US012807724B2

(12) United States Patent
Bienvenue et al.

(10) Patent No.: US 12,807,724 B2
(45) Date of Patent: Nov. 24, 2026

(54) 4-1BB AND OX40 BINDING PROTEINS AND RELATED COMPOSITIONS AND METHODS, ANTIBODIES AGAINST 4-1BB, ANTIBODIES AGAINST OX40

(71) Applicant: Aptevo Research and Development LLC, Seattle, WA (US)

(72) Inventors: David Leonard Bienvenue, Seattle, WA (US); Gabriela Hernandez-Hoyos, Seattle, WA (US); Lynda Misher, Seattle, WA (US); Danielle Van Citters, Seattle, WA (US); Michelle Hase Nelson, Seattle, WA (US); Peter Pavlik, Seattle, WA (US)

(73) Assignee: Aptevo Research and Development LLC, Seattle, WA (US)

( * ) Notice: Subject to any disclaimer, the term of this patent is extended or adjusted under 35 U.S.C. 154(b) by 1212 days.

(21) Appl. No.: 17/634,631

(22) PCT Filed: Aug. 12, 2020

(86) PCT No.: PCT/US2020/046005

§ 371 (c)(1),
(2) Date: Feb. 11, 2022

(87) PCT Pub. No.: WO2021/030488

PCT Pub. Date: Feb. 18, 2021

(65) Prior Publication Data

US 2022/0242962 A1 Aug. 4, 2022

Related U.S. Application Data

(60) Provisional application No. 63/056,115, filed on Jul. 24, 2020, provisional application No. 62/911,010, filed on Oct. 4, 2019, provisional application No. 62/902,318, filed on Sep. 18, 2019, provisional application No. 62/885,751, filed on Aug. 12, 2019.

(51) Int. Cl.

*C07K 16/28* (2006.01)
*A61K 39/00* (2006.01)
*A61P 35/00* (2006.01)

(52) U.S. Cl.

CPC .......... *C07K 16/2878* (2013.01); *A61P 35/00* (2018.01); *A61K 2039/505* (2013.01); *C07K 2317/24* (2013.01); *C07K 2317/31* (2013.01); *C07K 2317/52* (2013.01); *C07K 2317/622* (2013.01); *C07K 2317/75* (2013.01); *C07K 2317/92* (2013.01)

(58) Field of Classification Search

None
See application file for complete search history.

(56) References Cited

U.S. PATENT DOCUMENTS

| | | | |
|---|---|---|---|
| 4,474,893 | A | 10/1984 | Reading |
| 4,714,681 | A | 12/1987 | Reading |
| 4,925,648 | A | 5/1990 | Hansen et al. |
| 5,037,743 | A | 8/1991 | Welch et al. |
| 5,122,464 | A | 6/1992 | Wilson et al. |
| 5,143,830 | A | 9/1992 | Holland et al. |
| 5,223,409 | A | 6/1993 | Ladner et al. |
| 5,225,539 | A | 7/1993 | Winter |
| 5,403,484 | A | 4/1995 | Ladner et al. |
| 5,427,908 | A | 6/1995 | Dower et al. |
| 5,516,637 | A | 5/1996 | Huang et al. |
| 5,530,101 | A | 6/1996 | Queen et al. |
| 5,565,332 | A | 10/1996 | Hoogenboom et al. |
| 5,571,698 | A | 11/1996 | Ladner et al. |
| 5,573,920 | A | 11/1996 | Randle |
| 5,580,717 | A | 12/1996 | Dower et al. |
| 5,585,089 | A | 12/1996 | Queen et al. |
| 5,585,097 | A | 12/1996 | Bolt et al. |
| 5,601,819 | A | 2/1997 | Wong et al. |
| 5,624,821 | A | 4/1997 | Winter et al. |
| 5,648,260 | A | 7/1997 | Winter et al. |
| 5,658,727 | A | 8/1997 | Barbas et al. |
| 5,677,425 | A | 10/1997 | Bodmer et al. |
| 5,698,426 | A | 12/1997 | Huse |
| 5,731,168 | A | 3/1998 | Carter et al. |
| 5,733,743 | A | 3/1998 | Johnson et al. |
| 5,750,753 | A | 5/1998 | Kimae et al. |
| 5,766,886 | A | 6/1998 | Studnicka et al. |
| 5,780,225 | A | 7/1998 | Wigler et al. |
| 5,807,706 | A | 9/1998 | Carter et al. |
| 5,821,047 | A | 10/1998 | Garrard et al. |

(Continued)

FOREIGN PATENT DOCUMENTS

| | | | |
|---|---|---|---|
| CN | 101589062 | A | 11/2009 |
| CN | 107922480 | A | 4/2018 |

(Continued)

OTHER PUBLICATIONS

Winkler, et al., J Immunol, 2000, 165, 4505-4515 (Year: 2000).*

(Continued)

*Primary Examiner* — Misook Yu

*Assistant Examiner* — Samantha Lake Hopkins

(74) *Attorney, Agent, or Firm* — Sterne, Kessler, Goldstein & Fox P.L.L.C.

(57) ABSTRACT

The present disclosure provides antibodies that specifically bind to 4-1BB and/or OX40, including bispecific antibodies that bind to 4-1BB and OX40, and compositions comprising such antibodies. Also provided are methods for treating disorders, such as cancer, using such antibodies and compositions.

20 Claims, 34 Drawing Sheets

Specification includes a Sequence Listing.

(56) References Cited

U.S. PATENT DOCUMENTS

| | | | |
|---|---|---|---|
| 5,821,333 A | 10/1998 | Carter et al. | |
| 5,869,046 A | 2/1999 | Presta et al. | |
| 5,969,108 A | 10/1999 | McCafferty et al. | |
| 6,121,022 A | 9/2000 | Presta et al. | |
| 6,165,745 A | 12/2000 | Ward et al. | |
| 6,194,551 B1 | 2/2001 | Idusogie et al. | |
| 6,277,375 B1 | 8/2001 | Ward | |
| 6,407,213 B1 | 6/2002 | Carter et al. | |
| 6,737,056 B1 | 5/2004 | Presta | |
| 7,166,707 B2 | 1/2007 | Feige | |
| 7,658,921 B2 | 2/2010 | Dall'Acqua et al. | |
| 8,409,577 B2 | 4/2013 | Thompson et al. | |
| 8,591,886 B2 | 11/2013 | Ponath et al. | |
| 9,005,612 B2 | 4/2015 | Ledbetter et al. | |
| 9,782,478 B1 | 10/2017 | Blankenship et al. | |
| 10,774,150 B2 | 9/2020 | Ellmark et al. | |
| 11,008,396 B2 | 5/2021 | Ellmark et al. | |
| 11,352,426 B2 | 6/2022 | Tan et al. | |
| 2002/0155537 A1 | 10/2002 | Carter et al. | |
| 2003/0020734 A1 | 1/2003 | Yin et al. | |
| 2003/0118592 A1 | 6/2003 | Ledbetter et al. | |
| 2003/0133939 A1 | 7/2003 | Ledbetter et al. | |
| 2004/0014194 A1 | 1/2004 | Beyer et al. | |
| 2005/0042664 A1 | 2/2005 | Wu et al. | |
| 2005/0136049 A1 | 6/2005 | Ledbetter et al. | |
| 2006/0051844 A1 | 3/2006 | Heavner et al. | |
| 2009/0148447 A1 | 6/2009 | Ledbetter et al. | |
| 2013/0095097 A1 | 4/2013 | Blankenship et al. | |
| 2013/0129723 A1 | 5/2013 | Blankenship et al. | |
| 2015/0307620 A1 | 10/2015 | Vella et al. | |
| 2017/0089885 A1 | 3/2017 | Blankenship et al. | |
| 2018/0022819 A1 | 1/2018 | Blankenship et al. | |
| 2018/0118841 A1* | 5/2018 | Ellmark | A61P 35/00 |
| 2019/0022205 A1 | 1/2019 | Salih et al. | |
| 2019/0135943 A1 | 5/2019 | Boustany et al. | |
| 2021/0095046 A1 | 4/2021 | Blankenship et al. | |
| 2023/0303720 A1 | 9/2023 | Clapper et al. | |
| 2024/0150483 A1 | 5/2024 | Bienvenue | |
| 2024/0301086 A1 | 9/2024 | Pavlik et al. | |

FOREIGN PATENT DOCUMENTS

| | | | |
|---|---|---|---|
| EP | 0239400 | A2 | 9/1987 |
| EP | 0519596 | A1 | 12/1992 |
| EP | 0592106 | A1 | 4/1994 |
| JP | 2018535662 | A | 12/2018 |
| JP | 2018535665 | A | 12/2018 |
| WO | WO-1986005807 | A1 | 10/1986 |
| WO | WO-1989001036 | A1 | 2/1989 |
| WO | WO-1990002809 | A1 | 3/1990 |
| WO | WO-1991000360 | A1 | 1/1991 |
| WO | WO-1991009967 | A1 | 7/1991 |
| WO | WO-1991010737 | A1 | 7/1991 |
| WO | WO-1992001047 | A1 | 1/1992 |
| WO | WO-1992005793 | A1 | 4/1992 |
| WO | WO-1992008802 | A1 | 5/1992 |
| WO | WO-1992018619 | A1 | 10/1992 |
| WO | WO-1992022324 | A1 | 12/1992 |
| WO | WO-1993011236 | A1 | 6/1993 |
| WO | WO-1993017105 | A1 | 9/1993 |
| WO | WO-1993017715 | A1 | 9/1993 |
| WO | WO-1994029351 | A2 | 12/1994 |
| WO | WO-1995015982 | A2 | 6/1995 |
| WO | WO-1995020401 | A1 | 8/1995 |
| WO | WO-1997013844 | A1 | 4/1997 |
| WO | WO-1997034631 | A1 | 9/1997 |
| WO | WO-1998023289 | A1 | 6/1998 |
| WO | WO-2000042072 | A2 | 7/2000 |
| WO | WO-2000044788 | A1 | 8/2000 |
| WO | WO-2002060919 | A2 | 8/2002 |
| WO | WO-2002096948 | A2 | 12/2002 |
| WO | WO-2006028936 | A2 | 3/2006 |
| WO | WO-2007042261 | A2 | 4/2007 |
| WO | WO-2007146968 | A2 | 12/2007 |
| WO | WO-2008119353 | A1 | 10/2008 |
| WO | WO-2010003108 | A2 | 1/2010 |
| WO | WO-2010037838 | A2 | 4/2010 |
| WO | WO-2010040105 | A2 | 4/2010 |
| WO | WO-2011131746 | A2 | 10/2011 |
| WO | WO-2011147986 | A1 | 12/2011 |
| WO | WO-2012145714 | A2 | 10/2012 |
| WO | WO-2013060867 | A2 | 5/2013 |
| WO | WO-2018045110 | A1 | 3/2018 |
| WO | WO-2018057802 | A1 | 3/2018 |
| WO | WO-2018115003 | A2 | 6/2018 |
| WO | WO-2019016402 | A1 | 1/2019 |
| WO | WO-2020011966 | A1 | 1/2020 |
| WO | WO-2020150496 | A1 | 7/2020 |
| WO | WO-2021030488 | A1 | 2/2021 |
| WO | WO-2022178114 | A1 | 8/2022 |

OTHER PUBLICATIONS

Ahmad, et al., Clin Dev Immunol, 2012, 980250, 1-15 (Year: 2012).*

Herold, et al., Sci Rep, 2017, 7, 1-17 (Year: 2017).*

Janeway, et al., Immunobiology: The Immune System in Health and Disease, 5th edition, 2001 (Year: 2001).*

Chester, et al., Blood, 2018, 131, 49-57 (Year: 2018).*

International Search Report and Written Opinion for International Application No. PCT/US2022/016776, European Patent Office, Netherlands, mailed on May 27, 2022, 12 pages.

Wang, W., et al., "Antibody Structure, Instability, and Formulation," Journal of Pharmaceutical Sciences 96(1):1-26, American Pharmaceutical Association, United States (Jan. 2007).

Ames, R.S., et al., "Conversion of murine Fabs isolated from a combinatorial phage display library to full length immunoglobulins," *J Immunol Methods 184*:177-186, Elsevier, Netherlands (1995).

Baca, M., et al., "Antibody humanization using monovalent phage display," *J Biol Chem 272*(16):10678-84, American Society for Biochemistry and Molecular Biology, United States (1997).

Batzer, M.A., et al., "Enhanced evolutionary PCR using oligonucleotides with inosine at the 3'-terminus," *Nucleic Acid Res. 19*:5081, Oxford University Research, United Kingdom (1991).

Better, M., et al., "*Escherichia coli* secretion of an active chimeric antibody fragment," *Science* 240:1041-1043, American Association for the Advancement of Science, United States (1988).

Bremer, E., "Targeting of the tumor necrosis factor receptor superfamily for cancer immunotherapy," *ISRN Oncol.* 2013:371854, pp. 1-25, Hindawi Limited, United Kingdom (2013).

Bricogne, G., "[23] Bayesian statistical viewpoint on structure determination: Basic concepts and examples," *Methods Enzymol 276*:361-423, Academic Press, United States (1997).

Bricogne, G., "Direct phase determination by entropy maximization and likelihood ranking: status report and perspectives," *Acta Crystallogr D Biol Crystallogr 49*(Pt 1):37-60, Wiley, United States (1993).

Brinkmann, U., and Kontermann, R.E., "The making of bispecific antibodies," *MAbs 9*: 182-212, Taylor & Francis, United Kingdom (2017).

Brinkmann, U., et al., "Phage display of disulfide-stabilized Fv fragments," *J Immunol Methods 182*:41-50, Elsevier, Netherlands (1995).

Brochet, X., et al., "IMGT/V-QUEST: the highly customized and integrated system for IG and TR standardized V-J and V-D-J sequence analysis," *Nucl. Acids Res. 36*:W503-508, Oxford University Press, United Kingdom (2008).

Burton, D.R., and Barbas, C.F., "Human antibodies from combinatorial libraries," *Advan Immunol 57*:191-280, Elsevier, Netherlands (1994).

Caldas, C., et al., "Design and synthesis of germline-based hemi-humanized single-chain Fv against the CD18 surface antigen," *Protein Eng. 13*(5):353-60, Oxford University Press, United Kingdom (2000).

Champe, M., et al., "Monoclonal antibodies that block the activity of leukocyte function-associated antigen 1 recognize three discrete epitopes in the inserted domain of CD11a," *J Biol Chem 270*:1388-1394, American Society for Biochemistry and Molecular Biology, United States (1995).

(56) References Cited

OTHER PUBLICATIONS

Chayen, N.E., "The role of oil in macromolecular crystallization," *Structure 5*:1269-1274, Cell Press, United States (1997).
Chester, C., et al., "Immunotherapy targeting 4-1BB: mechanistic rationale, clinical results, and future strategies," *Blood 131*:49-57, American Society of Hematology, United States (2018).
Chothia, C., and Lesk, J., "Canonical structures for the hypervariable regions of immunoglobulins," *Mol. Biol. 196*:901-917, Elsevier, Netherlands (1987).
Coales, S.J., et al., "Epitope mapping by amide hydrogen/deuterium exchange coupled with immobilization of antibody, on-line proteolysis, liquid chromatography and mass spectrometry," *Rapid Commun. Mass Spectrom. 23*: 639-647, Wiley, United States (2009).
Couto, J.R., et al., "Anti-BA46 monoclonal antibody Mc3: humanization using a novel positional consensus and in vivo and in vitro characterization," *Cancer Res 55*(8):1717-22, American Association for Cancer Research, United States (1995).
Couto, J.R., et al., "Designing human consensus antibodies with minimal positional templates," *Cancer Res. 55*(23 Suppl):5973s-5977s, American Association for Cancer Research, United States (1995).
Cunningham, B.C., and Wells, J.A., "High-resolution epitope mapping of hGH-receptor interactions by alanine-scanning mutagenesis," *Science 244*:1081-1085, American Association for the Advancement of Science, United States (1989).
Curti, B.D., et al., "OX40 is a potent immune stimulating target in late-stage cancer patients," *Cancer Res. 73*(24):7189-7198, American Association for Cancer Research, United States (2013).
Dall'Acqua, W.F., et al., "Properties of human IgG1s engineered for enhanced binding to the neonatal Fc receptor (FcRn)," *J Biol Chem 281*: 23514-24, American Society for Biochemistry and Molecular Biology, United States (2006).
Edelman, G.M., et al., "The covalent structure of an entire gammaG immunoglobulin molecule," *Proc. Natl. Acad. USA*, 63:78-85, National Academy of Sciences, United States (1969).
Garber, K., "Bispecific antibodies rise again," *Nature Reviews Drug Discovery 13*:799-801, Springer Nature, Germany (2014).
Gaspar, M., et al., "CD137/OX40 Bispecific Antibody Induces Potent Antitumor Activity that Is Dependent on Target Coengagement," *Cancer Immunol Res. 8*(6):781-793, American Association for Cancer Research, United States (Apr. 2020).
Giege, R., et al., "Crystallogenesis of biological macromolecules: facts and perspectives," *Acta Crystallogr D Biol Crystallogr 50*(Pt 4):339-350, Wiley, United States (1994).
Gough, M.J., et al., "Adjuvant therapy with agonistic antibodies to CD134 (OX40) increases local control following surgical or radiation therapy of cancer in mice," *J Immunotherapy 33*(8):798-809, Future Medicine, United Kingdom (2010)).
Hennecke, F., et al., "Non-repetitive single-chain Fv linkers selected by selectively infective phage (SIP) technology," *Protein Eng. 11*:405-410, Oxford University Press, United Kingdom (1998).
Imura, A., et al., "The human OX40/gp34 system directly mediates adhesion of activated T cells to vascular endothelial cells," *J Exp. Med 183*:2185-2195, Rockefeller University Press, United States (1996).
International Search Report and Written Opinion for International Application No. PCT/US2020/046005, European Patent Office, Netherlands, mailed on Jan. 21, 2021, 20 pages.
Jones, P.T., et al., "Replacing the complementarity-determining regions in a human antibody with those from a mouse," *Nature 321*:522-525, Springer Nature, United Kingdom (1986).
Kabat, E.A. and Wu, T.T., "Attempts to locate complementarity-determining residues in the variable positions of light and heavy chains," *Ann NY Acad Sci 190*:382-393, New York Academy of Sciences, Wiley-Blackwell, United States (1971).
Kettleborough, C.A., et al., "Isolation of tumor cell-specific single-chain Fv from immunized mice using phage-antibody libraries and the re-construction of whole antibodies from these antibody fragments," *Eur J Immunol 24*:952-958, Wiley, United States (1994).
Kohler, G., and Milstein, C., "Continuous cultures of fused cells secreting antibody of predefined specificity," *Nature 256*:495-497, Springer Nature, Germany (1975).
Kostelny, S.A., et al., "Formation of a bispecific antibody by the use of leucine zippers," *J. Immunol. 148*:1547-1553, American Association of Immunologists, United States (1992).
Labrijn, A.F. et al., "Efficient generation of stable bispecific IgG1 by controlled Fab-arm exchange," *PNAS 110*(13):5145-5150, National Academy of Sciences, United States (2013).
Liu, H., et al., "Fc Engineering for Developing Therapeutic Bispecific Antibodies and Novel Scaffolds," *Front. Immunol. 8*(38): 1-15 doi:10.2289/fimmu.2017.00038, Frontiers Media S.A., Switzerland (2017).
Martinez-Lostao, L., et al., "How Do Cytotoxic Lymphocytes Kill Cancer Cells?," *Clin Cancer Re*; 21(22):5047-5056, American Association for Cancer Research, United States (2015).
Maxwell, J.R., et al., "Danger and OX40 Receptor Signaling Synergize to Enhance Memory T Cell Survival by Inhibiting Peripheral Deletion," *J Immunology 164*:107-112, American Association of Immunologists, United States (2000).
Mayes, P.A., et al., "The promise and challenges of immune agonist antibody development in cancer," *Nature Reviews Drug Discovery 17*:509-527, Springer Nature, Germany (2018).
Mcpherson, A., "Crystallization of proteins from polyethylene glycol," *J Biol Chem 251*: 6300-6303, American Society for Biochemistry and Molecular Biology, United States (1976).
Mcpherson, A., "Current approaches to macromolecular crystallization," *Eur J Biochem 189*: 1-23, Wiley, United Kingdom (1990).
Montler, R., et al., "OX40, PD-1 and CTLA-4 are selectively expressed on tumor-infiltrating T cells in head and neck cancer," *Clin Transl Immunology 5*:e70, 9 pages, Wiley, United States (2016).
Morea, V., et al., "Antibody modeling: implications for engineering and design," *Methods 20*(3):267-279, Elsevier, Netherlands (2000).
Mullinax, R.L., et al., "Expression of a heterodimeric Fab antibody protein in one cloning step," *BioTechniques 12*(6):864-869, Informa, United Kingdom (1992).
Ohshima, Y., et al., "Expression and function of OX40 ligand on human dendritic cells," *J Immunology 159*:3838-3848, American Association of Immunologists, United States (1997).
Ohtsuka, E., et al., "An alternative approach to deoxyoligonucleotides as hybridization probes by insertion of deoxyinosine at ambiguous codon positions," *J. Biol. Chem. 260*:2605-2608, American Society for Biochemistry and Molecular Biology, United States (1985).
Padlan, E.A., "A possible procedure for reducing the immunogenicity of antibody variable domains while preserving their ligand-binding properties," *Mol Immunol 28*:489-498, Pergamon Press, United Kingdom (1991).
Padlan, E.A., "Anatomy of the antibody molecule," *Mol. Immunol. 31*:169-217, Pergamon Press, United Kingdom (1994).
Pedersen, J.T., et al., "Comparison of surface accessible residues in human and murine immunoglobulin Fv domains. Implication for humanization of murine antibodies," *J Mol Biol 235*(3):959-973, Elsevier, United States (1994).
Persic, L., et al., "An integrated vector system for the eukaryotic expression of antibodies or their fragments after selection from phage display libraries," *Gene 187*:9-18, Elsevier, Netherlands (1997).
Putnam, F.W., "Immunoglobulins: Structure, Function, and Genes," in *The Plasma Proteins*, vol. 5, pp. 49-140, Academic Press, Inc., United States (1987).
Qui, H.Z., et al., "CD134 plus CD137 dual costimulation induces Eomesodermin in CD4 T cells to program cytotoxic Th1 differentiation," *J Jmmunol. 187*:3555-3564, American Association of Immunologists, United States (2011).
Ravetch, J.V., et al., "Fc receptors," *Annu. Rev. Immunol.*, 9:457-492, Annual Reviews, United States (1991).
Riechmann, L., et al., "Reshaping human antibodies for therapy," *Nature 332*:323-327, Springer Nature, United Kingdom (1988).
Rogers, P.R., et al., "OX40 promotes Bcl-xL and Bcl-2 expression and is essential for long-term survival of CD4 T cells," *Immunity 15*(3):445-455, Cell Press, United States (2001).

(56) References Cited

OTHER PUBLICATIONS

Roguska, M.A., et al., "A comparison of two murine monoclonal antibodies humanized by CDR-grafting and variable domain resurfacing," *Protein Eng. 9*(10):895-904, Oxford University Press, United Kingdom (1996).
Roguska, M.A., et al., "Humanization of murine monoclonal antibodies through variable domain resurfacing," *Proc. Natl. Acad. Sci.*, USA, 91(3):969-973, National Academy of Sciences, United States (1994).
Rossolini, G.M., et al., "Use of deoxyinosine-containing primers vs degenerate primers for polymerase chain reaction based on ambiguous sequence information," *Mol. Cell. Probes 8*:91-98, Elsevier, Netherlands (1994).
Roversi, P., et al., "Modelling prior distributions of atoms for macromolecular refinement and completion," *Acta Crystallogr D Biol Crystallogr 56*(Pt 10): 1316-1323, Wiley, United States (2000).
Ryan, J., et al., "A novel biologic platform elicits profound T cell costimulatory activity and antitumor immunity in mice," *Cancer Immunol Immunother. 67*(4):605-613, Springer, Germany (2018).
Sandhu, J.S., "A rapid procedure for the humanization of monoclonal antibodies," *Gene 150*(2):409-10, Elsevier, Netherlands (1994).
Sawai, H., et al., "Direct production of the Fab fragment derived from the sperm immobilizing antibody using polymerase chain reaction and cDNA expression vectors," *Am J Reprod Immunol 34*:26-34, Wiley, United States (1995).
Shields, R.L., et al., "High resolution mapping of the binding site on human IgG1 for Fc gamma RI, Fc gamma RII, Fc gamma RIII, and FcRn and design of IgG1 variants with improved binding to the Fc gamma R*," *J Biol Chem* 276:6591-6604, American Society for Biochemistry and Molecular Biology, United States (2001).
Smith, P., et al., "Mouse model recapitulating human Fcγ receptor structural and functional diversity," *PNAS 109*:6181-6186, National Academy of Sciences, United States (2012).
Spiess, C., et al., "Alternative molecular formats and therapeutic applications for bispecific antibodies," *Mol. Immun. 67*:95-106, Pergamon Press, United Kingdom (2015).
Studnicka, G.M., et al., "Human-engineered monoclonal antibodies retain full specific binding activity by preserving non-CDR complementarity-modulating residues," *Prot Engineering 7*(6):805-814, Oxford University Press, United Kingdom (1994).
Tan, P., et al., "'Superhumanized' antibodies: reduction of immunogenic potential by complementarity-determining region grafting with human germline sequences: application to an anti-CD28," *J Immunol 169*: 1119-25, American Association of Immunologists, United States (2002).
Tang, Y., et al., "Selection of linkers for a catalytic single-chain antibody using phage display technology," *J Biol. Chem. 271*:15682-15686, American Society for Biochemistry and Molecular Biology, United States (1996).
Tarcsa, E., et al., "Dual-Variable Domain Immunoglobulin (DVD-Ig™) Technology: A Versatile, Novel Format for the Next Generation of Dual-Targeting Biologics," *Bispecific Antibodies* 171-185, Springer, Germany (2011).
Tutt, A., et al., "Trispecific F(ab')3 derivatives that use cooperative signaling via the TCR/CD3 complex and CD2 to activate and redirect resting cytotoxic T cells," *J. Immunol. 147*:60-69, American Association of Immunologists, United States (1991).
Verhoeyen, M., et al., "Reshaping human antibodies: grafting an antilysozyme activity," *Science 239*:1534-1536, American Association for the Advancement of Science, United States (1988).
Wang, W., et al., "Monoclonal antibodies with identical Fc sequences can bind to FcRn differentially with pharmacokinetic consequences," *Drug Metab Dispos. 39*(9):1469-1477, American Society for Pharmacology and Experimental Therapeutics, United States (2011).
Ward, E.S., et al., "The effector functions of immunoglobulins: implications for therapy," *Therap. Immunol.* 2:77-94, Wiley, United States (1995).
Weatherhill, A.R., et al., "OX40 ligation enhances cell cycle turnover of Ag-activated CD4 T cells in vivo," *Cell Immunol*, 209(1):63-75, Cell Press, United States (2001).
Ye, Q., et al., "Finding a needle in a haystack: Activation—induced CD137 expression accurately identifies naturally occurring tumor-reactive T cells in cancer patients," *Oncoimmunology 2*:12, e27184, 3 pages, Taylor & Francis, United Kingdom (2013).
Zhou, S., et al., "Strategies for Bispecific Single Chain Antibody in Cancer Immunotherapy," *J Cancer 8*:3689-3696, Ivyspring International Publisher, Australia (2017).
Hummer, A.M., et al., "Advances in computational structure-based antibody design," Current Opinion in Structural Biology 74:102379, pp. 1-7, Elsevier, Netherlands (Jun. 2022).
Chiu, M. L., et al., "Antibody structure and function: The basis for engineering therapeutics," Antibodies 8(4):55, pp. 1-80, MDPI, Switzerland (Dec. 2019).
Rojas, G., "Understanding and Modulating Antibody Fine Specificity: Lessons from Combinatorial Biology," Antibodies 11(3):48, pp. 1-22, MDPI, Switzerland (Jul. 2022).
Nie, S., et al., "Biology drives the discovery of bispecific antibodies as innovative therapeutics," Antibody Therapeutics 3(1):18-62, Oxford University Press, United Kingdom (Feb. 2020).

* cited by examiner

Fig. 1A. FOB005 expressing human 4-1BB (clones 4, 13 and 6, left to right)
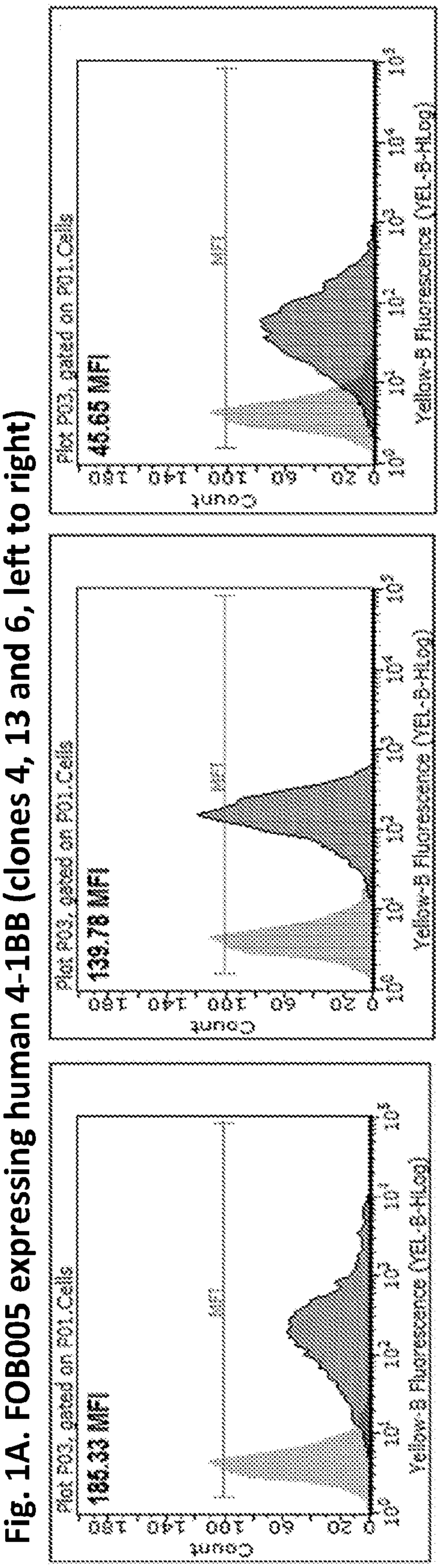
Fig. 1B FOB006 expressing cyno 4-1BB (clones 31, 26 and 30, left to right)
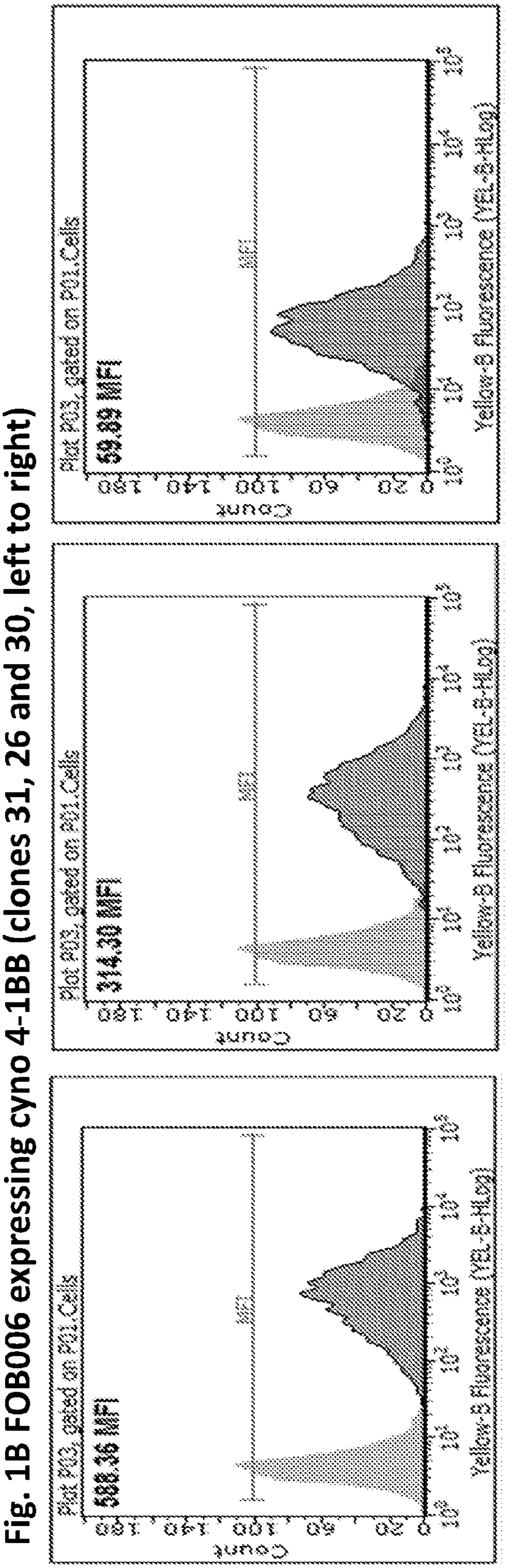

Binding of construct variants to human OX40 CHOK1SV

Binding of construct variants to cynomolgus OX40 CHOK1SV

Fig. 7

```
                         <-------FR1-IMGT-------->< -CDR1-><---FR2-IMGT----><-CDR2-><-------------FR3-IMGT------------->
IGHV1-46*01    QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCAR (SEQ ID NO:123)
FOBW006HLH40   EVQLVQSGAEVKKPGASVKVSCKASGYTFTSYWMNWVRQAPGQGLEWMGNIYPSGGSTNYAQKFQGRVTMTVDTSTSTVYMELSSLRSEDTAVYYCAS (SEQ ID NO:124)
FOBW006HLH26   EVQLVQSGAEVKKPGASVKVSCKASGYTFTSYWMNWVRQAPGQGLEWMGNIYPGSSTTNYAQKFQGRVTMTVDTSTSTVYMELSSLRSEDTAVYYCAS (SEQ ID NO:125)
FOBW006HLH20   EVQLVQSGAEVKKPGSSVKVSCKASGYTFTSYWINWVRQAPGQGLEWIGNIYPGSSTTNYNEKFKSRATLTVDTSTSTAYMELSSLRSEDTAVYYCAS (SEQ ID NO:126)
Mouse clone6   QVQLQQPGAELVKPGASVKLSCKASGYTFTSYWINWVKQRPGQGLEWIGNIYPGSSTTNYNEKFKSKATLTVDTSSSTAYMQLSSLTSDDSAVFYCAS (SEQ ID NO:127)

                   <---FR4--->
IGHJ4*01       YFDYWGQGTLVTVSS  (SEQ ID NO:128)
FOBW006HLH40   AMDYWGQGTLVTVSS  (SEQ ID NO:129)
FOBW006HLH26   AMDYWGQGTLVTVSS  (SEQ ID NO:130)
FOBW006HLH20   AMDYWGQGTLVTVSS  (SEQ ID NO:131)
Mouse clone6   AMDYWVQGTSVTVSS  (SEQ ID NO:132)

               <--------FR1-IMGT--------><CDR1-><---FR2-IMGT----><C><-------------FR3-IMGT------------>
IGKV3D-7*01    EIVMTQSPATLSLSPGERATLSCRASQSVSSSYLSWYQQKPGQAPRLLIYGASTRATGIPARFSGSGSGTDFTLTISSLQPEDFAVYYCQQDYNLP  (SEQ ID NO:133)
FOBW006HLH40   EIVMTQSPATLSLSPGERATLSCRASQSVSS-YLNWYQQKPGQAPRLLIYYASRRHTGIPARFSGSGSGTDFTLTISSLQPEDFAVYYCQQGYNLP  (SEQ ID NO:134)
FOBW006HLH26   EIVMTQSPATLSLSPGERATLSCRASQDISN-YLNWYQQKPGQAVRLLIYYTSRLHSGIPARFSGSGSGTDYTLTISSLQPEDFAVYFCQQGYTLP  (SEQ ID NO:135)
FOBW006HLH20   EIVMTQSPGTLSLSPGERATLSCRASQDISN-YLNWYQQKPGQAVRLLIYYTSRLHSGIPDRFSGSGSGTDYTLTISRLEPEDFAVYFCQQGYTLP  (SEQ ID NO:136)
Mouse clone6   DIQMTQTTSSLSASLGDRVTITCRASQDISN-YLNWYQQKPDGTVKLLIYYTSRLHSGVPSRFSGGGSGTDYSLTISNLEQEDIATYFCQQGYTLP  (SEQ ID NO:137)

                 <--FR4--->
IGKJ1*01       WTFGQGTKVEIK     (SEQ ID NO:138)
FOBW006HLH40   YTFGQGTKVEIK     (SEQ ID NO:139)
FOBW006HLH26   YTFGQGTKVEIK     (SEQ ID NO:140)
FOBW006HLH20   YTFGQGTKVEIK     (SEQ ID NO:141)
Mouse clone6   YTFGGGTKLEIK     (SEQ ID NO:142)
```

Binding of construct variants to parental CHOK1SV

Activity of construct variants in the human 4-1BB reporter assay

Activity of construct variants in the human OX40 reporter assay

Activity of construct variants in the cynomolgus 4-1BB reporter assay

Activity of construct variants in the cynomolgus OX40 reporter assay

NK cell proliferation

NK cell activation

4-1BB AND OX40 BINDING PROTEINS AND RELATED COMPOSITIONS AND METHODS, ANTIBODIES AGAINST 4-1BB, ANTIBODIES AGAINST OX40

CROSS REFERENCE TO RELATED APPLICATIONS

This application is a 35 U.S.C. § 371 National Phase Application of International Application No. PCT/US2020/046005 (filed Aug. 12, 2020), which claims the benefit of U.S. Provisional Application Nos. 62/885,751 (filed Aug. 12, 2019), 62/902,318 (filed Sep. 18, 2019), 62/911,010 (filed Oct. 4, 2019), and 63/056,115 (filed Jul. 24, 2020), each of which is hereby incorporated by reference in its entirety.

REFERENCE TO A SEQUENCE LISTING SUBMITTED ELECTRONICALLY VIA EFS-WEB

The content of the electronically submitted sequence listing in ASCII text file Name: 4897_0040004_Seglisting_ST25.txt; Size: 366,722 bytes; and Date of Creation: Jan. 14, 2022) is incorporated herein by reference in its entirety.

FIELD OF THE DISCLOSURE

The present disclosure relates to antibodies that specifically bind to 4-1BB and/or OX40, including bispecific antibodies that bind to 4-1BB and OX40, and compositions comprising the same. These antibodies are useful for enhancing immune responses and for the treatment of disorders, including solid tumor cancers.

BACKGROUND 4-1BB (CD137) and OX40 are members of the TNF-receptor (TNFR) family (Bremer, *ISRN Oncol.:* 371854 (2013)). These receptors are not constitutively present on naïve T or NK cells: their expression is triggered by stimulation of T cells through the T-cell Receptor (TCR), or other stimuli in NK cells. 4-1BB is primarily upregulated in CD8 T cells and NK cells, while OX40 is primarily upregulated on CD4 T cells. The function of these receptors is to provide a co-stimulatory signal to T and NK cells. Activation of these receptors is naturally triggered by trimerization through interaction with 4-1BB Ligand (4-1BBL) or OX40 Ligand (OX40L) trimers, leading to signal transduction and initiation of specific cellular functions. 4-1BB enhances the effector function of CD8 T cells and NK cells through increased expression of IFN-γ, granzymes, and anti-apoptotic genes leading to the generation of more and better effector CD8 T and NK cells. OX40 enhances the effector function of CD4 T cells by enhancing their ability to produce IL-2 and clonal expansion of memory CD4 T cells.

4-1BB and OX40 are often expressed on tumor infiltrating lymphocytes, and in fact, their expression has been used to identify tumor-specific T cells Human solid tumors are often infiltrated by lymphocytes, mostly CD8+ and CD4+ T cells. The accumulation of tumor infiltrating lymphocytes is often associated with improved survival among patients affected by various malignancies. (Ye et al., OncoImmunology 2: e27184 (2013); Montler et al., Clin Transl Immunology 5:e70 (2016)).

Trimerization of the 4-1BB receptors and OX40 receptors can be induced via monoclonal antibodies. In some published examples, monoclonal antibodies have been developed to induce signaling by binding to Fc gamma receptors through their Fc regions to induce higher-order clustering of the receptor (Mayes et al., *Nature Reviews Drug Discovery* 17: 509 (2018)).

Preclinical results in a variety of induced and spontaneous tumor models suggest that targeting 4-1BB with agonist antibodies can lead to tumor clearance and durable anti-tumor immunity. Urelumab and utomilumab, are agonist anti-4-1BB monoclonal antibodies with ongoing clinical trials in indications including treatment of solid tumors. Despite initial signs of efficacy, clinical development of urelumab has been hampered by inflammatory liver toxicity at doses above 1 mg/kg. Utomilumab is less potent that urelumab, but it has a improved safety profile as compared to urelumab (Chester et al., Blood 131: 39-57 (2018)). A need exists for an efficacious therapeutic that targets 4-1BB that does not cause liver toxicity as observed with urelumab or other systemic damage.

OX40 agonists have been reported to increase T-cell infiltration into tumors. Another advantage of targeting OX40 is that OX40 signaling can prevent Treg-mediated suppression of antitumor immune responses. In several preclinical mouse cancer models, including 4T-1 breast cancer, B16 melanoma, Lewis lung carcinoma and several chemically induced sarcomas, injection of an OX40 agonist has resulted in therapeutic responses. (Ohsima et al., J. Immunology 159:3838-3848 (1997); Imura et al., *J. Exp. Med.* 183:2185-2195 (1996); Maxwell et al., *J. Immunology* 164:107-112 (2000); Gough et al., *J. Immunotherapy* 33(8): 798-809 (2010)).

The murine anti-human OX40 mAb (clone 9B12) was the first OX40 agonistic reagent tested in a clinical trial of 30 patients with advanced solid tumors. In this phase I study, although none of the patients showed an objective response by RECIST criteria, some immune responses like Ki67-staining by antigen-experienced CD4+ and CD8+ T cells in blood was increased, suggesting enhanced activation of T cells. In addition, upregulation of OX40 by tumor-infiltrating Tregs was detected. Overall, agonist anti-OX40 mAb 9B12 was well tolerated with mild to moderate side effects. (Curti et al., Cancer Res. 73(24):7189-7198 (2013)).

In some cases, researchers have generated protein constructs that contain multiple binding domains (>2) against 4-1BB or OX40, or fusions of multiple OX40L and 4-1BBL extracellular domains to induce agonism. In other examples, there are bispecific proteins that contain binding domain(s) to 4-1BB or OX40 and binding domain(s) to a tumor-specific antigen. Binding and clustering via the tumor antigen binding induces clustering and signaling of 4-1BB and OX40. However, none of these constructs are expected to stimulate the function of tumor infiltrating lymphocytes, namely, CD8+ T cells CD4 T+ cells, and NK cells, and to do so with minimal to no off-target activation of effector cells (i.e., activation through binding to FcγR1, FcγRIIa, FcγRIIb, FcγRIIa, and FcγRIIIb). Therefore, in order to selectively bolster the activity of tumor infiltrating lymphocytes (with minimal to no effect on circulating lymphocytes), bispecific antibodies that bind to and stimulate both 4-1BB and OX40 are needed.

SUMMARY

As demonstrated herein, bispecific proteins that bind to 4-1BB and OX40 (e.g., ADAPTIR™ bispecifics) act by binding to one receptor to induce signaling of the other, and vice versa. Advantageously, this causes agonism of both receptors using one therapeutic protein. The Fc regions of the bispecific proteins can contain modifications that eliminate binding to Fc gamma receptors and complement-related proteins, so that the activity of the bispecific protein is strictly dependent on the presence of both receptors on either the same or different cells. Activity is not observed in the absence of one or both receptors. Importantly, the bispecific constructs provided herein result in dose-dependent increases in T and NK cell proliferation, while the combination of monospecific constructs targeting 4-1BB and OX40 fails to do so.

In certain instances, a bispecific antibody provided herein comprises a polypeptide comprising, in order from amino-terminus to carboxyl-terminus, (i) a first single chain variable fragment (scFv), (ii) a linker, optionally wherein the linker is a hinge region, (iii) an immunoglobulin constant region, and (iv) a second scFv, wherein (a) the first scFv comprises a human 4-1BB antigen-binding domain, and the second scFv comprises a human OX40 antigen-binding domain or (b) the first scFv comprises a human OX40 antigen-binding domain and the second scFv comprises a human 4-1BB antigen-binding domain.

In certain instances, an antibody provided herein comprises a human 4-1BB antigen-binding domain, wherein the 4-1BB antigen-binding domain competitively inhibits binding of an antibody comprising a heavy chain variable domain (VH) comprising SEQ ID NO:17 and a light chain variable domain (VL) comprising SEQ ID NO:18 to human 4-1BB.

In certain instances, an antibody provided herein comprises a human 4-1BB antigen-binding domain, wherein the 4-1BB antigen-binding domain specifically binds to the same epitope of human 4-1BB as an antibody comprising a VH comprising the amino acid sequence of SEQ ID NO:17 and a VL comprising the amino acid sequence of SEQ ID NO:18.

In certain instances, an antibody provided herein comprises a human 4-1BB antigen-binding domain, wherein the human 4-1BB antigen-binding domain comprises the six complementarity determining regions (CDRs) in the VH of SEQ ID NO:17 and the VL of SEQ ID NO:18 or the six CDRs in the VH of SEQ ID NO: 19 and the VL of SEQ ID NO:20.

In certain instances, the CDRs are the IMGT-defined CDRs, the Kabat-defined CDRs, the Chothia-defined CDRs, or the AbM-defined CDRs.

In certain instances, an antibody provided herein comprises a human 4-1BB antigen-binding domain, wherein the human 4-1BB antigen-binding domain comprises a VH and a VL, wherein the VH comprises the amino acid sequence of SEQ ID NO: 17.

In certain instances, an antibody provided herein comprises a human 4-1BB antigen-binding domain, wherein the human 4-1BB antigen-binding domain comprises a VH and a VL, wherein the VL comprises the amino acid sequence of SEQ ID NO:18.

In certain instances, an antibody provided herein comprises a human OX40 antigen-binding domain, wherein the OX40 antigen-binding domain competitively inhibits binding of an antibody comprising a VH comprising SEQ ID NO:29 and a VL comprising SEQ ID NO:28 to human OX40.

In certain instances, an antibody provided herein comprises a human OX40 antigen-binding domain, wherein the OX40 antigen-binding domain specifically binds to the same epitope of human OX40 as an antibody comprising a VH comprising the amino acid sequence of SEQ ID NO:29 and a VL comprising the amino acid sequence of SEQ ID NO:28.

In certain instances, an antibody provided herein comprises a human OX40 antigen-binding domain, wherein the human OX40 antigen-binding domain comprises the six CDRs in the VH of SEQ ID NO:29 and the VL of SEQ ID NO:28.

In certain instances, the CDRs are the IMGT-defined CDRs, the Kabat-defined CDRs, the Chothia-defined CDRs, or the AbM-defined CDRs.

In certain instances, an antibody provided herein comprises a human OX40 antigen-binding domain, wherein the human OX40 antigen-binding domain comprises a VH and a VL, wherein the VH comprises the amino acid sequence of SEQ ID NO:29.

In certain instances, an antibody provided herein comprises a human OX40 antigen-binding domain, wherein the human OX40 antigen-binding domain comprises a VH and a VL, wherein the VL comprises the amino acid sequence of SEQ ID NO:28.

In certain instances, the antibody is monospecific.

In certain instances, the antibody is an IgG antibody. In certain instances, the IgG antibody is an $IgG_1$ antibody.

In certain instances, the antibody further comprises a heavy chain constant region and a light chain constant region, optionally wherein the heavy chain constant region is a human $IgG_1$ heavy chain constant region, and optionally wherein the light chain constant region is a human $IgG_{\kappa}$ light chain constant region.

In certain instances, the antibody is an single chain Fv (scFv). In certain instances, the antibody comprises an a Fab, Fab', $F(ab')_2$, scFv, disulfide linked Fv, or scFv-Fc.

In certain instances, the antibody that comprises a 4-1BB binding domain is bispecific. In certain instances, the bispecific antibody comprises a human OX40 antigen-binding domain. In certain instances, the human OX40 antigen-binding domain (a) competitively inhibits binding of an antibody comprising a VH comprising SEQ ID NO:29 and a VL comprising SEQ ID NO:28 to human OX40, (b) specifically binds to the same epitope of human OX40 as an antibody comprising a VH comprising the amino acid sequence of SEQ ID NO:29 and a VL comprising the amino acid sequence of SEQ ID NO:28, (c) comprises the six CDRs in the VH of SEQ ID NO:29 and the VL of SEQ ID NO:28, optionally wherein the CDRs are the IMGT-defined CDRs, the Kabat-defined CDRs, the Chothia-defined CDRs, or the AbM-defined CDRs, (d) comprises a VH and a VL, wherein the VH comprises the amino acid sequence of SEQ ID NO:29, and/or (e) comprises a VH and a VL, wherein the VL comprises the amino acid sequence of SEQ ID NO:28.

In certain instances, the antibody that comprises an OX40 binding domain is bispecific. In certain instances, the bispecific antibody comprises a human 4-1BB antigen-binding domain. In certain instances, the human 4-1BB antigen-binding domain (a) competitively inhibits binding of an antibody comprising a VH comprising SEQ ID NO:17 and a VL comprising SEQ ID NO:18 to human 4-1BB, (b) specifically binds to the same epitope of human 4-1BB as an antibody comprising a VH comprising the amino acid sequence of SEQ ID NO:17 and a VL comprising the amino acid sequence of SEQ ID NO:18, (c) comprises the six CDRs in the VH of SEQ ID NO:17 and the VL of SEQ ID NO:18 or the six CDRs in the VH of SEQ ID NO:19 and the VL of SEQ ID NO:20, optionally wherein the CDRs are the IMGT-defined CDRs, the Kabat-defined CDRs, the Chothia-defined CDRs, or the AbM-defined CDRs, (d) comprises a VH and a VL, wherein the VH comprises the amino acid sequence of SEQ ID NO: 17, and/or (e) comprises a VH and a VL, wherein the VL comprises the amino acid sequence of SEQ ID NO:18.

In certain instances, bispecific antibody provided herein comprises (a) a human 4-1BB antigen-binding domain and (b) a human OX40 antigen-binding domain, wherein the 4-1BB antigen-binding domain comprises a (i) a VH-CDR 1 comprising the amino acid sequence of GYTFTSYW (SEQ ID NO:5); (ii) a VH-CDR2 comprising the amino acid sequence of IYPGSSTT (SEQ ID NO:6); (iii) a VH-CDR3 comprising the amino acid sequence of ASFSDGYYAYAMDY (SEQ ID NO:7); (iv) a light chain variable domain (VL)-CDR1 comprising the amino acid sequence of QDISNY (SEQ ID NO:8); (v) a VL-CDR2 comprising the amino acid sequence of YTS (SEQ ID NO:9); and (vi) a VL-CDR3 comprising the amino acid sequence of QQGYTLPYT (SEQ ID NO:10); and the OX40 antigen-binding domain comprises a (i) a VH-CDR1 comprising the amino acid sequence of GFTLSYYG (SEQ ID NO: 11); (ii) a VH-CDR2 comprising the amino acid sequence of ISHDGSDK (SEQ ID NO:12); (iii) a VH-CDR3 comprising the amino acid sequence of SNDQFDP (SEQ ID NO:13); (iv) a VL-CDR1 comprising the amino acid sequence of NIGSKS (SEQ ID NO: 14); (v) a VL-CDR2 comprising the amino acid sequence of DDS (SEQ ID NO: 15); and (vi) a VL-CDR3 comprising the amino acid sequence of QVWDSSSDHVV (SEQ ID NO:16).

In certain instances of the bispecific antibodies provided herein, the human 4-1BB antigen-binding domain (a) competitively inhibits binding of an antibody comprising a VH comprising SEQ ID NO:17 and a VL comprising SEQ ID NO:18 to human 4-1BB, (b) specifically binds to the same epitope of human 4-1BB as an antibody comprising a VH comprising the amino acid sequence of SEQ ID NO: 17 and a VL comprising the amino acid sequence of SEQ ID NO: 18, (c) comprises the six CDRs in the VH of SEQ ID NO:17 and the VL of SEQ ID NO:18 or the six CDRs in the VH of SEQ ID NO:19 and the VL of SEQ ID NO:20, optionally wherein the CDRs are the IMGT-defined CDRs, the Kabat-defined CDRs, the Chothia-defined CDRs, or the AbM-defined CDRs, (d) comprises a VH and a VL, wherein the VH comprises the amino acid sequence of SEQ ID NO:17, and/or (e) comprises a VH and a VL, wherein the VL comprises the amino acid sequence of SEQ ID NO:18.

In certain instances of the bispecific antibodies provided herein, the human OX40 antigen-binding domain (a) competitively inhibits binding of an antibody comprising a VH comprising SEQ ID NO:29 and a VL comprising SEQ ID NO:28 to human OX40, (b) specifically binds to the same epitope of human OX40 as an antibody comprising a VH comprising the amino acid sequence of SEQ ID NO:29 and a VL comprising the amino acid sequence of SEQ ID NO:28, (c) comprises the six CDRs in the VH of SEQ ID NO:29 and the VL of SEQ ID NO:28, optionally wherein the CDRs are the IMGT-defined CDRs, the Kabat-defined CDRs, the Chothia-defined CDRs, or the AbM-defined CDRs, (d) comprises a VH and a VL, wherein the VH comprises the amino acid sequence of SEQ ID NO:29, and/or (e) comprises a VH and a VL, wherein the VL comprises the amino acid sequence of SEQ ID NO:28.

In certain instances, the human 4-1BB binding domain comprises a VH comprising an amino acid sequence at least 75%, 80%, 85%, 90%, 95%, or 99% identical to an amino acid sequence selected from the group consisting of SEQ ID NOs:17, 19, 21, 23, 32, and 143. In certain instances, the human 4-1BB binding domain comprises a VH comprising the amino acid sequence of any one of SEQ ID NOs:17, 19, 21, 23, 32, and 143.

In certain instances, the human 4-1BB binding domain comprises a VL comprising an amino acid sequence at least 75%, 80%, 85%, 90%, 95%, or 99% identical to an amino acid sequence selected from the group consisting of SEQ ID NOs:18, 20, 22, and 24. In certain instances, the human 4-1BB binding domain comprises a VL comprising the amino acid sequence of any one of SEQ ID NOs:18, 20, 22, and 24.

In certain instances, the human 4-1BB binding domain comprises (a) a VH comprising the amino acid sequence of SEQ ID NO:17 and a VL comprising the amino acid sequence of SEQ ID NO:18, (b) a VH comprising the amino acid sequence of SEQ ID NO:19 and a VL comprising the amino acid sequence of SEQ ID NO:20, (c) a VH comprising the amino acid sequence of SEQ ID NO:21 and a VL comprising the amino acid sequence of SEQ ID NO:22, (d) a VH comprising the amino acid sequence of SEQ ID NO:23 and a VL comprising the amino acid sequence of SEQ ID NO:24, (e) a VH comprising the amino acid sequence of SEQ ID NO:32 and a VL comprising the amino acid sequence of SEQ ID NO:18, or (f) a VH comprising the amino acid sequence of SEQ ID NO:143 and a VL comprising the amino acid sequence of SEQ ID NO:20.

In certain instances, the human 4-1BB binding domain comprises a VH comprising the amino acid sequence of SEQ ID NO:17 and a VL comprising the amino acid sequence of SEQ ID NO:18.

In certain instances, the human 4-1BB binding domain comprises a VH and a VL on the same polypeptide chain. In certain instances, the VH of the human 4-1BB binding domain is N-terminal to the VL of the human 4-1BB binding domain. In certain instances, the VH of the human 4-1BB binding domain is C-terminal to the VL of the human 4-1BB binding domain. In certain instances, the human 4-1BB binding domain comprises a linker between the VH and the VL. In certain instances, the linker comprises the amino acid $(Gly_4Ser)_n$, wherein n=1-5 (SEQ ID NO: 117). In certain instances, n=3-5 or n=4-5. In certain instances n=4.

In certain instances, the human 4-1BB binding domain comprises an scFv comprising the amino acid sequence of any one of SEQ ID NOs:42, 44, 58, 63, 77, and 145.

In certain instances, the human 4-1BB binding domain comprises an scFv comprising the amino acid sequence of SEQ ID NO:58.

In certain instances, the human 4-1BB binding domain is capable of binding to cynomolgus 4-1BB.

In certain instances, the human 4-1BB binding domain is capable of agonizing human 4-1BB activity.

In certain instances, the human 4-1BB binding domain comprises humanized VH and VL sequences.

In certain instances, the human OX40 binding domain comprises a VH comprising an amino acid sequence at least 75%, 80%, 85%, 90%, 95%, or 99% identical to an amino acid sequence selected from the group consisting of SEQ ID NOs:25, 27, 29, 31, and 33. In certain instances, the human OX40 binding domain comprises a VH comprising the amino acid sequence of any one of SEQ ID NOs:25, 27, 29, 31, and 33.

In certain instances, the human OX40 binding domain comprises a VL comprising an amino acid sequence at least 75%, 80%, 85%, 90%, 95%, or 99% identical to an amino acid sequence selected from the group consisting of SEQ ID NOs:26, 28, 30, and 34-41. In certain instances, the human OX40 binding domain comprises a VL comprising the amino acid sequence of any one of SEQ ID NOs:26, 28, 30, and 34-41.

In certain instances, the human OX40 binding domain comprises (a) a VH comprising the amino acid sequence of SEQ ID NO:25 and a VL comprising the amino acid sequence of SEQ ID NO:26, (b) a VH comprising the amino acid sequence of SEQ ID NO:27 and a VL comprising the amino acid sequence of SEQ ID NO:28, (c) a VH comprising the amino acid sequence of SEQ ID NO:29 and a VL comprising the amino acid sequence of SEQ ID NO:26, (d) a VH comprising the amino acid sequence of SEQ ID NO:29 and a VL comprising the amino acid sequence of SEQ ID NO:30, (e) a VH comprising the amino acid sequence of SEQ ID NO:31 and a VL comprising the amino acid sequence of SEQ ID NO:28, (f) a VH comprising the amino acid sequence of SEQ ID NO:31 and a VL comprising the amino acid sequence of SEQ ID NO:30, (g) a VH comprising the amino acid sequence of SEQ ID NO:33 and a VL comprising the amino acid sequence of SEQ ID NO:28, (h) a VH comprising the amino acid sequence of SEQ ID NO:29 and a VL comprising the amino acid sequence of SEQ ID NO:34, (i) a VH comprising the amino acid sequence of SEQ ID NO:29 and a VL comprising the amino acid sequence of SEQ ID NO:35, (j) a VH comprising the amino acid sequence of SEQ ID NO:29 and a VL comprising the amino acid sequence of SEQ ID NO:36, (k) a VH comprising the amino acid sequence of SEQ ID NO:29 and a VL comprising the amino acid sequence of SEQ ID NO:37, (l) a VH comprising the amino acid sequence of SEQ ID NO:31 and a VL comprising the amino acid sequence of SEQ ID NO:34, (m) a VH comprising the amino acid sequence of SEQ ID NO:31 and a VL comprising the amino acid sequence of SEQ ID NO:35, (n) a VH comprising the amino acid sequence of SEQ ID NO:31 and a VL comprising the amino acid sequence of SEQ ID NO:36, (o) a VH comprising the amino acid sequence of SEQ ID NO:31 and a VL comprising the amino acid sequence of SEQ ID NO:37, (p) a VH comprising the amino acid sequence of SEQ ID NO:31 and a VL comprising the amino acid sequence of SEQ ID NO:38, (q) a VH comprising the amino acid sequence of SEQ ID NO:31 and a VL comprising the amino acid sequence of SEQ ID NO:39, (r) a VH comprising the amino acid sequence of SEQ ID NO:31 and a VL comprising the amino acid sequence of SEQ ID NO:40, or (s) a VH comprising the amino acid sequence of SEQ ID NO:31 and a VL comprising the amino acid sequence of SEQ ID NO:41.

In certain instances, the human OX40 binding domain comprises (a) a VH comprising the amino acid sequence of SEQ ID NO:29 and a VL comprising the amino acid sequence of SEQ ID NO:28, (b) a VH comprising the amino acid sequence of SEQ ID NO:31 and a VL comprising the amino acid sequence of SEQ ID NO:30, or (c) a VH comprising the amino acid sequence of SEQ ID NO:29 and a VL comprising the amino acid sequence of SEQ ID NO:35.

In certain instances, the human OX40 binding domain comprises a VH and a VL on the same polypeptide chain. In certain instances, the VH of the human OX40 binding domain is N-terminal to the VL of the human OX40 binding domain. In certain instances, the VH of the human OX40 binding domain is C-terminal to the VL of the human OX40 binding domain. In certain instances, the human OX40 binding domain comprises a linker between the VH and the VL. In certain instances, the linker comprises the amino acid sequence $(Gly_4Ser)_n$, wherein n=1-5 (SEQ ID NO:117). In certain instances, n=3-5. In certain instances, n=4.

In certain instances, the human OX40 binding domain comprises an scFv comprising the amino acid sequence of any one of SEQ ID NOs:46, 47, 52, 54, 56, 59-62, 64-76, and 146. In certain instances, the human OX40 binding domain comprises an scFv comprising the amino acid sequence of any one of SEQ ID NOs:59, 62, or 66.

In certain instances, the human OX40 binding domain is capable of binding to cynomolgus OX40.

In certain instances, the human OX40 binding domain is capable of agonizing human OX40 activity.

In certain instances, the human OX40 binding domain comprises murine or rat VH and VL sequences.

In certain instances, the human 4-1BB binding domain comprises a VH comprising the amino acid sequence of SEQ ID NO:17 and a VL comprising the amino acid sequence of SEQ ID NO:18 and wherein the human OX40 binding domain comprises (a) a VH comprising the amino acid sequence of SEQ ID NO:29 and a VL comprising the amino acid sequence of SEQ ID NO:28, (b) a VH comprising the amino acid sequence of SEQ ID NO:31 and a VL comprising the amino acid sequence of SEQ ID NO:30, or (c) a VH comprising the amino acid sequence of SEQ ID NO:29 and a VL comprising the amino acid sequence of SEQ ID NO:35.

In certain instances, the human 4-1BB binding domain comprises an scFv comprising the amino acid sequence of SEQ ID NO:58 and wherein the human OX40 binding domain comprises an scFv comprising the amino acid sequence of any one of SEQ ID NOs:59, 62, or 66.

In certain instances, the human 4-1BB binding domain and the human OX40 binding domain are on the same polypeptide. In certain instances, the human 4-1BB binding domain is N-terminal to the human OX40 binding domain. In certain instances, the human 4-1BB binding domain is C-terminal to the human OX40 binding domain.

In certain instances, the antibody comprises an immunoglobulin constant region. In certain instances, the immunoglobulin constant region comprises immunoglobulin CH2 and CH3 domains of IgG1, IgG2, IgG3, IgG4, IgA1, IgA2 or IgD. In certain instances, the immunoglobulin constant region comprises immunoglobulin CH2 and CH3 domains of IgG1. In certain instances, the antibody does not contain a CH1 domain.

In certain instances, the immunoglobulin constant region comprises one, two, three or more amino acid substitutions compared to a wild-type immunoglobulin constant region to prevent binding to FcγR1, FcγRIIa, FcγRIIb, FcγRIIa, and FcγRIIIb. In certain instances, the immunoglobulin constant region comprises one, two, three or more amino acid substitutions compared to a wild-type immunoglobulin constant region to prevent or reduce Fc-mediated T-cell activation. In certain instances, the immunoglobulin constant region comprises one, two, three or more amino acid substitutions compared to a wild-type immunoglobulin constant region to prevent or reduce CDC activity. In certain instances, the immunoglobulin constant region comprises one, two, three or more amino acid substitutions compared to a wild-type immunoglobulin constant region to prevent or reduce ADCC activity. In certain instances, the immunoglobulin constant region comprises a human IgG1 CH2 domain comprising the substitutions E233P, L234A, L235A, G237A, and K322A and a deletion of G236 according to the EU numbering system.

In certain instances, the antibody comprises a linker between the immunoglobulin constant region and the human 4-1BB binding domain and/or between the immunoglobulin constant region and the human OX40 binding domain. In certain instances, the linker between the immunoglobulin constant region and the human 4-1BB binding domain and/or between the immunoglobulin constant region and the human OX40 binding domain comprises 10-30 amino acids, 15-30 amino acids, or 20-30 amino acids. In certain instances, the linker between the immunoglobulin constant region and the human 4-1BB binding domain or between the immunoglobulin constant region and the human OX40 binding domain comprises the amino acid sequence $(Gly_4Ser)_n$, wherein n=1-5 (SEQ ID NO:117). In certain instances, n=1.

In certain instances, the antibody comprises a dimer of two polypeptides, each polypeptide comprising in order from amino-terminus to carboxyl-terminus, a first scFv, a hinge region, an immunoglobulin constant region, and a second scFv, wherein (a) the first scFv comprises a human 4-1BB antigen-binding domain, and the second scFv comprises a human OX40 antigen-binding domain or (b) the first scFv comprises a human OX40 antigen-binding domain and the second scFv comprises a human 4-1BB antigen-binding domain. In certain instances, the dimer is a homodimer.

In certain instances, the first scFv comprises a human 4-1BB binding domain and the second scFv comprises a human OX40 antigen-binding domain.

In certain instances, the hinge is an $IgG_1$ hinge. In certain instances, the hinge comprises amino acids 1-15 of SEQ ID NO:115.

In certain instances, the hinge and immunoglobulin constant region comprise the amino acid sequence of SEQ ID NO: 115.

In certain instances, the antibody comprises a linker between the immunoglobulin constant region and the human OX40 binding domain, wherein the linker comprises the amino acid sequence $(Gly_4Ser)_n$, wherein n=1-5 (SEQ ID NO:117). In certain instances, n=1.

In certain instances, the human 4-1BB binding domain comprises a VH comprising the amino acid sequence of SEQ ID NO:17 and a VL comprising the amino acid sequence of SEQ ID NO:18 and wherein the human OX40 binding domain comprises (a) a VH comprising the amino acid sequence of SEQ ID NO:29 and a VL comprising the amino acid sequence of SEQ ID NO:28, (b) a VH comprising the amino acid sequence of SEQ ID NO:31 and a VL comprising the amino acid sequence of SEQ ID NO:30, or (c) a VH comprising the amino acid sequence of SEQ ID NO:29 and a VL comprising the amino acid sequence of SEQ ID NO:35.

In certain instances, the human 4-1BB binding domain comprises the amino acid sequence of SEQ ID NO:58 and wherein the human OX40 binding domain comprises the amino acid sequence of any one of SEQ ID NOs:59, 62, or 66.

In certain instances, a bispecific antibody provided herein comprises a human 4-1BB antigen-binding domain and human OX40 antigen-binding domain, wherein the antibody comprises an amino acid sequence selected from the group consisting of SEQ ID NOs:78-100 and 144. In certain instances, the antibody is a homodimer comprising two polypeptides, each polypeptide comprising the same amino acid sequence selected from the group consisting of SEQ ID NOs:78-100 and 144.

In certain instances, a bispecific antibody provided herein comprises a human 4-1BB antigen-binding domain and human OX40 antigen-binding domain, wherein the antibody comprises the amino acid sequence of SEQ ID NO:78. In certain instances, the antibody is a homodimer comprising two polypeptides, each polypeptide comprising the amino acid sequence of SEQ ID NO:78.

In certain instances, a bispecific antibody provided herein comprises a human 4-1BB antigen-binding domain and a human OX40 antigen-binding domain, wherein the antibody comprises the amino acid sequence of SEQ ID NO:81. In certain instances, the antibody is a homodimer comprising two polypeptides, each polypeptide comprising the amino acid sequence of SEQ ID NO:81.

In certain instances, a bispecific antibody provided herein comprises a human 4-1BB antigen-binding domain and a human OX40 antigen-binding domain, wherein the antibody comprises the amino acid sequence of SEQ ID NO:90. In certain instances, the antibody is a homodimer comprising two polypeptides, each polypeptide comprising the amino acid sequence of SEQ ID NO:90.

In certain instances, the human 4-1BB binding domain and the human OX40 binding domain are on separate peptides. In certain instances, the human 4-1BB binding domain comprises a VH and VL on separate polypeptides. In certain instances, the human OX40 binding domain comprises a VH and VL on separate polypeptides.

In certain instances, the antibody is a knob-in-hole (KIH) antibody, an IgG1 antibody comprising matched mutations in the CH3 domain, two engineered Fv fragments with exchanged VHs, a diabody, an scFv×scFv, an scFv-Fc-scFv, a quadroma, a CrossMab Fab, a CrossMab VH-VL, or a strand-exchange engineered domain body (SEEDbody).

In certain instances, the antibody is capable of binding to human 4-1BB and human OX40 simultaneously.

In certain instances, the antibody is capable of promoting a dose-dependent expansion of CD8+T, CD4+T, and/or NK cells.

In certain instances, the antibody is capable of increasing secretion of IFN-γ, IL-2, and/or TNF-α from stimulated PBMCs.

In certain instances, the antibody is agonistic to human 4-1BB and human OX40.

In certain instances, the antibody is isolated.

In certain instances, the antibody is a monoclonal antibody.

In certain instances, the antibody further comprises a detectable label.

In certain instances, a polynucleotide provided herein encodes an antibody provided herein. In certain instances, a vector provided herein comprises a polynucleotide provided herein, optionally wherein the vector is an expression vector.

In certain instances, a host cell provided herein comprises a polynucleotide provided herein or a vector provided herein.

In certain instances a host cell provided herein comprises a combination of polynucleotides provided herein that encode an antibody provided herein. In certain instances, the polynucleotides are encoded on a single vector. In certain instances, the polynucleotides are encoded on multiple vectors.

In certain instances, the host cell is selected from the group consisting of a CHO, HEK293, or COS cell.

In certain instances, a method of producing an antibody that specifically binds to human 4-1BB and human OX40 provided herein comprises culturing a host cell provided herein so that the antibody is produced, optionally further comprising recovering the antibody.

In certain instances, a method for detecting 4-1BB and OX40 in a sample provided herein comprises contacting said sample with the antibody of any one of claims 1-106, optionally wherein the sample comprises cells.

In certain instances, a pharmaceutical composition provided herein comprises an antibody provided herein and a pharmaceutically acceptable excipient.

In certain instances, a method for increasing NK cell proliferation provided herein comprises contacting an NK cell with an antibody provided herein or a pharmaceutical composition provided herein.

In certain instances, a method for increasing T cell proliferation provided herein comprises contacting a T cell with an antibody provided herein or a pharmaceutical composition provided herein.

In certain instances, a method for increasing NK cell proliferation and T cell proliferation provided herein comprises contacting an NK cell and a T cell with an antibody provided herein or a pharmaceutical composition provided herein.

In certain instances, a method of agonizing a T cell co stimulatory pathway provided herein comprises contacting a T cell with antibody of an antibody provided herein or a pharmaceutical composition provided herein.

In certain instances, the T cell is a CD4+ T cell. In certain instances, the T cell is a CD8+ T cell.

In certain instances, the cell is in a subject and the contacting comprises administering the antibody or the pharmaceutical composition to the subject.

In certain instances, a method for enhancing an immune response in a subject provided herein comprises administering to the subject an effective amount of an antibody provided herein or a pharmaceutical composition provided herein.

In certain instances, a method of treating cancer in a subject provided herein comprises administering to the subject an effective amount of an antibody provided herein or a pharmaceutical composition provided herein. In certain instances, the cancer is selected from the group consisting of a melanoma, kidney cancer, pancreatic cancer, lung cancer, intestinal cancer, prostate cancer, breast cancer, liver cancer, brain cancer, or a hematological cancer.

In certain instances, the subject is human.

BRIEF DESCRIPTION OF THE FIGURES

FIGS. 1A and 1B show the surface expression of 4-1BB (CD137) in CHO clones. The two panels show representative cell staining on CHO clones expressing full-length human (1A) and cynomolgus monkey (1B) 4-1BB. Untransfected cells are shown in the light grey histogram; clones are in overlay in dark gray with the solid border. Samples were stained with antibody to 4-1BB (PE anti-hu. CD137 #309804, BioLegend) at 1:50 dilution then analyzed with GUAVA Easycyte HT. Parental CHO were used as negative control. (See Example 2.)

FIG. 7 shows multiple sequence alignment of human germline sequences IGHV1-46*01, IGHJ4*01, IGKV3D-7*01, and IGKJ1*01 to V- and J-regions of mouse clone 6 and its humanized variants FOBW006HLH20, FOBW006HLH26 and FOBW006HLH40. Frameworks and CDRs are specified using IMGT definitions. Differences between FOBW006HLH40 and human germlines are indicated in bold and differences between FOBW006HLH40 and murine clone 6 are underlined. (See Example 11.)

FIGS. 12A-12D show the binding of anti-4-1BB×anti-OX40 constructs, with additional humanization in 4-1BB and altered orientations of binding domains, human (12A) or cynomolgus (12C) 4-1BB-expressing Jurkat cells or human (12B) or cynomolgus (12D) OX40-expressing CHOK1SV cells. Serial dilutions of ADAPTIR™ constructs were incubated with transfected cells and subsequently labelled with a fluorescently-conjugated goat-α-human Fc secondary antibody. The y-axis displays the MFI. (See Example 19.)

Figure 13:
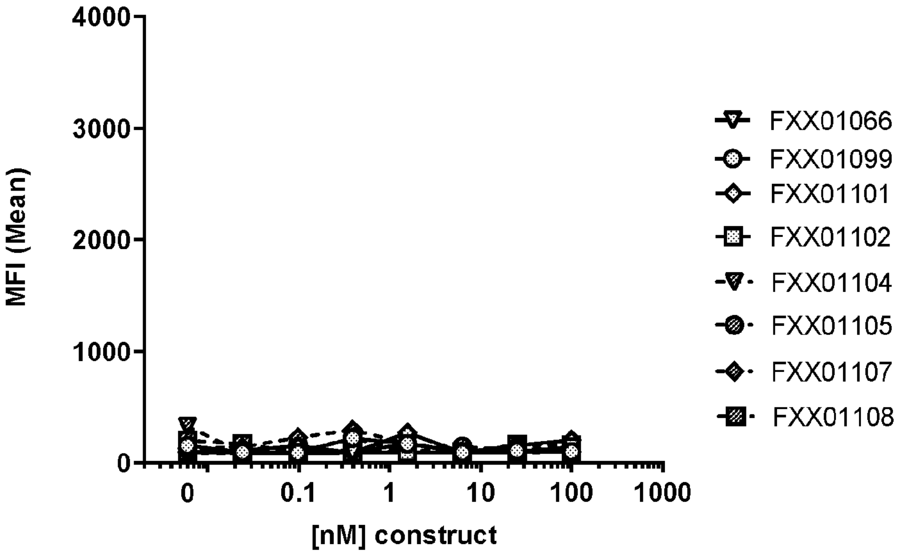

FIG. 13 shows binding of anti-4-1BB×anti-OX40 constructs to parental CHOK1SV cells. Serial dilutions of ADAPTIR™ constructs were incubated with parental CHOK1SV cells and then labelled with a fluorescently-conjugated goat-α-human Fc secondary antibody. The y-axis displays the MFI. (See Example 19.)

FIGS. 14A-14D show the functionality of anti-4-1BB× anti-OX40 constructs, with additional pI stabilizing mutations in OX40 and alternate orientation, to induce NFκB signaling. In the human (14A) and cynomolgus (14C) 4-1BB reporter assay, OX40-expressing CHOK1SV were used for crosslinking. In the human (14B) and cynomolgus (14D) OX40 reporter assay, 4-1BB expressing Jurkat cells were added for crosslinking. Serially diluted constructs were incubated with target cells and an NFκB reporter cell line for 5 hours, followed with the addition of Bio-Glo. The y-axis displays the RLU. (See Example 19.)

Figure 15A:
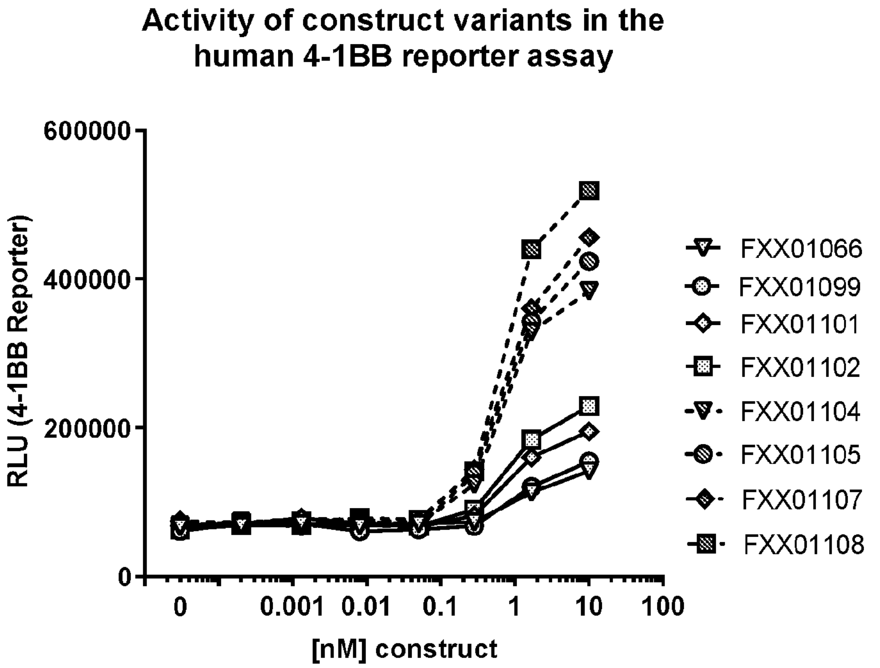
Figure 15B:
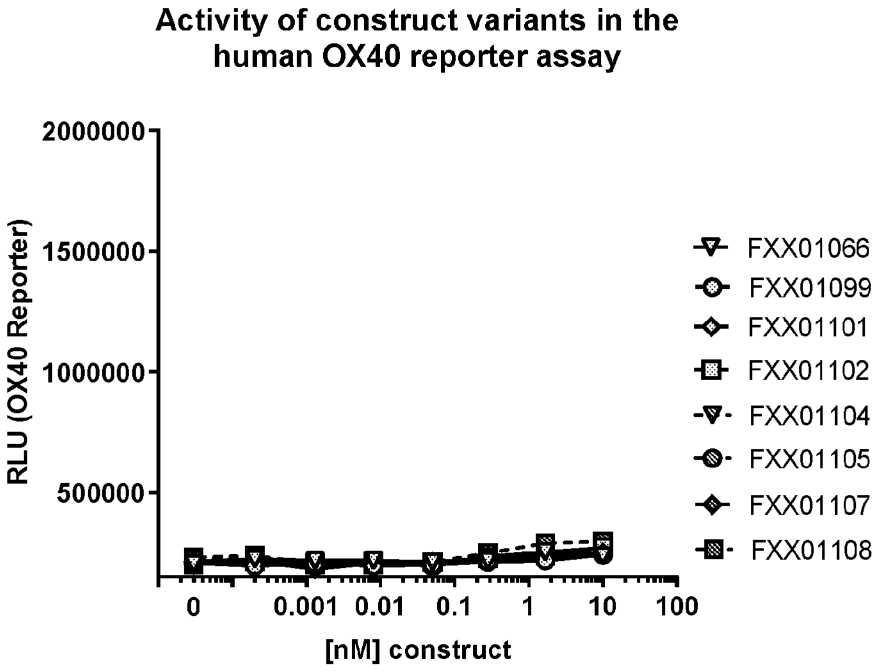

FIGS. 15A and 15B show the non-specific activity of anti-4-1BB×anti-OX40 constructs, with additional pI stabilizing mutations in OX40 and alternate orientation, to induce NFκB signaling. Serially diluted constructs were incubated with parental CHOK1SV cells target cells and either a 4-1BB/NFκB reporter cell (15A) or an OX40/NFκB reporter line (15B) for 5 hours, followed with the addition of Bio-Glo. The y-axis displays the RLU. (See Example 19.)

Figure 16:
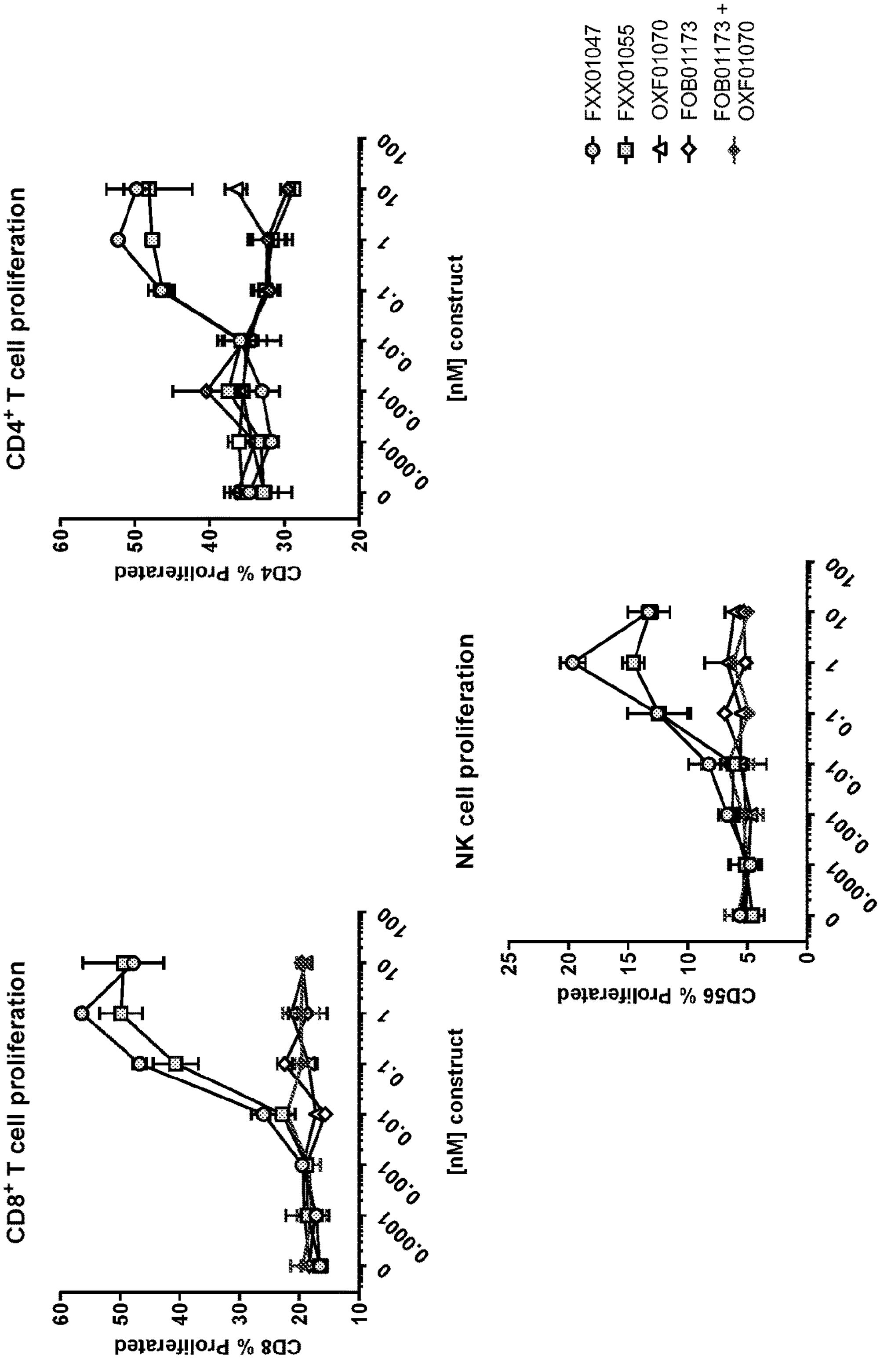

FIG. 16 shows expansion of PBMC cells in in vitro cultures incubated with non-humanized anti-4-1BB×non-optimized anti-OX40 constructs and compared to their monospecific counterparts that bind only to 4-1BB or OX40. Enriched PBMC were labeled with CellTrace Violet and cultured with anti-CD3 and a dilution of therapeutic construct. At day 5, cells were stained via FACS staining and analyzed for cell proliferation based on CellTrace Violet dilution. The y-axis displays the percent of CD8+, $CD4^+$ or NK cells that proliferated. (See Example 20.)

Figure 17:
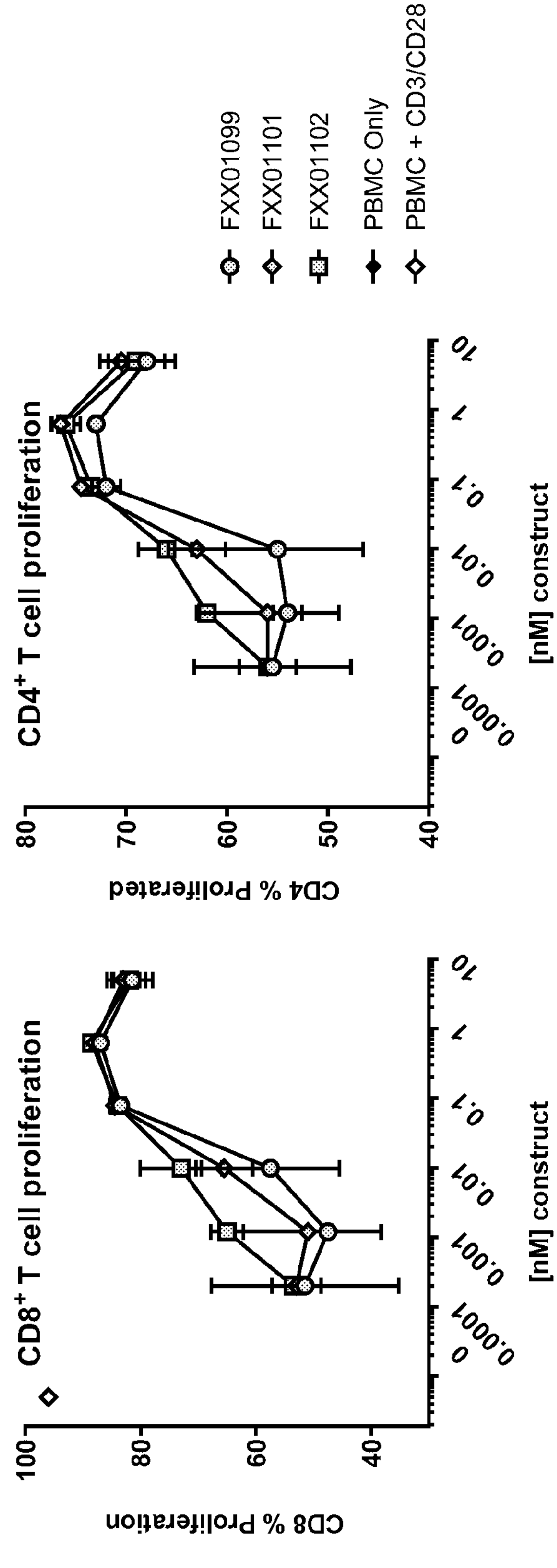

FIG. 17 shows expansion of PBMC cells in in vitro cultures incubated with humanized anti-4-1BB×optimized anti-OX40 constructs. Enriched PBMC were labeled with CellTrace Violet and cultured with αCD3 and a dilution of therapeutic construct. At 72 hours, cells were stained via FACS staining and analyzed for cell proliferation based on CellTrace Violet dilution. The y-axis displays the percent of $CD8^+$ or $CD4^+$ T cells that proliferated. (See Example 21.)

Figures 18A, 18B:
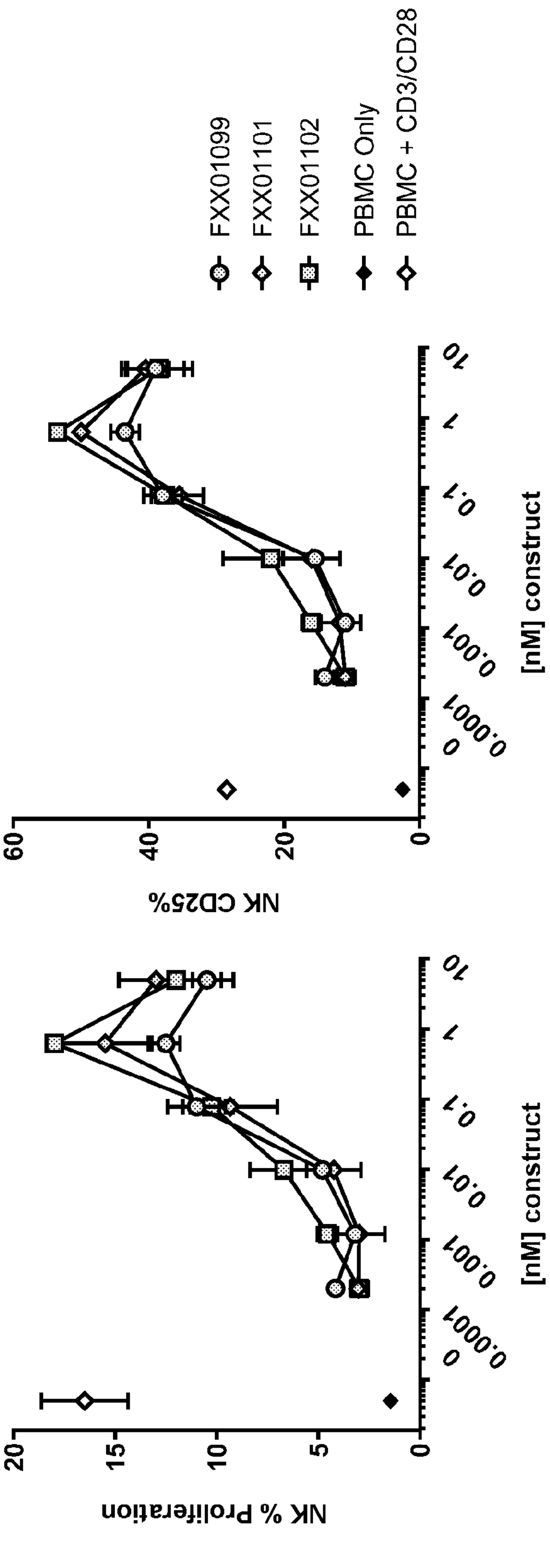

FIGS. 18A and 18B show the expansion of PBMC cells in in vitro cultures incubated with humanized anti-4-1BB× optimized anti-OX40 constructs. Enriched PBMC were labeled with CellTrace Violet and cultured with αCD3 and a dilution of therapeutic construct. At 72 hours, cells were stained via FACS staining and NK analyzed for cell proliferation based on CellTrace Violet dilution (18A) and CD25 expression (18B). The y-axis displays the percent of NK cells that proliferated and were positive for CD25, respectively. (See Example 21.)

Figure 19:
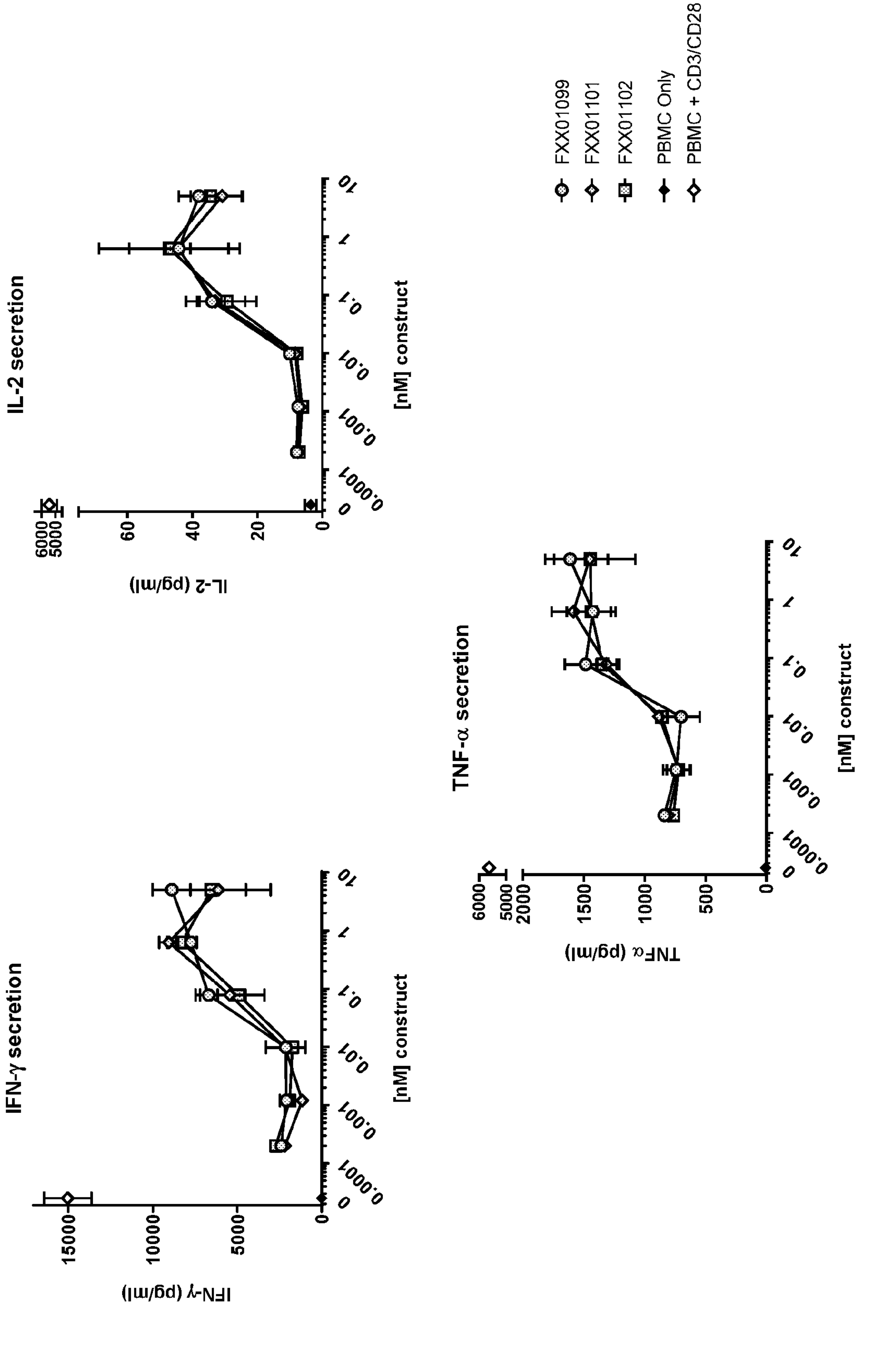
Figure 20A:
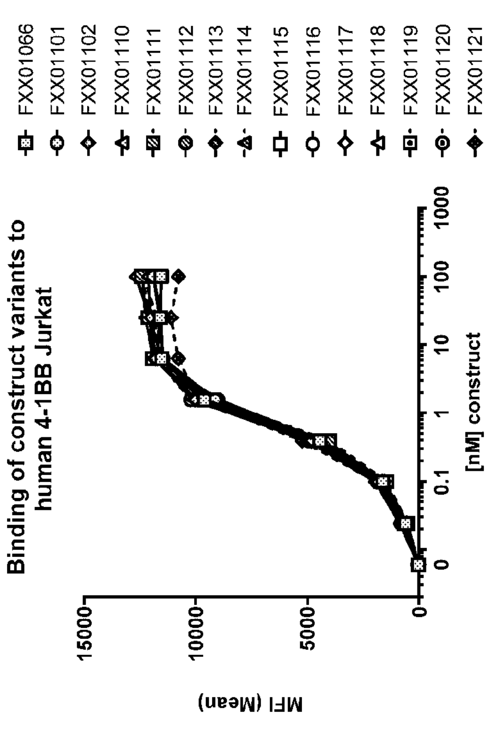
Figure 20B:
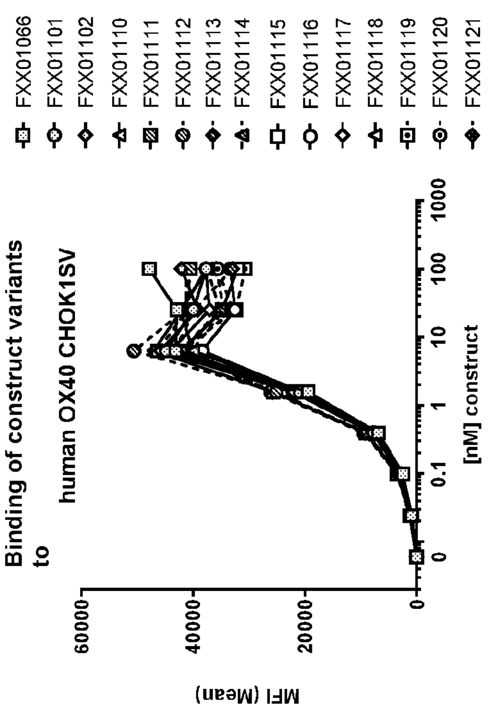
Figure 20C:
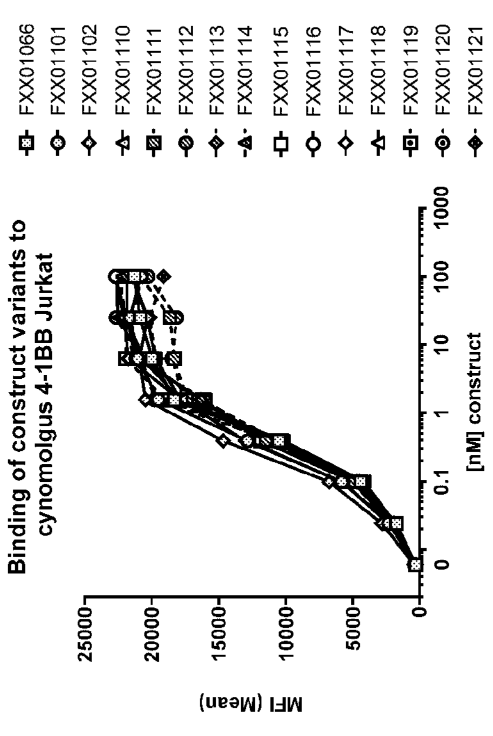
Figure 20D:
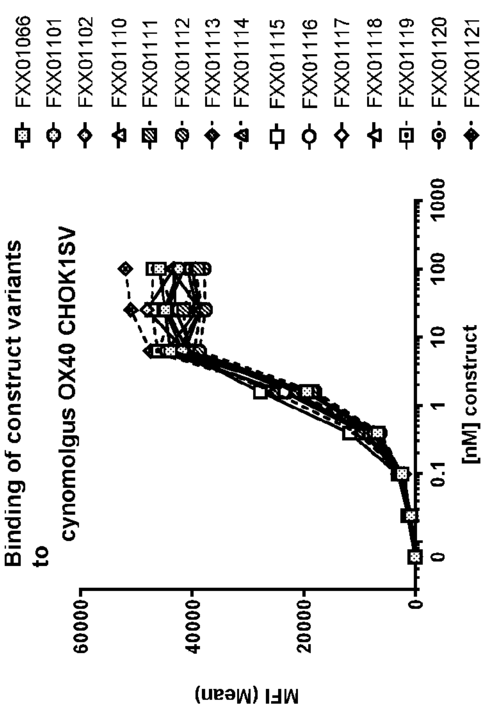

FIG. 19 shows cytokine secretion from PBMC cells in in vitro cultures incubated with humanized anti-4-1BB×optimized anti-OX40 constructs. Enriched PBMC were cultured with anti-CD3 and a dilution of therapeutic construct. At 48 hours, supernatants were harvested and analyzed for the levels of cytokines via multiplex-based assay (Milliplex). The y-axis displays the pg/ml amount cytokine secreted from each treated culture. (See Example 21.)

FIGS. 20A-D show the binding of anti-4-1BB×anti-OX40 constructs, with additional pI variations, to (20A) human 4-1BB-, (20B) human OX40-, (20C) cynomolgus 4-1BB- or (20D) cynomolgus OX40-expressing cells. Serial dilutions of ADAPTIR™ constructs were incubated with transfected target cells and subsequently labelled with a fluorescently-conjugated goat-α-human Fc secondary antibody. The y-axis displays the mean fluorescence intensity units (MFI). (See Example 25.)

Figure 21:
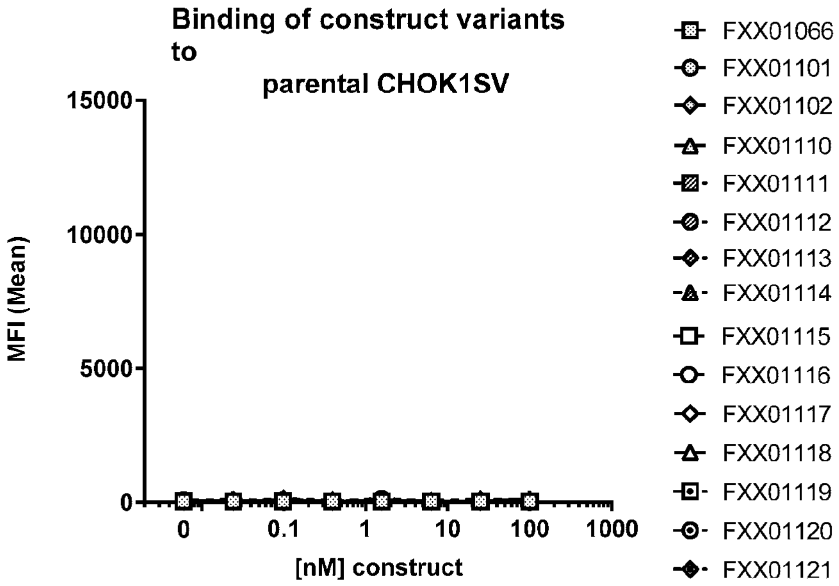
Figure 22A:
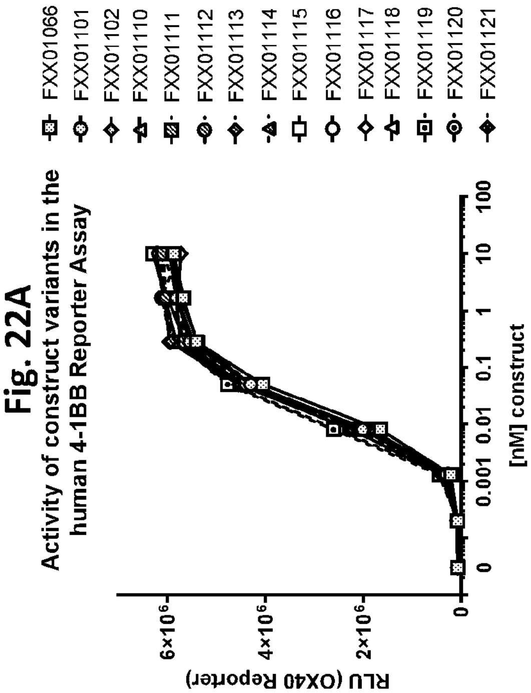
Figure 22B:
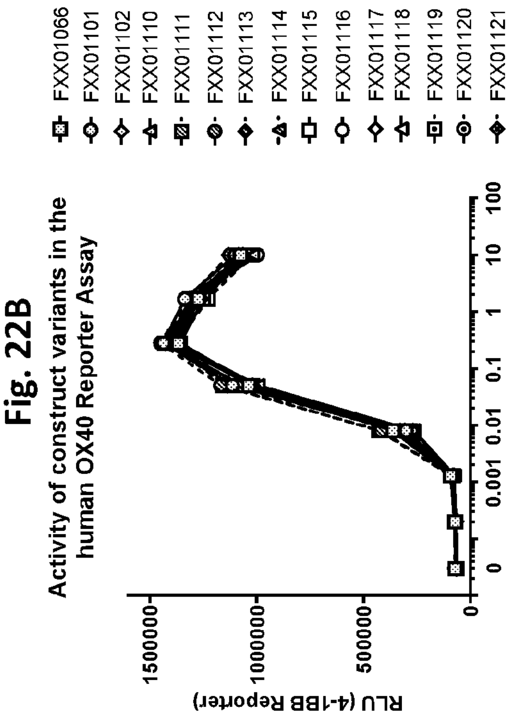
Figure 22C:
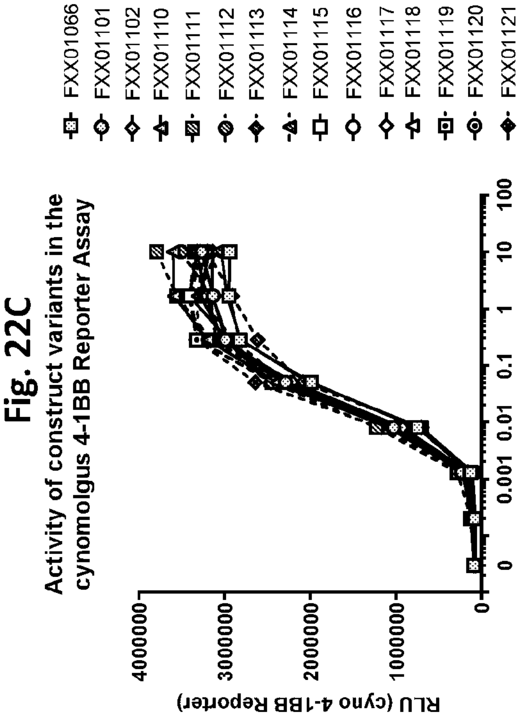
Figure 22D:
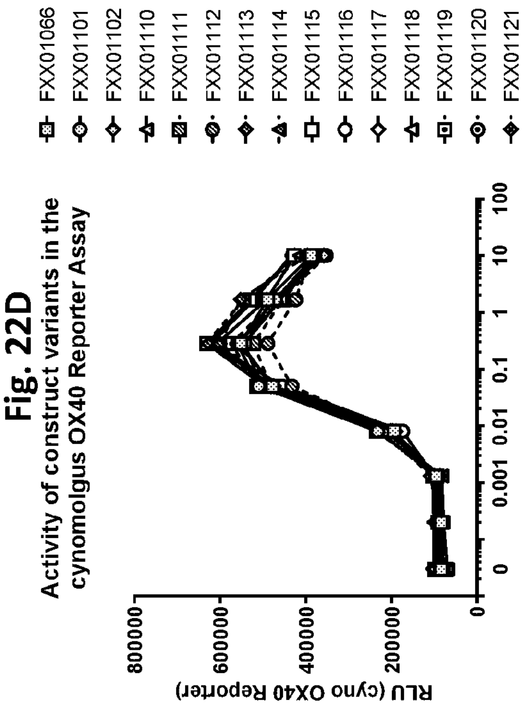

FIG. 21 shows binding of anti-4-1BB×anti-OX40 constructs to parental CHOK1SV cells. Serial dilutions of ADAPTIR™ constructs were incubated with parental CHOK1SV cells and then labelled with a fluorescently-conjugated goat-α-human Fc secondary antibody. The y-axis displays the mean fluorescence intensity units (MFI). (See Example 25.)

FIGS. 22A-D show the functionality of anti-4-1BB×anti-OX40 constructs, with additional pI stabilizing mutations in OX40, to induce NFκB signaling. Serially diluted constructs were incubated with CHO/OX40 target cells and either a (22A) human 4-1BB or a (22C) cynomolgus 4-1BB NFκB reporter cell line. Alternatively, constructs were incubated with Jurkat/4-1BB target cells and either a (22B) human OX40 or a (22B) cynomolgus OX40 NFκB reporter cell line. The assay was incubated for 5 hours, followed with the addition of Bio-Glo luciferase reagent. The y-axis displays the relative light units (RLU). (See Example 25.)

Figure 23B:
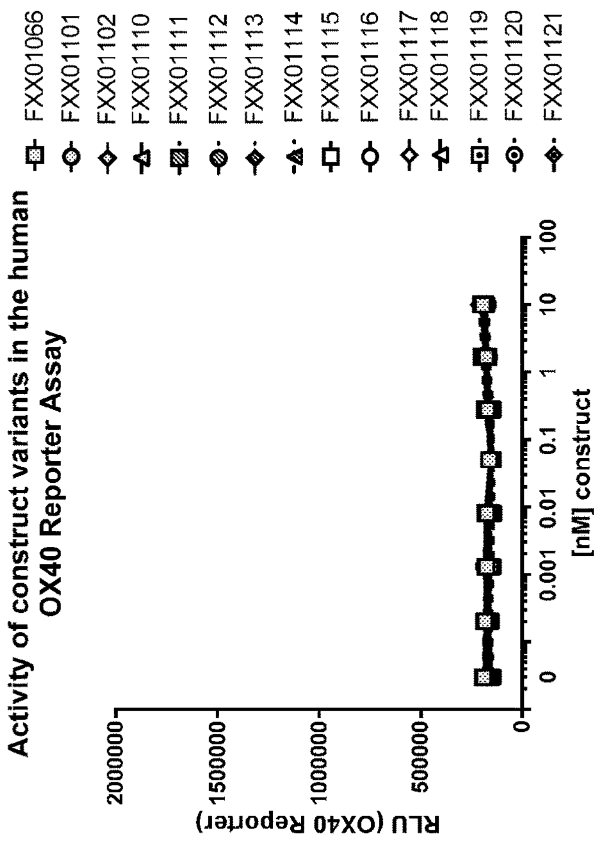
Figure 23A:
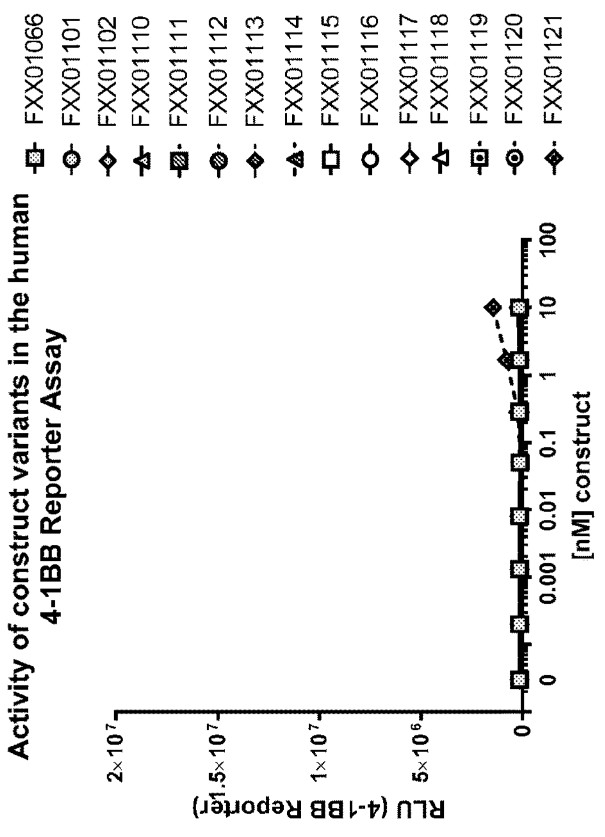

FIGS. 23A-B show the non-specific activity of anti-4-1BB×anti-OX40 constructs, with additional pI variation in OX40, to induce NFκB signaling. Serially diluted constructs were incubated with parental CHOK1SV cells target cells and either a (23A) 4-1BB NFκB reporter cell or an (23B) OX40 NFκB reporter line for 5 hours, followed with the addition of Bio-Glo luciferase reagent. The y-axis displays the relative light units (RLU). (See Example 25.)

Figure 24:
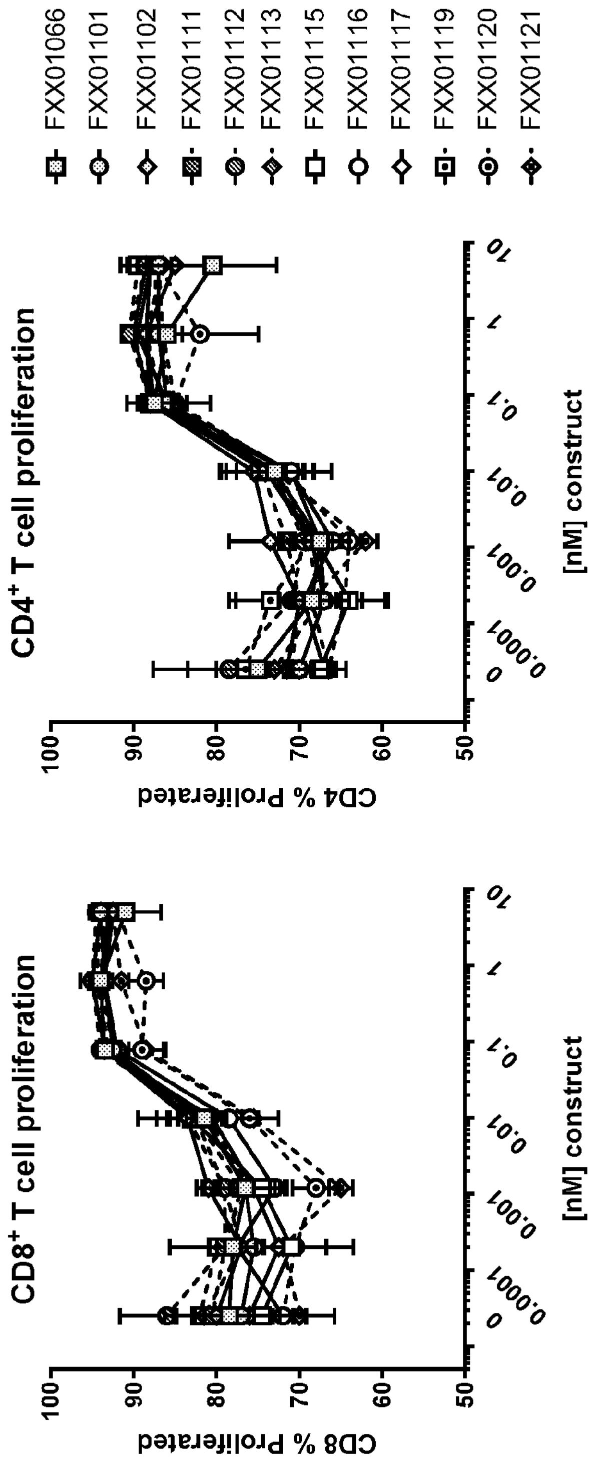

FIG. 24 shows the expansion of PBMC cells in in vitro cultures incubated with anti-4-1BB×anti-OX40 constructs. Enriched PBMC were labeled with CellTrace Violet and cultured with antiCD3 and a dilution of therapeutic construct in human serum-containing media. At 96 hours, cells were stained via FACS staining and analyzed for cell proliferation based on CellTrace Violet dilution. The y-axis displays the percent of $CD8^+$ or $CD4^+$ T cells that proliferated. (See Example 26.)

Figure 25:
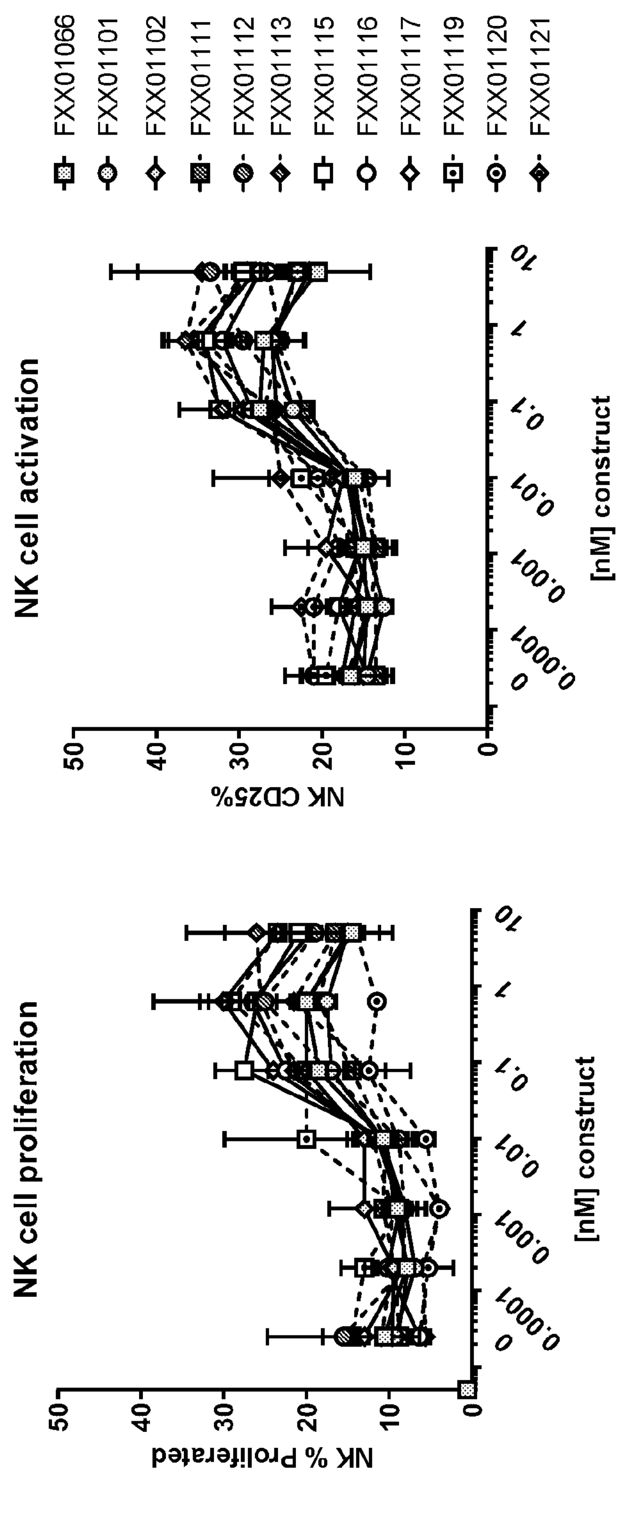

FIG. 25 shows the expansion of PBMC cells in in vitro cultures incubated with anti-4-1BB×anti-OX40 constructs. Enriched PBMC were labeled with CellTrace Violet and cultured with antiCD3 and a dilution of therapeutic construct in human serum-containing media. At 96 hours, NK cells were stained via FACS staining and analyzed for cell proliferation and CD25 expression. The y-axis displays the percentage of NK cells that proliferated and the percentage of NK cells that expressed the activation maker CD25. (See Example 26.)

Figure 26:
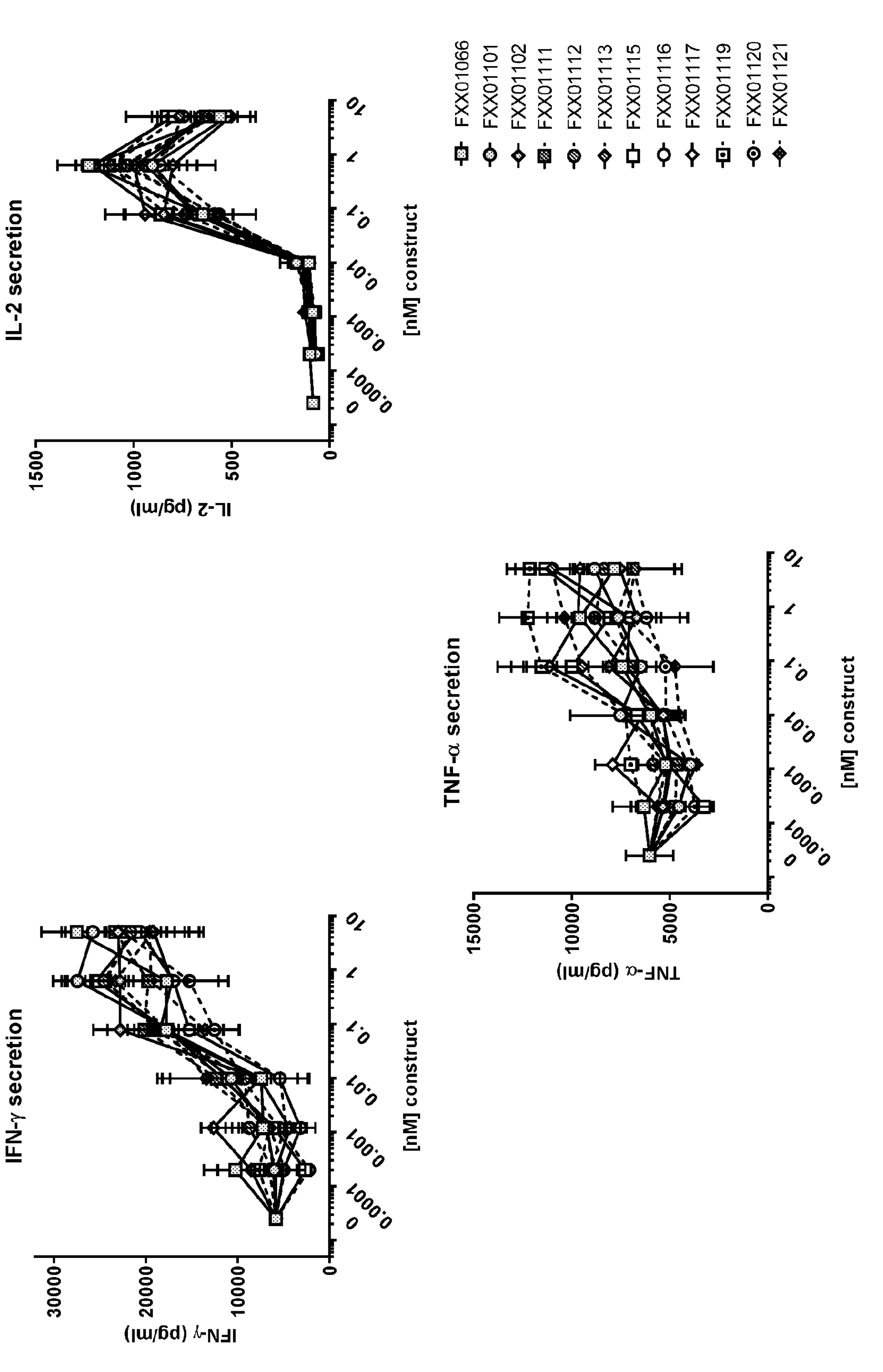

FIG. 26 shows cytokine secretion from PBMC cells in in vitro cultures incubated with anti-4-1BB×anti-OX40 constructs. Enriched PBMC were cultured with anti-CD3 and a dilution of therapeutic construct in fetal bovine serum-containing media. At 48 hours, supernatants were harvested and analyzed for the levels of cytokines via multiplex-based assay (Milliplex). The y-axis displays the pg/ml amount cytokine secreted from each treated culture. (See Example 26.)

Figure 27:
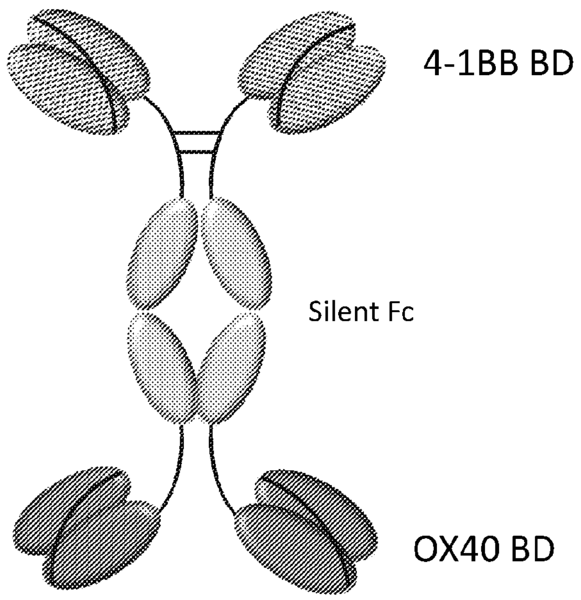

FIG. 27 illustrates an exemplary bispecific antibody in ADAPTIR™ format. The antibody comprises two identical polypeptides, each in order from amino-terminus to carboxyl-terminus, a first scFv antigen-binding domain that binds to 4-1BB, a hinge region, an immunoglobulin constant region, and a second scFv antigen-binding domain that binds to OX40.

Figures 28A, 28B:
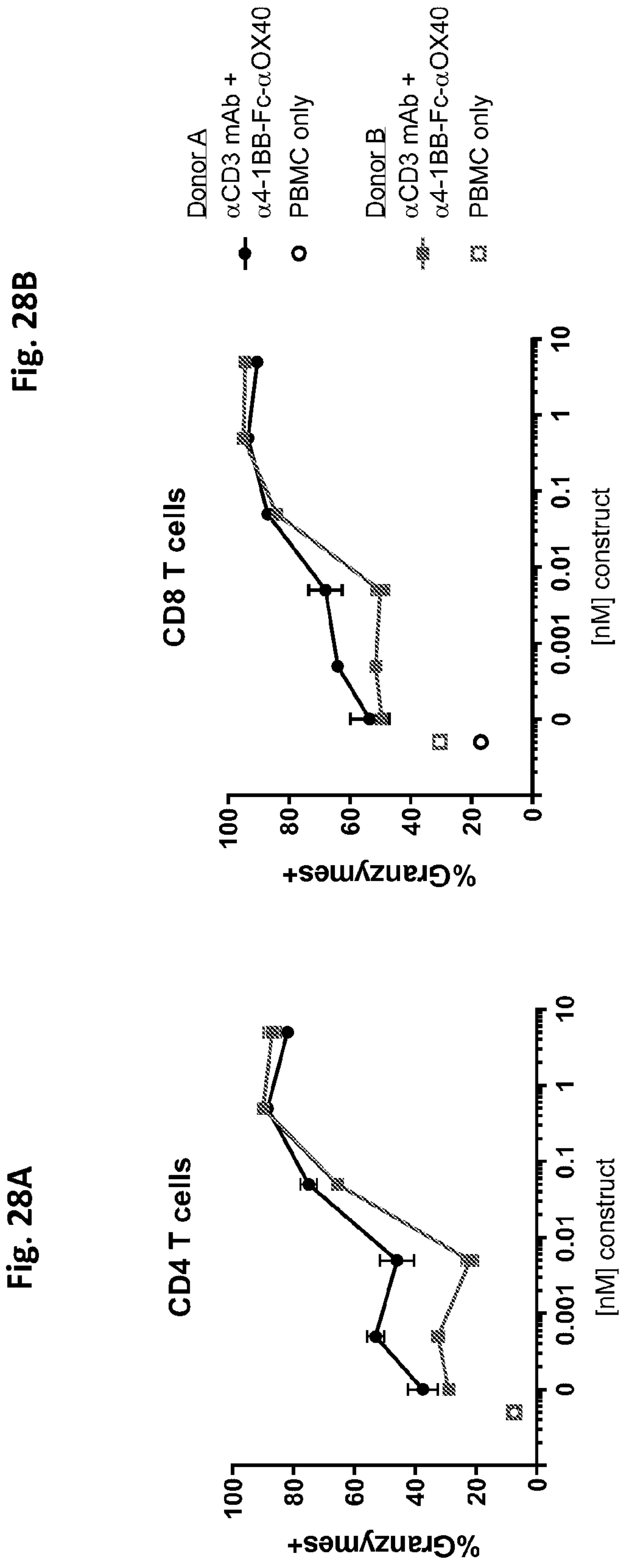

FIGS. 28A and 28B show expression of granzyme B in CD4 (28A) and CD8 (28B) T cells stimulated in vitro with bispecific antibody constructs. Enriched PBMC from 2 donors (Donor A and Donor B) were cultured with anti-CD3 antibody (Ab) and serial dilutions of FXX01102 (SEQ ID NO:81). At 72 hours, cells were harvested and analyzed for intracellular expression of granzyme B and surface markers by flow cytometry. The y-axis displays the percent of granzyme B+ cells within the CD4 or CD8 T cell subsets. Unstimulated PBMCs were used as a control. Cells treated with anti-CD3 antibody and no bispecific antibody are represented on the graphs as the points marked at 0 nM. (See Example 33.)

Figure 29:
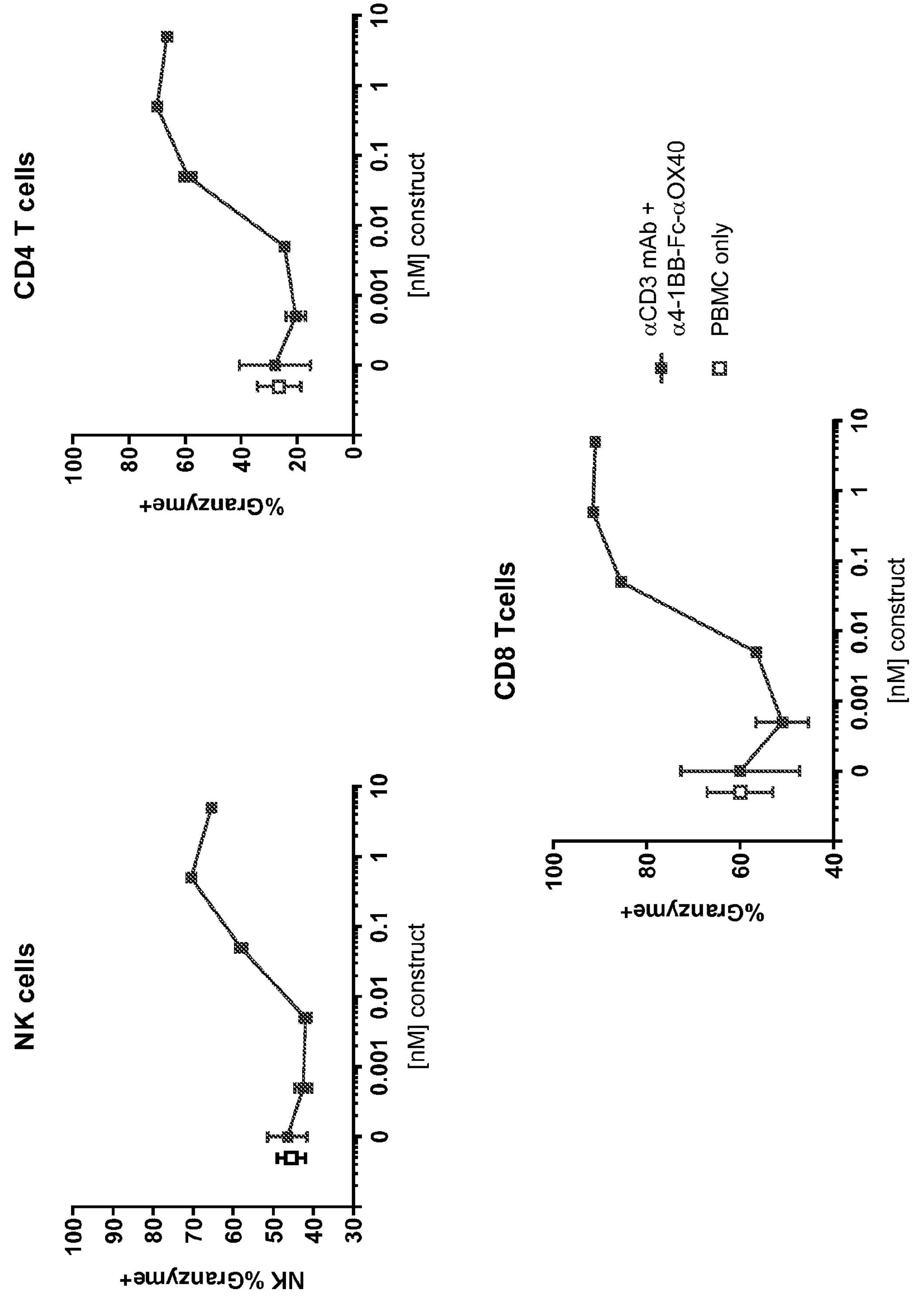

FIG. 29 shows expression of granzyme B in CD4 and CD8 T cells, and NK cells stimulated in vitro with bispecific antibody constructs. Enriched PBMC were cultured with anti-CD3 antibody (Ab) and serial dilutions of FXX01102 (SEQ ID NO:81). At 72 hours, cells were harvested and analyzed for intracellular expression of granzyme B and surface markers by flow cytometry. The y-axis displays the percent of granzyme B+ cells within the CD4 or CD8 T cell, or (CD335) NK cell subsets. Unstimulated PBMCs were used as a control. Cells treated with anti-CD3 antibody and no bispecific antibody are represented on the graphs as the points marked at 0 nM. (See Example 33.)

Figure 30:
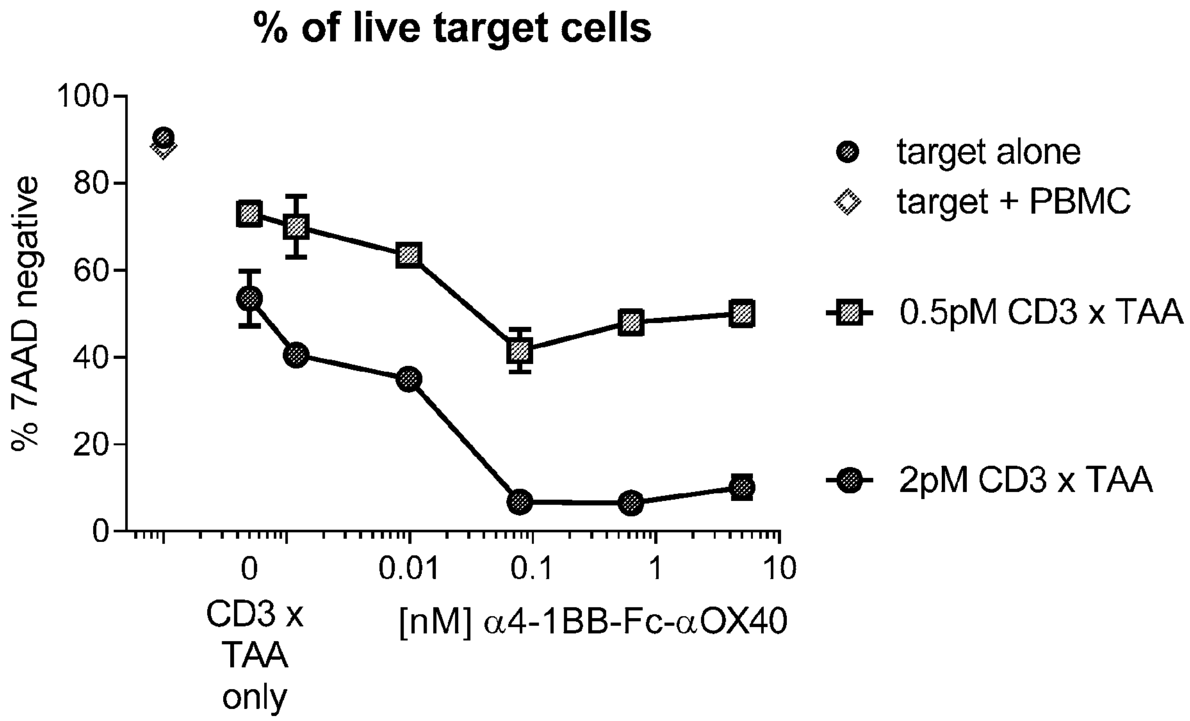

FIG. 30 shows the ability of PBMC to kill target cells in a dose-dependent manner with the addition of the anti-4-1BB×anti-OX40 ADAPTIR™ bispecific protein FXX01102 (SEQ ID NO:81). Enriched PBMC were cultured with 2 or 0.5 pM CD3×TAA T cell engager, TAA+ target cells, and serial dilutions of anti-4-1BB-Fc-anti-OX40. At 72 hours, cells were harvested and tumor cells were analyzed for their viability by flow cytometry. The y-axis displays the percent of target cells that did not stain for 7AAD (viable cells). Controls: target cells alone and target cells co-cultured with un-stimulated PBMC (See Example 34.)

Figure 31:
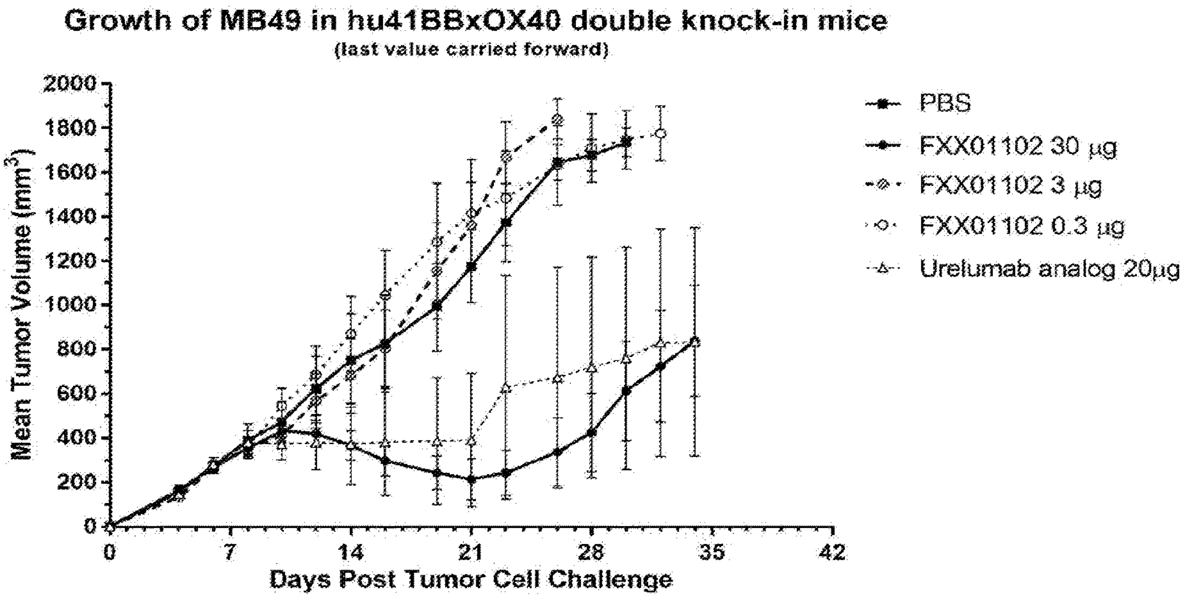

FIG. 31 shows treatment with FXX01102 at a dose of 30 μg/mouse resulted in statistically significant reduction of MB49 tumor growth in B-hOX40/h4-1BB mice. 500,000 MB49 cells were injected SC into the right flank of female B-hOX40/h41BB mice (n=4 or 8/group). Treatments were administered by intraperitoneal injection on days 6, 9, 12, 15, 18, 21 and 24. Mean tumor volume for each group is plotted±SEM. Mice that reached a tumor endpoint of equal to or greater than 1500 mm$^3$ had the last recorded tumor volume used at future time points. Differences in mean tumor volume from Day 6 through day 26 for the study groups were determined using JMP repeated measures analysis with Tukey multiple comparison test. Values of $p<0.05$ were considered significant.

Figure 32:
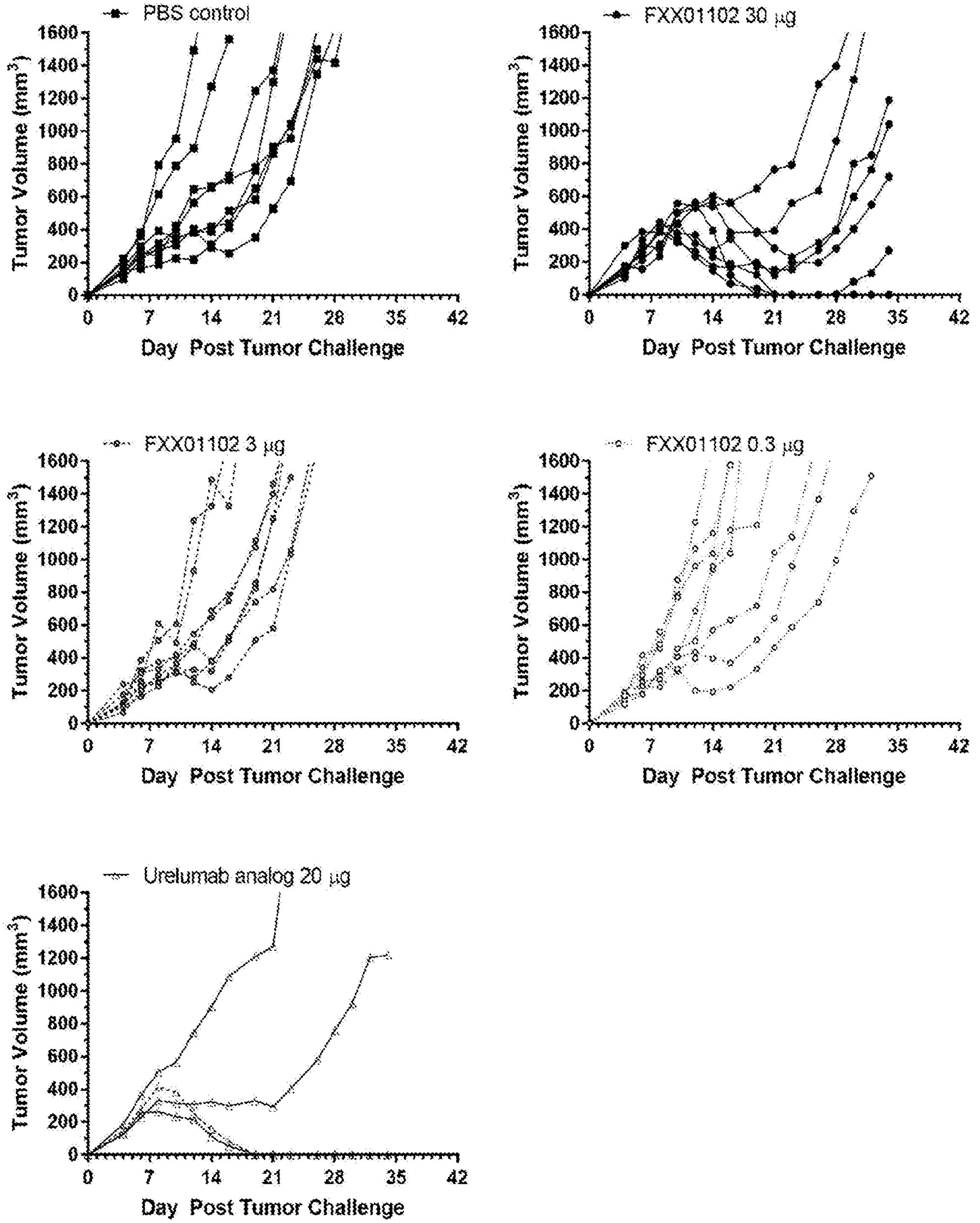

FIG. 32 shows treatment with FXX01102 at a dose of 30 μg/mouse resulted in complete tumor rejection in 2 of 8 mice treated and 1 transient tumor rejection. 500,000 MB49 cells were injected SC into the right flank of female B-hu41BB mice (n=4 or 8/group). Treatments were administered by intraperitoneal injection on days 6, 9, 12, 15, 18, 21 and 24. Data are expressed as tumor area (mm$^3$) on the days after tumor challenge as indicated; each line represents an individual mouse.

Figure 33:
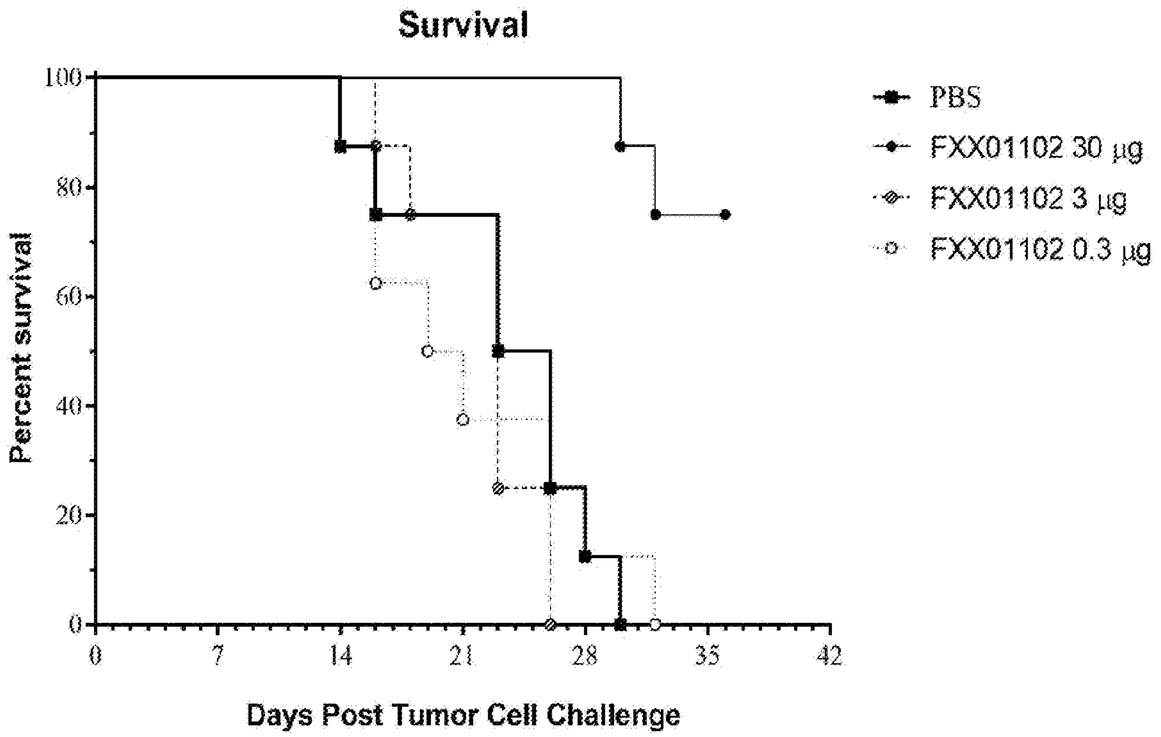

FIG. 33 shows treatment with FXX01102 at a dose of 30 μg/mouse resulted in significantly prolonged survival compared to the vehicle control group. Survival events were recorded each time a mouse reached the endpoint (tumor volume ≥1500 mm$^3$) and was euthanized. The survival was evaluated through study day 34. Median survival and statistical significance were calculated using JMP survival analysis with a log-rank test and Wilcoxon Test for comparison of survival curves. Values of $p<0.05$ were considered significant.

Figure 34:
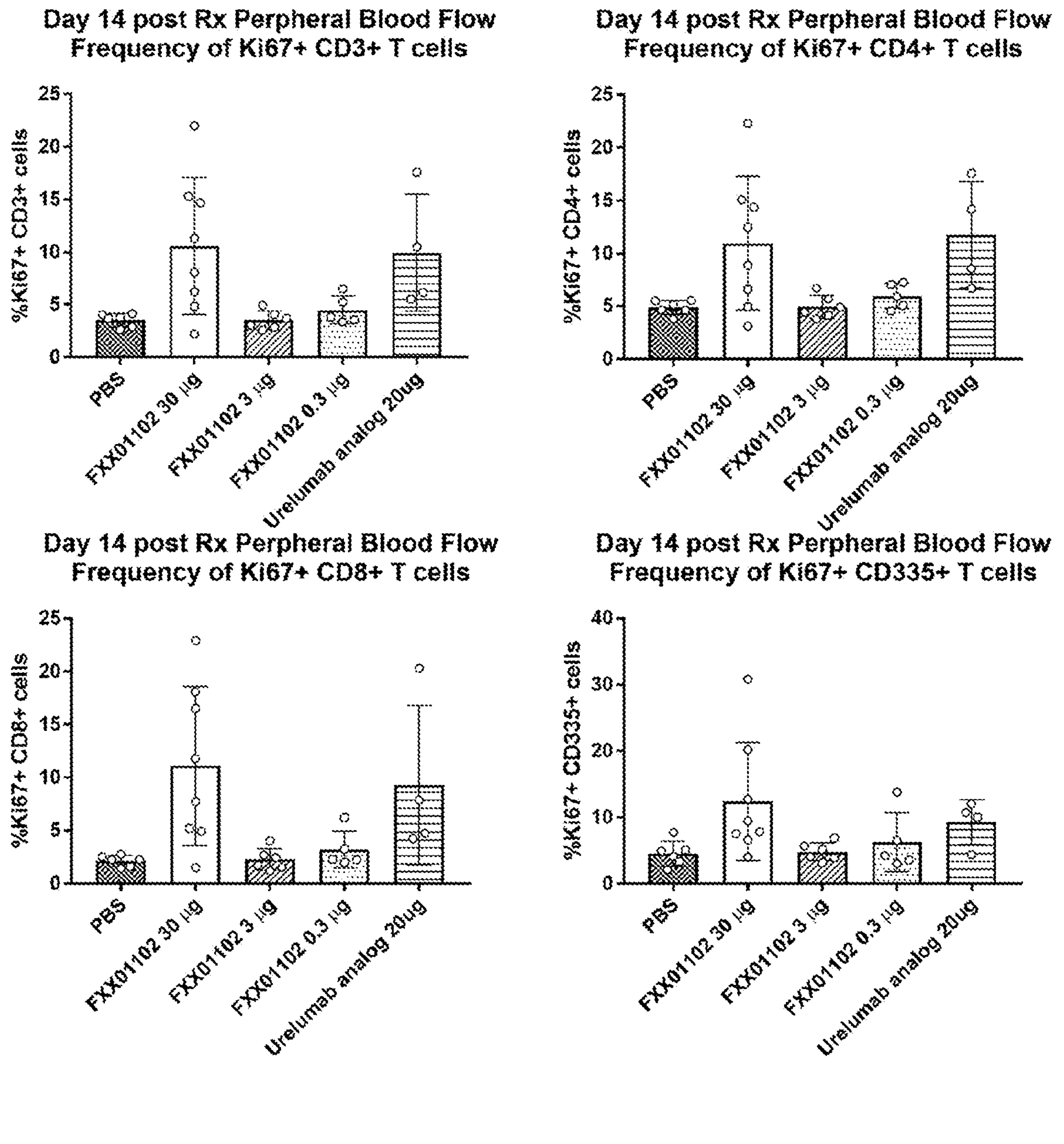

FIG. 34 shows the frequency of proliferating Ki67 positive T cells was increased after 14 days of treatment with FXX01102 at a dose of 30 μg/mouse in CD3 positive, CD4 positive, and CD8 positive T cells as well as CD335 positive NK cells. On day 20 post tumor challenge (after 14 days of treatment with FXX01102), 100 μL of peripheral blood was stained for T cell markers and expression of intracellular Ki67.

DETAILED DESCRIPTION

To facilitate an understanding of the present disclosure, a number of terms and phrases are defined below.

I. Terminology

As used herein, the term "4-1BB" refers to mammalian 4-1BB polypeptides including, but not limited to, native 4-1BB polypeptides and isoforms of 4-1BB polypeptides. "4-1BB" encompasses full-length, unprocessed 4-1BB polypeptides as well as forms of 4-1BB polypeptides that result from processing within the cell. As used herein, the term "CD137" should be understood to be interchangeable with the term "4-1BB." As used herein, the term "human 4-1BB" refers to a polypeptide comprising the amino acid sequence of SEQ ID NO:1. As used herein, the term "cynomolgus 4-1BB" refers to a polypeptide comprising the amino acid sequence of SEQ ID NO:2. A "4-1BB polynucleotide," "4-1BB nucleotide," or "4-1BB nucleic acid" refers to a polynucleotide encoding 4-1BB.

As used herein, the term "OX40" refers to mammalian OX40 polypeptides including, but not limited to, native OX40 polypeptides and isoforms of OX40 polypeptides. "OX40" encompasses full-length, unprocessed OX40 polypeptides as well as forms of OX40 polypeptides that result from processing within the cell. As used herein, the term "human OX40" refers to a polypeptide comprising the amino acid sequence of SEQ ID NO:3. As used herein, the term "cynomolgus OX40" refers to a polypeptide comprising the amino acid sequence of SEQ ID NO:4. An "OX40 polynucleotide," "OX40 nucleotide," or "OX40 nucleic acid" refers to a polynucleotide encoding OX40.

As used herein, the term "tumor infiltrating lymphocytes" or "TIL" refers to lymphocytes that directly oppose and/or surround tumor cells. Tumor infiltrating lymphocytes are typically non-circulating lymphocytes and include, CD8+ T cells, CD4+ T cells and NK cells. Tumor infiltrating lymphocytes can express OX40 and 4-1BB.

As used herein, the terms "antibody" and "antibodies" are terms of art and can be used interchangeably herein and refer to a molecule or a complex of molecules with at least one antigen-binding site that specifically binds an antigen.

Antibodies can include, for example, monoclonal antibodies, recombinantly produced antibodies, human antibodies, humanized antibodies, resurfaced antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, single domain antibodies, monovalent antibodies, single chain antibodies or single-chain Fvs (scFv), camelized antibodies, affybodies, Fab fragments, $F(ab')_2$ fragments, disulfide-linked Fvs (sdFv), anti-idiotypic (anti-Id) antibodies (including, e.g., anti-anti-Id antibodies), bispecific antibodies, and multi-specific antibodies. In certain embodiments, antibodies described herein refer to polyclonal antibody populations. Antibodies can be of any type (e.g., IgG, IgE, IgM, IgD, IgA, or IgY), any class (e.g., $IgG_1$, $IgG_2$, $IgG_3$, $IgG_4$, $IgA_1$, or $IgA_2$), or any subclass (e.g., $IgG_{2a}$ or $IgG_{2b}$) of immunoglobulin molecule. In certain embodiments, antibodies described herein are IgG antibodies, or a class (e.g., human $IgG_1$, $IgG_2$, or $IgG_4$) or subclass thereof. In a specific embodiment, the antibody is a humanized monoclonal antibody. In another specific embodiment, the antibody is a human monoclonal antibody, e.g., that is an immunoglobulin. In certain embodiments, an antibody described herein is an $IgG_1$, $IgG_2$, or $IgG_4$ antibody.

"Bispecific" antibodies are antibodies with two different antigen-binding sites (exclusive of the Fc region) that bind to two different antigens. Bispecific antibodies can include, for example, recombinantly produced antibodies, human antibodies, humanized antibodies, resurfaced antibodies, chimeric antibodies, immunoglobulins, synthetic antibodies, tetrameric antibodies comprising two heavy chain and two light chain molecules, an antibody light chain monomer, heteroconjugate antibodies, linked single chain antibodies or linked-single-chain Fvs (scFv), camelized antibodies, affybodies, linked Fab fragments, $F(ab')_2$ fragments, chemically-linked Fvs, and disulfide-linked Fvs (sdFv). Bispecific antibodies can be of any type (e.g., IgG, IgE, IgM, IgD, IgA, or IgY), any class (e.g., $IgG_1$, $IgG_2$, $IgG_3$, $IgG_4$, $IgA_1$, or $IgA_2$), or any subclass (e.g., $IgG_{2a}$ or $IgG_{2b}$) of immunoglobulin molecule. In certain embodiments, bispecific antibodies described herein are IgG antibodies, or a class (e.g., human $IgG_1$, $IgG_2$, or $IgG_4$) or subclass thereof. In certain embodiments, bispecific antibodies described herein comprise two polypeptides, optionally identical polypeptides, each polypeptide comprising in order from amino-terminus to carboxyl-terminus, a first scFv antigen-binding domain, a linker (optionally wherein the linker is a hinge region), an immunoglobulin constant region, and a second scFv antigen-binding domain. This particular type of antibody is exemplified by ADAPTIR™ technology, and it is illustrated in FIG. 27. Bispecific antibodies can be e.g., monovalent for each target (e.g., an IgG molecule with one arm targeting one antigen and the other arm targeting a second antigen) or bivalent for each target (e.g., a dual variable domain antibody, an IgG-scFv, a scFv-Fc-scFv, or an ADAPTIR™ antibody containing a dimer, wherein each polypeptide of the dimer contains two different antigen-binding domains).

As used herein, the terms "antigen-binding domain," "antigen-binding region," "antigen-binding site," and similar terms refer to the portion of antibody molecules which comprises the amino acid residues that confer on the antibody molecule its specificity for the antigen (e.g., the complementarity determining regions (CDR)). The antigen-binding region can be derived from any animal species, such as rodents (e.g., mouse, rat, or hamster) and humans. An antigen-binding domain that binds to 4-1BB can be referred to herein e.g., as a "4-1BB binding domain." An antigen-binding domain that binds to OX40 can be referred to herein e.g., as an "OX40 binding domain." As used herein, a "human 4-1BB binding domain" or "human 4-1BB antigen-binding domain" refers to an antigen-binding domain that specifically binds to human 4-1BB although it may also bind to a non-human 4-1BB (for instance, murine, rodent, or non-human primate 4-1BB). Likewise, a "human OX40 binding domain" or "human OX40 antigen-binding domain" refers to an antigen-binding domain that specifically binds to human OX40.

A used herein, the term "4-1BB/OX40 antibody," "anti-4-1BB/OX40 antibody" or "4-1BB×OX40 antibody" refers to a bispecific antibody that contains an antigen-binding domain that binds to 4-1BB (e.g., human 4-1BB) and an antigen-binding domain that binds to OX40 (e.g., human OX40).

A "monoclonal" antibody refers to a homogeneous antibody population involved in the highly specific recognition and binding of a single antigenic determinant, or epitope. This is in contrast to polyclonal antibodies that typically include different antibodies directed against different antigenic determinants. The term "monoclonal" antibody encompasses both intact and full-length immunoglobulin molecules as well Fab, Fab', F(ab')2, Fv), single chain (scFv), fusion proteins comprising an antibody portion, and any other modified immunoglobulin molecule comprising an antigen recognition site. Furthermore, a "monoclonal" antibody refers to such antibodies made in any number of manners including but not limited to by hybridoma, phage selection, recombinant expression, and transgenic animals.

The term "chimeric" antibodies refers to antibodies wherein the amino acid sequence is derived from two or more species. Typically, the variable region of both light and heavy chains corresponds to the variable region of antibodies derived from one species of mammals (e.g. mouse, rat, rabbit, etc.) with the desired specificity, affinity, and capability while the constant regions are homologous to the sequences in antibodies derived from another (usually human) to avoid eliciting an immune response in that species.

The term "humanized" antibody refers to forms of non-human (e.g. murine) antibodies that contain minimal non-human (e.g., murine) sequences. Typically, humanized antibodies are human immunoglobulins in which residues from the complementary determining region (CDR) are replaced by residues from the CDR of a non-human species (e.g. mouse, rat, rabbit, hamster) that have the desired specificity, affinity, and capability ("CDR grafted") (Jones et al., Nature 321:522-525 (1986); Riechmann et al., Nature 332:323-327 (1988); Verhoeyen et al., Science 239:1534-1536 (1988)). In some instances, the Fv framework region (FR) residues of a human immunoglobulin are replaced with the corresponding residues in an antibody from a non-human species that has the desired specificity, affinity, and capability. The humanized antibody thereof can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539; Roguska et al., Proc. Natl. Acad. Sci., USA, 91(3):969-973 (1994), and Roguska et al., Protein Eng. 9(10):895-904 (1996).

The term "human" antibody means an antibody having an amino acid sequence derived from a human immunoglobulin gene locus, where such antibody is made using any technique known in the art.

The variable region typically refers to a portion of an antibody, generally, a portion of a light or heavy chain, typically about the amino-terminal 110 to 125 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VH" and "VH domain" are used interchangeably to refer to the heavy chain variable region of an antibody.

The terms "VL" and "VL domain" are used interchangeably to refer to the light chain variable region of an antibody.

The term "Kabat numbering" and like terms are recognized in the art and refer to a system of numbering amino acid residues in the heavy and light chain variable regions of an antibody, or an antigen-binding portion thereof. In certain aspects, the CDRs of an antibody can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). In a specific embodiment, the CDRs of the antibodies described herein have been determined according to the Chothia numbering scheme.

The AbM hypervariable regions represent a compromise between the Kabat CDRs and Chothia structural loops, and are used by Oxford Molecular's AbM antibody modeling software. In a specific embodiment, the CDRs of the antibodies described herein have been determined according to the AbM numbering scheme.

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32. . . 34 |
| | | (Kabat Numbering) | |
| H1 | H31-H35 | H26-H35 | H26-H32 |
| | | (Chothia Numbering) | |
| H2 | H50-H65 | H50-H58 | H52-H56 |
| H3 | H95-H102 | H95-H102 | H95-H102 |

The IMGT numbering convention is described in Brochet, X, et al, *Nucl. Acids Res.* 36: W503-508 (2008). In a specific embodiment, the CDRs of the antibodies described herein have been determined according to the IMGT numbering convention. As used herein, unless otherwise provided, a position of an amino acid residue in a variable region of an immunoglobulin molecule is numbered according to the IMGT numbering convention.

As used herein, the term "constant region" or "constant domain" are interchangeable and have its meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain. An immunoglobulin "constant region" or "constant domain" can contain a CH1 domain, a hinge, a CH2 domain, and a CH3 domain or a subset of these domains, e.g., a CH2 domain and a CH3 domain. In certain embodiments provided herein, an immunoglobulin constant region does not contain a CH1 domain. In certain embodiments provided herein, an immunoglobulin constant region does not contain a hinge. In certain embodiments provided herein, an immunoglobulin constant region contains a CH2 domain and a CH3 domain.

"Fc region" or "Fc domain" refers to a polypeptide sequence corresponding to or derived from the portion of a source antibody that is responsible for binding to antibody receptors on cells and the C1q component of complement. Fc stands for "fragment crystalline," and refers to the fragment of an antibody that will readily form a protein crystal. Distinct protein fragments, which were originally described by proteolytic digestion, can define the overall general structure of an immunoglobulin protein. An "Fc region" or "Fc domain" contains a CH2 domain, a CH3 domain, and optionally all or a portion of a hinge. An "Fc region" or "Fc domain" can refer to a single polypeptide or to two disulfide-linked polypeptides. For a review of immunoglobulin structure and function, see Putnam, The Plasma Proteins, Vol. V (Academic Press, Inc., 1987), pp. 49-140; and Padlan, Mol. Immunol. 31:169-217, 1994. As used herein, the term Fc includes variants of naturally occurring sequences.

An "immunoglobulin dimerization domain" or "immunoglobulin heterodimerization domain," as used herein, refers to an immunoglobulin domain of a polypeptide chain that preferentially interacts or associates with a different immunoglobulin domain of a second polypeptide chain, wherein the interaction of the different immunoglobulin heterodimerization domains substantially contributes to or efficiently promotes heterodimerization of the first and second polypeptide chains (i.e., the formation of a dimer between two different polypeptide chains, which is also referred to as a "heterodimer"). The interactions between immunoglobulin heterodimerization domains "substantially contributes to or efficiently promotes" the heterodimerization of first and second polypeptide chains if there is a statistically significant reduction in the dimerization between the first and second polypeptide chains in the absence of the immunoglobulin heterodimerization domain of the first polypeptide chain and/or the immunoglobulin heterodimerization domain of the second polypeptide chain. In certain embodiments, when the first and second polypeptide chains are co-expressed, at least 60%, at least about 60% to about 70%, at least about 70% to about 80%, at least 80% to about 90%, 91%, 92%, 93%, 94%, 95%, 96%, 97%, 98%, or 99% of the first and second polypeptide chains form heterodimers with each other. Representative immunoglobulin heterodimerization domains include an immunoglobulin CH1 domain, an immunoglobulin CL domain (e.g., Cκ or Cλ isotypes), or derivatives thereof, including wild type immunoglobulin CH1 and CL domains and altered (or mutated) immunoglobulin CH1 and CL domains, as provided therein.

A "wild-type immunoglobulin hinge region" refers to a naturally occurring upper and middle hinge amino acid sequences interposed between and connecting the CH1 and CH2 domains (for IgG, IgA, and IgD) or interposed between and connecting the CH1 and CH3 domains (for IgE and IgM) found in the heavy chain of a naturally occurring antibody. In certain embodiments, a wild type immunoglobulin hinge region sequence is human, and can comprise a human IgG hinge region. An "altered wild-type immunoglobulin hinge region" or "altered immunoglobulin hinge region" refers to (a) a wild type immunoglobulin hinge region with up to 30% amino acid changes (e.g., up to 25%, 20%, 15%, 10%, or 5% amino acid substitutions or deletions), or (b) a portion of a wild type immunoglobulin hinge region that has a length of about 5 amino acids (e.g., about 5, 6, 7, 8, 9, 10, 11, 12, 13, 14, 15, 16, 17, 18, 19, or 20 amino acids) up to about 120 amino acids (for instance, having a length of about 10 to about 40 amino acids or about 15 to about 30 amino acids or about 15 to about 20 amino acids or about 20 to about 25 amino acids), has up to about 30% amino acid changes (e.g., up to about 25%, 20%, 15%, 10%, 5%, 4%, 3%, 2%, or 1% amino acid substitutions or deletions or a combination thereof), and has an IgG core hinge region as disclosed in US 2013/0129723 and US 2013/0095097. As provided herein, a "hinge region" or a "hinge" can be located between an antigen-binding domain (e.g., a 4-1BB or an OX40-binding domain) and an immunoglobulin constant region.

As used herein, a "linker" refers to a moiety, e.g., a polypeptide, that is capable of joining two compounds, e.g., two polypeptides. Non-limiting examples of linkers include flexible linkers comprising glycine-serine (e.g., (Gly4Ser)) repeats, and linkers derived from (a) an interdomain region of a transmembrane protein (e.g., a type I transmembrane protein); (b) a stalk region of a type II C-lectin; or (c) an immunoglobulin hinge. As provided herein, a linker can refer, e.g., to (1) a polypeptide region between VH and VL regions in a single-chain Fv (scFv) or (2) a polypeptide region between an immunoglobulin constant region and an antigen-binding domain. In certain embodiments, a linker is comprised of 5 to about 35 amino acids, for instance, about 15 to about 25 amino acids. In some embodiments, a linker is comprised of at least 5 amino acids, at least 7 amino acids or at least 9 amino acids.

As used herein, the term "heavy chain" when used in reference to an antibody can refer to any distinct type, e.g., alpha (α), delta (δ), epsilon (ε), gamma (γ), and mu (μ), based on the amino acid sequence of the constant region, which give rise to IgA, IgD, IgE, IgG, and IgM classes of antibodies, respectively, including subclasses of IgG, e.g., $IgG_1$, $IgG_2$, $IgG_3$, and $IgG_4$.

As used herein, the term "light chain" when used in reference to an antibody can refer to any distinct type, e.g., kappa (κ) or lambda (λ) based on the amino acid sequence of the constant regions. Light chain amino acid sequences are well known in the art. In specific embodiments, the light chain is a human light chain.

As used herein, the term "EU numbering system" refers to the EU numbering convention for the constant regions of an antibody, as described in Edelman, G. M. et al., Proc. Natl. Acad. USA, 63, 78-85 (1969) and Kabat et al, Sequences of Proteins of Immunological Interest, U.S. Dept. Health and Human Services, 5th edition, 1991, each of which is herein incorporated by reference in its entirety. As used herein, unless otherwise provided, a position of an amino acid residue in a constant region of an immunoglobulin molecule is numbered according to EU nomenclature (Ward et al., 1995 Therap. Immunol. 2:77-94).

As used herein, the term "dimer" refers to a biological entity that consists of two subunits associated with each other via one or more forms of intramolecular forces, including covalent bonds (e.g., disulfide bonds) and other interactions (e.g., electrostatic interactions, salt bridges, hydrogen bonding, and hydrophobic interactions), and is stable under appropriate conditions (e.g., under physiological conditions, in an aqueous solution suitable for expressing, purifying, and/or storing recombinant proteins, or under conditions for non-denaturing and/or non-reducing electrophoresis). A "heterodimer" or "heterodimeric protein," as used herein, refers to a dimer formed from two different polypeptides. A "homodimer" or "homodimeric protein," as used herein, refers to a dimer formed from two identical polypeptides.

"Antibody-dependent cell-mediated cytotoxicity" and "ADCC," as used herein, refer to a cell-mediated process in which nonspecific cytotoxic cells that express FcγRs (e.g., monocytic cells such as Natural Killer (NK) cells and macrophages) recognize bound antibody (or other protein capable of binding FcγRs) on a target cell and subsequently cause lysis of the target cell. In principle, any effector cell with an activating FcγR can be triggered to mediate ADCC. The primary cells for mediating ADCC are NK cells, which express only FcγRIII, whereas monocytes, depending on their state of activation, localization, or differentiation, can express FcγRI, FcγRII, and FcγRIII. For a review of FcγR expression on hematopoietic cells, see, e.g., Ravetch et al., Annu. Rev. Immunol., 9:457-92 (1991).

The term "having ADCC activity," as used herein in reference to a, means that the polypeptide (for example, one comprising an immunoglobulin hinge region and an immunoglobulin constant region having CH2 and CH3 domains, such as derived from IgG (e.g., IgG1)), is capable of mediating antibody-dependent cell-mediated cytotoxicity (ADCC) through binding of a cytolytic Fc receptor (e.g., FcγRIII) on a cytolytic immune effector cell expressing the Fc receptor (e.g., an NK cell).

"Complement-dependent cytotoxicity" and "CDC," as used herein, refer to a process in which components in normal serum ("complement"), together with an antibody or other C1q-complement-binding protein bound to a target antigen, exhibit lysis of a target cell expressing the target antigen. Complement consists of a group of serum proteins that act in concert and in an orderly sequence to exert their effect.

The terms "classical complement pathway" and "classical complement system," as used herein, are synonymous and refer to a particular pathway for the activation of complement. The classical pathway requires antigen-antibody complexes for initiation and involves the activation, in an orderly fashion, of nine major protein components designated C1 through C9. For several steps in the activation process, the product is an enzyme that catalyzes the subsequent step. This cascade provides amplification and activation of large amounts of complement by a relatively small initial signal.

The term "having CDC activity," as used herein in reference to a polypeptide, means that the polypeptide (for example, one comprising an immunoglobulin hinge region and an immunoglobulin constant region having CH2 and CH3 domains, such as derived from IgG (e.g., IgG1)) is capable of mediating complement-dependent cytotoxicity (CDC) through binding of C1q complement protein and activation of the classical complement system. In one embodiment of the invention, the recombinant polypeptide has been modified to abate CDC activity.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant (KA). The $K_D$ is calculated from the quotient of $k_{off}/k_{on}$, whereas KA is calculated from the quotient of $k_{on}/k_{off}$. $k_{on}$ refers to the association rate constant of, e.g., an antibody to an antigen, and $k_{off}$ refers to the dissociation of, e.g., an antibody from an antigen. The $k_{on}$ and $k_{off}$ can be determined by techniques known to one of ordinary skill in the art, such as BIAcore® or KinExA.

As used herein, the terms "immunospecifically binds," "immunospecifically recognizes," "specifically binds," and "specifically recognizes" are analogous terms in the context of antibodies. These terms indicate that the antibody binds to an epitope via its antigen-binding domain and that the binding entails some complementarity between the antigen-binding domain and the epitope. Accordingly, an antibody that "specifically binds" to human 4-1BB and/or OX40 may also, but the extent of binding to an un-related, non-4-1BB and/or OX40 protein is less than about 10% of the binding of the antibody to 4-1BB and/or OX40 as measured, e.g., by a radioimmunoassay (RIA).

Binding domains can be classified as "high affinity" binding domains and "low affinity" binding domains. "High affinity" binding domains refer to those binding domains with a $K_D$ value less than $10^{-7}$ M, less than $10^{-8}$ M, less than $10^{-9}$ M, less than $10^{-10}$ M. "Low affinity" binding domains refer to those binding domains with a KD greater than $10^{-7}$ M, greater than $10^{-6}$ M, or greater than $10^{-5}$ M. "High affinity" and "low affinity" binding domains bind their targets, while not significantly binding other components present in a test sample.

As used herein, an antibody is "capable of binding" if it will specifically bind its target (i.e., human 4-1BB or human OX40) when in close proximity to the target and under conditions one of skill in the art would consider to be necessary for binding. A "human 4-1BB antigen-binding domain" should be understood to mean a binding domain that specifically binds to human 4-1BB. A "human OX40 antigen-binding domain" should be understood to mean a binding domain that specifically binds to OX40.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligopeptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals can be studied using well known X-ray diffraction techniques and can be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies can be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques.

An antibody that "binds to the same epitope" as a reference antibody refers to an antibody that binds to the same amino acid residues on the antigen as the reference antibody. The ability of an antibody to bind to the same epitope as a reference antibody can be determined by a hydrogen/deuterium exchange assay (see Coales et al. Rapid Commun. Mass Spectrom. 2009; 23: 639-647)

An antibody that "binds to the same conformational epitope" as a reference antibody refers to an antibody that binds to the conformation or structure on the antigen as the reference antibody. The ability of an antibody to bind to the same conformational epitope as a reference antibody can be determined by methods known in the art, including, for instance, a hydrogen/deuterium exchange assay (see Coales et al. Rapid Commun. Mass Spectrom. 2009; 23: 639-647), comparison of the structures of the antibody(ies) complexed with the antigen as determined by X-ray crystallography, and alanine scanning. An antibody that binds to the same linear epitope" as a reference antibody refers to an antibody that binds to the same linear amino acid sequence on the antigen as the reference antibody. For linear epitopes, peptide mapping experiments, such as pepspot analysis, can be used to determine binding to the same linear epitope.

An antibody is said to "competitively inhibit" binding of a reference antibody to its epitope if the antibody preferentially binds to that epitope or an overlapping epitope to the extent that it blocks, to some degree, binding of the reference antibody to the epitope. Competitive inhibition may be determined by any method known in the art, for example, competition ELISA assays, surface plasmon resonance (SPR), or biolayer interferometry (BLI). An antibody may be said to competitively inhibit binding of the reference antibody to a given epitope if it prevents or reduces binding of the reference antibody to its target by at least 50%. In certain embodiments, an antibody competitively inhibits binding of a reference antibody to a given epitope by at least 90%, at least 80%, at least 70%, or at least 60%. In certain embodiments, the reference antibody is an anti-4-1BB antibody, an anti-OX40 antibody, an anti-4-1BB bispecific or multispecific antibody, or an anti-OX40 bispecific or multispecific antibody. For instance, a reference antibody may be an anti-4-1BB×anti-OX40 bispecific antibody. A reference antibody with a human 4-1BB antigen-binding domain may comprise a heavy chain variable domain (VH) of SEQ ID NO: 17 and a light chain variable domain (VL) of SEQ ID NO:18. A reference antibody with a human OX40 antigen-binding domain may comprise a heavy chain of SEQ ID NO:29 and a VL of SEQ ID NO:28.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain embodiments, the polypeptides can occur as single chains or associated chains.

As used herein, the terms "nucleic acid," "nucleic acid molecule," or "polynucleotide" refer to deoxyribonucleotides or ribonucleotides and polymers thereof in either single- or double-stranded form. Unless specifically limited, the terms encompass nucleic acids containing analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions can be achieved by generating sequences in which the third position of one or more selected (or all) codons is substituted with mixed-base and/or deoxyinosine residues (Batzer et al. (1991) Nucleic Acid Res. 19:5081; Ohtsuka et al. (1985) J. Biol. Chem. 260:2605-2608; Cassol et al. (1992); Rossolini et al. (1994) Mol. Cell. Probes 8:91-98). The term nucleic acid is used interchangeably with gene, cDNA, and mRNA encoded by a gene. As used herein, the terms "nucleic acid," "nucleic acid molecule," or "polynucleotide" are intended to include DNA molecules (e.g., cDNA or genomic DNA), RNA molecules (e.g., mRNA), analogs of the DNA or RNA generated using nucleotide analogs, and derivatives, fragments and homologs thereof.

The term "expression vector," as used herein, refers to a nucleic acid molecule, linear or circular, comprising one or more expression units. In addition to one or more expression units, an expression vector can also include additional nucleic acid segments such as, for example, one or more origins of replication or one or more selectable markers. Expression vectors are generally derived from plasmid or viral DNA, or can contain elements of both.

"Percent identity" refers to the extent of identity between two sequences (e.g., amino acid sequences or nucleic acid sequences). Percent identity can be determined by aligning two sequences, introducing gaps to maximize identity between the sequences. Alignments can be generated using programs known in the art. For purposes herein, alignment of nucleotide sequences can be performed with the blastn program set at default parameters, and alignment of amino acid sequences can be performed with the blastp program set at default parameters (see National Center for Biotechnology Information (NCBI) on the worldwide web, ncbi.nlm.nih.gov).

As used herein, a "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a CDR(s) or within a framework region(s) of an antibody can be replaced with an amino acid residue with a similar side chain.

As used herein, a polypeptide or amino acid sequence "derived from" a designated polypeptide refers to the origin of the polypeptide. In certain embodiments, the polypeptide or amino acid sequence which is derived from a particular sequence (sometimes referred to as the "starting" or "parent" or "parental" sequence) has an amino acid sequence that is essentially identical to the starting sequence or a portion thereof, wherein the portion consists of at least 10-20 amino acids, at least 20-30 amino acids, or at least 30-50 amino acids, or at least 50-150 amino acids, or which is otherwise identifiable to one of ordinary skill in the art as having its origin in the starting sequence. For example, a binding domain can be derived from an antibody, e.g., a Fab, $F(ab')_2$, Fab', scFv, single domain antibody (sdAb), etc.

Polypeptides derived from another polypeptide can have one or more mutations relative to the starting polypeptide, e.g., one or more amino acid residues which have been substituted with another amino acid residue or which has one or more amino acid residue insertions or deletions. The polypeptide can comprise an amino acid sequence which is not naturally occurring. Such variations necessarily have less than 100% sequence identity or similarity with the starting polypeptide. In one embodiment, the variant will have an amino acid sequence from about 60% to less than 100% amino acid sequence identity or similarity with the amino acid sequence of the starting polypeptide. In another embodiment, the variant will have an amino acid sequence from about 75% to less than 100%, from about 80% to less than 100%, from about 85% to less than 100%, from about 90% to less than 100%, from about 95% to less than 100% amino acid sequence identity or similarity with the amino acid sequence of the starting polypeptide.

As used herein, the term "host cell" can be any type of cell, e.g., a primary cell, a cell in culture, or a cell from a cell line. In specific embodiments, the term "host cell" refers to a cell transfected with a nucleic acid molecule and the progeny or potential progeny of such a cell. Progeny of such a cell may not be identical to the parent cell transfected with the nucleic acid molecule, e.g., due to mutations or environmental influences that may occur in succeeding generations or integration of the nucleic acid molecule into the host cell genome.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure. As used herein, "substantially pure" refers to material which is at least 50% pure (i.e., free from contaminants). In some instances, a material is at least 90% pure, at least 95% pure, at least 98% pure, or at least 99% pure.

The term "pharmaceutical formulation" refers to a preparation which is in such form as to permit the biological activity of the active ingredient to be effective, and which contains no additional components which are unacceptably toxic to a subject to which the formulation would be administered. The formulation can be sterile.

As used herein, the term "pharmaceutically acceptable" refers to molecular entities and compositions that do not generally produce allergic or other serious adverse reactions when administered using routes well known in the art. Molecular entities and compositions approved by a regulatory agency of the Federal or a state government or listed in the U.S. Pharmacopeia or other generally recognized pharmacopeia for use in animals, and more particularly in humans are considered to be "pharmaceutically acceptable."

The terms "administer", "administering", "administration", and the like, as used herein, refer to methods that may be used to enable delivery of a drug, e.g., a 4-1BB/OX40 antibody to the desired site of biological action (e.g., intravenous administration). Administration techniques that can be employed with the agents and methods described herein are found in e.g., Goodman and Gilman, The Pharmacological Basis of Therapeutics, current edition, Pergamon; and Remington's, Pharmaceutical Sciences, current edition, Mack Publishing Co., Easton, Pa.

As used herein, the terms "subject" and "patient" are used interchangeably. The subject can be an animal. In some embodiments, the subject is a mammal such as a non-human animal (e.g., cow, pig, horse, cat, dog, rat, mouse, monkey or other primate, etc.). In some embodiments, the subject is a human. As used herein, the term "patient in need" or "subject in need" refers to a patient at risk of, or suffering from, a disease, disorder or condition that is amenable to treatment or amelioration, e.g., with a 4-1BB/OX40 antibody provided herein. A patient in need may, for instance, be a patient diagnosed with a cancer.

The term "therapeutically effective amount" refers to an amount of a drug, e.g., an anti-4-1BB/OX40 antibody effective to treat a disease or disorder in a subject. In the case of cancer, the therapeutically effective amount of the drug can reduce the number of cancer cells; reduce the tumor size or burden; inhibit (i.e., slow to some extent and in a certain embodiment, stop) cancer cell infiltration into peripheral organs; inhibit (i.e., slow to some extent and in a certain embodiment, stop) tumor metastasis; inhibit, to some extent, tumor growth; relieve to some extent one or more of the symptoms associated with the cancer; and/or result in a favorable response such as increased progression-free survival (PFS), disease-free survival (DFS), or overall survival (OS), complete response (CR), partial response (PR), or, in some cases, stable disease (SD), a decrease in progressive disease (PD), a reduced time to progression (TTP), or any combination thereof.

Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already diagnosed with or suspected of having the disorder. In certain embodiments, a subject is successfully "treated" for cancer according to the methods of the present invention if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity, tumorigenic frequency, or tumorigenic capacity, of a tumor; reduction in the number or frequency of cancer stem cells in a tumor; differentiation of tumorigenic cells to a non-tumorigenic state; increased progression-free survival (PFS), disease-free survival (DFS), or overall survival (OS), complete response (CR), partial response (PR), stable disease (SD), a decrease in progressive disease (PD), a reduced time to progression (TTP), or any combination thereof.

The terms "cancer" and "cancerous" refer to or describe the physiological condition in mammals in which a population of cells are characterized by unregulated cell growth. Examples of cancer include, but are not limited to, melanoma, kidney cancer, pancreatic cancer, lung cancer, intestinal cancer, prostate cancer, breast cancer, liver cancer, brain cancer, and hematological cancers. The cancer may be a primary tumor or may be advanced or metastatic cancer.

A cancer can be a solid tumor cancer. The term "solid tumor" refers to an abnormal mass of tissue that usually does not contain cysts or liquid areas. Examples of solid tumors are sarcomas, carcinomas, and lymphomas. Leukemias (cancers of the blood) generally do not form solid tumors. A solid tumor can contain tumor infiltrating lymphocytes which express OX40 and 4-1BB.

It should be understood that the terms "a" and "an" as used herein refer to "one or more" of the enumerated components unless otherwise indicated.

Unless specifically stated or obvious from context, as used herein, the term "or" is understood to be inclusive. The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

It is understood that wherever embodiments are described herein with the language "comprising," otherwise analogous embodiments described in terms of "consisting of" and/or "consisting essentially of" are also provided and part of the present application's disclosure. In this disclosure, "comprises," "comprising," "containing" and "having" and the like can have the meaning ascribed to them in U.S. and European Patent law and can mean "includes," "including," and the like; "consisting essentially of" or "consists essentially" likewise has the meaning ascribed in U.S. and European Patent law. It should be appreciated that as far as U.S. patent law is concerned, the term is open-ended, allowing for the presence of more than that which is recited so long as basic or novel characteristics of that which is recited is not changed by the presence of more than that which is recited, but excludes prior art embodiments. It should also be appreciated that as far as European Patent law is concerned the use of "consisting essentially of" or "comprising substantially" means that specific further components can be present, namely those not materially affecting the essential characteristics of the compound or composition.

As used herein, the terms "about" and "approximately," when used to modify a numeric value or numeric range, indicate that deviations of up to 5% above or 5% below the value or range remain within the intended meaning of the recited value or range.

Any domains, components, compositions, and/or methods provided herein can be combined with one or more of any of the other domains, components, compositions, and/or methods provided herein.

II. 4-1BB and OX40 Antibodies

Provided herein are 4-1BB antibodies, OX40 antibodies, and 4-1BB×OX40 bispecific antibodies. The 4-1BB antibodies and the 4-1BB×OX40 bispecific antibodies comprise an antigen-binding domain that specifically binds to human 4-1BB (i.e., a human 4-1BB antigen-binding domain). The OX40 antibodies and the 4-1BB×OX40 bispecific antibodies comprise an antigen-binding domain that binds to human OX40 (i.e., a human OX40 antigen-binding domain). The 4-1BB×OX40 bispecific antibodies can comprise a human 4-1BB binding domain and a human OX40 binding domain. The 4-1BB×OX40 bispecific antibodies be monovalent for each target, i.e., containing one human 4-1BB binding domain and one human OX40 binding domain. The bispecific antibodies can also be bivalent for one or both target proteins, i.e., containing two 4-1BB binding domains and/or two OX40 binding domains. An exemplary 4-1BB×OX40 bispecific antibody format is shown in FIG. 27.

A. 4-1BB Binding Domains

Provided herein are antigen-binding domains that bind to human 4-1BB (i.e., 4-1BB binding domains) that can be used to assemble 4-1BB×OX40 bispecific antibodies. A 4-1BB binding domain can bind to 4-1BB from other species, e.g. cynomolgus monkey and/or mouse 4-1BB, in addition to binding to human 4-1BB. In certain instances, the 4-1BB binding domains bind to human 4-1BB and to cynomolgus monkey 4-1BB.

A 4-1BB binding domain can comprise six complementarity determining regions (CDRs), i.e., a variable heavy chain (VH) CDR1, a VH CDR2, a VH CDR3, a variable light chain (VL) CDR1, a VL CDR2, and a VL CDR3. A 4-1BB binding domain can comprise a variable heavy chain (VH) and a variable light chain (VL). The VH and the VL can be separate polypeptides or can parts of the same polypeptide (e.g., in an scFv).

In certain embodiments, a 4-1BB binding domain described herein comprises a combination of six CDRs listed in Tables A and B (e.g., SEQ ID NOs:5-10 or SEQ ID NOs:5, 119, 7, 120, 121, and 122).

TABLE A 4-1BB VH CDR Amino Acid Sequences[1]

| VH CDR1 (SEQ ID NO:) | VH CDR2 (SEQ ID NO:) | VH CDR3 (SEQ ID NO:) |
|---|---|---|
| GYTFTSYW (SEQ ID NO: 5) | IYPSGGST (SEQ ID NO: 6) | ASFSDGYYAYAMDY (SEQ ID NO: 7) |
| GYTFTSYW (SEQ ID NO: 5) | IYPGSSTT (SEQ ID NO: 119) | ASFSDGYYAYAMDY (SEQ ID NO: 7) |

[1]The CDRs are determined according to IMGT.

TABLE B 4-1BB VL CDR Amino Acid Sequences[2]

| VL CDR1 (SEQ ID NO:) | VL CDR2 (SEQ ID NO:) | VL CDR3 (SEQ ID NO:) |
|---|---|---|
| QSVSSY (SEQ ID NO: 8) | YAS (SEQ ID NO: 9) | QQGYNLPYT (SEQ ID NO: 10) |
| QDISNY (SEQ ID NO: 120) | YTS (SEQ ID NO: 121) | QQGYTLPYT (SEQ ID NO: 122) |

[2]The CDRs are determined according to IMGT.

A 4-1BB×OX40 bispecific antibody that is monovalent for 4-1BB can comprise a single 4-1BB binding domain with a combination of six CDRs listed in Tables A and B above (e.g., SEQ ID NOs:5-10 or SEQ ID NOs:5, 119, 7, 120, 121, and 122). A 4-1BB×OX40 bispecific antibody that is bivalent for 4-1BB can comprise two 4-1BB binding domains, each comprising a combination of six CDRs listed in Tables A and B above (e.g., SEQ ID NOs:5-10 or SEQ ID NOs:5, 119, 7, 120, 121, and 122).

As described herein, a 4-1BB binding can comprise the VH of an antibody listed in Table C.

TABLE C

| 4-1BB Variable Heavy Chain (VH) Amino Acid Sequences | |
|---|---|
| SEQ ID NO; | VH Amino Acid Sequence |
| 17 | EVQLVQSGAEVKKPGASVKVSCKASGYTFTSYWMNWVRQAPGQGL EWMGNIYPSGGSTNYAQKFQGRVTMTVDTSTSTVYMELSSLRSEDT AVYYCASFSDGYYAYAMDYWGQGTLVTVSS |
| 19 | QVQLQQPGAELVKPGASVKLSCKASGYTFTSWINWVKQRPGQGLE WIGNIYPGSSTTNYNEKFKSKATLTVDTSSSTAYMQLSSLTSDDSAVF YCASFSDGYYAYAMDWVQGTSVTVSS |
| 21 | EVQLVQSGAEVKKPGSSVKVSCKASGYTFTSYWINWVRQAPGQGLE WIGNIYPGSSTTNYNEKFKSRATLTVDTSTSTAYMELSSLRSEDTAVY YCASFSDGYYAYAMDYWGQGTLVTVSS |
| 23 | EVQLVQSGAEVKKPGASVKVSCKASGYTFTSYWMNWVRQAPGQGL EWMGNIYPGSSTTNYAQKFQGRVTMTVDTSTSTVYMELSSLRSEDT AVYYCASFSDGYYAYAMDWGQGTLVTVSS |
| 32 | EVQLVQSGAEVKKPGASVKVSCKASGYTFTSYWMNWVRQAPGQGL EWMGNIYPSGGSTNYAQKFQGRVTMTVDTSTSTVYMELSSLRSEDT AVYYCASFSDGYYAYAMDWGQGTLVTV |
| 143 | QVQLQQPGAELVKPGASVKLSCEASGYTFTSYWINWVKQRPGQGLE WIGNIYPGSSTTNYNEKFKSKATLTVDTSSSTAYMQLSSLTSDDSAVF YCASFSDGYYAYAMDWVQGTSVTVSS |

As described herein, a 4-1BB binding domain can comprise a VH having at least about 70%, at least about 75%, at least about 80%, at least about 85%, at least about 90%, at least about 95%, at least about 96%, at least about 97%, at least about 98%, at least about 99%, or 100% sequence identity to a sequence in Table C, optionally wherein the VH comprises VH CDR1, VH CDR2, and VH CDR3 sequences of SEQ ID NOs:5-7, respectively, or VH CDR1, VH CDR2, and VH CDR3 sequences of SEQ ID NOs:5, 119, and 7, respectively.

As described herein, a 4-1BB binding domain can comprise a VH comprising the CDRs of a VH sequence in Table C, e.g., the IMGT-defined CDRs, the Kabat-defined CDRs, the Chothia-defined CDRs, or the AbM-defined CDRs.

As described herein, a 4-1BB binding domain can comprise the VL of an antibody listed in Table D.

TABLE D

| 4-1BB Variable Light Chain (VL) Amino Acid Sequences | |
|---|---|
| SEQ ID NO | VL Amino Acid Sequence |
| 18 | EIVMTQSPATLSLSPGERATLSCRASQSVSSYLNAVYQQKPGQAPRLLI YYASRRHTGIPARFSGSGSGTDFTLTISSLQPEDFAVYYCQQGYNLPY TFGQGTKVEIK |
| 20 | DIQMTQTTSSLSASLGDRVTITCRASQDISNYLNWYQQKPDGTVKLLI YYTSRLHSGVPSRFSGGGSGTDYSLTISNLEQEDIATYFCQQGYTLPY TFGGGTKLEIK |
| 22 | EIVMTQSPGTLSLSPGERATLSCRASQDISNYLNWYQQKPGQAVRLLI YYTSRLHSGIPDRFSGSGSGTDYTLTISRLEPEDFAVYFCQQGYTLPYT FGQGTKVEIK |
| 24 | EIVMTQSPATLSLSPGERATLSCRASQDISNYLNWYQQKPGQAVRLLI YYTSRLHSGIPARFSGSGSGTDYTLTISSLQPEDFAVYFCQQGYTLPYT FGQGTKVEIK |

As described herein, a 4-1BB binding domain can comprise a VL having at least about 70%, at least about 75%, at least about 80%, at least about 85%, at least about 90%, at least about 95%, at least about 96%, at least about 97%, at least about 98%, at least about 99%, or 100% sequence identity to a sequence in Table D, optionally wherein the VL comprises VL CDR1, VL CDR2, and VL CDR3 sequences of SEQ ID NOs:8-10, respectively, or VL CDR1, VL CDR2, and VL CDR3 sequences of SEQ ID NOs:120-122, respectively.

As described herein, a 4-1BB binding domain can comprise a VL comprising the CDRs of a VL sequence in Table D, e.g., the IMGT-defined CDRs, the Kabat-defined CDRs, the Chothia-defined CDRs, or the AbM-defined CDRs.

As described herein, a 4-1BB binding domain can comprise a VH listed in Table C and a VL listed in Table D. A 4-1BB×OX40 bispecific antibody that is monovalent for 4-1BB can comprise a single 4-1BB binding domain comprising a VH listed in Table C and a VL listed in Table D. A 4-1BB×OX40 bispecific antibody that is bivalent for 4-1BB can comprise two 4-1BB binding domains, each comprising a VH listed in Table C and a VL listed in Table D. The VH listed in Table C and the VL listed in table D can be different polypeptides or can be on the same polypeptide. When the VH and VL are on the same polypeptide, they can be in either orientation (i.e., VH-VL or VL-VH), and they can be connected by a linker (e.g., a glycine-serine linker). In certain embodiments, the VH and VL are connected a glycine-serine linker that is at least 15 amino acids in length (e.g., 15-50 amino acids 15-40 amino acids, 15-30 amino acids, 15-25 amino acids or 15-20 amino acids). In certain embodiments, the VH and VL are connected a glycine-serine linker that is at least 20 amino acids in length (e.g., 20-50 amino acids 20-40 amino acids, 20-30 amino acids, or 20-25 amino acids).

As described herein, a 4-1BB binding domain can comprise a VH comprising the CDRs of a VH sequence in Table C, e.g., the IMGT-defined CDRs, the Kabat-defined CDRs, the Chothia-defined CDRs, or the AbM-defined CDRs and a VL comprising the CDRs of a VL sequence in Table D, e.g., the IMGT-defined CDRs, the Kabat-defined CDRs, the Chothia-defined CDRs, or the AbM-defined CDRs.

In certain embodiments, a 4-1BB binding domain comprises (i) a VH comprising the amino acid sequence of SEQ ID NO: 17 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:17, optionally wherein the VH comprises VH CDR1, VH CDR2, and VH CDR3 sequences of SEQ ID NOs:5-7, respectively) and (ii) a VL comprising the amino acid sequence of SEQ ID NO: 18 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:18, optionally wherein the VL comprises VL CDR1, VL CDR2, and VL CDR3 sequences of SEQ ID NOs:8-10, respectively).

In certain embodiments, a 4-1BB binding domain comprises (i) a VH comprising the amino acid sequence of SEQ ID NO: 19 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:19, optionally wherein the VH comprises VH CDR1, VH CDR2, and VH CDR3 sequences of SEQ ID NOs:5, 119, and 7, respectively) and (ii) a VL comprising the amino acid sequence of SEQ ID NO:20 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:20, optionally wherein the VL comprises VL CDR1, VL CDR2, and VL CDR3 sequences of SEQ ID NOs:120-122, respectively).

In certain embodiments, a 4-1BB binding domain comprises (i) a VH comprising the amino acid sequence of SEQ ID NO:21 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:21, optionally wherein the VH comprises VH CDR1, VH CDR2, and VH CDR3 sequences of SEQ ID NOs:5, 19, and 7, respectively) and (ii) a VL comprising the amino acid sequence of SEQ ID NO:22 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:22, optionally wherein the VL comprises VL CDR1, VL CDR2, and VL CDR3 sequences of SEQ ID NOs:120-122, respectively).

In certain embodiments, a 4-1BB binding domain comprises (i) a VH comprising the amino acid sequence of SEQ ID NO:23 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:23, optionally wherein the VH comprises VH CDR1, VH CDR2, and VH CDR3 sequences of SEQ ID NOs: 5, 119, and 7, respectively) and a (ii) VL comprising the amino acid sequence of SEQ ID NO:24 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:24, optionally wherein the VL comprises VL CDR1, VL CDR2, and VL CDR3 sequences of SEQ ID NOs:120-122, respectively).

In certain embodiments, a 4-1BB binding domain comprises (i) a VH comprising the amino acid sequence of SEQ ID NO:32 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:32, optionally wherein the VH comprises VH CDR1, VH CDR2, and VH CDR3 sequences of SEQ ID NOs:5-7, respectively) and (ii) a VL comprising the amino acid sequence of SEQ ID NO: 18 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:18, optionally wherein the VL comprises VL CDR1, VL CDR2, and VL CDR3 sequences of SEQ ID NOs:8-10, respectively).

In certain embodiments, a 4-1BB binding domain comprises (i) a VH comprising the amino acid sequence of SEQ ID NO: 143 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:143, optionally wherein the VH comprises VH CDR1, VH CDR2, and VH CDR3 sequences of SEQ ID NOs:5, 119, and 7, respectively) and (ii) a VL comprising the amino acid sequence of SEQ ID NO:20 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:20, optionally wherein the VL comprises VL CDR1, VL CDR2, and VL CDR3 sequences of SEQ ID NOs:120-122, respectively).

In certain embodiments, a 4-1BB binding domain (e.g., an scFv) described herein binds to human 4-1BB and comprises one of the amino acid sequences set forth in Table E.

TABLE E 4-1BB Binding Sequences

| 4-1BB Binding Construct | SEQ ID NO | VH SEQ ID NO | VL SEQ ID NO |
|---|---|---|---|
| FOB01143 scFv | 42 | 21 | 22 |
| FOB01143 Full Construct | 43 | 21 | 22 |
| FOB01188 scFv and FX01047 and FX01055 4-1BB scFv | 44 | 23 | 24 |
| FOB01188 Full Construct | 45 | 23 | 24 |
| FX01066, FXX01099, FXX01101, FXX01102, FXX01079, and FXX01110-FXX01121 4-1BB scFv | 58 | 17 | 18 |
| FXX01104, FXX01105, FXX01107, and FXX01108 4-1BB scFv | 63 | 32 | 18 |
| FOB01173 scFv | 77 | 143 | 20 |
| FOB01173 Full Construct | 101 | 143 | 20 |
| FXX01028 | 145 | 19 | 20 |

As described herein, a 4-1BB×OX40 bispecific antibody that is monovalent for 4-1BB can comprise a single 4-1BB binding domain comprising a sequence listed in Table E. A 4-1BB×OX40 bispecific antibody that is bivalent for 4-1BB can comprise two 4-1BB binding domains, each comprising a sequence listed in Table E.

As described herein, a 4-1BB binding domain can comprises an amino acid sequence at least about 70%, at least about 75%, at least about 80%, at least about 85%, at least about 90%, at least about 95%, at least about 96%, at least about 97%, at least about 98%, at least about 99% identical to a sequence in Table E, optionally wherein the sequence comprises VH CDR1, VH CDR2, and VH CDR3 sequences of SEQ ID NOs:5-7, respectively, and VL CDR1, VL CDR2, and VL CDR3 sequences of SEQ ID NOs:8-10, respectively or VH CDR1, VH CDR2, and VH CDR3 sequences of SEQ ID NOs:5, 119, and 7, respectively, and VL CDR1, VL CDR2, and VL CDR3 sequences of SEQ ID NOs:120-122, respectively.

In certain embodiments, a 4-1BB binding domain provided herein competitively inhibits binding of an antibody comprising a VH sequence in Table C (e.g., a VH comprising SEQ ID NO:17) and a VL sequence in Table D (e.g., a VL comprising SEQ ID NO:18) to human 4-1BB.

In certain embodiments, a 4-1BB binding domain provided herein specifically binds to the same epitope of human 4-1BB as an antibody comprising a VH sequence in Table C (e.g., a VH comprising SEQ ID NO:17) and a VL sequence in Table D (e.g., a VL comprising SEQ ID NO:18) to human 4-1BB.

In certain embodiments, a 4-1BB binding domain provided herein is capable of agonizing 4-1BB. In certain embodiments, a 4-1BB binding domain provided herein in a 4-1BB×OX40 bispecific antibody only agonizes 4-1BB in the presence of both 4-1BB and OX40.

B. OX40 Binding Domains

Provided herein are antigen-binding domains that bind to human OX40 (i.e., OX40 binding domains) that can be used to assemble 4-1BB×OX40 bispecific antibodies. An OX40 binding domain can bind to OX40 from other species, e.g. cynomolgus monkey and/or mouse OX40, in addition to binding to human OX40. In certain instances, the OX40 binding domains bind to human OX40 and to cynomolgus monkey OX40.

An OX40 binding domain can comprise six complementarity determining regions (CDRs), i.e., a variable heavy chain (VH) CDR1, a VH CDR2, a VH CDR3, a variable light chain (VL) CDR1, a VL CDR2, and a VL CDR3. An OX40 binding domain can comprise a variable heavy chain (VH) and a variable light chain (VL). The VH and the VL can be separate polypeptides or can parts of the same polypeptide (e.g., in an scFv).

In certain embodiments, an OX40 binding domain described herein comprises the six CDRs listed in Tables F and G.

TABLE F

OX40 VH CDR Amino Acid Sequences[3]

| VH CDR1 (SEQ ID NO:) | VH CDR2 (SEQ ID NO:) | VH CDR3 (SEQ ID NO:) |
|---|---|---|
| GFTLSYYG (SEQ ID NO: 11) | ISHDGSDK (SEQ ID NO: 12) | SNDQFDP (SEQ ID NO: 13) |

[3]The CDRs are determined according to IMGT.

TABLE G

OX40 VL CDR Amino Acid Sequences[4]

| VL CDR1 (SEQ ID NO:) | VL CDR2 (SEQ ID NO:) | VL CDR3 (SEQ ID NO:) |
|---|---|---|
| NIGSKS (SEQ IDNO: 14) | DDS (SEQ ID NO: 15) | QVWDSSSDHVV (SEQ ID NO: 16) |

[4]The CDRs are determined according to IMGT.

A 4-1BB×OX40 bispecific antibody that is monovalent for OX40 can comprise a single OX40 binding domain with the six CDRs listed in Tables F and G above. A 4-1BB×OX40 bispecific antibody that is bivalent for OX40 can comprise two OX40 binding domains, each comprising the six CDRs listed in Tables F and G above.

As described herein, an OX40 binding can comprise the VH of an antibody listed in Table H.

TABLE H

OX40 Variable Heavy Chain (VH) Amino Acid Sequences

| SEQ ID NO | VH Amino Acid Sequence |
|---|---|
| 25 | QVQLVESGGGVVQPGRSLRLSCAASGFTLSYYGMHWVRQAPGKGLE WVAVISHDGSDKYYADSVKGRFTISRDNSKNTLYLQMDSLRAEDTA LYYCSNDQFDPWGQGTLVTVSS |

TABLE H-continued

| OX40 Variable Heavy Chain (VH) Amino Acid Sequences | |
|---|---|
| SEQ ID NO | VH Amino Acid Sequence |
| 27 | QVQLVESGGGVVQPGRSLRLSCAASGFTLSYYGMHWVRQAPGKGLE<br>WVAVISHDGSDKYYADSVKGRFTISRDNSKNTLYLQMNSLRAEDTA<br>VYYCSNDQFDPWGQGTLVTVSS |
| 29 | QVQLVESGGGVVQPGRSLRLSCAASGFTLSYYGMHWVRQAPGKGLE<br>WVAAISFIDGSDKYYADSVKGRFTISRDNSKNTLYLQMNSLRAEDTA<br>VYYCSNDQFDPWGQGTLVTVSS |
| 31 | QVQLVESGGGVVQPGRSLRLSCAASGFTLSYYGMHWVRQAPGKGLE<br>WVAAISHDGSDKYYADSVKGRFTISRDNSKNRLYLQMNSLRAEDTA<br>VYYCSNDQFDPWGQGTLVTVSS |
| 33 | QVQLVESGGGVVQPGRSLRLSCAASGFTLSYYGMHWVRQAPGKGLE<br>WVAVISHDGSDKYYADSVKGRFTISRDNSKNTLYLQMNSLRAEDTA<br>VYYCSNDQFDPWGQGTLVTV |

As described herein, an OX40 binding domain can comprise a VH having at least about 70%, at least about 75%, at least about 80%, at least about 85%, at least about 90%, at least about 95%, at least about 96%, at least about 97%, at least about 98%, at least about 99%, or 100% sequence identity to a sequence in Table H, optionally wherein the VH comprises VH CDR1, VH CDR2, and VH CDR3 sequences of SEQ ID NOs:11-13, respectively.

As described herein, an OX40 binding domain can comprise a VH comprising the CDRs of a VH sequence in Table H, e.g., the IMGT-defined CDRs, the Kabat-defined CDRs, the Chothia-defined CDRs.

As described herein, an OX40 binding domain can comprise the VL of an antibody listed in Table I.

TABLE I

| Variable Light Chain (VL) Amino Acid Sequences | |
|---|---|
| SEQ ID NO. | VL Amino Acid Sequence |
| 26 | SYVLTQPPSVSVAPGQTARITCGGNNIGSKSVHWFQQKPGQAPALVV<br>YDDSGRPSGIPERFSGSTSGNTATLTISRVEAGDEADYYCQVWDSSSD<br>HVVFGGGTKLTVL |
| 28 | SYVLTQPPSVSVAPGQTARITCGGNNIGSKSVNWFQQKPGQAPVLVV<br>YDDSGRPSGIPERFSGSTSGNTATLTISRVEAGDEADYYCQVWDSSSD<br>HVVFGGGTKLTVL |
| 30 | SYVLTQPPSVSVAPGKTARITCGGNNIGSKSVNWFQQKPGQAPVLVV<br>YDDSGRPSGIPERFSGSTSGNTATLTISRVEAGDEADYYCQVWDSSSD<br>HVVFGGGTKLTVL |
| 34 | SYVLTQPPSVSVAPGQTARITCGGNNIGSKSVNWFQQKPGQAPVLVV<br>YDDSGRPSGIPARFSGSTSGNTATLTISRVEAGDEADYYCQVWDSSSD<br>HVVFGGGTKLTVL |
| 35 | SYVLTQPPSVSVAPGQTARITCGGNNIGSKSVNWFQQKPGQAPVLVV<br>YDDSGRPSGVPNRFSGSTSGNTATLTISRVEAGDEADYYCQVWDSSS<br>DHVVFGGGTKLTVL |
| 36 | SYVLTQPPSVSVAPGQTARITCGGNNIGSKSVNWFQQKPGQAPVLVV<br>YDDSGRPSGVPSRFSGSTSGNTATLTISRVEAGDEADYYCQVWDSSS<br>DHVVFGGGTKLTVL |
| 37 | SYVLTQPPSVSVAPGQTARITCGGNNIGSKSVNWFQQKPGQAPVLVV<br>YDDSGRPSGIPKRFSGSTSGNTATLTISRVEAGDEADYYCQVWDSSSD<br>HVVFGGGTKLTVL |
| 38 | SYVLTQPPSVSVAPGKTARITCGGNNIGSKSVNWFQQKPGQAPVLVV<br>YDDSGRPSGIPARFSGSTSGNTATLTISRVEAGDEADYYCQVWDSSSD<br>HVVFGGGTKLTVL |

TABLE I-continued

| Variable Light Chain (VL) Amino Acid Sequences | |
|---|---|
| SEQ ID NO. | VL Amino Acid Sequence |
| 39 | SYVLTQPPSVSVAPGKTARITCGGNNIGSKSVNWFQQKPGQAPVLVV YDDSGRPSGVPNRFSGSTSGNTATLTISRVEAGDEADYYCQVWDSSS DHVVFGGGTKLTVL |
| 40 | SYVLTQPPSVSVAPGKTARITCGGNNIGSKSVNWFQQKPGQAPVLVV YDDSGRPSGVPSRFSGSTSGNTATLTISRVEAGDEADYYCQVWDSSS DHVVFGGGTKLTVL |
| 41 | SYVLTQPPSVSVAPGKTARITCGGNNIGSKSVNWFQQKPGQAPVLVV YDDSGRPSGIPKRFSGSTSGNTATLTISRVEAGDEADYYCQVWDSSSD HVVFGGGTKLTVL |

As described herein, an OX40 binding domain can comprise a VL having at least about 70%, at least about 75%, at least about 80%, at least about 85%, at least about 90%, at least about 95%, at least about 96%, at least about 97%, at least about 98%, at least about 99%, or 100% sequence identity to a sequence in Table I, optionally wherein the VL comprises VL CDR1, VL CDR2, and VL CDR3 sequences of SEQ ID NOs:14-16, respectively.

As described herein, an OX40 binding domain can comprise a VL comprising the CDRs of a VL sequence in Table I, e.g., the IMGT-defined CDRs, the Kabat-defined CDRs, the Chothia-defined CDRs, or the AbM-defined CDRs.

As described herein, an OX40 binding domain can comprise a VH listed in Table H and a VL listed in Table I. A 4-1BB×OX40 bispecific antibody that is monovalent for 4-1BB can comprise a single 4-1BB binding domain comprising a VH listed in Table H and a VL listed in Table I. A 4-1BB×OX40 bispecific antibody that is bivalent for 4-1BB can comprise two 4-1BB binding domains, each comprising a VH listed in Table H and a VL listed in Table I. The VH listed in Table H and the VL listed in table I can be different polypeptides or can be on the same polypeptide. When the VH and VL are on the same polypeptide, they can be in either orientation (i.e., VH-VL or VL-VH), and they can be connected by a linker (e.g., a glycine-serine linker). In certain embodiments, the VH and VL are connected a glycine-serine linker that is at least 15 amino acids in length (e.g., 15-50 amino acids 15-40 amino acids, 15-30 amino acids, 15-25 amino acids or 15-20 amino acids). In certain embodiments, the VH and VL are connected a glycine-serine linker that is at least 20 amino acids in length (e.g., 20-50 amino acids 20-40 amino acids, 20-30 amino acids, or 20-25 amino acids).

As described herein, an OX40 binding domain can comprise a VH comprising the CDRs of a VH sequence in Table H, e.g., the IMGT-defined CDRs, the Kabat-defined CDRs, the Chothia-defined CDRs, or the AbM-defined CDRs and a VL comprising the CDRs of a VL sequence in Table I, e.g., the IMGT-defined CDRs, the Kabat-defined CDRs, the Chothia-defined CDRs, or the AbM-defined CDRs.

In certain embodiments, an OX40 binding domain comprises a (i) VH comprising the amino acid sequence of SEQ ID NO:25 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:25, optionally wherein the VH comprises VH CDR1, VH CDR2, and VH CDR3 sequences of SEQ ID NOs:11-13, respectively) and (ii) a VL comprising the amino acid sequence of SEQ ID NO:26 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:18, optionally wherein the VL comprises VL CDR1, VL CDR2, and VL CDR3 sequences of SEQ ID NOs:14-16, respectively).

In certain embodiments, an OX40 binding domain comprises (i) a VH comprising the amino acid sequence of SEQ ID NO:27 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:27, optionally wherein the VH comprises VH CDR1, VH CDR2, and VH CDR3 sequences of SEQ ID NOs:11-13, respectively) and (ii) a VL comprising the amino acid sequence of SEQ ID NO:28 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:28, optionally wherein the VL comprises VL CDR1, VL CDR2, and VL CDR3 sequences of SEQ ID NOs:14-16, respectively).

In certain embodiments, an OX40 binding domain comprises (i) a VH comprising the amino acid sequence of SEQ ID NO:29 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:29, optionally wherein the VH comprises VH CDR1, VH CDR2, and VH CDR3 sequences of SEQ ID NOs:11-13, respectively) and (ii) a VL comprising the amino acid sequence of SEQ ID NO:28 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:28, optionally wherein the VL comprises VL CDR1, VL CDR2, and VL CDR3 sequences of SEQ ID NOs:14-16, respectively).

In certain embodiments, an OX40 binding domain comprises (i) a VH comprising the amino acid sequence of SEQ ID NO:29 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:29, optionally wherein the VH comprises VH CDR1, VH CDR2, and VH CDR3 sequences of SEQ ID NOs:11-13, respectively) a (ii) VL comprising the amino acid sequence of any one of SEQ ID NOs:26, 30, and 34-37 (or a sequence that is at least about 70%, at least about 75%, at least about 80%, at least about 85%, at least about 90%, at least about 95%, at least about 96%, at least about 97%, at least about 98%, at least about 99% identical to any one of SEQ ID NOs:28 and 34-37, optionally wherein the VL comprises VL CDR1, VL CDR2, and VL CDR3 sequences of SEQ ID NOs:14-16, respectively).

In certain embodiments, an OX40 binding domain comprises (i) a VH comprising the amino acid sequence of SEQ ID NO:31 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:31, optionally wherein the VH comprises VH CDR1, VH CDR2, and VH CDR3 sequences of SEQ ID NOs:11-13, respectively) and a (ii) VL comprising the amino acid sequence of any one of SEQ ID NOs:28, 30, and 34-41 (or a sequence that is at least about 70%, at least about 75%, at least about 80%, at least about 85%, at least about 90%, at least about 95%, at least about 96%, at least about 97%, at least about 98%, at least about 99% identical to any one of SEQ ID NOs:28, 30, and 34-41, optionally wherein the VL comprises VL CDR1, VL CDR2, and VL CDR3 sequences of SEQ ID NOs:14-16, respectively)

In certain embodiments, an OX40 binding domain comprises (i) a VH comprising the amino acid sequence of SEQ ID NO:33 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:33, optionally wherein the VH comprises VH CDR1, VH CDR2, and VH CDR3 sequences of SEQ ID NOs:11-13, respectively) and a (ii) VL comprising the amino acid sequence of SEQ ID NO:28 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:28, optionally wherein the VL comprises VL CDR1, VL CDR2, and VL CDR3 sequences of SEQ ID NOs:14-16, respectively).

In certain embodiments, an OX40 binding domain (e.g., an scFv) described herein binds to human OX40 and comprises one of the amino acid sequences set forth in Table J.

TABLE J

OX40 Binding Sequences

| OX40 Binding Construct | SEQ ID NO. | VH SEQ ID NO | VL SEQ ID NO |
|---|---|---|---|
| OXF169 and OXF170 scFv | 46 | 25 | 26 |
| OXF171 and OXF172 scFv | 47 | 25 | 26 |
| OXF169 Full Construct | 48 | 25 | 26 |
| OXF170 Full Construct | 49 | 25 | 26 |
| OXF171 Full Construct | 50 | 25 | 26 |
| OXF172 Full Construct | 51 | 25 | 26 |
| OXF01099 scFv | 52 | 27 | 28 |
| OXF01099 Full Construct | 53 | 27 | 28 |
| OXF01115 scFv | 54 | 29 | 28 |
| OXF01115 Full Construct | 55 | 29 | 28 |
| OXF01122 scFv | 56 | 25 | 26 |
| OXF01122 Full Construct | 57 | 25 | 26 |
| OXF01070 scFv -Fc | 102 | 25 | 26 |
| FX01066, FX01104, and FX01047 anti-OX40 scFv | 59 | 29 | 28 |
| FX01099 and FX01105 anti-OX40 scFv | 60 | 29 | 30 |
| FX01101 and FX01107 anti-OX40 scFv | 61 | 31 | 28 |
| FX01102 anti-OX40 scFv | 62 | 31 | 30 |
| FXX01055 and FX01079 anti-OX40 scFv | 64 | 33 | 28 |

TABLE J-continued

OX40 Binding Sequences

| OX40 Binding Construct | SEQ ID NO. | VH SEQ ID NO | VL SEQ ID NO |
|---|---|---|---|
| FXX01110 anti-OX40 scFv | 65 | 29 | 34 |
| FXX01111 anti-OX40 scFv | 66 | 29 | 35 |
| FXX01112 anti-OX40 scFv | 67 | 29 | 36 |
| FXX01113 anti-OX40 scFv | 68 | 29 | 37 |
| FXX01114 anti-OX40 scFv | 69 | 31 | 34 |
| FXX01115 anti-OX40 scFv | 70 | 31 | 35 |
| FXX01116 anti-OX40 scFv | 71 | 31 | 36 |
| FXX01117 anti-OX40 scFv | 72 | 31 | 37 |
| FXX01118 anti-OX40 scFv | 73 | 31 | 38 |
| FXX01119 anti-OX40 scFv | 74 | 31 | 39 |
| FXX01120 anti-OX40 scFv | 75 | 31 | 40 |
| FXX01121 anti-OX40 scFv | 76 | 31 | 41 |
| FXX01028 anti-OX40 scFv | 146 | 25 | 26 |

As described herein, a 4-1BB×OX40 bispecific antibody that is monovalent for OX40 can comprise a single OX40 binding domain comprising a sequence listed in Table J. A 4-1BB×OX40 bispecific antibody that is bivalent for OX40 can comprise two OX40 binding domains, each comprising a sequence listed in Table J.

As described herein, an OX40 binding domain can comprises an amino acid sequence at least about 70%, at least about 75%, at least about 80%, at least about 85%, at least about 90%, at least about 95%, at least about 96%, at least about 97%, at least about 98%, at least about 99% identical to a sequence in Table J, optionally wherein the sequence comprises VH CDR1, VH CDR2, and VH CDR3 sequences of SEQ ID NOs:11-13, respectively, and VL CDR1, VL CDR2, and VL CDR3 sequences of SEQ ID NOs:14-16, respectively.

In certain embodiments, an OX40 binding domain provided herein competitively inhibits binding of an antibody comprising a VH sequence in Table H (e.g., a VH comprising SEQ ID NO:29) and a VL sequence in Table I (e.g., a VL comprising SEQ ID NO:28) to human OX40.

In certain embodiments, an OX40 binding domain provided herein specifically binds to the same epitope of human OX40 as an antibody comprising a VH sequence in Table H (e.g., a VH comprising SEQ ID NO:29) and a VL sequence in Table I (e.g., a VL comprising SEQ ID NO:28) to human OX40.

In certain embodiments, an OX40 binding domain provided herein is capable of agonizing OX40. By "capable" it is meant that the OX40 binding domain can perform an activity but may only do so under appropriate conditions as can be appreciated by one of skill in the art. In certain embodiments, an OX40 binding domain provided herein in a 4-1BB×OX40 bispecific antibody only agonizes OX40 in the presence of both 4-1BB and OX40.

C. 4-1BB and/or OX40 Binding Domains

In a 4-1BB or OX40 binding domain, the VH CDRs or VH and the VL CDRs or VL can be separate polypeptides or can be on the same polypeptide. When the VH CDRs or VH and the VL CDRs or VL are on the same polypeptide, they can be in either orientation (i.e., VH-VL or VL-VH).

When the VH CDRs or VH and the VL CDRs or VL are on the same polypeptide, they can be connected by a linker (e.g., a glycine-serine linker). The VH can be positioned N-terminally to a linker sequence, and the VL can be positioned C-terminally to the linker sequence. Alternatively, the VL can be positioned N-terminally to a linker sequence, and the VH can be positioned C-terminally to the linker sequence.

The use of peptide linkers for joining VH and VL regions is well-known in the art, and a large number of publications exist within this particular field. In some embodiments, a peptide linker is a 15mer consisting of three repeats of a Gly-Gly-Gly-Gly-Ser amino acid sequence ($(Gly_4Ser)_3$) (SEQ ID NO:116). Other linkers have been used, and phage display technology, as well as selective infective phage technology, has been used to diversify and select appropriate linker sequences (Tang et al., *J. Biol. Chem.* 271, 15682-15686, 1996; Hennecke et al., *Protein Eng.* 11, 405-410, 1998). In certain embodiments, the VH and VL regions are joined by a peptide linker having an amino acid sequence comprising the formula $(Gly_4Ser)_n$, wherein n=1-5 (SEQ ID NO: 117). In certain embodiments, n=3-10. In certain embodiments, n=3-5. In certain embodiments, n=4-10. In certain embodiments, n=4-5. In certain embodiments, n=4. Other suitable linkers can be obtained by optimizing a simple linker (e.g., $(Gly_4Ser)_n$), wherein n=1-5 (SEQ ID NO: 117) through random mutagenesis.

The 4-1BB and/or OX40 binding domain can be a humanized binding domain. The 4-1BB and/or OX40 binding domain can be a rat binding domain. The 4-1BB and/or OX40 binding domain can be a murine binding domain. In certain embodiments, a 4-1BB×OX40 bispecific antibody comprises a humanized 4-1BB binding domain and a rat OX40 binding domain. In certain embodiments, a 4-1BB×OX40 bispecific antibody comprises a humanized 4-1BB binding domain and a murine OX40 binding domain. In certain embodiments, a 4-1BB×OX40 bispecific antibody comprises a humanized 4-1BB binding domain and a humanized OX40 binding domain.

The 4-1BB and/or OX40 binding domain can be an scFv. In certain embodiments, all of the 4-1BB and OX40 binding domains in a 4-1BB×OX40 bispecific antibody are scFvs. In certain embodiments, a 4-1BB binding domain and an OXO binding domain in a 4-1BB×OX40 bispecific antibody are scFvs. In certain embodiments, at least one 4-1BB or OX40 binding domain in a 4-1BB×OX40 bispecific antibody is an scFv. In certain embodiments, a polypeptide comprises a 4-1BB binding domain (e.g., an scFv) and an OX40 binding domain (e.g., an scFv).

The 4-1BB and/or OX40 binding domain can comprise a VH and a VL on separate polypeptide chains. In certain embodiments, all of the 4-1BB and OX40 binding domains in a 4-1BB×OX40 bispecific antibody comprise a VH and a VL on separate polypeptide chains. In certain embodiments, at least one 4-1BB or OX40 binding domain in a 4-1BB×OX40 bispecific antibody comprises a VH and a VL on separate polypeptide chains.

D. 4-1BB×OX40 Bispecific Antibodies

Provided herein are bispecific antibodies that bind to human 4-1BB and to human OX40 (4-1BB×OX40 bispecific antibodies). Such bispecific antibodies comprise at least one 4-1BB binding domain and at least one human OX40 binding domain. The 4-1BB binding domain in the bispecific antibody can be any human 4-1BB binding domain, including, e.g., any 4-1BB binding domain discussed above. The OX40 binding domain in the bispecific antibody can be any human OX40 binding domain, including, e.g., any OX40 binding domain discussed above.

In certain embodiments, the 4-1BB×OX40 bispecific antibodies provided herein can bind to 4-1BB and OX40 simultaneously.

In certain embodiments, the 4-1BB×OX40 bispecific antibodies provided herein can agonize a T cell co stimulatory pathway. In certain embodiments, the 4-1BB×OX40 bispecific antibodies provided herein can agonize 4-1BB only in the presence of OX40. In certain embodiments, the 4-1BB×OX40 bispecific antibodies provided herein can agonize OX40 only in the presence of 4-1BB.

In certain embodiments, the 4-1BB×OX40 bispecific antibodies provided herein can increase natural killer (NK) cell proliferation. In certain embodiments, the 4-1BB×OX40 bispecific antibodies provided herein can increase T cell proliferation. In certain embodiments, the 4-1BB×OX40 bispecific antibodies provided herein can increase CD8 T cell proliferation. In certain embodiments, the 4-1BB×OX40 bispecific antibodies provided herein can increase CD4 T cell proliferation. In certain embodiments, the 4-1BB×OX40 bispecific antibodies provided herein can increase CD8 T cell proliferation and CD4 T cell proliferation. In certain embodiments, the 4-1BB×OX40 bispecific antibodies provided herein can increase NK cell proliferation and T cell proliferation.

In certain embodiments, a 4-1BB×OX40 bispecific antibody costimulates 4-1BB and OX40. In certain embodiments, a 4-1BB×OX40 bispecific antibody provides synergistic co-stimulation of T cells. In certain embodiments, a 4-1BB×OX40 bispecific antibody provides synergistic tumor lysis. In certain embodiments, a 4-1BB×OX40 bispecific antibody provides synergistic effect in enhancing an anti-tumor immune response.

In certain embodiments, a 4-1BB×OX40 bispecific antibody enhances T-cell activation and/or prolongs T-cell survival.

In certain embodiments, a 4-1BB×OX40 bispecific antibody comprises two 4-1BB binding domains and two OX40 binding domains. Where a 4-1BB×OX40 bispecific antibody comprises two antigen-binding domains that bind to the same target (e.g., 4-1BB or OX40), those two antigen-binding domains can comprise the same amino acid sequence(s) or can comprise different amino acid sequences. In certain embodiments, the two 4-1BB binding domains comprise the same amino acid sequence(s). In certain embodiments, the two OX40 binding domains comprise the same amino acid sequence(s). In certain embodiments, the two 4-1BB binding domains comprise the same acid sequences(s), and the two OX40 binding domains comprise the same amino acid sequences(s).

A 4-1BB×OX40 bispecific antibody as provided herein can be prepared by chemically linking two different monoclonal antibodies or by fusing two hybridoma cell lines to produce a hybrid-hybridoma. Other multivalent formats that can be used include, for example, quadromas, Kλ-bodies, dAbs, diabodies, TandAbs, nanobodies, Small Modular ImmunoPharmaceutials (SMIPsT™), DOCK-AND-LOCKs® (DNLs®), CrossMab Fabs, CrossMab VH-VLs, strand-exchange engineered domain bodies (SEEDbodies), Affibodies, Fynomers, Kunitz Domains, Albu-dabs, two engineered Fv fragments with exchanged VHs (e.g., a dual-affinity re-targeting molecules (D.A.R.T.s)), scFv×scFv (e.g., BiTE), DVD-IG, Covx-bodies, peptibodies, scFv-Igs, SVD-Igs, dAb-Igs, Knobs-in-Holes, IgG1 antibodies comprising matched mutations in the CH3 domain (e.g., DuoBody antibodies) and triomAbs. Exemplary bispecific formats are discussed in Garber et al., *Nature Reviews Drug Discovery* 13:799-801 (2014), which is herein incorporated by reference in its entirety. Additional exemplary bispecific formats are discussed in Liu et al. *Front. Immunol.* 8:38 doi: 10.2289/fimmu.2017.00038, and Brinkmann and Kontermann, MABS 9: 2, 182-212 (2017), each of which is herein incorporated by reference in its entirety. In certain embodiments, a bispecific antibody can be a $F(ab')_2$ fragment. A $F(ab')_2$ fragment contains the two antigen-binding arms of a tetrameric antibody molecule linked by disulfide bonds in the hinge region.

4-1BB×OX40 bispecific antibodies disclosed herein can incorporate a multi-specific binding protein scaffold. Multi-specific binding proteins using scaffolds are disclosed, for instance, in PCT Application Publication No. WO 2007/146968, U.S. Patent Application Publication No. 2006/0051844, PCT Application Publication No. WO 2010/040105, PCT Application Publication No. WO 2010/003108, U.S. Pat. Nos. 7,166,707, and 8,409,577, each of which is herein incorporated by reference in its entirety. A 4-1BB×OX40 bispecific antibody can comprise two binding domains (the domains can be designed to specifically bind the same or different targets), a hinge region, a linker (e.g., a carboxyl-terminus or an amino-terminus linker), and an immunoglobulin constant region. A 4-1BB×OX40 bispecific antibody can be a homodimeric protein comprising two identical, disulfide-bonded polypeptides.

In one embodiment, the 4-1BB×OX40 bispecific antibody comprises two polypeptides, each polypeptide comprising, in order from amino-terminus to carboxyl-terminus, a first antigen-binding domain, a linker (e.g., wherein the linker is a hinge region), an immunoglobulin constant region, and a second antigen-binding domain. FIG. 27 illustrates a 4-1BB×OX40 bispecific antibody in this configuration. This configuration is also referred to herein as an ADAPTIR™ format.

In some embodiments, a 4-1BB×OX40 bispecific antibody comprises a polypeptide comprising in order from amino-terminus to carboxyl-terminus, a 4-1BB binding domain (e.g., scFv), a linker (e.g., wherein the linker is a hinge region), an immunoglobulin constant region, a linker, and an OX40 binding domain (e.g., scFv). In certain embodiments, the 4-1BB binding domain (e.g., scFv) comprises in order from amino-terminus to carboxyl-terminus a VH, a linker (e.g., glycine-serine linker), and a VL. In certain embodiments, linker between the 4-1BB binding domain and the immunoglobulin constant region is a hinge, and the hinge is an IgG1 hinge. In certain embodiments, the immunoglobulin constant region comprises a CH2 domain and a CH3 domain. In certain embodiments, the OX40 binding domain (e.g., scFv) comprises in order from amino-terminus to carboxyl-terminus a VL, a linker (e.g., glycine-serine linker), and a VH.

Accordingly, in some embodiments, a 4-1BB×OX40 bispecific antibody comprises a polypeptide comprising in order from amino-terminus to carboxyl-terminus a VH of a 4-1BB binding domain, a linker (e.g., a glycine-serine linker), a VL of a 4-1BB binding domain, an IgG1 hinge, an immunoglobulin constant region comprising a CH2 domain and a CH3 domain, a linker (e.g., a glycine-serine linker), a VL of an OX40 binding domain, a linker (e.g., a glycine-serine linker), and a VH of an OX40 binding domain. In some embodiments, a 4-1BB×OX40 bispecific antibody comprises a dimer of such polypeptides.

In some embodiments, a 4-1BB×OX40 bispecific antibody comprises a protein scaffold as generally disclosed in, for example, in US Patent Application Publication Nos. 2003/0133939, 2003/0118592, and 2005/0136049. A 4-1BB×OX40 bispecific antibody may comprise a dimer (e.g., a homodimer) of two peptides, each comprising, in order from amino-terminus to carboxyl-terminus: a first antigen-binding domain, a linker (e.g., wherein the linker is a hinge region), and an immunoglobulin constant region. In other embodiments, a 4-1BB×OX40 bispecific antibody comprises a protein scaffold as generally disclosed in, for example, in US Patent Application Publication No. 2009/0148447. A 4-1BB/OX40 antibody may comprise a dimer (e.g., a homodimer) of two peptides, each comprising, in order from amino-terminus to carboxyl-terminus: an immunoglobulin constant region, a linker (e.g., wherein the linker is a hinge region) and a first antigen-binding domain.

In some embodiments, a 4-1BB×OX40 bispecific antibody comprises two antigen-binding domains that are scFvs and two antigen-binding domains that comprises VHs and VLs on separate polypeptides. In such embodiments, the scFvs can be fused to the N- or C-terminal of the polypeptide comprising the VH. The scFvs can also be fused to the N- or C-terminal of the polypeptide comprising the VL.

Additional exemplary bispecific antibody molecules of the invention comprise (i) an antibody that has two arms, each comprising two different antigen-binding regions, one with a specificity to 4-1BB and one with a specificity to OX40, (ii) an antibody that has one antigen-binding region or arm specific to 4-1BB and a second antigen-binding region or arm specific to OX40, (iii) a single chain antibody that has a first specificity to 4-1BB and a second specificity to OX40, e.g., via two scFvs linked in tandem by an extra peptide linker; (iv) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (v) a chemically-linked bispecific $(Fab')_2$ fragment; (vi) a Tandab, which is a fusion of two single chain diabodies resulting in a tetravalent bispecific antibody that has two binding sites for each of the target antigens; (vii) a flexibody, which is a combination of scFvs with a diabody resulting in a multivalent molecule; (viii) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (ix) a so-called Scorpion molecule, comprising, e.g., two scFvs fused to both termini of a human Fab-arm; and (x) a diabody.

Examples of different classes of bispecific antibodies include but are not limited to IgG-like molecules with complementary CH3 domains to force heterodimerization; recombinant IgG-like dual targeting molecules, wherein the two sides of the molecule each contain the Fab fragment or part of the Fab fragment of at least two different antibodies; IgG fusion molecules, wherein full length IgG antibodies are fused to extra Fab fragment or parts of Fab fragment; Fc fusion molecules, wherein single chain Fv molecules or stabilized diabodies are fused to heavy-chain constant-domains, Fc-regions or parts thereof; Fab fusion molecules, wherein different Fab-fragments are fused together; ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule.

Examples of Fab fusion bispecific antibodies include but are not limited to $F(ab)_2$ (Medarex/AMGEN), Dual-Action or Bis-Fab (Genentech), Dock-and-Lock (DNL) (ImmunoMedics), Bivalent Bispecific (Biotecnol) and Fab-Fv (UCB-Celltech). Examples of ScFv-, diabody-based and domain antibodies include but are not limited to Bispecific T Cell Engager (BITE) (Micromet, Tandem Diabody (Tandab) (Affimed), Dual Affinity Retargeting Technology (D.A.R.T.) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), and dual targeting heavy chain only domain antibodies.

As provided herein, a 4-1BB×OX40 bispecific antibody can comprise the 4-1BB VH CDR1, CDR2, and CDR3 sequences of SEQ ID NOs:5-7, respectively, the 4-1BB VL CDR1, CDR2, and CDR3 sequences of SEQ ID NOs:8-10, respectively, the OX40 VH CDR1, CDR2, and CDR3 sequences of SEQ ID NOs:11-13, respectively, and the OX40 VL CDR1, CDR2, and CDR3 sequences of SEQ ID NOs:14-16, respectively.

As provided herein, a 4-1BB×OX40 bispecific antibody can comprise the 4-1BB VH CDR1, CDR2, and CDR3 sequences of SEQ ID NOs:5, 119, and 7, respectively, the 4-1BB VL CDR1, CDR2, and CDR3 sequences of SEQ ID NOs:120-122, respectively, the OX40 VH CDR1, CDR2, and CDR3 sequences of SEQ ID NOs:11-13, respectively, and the OX40 VL CDR1, CDR2, and CDR3 sequences of SEQ ID NOs:14-16, respectively As provided herein, a 4-1BB×OX40 bispecific antibody can comprise any combination of 4-1BB VH and VL sequences and OX40 VH and VL sequences provided herein.

For example, a 4-1BB×OX40 bispecific antibody can comprise a 4-1BB binding domain and an OX40 binding domain, wherein the 4-1BB binding domain comprises a VH comprising the amino acid sequence of SEQ ID NO: 17 and a VL comprising the amino acid sequence of SEQ ID NO:18, and wherein the OX40 binding domain comprises (i) a VH comprising the amino acid sequence of SEQ ID NO:29 and a VL comprising the amino acid sequence of SEQ ID NO:28, (ii) a VH comprising the amino acid sequence of SEQ ID NO:29 and a VL comprising the amino acid sequence of SEQ ID NO:30, (iii) a VH comprising the amino acid sequence of SEQ ID NO:31 and a VL comprising the amino acid sequence of SEQ ID NO:28, (iv) a VH comprising the amino acid sequence of SEQ ID NO:31 and a VL comprising the amino acid sequence of SEQ ID NO:30, (v) a VH comprising the amino acid sequence of SEQ ID NO:33 and a VL comprising the amino acid sequence of SEQ ID NO:28, (vi) a VH comprising the amino acid sequence of SEQ ID NO:29 and a VL comprising the amino acid sequence of SEQ ID NO:34; (vii) a VH comprising the amino acid sequence of SEQ ID NO:29 and a VL comprising the amino acid sequence of SEQ ID NO:35; (viii) a VH comprising the amino acid sequence of SEQ ID NO:29 and a VL comprising the amino acid sequence of SEQ ID NO:36; (ix) a VH comprising the amino acid sequence of SEQ ID NO:29 and a VL comprising the amino acid sequence of SEQ ID NO:37; (x) a VH comprising the amino acid sequence of SEQ ID NO:31 and a VL comprising the amino acid sequence of SEQ ID NO:34, (xi) a VH comprising the amino acid sequence of SEQ ID NO:31 and a VL comprising the amino acid sequence of SEQ ID NO:35, (xii) a VH comprising the amino acid sequence of SEQ ID NO:31 and a VL comprising the amino acid sequence of SEQ ID NO:36, (xiii) a VH comprising the amino acid sequence of SEQ ID NO:31 and a VL comprising the amino acid sequence of SEQ ID NO:37, (xiv) a VH comprising the amino acid sequence of SEQ ID NO:31 and a VL comprising the amino acid sequence of SEQ ID NO:38, (xv) a VH comprising the amino acid sequence of SEQ ID NO:31 and a VL comprising the amino acid sequence of SEQ ID NO:39, (xvi) a VH comprising the amino acid sequence of SEQ ID NO:31 and a VL comprising the amino acid sequence of SEQ ID NO:40, (xvii) a VH comprising the amino acid sequence of SEQ ID NO:31 and a VL comprising the amino acid sequence of SEQ ID NO:41, or (xviii) a VH comprising the amino acid sequence of SEQ ID NO:25 and a VL comprising the amino acid sequence of SEQ ID NO:26. In some embodiments, both VH sequences and both VL sequences are on a single polypeptide chain (e.g., a single polypeptide containing one 4-1BB scFv and one OX40 scFv). In some embodiments, one polypeptide comprises both VH sequences and another polypeptide comprises both VL sequences.

A 4-1BB×OX40 bispecific antibody can comprise a 4-1BB binding domain and an OX40 binding domain, wherein the 4-1BB binding domain comprises a VH comprising the amino acid sequence of SEQ ID NO:32 and a VL comprising the amino acid sequence of SEQ ID NO:18, and wherein the OX40 binding domain comprises (i) a VH comprising the amino acid sequence of SEQ ID NO:29 and a VL comprising the amino acid sequence of SEQ ID NO:28, (ii) a VH comprising the amino acid sequence of SEQ ID NO:29 and a VL comprising the amino acid sequence of SEQ ID NO:30, (iii) a VH comprising the amino acid sequence of SEQ ID NO:31 and a VL comprising the amino acid sequence of SEQ ID NO:28, (iv) a VH comprising the amino acid sequence of SEQ ID NO:31 and a VL comprising the amino acid sequence of SEQ ID NO:30, (v) a VH comprising the amino acid sequence of SEQ ID NO:33 and a VL comprising the amino acid sequence of SEQ ID NO:28, (vi) a VH comprising the amino acid sequence of SEQ ID NO:29 and a VL comprising the amino acid sequence of SEQ ID NO:34; (vii) a VH comprising the amino acid sequence of SEQ ID NO:29 and a VL comprising the amino acid sequence of SEQ ID NO:35; (viii) a VH comprising the amino acid sequence of SEQ ID NO:29 and a VL comprising the amino acid sequence of SEQ ID NO:36; (ix) a VH comprising the amino acid sequence of SEQ ID NO:29 and a VL comprising the amino acid sequence of SEQ ID NO:37; (x) a VH comprising the amino acid sequence of SEQ ID NO:31 and a VL comprising the amino acid sequence of SEQ ID NO:34, (xi) a VH comprising the amino acid sequence of SEQ ID NO:31 and a VL comprising the amino acid sequence of SEQ ID NO:35, (xii) a VH comprising the amino acid sequence of SEQ ID NO:31 and a VL comprising the amino acid sequence of SEQ ID NO:36, (xiii) a VH comprising the amino acid sequence of SEQ ID NO:31 and a VL comprising the amino acid sequence of SEQ ID NO:37, (xiv) a VH comprising the amino acid sequence of SEQ ID NO:31 and a VL comprising the amino acid sequence of SEQ ID NO:38, (xv) a VH comprising the amino acid sequence of SEQ ID NO:31 and a VL comprising the amino acid sequence of SEQ ID NO:39, (xvi) a VH comprising the amino acid sequence of SEQ ID NO:31 and a VL comprising the amino acid sequence of SEQ ID NO:40, (xvii) a VH comprising the amino acid sequence of SEQ ID NO:31 and a VL comprising the amino acid sequence of SEQ ID NO:41, or (xviii) a VH comprising the amino acid sequence of SEQ ID NO:25 and a VL comprising the amino acid sequence of SEQ ID NO:26. In some embodiments, both VH sequences and both VL sequences are on a single polypeptide chain (e.g., a single polypeptide containing one 4-1BB scFv and one OX40 scFv). In some embodiments, one polypeptide comprises both VH sequences and another polypeptide comprises both VL sequences.

A 4-1BB×OX40 bispecific antibody can comprise a 4-1BB binding domain and an OX40 binding domain, wherein the 4-1BB binding domain comprises a VH comprising the amino acid sequence of SEQ ID NO:23 and a VL comprising the amino acid sequence of SEQ ID NO:24, and wherein the OX40 binding domain comprises (i) a VH comprising the amino acid sequence of SEQ ID NO:29 and a VL comprising the amino acid sequence of SEQ ID NO:28, (ii) a VH comprising the amino acid sequence of SEQ ID NO:29 and a VL comprising the amino acid sequence of SEQ ID NO:30, (iii) a VH comprising the amino acid sequence of SEQ ID NO:31 and a VL comprising the amino acid sequence of SEQ ID NO:28, (iv) a VH comprising the amino acid sequence of SEQ ID NO:31 and a VL comprising the amino acid sequence of SEQ ID NO:30, (v) a VH comprising the amino acid sequence of SEQ ID NO:33 and a VL comprising the amino acid sequence of SEQ ID NO:28, (vi) a VH comprising the amino acid sequence of SEQ ID NO:29 and a VL comprising the amino acid sequence of SEQ ID NO:34; (vii) a VH comprising the amino acid sequence of SEQ ID NO:29 and a VL comprising the amino acid sequence of SEQ ID NO:35; (viii) a VH comprising the amino acid sequence of SEQ ID NO:29 and a VL comprising the amino acid sequence of SEQ ID NO:36; (ix) a VH comprising the amino acid sequence of SEQ ID NO:29 and a VL comprising the amino acid sequence of SEQ ID NO:37; (x) a VH comprising the amino acid sequence of SEQ ID NO:31 and a VL comprising the amino acid sequence of SEQ ID NO:34, (xi) a VH comprising the amino acid sequence of SEQ ID NO:31 and a VL comprising the amino acid sequence of SEQ ID NO:35, (xii) a VH comprising the amino acid sequence of SEQ ID NO:31 and a VL comprising the amino acid sequence of SEQ ID NO:36, (xiii) a VH comprising the amino acid sequence of SEQ ID NO:31 and a VL comprising the amino acid sequence of SEQ ID NO:37, (xiv) a VH comprising the amino acid sequence of SEQ ID NO:31 and a VL comprising the amino acid sequence of SEQ ID NO:38, (xv) a VH comprising the amino acid sequence of SEQ ID NO:31 and a VL comprising the amino acid sequence of SEQ ID NO:39, (xvi) a VH comprising the amino acid sequence of SEQ ID NO:31 and a VL comprising the amino acid sequence of SEQ ID NO:40, (xvii) a VH comprising the amino acid sequence of SEQ ID NO:31 and a VL comprising the amino acid sequence of SEQ ID NO:41, or (xviii) a VH comprising the amino acid sequence of SEQ ID NO:25 and a VL comprising the amino acid sequence of SEQ ID NO:26. In some embodiments, both VH sequences and both VL sequences are on a single polypeptide chain (e.g., a single polypeptide containing one 4-1BB scFv and one OX40 scFv). In some embodiments, one polypeptide comprises both VH sequences and another polypeptide comprises both VL sequences.

A 4-1BB×OX40 bispecific antibody can comprise a 4-1BB binding domain and an OX40 binding domain, wherein the 4-1BB binding domain comprises a VH comprising the amino acid sequence of SEQ ID NO:19 and a VL comprising the amino acid sequence of SEQ ID NO:20, and wherein the OX40 binding domain comprises (i) a VH comprising the amino acid sequence of SEQ ID NO:20 and a VL comprising the amino acid sequence of SEQ ID NO:28, (ii) a VH comprising the amino acid sequence of SEQ ID NO:29 and a VL comprising the amino acid sequence of SEQ ID NO:30, (iii) a VH comprising the amino acid sequence of SEQ ID NO:31 and a VL comprising the amino acid sequence of SEQ ID NO:28, (iv) a VH comprising the amino acid sequence of SEQ ID NO:31 and a VL comprising the amino acid sequence of SEQ ID NO:30, (v) a VH comprising the amino acid sequence of SEQ ID NO:33 and a VL comprising the amino acid sequence of SEQ ID NO:28, (vi) a VH comprising the amino acid sequence of SEQ ID NO:29 and a VL comprising the amino acid sequence of SEQ ID NO:34; (vii) a VH comprising the amino acid sequence of SEQ ID NO:29 and a VL comprising the amino acid sequence of SEQ ID NO:35; (viii) a VH comprising the amino acid sequence of SEQ ID NO:29 and a VL comprising the amino acid sequence of SEQ ID NO:36; (ix) a VH comprising the amino acid sequence of SEQ ID NO:29 and a VL comprising the amino acid sequence of SEQ ID NO:37; (x) a VH comprising the amino acid sequence of SEQ ID NO:31 and a VL comprising the amino acid sequence of SEQ ID NO:34, (xi) a VH comprising the amino acid sequence of SEQ ID NO:31 and a VL comprising the amino acid sequence of SEQ ID NO:35, (xii) a VH comprising the amino acid sequence of SEQ ID NO:31 and a VL comprising the amino acid sequence of SEQ ID NO:36, (xiii) a VH comprising the amino acid sequence of SEQ ID NO:31 and a VL comprising the amino acid sequence of SEQ ID NO:37, (xiv) a VH comprising the amino acid sequence of SEQ ID NO:31 and a VL comprising the amino acid sequence of SEQ ID NO:38, (xv) a VH comprising the amino acid sequence of SEQ ID NO:31 and a VL comprising the amino acid sequence of SEQ ID NO:39, (xvi) a VH comprising the amino acid sequence of SEQ ID NO:31 and a VL comprising the amino acid sequence of SEQ ID NO:40, (xvii) a VH comprising the amino acid sequence of SEQ ID NO:31 and a VL comprising the amino acid sequence of SEQ ID NO:41, or (xviii) a VH comprising the amino acid sequence of SEQ ID NO:25 and a VL comprising the amino acid sequence of SEQ ID NO:26. In some embodiments, both VH sequences and both VL sequences are on a single polypeptide chain (e.g., a single polypeptide containing one 4-1BB scFv and one OX40 scFv). In some embodiments, one polypeptide comprises both VH sequences and another polypeptide comprises both VL sequences.

A 4-1BB×OX40 bispecific antibody can comprise a 4-1BB binding domain and an OX40 binding domain, wherein the 4-1BB binding domain comprises a VH comprising the amino acid sequence of SEQ ID NO:17 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:17, optionally wherein the VH comprises VH CDR1, VH CDR2, and VH CDR3 sequences of SEQ ID NOs:5-7, respectively) and a VL comprising the amino acid sequence of SEQ ID NO:18 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:18, optionally wherein the VL comprises VL CDR1, VL CDR2, and VL CDR3 sequences of SEQ ID NOs:8-10, respectively), and wherein the OX40 binding domain comprises a VH comprising the amino acid sequence of SEQ ID NO:29 or a sequence that is at least about 70%, at least about 75%, at least about 80%, at least about 85%, at least about 90%, at least about 95%, at least about 96%, at least about 97%, at least about 98%, at least about 99% identical to SEQ ID NO:17, optionally wherein the VH comprises VH CDR1, VH CDR2, and VH CDR3 sequences of SEQ ID NOs:11-13, respectively) and a VL comprising the amino acid sequence of SEQ ID NO:28 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:28, optionally wherein the VL comprises VL CDR1, VL CDR2, and VL CDR3 sequences of SEQ ID NOs:14-16, respectively). In some embodiments, both VH sequences and both VL sequences are on a single polypeptide chain (e.g., a single polypeptide containing one 4-1BB scFv and one OX40 scFv). In some embodiments, one polypeptide comprises both VH sequences and another polypeptide comprises both VL sequences.

A 4-1BB×OX40 bispecific antibody can comprise a 4-1BB binding domain and an OX40 binding domain, wherein the 4-1BB binding domain comprises a VH comprising the amino acid sequence of SEQ ID NO:17 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:17, optionally wherein the VH comprises VH CDR1, VH CDR2, and VH CDR3 sequences of SEQ ID NOs:5-7, respectively) and a VL comprising the amino acid sequence of SEQ ID NO:18 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:18, optionally wherein the VL comprises VL CDR1, VL CDR2, and VL CDR3 sequences of SEQ ID NOs:8-10, respectively), and wherein the OX40 binding domain comprises a VH comprising the amino acid sequence of SEQ ID NO:31 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:31, optionally wherein the VH comprises VH CDR1, VH CDR2, and VH CDR3 sequences of SEQ ID NOs:11-13, respectively) and a VL comprising the amino acid sequence of SEQ ID NO:30 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:30, optionally wherein the VL comprises VL CDR1, VL CDR2, and VL CDR3 sequences of SEQ ID NOs:14-16, respectively). In some embodiments, both VH sequences and both VL sequences are on a single polypeptide chain (e.g., a single polypeptide containing one 4-1BB scFv and one OX40 scFv). In some embodiments, one polypeptide comprises both VH sequences and another polypeptide comprises both VL sequences.

A 4-1BB×OX40 bispecific antibody can comprise a 4-1BB binding domain and an OX40 binding domain, wherein the 4-1BB binding domain comprises a VH comprising the amino acid sequence of SEQ ID NO:17 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:17, optionally wherein the VH comprises VH CDR1, VH CDR2, and VH CDR3 sequences of SEQ ID NOs:5-7, respectively) and a VL comprising the amino acid sequence of SEQ ID NO:18 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:18, optionally wherein the VL comprises VL CDR1, VL CDR2, and VL CDR3 sequences of SEQ ID NOs:8-10, respectively), and wherein the OX40 binding domain comprises a VH comprising the amino acid sequence of SEQ ID NO:29 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:29, optionally wherein the VH comprises VH CDR1, VH CDR2, and VH CDR3 sequences of SEQ ID NOs:11-13, respectively) and a VL comprising the amino acid sequence of SEQ ID NO:35 (or a sequence that is at least about 70%, at least about 75%, at least about 80%, at least about 85%, at least about 90%, at least about 95%, at least about 96%, at least about 97%, at least about 98%, at least about 99% identical to SEQ ID NO:35, optionally wherein the VL comprises VL CDR1, VL CDR2, and VL CDR3 sequences of SEQ ID NOs:14-16, respectively). In some embodiments, both VH sequences and both VL sequences are on a single polypeptide chain (e.g., a single polypeptide containing one 4-1BB scFv and one OX40 scFv). In some embodiments, one polypeptide comprises both VH sequences and another polypeptide comprises both VL sequences.

As provided herein, a 4-1BB×OX40 bispecific antibody can comprise any combination of 4-1BB scFv sequences and OX40 scFv sequences provided herein. For example, a 4-1BB×OX40 bispecific antibody can comprise the scFvs of SEQ ID NOs:58 and 59. A 4-1BB×OX40 bispecific antibody can comprise the scFvs of SEQ ID NOs:58 and 60. A 4-1BB×OX40 bispecific antibody can comprise the scFvs of SEQ ID NOs:58 and 61. A 4-1BB×OX40 bispecific antibody can comprise the scFvs of SEQ ID NOs:58 and 62. A 4-1BB×OX40 bispecific antibody can comprise the scFvs of SEQ ID NOs:63 and 59. A 4-1BB×OX40 bispecific antibody can comprise the scFvs of SEQ ID NOs:63 and 60. A 4-1BB×OX40 bispecific antibody can comprise the scFvs of SEQ ID NOs:63 and 61. A 4-1BB×OX40 bispecific antibody can comprise the scFvs of SEQ ID NOs:63 and 62. A 4-1BB×OX40 bispecific antibody can comprise the scFvs of SEQ ID NOs:44 and 59. A 4-1BB×OX40 bispecific antibody can comprise the scFvs of SEQ ID NOs:44 and 64. A 4-1BB×OX40 bispecific antibody can comprise the scFvs of SEQ ID NOs:58 and 64. A 4-1BB×OX40 bispecific antibody can comprise the scFvs of SEQ ID NOs:58 and 65. A 4-1BB×OX40 bispecific antibody can comprise the scFvs of SEQ ID NOs:58 and 66. A 4-1BB×OX40 bispecific antibody can comprise the scFvs of SEQ ID NOs:58 and 67. A 4-1BB×OX40 bispecific antibody can comprise the scFvs of SEQ ID NOs:58 and 68. A 4-1BB×OX40 bispecific antibody can comprise the scFvs of SEQ ID NOs:58 and 69. A 4-1BB×OX40 bispecific antibody can comprise the scFvs of SEQ ID NOs:58 and 70. A 4-1BB×OX40 bispecific antibody can comprise the scFvs of SEQ ID NOs:58 and 71. A 4-1BB×OX40 bispecific antibody can comprise the scFvs of SEQ ID NOs:58 and 72. A 4-1BB×OX40 bispecific antibody can comprise the scFvs of SEQ ID NOs:58 and 73. A 4-1BB×OX40 bispecific antibody can comprise the scFvs of SEQ ID NOs:58 and 74. A 4-1BB×OX40 bispecific antibody can comprise the scFvs of SEQ ID NOs:58 and 75. A 4-1BB×OX40 bispecific antibody can comprise the scFvs of SEQ ID NOs:58 and 76. A 4-1BB×OX40 bispecific antibody can comprise the scFvs of SEQ ID NOs:145 and 146. Such scFv pairs can be on the same polypeptide or on separate polypeptides. Where the scFv pairs are on the same polypeptide, the 4-1BB scFv can be N-terminal to the OX40 scFv or the 4-1BB scFv can be C-terminal to the OX40 scFv.

As provided herein, an antibody or polypeptide comprising any of the CDR, VH, VL, and/or scFv sequences provided herein may further comprise a hinge. A hinge can be located, for example between a 4-1BB binding domain (e.g., an scFv) and an immunoglobulin constant region. A hinge can also be located between an OX40-binding domain (e.g., an scFv) and an immunoglobulin constant region. In some embodiments, a polypeptide comprises, in order from amino-terminus to carboxyl-terminus, an antigen-binding domain (e.g., an scFv), a hinge region, and an immunoglobulin constant region.

The hinge can be an immunoglobulin hinge, e.g., a human IgG hinge. In some embodiments, the hinge is a human IgG1 hinge. In some embodiments, the hinge comprises amino acids 216-230 (according to EU numbering) of human IgG1 or a sequence that is at least 90% identical thereto. For example, the hinge can comprise a substitution at amino acid C220 according to EU numbering of human IgG1. If derived from a non-human source, a hinge can be humanized. In some embodiments, the hinge comprises amino acids 1-15 of SEQ ID NO:115. Non-limiting examples of hinges are provided in Tables K and L below.

In certain embodiments, a hinge comprises or is a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a wild type immunoglobulin hinge region, such as a wild type human IgG1 hinge, a wild type human IgG2 hinge, or a wild type human IgG4 hinge.

Exemplary altered immunoglobulin hinges include an immunoglobulin human IgG1 hinge region having one, two or three cysteine residues found in a wild type human IgG1 hinge substituted by one, two or three different amino acid residues (e.g., serine or alanine). An altered immunoglobulin hinge can additionally have a proline substituted with another amino acid (e.g., serine or alanine). For example, the above-described altered human IgG1 hinge can additionally have a proline located carboxyl-terminal to the three cysteines of wild type human IgG1 hinge region substituted by another amino acid residue (e.g., serine, alanine). In one embodiment, the prolines of the core hinge region are not substituted.

In certain embodiments, hinge comprises about 5 to 150 amino acids, 5 to 10 amino acids, 10 to 20 amino acids, 20 to 30 amino acids, 30 to 40 amino acids, 40 to 50 amino acids, 50 to 60 amino acids, 5 to 60 amino acids, 5 to 40 amino acids, 8 to 20 amino acids, or 10 to 15 amino acids. The hinge can be primarily flexible, but can also provide more rigid characteristics or can contain primarily α-helical structure with minimal j-sheet structure. The lengths or the sequences of the hinges can affect the binding affinities of the binding domains to which the hinges are directly or indirectly (via another region or domain) connected as well as one or more activities of the Fc region portions to which the hinges or linkers are directly or indirectly connected.

In certain embodiments, a hinge is stable in plasma and serum and is resistant to proteolytic cleavage. The first lysine in the IgG1 upper hinge region can be mutated to minimize proteolytic cleavage. For instance, the lysine can be substituted with methionine, threonine, alanine or glycine, or it can be deleted.

In some embodiments, a 4-1BB×OX40 bispecific antibody does not comprise a hinge. For instance, in some embodiments, a 4-1BB×OX40 bispecific antibody comprises a linker in the place of a hinge.

As provided herein, an antibody or polypeptide comprising any of the CDR, VH, VL, scFv, and/or hinge provided herein may further comprise an immunoglobulin constant region. An immunoglobulin constant region can be located, for example between a hinge and a 4-1BB binding domain (e.g., a 4-1BB binding scFv). An immunoglobulin constant region can also be located between a hinge and an OX40-binding domain (e.g., an OX-40 binding scFv). In some embodiments, a polypeptide comprises, in order from amino-terminus to carboxyl-terminus, a hinge region, an immunoglobulin constant region, and an antigen-binding domain (e.g., an scFv).

In some embodiments, the immunoglobulin constant region comprises immunoglobulin CH2 and CH3 domains of IgG1, IgG2, IgG3, IgG4, IgA1, IgA2 or IgD, optionally wherein the IgG is human. In some cases, the immunoglobulin constant region comprises immunoglobulin CH2 and CH3 domains of IgG1 (e.g., human IgG1). In some embodiments, the polypeptide does not contain a CH1 domain.

In some embodiments, the immunoglobulin constant region comprises one, two, three, four, five or more amino acid substitutions and/or deletions to prevent binding to FcγR1, FcγRIIa, FcγRIIb, FcγRIIa, and FcγRIIIb.

In certain embodiments, the immunoglobulin constant region comprises one, two, three or more amino acid substitutions to prevent or reduce Fc-mediated T-cell activation.

In some embodiments, the immunoglobulin constant region comprises one, two, three, four or more amino acid substitutions and/or deletions to prevent or reduce CDC and/or ADCC activity. In some embodiments, the immunoglobulin constant region comprises one, two, three, four, five or more amino acid substitutions and/or deletions to prevent or abate FcγR or C1q interactions.

The invention includes an antibody with a human 4-1BB antigen-binding domain containing the CDRs of the VH of SEQ ID NO: 17 and the CDRs of the VL of SEQ ID NO:18 and a human OX40 antigen binding domain containing the CDRs of the VH of SEQ ID NO:31 and CDRs of the VL of SEQ ID NO:30 (e.g., the antibody of SEQ ID NO:81). In this embodiment, the human 4-1BB antigen-binding domain and the human OX40 binding domain can be separated by a "null" constant region that contains mutations that prevent binding to FcγRI, FcγRIIa, FcγRIIb, FcγRIIa, and FcγRIIIb. Such a "null" constant region allows the bispecific antibodies of the invention to activate tumor infiltrating lymphocytes while at the same time not activating or minimally activating other effector cells. The presence of the constant region extends the half-life of the bispecific antibody as compared to a similar bispecific antibody without a constant region.

In certain embodiments, the immunoglobulin constant region comprises a human IgG1 CH2 domain comprising the substitutions L234A, L235A, G237A, and K322A, according to the EU numbering system.

In certain embodiments, the immunoglobulin constant region comprises a human IgG1 CH2 domain comprising one or more of the following substitutions: E233P, L234A, L234V, L235A, G237A, E318A, K320A, and K322A, and/or a deletion of G236, according to the EU numbering system.

In certain embodiments, the immunoglobulin constant region comprises a human IgG1 CH2 domain comprising one or more of the following substitutions: E233P, L234A, L234V, L235A, G237A, and K322A, and/or a deletion of G236, according to the EU numbering system.

In certain embodiments, the immunoglobulin constant region comprises a human IgG1 CH2 domain comprising the substitutions L234A, L235A, G237A, E318A, K320A, and K322A, according to the EU numbering system.

In certain embodiments, the immunoglobulin constant region comprises a human IgG1 CH2 domain comprising the substitutions L234A, L235A, G237A, and K322A, according to the EU numbering system.

In certain embodiments, the immunoglobulin constant region comprises a human IgG1 CH2 domain comprising the substitutions E233P, L234V, L235A, G237A, and K322A, according to the EU numbering system.

In certain embodiments, the immunoglobulin constant region comprises a human IgG1 CH2 domain comprising the substitutions E233P, L234V, L235A, G237A, and K322A, and a deletion of G236, according to the EU numbering system.

In certain embodiments, the immunoglobulin constant region comprises a human IgG1 CH2 domain comprising the substitutions E233P, L234A, L235A, G237A, and K322A, according to the EU numbering system. For instance, the invention includes a bispecific antibody comprising, from amino terminus to carboxyl terminus, a first scFV, an immunoglobulin hinge, an IgG1 CH2 domain comprising the substitutions E233P, L234A, L235A, G237A, and K322A, according to the EU numbering system, an IgG1 CH3, and a second scFv. In one embodiment, the first scFv specifically binds to human 4-1BB and the second scFv specifically binds to human OX40. In one embodiment, the first scFv specifically binds to human OX40 and the second scFv specifically binds to human OX40.

In certain embodiments, the immunoglobulin constant region comprises a human IgG1 CH2 domain comprising the substitutions E233P, L234A, L235A, G237A, and K322A, and a deletion of G236, according to the EU numbering system. For instance, the invention includes a bispecific antibody comprising, from amino terminus to carboxyl terminus, a first scFV, an immunoglobulin hinge, an IgG1 CH2 comprising the substitutions E233P, L234A, L235A, G237A, and K322A, and a deletion of G236, according to the EU numbering system, an IgG1 CH3, and a second scFv. In one embodiment, the first scFv specifically binds to human 4-1BB and the second scFv specifically binds to human OX40. In one embodiment, the first scFv specifically binds to human OX40 and the second scFv specifically binds to human OX40.

In certain embodiments, the immunoglobulin constant region comprises a human IgG1 CH3 domain.

In certain embodiments, the immunoglobulin constant region comprises amino acids 16-231 of SEQ ID NO:111, 112, or 114 or amino acids 16-230 of SEQ ID NO: 113 or 115. In certain embodiments, the immunoglobulin constant region comprises amino acids 16-230 of SEQ ID NO: 115.

Additional immunoglobulin constant regions that can be present in the 4-1BB×OX40 antibodies provided herein are discussed in more detail below.

In some embodiments, the hinge and the immunoglobulin constant region comprise the amino acid sequence of any one of SEQ ID NOs:111-115. In some embodiments, the hinge and the immunoglobulin constant region comprise the amino acid sequence of SEQ ID NO:115.

In some embodiments, a 4-1BB×OX40 bispecific antibody does not comprise an immunoglobulin constant region. In some embodiments, a 4-1BB×OX40 bispecific antibody does not comprise a hinge and does not comprise an immunoglobulin constant region.

As provided herein, an antibody or polypeptide comprising any of the CDR, VH, VL, scFv, hinge, and/or immunoglobulin constant region provided herein may further comprise a linker. A linker can be located, for example between an immunoglobulin constant region and a C-terminus binding domain. For instance, a linker can be located between an immunoglobulin constant region and a C-terminus 4-1BB binding domain. A linker can also be located between an immunoglobulin constant region and a C-terminus OX40-binding domain In some embodiments, a polypeptide comprises, in order from amino-terminus to carboxyl-terminus, an immunoglobulin constant region, a linker, and an antigen-binding domain.

In some embodiments, the linker (e.g., between an immunoglobulin constant region and an antigen-binding domain) comprises 3-30 amino acids, 3-15 amino acids, or about 3-10 amino acids. In some embodiments, the linker (e.g., between an immunoglobulin constant region and an antigen-binding domain) comprises 5-30 amino acids, 5-15 amino acids, or about 5-10 amino acids. In some embodiments, the linker (e.g., between an immunoglobulin constant region and an antigen-binding domain) comprises the amino acid sequence $(Gly_4Ser)_n$, wherein n=1-5 (SEQ ID NO:117), optionally wherein n=1. In some embodiments, the linker (e.g., between an immunoglobulin constant region and an antigen-binding domain) comprises the amino acid sequence GGGSPS (SEQ ID NO: 118). In some embodiments, the linker (e.g., between an immunoglobulin constant region and an antigen-binding domain) comprises the amino acid sequence of SEQ ID NO: 109 or 110.

Non-limiting examples of linkers are provided in Tables K and L below.

TABLE K

Exemplary hinges and linkers

| Name | Amino Acid Sequence | SEQ ID NO |
|---|---|---|
| sss(s)-hIgG1 hinge | EPKSSDKTHTSPPSS | 150 |
| csc(s)-hIgG1 hinge | EPKSCDKTHTSPPCS | 151 |
| ssc(s)-hIgG1 hinge | EPKSSDKTHTSPPCS | 152 |
| scc(s)-hIgG1 hinge | EPKSSDKTHTCPPCS | 153 |
| css(s)-hIgG1 hinge | EPKSCDKTHTSPPSS | 154 |
| scs(s)-hIgG1 hinge | EPKSSDKTHTCPPSS | 155 |

TABLE K-continued

| Exemplary hinges and linkers | | |
|---|---|---|
| Name | Amino Acid Sequence | SEQ ID NO |
| ccc(s)-hIgG1 hinge | EPKSCDKTHTSPPCS | 156 |
| ccc(p)-hIgG1 hinge | EPKSCDKTHTSPPCP | 157 |
| sss(p)-hIgG1 hinge | EPKSSDKTHTSPPSP | 158 |
| csc(p)-hIgG1 hinge | EPKSCDKTHTSPPCP | 159 |
| ssc(p)-hIgG1 hinge | EPKSSDKTHTSPPCP | 160 |
| scc(p)-hIgG1 hinge | EPKSSDKTHTCPPCP | 161 |
| css(p)-hIgG1 hinge | EPKSCDKTHTSPPSP | 162 |
| scs(p)-hIgG1 hinge | EPKSSDKTHTCPPSP | 163 |
| Scppcp | SCPPCP | 164 |
| STD1 | NYGGGGSGGGGSGGGGSGNS | 165 |
| STD2 | NYGGGGSGGGGSGGGGSGNYGGGGSGGGGSG GGGSGNS | 166 |
| H1 | NS | 167 |
| H2 | GGGGSGNS | 168 |
| H3 | NYGGGGSGNS | 169 |
| H4 | GGGGSGGGGSGNS | 170 |
| H5 | NYGGGGSGGGGSGNS | 171 |
| H6 | GGGGSGGGGSGGGGSGNS | 172 |
| H7 | GCPPCPNS | 173 |
| $(G_4S)_3$ | GGGGSGGGGSGGGGS | 174 |
| H105 | SGGGGSGGGGSGGGGS | 175 |
| $(G_4S)_4$ | GGGGSGGGGSGGGGSGGGGS | 176 |
| H75 (NKG2A quadruple mutant) | QRHNNSSLNTGTQMAGHSPNS | 177 |
| H83 (NKG2A derived) | SSLNTGTQMAGHSPNS | 178 |
| H106 (NKG2A derived) | QRHNNSSLNTGTQMAGHS | 179 |
| H81 (NKG2D derived) | EVQIPLTESYSPNS | 180 |
| H91 (NKG2D derived) | NSLANQEVQIPLTESYSPNS | 181 |
| H94 | SGGGGSGGGGSGGGGSPNS | 182 |
| H111 | SGGGGSGGGGSGGGGSPGS | 183 |
| H114 | GGGGSGGGGSGGGGSPS | 184 |

In some embodiments, a 4-1BB×OX40 antibody comprises a polypeptide comprising in order from amino-terminus to carboxyl-terminus (i) a VH comprising the amino acids sequence of SEQ ID NO: 17, (ii) a linker (e.g., glycine-serine linker), (iii) a VL comprising the amino acid sequence of SEQ ID NO: 18, (iv) an IgG1 hinge comprising a C220S substitution according to EU numbering, (v) an immunoglobulin constant region comprising a CH2 domain comprising the following substitutions: E233P, L234A, L234V, L235A, G237A, and K322A, and a deletion of G236, according to the EU numbering system) and a wild-type CH3 domain, (vi) a VL comprising the amino acid sequence of SEQ ID NO:28, (vii) a linker (e.g., glycine-serine linker), and (viii) a VH comprising the amino acid sequence of SEQ ID NO:29. In some embodiments, a 4-1BB×OX40 antibody comprises a dimer of such a polypeptide.

glycine-serine linker), (iii) a VL comprising the amino acid sequence of SEQ ID NO:18, (iv) an IgG1 hinge comprising a C220S substitution according to EU numbering, (v) an immunoglobulin constant region comprising a CH2 domain comprising the following substitutions: E233P, L234A, L234V, L235A, G237A, and K322A, and a deletion of G236, according to the EU numbering system) and a wild-type CH3 domain, (vi) a VL comprising the amino acid sequence of SEQ ID NO:35, (vii) a linker (e.g., glycine-serine linker), and (viii) a VH comprising the amino acid sequence of SEQ ID NO:29. In some embodiments, a 4-1BB×OX40 antibody comprises a dimer of such a polypeptide.

In some embodiments, a 4-1BB×OX40 bispecific antibody comprises the amino acid sequence of any one of SEQ ID NOs:78-100.

TABLE L

| FXX Antibody SEQ ID NOs | | | | | | | |
|---|---|---|---|---|---|---|---|
| Antibody | Full Construct | 4-1BB VH | 4-1BB VL | 4-1BB scFv | OX40 VH | OX40 VL | OX40 scFv |
| FXX01066 | 78 | 17 | 18 | 58 | 29 | 28 | 59 |
| FXX01099 | 79 | 17 | 18 | 58 | 29 | 30 | 60 |
| FXX01101 | 80 | 17 | 18 | 58 | 31 | 28 | 61 |
| FXX01102 | 81 | 17 | 18 | 58 | 31 | 30 | 62 |
| FXX01104 | 82 | 32 | 18 | 63 | 29 | 28 | 59 |
| FXX01105 | 83 | 32 | 18 | 63 | 29 | 30 | 60 |
| FXX01107 | 84 | 32 | 18 | 63 | 31 | 28 | 61 |
| FXX01108 | 85 | 32 | 18 | 63 | 31 | 30 | 62 |
| FXX01047 | 86 | 23 | 24 | 44 | 29 | 28 | 59 |
| FXX01055 | 87 | 23 | 24 | 44 | 33 | 28 | 64 |
| FXX01079 | 88 | 17 | 18 | 58 | 33 | 28 | 64 |
| FXX01110 | 89 | 17 | 18 | 58 | 29 | 34 | 65 |
| FXX01111 | 90 | 17 | 18 | 58 | 29 | 35 | 66 |
| FXX01112 | 91 | 17 | 18 | 58 | 29 | 36 | 67 |
| FXX01113 | 92 | 17 | 18 | 58 | 29 | 37 | 68 |
| FXX01114 | 93 | 17 | 18 | 58 | 31 | 34 | 69 |
| FXX01115 | 94 | 17 | 18 | 58 | 31 | 35 | 70 |
| FXX01116 | 95 | 17 | 18 | 58 | 31 | 36 | 71 |
| FXX01117 | 96 | 17 | 18 | 58 | 31 | 37 | 72 |
| FXX01118 | 97 | 17 | 18 | 58 | 31 | 38 | 73 |
| FXX01119 | 98 | 17 | 18 | 58 | 31 | 39 | 74 |
| FXX01120 | 99 | 17 | 18 | 58 | 31 | 40 | 75 |
| FXX01121 | 100 | 17 | 18 | 58 | 31 | 41 | 76 |
| FXX01028 | 144 | 19 | 20 | 145 | 25 | 26 | 146 |

In some embodiments, a 4-1BB×OX40 antibody comprises a polypeptide comprising in order from amino-terminus to carboxyl-terminus (i) a VH comprising the amino acids sequence of SEQ ID NO: 17, (ii) a linker (e.g., glycine-serine linker), (iii) a VL comprising the amino acid sequence of SEQ ID NO:18, (iv) an IgG1 hinge comprising a C220S substitution according to EU numbering, (v) an immunoglobulin constant region comprising a CH2 domain comprising the following substitutions: E233P, L234A, L234V, L235A, G237A, and K322A, and a deletion of G236, according to the EU numbering system) and a wild-type CH3 domain, (vi) a VL comprising the amino acid sequence of SEQ ID NO:30, (vii) a linker (e.g., glycine-serine linker), and (viii) a VH comprising the amino acid sequence of SEQ ID NO:31. In some embodiments, a 4-1BB×OX40 antibody comprises a dimer of such a polypeptide.

In some embodiments, a 4-1BB×OX40 antibody comprises a polypeptide comprising in order from amino-terminus to carboxyl-terminus (i) a VH comprising the amino acids sequence of SEQ ID NO: 17, (ii) a linker (e.g., In some embodiments, a 4-1BB1×OX40 bispecific antibody comprises the amino acid sequence of SEQ ID NO:78. In some embodiments, a 4-1BB×OX40 bispecific antibody comprises the amino acid sequence of 81. In some embodiments, a 4-1BB×OX40 bispecific antibody comprises the amino acid sequence of SEQ ID NO:90. In some embodiments, a 4-1BB×OX40 bispecific antibody consists essentially of the amino acid sequence of SEQ ID NO:78. In some embodiments, a 4-1BB×OX40 bispecific antibody consists essentially of the amino acid sequence of 81. In some embodiments, a 4-1BB×OX40 bispecific antibody consists essentially of the amino acid sequence of SEQ ID NO:90. In some embodiments, a 4-1BB×OX40 bispecific antibody consists of the amino acid sequence of SEQ ID NO:78. In some embodiments, a 4-1BB×OX40 bispecific antibody consists of the amino acid sequence of 81. In some embodiments, a 4-1BB×OX40 bispecific antibody consists of the amino acid sequence of SEQ ID NO:90.

In some embodiments, a 4-1BB×OX40 bispecific antibody is a homodimer capable of binding to human 4-1BB and human OX40 and comprising two polypeptides, wherein each polypeptide comprises an amino acid sequence selected from the group consisting of SEQ ID NOs:78-100.

In some embodiments, a 4-1BB×OX40 bispecific antibody is a homodimer capable of binding to human 4-1BB and human OX40 and comprising two identical polypeptides, with each polypeptide comprising an amino acid sequence that is at least 75%, 80%, 85%, 90%, 95%, 96%, 97%, 98%, or 99% or more to the amino acid sequence of SEQ ID NO:78. In some embodiments, a 4-1BB×OX40 bispecific antibody is a homodimer comprising two polypeptides, wherein each polypeptide comprises the amino acid sequence of SEQ ID NO:78. In some embodiments, a bispecific antibody that binds to human 4-1BB and human OX40 is a dimer consisting essentially of or consisting of two polypeptides, wherein each polypeptide comprises the amino acid sequence of SEQ ID NO:78.

In some embodiments, a 4-1BB×OX40 bispecific antibody is a homodimer capable of binding to human 4-1BB and human OX40 and comprising two identical polypeptides, with each polypeptide comprising an amino acid sequence that is at least 75%, 80%, 85%, 90%, 95%, 96%, 97%, 98%, or 99% or more to the amino acid sequence of SEQ ID NO:81.

In some embodiments, a 4-1BB×OX40 bispecific antibody is a homodimer capable of binding to human 4-1BB and human OX40 and comprising two polypeptides, wherein each polypeptide comprises the amino acid sequence of SEQ ID NO:81. In some embodiments, a bispecific antibody that binds to human 4-1BB and human OX40 is a dimer consisting essentially of or consisting of two polypeptides, wherein each polypeptide comprises the amino acid sequence of SEQ ID NO:81.

In some embodiments, a 4-1BB×OX40 bispecific antibody is a homodimer capable of binding to human 4-1BB and human OX40 and comprising two identical polypeptides, with each polypeptide comprising an amino acid sequence that is at least 75%, 80%, 85%, 90%, 95%, 96%, 97%, 98%, or 99% or more to the amino acid sequence of SEQ ID NO:90. In some embodiments, a 4-1BB×OX40 bispecific antibody is a homodimer capable of binding human 4-1BB and human OX40 and comprising two polypeptides, wherein each polypeptide comprises the amino acid sequence of SEQ ID NO:90. In some embodiments, a bispecific antibody that binds to human 4-1BB and human OX40 is a dimer consisting essentially of or consisting of two polypeptides, wherein each polypeptide comprises the amino acid sequence of SEQ ID NO:90.

The bispecific antibodies of the invention are capable of lysing tumor cells. By "capable" it is meant that the bispecific antibodies are able to perform an activity under the appropriate laboratory conditions. Tumor lysis can be determined in vitro and in vivo using methods known in the art. For instance, tumor lysis can be assessed by co-incubating PBMC (or purified T cells) and tumor cells with an anti-CD3×anti-tumor associated antigen (TAA) bispecific molecule (CD3×TAA engager). The CD3×TAA engager is a polyclonal stimulator of T cells, providing signal to the T cells, and resulting in the upregulation of 4-1BB and OX40. In this type of experiment, the CD3×TAA engager is added to the cultures at a suboptimal concentration, while addition of the anti-4-1BB and anti-OX40 bispecific antibodies (e.g., the antibody comprising SEQ ID NO:81) to the cultures further increases the target cell lysis induced by the CD3×TAA engager, in a dose-dependent manner. In a similar manner, lysis of target cells can also be assessed using a chromium-51 release assay.

Tumor lysis can also be assessed using a syngeneic tumor model using host mice expressing human 4-1BB and human OX40 (e.g., mice expressing human 4-1BB and human OX40 under the control of the corresponding endogenous murine promoter genes, for example female B-hOX40/h4-1BB mice (C57BL/6-Tnfrsf4$^{tm1(TNFRSF4)}$CD137$^{tm1(CD137)}$/Bcgen) from Biocytogen, China). For example, the mice can be inoculated with a syngeneic tumor line such as MB49 or MC38 tumor cells. Once tumor growth is visible, for example around day 6, an anti-4-1BB and anti-OX40 bispecific antibody or a control antibody can be administered (e.g., intraperitoneally). Decreased tumor sizes in the mice treated with the anti-4-1BB and anti-OX40 bispecific antibody as compared to the mice treated with the control antibody indicate that the bispecific antibody is capable of lysing tumor cells. Tumor lysis can also be assessed in xenograft models in immunodeficient mice transplanted with human T cells, dosed in combination with a CD3 bispecific engager to prime the T cells.

In one embodiment, the antibodies of the invention are thermostable. The antibodies of the invention exhibit improved stability over many prior art antibodies (e.g., those antibodies disclosed in US2018/0118841 and US2015/0307620). Tm is a measurement of thermostability and can be determined by methods known in the art (for instance, according to any of the methods described in the Examples). In one embodiment, the bispecific antibodies of the invention have a Tm of about 63, 64, 65, 66, 67, 68 or 69. For instance, the invention includes a bispecific antibody wherein the human 4-1BB binding domain comprises a VH comprising an amino acid sequence at least 85%, 90%, 95%, or 99% identical to an amino acid sequence SEQ ID NO:17 and a VL comprising an amino acid sequence at least 85%, 90%, 95%, or 99% identical to an amino acid sequence of SEQ ID NO: 18 and wherein the human OX40 binding domain comprises a VH comprising an amino acid sequence at least 85%, 90%, 95%, or 99% identical to an amino acid sequence SEQ ID NO:31 and a VL comprising an amino acid sequence at least 85%, 90%, 95%, or 99% identical to an amino acid sequence SEQ ID NO:30, wherein the bispecific antibody has a Tm of 64 to 68.

In another embodiment, the antibody of the invention has a theoretical pI of less than 7.5, 7.6, 7.7, 7.8, 7.9 or 8. Theoretical pI can be determined by methods known in the art (for instance, according to any methods described in the Examples). In one embodiment, the invention includes a bispecific antibody wherein the human 4-1BB binding domain comprises a VH comprising an amino acid sequence at least 85%, 90%, 95%, or 99% identical to an amino acid sequence SEQ ID NO:17 and a VL comprising an amino acid sequence at least 85%, 90%, 95%, or 99% identical to an amino acid sequence of SEQ ID NO:18 and wherein the human OX40 binding domain comprises a VH comprising an amino acid sequence at least 85%, 90%, 95%, or 99% identical to an amino acid sequence SEQ ID NO:31 and a VL comprising an amino acid sequence at least 85%, 90%, 95%, or 99% identical to an amino acid sequence SEQ ID NO:30, wherein the bispecific antibody has a pI of less than 7.8.

E. 4-1BB and OX40 Monospecific Antibodies

Provided herein are monospecific antibodies that bind to either human 4-1BB or to human OX40. An anti-4-1BB antibody provided herein can comprise one or more of any of the 4-1BB binding domains described herein. An anti-OX40 antibody provided herein can comprise one or more of any of the anti-OX40 binding domain described herein.

In some embodiments, an anti-4-1BB antibody or an anti-OX40 antibody provided herein is an IgG antibody. In some embodiments, an anti-4-1BB antibody or an anti-OX40 antibody provided herein is an $IgG_1$ antibody.

In some embodiments, an anti-4-1BB antibody comprises the six CDRs of SEQ ID NOs:5-10, the six CDRs of SEQ ID NOs:5, 119, 7, 120, 121, and 122, or a combination of 4-1BB binding VH and VL sequences provided herein and a heavy chain constant region. In some embodiments, an anti-4-1BB antibody comprises the six CDRs of SEQ ID NOs:5-10, the six CDRs of SEQ ID NOs:5, 119, 7, 120, 121, and 122, or a combination of 4-1BB binding VH and VL sequences provided herein and a light chain constant region. In some embodiments, an anti-4-1BB antibody comprises the six CDRs of SEQ ID NOs:5-10, the six CDRs of SEQ ID NOs:5, 119, 7, 120, 121, and 122, or a combination of 4-1BB binding VH and VL sequences provided herein and, a heavy chain constant region, and a light chain constant region.

In some embodiments, an anti-OX40 antibody comprises the six CDRs of SEQ ID NOs:11-16, or a combination of OX40 binding VH and VL sequences provided herein and a heavy chain constant region. In some embodiments, an anti-OX40 antibody comprises the six CDRs of SEQ ID NOs:11-16, or a combination of OX40 binding VH and VL sequences provided herein and a light chain constant region. In some embodiments, an anti-OX40 antibody comprises the six CDRs of SEQ ID NOs:11-16, or a combination of OX40 binding VH and VL sequences provided herein and, a heavy chain constant region, and a light chain constant region.

The constant region of an anti-4-1BB antibody or an OX40 antibody can be any constant region discussed herein. Constant regions that can be present in these antibodies are discussed in more detail below.

In some embodiments, an anti-4-1BB antibody or an anti-OX40 antibody is a Fab, Fab', $F(ab')_2$, scFv, disulfide linked Fv, or scFv-Fc. In some embodiments, an anti-4-1BB antibody or an anti-OX40 antibody comprises a Fab, Fab', $F(ab')_2$, scFv, disulfide linked Fv, or scFv-Fc. For instance, the invention includes an anti-4-1BB antibody or an anti-OX40 antibody in the SMIP format (i.e., scFv-Fc) as disclosed in U.S. Pat. No. 9,005,612. A SMIP antibody may comprise, from amino-terminus to carboxyl-terminus, an scFv and a modified constant domain comprising an immunoglobulin hinge and a CH2/CH3 region. The invention also includes an anti-4-1BB antibody or an anti-OX40 antibody in the PIMS format as disclosed in published US patent application 2009/0148447. A PIMS antibody may comprise, from amino-terminus to carboxyl-terminus, a modified constant domain comprising an immunoglobulin hinge and CH2/CH3 region, and an scFv.

An anti-4-1BB antibody can be monovalent for 4-1BB (i.e., contain one 4-1BB binding domain), bivalent for 4-1BB (i.e., contain two 4-1BB binding domains), or can have three or more 4-1BB binding domains.

An anti-OX40 antibody can be monovalent for OX40 (i.e., contain one OX40 binding domain), bivalent for OX40 (i.e., contain two OX40 binding domains), or can have three or more OX40 binding domains.

F. Constant Regions

As discussed above antibodies provided herein, including monospecific antibodies that bind to 4-1BB or OX40 as well as 4-1BB×OX40 bispecific antibodies, can comprise immunoglobulin constant regions. In certain embodiments, the immunoglobulin constant region does not interact with Fc gamma receptors.

In a specific embodiment, an antibody described herein, which immunospecifically binds to 4-1BB and/or OX40 comprises a VH domain and a VL domain comprising any amino acid sequence described herein, and wherein the constant regions comprise the amino acid sequences of the constant regions of an IgG, IgE, IgM, IgD, IgA, or IgY immunoglobulin molecule, or a human IgG, IgE, IgM, IgD, IgA, or IgY immunoglobulin molecule. In another specific embodiment, an antibody described herein, which immunospecifically binds to 4-1BB and/or OX40 comprises a VH domain and a VL domain comprising any amino acid sequence described herein, and wherein the constant regions comprise the amino acid sequences of the constant regions of an IgG, IgE, IgM, IgD, IgA, or IgY immunoglobulin molecule, any class (e.g., IgG1, IgG2, IgG3, IgG4, IgA1, and IgA2), or any subclass (e.g., IgG2a and IgG2b) of immunoglobulin molecule. In a particular embodiment, the constant regions comprise the amino acid sequences of the constant regions of a human IgG, IgE, IgM, IgD, IgA, or IgY immunoglobulin molecule, any class (e.g., IgG1, IgG2, IgG3, IgG4, IgA1, and IgA2), or any subclass (e.g., IgG2a and IgG2b) of immunoglobulin molecule In one embodiment, the heavy chain constant region is a human $IgG_1$ heavy chain constant region, and the light chain constant region is a human $IgG_\kappa$ light chain constant region.

In some embodiments, the constant region comprises one, two, three or more amino acid substitutions to prevent binding to FcγR1, FcγRIIa, FcγRIIb, FcγRIIa, and FcγRIIIb.

In certain embodiments, the constant region comprises one, two, three or more amino acid substitutions to prevent or reduce Fc-mediated T-cell activation.

In some embodiments, the constant region comprises one, two, three or more amino acid substitutions to prevent or reduce CDC and/or ADCC activity.

In some embodiments, one, two, or more mutations (e.g., amino acid substitutions) are introduced into the Fc region of an antibody or antigen-binding fragment thereof described herein (e.g., CH2 domain (residues 231-340 of human IgG1) and/or CH3 domain (residues 341-447 of human IgG1) and/or the hinge region, with numbering according to the Kabat numbering system (e.g., the EU index in Kabat)) to alter one or more functional properties of the antibody or antigen-binding fragment thereof, such as serum half-life, complement fixation, Fc receptor binding, and/or antigen-dependent cellular cytotoxicity.

In certain embodiments, one, two, or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425. The number of cysteine residues in the hinge region of the CH1 domain may be altered to, e.g., facilitate assembly of the light and heavy chains, or to alter (e.g., increase or decrease) the stability of the antibody or antigen-binding fragment thereof.

In some embodiments, one, two, or more mutations (e.g., amino acid substitutions) are introduced into the Fc region of an antibody or antigen-binding fragment thereof described herein (e.g., CH2 domain (residues 231-340 of human IgG1) and/or CH3 domain (residues 341-447 of human IgG1) and/or the hinge region, with numbering according to the Kabat numbering system (e.g., the EU index in Kabat)) to increase or decrease the affinity of the antibody or antigen-binding fragment thereof for an Fc receptor (e.g., an activated Fc receptor) on the surface of an effector cell. Mutations in the Fc region that decrease or increase affinity for an Fc receptor and techniques for introducing such mutations into the Fc receptor or fragment thereof are known to one of skill in the art. Examples of mutations in the Fc receptor that can be made to alter the affinity of the antibody or antigen-binding fragment thereof for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, which are incorporated herein by reference.

In a specific embodiment, one, two, or more amino acid mutations (i.e., substitutions, insertions or deletions) are introduced into an IgG constant domain, or FcRn-binding fragment thereof (preferably an Fc or hinge-Fc domain fragment) to alter (e.g., decrease or increase) half-life of the antibody or antigen-binding fragment thereof in vivo. See, e.g., International Publication Nos. WO 02/060919; WO 98/23289; and WO 97/34631; and U.S. Pat. Nos. 5,869,046, 6,121,022, 6,277,375 and 6,165,745 for examples of mutations that will alter (e.g., decrease or increase) the half-life of an antibody or antigen-binding fragment thereof in vivo. In some embodiments, one, two or more amino acid mutations (i.e., substitutions, insertions, or deletions) are introduced into an IgG constant domain, or FcRn-binding fragment thereof (preferably an Fc or hinge-Fc domain fragment) to decrease the half-life of the antibody or antigen-binding fragment thereof in vivo. In other embodiments, one, two or more amino acid mutations (i.e., substitutions, insertions or deletions) are introduced into an IgG constant domain, or FcRn-binding fragment thereof (preferably an Fc or hinge-Fc domain fragment) to increase the half-life of the antibody or antigen-binding fragment thereof in vivo. In a specific embodiment, the antibodies or antigen-binding fragments thereof may have one or more amino acid mutations (e.g., substitutions) in the second constant (CH2) domain (residues 231-340 of human IgG1) and/or the third constant (CH3) domain (residues 341-447 of human IgG1), with numbering according to the EU index in Kabat (Kabat E A et al., (1991) supra). In a specific embodiment, the constant region of the IgG1 comprises a methionine (M) to tyrosine (Y) substitution in position 252, a serine (S) to threonine (T) substitution in position 254, and a threonine (T) to glutamic acid (E) substitution in position 256, numbered according to the EU index as in Kabat. See U.S. Pat. No. 7,658,921, which is incorporated herein by reference. This type of mutant IgG, referred to as "YTE mutant" has been shown to display fourfold increased half-life as compared to wild-type versions of the same antibody (see Dall'Acqua W F et al., (2006) J Biol Chem 281: 23514-24). In certain embodiments, an antibody or antigen-binding fragment thereof comprises an IgG constant domain comprising one, two, three or more amino acid substitutions of amino acid residues at positions 251-257, 285-290, 308-314, 385-389, and 428-436, numbered according to the EU index as in Kabat.

In a further embodiment, one, two, or more amino acid substitutions are introduced into an IgG constant domain Fc region to alter the effector function(s) of the antibody or antigen-binding fragment thereof. For example, one or more amino acids selected from amino acid residues 234, 235, 236, 237, 297, 318, 320 and 322, numbered according to the EU index as in Kabat, can be replaced with a different amino acid residue such that the antibody or antigen-binding fragment thereof has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260. In some embodiments, the deletion or inactivation (through point mutations or other means) of a constant region domain may reduce Fc receptor binding of the circulating antibody or antigen-binding fragment thereof thereby increasing tumor localization. See, e.g., U.S. Pat. Nos. 5,585,097 and 8,591,886 for a description of mutations that delete or inactivate the constant domain and thereby increase tumor localization. In certain embodiments, one or more amino acid substitutions can be introduced into the Fc region to remove potential glycosylation sites on Fc region, which may reduce Fc receptor binding (see, e.g., Shields R L et al., (2001) J Biol Chem 276: 6591-604).

In certain embodiments, one or more amino acids selected from amino acid residues 329, 331, and 322 in the constant region, numbered according to the EU index as in Kabat, can be replaced with a different amino acid residue such that the antibody or antigen-binding fragment thereof has altered C1q binding and/or reduced or abolished complement dependent cytotoxicity (CDC). This approach is described in further detail in U.S. Pat. No. 6,194,551 (Idusogie et al). In some embodiments, one or more amino acid residues within amino acid positions 231 to 238 in the N-terminal region of the CH2 domain are altered to thereby alter the ability of the antibody to fix complement. This approach is described further in International Publication No. WO 94/29351. In certain embodiments, the Fc region is modified to increase the ability of the antibody or antigen-binding fragment thereof to mediate antibody dependent cellular cytotoxicity (ADCC) and/or to increase the affinity of the antibody or antigen-binding fragment thereof for an Fcγ receptor by mutating one or more amino acids (e.g., introducing amino acid substitutions) at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 328, 329, 330, 331, 333, 334, 335, 337, 338, 340, 360, 373, 376, 378, 382, 388, 389, 398, 414, 416, 419, 430, 434, 435, 437, 438, or 439, numbered according to the EU index as in Kabat. This approach is described further in International Publication No. WO 00/42072.

In certain embodiments, an antibody or antigen-binding fragment thereof described herein comprises the constant domain of an IgG1 with a mutation (e.g., substitution) at position 267, 328, or a combination thereof, numbered according to the EU index as in Kabat. In certain embodiments, an antibody or antigen-binding fragment thereof described herein comprises the constant domain of an IgG1 with a mutation (e.g., substitution) selected from the group consisting of S267E, L328F, and a combination thereof. In certain embodiments, an antibody or antigen-binding fragment thereof described herein comprises the constant domain of an IgG1 with a S267E/L328F mutation (e.g., substitution). In certain embodiments, an antibody or antigen-binding fragment thereof described herein comprising the constant domain of an IgG1 with a S267E/L328F mutation (e.g., substitution) has an increased binding affinity for FcγRIIA, FcγRIIB, or FcγRIIA and FcγRIIB.

In certain embodiments, any of the constant region mutations or modifications described herein can be introduced into one or both heavy chain constant regions of an antibody or antigen-binding fragment thereof described herein having two heavy chain constant regions.

III. Antibody Production

Antibodies that immunospecifically bind to human 4-1BB and/or human OX40 can be produced by any method known in the art for the synthesis of antibodies, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, NY; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press.

Bispecific antibodies as provided herein can be prepared by expressing a polynucleotide in a host cell, wherein the polynucleotide encodes a polypeptide comprising, in order from amino-terminus to carboxyl-terminus, a first scFv, a hinge region, an immunoglobulin constant region, and a second scFv, wherein (a) the first scFv comprises a human 4-1BB antigen-binding domain, and the second scFv comprises a human OX40 antigen-binding domain or (b) the first scFv comprises a human OX40 antigen-binding domain and the second scFv comprises a human 4-1BB antigen-binding domain. The polypeptide can be expressed in the host cell as a dimer.

Bispecific antibodies as provided herein can be prepared by chemically linking two different monoclonal antibodies or by fusing two hybridoma cell lines to produce a hybrid-hybridoma. Bispecific, bivalent antibodies, and methods of making them, are described, for instance in U.S. Pat. Nos. 5,731,168, 5,807,706, 5,821,333, and U.S. Appl. Publ. Nos. 2003/020734 and 2002/0155537; each of which is herein incorporated by reference in its entirety. Bispecific tetravalent antibodies, and methods of making them are described, for instance, in Int. Appl. Publ. Nos. WO02/096948 and WO00/44788, the disclosures of both of which are herein incorporated by reference in its entirety. See generally, Int. Appl. Publ. Nos. WO93/17715, WO92/08802, WO91/00360, and WO92/05793; Tutt et al., J. Immunol. 147:60-69 (1991); U.S. Pat. Nos. 4,474,893; 4,714,681; 4,925,648; 5,573,920; and 5,601,819; and Kostelny et al., J. Immunol. 148:1547-1553 (1992); each of which is herein incorporated by reference in its entirety.

A bispecific antibody as described herein can be generated according to the DuoBody technology platform (Genmab A/S) as described, e.g., in International Publication Nos. WO 2011/131746, WO 2011/147986, WO 2008/119353, and WO 2013/060867, and in Labrijn A F et al., (2013) PNAS 110(13): 5145-5150. The DuoBody technology can be used to combine one half of a first monospecific antibody containing two heavy and two light chains with one half of a second monospecific antibody containing two heavy and two light chains. The resultant heterodimer contains one heavy chain and one light chain from the first antibody paired with one heavy chain and one light chain from the second antibody. When both of the monospecific antibodies recognize different epitopes on different antigens, the resultant heterodimer is a bispecific antibody.

The DuoBody technology requires that each of the monospecific antibodies includes a heavy chain constant region with a single point mutation in the CH3 domain. The point mutations allow for a stronger interaction between the CH3 domains in the resultant bispecific antibody than between the CH3 domains in either of the monospecific antibodies. The single point mutation in each monospecific antibody is at residue 366, 368, 370, 399, 405, 407, or 409, numbered according to the EU numbering system, in the CH3 domain of the heavy chain constant region, as described, e.g., in International Publication No. WO 2011/131746. Moreover, the single point mutation is located at a different residue in one monospecific antibody as compared to the other monospecific antibody. For example, one monospecific antibody can comprise the mutation F405L (i.e., a mutation from phenylalanine to leucine at residue 405), while the other monospecific antibody can comprise the mutation K409R (i.e., a mutation from lysine to arginine at residue 409), numbered according to the EU numbering system. The heavy chain constant regions of the monospecific antibodies can be an IgG1, IgG2, IgG3, or IgG4 isotype (e.g., a human IgG1 isotype), and a bispecific antibody produced by the DuoBody technology can retain Fc-mediated effector functions.

Another method for generating bispecific antibodies has been termed the "knobs-into-holes" strategy (see, e.g., Intl. Publ. WO2006/028936). The mispairing of Ig heavy chains is reduced in this technology by mutating selected amino acids forming the interface of the CH3 domains in IgG. At positions within the CH3 domain at which the two heavy chains interact directly, an amino acid with a small side chain (hole) is introduced into the sequence of one heavy chain and an amino acid with a large side chain (knob) into the counterpart interacting residue location on the other heavy chain. In some embodiments, compositions of the invention have immunoglobulin chains in which the CH3 domains have been modified by mutating selected amino acids that interact at the interface between two polypeptides so as to preferentially form a bispecific antibody. The bispecific antibodies can be composed of immunoglobulin chains of the same subclass (e.g., IgG1 or IgG3) or different subclasses (e.g., IgG1 and IgG3, or IgG3 and IgG4).

In one embodiment, a bispecific antibody that binds to 4-1BB and OX40 comprises a T366W mutation in the "knobs chain" and T366S, L368A, Y407V mutations in the "hole chain," and optionally an additional interchain disulfide bridge between the CH3 domains by, e.g., introducing a Y349C mutation into the "knobs chain" and a E356C mutation or a S354C mutation into the "hole chain;" R409D, K370E mutations in the "knobs chain" and D399K, E357K mutations in the "hole chain;" R409D, K370E mutations in the "knobs chain" and D399K, E357K mutations in the "hole chain;" a T366W mutation in the "knobs chain" and T366S, L368A, Y407V mutations in the "hole chain;" R409D, K370E mutations in the "knobs chain" and D399K, E357K mutations in the "hole chain;" Y349C, T366W mutations in one of the chains and E356C, T366S, L368A, Y407V mutations in the counterpart chain; Y349C, T366W mutations in one chain and S354C, T366S, L368A, Y407V mutations in the counterpart chain; Y349C, T366W mutations in one chain and S354C, T366S, L368A, Y407V mutations in the counterpart chain; and Y349C, T366W mutations in one chain and S354C, T366S, L368A, Y407V mutations in the counterpart chain (numbering according to the EU numbering system).

Bispecific antibodies that bind to 4-1BB and OX40 can, in some instances contain, IgG4 and IgG1, IgG4 and IgG2, IgG4 and IgG2, IgG4 and IgG3, or IgG1 and IgG3 chain heterodimers. Such heterodimeric heavy chain antibodies, can routinely be engineered by, for example, modifying selected amino acids forming the interface of the CH3 domains in human IgG4 and the IgG1 or IgG3 so as to favor heterodimeric heavy chain formation.

Bispecific antibodies described herein can be generated by any technique known to those of skill in the art. For example, $F(ab')_2$ fragments described herein can be produced by proteolytic cleavage of immunoglobulin molecules, using enzymes such as pepsin.

In a certain aspect, provided herein is a method of making an antibody which immunospecifically binds to human 4-1BB and/or human OX40 comprising culturing a cell or cells described herein. In a certain aspect, provided herein is a method of making an antibody that immunospecifically binds to human 4-1BB and/or human OX40 comprising expressing (e.g., recombinantly expressing) the antibody using a cell or host cell described herein (e.g., a cell or a host cell comprising polynucleotides encoding an antibody described herein). In a particular embodiment, the cell is an isolated cell. In a particular embodiment, the exogenous polynucleotides have been introduced into the cell. In a particular embodiment, the method further comprises the step of purifying the antibody from the cell or host cell.

Monoclonal antibodies can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981). The term “monoclonal antibody” as used herein is not limited to antibodies produced through hybridoma technology. For example, monoclonal antibodies can be produced recombinantly from host cells exogenously expressing an antibody described herein. Monoclonal antibodies described herein can, for example, be made by the hybridoma method as described in Kohler G & Milstein C (1975) Nature 256: 495 or can, e.g., be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel F M et al., supra).

Further, the antibodies described herein can also be generated using various phage display methods known in the art. In phage display methods, proteins are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in *E. coli* and the *E. coli* is infected with helper phage. Phage used in these methods are typically filamentous phage including fd and M13, and the VH and VL domains are usually recombinantly fused to either the phage gene III or gene VIII. Phage expressing an antibody that binds to a particular antigen can be selected or identified with antigen, e.g., using labeled antigen or antigen bound or captured to a solid surface or bead. Examples of phage display methods that can be used to make the antibodies described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/1 1236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, and 5,969,108.

As described in the above references, after phage selection, the antibody coding regions from the phage can be isolated and used to generate antibodies, including human antibodies, and expressed in any desired host, including mammalian cells, insect cells, plant cells, yeast, and bacteria, e.g., as described below. Techniques to recombinantly produce antibodies such as Fab, Fab' and $F(ab')_2$ fragments can also be employed using methods known in the art such as those disclosed in PCT publication No. WO 92/22324; Mullinax R L et al., (1992) BioTechniques 12(6): 864-9; Sawai H et al., (1995) Am J Reprod Immunol 34: 26-34; and Better M et al., (1988) Science 240: 1041-1043.

In one aspect, to generate antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express antibodies, e.g., IgG, using techniques known to those of skill in the art.

A humanized antibody is capable of binding to a predetermined antigen and comprises a framework region having substantially the amino acid sequence of a human immunoglobulin and CDRs having substantially the amino acid sequence of a non-human immunoglobulin (e.g., a murine immunoglobulin). In particular embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA and IgE, and any isotype, including IgG1, IgG2, IgG3 and IgG4. Humanized antibodies can be produced using a variety of techniques known in the art, including but not limited to, CDR-grafting (European Patent No. EP 239400; International Publication No. WO 91/09967; and U.S. Pat. Nos. 5,225,539, 5,530,101, and 5,585,089), veneering or resurfacing (European Patent Nos. EP 592106 and EP 519596; Padlan E A (1991) Mol Immunol 28(4/5): 489-498; Studnicka G M et al., (1994) Prot Engineering 7(6): 805-814; and Roguska M A et al., (1994) PNAS 91: 969-973), chain shuffling (U.S. Pat. No. 5,565,332), and techniques disclosed in, e.g., U.S. Pat. Nos. 6,407,213, 5,766,886, International Publication No. WO 93/17105; Tan P et al., (2002) J Immunol 169: 1119-25; Caldas C et al., (2000) Protein Eng. 13(5): 353-60; Morea V et al., (2000) Methods 20(3): 267-79; Baca M et al., (1997) J Biol Chem 272(16): 10678-84; Roguska M A et al., (1996) Protein Eng 9(10): 895 904; Couto J R et al., (1995) Cancer Res. 55 (23 Supp): 5973s-

5977s; Couto J R et al., (1995) Cancer Res 55(8): 1717-22; Sandhu J S (1994) Gene 150(2): 409-10 and Pedersen J T et al., (1994) J Mol Biol 235(3): 959-73. See also U.S. Application Publication No. US 2005/0042664 A1 (Feb. 24, 2005), which is herein incorporated by reference in its entirety.

IV. Polynucleotides Encoding Antibodies

In certain embodiments, the disclosure encompasses polynucleotides comprising a nucleic acid that encodes an antibody that binds to 4-1BB and/or OX40, or polypeptide of such an antibody, e.g., a VH, a VL, a VH with a VL (e.g., in an scFv), a heavy chain, a light chain, a heavy chain with an scFv, a light chain with an scFv, a fusion protein comprising an scFv, a linker (e.g., wherein the linker is a hinge), an immunoglobulin constant region, and an scFv, a constant region, or a constant region with an scFv.

Accordingly, provided herein are polynucleotides or combinations of polynucleotides encoding the six CDRs of SEQ ID NOs:5-10. The polynucleotides can comprise the nucleotide sequences set forth as nucleotides 76-99, 151-174, 289-330, 502-519, 571-579, and 688-714, respectively, of SEQ ID NO:147.

Provided herein are also polynucleotides or combinations of polynucleotides encoding the six CDRs of SEQ ID NOs:5, 119, 7, 120, 121, and 122.

Provided herein are also polynucleotides or combinations of polynucleotides encoding the six CDRs of SEQ ID NOs:11-16. The polynucleotides can comprise the nucleotide sequences set forth as nucleotides 1912-1935, 1987-2010, 2125-2145, 1528-1545, 1597-1605, and 1714-1746, respectively, of SEQ ID NO:147.

Provided herein are also polynucleotides or combinations of polynucleotides encoding the six CDRs of SEQ ID NOs:5-10 and the six CDRs of SEQ ID NOs:11-16.

Provided herein are also polynucleotides or combinations of polynucleotides encoding the six CDRs of SEQ ID NOs:5, 119, 7, 120, 121, and 122 and the six CDRs of SEQ ID NOs:11-16.

Also provided herein are polynucleotides encoding a VH provided herein, e.g., a VH comprising the amino acid sequence of SEQ ID NO:17, 19, 21, 23, 25, 27, 29, 31-33, or 143. The polynucleotides can comprise the nucleotide sequences set forth as nucleotides 1-363 of SEQ ID NO: 147; 1837-2178 of SEQ ID NO:147; nucleotides 1-363 of SEQ ID NO:148; 1837-2178 of SEQ ID NO:148; nucleotides 1-363 of SEQ ID NO:149; or 1837-2178 of SEQ ID NO:149.

Also provided herein are polynucleotides encoding a VL provided herein, e.g., a VL comprising the amino acid sequence of SEQ ID NO:18, 20, 22, 24, 26, 28, 30 or 34-41. The polynucleotides can comprise the nucleotide sequences set forth as nucleotides 424-744 of SEQ ID NO:147; 1453-1776 of SEQ ID NO: 147; 424-744 of SEQ ID NO:148; 1453-1776 of SEQ ID NO: 148; 424-744 of SEQ ID NO:149; or 1453-1776 of SEQ ID NO:149.

Also provided herein are polynucleotides encoding a 4-1BB binding sequence (e.g., scFv) provided herein, e.g., a 4-1BB binding sequence comprising the amino acid sequence of SEQ ID NO:42-45, 58, 63, 77, or 101. The polynucleotides can comprise the nucleotide sequences set forth as nucleotides 1-744 of SEQ ID NO:147; 1-744 of SEQ ID NO:148; or 1-744 of SEQ ID NO:149.

Also provided herein are polynucleotides encoding an OX40 binding sequence (e.g., scFv) provided herein, e.g., an OX40 binding sequence comprising the amino acid sequence of SEQ ID NO:46-57, 59-76, or 102. The polynucleotides can comprise the nucleotide sequences set forth as nucleotides 1453-2181 of SEQ ID NO:147; 1453-2181 of SEQ ID NO:148; or 1453-2181 of SEQ ID NO:149

Also provided herein are polynucleotides encoding 4-1BB×OX40 bispecific antibodies provided herein, e.g., an antibody comprising the amino acid sequence of SEQ ID NO:78-100. The polynucleotides can comprise the nucleotide sequences set forth in any one of SEQ ID NOs:147-149.

In certain embodiments, a polynucleotide encodes a polypeptide comprising, in order from amino-terminus to carboxyl-terminus, a first scFv, a linker (e.g., wherein the linker is a hinge region), an immunoglobulin constant region, and a second scFv, wherein (a) the first scFv comprises a human 4-1BB antigen-binding domain, and the second scFv comprises a human OX40 antigen-binding domain or (b) the first scFv comprises a human OX40 antigen-binding domain and the second scFv comprises a human 4-1BB antigen-binding domain.

As discussed in more detail below, vectors comprising the polynucleotides disclosed herein are also provided.

The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand. In some embodiments, the polynucleotide is a cDNA or a DNA lacking one more endogenous introns.

In some embodiments, a polynucleotide is a non-naturally occurring polynucleotide. In some embodiments, a polynucleotide is recombinantly produced.

In certain embodiments, the polynucleotides are isolated. In certain embodiments, the polynucleotides are substantially pure. In some embodiments, a polynucleotide is purified from natural components.

In some embodiments, a polynucleotide provided herein is codon optimized for expression in a particular host (change codons in the human mRNA to those preferred by a bacterial host such as *E. coli*).

V. Cells and Vectors

Vectors and cells comprising the polynucleotides described herein are also provided herein.

In certain aspects, provided herein are cells (e.g., host cells) expressing (e.g., recombinantly) antibodies described herein which specifically bind to 4-1BB and/or OX40 and comprising related polynucleotides and expression vectors. Provided herein are vectors (e.g., expression vectors) comprising polynucleotides comprising nucleotide sequences encoding antibodies that specifically bind to 4-1BB and/or OX40 for recombinant expression in host cells, e.g., mammalian host cells. Also provided herein are host cells comprising such vectors for recombinantly expressing antibodies that specifically bind to 4-1BB and/or OX40 described herein. In a particular aspect, provided herein are methods for producing an antibody that specifically bind to 4-1BB and/or OX40 described herein, comprising expressing such antibody in a host cell.

Recombinant expression of an antibody that specifically bind to 4-1BB and/or OX40 described herein involves construction of an expression vector containing a polynucleotide that encodes the antibody or a polypeptide thereof (e.g., a fusion protein comprising an scFv, a linker (e.g., wherein the linker is a hinge), an immunoglobulin constant region; a heavy or light chain; a polypeptide comprising one or more variable domains; a polypeptide comprising one or more antigen-binding domains (e.g., scFvs), optionally fused to a linker (e.g., wherein the linker is a hinge), immunoglobulin constant region and/or linker, etc.). Once a polynucleotide encoding an antibody or a polypeptide thereof described herein has been obtained, the vector for the production of the antibody or polypeptide thereof can be produced by recombinant DNA technology using techniques well known in the art. Thus, methods for preparing a protein by expressing a polynucleotide a nucleotide sequence encoding an antibody or fragment thereof are described herein. Methods which are well known to those skilled in the art can be used to construct expression vectors containing coding sequences for an antibody or a polypeptide thereof and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody or a fragment thereof, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122,464), and variable domains of the antibody can be cloned into such a vector for expression of the entire heavy, the entire light chain, or both the entire heavy and light chains. A nucleotide sequence encoding an additional variable domain, a 4-1BB binding domain (e.g., scFv), and/or an OX40 binding domain can also be cloned into such a vector for expression of fusion proteins comprising a heavy or light chain fused to an additional variable domain, a 4-1BB binding domain (e.g., scFv), and/or an OX40 binding domain.

To direct a recombinant protein into the secretory pathway of a host cell, a secretory signal sequence (also known as a leader sequence) can be provided in the expression vector. The secretory signal sequence can be that of the native form of the recombinant protein, or can be derived from another secreted protein or synthesized de novo. The secretory signal sequence can be operably linked to the polypeptide-encoding DNA sequence. Secretory signal sequences are commonly positioned 5' to the DNA sequence encoding the polypeptide of interest, although certain signal sequences can be positioned elsewhere in the DNA sequence of interest (see, e.g., Welch et al., U.S. Pat. No. 5,037,743; Holland et al., U.S. Pat. No. 5,143,830).

An expression vector can be transferred to a cell (e.g., host cell) by conventional techniques and the resulting cells can then be cultured by conventional techniques to produce an antibody or polypeptide thereof (e.g., a fusion protein comprising an scFv, a linker (e.g., wherein the linker is a hinge), an immunoglobulin constant region; a heavy or light chain; a polypeptide comprising one or more variable domains; a polypeptide comprising one or more antigen-binding domains (e.g., scFvs), optionally fused to a hinge, immunoglobulin constant region and/or linker, etc.) described herein. Thus, provided herein are host cells containing a polynucleotide encoding an antibody or a polypeptide thereof described herein operably linked to a promoter for expression of such sequences in the host cell.

In certain embodiments, for the expression of multiple-polypeptide antibodies, vectors encoding all of polypeptides, individually, can be co-expressed in the host cell for expression of the entire antibody.

In certain embodiments, a host cell contains a vector comprising polynucleotides encoding all of the polypeptides of an antibody described herein. In specific embodiments, a host cell contains multiple different vectors encoding all of the polypeptides of an antibody described herein.

A vector or combination of vectors can comprise polynucleotides encoding two or more polypeptides that interact to form an antibody described herein: e.g., a first polynucleotide encoding a heavy chain and a second polynucleotide encoding a light chain; a first polynucleotide encoding a fusion protein comprising a heavy chain and an scFv with a second polynucleotide encoding a light chain; a first polynucleotide encoding a fusion protein comprising a light chain and an scFv with a second polynucleotide encoding a heavy chain; a first polynucleotide encoding a fusion protein comprising a heavy chain and a VH with a second polynucleotide encoding a fusion protein comprising a light chain and a VL, etc. Where the two polypeptides are encoded by polynucleotides in two separate vectors, the vectors can be transfected into the same host cell.

A variety of host-expression vector systems can be utilized to express antibodies or polypeptides thereof (e.g., a fusion protein comprising an scFv, a linker (e.g., wherein the linker is a hinge), an immunoglobulin constant region; a heavy or light chain; a polypeptide comprising one or more variable domains; a polypeptide comprising one or more antigen-binding domains (e.g., scFvs), optionally fused to a hinge, immunoglobulin constant region and/or linker, etc.) described herein. Such host-expression systems represent vehicles by which the coding sequences of interest can be produced and subsequently purified, but also represent cells which can, when transformed or transfected with the appropriate nucleotide coding sequences, express an antibody or polypeptide thereof described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

Once an antibody or a polypeptide thereof (e.g., a fusion protein comprising an scFv, a linker (e.g., wherein the linker is a hinge), an immunoglobulin constant region; a heavy or light chain; a polypeptide comprising one or more variable domains; a polypeptide comprising one or more antigen-binding domains (e.g., scFvs), optionally fused to a hinge, immunoglobulin constant region and/or linker, etc.) described herein has been produced by recombinant expression, it can be purified by any method known in the art for purification of an antibody, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein (e.g., a FLAG tag, a his tag, or avidin) or otherwise known in the art to facilitate purification.

VI. Compositions and Kits

Provided herein are compositions comprising an antibody described herein having the desired degree of purity in a physiologically acceptable carrier, excipient or stabilizer (Remington's Pharmaceutical Sciences (1990) Mack Publishing Co., Easton, PA). Acceptable carriers, excipients, or stabilizers are nontoxic to recipients at the dosages and concentrations employed.

A pharmaceutical composition may be formulated for a particular route of administration to a subject. For example, a pharmaceutical composition can be formulated for parenteral, e.g., intravenous, administration. The compositions to be used for in vivo administration can be sterile. This is readily accomplished by filtration through, e.g., sterile filtration membranes.

The pharmaceutical compositions described herein are in one embodiment for use as a medicament. Pharmaceutical compositions described herein can be useful in enhancing an immune response. Pharmaceutical compositions described herein can be useful in increasing natural killer (NK) cell and/or T cell (e.g., CD4 T cell and/or CD8 T cell) proliferation in a subject. Pharmaceutical compositions described herein can be useful in agonizing a T cell co stimulatory pathway in a subject.

Pharmaceutical compositions described herein can be useful in treating a condition such as cancer. Examples of cancer that can be treated as described herein include, but are not limited to, melanoma, kidney cancer, pancreatic cancer, lung cancer, intestinal cancer, prostate cancer, breast cancer, liver cancer, brain cancer, and hematological cancers such as a lymphoma. In certain instances, the cancer is a solid tumor.

VII. Methods and Uses

The antibodies of the disclosure that bind to 4-1BB and/or OX40 are useful in a variety of applications including, but not limited to, therapeutic treatment methods, such as the treatment of cancer. In certain embodiments, the agents are useful for inhibiting tumor growth and/or reducing tumor volume. The methods of use may be in vitro or in vivo methods. The invention includes the use of any of the disclosed antibodies (and pharmaceutical compositions comprising the disclosed antibodies) for use in therapy.

The present disclosure provides for methods of treating cancer in a subject comprising administering a therapeutically effective amount of an antibody that binds to 4-1BB and/or OX40 to the subject. The invention includes the use of any of the disclosed antibodies for treatment of cancer.

In certain embodiments, the cancer is a cancer including, but are not limited to, melanoma, kidney cancer, pancreatic cancer, lung cancer, colon cancer/intestinal cancer, stomach cancer, prostate cancer, ovarian cancer, breast cancer, liver cancer, brain cancer, and hematological cancers. The cancer may be a primary tumor or may be advanced or metastatic cancer. In certain instances, the cancer is a solid tumor. For instance, the present disclosure includes use of the bispecific antibodies for treatment of sarcoma, carcinoma, and lymphoma. The invention includes, for instance, treating a human subject with a sarcoma, carcinoma, or lymphoma by administering to the subject a therapeutically effective amount of a pharmaceutical composition of the invention (e.g., a pharmaceutical composition comprising a bispecific antibody that specifically binds human 4-1BB and human OX40 and comprising an amino acid sequence at least 85%, 90%, 95%, or 99% identical to an amino acid sequence selected from the group of SEQ ID NOs:78-100 and 144).

The invention includes methods of treating a human subject with a tumor or cancerous tissue that contains tumor infiltrating lymphocytes. The invention includes treating a human subject with a tumor containing lymphocytes that express 4-1BB and OX40. In one embodiment, the invention includes administering to a human subject with a solid tumor a therapeutically effective amount of a pharmaceutical composition comprising an anti-4-BB×anti-OX40 bispecific antibody wherein the human 4-1BB binding domain comprises a VH comprising an amino acid sequence at least 85%, 90%, 95%, or 99% identical to an amino acid sequence SEQ ID NO:17 and a VL comprising an amino acid sequence at least 85%, 90%, 95%, or 99% identical to an amino acid sequence of SEQ ID NO:18 and wherein the human OX40 binding domain comprises a VH comprising an amino acid sequence at least 85%, 90%, 95%, or 99% identical to an amino acid sequence SEQ ID NO:31 and a VL comprising an amino acid sequence at least 85%, 90%, 95%, or 99% identical to an amino acid sequence SEQ ID NO:30. For instance, the invention includes administering to a human subject with a tumor an effective amount of a pharmaceutical composition comprising an anti-4-BB×anti-OX40 bispecific antibody wherein the human 4-1BB binding domain comprises an amino acid sequence at least 85%, 90%, 95%, or 99% identical to an amino acid sequence SEQ ID NO:58 and wherein the human OX40 binding domain comprises an amino acid sequence at least 85%, 90%, 95%, or 99% identical to an amino acid sequence SEQ ID NO:62. In one embodiment, the invention includes administering to a human subject with a tumor a therapeutically effective amount of a pharmaceutical composition comprising an anti-4-BB×anti-OX40 bispecific antibody comprising an amino acid sequence at least 85%, 90%, 95%, or 99% identical to an amino acid sequence SEQ ID NO:81.

The present disclosure provides for methods of enhancing an immune response in a subject comprising administering a therapeutically effective amount of an antibody that binds to 4-1BB and/or OX40 to the subject.

The present disclosure provides for methods of agonizing a T cell co stimulatory pathway in a subject comprising administering a therapeutically effective amount of an antibody that binds to 4-1BB and/or OX40 to the subject.

The present disclosure provides for methods of increasing the proliferation of NK cells and/or T cells (e.g., CD4+ T cells and/or CD8+ T cells) in a subject comprising administering a therapeutically effective amount of an antibody that binds to 4-1BB and/or OX40 to the subject. The present disclosure provides for methods of increasing the proliferation of NK cells, CD4+ T cells, and CD8+ T cells in a subject comprising administering a therapeutically effective amount of an antibody that binds to 4-1BB and OX40 to the subject. For instance, the invention includes methods for increasing the proliferation of NK cells, CD4+ T cells and CD8+ T cells in a subject comprising administering a therapeutically effective amount of a pharmaceutical composition comprising a bispecific antibody that specifically binds human 4-1BB and human OX40 and comprising an amino acid sequence at least 85%, 90%, 95%, or 99% identical to an amino acid sequence selected from the group of SEQ ID NOs:78-100 and 144.

The invention includes methods of increasing the number of tumor infiltrating lymphocytes in a subject by administering to the subject a therapeutically effective amount of a pharmaceutical composition of the invention. For instance, the invention includes a method of increasing the number of tumor infiltrating lymphocytes in a subject by administering a pharmaceutical composition comprising a bispecific antibody that specifically binds human 4-1BB and human OX40 and comprising an amino acid sequence at least 85%, 90%, 95%, or 99% identical to an amino acid sequence selected from the group of SEQ ID NOs:78-100 and 144.

The invention also includes methods of increasing the expression of granzymes by tumor infiltrating lymphocytes in a subject by administering to the subject a therapeutically effective amount of an antibody or pharmaceutical composition of the invention. For instance, the invention includes a method of increasing the expression of granzymes by tumor infiltrating lymphocytes in a subject by administering to the subject a therapeutically effective amount of any antibody or pharmaceutical composition provided herein.

In certain embodiments, the subject is a human.

Administration of an antibody that binds to 4-1BB and/or OX40 can be parenteral, including intravenous, administration.

In some embodiments, provided herein are antibodies that bind to 4-1BB and/or OX40, or pharmaceutical compositions comprising the same, for use as a medicament. In some aspects, provided herein are antibodies that bind to 4-1BB and/or OX40, or pharmaceutical compositions comprising the same for use in a method for the treatment of cancer. For instance, the invention includes a pharmaceutical composition comprising a bispecific antibody containing a human 4-1BB binding domain comprises a VH comprising an amino acid sequence at least 85%, 90%, 95%, or 99% identical to an amino acid sequence SEQ ID NO:17 and a VL comprising an amino acid sequence at least 85%, 90%, 95%, or 99% identical to an amino acid sequence of SEQ ID NO:18 and wherein the human OX40 binding domain comprises a VH comprising an amino acid sequence at least 85%, 90%, 95%, or 99% identical to an amino acid sequence SEQ ID NO:31 and a VL comprising an amino acid sequence at least 85%, 90%, 95%, or 99% identical to an amino acid sequence SEQ ID NO:30.

In one aspect, antibodies that bind to 4-1BB and/or OX40 provided herein are useful for detecting the presence of 4-1BB and/or OX40, e.g., in a biological sample. The term "detecting" as used herein encompasses quantitative or qualitative detection. In certain embodiments, a biological sample comprises a cell or tissue. In certain embodiments, the method of detecting the presence of 4-1BB and/or OX40 in a biological sample comprises contacting the biological sample with an antibody that binds to 4-1BB and/or OX40 provided herein under conditions permissive for binding of the antibody, and detecting whether a complex is formed between the antibody and 4-1BB and/or OX40.

In certain embodiments, an antibody that binds to 4-1BB and/or OX40 provided herein is labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction.

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

EXAMPLES

It is understood that the examples and embodiments described herein are for illustrative purposes only and that various modifications or changes in light thereof will be suggested to persons skilled in the art and are to be included within the spirit and purview of this application.

Example 1. Generation of OX40 and 4-1BB Expressing CHO Cells and Recombinant OX40 and 4-1BB Extracellular Domain Proteins The nucleotide sequences defining the human and cynomolgus OX40 and 4-1BB full length and extracellular domains (ECDs) were obtained from Genbank database and are listed in Table 1.

TABLE 1

SEQ IDs of constructs for production of cell lines and recombinant proteins

| Construct Name | Construct Description | SEQ ID Protein |
|---|---|---|
| FOB005 | Full-length Human 4-1BB | 1 |
| FOB006 | Full-length Cyno 4-1BB | 2 |
| OXF001 | Full-length Human OX40 | 3 |
| OXF004 | Full-length Cyno OX40 | 4 |
| FOB003 | Human 4-1BB ECD-AFH | 103 |
| FOB001 | Human 4-1BB ECD-mFc | 104 |
| FOB004 | Cyno 4-1BB ECD-AFH | 105 |
| FOB002 | Cyno 4-1BB ECD-mFc | 106 |
| OXF003 | Human OX40 ECD-AFH | 107 |
| OXF005 | Cyno OX40-AFH | 108 |

Human and cynomolgus ECDs contained C-terminal tags for purification, detection and biotin-based labeling purposes. DNA containing the nucleotide sequences in Table 1 were synthesized and inserted into an expression vector appropriate for mammalian cell expression and secretion. The non-human primate OX40 and 4-1BB ECD proteins were used to assess the cross reactivity and affinity of binding domains to the species to be used in potential toxicology assessments. These proteins were also utilized for immunization and screening to isolate binding domains to both targets. DNA expression vectors encoding ECD were used to transiently transfect HEK-293 cells grown in suspension culture. After several days in culture, the conditioned media was clarified via centrifugation and sterile filtration. Protein purification was performed, utilizing a combination of the appropriate affinity purification step (typically Immobilized Metal Affinity Chromatography, Protein A, or Protein G chromatography), followed by size exclusion chromatography (SEC) to remove aggregated and clipped product and other host cell contaminants. SEC was also used to buffer-exchange the protein into phosphate-buffered saline (PBS). Final purity of the sample was determined by analytical SEC and typically exceeded 90% final purity. Protein batches were sterile-filtered and stored at 4° C. until needed.

Figure 2A:
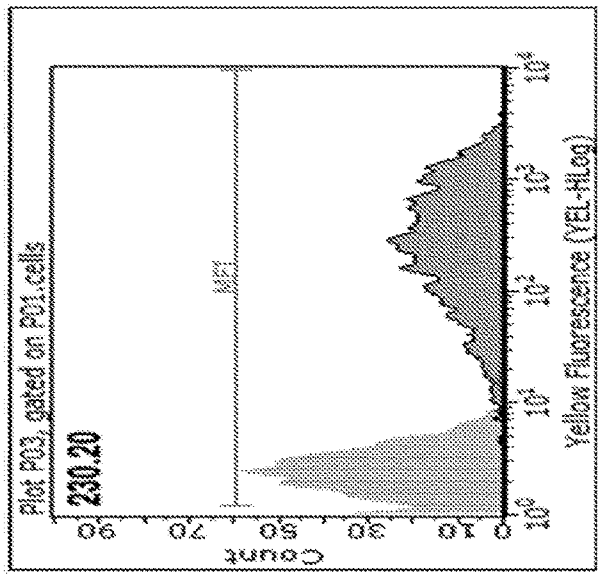
FIGS. 2A-2C show the surface expression of OX40 in CHO clones. The three panels show representative staining of three human OX40-expressing CHO clones (2A: OXF001a_9G10; 2B: OXF001a_6B1; 2C: OXF004a_11H7). Untransfected cells are shown in the light grey histogram; clones are in overlay in dark gray with the solid border. Clones in (2A) and (2B) express human OX40 while the Clone in (2C) expresses cynomolgus OX40. Samples were stained with antibody to human OX40 (clone L106, BD Biosciences) at 1:30 dilution then analyzed with GUAVA Easycyte. Parental CHO were used as negative control. (See Example 2.)
Figure 2B:
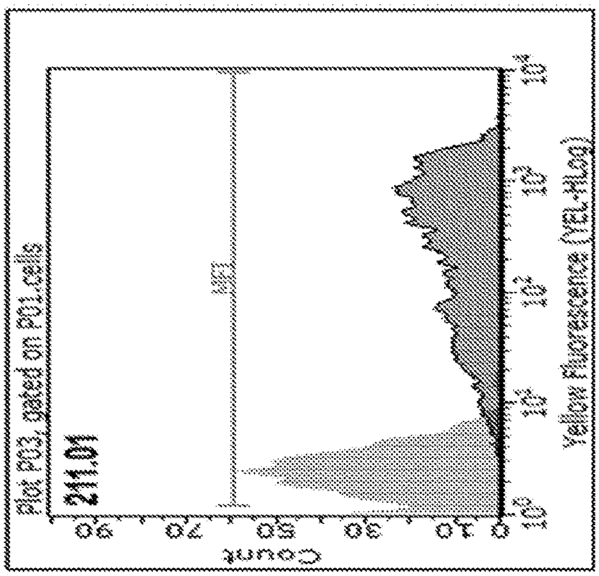
Figure 2C:
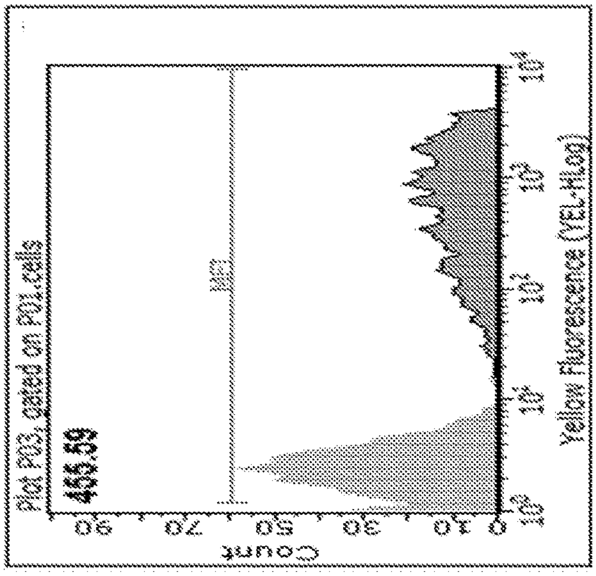

Example 2. Generation of CHO Cell Lines Expressing Full-Length OX40 and 4-1BB for Screening Plasmid DNA encoding the two targets (OX40: OXF 001 (hu) and OXF004 (cyno); 4-1BB: FOB 005 (hu) and FOB006 (cyno)) was digested with PvuI and ethanol precipitated, and the OX40 constructs were dissolved in ultrapure water, then Maxcyte Electroporation Buffer. Linearized DNA was transfected into CHO-K1SV cells (CDACF-CHO-K1 SV cells (ID code 269-W3), Lonza Biologics) using the MaxCyte instrument for electroporation. Transfected cells were transferred from the electroporation cuvette to a T150 culture flask, rested, and then gently resuspended in 40 mL of CD CHO media supplemented with 6 mM L-Glutamine in the T150 flask. The flask was put in a 37° C., 5% $CO_2$ incubator and allowed to recover for 24 hours prior to placing in the selection conditions. On the day following transfection, the cells were centrifuged for 5 minutes at 1000 RPM and resuspended in CD CHO medium with 1×GS supplement and 50 μM MSX. After the bulk populations were recovered from initial selection, cells were evaluated for surface expression with commercially available reagents, and representative vials were frozen. To obtain clones with varying levels of expression, cells were sorted by flow cytometry, plated by limiting dilution, and allowed to grow for 2 weeks. Clones from the FOB005 and FOB006 sorted pools were identified by imaging with CLD Cell Metric (Solentim) at 3 hours, 24 hours, 48 hours, 7 days, and 14 days after plating. Only wells with good quality images and an identified single cell at 3 hours after plating were selected for further expansion and characterization for surface expression by flow cytometry (FIGS. 1A and 1B). Clones from the OXF001 and OXF004 sorted pools were imaged 14 days after plating. Only wells with good quality images on day 14 after plating were selected for further expansion and characterization for surface expression by flow cytometry (FIGS. 2A-2C). All clones were frozen in banks at up to 30 vials per clone.

Example 3. General Expression and Purification of 4-1BB and OX40-Binding Molecules and Antibodies Monospecific and bispecific 4-1BB and OX40-binding molecules disclosed herein were produced by transient transfection of either human HEK293 or Chinese Hamster Ovary (CHO) cells. Cultures were clarified of cells, cell debris, and insoluble matter by centrifugation and/or filtration. Recombinant protein was purified from the clarified, conditioned media using Protein A affinity chromatography. Preparative Size exclusion chromatography (Prep SEC) was typically performed to further purify the protein to homogeneity and buffer-exchange into PBS. Protein purity was verified by analytical size exclusion chromatography (analytical SEC) on an Agilent HPLC after each of the Protein A and Prep SEC purification steps. Endotoxin levels were determined by using the Endosafe PTS instrument according to the manufacturer's instructs to assure that the in vitro activity assay results would not be confounded by the presence of endotoxin. The resulting protein was buffer-exchanged into PBS as part of the SEC purification process, concentrated to 1 mg/mL, sterile-filtered and stored at 4° C. until needed or otherwise specified. Protein concentration was determined from the absorbance at 280 nm and using the theoretical extinction coefficient calculated from the amino acid sequence.

Example 4. Generation of OX40 Antibodies by Hybridoma

Anti-OX40-specific antibodies were isolated from a hybridoma library generated after immunizing OmniRats and OmniMice (Ligand Inc, San Diego, CA) with DNA encoding human OX40 protein (Aldevron Freiburg, Germany). Binding specificity of individual clones was confirmed by testing binding using flow cytometry on CHO cells transfected with human and cynomolgus monkey variants of OX40 and further confirmed by lack of binding to untransfected CHO cells. The variable heavy (VH) and light (VL) domain sequences for selected hybridoma clones were obtained by RT-PCR after isolating total RNA. Briefly, total RNA was isolated from the hybridoma clone cell banks using Qiagen's RNeasy Plus Kit (Qiagen, Venlo Netherlands). 200 ng of total RNA was then used in a First Stand cDNA synthesis reaction using Superscript IV (Thermo Fisher Scientific Waltham, MA), following manufacturer's protocol. PCR was performed using 2 μl of cDNA as template and specific primer mixes defined by Ligand/OMT for the amplification of either VH or VL regions. PCR products for each clone were directly sequenced using a reverse primer in the constant domains and standard Sanger sequencing methods. Sequences were then converted to scFv by amplifying the variable domains using specific primers that contain overlapping sequences and were assembled into a mammalian expression vector using NEBuilder HiFi DNA Assembly Cloning Kit (New England Biolabs, Beverly MA).

Example 5. Surface Plasmon Resonance (SPR) Methodology to Determine the Binding Affinity of OX40 and 4-11313 Binding Domains to Recombinant Human, Mouse and Cynomolgus Monkey Extracellular Domains SPR binding affinity studies of mono- and bispecific proteins binding to recombinant monomeric human and cynomolgus monkey OX40 and 4-1BB ectodomain (ECD) were conducted at 25° C. in HBS-EP+ with 0.2% BSA buffer on either a Biacore T200 or Biacore 8K system. Mouse anti-human IgG (GE, BR-1008-39) at 25 μg/ml in 10 mM sodium acetate pH 5.0 was immobilized at a density of ~10,000 response units (RU) onto each flow cell of a CM5 research-grade sensor chip (GE) by standard amine coupling chemistry. Each binding protein at approximately 100 nM in HBS-EP+ with 0.2% BSA buffer was captured in a flow cell with the immobilized anti-human IgG at a flow rate of 10 μL/min for 20 seconds, leaving one flow cell surface unmodified as the reference. Using a single-cycle kinetics mode, five different concentrations of ECD were sequentially injected through each flow cell at 30 μL/min for 300 seconds followed by a 600 second dissociation period. Regeneration was achieved by injection of 3 M $MgCl_2$ at a flow rate of 30 μL/min for 30 seconds followed by HBS-EP+ with 0.2% BSA buffer stabilization for 1 min.

Sensorgrams obtained from kinetic SPR measurements were analyzed by the double subtraction method. The signal from the reference flow cell was subtracted from the analyte binding response obtained from flow cells with immobilized or captured ligands. Buffer reference responses were then averaged from multiple injections. The averaged buffer reference responses were then subtracted from analyte binding responses, and the final double-referenced data were analyzed with Biacore T200 Evaluation software (2.0, GE), globally fitting data to derive kinetic parameters. All sensorgrams were fitted using a simple one-to-one binding model.

Example 6. Screening OX40 Binding Domains in ADAPTIR™ Format with a Control scFv on the N-Terminus and the OX40 scFv on the C-Terminus for Cell Binding and Activity Based on the cell binding data obtained by screening hybridoma supernatants, select anti-OX40 antibodies were converted to scFvs and incorporated into the ADAPTIR™ bispecific format (N-terminal scFv-IgG1 Fc-C-terminal scFv) in the C-terminal position and screened for cell binding and activity in an OX40 reporter assay. In the N-terminal position, a control anti-tumor antigen scFv was used, and held constant across the set. Both orientations of the anti-OX40 scFv variable domains were evaluated (VH-VL and VL-VH), as well as two different linker lengths used to connect the Fc region to the C-terminal scFv (either a single Gly4Ser linker, or a series of three Gly4Ser repeats).

Flow cytometry was used to quantitate and confirm binding of OX40-specific scFv to human and cynomolgus OX40 expressed on the surface of transfected cells. Binding studies were performed on CHO-K1 cells stably expressing the full length human or cynomolgus OX40 protein that were developed and subsequently cloned in-house. Typically, 100,000 cells were incubated with a dilution of bispecific construct in 50 μl of PBS buffer containing 0.2% BSA and 2 mM EDTA, for 40 minutes at 4° C., followed by washes. Subsequent incubation was with PE-labeled, minimum cross species reactive secondary antibody, goat anti-human IgG Fcγ, F(ab')2 (Jackson ImmunoResearch) for 30 minutes at 4° C. Signal from bound molecules was detected using an LSR-II or FACSymphony A3 flow cytometer (BD Biosciences) and analyzed by FlowJo flow cytometry analysis software. Mean fluorescence intensity (MFI) of bound molecules on cells was determined after exclusion of doublets. Nonlinear regression analysis to determine $EC_{50}$ values was performed in GraphPad Prism 7® graphing and statistics software.

Figure 3A:
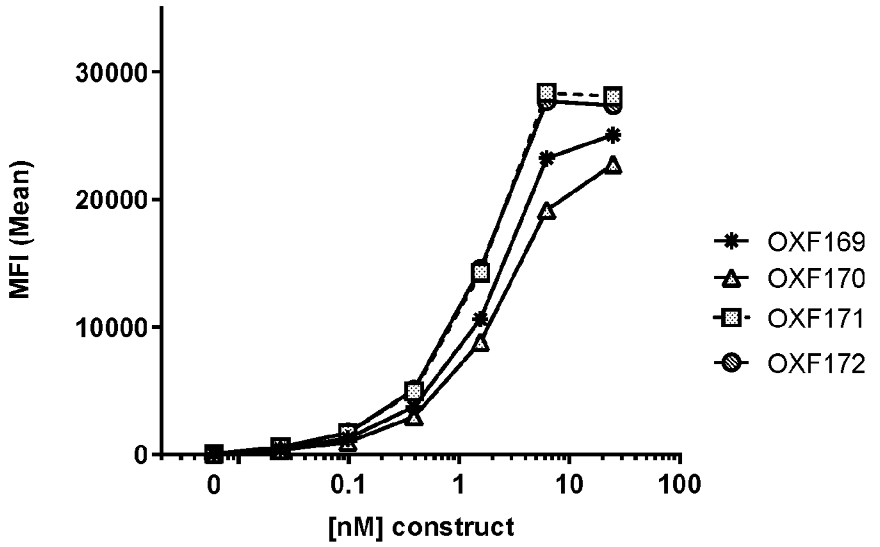
FIGS. 3A and 3B show binding of anti-OX40 constructs to human (3A) or cynomolgus (3B) OX40-expressing CHOK1SV cells. Serial dilutions of ADAPTIR™ constructs were incubated with CHOK1SV cells transfected with human or cynomolgus OX40 and subsequently labelled with a fluorescently-conjugated goat-α-human Fc secondary antibody. The y-axis displays the mean fluorescence intensity units (MFI). (See Example 6.)
Figure 3B:
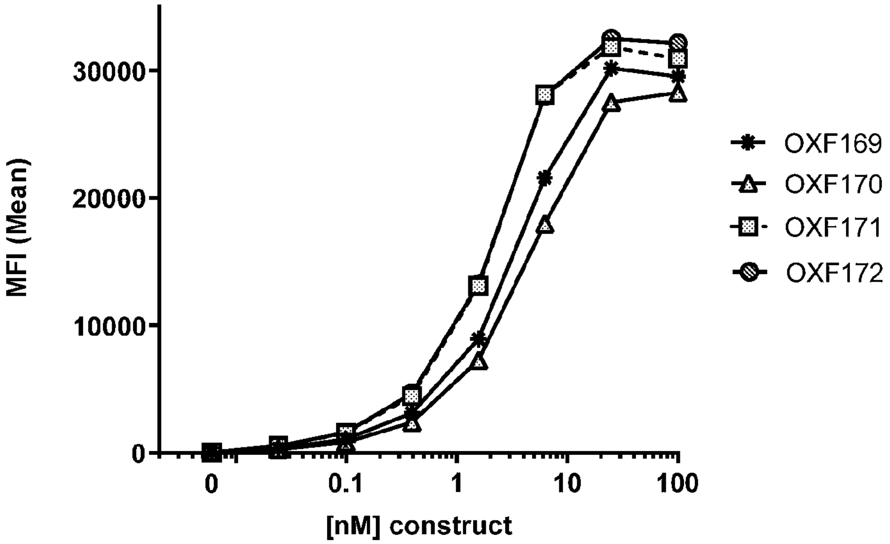

FIGS. 3A and 3B show the binding of 4 different bispecific anti-ROR243×anti-OX40 constructs (OXF169, OXF170, OXF171, and OXF172) to CHO cells stably expressing either human OX40 or cynomolgus OX40 protein. Observed $EC_{50}$ are reported in Table 2.

TABLE 2

Cell binding and activity data examining the impact of scFv orientation and linker length

| | Construct Details | | | | | |
|---|---|---|---|---|---|---|
| | OX40 Reporter Assay | | Binding to human OX40/CHO | | Binding to cyno OX40CHO | |
| Name | EC50 pM | Max induction | EC50 nM | max MFI | EC50 nM | max MFI |
| OXF169 Anti-tumor scFv-Fc-3X(G4S)- Anti-OX40 VHVL | 12 | 481003 | 1.9 | 25068 | 3.2 | 30168 |
| OXF170 Anti-tumor scFv-Fc-1X(G4S)- Anti-OX40 VHVL | 10 | 557623 | 2.3 | 22733 | 4.2 | 28248 |
| OXF171 Anti-tumor scFv-Fc-3X(G4S)- Anti-OX40 VLVH | 4 | 582852 | 1.6 | 28371 | 1.9 | 31803 |
| OXF172 Anti-tumor scFv-Fc-1X(G4S)- Anti-OX40 VLVH | 7 | 540132 | 1.5 | 27698 | 2.0 | 32481 |

Figure 4:
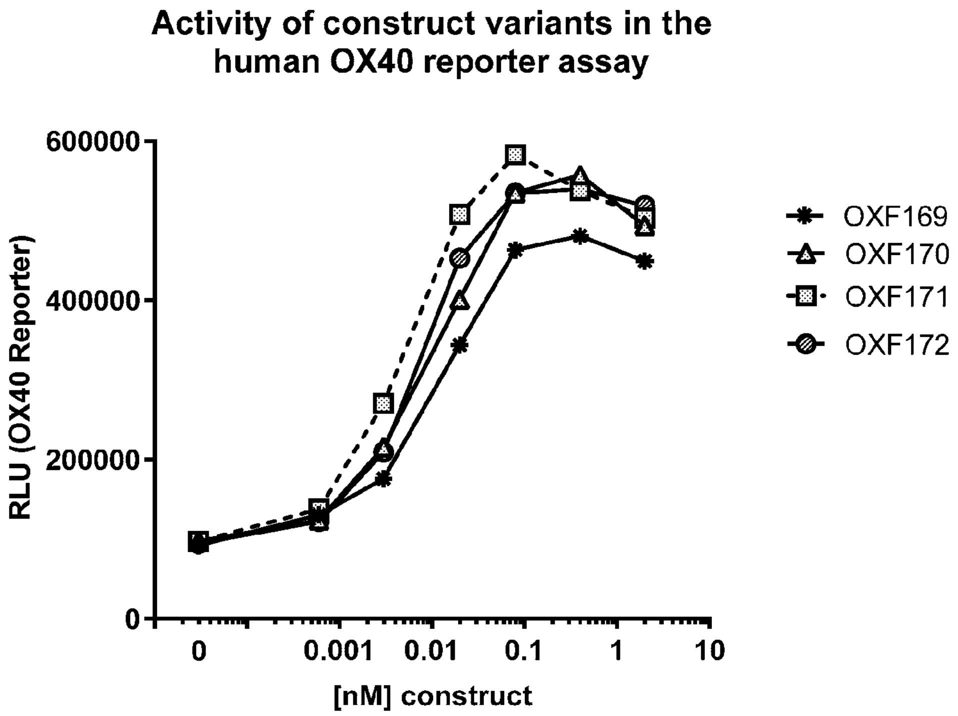
FIG. 4 shows a comparison of the functionality of anti-tumor×anti-OX40 constructs with binding domains in either the VH-VL or VL-VH orientation with two different linkers using the MDA-MB-231 tumor line in the functional OX40 reporter assay. Serially diluted constructs were run side-by-side with an NFκB/OX40 reporter cell line and MDA-MB-231 target cells for five hours, followed with the addition of Bio-Glo. The y-axis displays the relative light units (RLU). (See Example 6.)

To compare the activity of different OX40-binding bispecific constructs to induce target-dependent activation of OX40, a luciferase reporter assay was used. Thirty thousand Jurkat cells transfected to expressed human OX40, carrying a luciferase reporter gene under the control of an NFκB promoter (generated in-house), were cultured with 120,000 ROR-expressing MDA-MB-231 cancer (target) cells in 96-well plates. Five-fold dilutions of the bispecific constructs were added. Cells were cultured in a total volume of 100 μL of RPMI 1640 media supplemented with 5% fetal bovine serum, sodium pyruvate, antibiotics, and non-essential amino acids. Plates were incubated at 37° C., 5% $CO_2$ in humidified incubators for 5 hours. One hundred microliters of Bio-Glow buffer (Promega) was added to each well, mixed, and incubated for 10 minutes. Luminescence was measured in a MicroBeta$^2$ 2450 Microplate Counter (Perkin Elmer). Nonlinear regression analysis to determine $EC_{50}$ values was performed in GraphPad Prism 6® graphing and statistics software. The results are shown in FIG. 4, where the y-axis shows values in relative fluorescence units (RLU).

FIGS. 3A and 3B and Table 2 demonstrate the activity of ROR243×OX40 constructs (OXF169, OXF170, OXF171 and OXF172) using an OX40-expressing NFκB Jurkat reporter line. MDA-MB-231 target cells were used for crosslinking. Observed $EC_{50}$ values for activity ranged between 4.4 and 12.2 pM.

In summary, a series of ADAPTIR™ constructs was generated from the same anti-OX40 hybridoma clone (containing a VH of SEQ ID NO:25 and a VL of SEQ ID NO:26). Based on the reporter assay, the linker length did not appear to impact the activity (OXF171 vs. OXF172, or OXF169 vs. OXF170). However, the activity appeared to be higher when the anti-OX40 scFv was in the VL-VH orientation (Table 2, FIGS. 3 and 4).

Example 7. Optimization of Thermostability of the OXF171 Anti-OX40 scFv

An optimization campaign was performed in order to increase the thermostability of the anti-OX40 binding domain used in OXF171 (BZG-12C3 scFv in VL-VH orientation). Random mutagenesis phage libraries were generated for the OXF171 scFv using error-prone PCR, and panning from phage display libraries under mildly denaturing conditions was used to enrich for clones with increases stability. A combination of well-established molecular biology and phage-display protocols was used. Briefly, the gene encoding the anti-OX40 scFv binding domain used in OXF171 was used as template in an error-prone PCR reaction using a commercial mutagenesis kit (GeneMorph II Random Mutagenesis Kit, Agilent Technologies, USA) following the manufacturer's protocol. The PCR products were digested by restriction enzymes and ligated into the phagemid vector to create a pIII phage coat protein N-terminal fusion library. This library was transformed into *E. coli* SS320/M13KO7 competent cells to generate the phage libraries. Five rounds of panning were performed on the library using biotinylated OX40 ECD (SEQ ID NO: 107 as bait. Increased stringency of panning was used for each successive round by decreasing the antigen concentration and increasing the wash times. Additional rounds of panning were performed that replaced standard PBS-T washes with guanidine hydrochloride or magnesium chloride washes, or that used phage that had been pre-incubated at high temperatures, as methods for selecting more stable binders. Following the final round of panning, phage output was plated and prepared for a bulk cloning of the scFv pool into a prepared expression vector for mammalian expression and screening. Approximately 600 individual colonies were picked and sequenced. Plasmid DNA for approximately 200 unique sequences was isolated and used in high-throughput 293 transient transfections (~0.6 mL culture volume). After cultivating for 3 days, cell supernatants were purified, and the thermostability was measured using differential scanning fluorimetry (DSF). Two amino acid changes were identified that had improved thermostability compared to the parental OXF171 sequence: H40N in variable light chain and V55A in variable heavy chain. Next, the H40N and V55A mutations were combined individually or in combinations with framework germlining mutation A51V in variable light chain (to revert to IGLV3-21*02), and D92N and L101V in variable heavy chain (to revert to IGHV3-30*03). Combination of germlining mutations with H40N is present in molecules OXF01099, FXX01055 and FXX01079. Combination of germlining mutations with H40N and V55A is present in molecules OXF01115, FXX01047 and FXX01066.

Example 8. Production and Evaluation of the Biophysical Characteristics of the OXF171 Anti-OX40 scFv Variants Following phage panning the isolated scFvs were sequenced and incorporated into monospecific constructs by attaching the anti-OX40 scFv to the C-terminus of a wild-type IgG1 Fc region (wtFc-anti-OX40 scFv). Following transient expression from Chinese Hamster Ovary cells and purification, these constructs were characterized for expression, thermal stability by differential scanning calorimetry (DSC), binding affinity to human OX40 ECD by SPR, cell binding, and activity in an OX40 reporter assay.

DSC to determine the mid-point of the temperature-induced unfolding (Tm) of the anti-OX40 scFv was conducted using a MicroCal VP-Capillary DSC system (Malvern Instrument). An exact match of buffer, PBS pH 7.4, was used as the reference. 500 μL of a 0.5 mg/mL solution of each protein sample with reference was loaded on the instrument and heated from 25° C. to 100° C. at a rate of one degree Celsius per minute. Melting curves were analyzed using Origin 7 platform software MicroCal VP-Capillary DSC Automated Analysis Software to derive the Tm values. Surface plasmon resonance was used to determine the binding affinity of the OX40 binding domains as described in Example 5.

As shown in Table 3, a significant increase in expression was obtained with two variants (OXF01099 and OXF01115) compared to the unmodified parent construct (OXF01022). The thermal stability was improved from 55.7 to greater than 60° C., while retaining similar binding affinity to the parent binding domain. The improved expression and Tm values suggest that the variants have improved stability and solubility, which are considered beneficial properties of therapeutic protein drugs.

TABLE 3

Summary of expression, thermostability and affinity of preferred anti-OX40 variants compared to the parent sequence

| Construct Details | Expression Titer | DSC Tm1 | Affinity to human OX40 ECD by SPR | | |
|---|---|---|---|---|---|
| Name | μg/mL | (° C.) | Ka (1/Ms) | Kd (1/s) | KD (nM) |
| OXF01122 (Parent) | 163 | 55.7 | 3.4E+05 | 2.1E−04 | 0.6 |
| OXF01099 | 285 | 61.4 | 5.3E+05 | 1.4E−04 | 0.3 |
| OXF01115 | 326 | 66.6 | 3.9E+05 | 2.6E−04 | 0.7 |

Figure 5A:
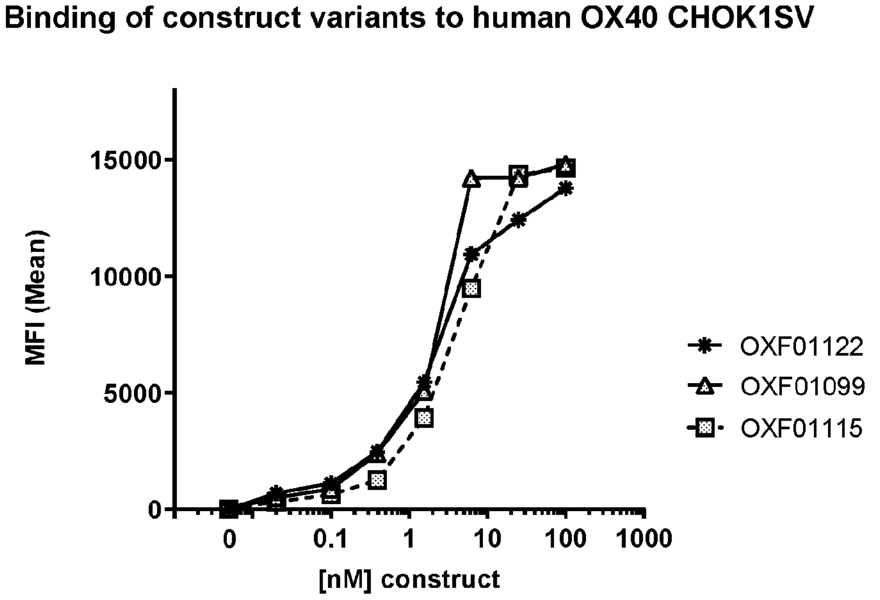
FIGS. 5A and 5B show binding of anti-OX40 constructs to human (5A) or cynomolgus (5B) OX40-expressing CHOK1SV cells. Serial dilutions of ADAPTIR™ constructs were incubated with CHOK1SV cells transfected with human or cynomolgus OX40 and subsequently labelled with a fluorescently-conjugated goat-α-human Fe secondary antibody. The y-axis displays the MFI. (See Example 9.)
Figure 5B:
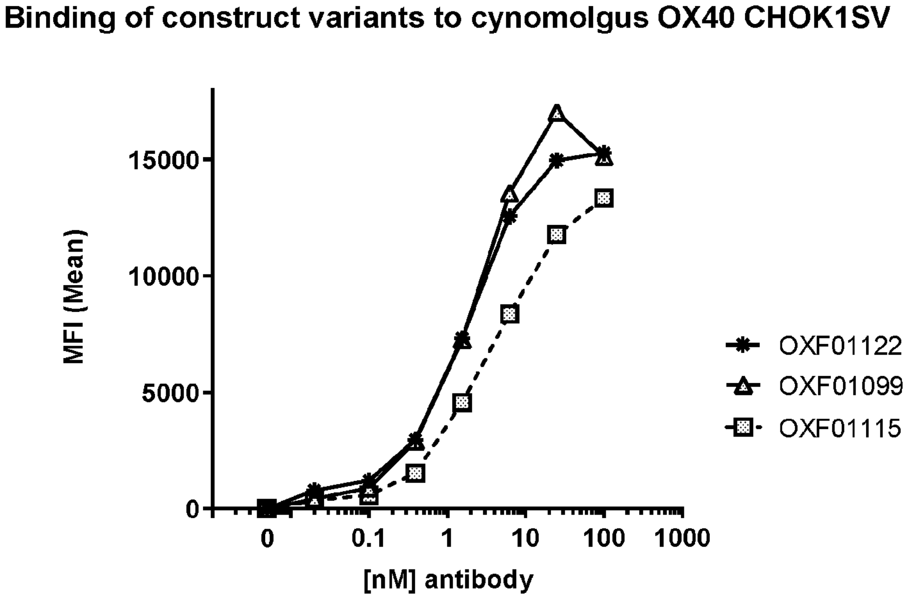

Example 9. Evaluation of Cell Binding and In Vitro Activity of OXF171 Anti-OX40 scFv Variants Binding studies were used to confirm binding of preferred anti-OX40 variants to human and cynomolgus OX40. As shown in FIGS. 5A and 5B, binding of various anti-OX40 constructs (OXF01122, OXF01099 and OXF01115) to CHO cells stably expressing either human OX40 or cynomolgus OX40 protein. There was no detectable differences in binding between the parent and anti-OX40 scFv variants.

Figure 6:
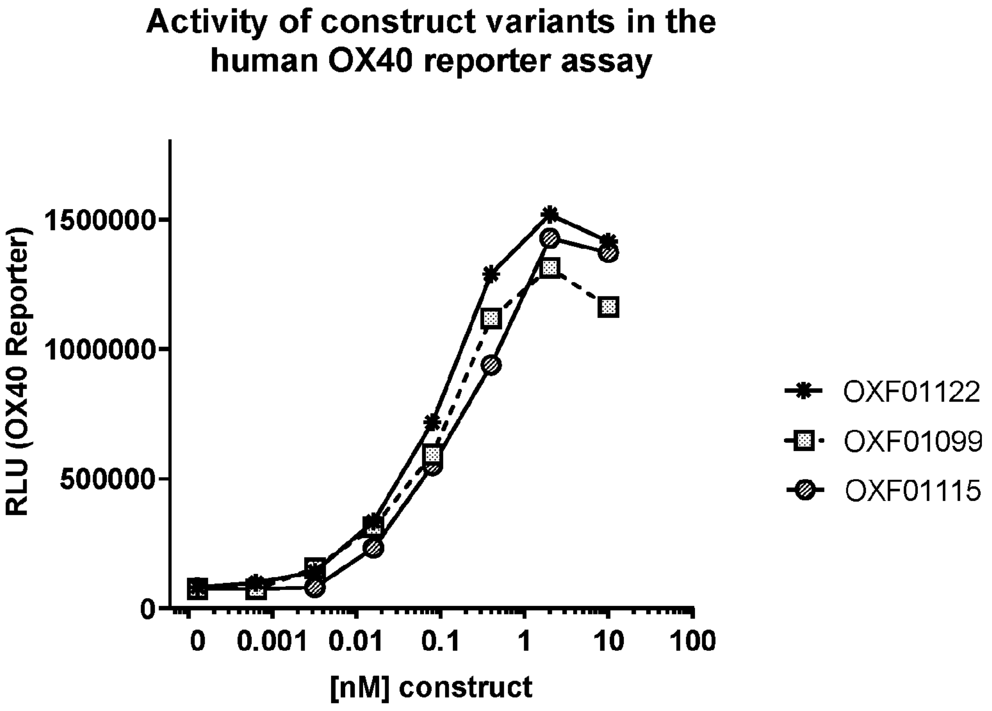
FIG. 6 shows a comparison of the activity of anti-OX40 constructs in their preferred orientation in the functional OX40 reporter assay. Serially diluted constructs were run side-by-side with an NFκB/OX40 reporter cell line and CHO/CD64 target cells for five hours, followed with the addition of Bio-Glo. The y-axis displays the RLU. (See Example 9.)

To compare the ability of different OX40-binding constructs to induce target-dependent activation of OX40, a luciferase reporter assay was used. The experimental setup was described in Example 6, with modifications. CHO-K1 expressing CD64 (FcγRI) were used to crosslink the wild-type Fc of these constructs. FIG. 6 demonstrates the activity of anti-OX40 constructs as being similar. A summary of the binding and reporter assay is shown in Table 4.

TABLE 4

Summary of cell binding and reporter assay data of preferred anti-OX40 variants compared to the parent sequence.

| | Construct Details | | | | | |
|---|---|---|---|---|---|---|
| | OX40 Reporter Assay | | Binding to human OX40/CHO | | Binding to cyno OX40CHO | |
| Name | EC50 pM | Max induction | EC50 nM | max MFI | EC50 nM | max MFI |
| OXF01122 (Parent) | 89 | 1519155 | 2.2 | 13783 | 1.8 | 15269 |
| OXF01099 | 182 | 1427969 | 4.0 | 14647 | 4.0 | 13336 |
| OXF01115 | 88 | 1313128 | 2.1 | 14806 | 1.8 | 17019 |

Example 10. Generation of 4-1BB Antibodies by Immunization of Wild-Type Mice 4-1BB-specific antibodies were isolated from a hybridoma library generated after immunizing BABLB/c and NZB/W mice with recombinant human 4-1BB protein antigen (ImmunoPrecise Antibodies Victoria, B.C. CAN). Supernatants from hybridoma clones were assayed by ELISA, and identified wells were confirmed for specific binding using flow cytometry on CHO cells transfected with human and cynomolgus 4-1BB. Positive clones were selected for expansion, and viable cells were frozen for RNA extraction and variable domain analysis. Supernatants were saved for additional analyses.

The variable heavy (VH) and light (VL) domain sequences for selected hybridoma clones were obtained by RT-PCR after isolating total RNA. Briefly, total RNA was isolated from the hybridoma clone cell banks using Qiagen's RNeasy Plus Kit (Qiagen, Venlo Netherlands), and 400 ng of total RNA were used in a First Stand cDNA synthesis reaction using oligo dT and Superscript IV (Thermo Fisher Scientific Waltham, MA), following manufacturer's protocol. Following cDNA synthesis, the variable region cDNA was amplified using 1 μL of cDNA and a series of primer mixes for mouse IgG VH, $V_\kappa$, and $V_\lambda$ (Novagen Mouse Ig-Primer Set, EMD Millipore Temecula, CA). PCR products for each clone were directly sequenced using the reverse (constant domain) PCR primer and standard Sanger sequencing methods. Sequences were then converted to scFv by amplifying the variable domains using specific primers that contain overlapping sequences and were assembled into a mammalian expression vector using NEBuilder HiFi DNA Assembly Cloning Kit (New England Biolabs, Beverly MA).

Example 11. Humanization of Clone 6, 41BB Antibody in scFv Format

After evaluation of the hybridoma derived antibodies, Clone 6 was selected for humanization and further optimization. The primary purpose was to eliminate as much of the mouse derived sequence as possible to minimize potential immunogenicity and optimize the binding and stability properties of the binding domain. Clone 6 anti-41BB murine monoclonal antibody (VH SEQ ID NO:19; VL SEQ ID NO:20; see also FIG. 7) was humanized in 3 stages. Stage 1 used the BioLuminate software package release 2018-2 (Schrodinger, LLC, New York, USA). A homology model of mouse Clone 6 was created based on PDB ID 1JV5, and the most geometrically suitable and homologous human frameworks for CDR grafting were identified using the software's default and modified settings. Nineteen CDR-grafted molecules were produced and tested for binding to cells expressing full length human- or cyno-41BB (data not shown). Molecule FOB01143 (FOBW006HLH20) SEQ ID NO:43, graft based on PDB ID 5117, was shown to have similar binding properties to the parental mAb Clone 6 (data not shown). In Stage 2, framework residues were mutated in sets and combinations of sets to convert mouse residues of FOB01143 to human germline sequences IGHV1-46*01 and IGHJ4*01 for heavy chain and IGKV3D-7*01 and IGKJ1*01 for light chain. Molecule FOB01188 (FOBW0061HLH26), SEQ ID NO:45, was identified to carry the best combination of binding, functional, and developability properties (data not shown). In Stage 3, each individual residue different from human V-gene germline was mutated to germline, and the set of mutant molecules was characterized first for binding to human- and cyno-41BB recombinant proteins (SEQ ID NOs:1 and 2, respectively) using Biacore 8K (GE Healthcare Life Sciences, USA) and then for stability by measuring Tm and Tagg using the Uncle instrument (Unchained Labs, USA) (data not shown). By incorporating all benign mouse-to-human germline amino acid changes into FOB01188 molecule, a final molecule FOBW006HLH40 was created. The sequence of this molecule is 92% identical to IGHV1-46*01 and 94% identical to IGKV3D-7*01. All non-germline residues are essential for either binding of stability. The progression from mouse to humanized sequences in amino acid alignment is shown in FIG. 7 (from mouse Clone 6 to humanized FOBW006HLH40).

Example 12. Production and Biophysical Evaluation of Partial Humanized Versions of Anti-41BB Clone 6

Different humanized versions of the Clone 6 scFv were produced as monospecific DNA constructs by attaching the scFv sequence to the C-terminus of a wildtype IgG1 Fc in the VH-VL orientation. Following transient expression and purification, these constructs were characterized for thermal stability by differential scanning fluorimetry (DSF) and binding affinity to human and cyno 41BB ECD. DSF was performed on samples and examined in triplicate on a 7500 Fast Real-Time PCR System (Thermo Fisher Scientific) in dPBS at 0.125 mg/mL with SYPRO Orange (Life Technologies) added to a final concentration of 5×. Samples were heated from 25° C. to 95° C. at a scan rate of 0.9° C./min. Average transition mid-point values (Tm) were determined using the ProteoStat® ProProtein Thermal Shift™ Software v1.0 (Thermo Fisher Scientific). Binding affinity was performed as described above.

This data verified that the binding and thermal stability was not negatively impacted by elimination of the mouse sequence. The humanized construct (FOB01188) was compared to a chimeric molecule that consisted of the human IgG1 Fc and mouse scFv sequence (FOB01143). The Tm values for both the mouse and humanized scFv were both 69° C., suggesting that the stability of the molecule was unchanged (Table 5). The binding affinity determined by SPR indicated that tighter binding was achieved to both human and cyno 4-1BB ECD (Table 5) as a result of the humanization process.

TABLE 5

Summary of thermostability and binding affinity of partial humanized variant of Clone 6 anti-41BB scFv

| | DSF | Affinity to Human 4-1BB | | | Affinity to Cyno 4-1BB | | |
|---|---|---|---|---|---|---|---|
| Construct ID | Tm1 (° C.) | KD (nM) | Ka (1/Ms) | Kd (1/s) | KD (nM) | Ka (1/Ms) | Kd (1/s) |
| FOB01143 (Mouse) | 69.4 | 38 | 6.8E+04 | 2.6E−03 | 89 | 4.4E+04 | 3.9E−03 |
| FOB01188 (Partially Humanized) | 69.0 | 25 | 8.2E+04 | 2.1E−03 | 61 | 5.3E+04 | 3.2E−03 |

Figure 8A:
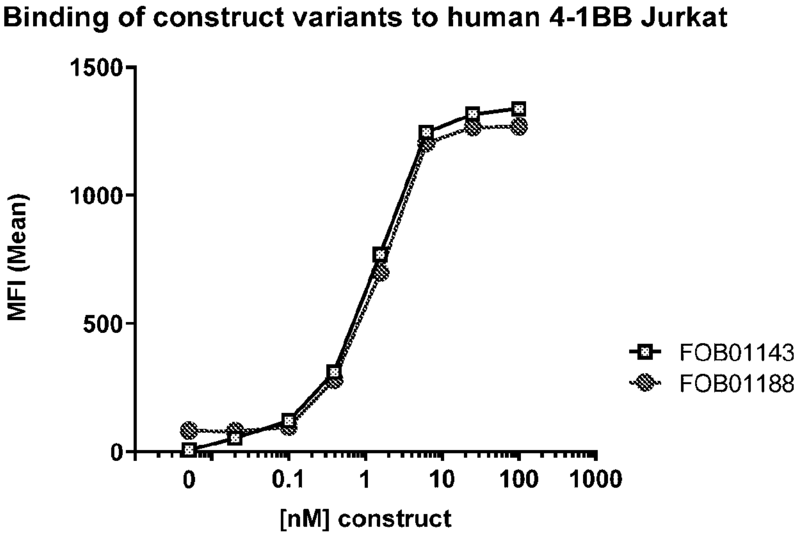
FIGS. 8A and 8B show binding to human (8A) or cynomolgus (8B) 4-1BB-expressing Jurkat cells. FOB011043 (mouse) and FOB01188 (partially humanized) 4-1BB constructs are shown, respectively. Serial dilutions of ADAPTIR™ constructs were incubated with Jurkat cells transfected with human or cynomolgus 4-1BB and subsequently labelled with a fluorescently-conjugated goat-α-human Fc secondary antibody. The y-axis displays the MFI. (See Example 13.)
Figure 8B:
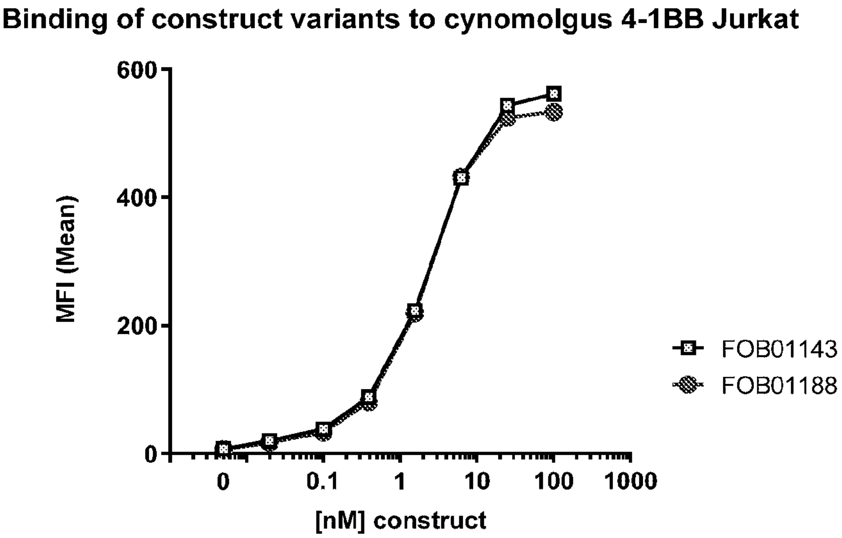

Example 13. Cell Binding and In Vitro Activity of Partially Humanized Version of Anti-41BB Clone 6 scFv Using the general methods described in Example 6, using Jurkat cells, stably expressing the full length human or cynomolgus 4-1BB protein, it was verified that the human modifications made to FOB01143, resulting in construct FOB01188, did not negatively inhibit binding affinity to either human 4-1BB or cynomolgus 4-1BB protein (Table 6, FIGS. 8A and 8B).

Figure 9:
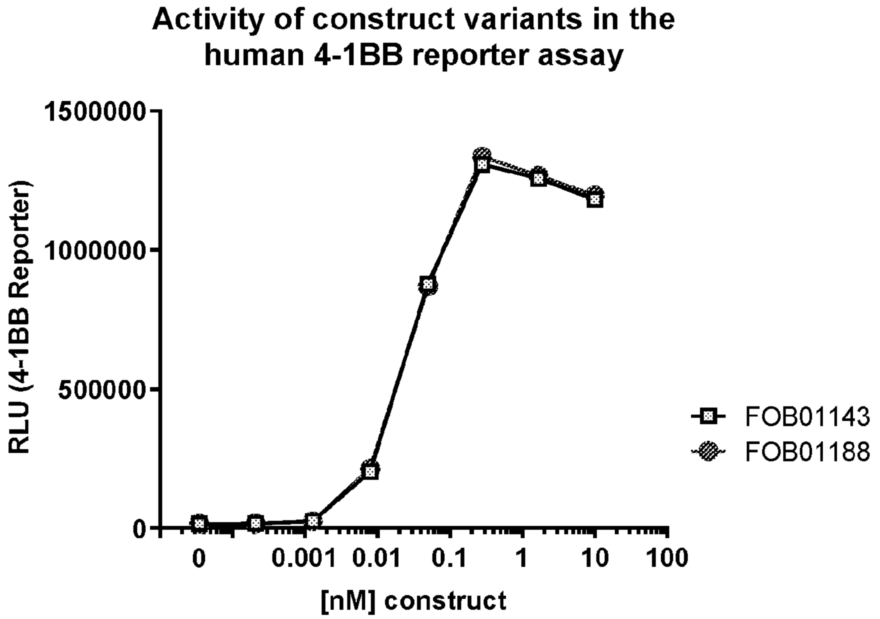
FIG. 9 shows a comparison of activity of murine (FOB01143) and partially humanized (FOB01188) anti-4-1BB constructs in the functional human 4-1BB reporter assay. Serially diluted constructs were run side-by-side with an NFκB/4-1BB reporter cell line and CHO/CD64 target cells for 5 hours, followed with the addition of Bio-Glo. The y-axis displays the RLU. (See Example 13.)
Figure 10A:
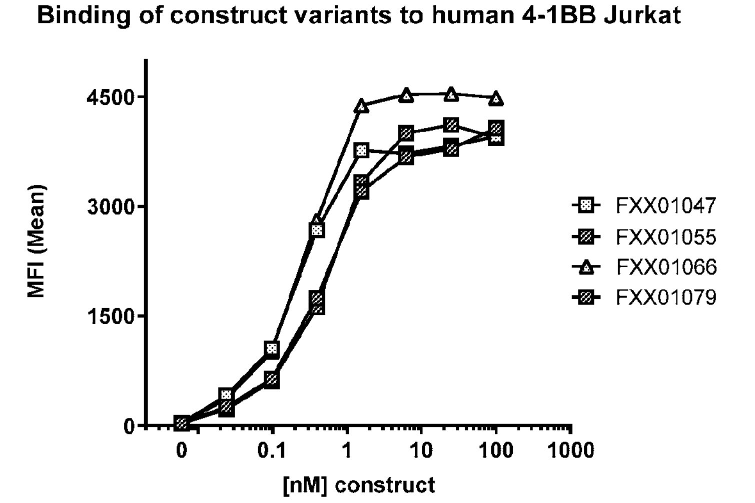
FIGS. 10A-10D show binding of anti-4-1BB×anti-OX40 constructs, with Tm stabilizing mutations in OX40 and additional humanization in 4-1BB, to human (10A) or cynomolgus (10C) 4-1BB-expressing Jurkat cells or human (10B) or cynomolgus (10D) OX40-expressing CHOK1SV cells. Serial dilutions of ADAPTIR™ constructs were incubated with cells transfected with human or cynomolgus ECD and subsequently labelled with a fluorescently-conjugated goat-α-human Fc secondary antibody. The y-axis displays the mean MFI. (See Example 16.)
Figure 10B:
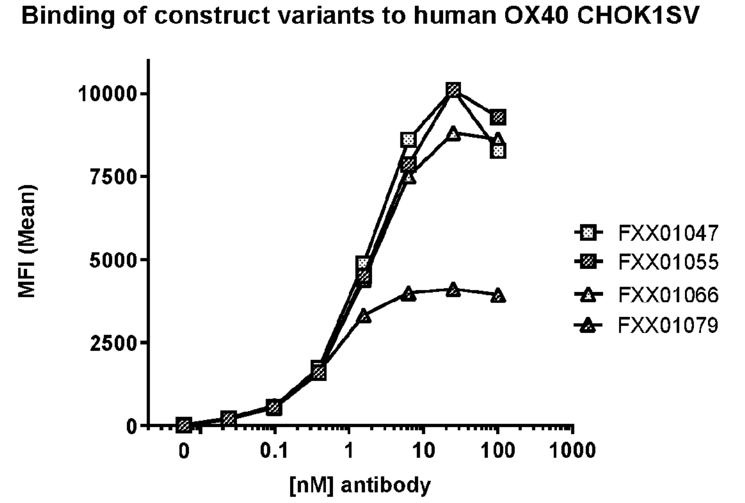
Figure 10C:
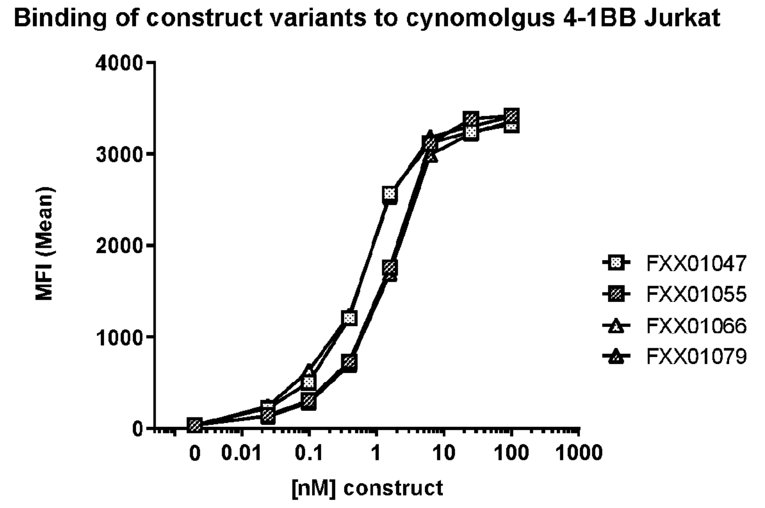
Figure 10D:
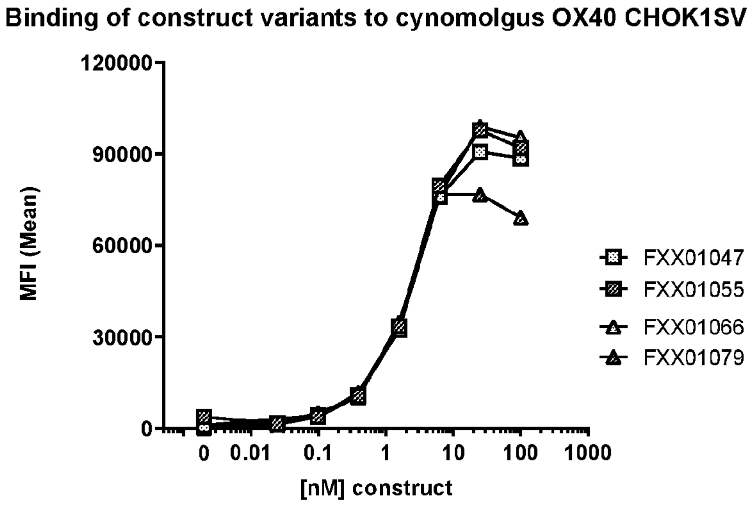

To compare the activity of different 4-1BB-binding constructs to induce target-dependent activation of 4-1BB, a luciferase reporter assay was used. The experimental setup was as described in Example 6, but using CHO-K1 expressing CD64 (FcγRI) as the target cell to crosslink 4-1BB via binding to the wildtype Fc of these constructs. A human 4-1BB-expressing NFκB reporter line was generated in-house and utilized herein to determine activity. The observed $EC_{50}$ values for activity of both constructs was 28 pM. These data (Table 6, FIG. 9) demonstrated that activity was not impacted by eliminating mouse sequence.

TABLE 6

Summary of cell binding and reporter assay data of humanized variants of the Clone 6 anti-41BB scFv

| | Construct Details | | | | | | | |
|---|---|---|---|---|---|---|---|---|
| | Reporter Assay CD64/CHO | | Reporter Assay CD64/CHO | | Binding to human 41BB/CHO | | Binding to cyno 41BB/CHO | |
| Name | EC50 pM | Max induction | EC50 pM | Max induction | EC50 nM | max MFI | EC50 nM | max MFI |
| FOB01143 (Mouse) | 28 | 1307559 | 54 | 1098725 | 1.2 | 1338 | 2.4 | 561 |
| FOB01188 (Partially Humanized) | 28 | 1336019 | 59 | 1081756 | 1.4 | 1268 | 2.2 | 533 |

Example 14: Assembly of 41BB×OX40 Bispecific Proteins

A subset of 41BB and OX40 binding domains were combined into bispecific proteins FXX01047, FXX01055, FXX01066, and FXX01079 (see Table 7; SEQ ID NOs:86, 87, 78, 88). Individual binding domains were amplified by PCR and assembled with DNA fragment encoding Fc and linearized expression vector using standard molecular biology techniques.

Example 15: Production and Biophysical Characterization of 4-1BB and OX40 Bispecific Proteins with Additional Humanization Mutations and Altering Position of OX40 and 4-1BB Binding Domains Following transient expression in CHO cells and purification, 4-1BB×OX40 bispecific proteins were examined for the impact of incorporation of additional human sequences to the anti-4-1BB scFv (FOB01188), as well as to determine the preferred orientation. These comparisons were performed with the set of constructs described in Table 7.

TABLE 7

Description of bispecific constructs evaluated for preferred position of anti-OX40 and anti-4-1BB scFvs

| Construct Name | N-Term scFv | C-Term scFv | Additional Humanization Mutations in 41BB Binding Domain? | Additional Tm Stabilizing Mutation in OX40 Binding Domain? |
|---|---|---|---|---|
| FXX01047 | Anti-4-1BB | Anti-OX40 | No | Yes |
| FXX01055 | Anti-OX40 | Anti-4-1BB | No | No |
| FXX01066 | Anti-4-1BB | Anti-OX40 | Yes | Yes |
| FXX01079 | Anti-OX40 | Anti-4-1BB | Yes | No |

Comparison of the constructs indicates that the transient CHO expression levels are improved when the anti-OX40 binding domain is located on the N-terminus of the protein (Table 8, FXX01055 vs FXX01047 and FXX01079 vs FXX01066). Presence of the additional human residues in FXX01066 and FXX01079 results in better expression of both orientations of the target binding domains when compared to the pair of proteins without these changes. FXX01066 and FXX01079 also had better resistance to aggregation, based on the % change in purity after storage for one week at 4 and 40° C., determined by integrating the product peak area on analytical SEC. Comparison of constructs with the same orientation, but differing in the inclusion of the humanization mutations shows a smaller amount of aggregate is formed with the more human constructs (FXX01066 vs. FXX01047, FXX01079 vs FXX01055) supporting that they are more stable. The position of the target binding domains impacted the amount of degraded product measured after the initial ProA purification step had been performed. ProA eluate samples were also analyzed on analytical Size Exclusion Ultra Performance Liquid Chromatography (analytical SE-UPLC) due to the greater resolving power of this method. Analysis was performed on a Waters ACQUITY UPLC instrument and utilized two BEH SEC columns (200 Å, 1.7 μm, 4.6 mm×300 mm) connected in tandem, using a potassium phosphate/potassium chloride running buffer. Generally, 10 μg was injected and a 75 minute method running at a 0.15 mL/min flow rate. Following integration to obtain the peak areas, the data indicated that constructs with the anti-4-1BB scFv in the N-terminal position were more resistant to the formation of clipped product. This is based on the larger percentage of low molecular weight contaminants present in FXX01055 and FXX01079 compared to FXX01047 and FXX01066.

TABLE 8

Comparison of expression, homogeneity and stability of select 4-1BB × OX40 bispecific proteins

| Construct | Expression (μg/mL) | Change in % MP Day 7 @ 4° C. | Change in % MP Day 7 @ 40° C. | % Low Molecular Weight Contaminants |
|---|---|---|---|---|
| FXX01047 | 109 | −0.3 | −1.8 | 0.0 |
| FXX01055 | 155 | −2.3 | 0.0 | 12.0 |
| FXX01066 | 179 | −0.2 | −2.0 | 0.0 |
| FXX01079 | 242 | 0.6 | −0.1 | 19.9 |

The binding affinity of these four variants to the human extracellular domains of OX40 and 4-1BB was determined (Table 9). The binding affinity to OX40 was not significantly impacted by either the relative position of the anti-target scFvs or the additional humanization mutants included in FXX01066 and FXX01079. The affinity to 4-1BB was determined to be tighter when the anti-4-1BB scFv was positioned on the N-terminus of the bispecific construct.

TABLE 9

Binding affinity of select 4-1BB × OX40 bispecific proteins

| | Affinity to human 41BB ECD by SPR (T200) | | | Affinity to human OX40 ECD by SPR (T200) | | |
|---|---|---|---|---|---|---|
| Construct Name | KD (nM) | Ka (1/Ms) | Kd (1/s) | KD (nM) | Ka (1/Ms) | Kd (1/s) |
| FXX01047 | 7 | 2.8E+05 | 2.0E−03 | 0.4 | 4.0E+05 | 1.6E−04 |
| FXX01055 | 21 | 8.4E+04 | 1.8E−03 | 0.3 | 4.4E+05 | 1.3E−04 |
| FXX01066 | 14 | 3.0E+05 | 4.4E−03 | 0.4 | 3.8E+05 | 1.4E−04 |
| FXX01079 | 37 | 1.0E+05 | 3.8E−03 | 0.3 | 4.5E+05 | 1.2E−04 |

Example 16: Cell Binding and In Vitro Activity of 4-1BB and OX40 Bispecific Proteins with Additional Humanization Mutations and Altering Position of OX40 and 4-1BB Binding Domains Flow cytometry was used to quantitate and confirm binding of 4-1BB×OX40 bispecific proteins using cell lines expressing either human or cynomolgus OX40 and human or cynomolgus 4-1BB. As shown in FIGS. 10A-D and Table 10, the variants do not display a difference in binding due either the additional humanization or position of the binding domains. There is a preference for the anti-4-1BB scFv to reside on the N terminus, as FXX01047 and FXX01066 have slightly lower EC50 than FXX01055 and FXX01079. Additionally, cynomolgus OX40 binding is reduced in FXX01079.

Figure 11A:
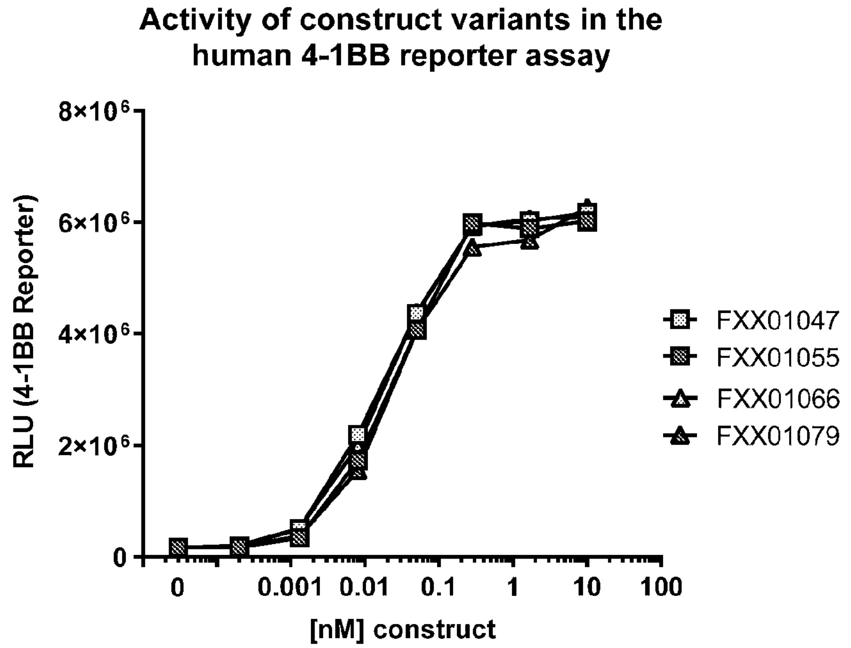
FIGS. 11A and 11B show the functionality of anti-4-1BB×anti-OX40 constructs, with Tm stabilizing mutations in OX40 and additional humanization in 4-1BB, to induce NFκB signaling. (11A) In the 4-1BB reporter assay, OX40-expressing CHOK1SV were used for crosslinking. (11B) In the OX40 reporter assay, 4-1BB expressing Jurkat cells were added for crosslinking. Serially diluted constructs were incubated with target cells and an NFκB reporter cell line for 5 hours, followed with the addition of Bio-Glo. The y-axis displays the RLU. (See Example 16.)
Figure 11B:
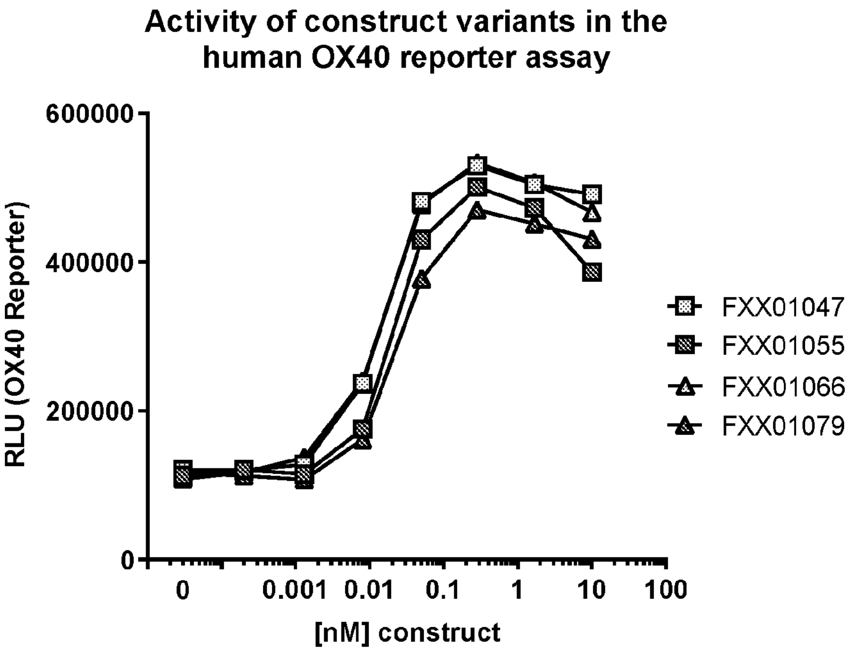
Figure 12A:
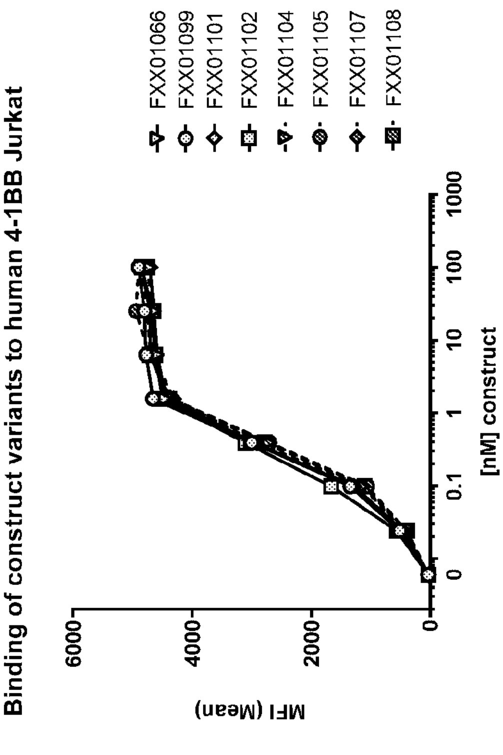
Figure 12B:
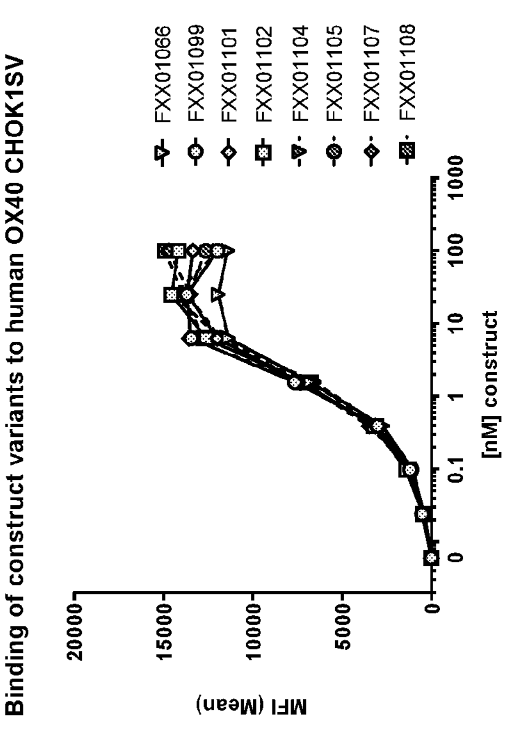
Figure 12C:
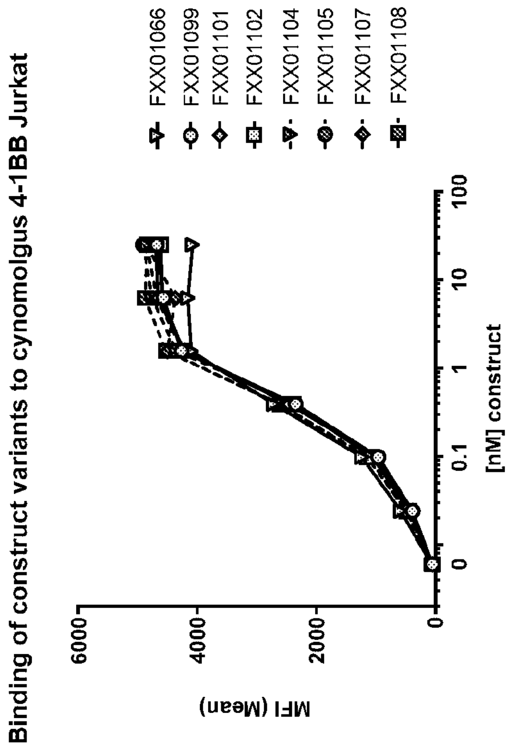
Figure 12D:
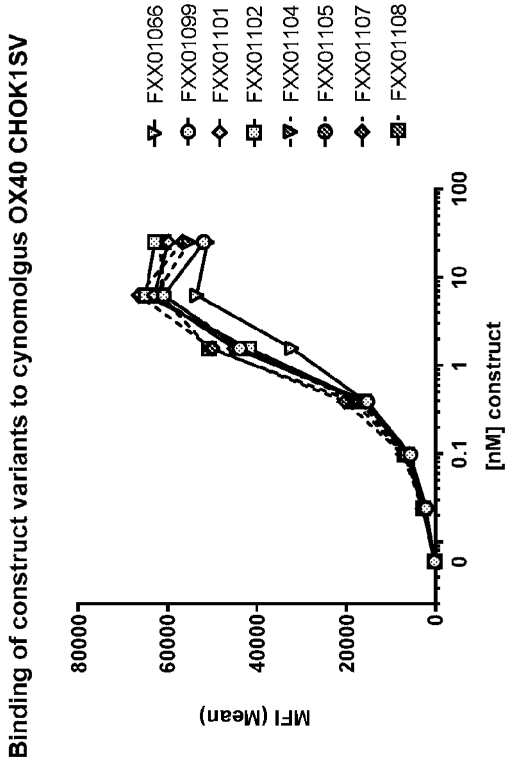

To compare the activity of 4-1BB×OX40 bispecific proteins, two luciferase reporter lines were utilized in separate assays. OX40- or 4-1BB-expressing cells were used to bind and induce crosslinking via the anti-receptor binding domain on the other end of the bispecific. To quantitate 4-1BB activity, the human 4-1BB NFκB luciferase reporter line was incubated with OX40-expressing CHO-K1 target cells. Conversely, to examine OX40 activity, the human OX40 NFκB luciferase reporter line was added along with the target 4-1BB-expressing Jurkat cells. In both assays 30,000 reporter and target cells were added to diluted 4-1BB×OX40 protein and incubated in reporter media containing 5% FBS for 5 hours. As demonstrated in FIG. 11A, the 4-1BB activity of FXX01047, FXX01055, FXX01066, and FXX01079 are undistinguishable and are not impacted by the scFv position or sequence modifications in the anti-4-1BB binding domain. The OX40 reporter assay indicates that there is a preference for the anti-OX40 scFv to be positioned on the C-terminus (FIG. 11B), whereas the alterations to sequence did not influence activity. A summary of human binding and reporter assays is displayed in Table 10.

TABLE 10

Summary of cell binding and reporter assay data of humanized variants of the Clone 6 anti-41BB scFv

| | Construct Details | | | | | | | |
|---|---|---|---|---|---|---|---|---|
| | 4-1BB Reporter Assay | | OX40 Reporter Assay | | Binding to human 41BB/Jurkat | | Binding to human OX40/CHO | |
| Name | EC50 pM | Max induction | EC50 pM | Max induction | EC50 nM | Max MFI | EC50 nM | Max MFI |
| FXX01047 | 14 | 6581841 | 10 | 1968922 | 0.32 | 4945 | 0.35 | 10487 |
| FXX01055 | 13 | 6818255 | 13 | 2029136 | 0.27 | 4747 | 0.40 | 10407 |
| FXX01166 | 19 | 6104367 | 12 | 533567 | 0.27 | 4542 | 1.5 | 8621 |
| FXX01179 | 25 | 6264343 | 23 | 470294 | 0.53 | 4115 | 1.4 | 9822 |

Example 17: Evaluation of Orientation of 4-1BB scFv and Framework Sequence Modifications of the Anti-OX40 scFv to Modify Isoelectric Point (pI)

To further optimize the bispecific molecule, the order of domains was evaluated in the anti-41BB scFv and germline-derived mutations were included to increase isoelectric point of the anti-OX40 scFv. The anti-41BB clone 6 mAb in scFv format was humanized in all stages in the VH-VL format. A set of variants was produced to evaluate the behavior of the anti-41BB in the VL-VH and VH-VL orientation. As part of this set of constructs, modifications to alter the pI of the anti-OX40 scFv were also included. These were constructed by first analyzing highly homologous germline human frameworks of IGHV3-30*03 and IGLV3-21*02 and identifying charge-changing and surface exposed positions distant from the CDRs. T86R is present in IGHV3-30*13 and Q17K in IGLV3-21*01 and was included to increase the overall pI of the protein. Side-directed mutagenesis was performed to create T86R and Q17K changes individually and in the combination.

Example 18: Production and Characterization of Anti-4-1BB×Anti-OX40 Bispecifics to Evaluate the Orientation of 4-1BB scFv and Framework Sequence Modifications of the Anti-OX40 scFv to Modify Isoelectric Point (pI)

Protein was produced by transient expression, purified by ProA chromatography and prep SEC. Following purification, the protein concentration of each sample was adjusted to 1 mg/mL in PBS and examined via several assessments of stability and binding affinity. The orientation of the anti-4-1BB scFv, when in the N-terminal position of the bispecific construct, did not have a significant impact on the binding affinity to human 4-1BB ECD as measured by SPR (Table 11). Similarly, changes made in the framework regions of the anti-OX40 binding domain did not alter the tight binding to Human OX40 ECD. Assessments of protein stability did not show significant differences as a result of these changes (data not shown).

TABLE 11

Binding affinity of 4-1BB × OX40 bispecific proteins with both orientations of the anti-4-1BB

| | Construct composition | | | Affinity to human 41BB ECD | | | Affinity to human OX40 ECD | | |
|---|---|---|---|---|---|---|---|---|---|
| Construct Name | OXF pI changes Q -> K | OXF pI changes T -> R | Anti-41BB scFv Orientation | KD (nM) | Ka (1/Ms) | Kd (1/s) | KD (nM) | Ka (1/Ms) | Kd (1/s) |
| FXX01066 | no | no | HL | 15 | 2.9E+05 | 4.5E−03 | 0.5 | 6.8E+05 | 3.1E−04 |
| FXX01099 | yes | no | HL | 14 | 3.3E+05 | 4.6E−03 | 0.4 | 7.7E+05 | 2.8E−04 |
| FXX01101 | no | yes | HL | 16 | 2.9E+05 | 4.6E−03 | 0.6 | 6.3E+05 | 4.1E−04 |
| FXX01102 | yes | yes | HL | 15 | 2.9E+05 | 4.3E−03 | 0.4 | 7.1E+05 | 3.0E−04 |
| FXX01104 | no | no | LH | 17 | 3.2E+05 | 5.5E−03 | 0.5 | 7.1E+05 | 3.2E−04 |
| FXX01105 | yes | no | LH | 19 | 2.9E+05 | 5.5E−03 | 0.4 | 7.1E+05 | 2.7E−04 |
| FXX01107 | no | yes | LH | 18 | 3.1E+05 | 5.6E−03 | 0.5 | 6.3E+05 | 2.9E−04 |
| FXX01108 | yes | yes | LH | 18 | 3.1E+05 | 5.5E−03 | 0.8 | 4.8E+05 | 3.9E−04 |

Example 19: Cell Binding and In Vitro Activity of 4-1BB and OX40 Bispecific Proteins to Evaluate the Orientation of 4-1BB scFv and Framework Sequence Modifications of the Anti-OX40 scFv to Modify Isoelectric Point (pI)

Cell binding studies were completed to demonstrate that the ADAPTIR™ scFv binding domains bound sufficiently to cells expressing human or cynomolgus 4-1BB or OX40. Binding studies were performed using the flow cytometry-based staining procedures described above. These data show that there is little variation in either human (FIGS. 12A and 12B) or cynomolgus (FIGS. 12C and 12D) binding for proteins FXX01066, FXX01099, FXX01101, FXX01102, FXX01104, FXX01105, FXX01107 and FXX01108. In addition, these proteins did not show any non-specific binding to parental CHO-K1 SV (FIG. 13). Thus, there this no detriment to binding with the addition of pI changes to the anti-OX40 scFv or with alternative orientations of the anti-4-1BB scFv.

Figure 14A:
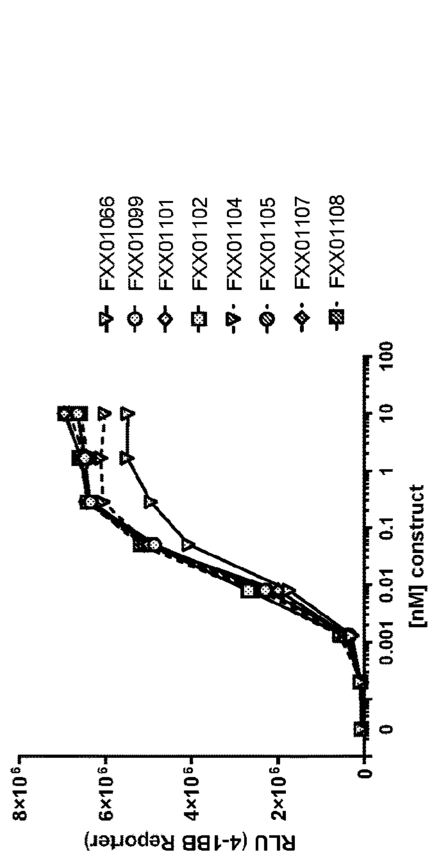
Figure 14B:
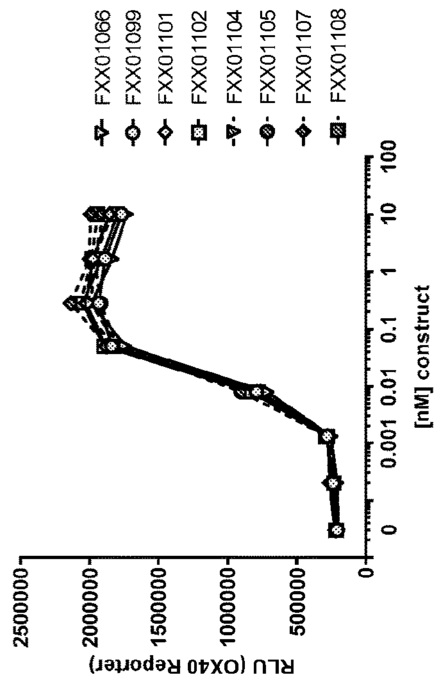
Figure 14C:
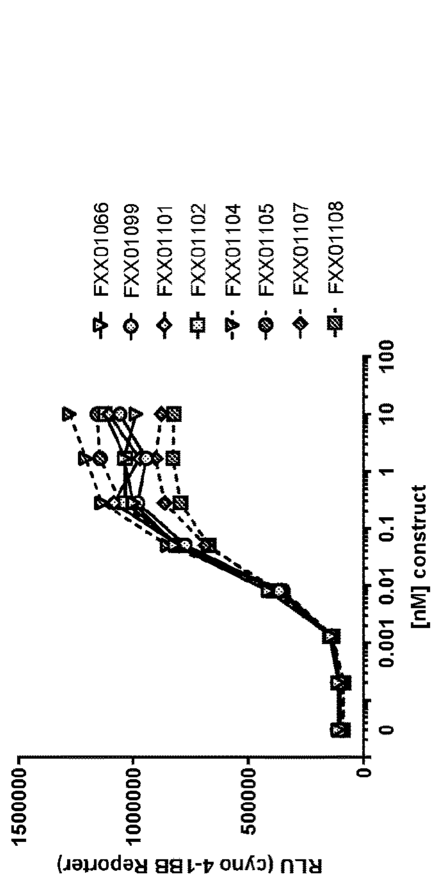
Figure 14D:
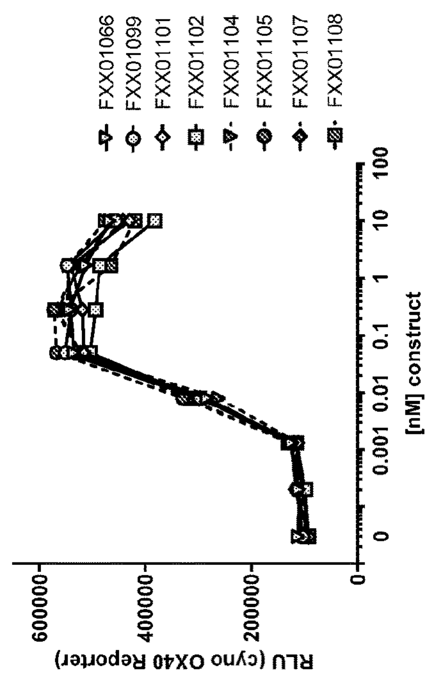

Activity assays were utilized to demonstrate the ability to induce NFκB signaling when crosslinking either OX40 or 4-1BB in the 4-1BB or OX40 reporter assay, respectively. In this set of experiments, both human and cynomolgus expressing 4-1BB or OX40 NFκB reporter lines were assessed in this screen. The cynomolgus reporter lines were generated and cloned in-house. The data in FIG. 14A show that there is a small increase in the maximum activity in the human 4-1BB activity in proteins above those generated by the parental FXX01066. In contrast, activity in the cynomolgus 4-1BB reporter (FIG. 14C) displays variation in the maximum RLU, such that constructs with the anti-4-1BB scFv in the VLVH orientation with the T86R pI mutation was marginally lower than any constructs in the VHVL orientation and significantly lower than constructs without the T86R pI mutation. FIGS. 14B and 14D display no differences in the EC50 or max RLU in the human or cynomolgus OX40 reporter assay. A summary of human binding and reporter assays displayed in Table 12.

To determine the non-specific activity induced by these various constructs, 4-1BB and OX40 reporter assays were conducted. Instead of using OX40- or 4-1BB-expressing cell lines (respectively) for crosslinking, parental CHO-K1 SV cells were used in their place. Without crosslinking, these constructs should not induce NFκB signaling. Without crosslinking, 4-1BB in the VLVH orientation induces significant NFκB signaling (FIG. 15A). The non-specific activity was significantly less when 4-1BB was in the VHVL orientation. These proteins did not induce non-specific activity in the human OX40 reporter assay when crosslinked with parental CHO-K1 SV (FIG. 15B).

TABLE 12

Summary of cell binding and reporter assay data of humanized variants of the Clone 6 anti-41BB scFv

| | Construct Details | | | | | | | |
|---|---|---|---|---|---|---|---|---|
| | 4-1BB Reporter Assay | | 0X40 Reporter Assay | | Binding to human 41BB/Jurkat | | Binding to human OX40/CHO | |
| Name | EC50 pM | Max induction | EC50 pM | Max induction | EC50 nM | max MFI | EC50 nM | max MFI |
| FXX01066 | 18 | 5498052 | 12 | 1988345 | 0.23 | 4712 | 0.29 | 10356 |
| FXX01099 | 17 | 6650047 | 10 | 1934075 | 0.25 | 4903 | 0.36 | 10407 |
| FXX01101 | 19 | 6957507 | 11 | 2028891 | 0.25 | 4850 | 0.31 | 10452 |
| FXX01102 | 14 | 6936322 | 10 | 2052673 | 0.18 | 4847 | 0.34 | 10549 |
| FXX01104 | 11 | 6106857 | 13 | 1991890 | 0.31 | 4855 | 0.32 | 10418 |
| FXX01105 | 14 | 6581841 | 10 | 1968922 | 0.33 | 4945 | 0.35 | 10487 |
| FXX01107 | 16 | 6847288 | 13 | 2137685 | 0.26 | 4703 | 0.29 | 10254 |
| FXX01108 | 13 | 6613976 | 13 | 2069456 | 0.29 | 4766 | 0.32 | 10337 |

Example 20: Anti-4-1BB×Anti-OX40 ADAPTIR™ Bispecific Treatment is Synergistic Compared to Treatment with Anti-4-1BB Plus Anti-OX40 Monospecific Proteins In Vitro Co-stimulation of OX40 during clonal expansion has been demonstrated to promote the increased survival of activated T cells (Rogers, P. R., et al., *Immunity,* 15(3): 445-55 (2001) and Weatherill, A. R., et al., *Cell Immunol,* 209(1): 63-75 (2001)). Therefore, the ability of anti-4-1BB× anti-OX40 ADAPTIR™ constructs to augment the number of T and NK cells in vitro was examined. Peripheral blood mononuclear cells (PBMC) were isolated from normal donor and incubated with serially diluted concentrations of ADAPTIRs™ in the presence α-CD3 (signal 1), which upregulates 4-1BB and OX40 expression (signal 2). In this particular experiment, an anti-OX40 monospecific construct with the scFv on the N-terminus of the Fc region of a wildtype IgG1 (OXF01070) and an anti-4-1BB monospecific construct with the scFv on the C-terminus of the Fc region of a wildtype IgG1 (FOB01173) were compared for their ability to induce PBMC proliferation. The monospecific therapies were compared alongside bispecific therapies with OX40 and 4-1BB synergistic effects. PBMC were isolated from human blood using standard density-gradient separation methods and stained with 5 μM CellTrace™ Violet (Molecular Probes) as recommended by the manufacturer. 120,000 PBMC were incubated with 10-fold concentrations of test molecules (ranging from 10 μM to 1 pM) and were added to the cell mixtures to a final volume of 200 l/well in complete RPMI 1640 media supplemented with 10% FBS and 5 ng/ml of α-CD3 per well in 96-well plates. Plates were incubated at 37° C., 5% $CO_2$ in humidified incubators for 24 to 6 days.

NK and T cell proliferation was assessed by flow cytometry. Cells were fluorescently-labeled with 7AAD (Sigma), PE/Cy7-αhCD25, APC/Cy7-αhCD5, BV605-αhCD56, BV650αhCD8 and BV510-α-hCD4 (Biolegend) and incubated for 30 minutes at 4° C. Cells were washed twice, resuspended, and acquired on a BD FACSymphony™ flow cytometer. All samples were analyzed using FlowJo software to calculate the percentages of NK, $CD8^+$, and $CD4^+$ T cells that had proliferated via the dilution of CellTrace™ Violet (CTV). GraphPad Prism 7.0 was used to plot graphs.

As shown in FIG. 16, the 4-1BB×OX40 bispecific proteins FXX01047 and FXX01055 promote a dose-dependent expansion of $CD8^+$ T, $CD4^+$ T, and NK cells (grey symbols). The $EC_{50}$ values ranged from 13 to 41 nM for the 3 cell subsets. This experiment clearly demonstrates that the monospecific constructs OXF01070 or FOB01173 alone are unable to promote proliferation (open symbols). Of importance, the combination of the two monospecific constructs are not sufficient to induce T or NK cell proliferation (black diamond). These results are clinically relevant as 4-1BB and OX40 monospecific therapies, containing wildtype Fc, have dramatically impaired functionality. Only in the synergistic bispecific forms of 4-1BB×OX40 antibodies promote robust proliferation.

Example 21: Human T Cell Proliferation in Response to Anti-4-1BB×Anti-OX40 ADAPTIR™ Bispecific Protein Treatment In Vitro Additional bispecific constructs were analyzed in a primary PBMC assay for function. Methods are similar to those used in Example 20, with modifications. Cells were additionally stained for PE/Cy7-αhCD25 (Biolegend). All samples were analyzed to calculate the percentages of NK, $CD8^+$, and $CD4^+$ T cells that had proliferated and the activation status via percent $CD25^+$.

Additionally, cytokine secretion was assessed using multiplex-based assays (Milliplex) for IFN-γ, IL-2, and TNF-α from 72 hour supernatants diluted 1:3 in assay buffer prior to analysis on the Magpix. $EC_{50}$ was determined by nonlinear regression using GraphPad Prism 7. Constructs were tested using two individual healthy donor PBMCs.

These data demonstrate that anti-CD3 stimulated PBMCs treated with 4-1BB×OX40 constructs can robustly increase the percentage of proliferating CD8+ and CD4+ T cells over a 96 hour culture in a dose-dependent manner (FIG. 17). Additionally, cytokines from stimulated T cells induce the proliferation (FIG. 18A) and activation (FIG. 18B) of NK cells. Furthermore, supernatants taken from culture at 72 hours reveal a marked dose-dependent secretion of IFN-γ, IL-2, and TNF-α when constructs are added exogenously (FIG. 19). There was no difference in the in vitro function of the tested 4-1BB×OX40 bispecific proteins. Taken together these results demonstrate dose-dependent in vitro NK and T cell proliferation and cytokine production when 4-1BB× OX40 constructs are added to stimulated PBMC. The levels of maximum proliferation induced by the top constructs was similar in both the maximal percentage of proliferating cells and the concentration at which the ADAPTIR™ induced peak proliferation.

Example 22. Evaluation of Additional Framework Sequence Modifications to Optimize the Anti-OX40 scFv After analysis of experimental data and in combination with modeling of surface properties of the binding domains, several variants were constructed and tested. Mutations were designed to mimic sequence and structure of human germline frameworks. Shortly, parental IGLV3-21*01 amino acid sequence IPE (IMGT numbering 71-74) was mutated to IPA, VPN, VPS and IPK. Bispecific molecules FXX01110 to 01121 (SEQ ID NOs:89-100) represent additional variants of the OX40 domain.

Example 23. Characterization of Bispecific Anti-4-1BB×Anti-OX40 ADAPTIR™ Constructs with Additional Modification to the Anti-OX40 scFv Following transient transfection and purification using methods described above, additional constructs containing changes that altered the calculated isoelectric point (pI) were evaluated for impact on expression levels, purity, and stability characteristics. The change in pI was generated via amino acid changes to the anti-OX40 scFv. The isoelectric point was calculated using the algorithm in the Genedata Biologics Platform®. Theoretical pI values can vary depending on the methodology. These values were used to look for general trends as the pI, a measure of net charge of a protein, can impact the solubility and stability of proteins under different conditions. The expression levels were calculated based on the mass recovered from Protein A purification from the volume of supernatant that was purified (assuming 100% of the protein was captured by Protein A). As shown in Table 13 below, there was no specific trend observed with expression and the changes made to the amino acid sequence that altered pI. Among this set of proteins, FXX01111 showed the highest expression levels. Preparative SEC was performed following the Protein A affinity capture step, which removed high molecular weight aggregate (HMW) and some low molecular material (LMW), if present, as well as simultaneously buffer-exchanged the sample into PBS. Samples of each of the construct were analyzed by analytical SE-HPLC and SE-UPLC to evaluate product homogeneity. All the constructs shown in Table 13 had high purity levels with minimal HMW product detected by either SE-HPLC or SE-UPLC. Using the SE-UPLC method, with higher resolution, there was no significant clipped/low molecular weight species peak area measured for these proteins.

TABLE 13

Expression level and purity of bispecific anti-4-1BB × anti-OX40 ADAPTIR ™ constructs with varied calculated isoelectric points

| Name | Theoretical pI | Titer, μg/mL | SE-HPLC % MP | SE-UPLC % HMW | SE-UPLC % MP | SE-UPLC % LMW |
|---|---|---|---|---|---|---|
| FXX01066 | 7.42 | 69 | 98.3 | 1.89 | 98.1 | Not detected |
| FXX01101 | 7.61 | 80 | 97.8 | 2.6 | 97.4 | Not detected |
| FXX01102 | 7.79 | 93 | 97.8 | 2.29 | 97.7 | Not detected |
| FXX01110 | 7.61 | 127 | 97.8 | 2.1 | 97.9 | Not detected |
| FXX01111 | 7.61 | 153 | 99.0 | 1.0 | 99.0 | Not detected |
| FXX01112 | 7.61 | 99 | 98.8 | 0.9 | 99.1 | Not detected |
| FXX01113 | 7.79 | 71 | 97.4 | 3.3 | 96.7 | Not detected |
| FXX01114 | 7.79 | 62 | 97.7 | 2.7 | 97.3 | Not detected |
| FXX01115 | 7.79 | 97 | 95.6 | 4.2 | 95.8 | Not detected |
| FXX01116 | 7.79 | 93 | 97.5 | 2.0 | 98.0 | Not detected |
| FXX01117 | 7.93 | 87 | 96.0 | 4.8 | 95.2 | Not detected |
| FXX01118 | 7.93 | 89 | 96.4 | 3.9 | 96.1 | Not detected |
| FXX01119 | 7.93 | 108 | 95.6 | 3.9 | 96.1 | Not detected |
| FXX01120 | 7.93 | 136 | 97.5 | 2.2 | 97.8 | Not detected |
| FXX01121 | 8.06 | 86 | 94.3 | 5.3 | 94.7 | Not detected |

Following purification and purity measurements, samples of each protein were stored under multiple conditions to assess their propensity to aggregate when formulated only in PBS at 1 mg/mL, in the absence of any additional excipients under different storage conditions. This included storage at 4° C. and 40° C. In addition, each variant was tested for the formation of aggregates after freezing, then thawing the protein from a −20° C. freezer. The percent change in the product peak area was calculated and reflected the increase in aggregated protein present in the sample immediately after purification and after the treatment indicated in Table 14 below. All constructs showed minimal change after one week at 4° C., with greater change detected in the samples stored under the accelerated stability condition of 40° C. The samples showed minor changes after a single freeze/thaw cycle from −20° C. storage. There did not appear to be a correlation with these values and the theoretical pI.

TABLE 14

Evaluation of storage stability at 4 and 40° C., and −20° C. Free/Thaw of bispecific anti-4-1BB × anti-OX40 ADAPTIR ™ constructs with varied calculated isoelectric points

| Name | Theoretical pI | Change in % MP Day 7 @ 4° C. | Change in % MP Day 7 @ 40° C. | Change in % MP −20° C. Freeze/Thaw |
|---|---|---|---|---|
| FXX01066 | 7.42 | −0.5 | −2.3 | −1.5 |
| FXX01101 | 7.61 | −0.4 | −2.2 | −1.4 |
| FXX01102 | 7.79 | −0.7 | −7.1 | −1.8 |
| FXX01110 | 7.61 | −0.3 | −4.1 | −0.9 |
| FXX01111 | 7.61 | −0.2 | −2.6 | −1.1 |
| FXX01112 | 7.61 | −0.2 | −2.1 | −1.1 |
| FXX01113 | 7.79 | −1 | −8.5 | −1.5 |
| FXX01114 | 7.79 | −0.7 | −4.5 | −1.3 |
| FXX01115 | 7.79 | −0.1 | −1.0 | −1.1 |
| FXX01116 | 7.79 | −0.3 | −1.6 | −1.1 |
| FXX01117 | 7.93 | −1 | −8.3 | −1.5 |
| FXX01118 | 7.93 | −0.6 | −9.9 | −1.9 |
| FXX01119 | 7.93 | −0.2 | −3.8 | −1.5 |
| FXX01120 | 7.93 | −0.2 | −2.7 | −1.0 |
| FXX01121 | 8.06 | −2.1 | −8.9 | −1.9 |

The Tm1 (mid-point of the first melting transition) and Tagg, the temperature of onset of aggregation based on dynamic light scattering, was measured for these constructs using the Uncle instrument from Unchained Labs. All of the constructs shown in Table 15 had Tm1 and Tagg values that exceeded 60° C., indicative of having high thermal stability. There did not appear to be a specific trend in the thermostability values that correlated with the calculated pI of the protein.

TABLE 15

Tm1 and Tagg values for bispecific anti-4-1BB × anti-OX40 ADAPTIR ™ constructs with varied calculated isoelectric points

| Name | pI | Tm1 (° C.) | Tagg (° C.) |
|---|---|---|---|
| FXX01066 | 7.42 | 66.8 | 64.1 |
| FXX01101 | 7.61 | 64.3 | 62.1 |
| FXX01102 | 7.79 | 64.6 | 61.6 |
| FXX01110 | 7.61 | 66.5 | 62.1 |
| FXX01111 | 7.61 | 67.5 | 63.7 |
| FXX01112 | 7.61 | 67.5 | 64.0 |
| FXX01113 | 7.79 | 67.0 | 63.5 |
| FXX01114 | 7.79 | 65.5 | 62.1 |
| FXX01115 | 7.79 | 66.1 | 63.6 |
| FXX01116 | 7.79 | 66.8 | 64.1 |
| FXX01117 | 7.93 | 67.1 | 63.1 |
| FXX01118 | 7.93 | 65.5 | 61.5 |
| FXX01119 | 7.93 | 65.6 | 62.5 |
| FXX01120 | 7.93 | 65.7 | 63.4 |
| FXX01121 | 8.06 | 65.7 | 62.7 |

Using the BIACORE 8K SPR system, the affinity of these constructs for human and cyno 4-1BB, and human and cyno OX40 ECD, were determined using the methods described above. Monovalent binding affinity was determined by capturing the ADAPTIR™ bispecific construct on the chip and injecting monovalent ECD of the target at multiple concentrations. The affinity of the OX40 scFv was not measurably impacted by the changes that were made to alter the pI, as all the values remained in the sub-nM range (Table 16). Since the anti-4-1BB scFv was unchanged across this set of constructs, binding to human and cyno 4-1BB was not impacted.

TABLE 16

Affinity values determined by Surface Plasmon Resonance for the ADAPTIR™ bispecific anti-4-1BB × anti-OX40 ADAPTIR™ constructs with varied calculated isoelectric points

| TPP Name | Affinity to human 4-1BB ECD KD (nM) | Ka (1/Ms) | Kd (1/s) | Affinity to human OX40 ECD KD (nM) | Ka (1/Ms) | Kd (1/s) | Affinity to cyno 411BB ECD KD (nM) | Ka (1/Ms) | Kd (1/s) | Affinity to cyno OX40 ECD KD (nM) | Ka (1/Ms) | Kd (1/s) |
|---|---|---|---|---|---|---|---|---|---|---|---|---|
| FXX01066 | 16 | 2.7E+05 | 4.3E−03 | <1 | 1.1E+06 | 2.7E−04 | 92 | 1.0E+05 | 9.2E−03 | <1 | 1.5E+06 | 1.9E−04 |
| FXX01101 | 17 | 2.7E+05 | 4.6E−03 | <1 | 9.8E+05 | 2.9E−04 | 76 | 1.0E+05 | 7.7E−03 | <1 | 1.1E+06 | 2.7E−04 |
| FXX01102 | 16 | 2.9E+05 | 4.7E−03 | <1 | 1.0E+06 | 2.5E−04 | 75 | 9.8E+04 | 7.4E−03 | <1 | 1.1E+06 | 2.3E−04 |
| FXX01110 | 18 | 2.6E+05 | 4.8E−03 | <1 | 9.1E+05 | 3.6E−04 | 70 | 1.1E+05 | 7.7E−03 | <1 | 1.1E+06 | 2.9E−04 |
| FXX01111 | 17 | 2.7E+05 | 4.5E−03 | <1 | 9.3E+05 | 3.8E−04 | 81 | 9.9E+04 | 8.0E−03 | <1 | 1.1E+06 | 2.9E−04 |
| FXX01112 | 17 | 2.6E+05 | 4.5E−03 | <1 | 7.9E+05 | 5.7E−04 | 77 | 1.0E+05 | 8.0E−03 | <1 | 8.7E+05 | 3.1E−04 |
| FXX01113 | 15 | 3.0E+05 | 4.6E−03 | <1 | 8.9E+05 | 3.1E−04 | 82 | 9.5E+04 | 7.8E−03 | <1 | 9.8E+05 | 2.8E−04 |
| FXX01114 | 17 | 2.7E+05 | 4.5E−03 | <1 | 1.1E+06 | 2.6E−04 | 116 | 7.9E+04 | 9.1E−03 | <1 | 1.1E+06 | 2.8E−04 |
| FXX01115 | 16 | 2.6E+05 | 4.1E−03 | <1 | 9.8E+05 | 3.0E−04 | 72 | 1.0E+05 | 7.4E−03 | <1 | 1.1E+06 | 2.1E−04 |
| FXX01116 | 17 | 2.7E+05 | 4.6E−03 | <1 | 8.8E+05 | 4.4E−04 | 81 | 9.8E+04 | 7.9E−03 | <1 | 1.0E+06 | 2.7E−04 |
| FXX01117 | 17 | 2.5E+05 | 4.2E−03 | <1 | 9.7E+05 | 3.0E−04 | 76 | 9.6E+04 | 7.2E−03 | <1 | 1.0E+06 | 2.0E−04 |
| FXX01118 | 17 | 2.7E+05 | 4.6E−03 | <1 | 8.4E+05 | 3.1E−04 | 80 | 9.6E+04 | 7.7E−03 | <1 | 1.1E+06 | 2.4E−04 |
| FXX01119 | 18 | 2.6E+05 | 4.6E−03 | 0.3 | 9.2E+05 | 3.1E−04 | 79 | 9.5E+04 | 7.5E−03 | 0.2 | 1.0E+06 | 2.3E−04 |
| FXX01120 | 18 | 2.6E+05 | 4.6E−03 | 0.4 | 1.0E+06 | 3.9E−04 | 77 | 9.7E+04 | 7.5E−03 | 0.2 | 9.5E+05 | 2.3E−04 |
| FXX01121 | 9 | 3.9E+05 | 3.6E−03 | 0.1 | 1.2E+06 | 1.3E−04 | 30 | 4.2E+05 | 1.3E−02 | 0.2 | 1.0E+06 | 1.8E−04 |

Example 24: Characterization of Fc Receptor Binding to Bispecific Anti-4-1BB×Anti-OX40 ADAPTIR™ Constructs with Varied Calculated Isoelectric Points Fcγ receptor binding to bispecific proteins was measured by Surface Plasmon Resonance on a Biacore 8K instrument at room temperature. Bispecific proteins with modified Fc regions to reduce binding to Fcγ receptors were directly immobilized on the surface of a CM5 sensor chip to a surface density of 4000 RU. A bispecific ADAPTIR™ protein with a wild type Fc was similarly immobilized to the surface as a positive control and used as a comparator to evaluate the reduction in binding resulting from changes incorporated into the Fc region amino acid sequence. Fcγ receptors (purchased from R&D Systems) were diluted to either 100 nM (FcγRI) or 2 μM (all other Fcγ receptors) in HBS-EP+ buffer before injecting over the surface of the prepared sensor chip at 30 μL/min for 60 seconds. Maximum RU values during association phase of each injection were used to compare the extent of binding of the modified Fc to wild type value and are reported in Table 17 below. There is a significant reduction of binding to all the receptors tested, with some apparent residual binding to FcγRIIA and RIIB/C receptors. As expected, the different FXX bispecifics show similar levels of binding, as they all share the same Fc sequence.

TABLE 17

Binding of ADAPTIR™ bispecific constructs with a modified Fc sequence to different Fc receptors

| Sample | Fc type | Immob. level (RU) | Max RU value during association RI | RIIA R167 | RIIA H167 | RIIB/C | RIIIA | RIIIA V176F | RIIIB |
|---|---|---|---|---|---|---|---|---|---|
| FXX01028 | wt | 4756 | 1085 | 430 | 378 | 231 | 532 | 203 | 91 |
| FXX01066 | PAA (del) | 4063 | 0 | 92 | 14 | 21 | 5 | 3 | 3 |
| FXX01101 | PAA (del) | 4318 | 0 | 94 | 14 | 21 | 3 | 2 | 2 |
| FXX01102 | PAA (del) | 4135 | 1 | 88 | 13 | 19 | 2 | 2 | 1 |
| FXX01111 | PAA (del) | 3923 | 0 | 86 | 13 | 20 | 3 | 3 | 2 |
| FXX01115 | PAA (del) | 4179 | 1 | 89 | 12 | 19 | 0 | 1 | 0 |
| FXX01119 | PAA (del) | 4854 | 1 | 103 | 14 | 22 | 0 | 1 | 1 |

Example 25: Evaluation of Cell Binding and Functional Activity of Anti-4-1BB×Anti-OX40 ADAPTIR™ Constructs with Modified Isoelectric Points (pI)

Human and cynomolgus binding studies were completed to demonstrate that our optimized ADAPTIR™ scFv binding domains bound sufficiently to cells using our standard flow cytometry-based staining procedures. These data show that there is minimal variation in either human (FIGS. 20A and 20B) or cynomolgus (FIGS. 20C and 20D) binding for constructs to either 4-1BB or OX40 expressed by cloned cell lines. Additionally, when examined for non-specificity, these constructs did not bind to parental CHO-K1 SV (FIG. 21). Therefore, there is no unfavorable binding alterations with the addition of these pI changes to the anti-OX40 scFv.

All screened constructs were run in the reporter assay using both human and cynomolgus expressing 4-1BB or OX40 reporter lines to demonstrate functionality. As shown in FIG. 22, there is little difference in the EC50 or max RLU in these reporter assays. In addition, these proteins did not induce non-specific activity in the human 4-1BB (FIG. 23A) or OX40 (FIG. 23B) reporter assay when crosslinked with parental CHO-K1 SV. Thus, the functionality of these optimized ADAPTIR™ constructs were not altered with the introduction of pI mutations. Table 18 summarizes the EC50 and maximum binding/induction in the human binding and reporter assays.

TABLE 18

Summary of human cell binding and reporter assay data with anti-4-1BB × anti-OX40 ADAPTIR ™ constructs with varied calculated isoelectric points

| | Construct Details | | | | | | | |
|---|---|---|---|---|---|---|---|---|
| | 4-1BB Reporter Assay | | OX40 Reporter Assay | | Binding to human 41BB/Jurkat | | Binding to human OX40/CHO | |
| Name | EC50 pM | Max induction | EC50 pM | Max induction | EC50 nM | max MFI | EC50 nM | max MFI |
| FXX01066 | 17 | 1365666 | 21 | 5863939 | 0.57 | 11601 | 0.57 | 11601 |
| FXX01101 | 18 | 1435671 | 17 | 5889413 | 0.60 | 11898 | 0.60 | 11898 |
| FXX01102 | 21 | 1397056 | 16 | 5784185 | 0.54 | 12115 | 0.54 | 12115 |
| FXX01110 | 21 | 1379619 | 17 | 5904888 | 0.50 | 11774 | 0.50 | 11774 |
| FXX01111 | 19 | 1429221 | 17 | 6092237 | 0.69 | 12442 | 0.69 | 12442 |
| FXX01112 | 14 | 1449547 | 19 | 6167694 | 0.53 | 12390 | 0.53 | 12390 |
| FXX01113 | 19 | 1367842 | 16 | 6099691 | 0.56 | 12177 | 0.56 | 12177 |
| FXX01114 | 18 | 1433016 | 18 | 6077716 | 0.58 | 12314 | 0.58 | 12314 |
| FXX01115 | 18 | 1357853 | 19 | 6288476 | 0.62 | 12119 | 0.62 | 12119 |
| FXX01116 | 19 | 1394988 | 17 | 5951223 | 0.65 | 11894 | 0.65 | 11894 |
| FXX01117 | 20 | 1405760 | 18 | 6222166 | 0.65 | 12667 | 0.65 | 12667 |
| FXX01118 | 18 | 1384094 | 16 | 6283088 | 0.58 | 12382 | 0.58 | 12382 |
| FXX01119 | 11 | 1374727 | 12 | 6067294 | 0.61 | 12207 | 0.61 | 12207 |
| FXX01120 | 15 | 1380059 | 12 | 6115030 | 0.53 | 12235 | 0.53 | 12235 |
| FXX01121 | 16 | 1428053 | 16 | 6191687 | 0.42 | 11105 | 0.42 | 11105 |

Example 26: Human T Cell Proliferation and Cytokine Production in Response to Anti-4-1BB×Anti-OX40 ADAPTIR™ Bispecific Protein Treatment In Vitro ADAPTIR™ bispecific constructs were analyzed in a primary PBMC assay for functional differences. Similar to methods described above, isolated PBMC were treated with 10 ug/mL of αCD3, alongside titrated test constructs, for 96 hours. After 96 hours, all samples were analyzed via flow cytometry to calculate the percentages of NK, $CD8^+$, and $CD4^+$ T cells that had proliferated. As displayed in FIG. 24, each of the anti-4-1BB×anti-OX40 ADAPTIR™ constructs were able to robustly enhance the number of proliferated $CD8^+$ and $CD4^+$ T cells in culture in a dose-dependent manner. There are slight variations in the function of these antibodies, but they do not correlate with differences in their calculated pI. Interestingly, there is an enhancement of NK cell proliferation and activation, as measured by CTV dilution and CD25 expression, respectively (FIG. 25). Furthermore, as shown in FIG. 26, the supernatants harvested from 72-hour cultures treated with anti-4-1BB×anti-OX40 bispecific proteins all promote dose-dependent secretion of IFN-γ, IL-2 and TNF-α. Variation in the calculated pI of the constructs does not alter their ability to induce cytokine secretion. Taken together, these results demonstrate dose-dependent in vitro NK and T cell proliferation and cytokine production when anti-4-1BB×anti-OX40 constructs are added to stimulated PBMC.

Example 27: Fc Mutations to Eliminate Binding to Fc Receptors and Complement It may be advantageous in an ADAPTIR™ bispecific molecule to make mutations to the Fc region to eliminate the ability to interact and signal through interactions with the Fc receptors and compliment. Table 19 below shows different mutations that could be made to the Fc regions included in an ADAPTIR™ bispecific construct (Null2, K322A Fc, TSC1004, TSC1005, TSC1006 and TSC1007), compared to the sequence of a wild type Fc (WT).

TABLE 19

Fc Mutations for ADAPTIR ™ bispecific construct

| Fc AA Position according to EU/Kabat/IMGT | 233/246/3 | 234/247/4 | 235/248/5 | 236/249/6 | 237/250/7 | 318/337/88 | 320/339/90 | 322/341/92 |
|---|---|---|---|---|---|---|---|---|
| WT IgG1 | Glu | Leu | Leu | Gly | Gly | Glu | Lys | Lys |
| Null2 Fc | Glu | Ala | Ala | Gly | Ala | Ala | Ala | Ala |
| EU-1 | | L234A | L235A | | G237A | E318A | K320A | K322A |
| EU-3 | | Leu234Ala | Leu235Ala | | Gly237Ala | Glu318Ala | Lys320Ala | Lys322Ala |
| Kabat-1 | | L247A | L248A | | G250A | E337A | K339A | K341A |
| Kabat-3 | | Leu247Ala | Leu248Ala | | Gly250Ala | Glu337Ala | Lys339Ala | Lys341Ala |
| IMGT-1 | | 4 | 5 | | 7 | 88 | 90 | 92 |
| IMGT-3 | | 4 | 5 | | 7 | 88 | 90 | 92 |
| K322A Fc | Glu | Ala | Ala | Gly | Ala | Glu | Lys | Ala |
| EU-1 | | L234A | L235A | | G237A | | | K322A |
| EU-3 | | Leu234Ala | Leu235Ala | | Gly237Ala | | | Lys322Ala |
| Kabat-1 | | L247A | L248A | | G250A | | | K341A |
| Kabat-3 | | Leu247Ala | Leu248Ala | | Gly250Ala | | | Lys341Ala |
| IMGT-1 | | 4 | 5 | | 7 | | | 92 |
| IMGT-3 | | 4 | 5 | | 7 | | | 92 |
| TSC 1004 | Pro | Val | Ala | Gly | Ala | Glu | Lys | Ala |
| EU-1 | E233P | L234V | L235A | | G237A | | | K322A |
| EU-3 | Glu233Pro | Leu234Val | Leu235Ala | | Gly237Ala | | | Lys322Ala |
| Kabat-1 | E246E | L247V | L248A | | G250A | | | K341A |
| Kabat-3 | Glu246Pro | Leu247Val | Leu248Ala | | Gly250Ala | | | Lys341Ala |
| IMGT-1 | 3 | 4 | 5 | | 7 | | | 92 |
| IMGT-3 | 3 | 4 | 5 | | 7 | | | 92 |
| TSC 1005 | Pro | Val | Ala | Deletion | Ala | Glu | Lys | Ala |
| EU-1 | E233P | L234V | L235A | | G237A | | | K322A |
| EU-3 | Glu233Pro | Leu234Val | Leu235Ala | Gly | Gly237Ala | | | Lys322Ala |
| Kabat-1 | E246E | L247V | L248A | | G250A | | | K341A |
| Kabat-3 | Glu246Pro | Leu247Val | Leu248Ala | Gly | Gly250Ala | | | Lys341Ala |
| IMGT-1 | 3 | 4 | 5 | 6 | 7 | | | 92 |
| IMGT-3 | 3 | 4 | 5 | 6 | 7 | | | 92 |
| TSC 1006 | Pro | Ala | Ala | Gly | Ala | Glu | Lys | Ala |
| EU-1 | E233P | L234A | L235A | | G237A | | | K322A |
| EU-3 | Glu233Pro | Leu234Ala | Leu235Ala | | Gly237Ala | | | Lys322Ala |
| Kabat-1 | E246E | L247A | L248A | | G250A | | | K341A |
| Kabat-3 | Glu246Pro | Leu247Ala | Leu248Ala | | Gly250Ala | | | Lys341Ala |
| IMGT-1 | 3 | 4 | 5 | 6 | 7 | 88 | 90 | 92 |
| IMGT-3 | 3 | 4 | 5 | 6 | 7 | 88 | 90 | 92 |
| TSC 1007 | Pro | Ala | Ala | Deletion | Ala | Glu | Lys | Ala |
| EU-1 | E233P | L234A | L235A | | G237A | | | K322A |
| EU-3 | Glu233Pro | Leu234Ala | Leu235Ala | Gly | Gly237Ala | | | Lys322Ala |
| Kabat-1 | E246E | L247A | L248A | | G250A | | | K341A |
| Kabat-3 | Glu246Pro | Leu247Ala | Leu248Ala | Gly | Gly250Ala | | | Lys341Ala |
| IMGT-1 | 3 | 4 | 5 | 6 | 7 | | | 92 |
| IMGT-3 | 3 | 4 | 5 | 6 | 7 | | | 92 |

Example 28: SPR Analysis Impact of Fc Mutations on Binding to Fc Receptors and Complement Fc mutations to be potentially integrated into an ADAPTIR™ bispecific construct were analyzed for binding to the common Fc receptors (human and cyno) and C1Q, which is a component of the complement activation system. SPR experiments were conducted at 25° C. in HBS-EP+ buffer on a Biacore T200 system.

For these experiments, all four flow cells of a CM5 sensor chip were immobilized with goat $F(ab')_2$ anti-human Fc (Jackson ImmunoResearch) to a response level of ~4000 RU. Fc variants and wild type Fc were diluted to 100 nM in HBS-EP+ and captured on the surface of the chip for 120 seconds at a flow rate of 10 μL/min. Fcγ receptors (human and cyno, all purchased from R&D Systems) and complement (C1Q, purchased from Quidel Corporation and Complement Technology, Inc) were diluted in HBS-EP+ and then flowed as analytes at 30 μL/min for 120 seconds followed by a 120 seconds dissociation. Regeneration was achieved by flowing 10 mM glycine pH 1.7 at 30 μL/min for 30 seconds followed by a 60 seconds stabilization. Flow cell 1 was always left as a blank (no captured protein) for purposes of background signal subtraction. Blank-subtracted sensorgrams for each captured Fc variant were inspected for the presence of binding to any of the Fcγ receptor proteins or complement. There are polymorphisms in the Human Fc receptors IIA and RIIIA, so both sequences were tested for binding. As indicated below, all mutation sets resulted in ablation of C1Q, RIIA H167 variant, RIIB/C and RIIIB binding. Some mutation variants showed residual binding to RI, RIIA R167 or RIIIA V176.

TABLE 20

Results summary of human Fcγ Receptor and C1Q binding

| Sample | Strength of Binding (relative to wild type Human Fc) | | | | | | | |
|---|---|---|---|---|---|---|---|---|
| | RI | RIIA R167 | RIIA H167 | RIIB/C | RIIIA V176 | RIIIA F176 | RIIIB | C1Q |
| Wild type IgG1 Fc | +++ | +++ | +++ | +++ | +++ | +++ | +++ | +++ |
| TSC 421 | BLOD | + | BLOD | BLOD | BLOD | BLOD | BLOD | BLOD |
| TSC 1004 | BLOD | + | BLOD | BLOD | BLOD | BLOD | BLOD | BLOD |
| TSC 1005 | + | BLOD | BLOD | BLOD | + | BLOD | BLOD | BLOD |
| TSC 1006 | BLOD | + | BLOD | BLOD | + | BLOD | BLOD | BLOD |
| TSC 1007 | BLOD | + | BLOD | BLOD | BLOD | BLOD | BLOD | BLOD |

These Fc variants were also evaluated for binding to recombinant Fc receptor extracellular domains from cynomolgus monkeys to verify that these mutations also ablated binding in species that could be used to evaluate the toxicity of ADAPTIR™ protein therapeutics. As the results in the table below indicate, the mutation sets ablated binding to cyno RIIB and cyno RIII. Two variants, TSC1004 and TSC1007, showed some residual binding to the cyno RI receptor.

TABLE 21

Results summary of Cyno Fcγ Receptor binding

| Sample | Strength of Binding (relative to Wild type Human IgG1 Fc) | | |
|---|---|---|---|
| | Cyno RI | Cyno RIIB | Cyno RIII |
| Wild type Fc | +++ | +++ | +++ |
| TSC 421 | BLOD | BLOD | BLOD |
| TSC 1004 | + | BLOD | BLOD |
| TSC 1005 | BLOD | BLOD | BLOD |
| TSC 1006 | + | BLOD | BLOD |
| TSC 1007 | BLOD | BLOD | BLOD |

Example 29: Differential Scanning Calorimetry (DSC) to Assess Impact of Fe Mutations on Thermal Stability Thermal stability of the different Fc regions that could be used in building ADAPTIR™ bispecifics was assessed using Differential Scanning Calorimetry (DSC). DSC measures heat capacity changes associated with the molecule's thermal denaturation when heated at a constant rate. The Fc proteins, containing just the hinge, CH2, and CH3 domains, were expressed via transient transfection, then purified via Protein A purification and SEC. No additional domains were attached to either the N- or C-terminus of the protein so that the melting temperatures of the individual domains could be clearly identified. The objective was to identify mutations in the Fe region that ablate binding to the different Fc receptors and complement, but retain the thermal stability of a wild-type IgG1 Fe region.

DSC was conducted using a MicroCal VP-Capillary DSC system (Malvern Instrument). An exact match of buffer, PBS pH7.4, was used as the reference. 500 μL of a 0.5 mg/mL solution of each protein sample with reference was loaded on the instrument and heated from 25° C. to 100° C. at a rate of one degree Celsius per minute. Melting curve was analyzed using Origin 7 platform software MicroCal VP-Capillary DSC Automated Analysis Software.

Table 22 shows the thermal stability of the Fc domains that can be used in bispecific constructs where it is desirable to eliminate Fc receptor and complement binding, compared to a wild-type IgG1 sequence. All variants tested had Tm values equivalent to the WT Fc region.

TABLE 22

Thermal stability of different Fc regions compared to wild-type IgG1 Fc

| ID | CH2 Tm (° C.) | CH3 Tm (° C.) |
|---|---|---|
| Wild-type IgG1 Fc | 70 | 82 |
| TSC 421 | 68 | 82 |
| TSC 1004 | 71 | 83 |
| TSC 1005 | 72 | 83 |
| TSC 1006 | 71 | 83 |
| TSC 1007 | 71 | 83 |

Example 30: Cell Binding Data to Evaluate Fc Mutations Using Cell Lines Expressing Fcγ Receptors To confirm the absence of FcγR binding, the Fc mutant constructs were tested in binding assays on a set of FcγR transfectants. CHO-K1SV cells stably transfected with a series of FcγR receptors were incubated with each of the transfectants listed in Table 23. A typical experiment labeled approximately 100,000 cells per well, in 96-well plates, with a range of binding molecule concentrations of 1 to 1000 nM, in 100 μl of PBS buffer with 0.2% BSA and 2 mM EDTA, for 30 minutes on ice, followed by washes and incubation with PE-labeled minimum cross species reactive secondary antibody, goat anti-human IgG Fcγ, F(ab')2 (Jackson Laboratory) for 30 minutes to 1 hour on ice. Signal from bound molecules was detected using a LSR-II™ flow cytometer (BD Biosciences) and analyzed by FlowJo flow cytometry analysis software. Mean fluorescence intensity (MFI) of bound molecules on cells was determined after exclusion of doublets.

As listed in Table 23, the wildtype Fc construct bound to the FcγR transfectants: the tightest binding was observed on FcγR1 cells, as expected. Binding to the rest of the Fcγ receptors did not show saturation, but was measurable. Binding to FcγRIIB was barely detectable. In contrast, binding was not detected when using the 1003, 1004, 1005, 1006, or 1007 Fc mutants.

TABLE 23

Summary of binding to human Fcγ Receptor expressing cell lines

| Sample | Binding to RI | RIIA R131 | RIIA H131 | RIIB/C | RIIIA F158 | RIIIA V158 | RIIIB |
|---|---|---|---|---|---|---|---|
| Wild type Fc | +++ | + | + | + | + | + | − |
| TSC1004 | − | − | − | − | − | − | − |
| TSC1005 | − | − | − | − | − | − | − |
| TSC1006 | − | − | − | − | − | − | − |
| TSC1007 | − | − | − | − | − | − | − |

Example 31: SPR Experiments of Binding to the Neonatal Fc Receptor (FcRn

The neonatal Fc receptor, FcRn, is responsible for extending the serum half-life of immunoglobulins and Fc-containing proteins by reducing degradation in the lysosomal compartment of cells. For FcRn to properly bind to immunoglobulins, it must be complexed with another protein, beta-2-macroglobulin. For simplicity, this complex will just be referred to as FcRn for the remainder of the document. IgGs and other serum proteins are continually internalized by cells through pinocytosis. They are transported from the endosome to the lysosome for degradation. However, serum albumin and IgG bind to FcRn under the acidic condition that is present in the vesicle and avoid the lysosome. Upon returning to the cell surface, IgG is unable to bind to FcRn under neutral pH and is released back into circulation. This recycling leads to IgG having serum half-lives >7 days, but can be impacted by other mechanisms of serum clearance (target-mediated disposition, degradation, aggregation, etc.).

For antibody-like protein therapeutics that contain an Fc region, it is critical that they have the ability to bind to FcRn under acidic conditions. Protein constructs consisting of only the Fc region with different mutations (no scFvs attached) were evaluated for their binding to FcRn to verify that the mutations did not impact the FcRn binding under acidic conditions using SPR at pH 6.0.

Recombinant FcRn/b2M protein was generated via transient transfection of HEK-293 cells with a bi-cistronic vector containing the genes for both FcRn and beta-2-macroglobulin. The complex was purified using IMAC chromatography and subsequently buffer exchanged into IMAC elution buffer after verifying purity of the IMAC eluate by analytical SEC. hFcRn/b2M at 10 μg/ml in 10 mM sodium acetate (pH 4.5) was immobilized on a CM5 chip by direct amine coupling chemistry to a level of ~600 RU. A reference flow cell was left blank.

Different concentrations of the Fc variant protein (5-80 nM by 2-fold dilutions in pH 6.0 running buffer) including running buffer as blank were injected in randomized order at 30 μL/min for 180 seconds followed by a 120 second dissociation period.

Optimal regeneration was achieved by two injections of Dulbecco's PBS with 0.05% Tween-20 and adjusting to pH 7.5 at a flow rate of 30 μL/min for 30 seconds followed by running buffer stabilization for 1 minute.

Sensorgrams obtained from kinetic SPR measurements were analyzed by the double subtraction method. The signal from the reference flow cell was subtracted from the analyte binding response obtained from flow cell with immobilized ligands. Buffer reference was subtracted from analyte binding responses, and the final double-referenced data were analyzed with Biacore T200 Evaluation software (2.0, GE), globally fitting data to derive kinetic parameters. All sensorgrams were fitted using two-state reaction model, as described in Weirong Wang et al, DrugMetab Dispos.: 39(9): 1469-77 (2011).

As shown in Table 24 below, the KD values for ADAPTIR™ bispecifics containing the different Fc mutation sets are all within a range consistent with that reported in the literature for monoclonal antibodies containing a wild-type IgG1 Fc.

TABLE 24

Dissociation Constant (KD) for ADAPTIR ™ bispecifics containing different Fc mutations

| Fc Variant | KD (nM) |
|---|---|
| Null2 | 33 |
| K322A | 22 |
| TSC1004 | 20 |
| TSC1005 | 20 |
| TSC1006 | 19 |
| TSC1007 | 19 |

Example 32. Incorporation of Binding Domains into Other Protein Formats, Characterization of Biophysical, Stability, Binding, and Activity In addition to utilizing the anti-OX40 and anti-41BB binding domains in the ADAPTIR™/scFv-Fc-scFv format, they can also be incorporated into other protein structures that enable binding to OX40 and 4-1BB individually or simultaneously and can cause signaling via both receptors. These other formats include but are not limited to those described by Spiess et al, *Mol. Immun.* 67: 95-106(2015). This also includes formats such as the RUBY™, Azymetric™ and TriTAC™ bispecific platforms. Generating alternative compositions of the anti-OX40 and anti-4-1BB binding domains disclosed herein can be performed by using molecular biology techniques to amplify the genetic sequences encoding the variable heavy and/or variable light domains or the CDR regions of the anti-4-1BB and anti-OX40 binding domains. These genetic fragments can then be spliced into the appropriate frameworks of the intended bispecific formats in a DNA plasmid appropriate for protein expression. Following expression, purification techniques can be employed to isolate the bispecific protein. These techniques could include affinity purification steps such as Protein A, Protein L, Protein G, anion exchange, cation exchange, or hydrophobic interaction chromatography. After protein purification, the molecules can be examined by biophysical techniques such as those described earlier, including differential scanning fluorimetry or differential scanning calorimetry. These alternative protein structures can also be assessed for solubility and resistance to aggregation by incubation in serum from different species, different salt concentrations, mechanical force, etc. The alternative protein formats can be assessed for binding to cells expressing one or both targets. Additionally, the alternative protein formats can be evaluated for biological activity by measuring the stimulation of cells expressing either OX40 and/or 4-1BB. Stimulation, or activation of these cell populations can be measured, among other outputs, by determining the increase in concentration of interferon gamma or other cytokines, measuring the expression of other cell surface markers that are indicative of activation, such as CD25 or CD69. Following in vitro analysis, these formats can also be developed as therapeutics for the treatment of human diseases such as cancer.

Example 33: Expression of Granzyme B in T Cells in Response to Anti-4-1BB×Anti-OX40 ADAPTIR™ Bispecific Protein Treatment In Vitro T and NK cells directly lyse tumor cells through the secretion of granzymes and perforin at the lymphocyte: target cell interphase. Perforin and granzyme mediate the cytotoxic responses of CD8 T and NK cells, by inducing cell death of the target cell (Martinze-Lostao et al., Clin Cancer Re; 21(22) Nov. 15, 2015). Expression of granzyme B is normally acquired following stimulation of CD8 T cells and NK cells, as they differentiate into effector cytotoxic cells. Therefore, expression of granzyme B is a measure of the cytotoxic potential of CD8 T cells and NK cells. Stimulation of T cells and NK cells through the 4-1BB receptor has been shown to enhance the expression of granzyme B, in addition to the secretion of IFN-γ. Therefore, the ability of the anti-4-1BB×anti-OX40 ADAPTIR™ bispecific (scFv-Fc-scFv) protein FXX01102 to enhance granzyme B expression was determined using blood cells from individual healthy donors.

Peripheral blood mononuclear cells (PBMC) were isolated from normal donors using standard density-gradient separation methods. PBMC were activated with anti-CD3, to induce expression of 4-1BB and OX40. This was done by incubating isolated PBMCs with serially diluted concentrations of bispecific polypeptide in the presence of an α-CD3 antibody. 120,000 PBMC were incubated with 10-fold serial dilutions of test molecules in a final volume of 200 ml/well in complete RPMI 1640 media supplemented with 10% FBS and 5 ng/ml of α-CD3 per well in 96-well plates. Plates were incubated at 37° C., 5% $CO_2$ in humidified incubators for 72 hours. Cells were harvested, fluorescently-labeled with APC/Cy7-αhCD5, BV605-αhCD56, BV650αhCD8 and BV510-α-hCD4 (Biolegend), and incubated for 30 minutes at 4° C. Cells were washed twice, and fixed and permeabilized for intracellular staining (Invitrogen). After permeabilization, cells were labeled with APC-α-granzyme B antibody and washed. Samples were resuspended and acquired on a BD FACSymphony™ flow cytometer. All samples were analyzed using FlowJo software to calculate the percentages of NK, CD8+, and CD4+ T cells expressing granzyme B. GraphPad Prism 7.0 was used to plot graphs.

As shown in FIGS. 28A and 28B, anti-CD3 stimulation alone (shown at 0 nM) can induce granzyme B expression in a fraction of the CD8 T cells, and normally a smaller fraction of CD4 T cells. Addition of the 4-1BB×OX40 bispecific protein FXX01102 (SEQ ID NO:81) boosts the expression of granzyme B in the CD8+ T cells. Furthermore, FXX01102 (SEQ ID NO:81) also boosts the expression of granzyme B in the CD4+ T cells. Results were consistent in two individual donor samples. The experiment was conducted on a third donor in which analysis of NK cells was included: the 4-1BB×OX40 bispecific protein FXX01102 (SEQ ID NO:81) boosts granzyme B expression on the NK cell population, in addition to the CD4 and CD8 T cells (FIG. 29).

These results are consistent with the described function of 4-1BB in stimulating the expression of molecules involved in the cytotoxic function of CD8 T cells and NK cells. In addition, these results demonstrate that co-targeting 4-1BB and OX40 through a bispecific molecule can enhance the cytotoxic potential of CD4 T cells.

Example 34: Enhanced In Vitro Tumor Cell Lysis in Response to Anti-4-1BB×Anti-OX40 ADAPTIR™ Bispecific Protein Treatment Since the anti-4-1BB×anti-OX40 ADAPTIR™ bispecific protein enhances granzyme B expression and secretion of INF-γ, it is expected to enhance the cytotoxic function of T cells. One method of initiating an anti-tumor response is to co-incubate peripheral blood mononuclear cells (PBMC) and tumor cells with an anti-CD3×anti-tumor associated antigen (TAA) bispecific molecule (CD3×TAA engager). The CD3×TAA engager is a polyclonal stimulator of T cells, providing signal 1 to the T cells, and resulting in the upregulation of 4-1BB and OX40 (signal 2).

PBMC were isolated from human blood using standard density-gradient separation methods and labelled with a fluorescent Cell Trace. 120,000 PBMC were co-cultured with 30,000 TAA+ target cells in the presence of CD3×TAA engager (0.5 or 2 pM). Eight-fold concentrations of the anti-4-1BB×anti-OX40 ADAPTIR™ bispecific protein FXX01102 (SEQ ID NO:81) (ranging from 5 μM to 1.2 pM) were added to the cell cultures at a final volume of 200 al/well in complete RPMI 1640 media supplemented with 10% FBS in 96-well plates. Plates were incubated at 37° C., 5% $CO_2$ in humidified incubators for 72 hours. Cells were harvested, fluorescently-labeled with antibodies for CD5, CD4, CD8, NK cells, tumor cells, and a live/dead discrimination dye (7AAD), for 30 minutes at 4° C. Cells were washed and resuspended for acquisition on a BD FACSymphony™ flow cytometer. Immune cells and tumor cells were distinguished based on Cell Trace and tumor cell markers, respectively. All samples were analyzed using FlowJo software to calculate the percentages of live or dead tumor cells. GraphPad Prism 7.0 is used to plot graphs.

As shown in FIG. 30, PBMC can kill TAA+ target cells in a dose-dependent manner when activated using a CD3×TAA engager. This bolus of data demonstrates that co-targeting 4-1BB and OX40 through a bispecific molecule can enhance the cytotoxic capabilities of lymphocytes from PBMC (Qui H Z et al., J. Immunol. 187: 3555-64 (2011)).

Example 35: Enhanced In Vivo Tumor Cell Lysis in Response to Anti-4-1BB×Anti-OX40 ADAPTIR™ Bispecific Protein Treatment Female B-hOX40/h4-1BB mice (C57BL/6-Tnfrsf4$^{tm1(TNFRSF4)}$ CD137$^{tm1(CD137)}$/Bcgen) from Biocytogen, China were acclimated for two weeks before initiation of the study. Animals were checked daily for general health. Treatment of study animals was in accordance with conditions specified in the Guide for the Care and Use of Laboratory Animals, and the study protocol was approved by the Institutional Animal Care and Use Committee (IACUC).

The mouse bladder carcinoma cell line MB49 (Millipore) was thawed and expanded in culture. B-hOX40/h4-1BB mice were challenged on day 0 by injecting $5\times10^5$ MB49 murine bladder carcinoma cells in 100 μL subcutaneously on their right flank.

Starting day 6 after tumor challenge, treatment groups were normalized for tumor burden by ranked random assignment and received treatment with either vehicle (PBS) or FXX01102 (SEQ ID NO:81) at dosages between 0.3 μg/mouse and 30 μg/mouse (n=8/group) or Urelumab analog at 20 μg/mouse (n=4). Treatments were administered intraperitoneally every three days until day 24. Tumor growth was observed and measured three times/week with a caliper. Tumor volumes are calculated using the formula: Volume=½[length×(width)2]. The experimental endpoint was either tumor volume ≥1500 $cm^3$, wounding, or affected health of the mice.

To evaluate the effects of treatment on circulating peripheral T cell numbers, mice were bled after 14 days of treatment. Blood samples were collected into a Sarstedt microvette K3E tube (#20-1278-100). 500 μl of 1×BD Pharm Lyse™ lysing solution was added, and the contents transferred to a 15 mL centrifuge tube. After 10 min, 9.5 mL of PBS was added and centrifuged. The resulting cell pellet was resuspended in 200 μL of PBE (DPBS+0.5% BSA+2 mM EDTA) and transferred to a 96 well plate. Cells were pelleted by centrifugation and decanted. The cell pellet was resuspended in 200 μL 1×BD Pharm Lyse™ lysing solution and incubated at RT for 5 min. Cells were washed once and stained with LIVE/DEAD™ Fixable Aqua Dead Cell Stain (Invitrogen). Cells were washed once and non-specific binding to cells was blocked by incubating cells with 100 μg/ml anti-CD16/CD32 clone 2.4G2 (in house). Cells were surface stained with PE@CD62L (eBioscience), PE-cy7@CD25 (Biolegend), BV421@CD3 (Biolegend), BV605@CD8a (Biolegend), APC@CD335 (Biolegend), AF700@CD44 (Biolegend) and APC-eF780@CD4 (eBioscience). Cells were washed twice, and fixed and permeabilized for intracellular staining Foxp3/Transcription Factor Staining Buffer (eBioscience). After permeabilization, cells were labeled with AF488@ Ki-67 and washed. Samples were resuspended and acquired on a BD FAC LSRII flow cytometer. All samples were analyzed using FlowJo software to calculate the percentages of NK, CD8+, and CD4+ T cells expressing Ki67. GraphPad Prism 7.0 was used to plot graphs.

Statistical analyses are performed using SAS/JMP software (SAS Institute). A repeated measures ANOVA model is fitted using Fit Model Standard Least Squares to evaluate overall effects of treatment, day and treatment-by-day interactions on tumor volumes for in vivo studies. Significant differences in tumor size between treatment groups for the s.c. xenograft model were evaluated by a Tukey multiple comparison test using the LSMeans platform and further time and treatment combinations are evaluated using the LSMeans Tukey multiple comparison test for each treatment-by-day combination as needed. Significant differences in time to tumor progression (as defined at median time to a tumor volume of ≥1500 $cm^3$) between treatment mouse groups is determined employing Kaplan-Meier survival analysis with a Log-rank (Mantel-Cox) test for comparison of tumor progression curves.

Treatment with FXX01102 at a dose of 30 μg/mouse resulted in statistically significant reduction of MB49 tumor growth in B-hOX40/h4-1BB mice (See FIG. 31, Table 25). The level of tumor reduction was similar to that seen with Urelumab analog.

TABLE 25

Statistical Comparison of Mean Tumor Volume through Day 26
JMP One-way ANOVA Analysis with Tukey-Kramer HSD Method

| Treatment | p-Value |
|---|---|
| PBS Control vs. FXX01102 30 μg | 0.0232 |
| PBS Control vs. FXX01102 3 μg | 0.9965 |
| PBS Control vs. FXX01102 0.3 μg | 0.9662 |
| PBS Control vs. Urelumab Analog 20 μg | 0.2450 |

TABLE 25-continued

| Statistical Comparison of Mean Tumor Volume through Day 26 JMP One-way ANOVA Analysis with Tukey-Kramer HSD Method | |
|---|---|
| Treatment | p-Value |
| FXX01102 30 μg vs. FXX01102 3 μg | 0.0096 |
| FXX01102 30 μg vs. FXX01102 0.3 μg | 0.0045 |
| FXX01102 3 μg vs. FXX01102 0.3 μg g | 0.9983 |
| FXX01102 30 μg vs. Urelumab Analog 20 μg | 0.9837 |
| FXX01102 3 μg vs. Urelumab Analog 20 μg | 0.1452 |
| FXX01102 0.3 μg vs. Urelumab Analog 20 μg | 0.0895 |

Treatment with 30 μg/mouse of FXX01102 resulted in complete tumor rejection in 2 of 8 mice treated and 1 transient tumor rejection (FIG. 32). In addition to effect on tumor growth, treatment with FXX01102 at a dose of 30 μg/mouse resulted in significantly prolonged survival compared to the vehicle control group (FIG. 33, Table 26).

TABLE 26

| Survival Statistical Analysis through Day 34 | | | |
|---|---|---|---|
| | Median Survival | P value relative to PBS control | |
| Group | Time (days) | Log-Rank | Wilcoxon |
| PBS | 24.5 | | |
| FXX01102 30 μg | Undefined | <0.0001 | 0.0003 |

TABLE 26-continued

| Survival Statistical Analysis through Day 34 | | | |
|---|---|---|---|
| | Median Survival | P value relative to PBS control | |
| Group | Time (days) | Log-Rank | Wilcoxon |
| FXX01102 3 μg | 23 | 0.2851 | 0.4812 |
| FXX01102 0.3 μg | 20 | 0.9120 | 0.598 |

The nuclear protein Ki-67 is strongly expressed in proliferating cells and can be used as a flow cytometric marker of proliferating cells. The frequency of proliferating Ki67 positive T cells was increased after 14 days of treatment of 30 μg/mouse of FXX01102 in CD3 positive, CD4 positive, and CD8 positive T cells, as well as CD335 positive NK cells (FIG. 34).

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes.

Other embodiments are within the following claims.

SEQUENCES

```
SEQ ID NO: 1
LQDPCSNCPAGTFCDNNRNQICSPCPPNSFSSAGGQRTCDICRQCKGVFRTRKECSSTSNA
ECDCTPGFHCLGAGCSMCEQDCKQGQELTKKGCKDCCFGTFNDQKRGICRPWTNCSLDGKSVL
VNGTKERDVVCGPSPADLSPGASSVTPPAPAREPGHSPQIISFFLALTSTALLFLLFFLTLRFSVVKR
GRKKLLYIFKQPFMRPVQTTQEEDGCSCRFPEEEEGGCEL

SEQ ID NO: 2
LQDLCSNCPAGTFCDNNRSQICSPCPPNSFSSAGGQRTCDICRQCKGVFKTRKECSSTSNA
ECDCISGYHCLGAECSMCEQDCKQGQELTKKGCKDCCFGTFNDQKRGICRPWTNCSLDGKSVL
VNGTKERDVVCGPSPADLSPGASSATPPAPAREPGHSPQIIFFLALTSTVVLFLLFFLVLRFSVVKR
SRKKLLYIFKQPFMRPVQTTQEEDGCSCRFPEEEEGGCEL

SEQ ID NO: 3
LHCVGDTYPSNDRCCHECRPGNGMVSRCSRSQNTVCRPCGPGFYNDVVSSKPCKPCTW
CNLRSGSERKQLCTATQDTVCRCRAGTQPLDSYKPGVDCAPCPPGHFSPGDNQACKPWTNCTLA
GKHTLQPASNSSDAICEDRDPPATQPQETQGPPARPITVQPTEAWPRTSQGPSTRPVEVPGGRAVA
AILGLGLVLGLLGPLAILLALYLLRRDQRLPPDAHKPPGGGSFRTPIQEEQADAHSTLAKI

SEQ ID NO: 4
KLHCVGDTYPSNDRCCQECRPGNGMVSRCNRSQNTVCRPCGPGFYNDVVSAKPCKACT
WCNLRSGSERKQPCTATQDTVCRCRAGTQPLDSYKPGVDCAPCPPGHFSPGDNQACKPWTNCT
LAGKHTLQPASNSSDAICEDRDPPPTQPQETQGPPARPTTVQPTEAWPRTSQRPSTRPVEVPRGPA
VAAILGLGLALGLLGPLAMLLALLLLRRDQRLPPDAPKAPGGGSFRTPIQEEQADAHSALAKI

SEQ ID NO: 42
EVQLVQSGAEVKKPGSSVKVSCKASGYTFTSYWINWVRQAPGQGLEWIGNIYPGSSTTNYNEKF
KSRATLTVDTSTSTAYMELSSLRSEDTAVYYCASFSDGYYAYAMDYWGQGTLVTVSSGGGGSG
GGGSGGGGSGGGGSEIVMTQSPGTLSLSPGERATLSCRASQDISNYLNWYQQKPGQAVRLLIYYT
SRLHSGIPDRFSGSGSGTDYTLTISRLEPEDFAVYFCQQGYTLPYTFGQGTKVEIKR

SEQ ID NO: 43
SSEPKSSDKTHTCPPCPAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYKTTPPVLDSDGSFFLYS
KLTVDKSRWQQGNVFSCSVMHEALHNHYTQKSLSLSPGSGGGGSGGGGSGGGGSPSEVQLVQS
GAEVKKPGSSVKVSCKASGYTFTSYWINWVRQAPGQGLEWIGNIYPGSSTTNYNEKFKSRATLT
VDTSTSTAYMELSSLRSEDTAVYYCASFSDGYYAYAMDYWGQGTLVTVSSGGGGSGGGGSGG
GGSGGGGSEIVMTQSPGTLSLSPGERATLSCRASQDISNYLNWYQQKPGQAVRLLIYYTSRLHSGI
PDRFSGSGSGTDYTLTISRLEPEDFAVYFCQQGYTLPYTFGQGTKVEIKR
```

-continued

| SEQUENCES |
|---|
| SEQ ID NO: 44:<br>EVQLVQSGAEVKKPGASVKVSCKASGYTFTSYWMNWVRQAPGQGLEWMGNIYPGSSTTNYAQ<br>KFQGRVTMTVDTSTSTVYMELSSLRSEDTAVYYCASFSDGYYAYAMDYWGQGTLVTVSSGGG<br>GSGGGGSGGGGSGGGGSEIVMTQSPATLSLSPGERATLSCRASQDISNYLNWYQQKPGQAVRLLI<br>YYTSRLHSGIPARFSGSGSGTDYTLTISSLQPEDFAVYFCQQGYTLPYTFGQGTKVEIKR |
| SEQ ID NO: 45<br>SSEPKSSDKTHTCPPCPAPELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIEKTISKAKGQ<br>PREPQVYTLPPSRDELTKNQVSLTCLVKGFYPSDIAVEWESNGQPENNYKTTPPVLDSDGSFFLYS<br>KLTVDKSRWQQGNVFSCSVMHEALHNHYTQKSLSLSPGSGGGGSGGGGSGGGGSPSEVQLVQS<br>GAEVKKPGASVKVSCKASGYTFTSWMNWVRQAPGQGLEWMGNIYPGSSTTNYAQKFQGRVT<br>MTVDTSTSTVYMELSSLRSEDTAVYYCASFSDGYYAYAMDYWGQGTLVTVSSGGGGSGGGGS<br>GGGGSGGGGSEIVMTQSPATLSLSPGERATLSCRASQDISNYLNWYQQKPGQAVRLLIYYTSRLH<br>SGIPARFSGSGSGTDYTLTISSLQPEDFAVYFCQQGYTLPYTFGQGTKVEIKR |
| SEQ ID NO: 46<br>QVQLVESGGGVVQPGRSLRLSCAASGFTLSYYGMHWVRQAPGKGLEWVAVISHDGSDKYYAD<br>SVKGRFTISRDNSKNTLYLQMDSLRAEDTALYYCSNDQFDPWGQGTLVTVSSGGGGSGGGGSG<br>GGGSGGGGSSYVLTQPPSVSVAPGQTARITCGGNNIGSKSVHWFQQKPGQAPALVVYDDSGRPS<br>GIPERFSGSTSGNTATLTISRVEAGDEADYYCQVWDSSSDHVVFGGGTKLTVLR |
| SEQ ID NO: 47<br>SYVLTQPPSVSVAPGQTARITCGGNNIGSKSVFIWFQQKPGQAPALVVYDDSGRPSGIPERFSGSTS<br>GNTATLTISRVEAGDEADYYCQVWDSSSDHVVFGGGTKLTVLGGGGSGGGGSGGGGSGGGGSQ<br>VQLVESGGGVVQPGRSLRLSCAASGFTLSYYGMHWVRQAPGKGLEWVAVISHDGSDKYYADS<br>VKGRFTISRDNSKNTLYLQMDSLRAEDTALYYCSNDQFDPWGQGTLVTVSSR |
| SEQ ID NO: 48<br>DIQMTQSPSSLSASVGDRVTINCQASQSIDSNLAWFQQKPGQPPKWYRASNLASGVPDRFSGSG<br>SGTDFTLTISSLEAEDVATYYCLGGVGAVSYRTSFGGGTKVEIKGGGGSGGGGSGGGGSGGGGS<br>EVQLVESGGGLVQPGRSLRLSCTASGSDINDYPITWVRQAPGQGLEWIGFINSGGSTWYASWVK<br>GRFTISRDDSKSIAYLQMNSLKTEDTAVYYCARGYSTYYRDFNIWGQGTLVTVSSSEPKSSDKTH<br>TCPPCPAPEAAGAPSVFLFPPKPKDTLMISRTPEVTCVVVDVSHEDPEVKFNWYVDGVEVHNAK<br>TKPREEQYNSTYRVVSVLTVLHQDWLNGKEYKCAVSNKALPAPIEKTISKAKGQPREPQVYTLP<br>PSRDELTKNQVSLTCLVKGFYPSDIAVEWESNGQPENNYKTTPPVLDSDGSFFLYSKLTVDKSRW<br>QQGNVFSCSVMHEALHNHYTQKSLSLSPGAGGGGSGGGGSGGGGSPSQVQLVESGGGVVQPGR<br>SLRLSCAASGFTLSYYGMHWVRQAPGKGLEWVAVISHDGSDKYYADSVKGRFTISRDNSKNTL<br>YLQMDSLRAEDTALYYCSNDQFDPWGQGTLVTVSSGGGGSGGGGSGGGGSGGGGSSYVLTQPP<br>SVSVAPGQTARITCGGNNIGSKSVHWFQQKPGQAPALVVYDDSGRPSGIPERFSGSTSGNTATLTI<br>SRVEAGDEADYYCQVWDSSSDHVVFGGGTKLTVLR |
| SEQ ID NO: 49<br>DIQMTQSPSSLSASVGDRVTINCQASQSIDSNLAWFQQKPGQPPKWYRASNLASGVPDRFSGSG<br>SGTDFTLTISSLEAEDVATYYCLGGVGAVSYRTSFGGGTKVEIKGGGGSGGGGSGGGGSGGGGS<br>EVQLVESGGGLVQPGRSLRLSCTASGSDINDYPITWVRQAPGQGLEWIGFINSGGSTWYASWVK<br>GRFTISRDDSKSIAYLQMNSLKTEDTAVYYCARGYSTYYRDFNIWGQGTLVTVSSSEPKSSDKTH<br>TCPPCPAPEAAGAPSVFLFPPKPKDTLMISRTPEVTCVVVDVSHEDPEVKFNWYVDGVEVHNAK<br>TKPREEQYNSTYRVVSVLTVLHQDWLNGKEYKCAVSNKALPAPIEKTISKAKGQPREPQVYTLP<br>PSRDELTKNQVSLTCLVKGFYPSDIAVEWESNGQPENNYKTTPPVLDSDGSFFLYSKLTVDKSRW<br>QQGNVFSCSVMHEALHNHYTQKSLSLSPGAGGGGSPSQVQLVESGGGVVQPGRSLRLSCAASGF<br>TLSYYGMHWVRQAPGKGLEWVAVISHDGSDKYYADSVKGRFTISRDNSKNTLYLQMDSLRAE<br>DTALYYCSNDQFDPWGQGTLVTVSSGGGGSGGGGSGGGGSGGGGSSYVLTQPPSVSVAPGQTA<br>RITCGGNNIGSKSVHWFQQKPGQAPALVVYDDSGRPSGIPERFSGSTSGNTATLTISRVEAGDEAD<br>YYCQVWDSSSDHVVFGGGTKLTVLR |
| SEQ ID NO: 50<br>DIQMTQSPSSLSASVGDRVTINCQASQSIDSNLAWFQQKPGQPPKWYRASNLASGVPDRFSGSG<br>SGTDFTLTISSLEAEDVATYYCLGGVGAVSYRTSFGGGTKVEIKGGGGSGGGGSGGGGSGGGGS<br>EVQLVESGGGLVQPGRSLRLSCTASGSDINDYPITWVRQAPGQGLEWIGFINSGGSTWYASWVK<br>GRFTISRDDSKSIAYLQMNSLKTEDTAVYYCARGYSTYYRDFNIWGQGTLVTVSSSEPKSSDKTH<br>TCPPCPAPEAAGAPSVFLFPPKPKDTLMISRTPEVTCVVVDVSHEDPEVKFNWYVDGVEVHNAK<br>TKPREEQYNSTYRVVSVLTVLHQDWLNGKEYKCAVSNKALPAPIEKTISKAKGQPREPQVYTLP<br>PSRDELTKNQVSLTCLVKGFYPSDIAVEWESNGQPENNYKTTPPVLDSDGSFFLYSKLTVDKSRW<br>QQGNVFSCSVMHEALHNHYTQKSLSLSPGAGGGGSGGGGSGGGGSPSSYVLTQPPSVSVAPGQT<br>ARITCGGNNIGSKSVHWFQQKPGQAPALVVYDDSGRPSGIPERFSGSTSGNTATLTISRVEAGDEA<br>DYYCQVWDSSSDHVVFGGGTKLTVLGGGGSGGGGSGGGGSGGGGSQVQLVESGGGVVQPGRS<br>LRLSCAASGFTLSYYGMHWVRQAPGKGLEWVAVISHDGSDKYYADSVKGRFTISRDNSKNTLY<br>LQMDSLRAEDTALYYCSNDQFDPWGQGTLVTVSSR |
| SEQ ID NO: 51<br>DIQMTQSPSSLSASVGDRVTINCQASQSIDSNLAWFQQKPGQPPKWYRASNLASGVPDRFSGSG<br>SGTDFTLTISSLEAEDVATYYCLGGVGAVSYRTSFGGGTKVEIKGGGGSGGGGSGGGGSGGGGS<br>EVQLVESGGGLVQPGRSLRLSCTASGSDINDYPITWVRQAPGQGLEWIGFINSGGSTWYASWVK<br>GRFTISRDDSKSIAYLQMNSLKTEDTAVYYCARGYSTYYRDFNIWGQGTLVTVSSSEPKSSDKTH<br>TCPPCPAPEAAGAPSVFLEPPKPKDTLMISRTPEVTCVVVDVSHEDPEVKFNWYVDGVEVHNAK<br>TKPREEQYNSTYRVVSVLTVLHQDWLNGKEYKCAVSNKALPAPIEKTISKAKGQPREPQVYTLP |

-continued

| SEQUENCES |
|---|
| PSRDELTKNQVSLTCLVKGFYPSDIAVEWESNGQPENNYKTTPPVLDSDGSFFLYSKLTVDKSRW<br>QQGNVFSCSVMHEALHNHYTQKSLSLSPGAGGGGSPSSYVLTQPPSVSVAPGQTARITCGGNNIG<br>SKSVFIWFQQKPGQAPALVVYDDSGRPSGIPERFSGSTSGNTATLTISRVEAGDEADYYCQVWDS<br>SSDHVVFGGGTKLTVLGGGGSGGGGSGGGGSGGGGSQVQLVESGGGVVQPGRSLRLSCAASGF<br>TLSYYGMHWVRQAPGKGLEWVAVISHDGSDKYYADSVKGRFTISRDNSKNTLYLQMDSLRAE<br>DTALYYCSNDQFDPWGQGTLVTVSSR |
| SEQ ID NO: 52<br>SYVLTQPPSVSVAPGQTARITCGGNNIGSKSVNWFQQKPGQAPVLVVYDDSGRPSGIPERFSGSTS<br>GNTATLTISRVEAGDEADYYCQVWDSSSDHVVFGGGTKLTVLGGGGSGGGGSGGGGSGGGGSQ<br>VQLVESGGGVVQPGRSLRLSCAASGETLSYYGMHWVRQAPGKGLEWVAVISHDGSDKYYADS<br>VKGRFTISRDNSKNTLYLQMNSLRAEDTAVYYCSNDQFDPWGQGTLVTVSSR |
| SEQ ID NO: 53<br>SSEPKSSDKTHTCPPCPAPELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIEKTISKAKGQ<br>PREPQVYTLPPSRDELTKNQVSLTCLVKGFYPSDIAVEWESNGQPENNYKTTPPVLDSDGSFFLYS<br>KLTVDKSRWQQGNVFSCSVMHEALHNHYTQKSLSLSPGGGGSPSSYVLTQPPSVSVAPGQTARI<br>TCGGNNIGSKSVNWFQQKPGQAPVLVVYDDSGRPSGIPERFSGSTSGNTATLTISRVEAGDEADY<br>YCQVWDSSSDHVVFGGGTKLTVLGGGGSGGGGSGGGGSGGGGSQVQLVESGGGVVQPGRSLR<br>LSCAASGFTLSYYGMHAVVRQAPGKGLEWVAVISEIDGSDKYYADSVKGRFTISRDNSKNTLYLQ<br>MNSLRAEDTAVYYCSNDQFDPWGQGTLVTVSSR |
| SEQ ID NO: 54<br>SYVLTQPPSVSVAPGQTARITCGGNNIGSKSVNWFQQKPGQAPVLVVYDDSGRPSGIPERFSGSTS<br>GNTATLTISRVEAGDEADYYCQVWDSSSDHVVFGGGTKLTVLGGGGSGGGGSGGGGSGGGGSQ<br>VQLVESGGGVVQPGRSLRLSCAASGFTLSYYGMHWVRQAPGKGLEWVAAISHDGSDKYYADS<br>VKGRFTISRDNSKNTLYLQMNSLRAEDTAVYYCSNDQFDPWGQGTLVTVSSR |
| SEQ ID NO: 55<br>SSEPKSSDKTHTCPPCPAPELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIEKTISKAKGQ<br>PREPQVYTLPPSRDELTKNQVSLTCLVKGFYPSDIAVEWESNGQPENNYKTTPPVLDSDGSFFLYS<br>KLTVDKSRWQQGNVFSCSVMHEALHNHYTQKSLSLSPGGGGSPSSYVLTQPPSVSVAPGQTARI<br>TCGGNNIGSKSVNWFQQKPGQAPVLVVYDDSGRPSGIPERFSGSTSGNTATLTISRVEAGDEADY<br>YCQVWDSSSDHVVFGGGTKLTVLGGGGSGGGGSGGGGSGGGGSQVQLVESGGGVVQPGRSLR<br>LSCAASGFTLSYYGMHWVRQAPGKGLEWVAAISHIDGSDKYYADSVKGRFTISRDNSKNTLYLQ<br>MNSLRAEDTAVYYCSNDQFDPWGQGTLVTVSSR |
| SEQ ID NO: 56<br>SYVLTQPPSVSVAPGQTARITCGGNNIGSKSVFIWFQQKPGQAPALVVYDDSGRPSGIPERFSGSTS<br>GNTATLTISRVEAGDEADYYCQVWDSSSDHVVFGGGTKLTVLGGGGSGGGGSGGGGSGGGGSQ<br>VQLVESGGGVVQPGRSLRLSCAASGFTLSYYGMHWVRQAPGKGLEWVAVISHDGSDKYYADS<br>VKGRFTISRDNSKNTLYLQMDSLRAEDTALYYCSNDQFDPWGQGTLVTVSSR |
| SEQ ID NO: 57<br>SSEPKSSDKTHTCPPCPAPELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIEKTISKAKGQ<br>PREPQVYTLPPSRDELTKNQVSLTCLVKGFYPSDIAVEWESNGQPENNYKTTPPVLDSDGSFFLYS<br>KLTVDKSRWQQGNVFSCSVMHEALHNHYTQKSLSLSPGGGGSPSSYVLTQPPSVSVAPGQTARI<br>TCGGNNIGSKSVFIWFQQKPGQAPALVVYDDSGRPSGIPERFSGSTSGNTATLTISRVEAGDEADY<br>YCQVWDSSSDHVVFGGGTKLTVLGGGGSGGGGSGGGGSGGGGSQVQLVESGGGVVQPGRSLR<br>LSCAASGFTLSYYGMHWVRQAPGKGLEWVAVISHIDGSDKYYADSVKGRFTISRDNSKNTLYLQ<br>MDSLRAEDTALYYCSNDQFDPWGQGTLVTVSSR |
| SEQ ID NO: 58<br>EVQLVQSGAEVKKPGASVKVSCKASGYTFTSYWMNWVRQAPGQGLEWMGNIYPSGGSTNYAQ<br>KFQGRVTMTVDTSTSTVYMELSSLRSEDTAVYYCASFSDGYYAYAMDYWGQGTLVTVSSGGG<br>GSGGGGSGGGGSGGGGSEIVMTQSPATLSLSPGERATLSCRASQSVSSYLNWYQQKPGQAPRLLI<br>YYASRRHTGIPARFSGSGSGTDFTLTISSLQPEDFAVYYCQQGYNLPYTFGQGTKVEIK |
| SEQ ID NO: 59<br>SYVLTQPPSVSVAPGQTARITCGGNNIGSKSVNWFQQKPGQAPVLVVYDDSGRPSGIPERFSGSTS<br>GNTATLTISRVEAGDEADYYCQVWDSSSDHVVFGGGTKLTVLGGGGSGGGGSGGGGSGGGGSQ<br>VQLVESGGGVVQPGRSLRLSCAASGFTLSYYGMHWVRQAPGKGLEWVAAISHDGSDKYYADS<br>VKGRFTISRDNSKNTLYLQMNSLRAEDTAVYYCSNDQFDPWGQGTLVTVSSR |
| SEQ ID NO: 60<br>SYVLTQPPSVSVAPGKTARITCGGNNIGSKSVNWFQQKPGQAPVLVVYDDSGRPSGIPERFSGSTS<br>GNTATLTISRVEAGDEADYYCQVWDSSSDHVVFGGGTKLTVLGGGGSGGGGSGGGGSGGGGSQ<br>VQLVESGGGVVQPGRSLRLSCAASGETLSYYGMHWVRQAPGKGLEWVAAISHDGSDKYYADS<br>VKGRFTISRDNSKNTLYLQMNSLRAEDTAVYYCSNDQFDPWGQGTLVTVSSR |

-continued

| SEQUENCES |
| --- |
| SEQ ID NO: 61<br>SYVLTQPPSVSVAPGQTARITCGGNNIGSKSVNWFQQKPGQAPVLVVYDDSGRPSGIPERFSGSTS<br>GNTATLTISRVEAGDEADYYCQVWDSSSDHVVFGGGTKLTVLGGGGSGGGGSGGGGSGGGGSQ<br>VQLVESGGGVVQPGRSLRLSCAASGFTLSYYGMHWVRQAPGKGLEWVAAISHDGSDKYYADS<br>VKGRFTISRDNSKNRLYLQMNSLRAEDTAVYYCSNDQFDPWGQGTLVTVSSR |
| SEQ ID NO: 62<br>SYVLTQPPSVSVAPGKTARITCGGNNIGSKSVNWFQQKPGQAPVLVVYDDSGRPSGIPERFSGSTS<br>GNTATLTISRVEAGDEADYYCQVWDSSSDHVVFGGGTKLTVLGGGGSGGGGSGGGGSGGGGSQ<br>VQLVESGGGVVQPGRSLRLSCAASGETLSYYGMHWVRQAPGKGLEWVAAISHDGSDKYYADS<br>VKGRFTISRDNSKNRLYLQMNSLRAEDTAVYYCSNDQFDPWGQGTLVTVSSR |
| SEQ ID NO: 63<br>EIVMTQSPATLSLSPGERATLSCRASQSVSSYLNWYQQKPGQAPRLLIYYASRRHTGIPARFSGSG<br>SGTDFTLTISSLQPEDFAVYYCQQGYNLPYTFGQGTKVEIKGGGGSGGGGSGGGGSGGGGSEVQ<br>LVQSGAEVKKPGASVKVSCKASGYTFTSYWMNWVRQAPGQGLEWMGNIYPSGGSTNYAQKFQ<br>GRVTMTVDTSTSTVYMELSSLRSEDTAVYYCASFSDGYYAYAMDYWGQGTLVTV |
| SEQ ID NO: 64<br>SYVLTQPPSVSVAPGQTARITCGGNNIGSKSVNWFQQKPGQAPVLVVYDDSGRPSGIPERFSGSTS<br>GNTATLTISRVEAGDEADYYCQVWDSSSDHVVFGGGTKLTVLGGGGSGGGGSGGGGSGGGGSQ<br>VQLVESGGGVVQPGRSLRLSCAASGETLSYYGMHWVRQAPGKGLEWVAVISHDGSDKYYADS<br>VKGRFTISRDNSKNTLYLQMNSLRAEDTAVYYCSNDQFDPWGQGTLVTV |
| SEQ ID NO: 65<br>SYVLTQPPSVSVAPGQTARITCGGNNIGSKSVNWFQQKPGQAPVLVVYDDSGRPSGIPARFSGST<br>SGNTATLTISRVEAGDEADYYCQVWDSSSDHVVFGGGTKLTVLGGGGSGGGGSGGGGSGGGGS<br>QVQLVESGGGVVQPGRSLRLSCAASGFTLSYYGMHWVRQAPGKGLEWVAAISHDGSDKYYAD<br>SVKGRFTISRDNSKNTLYLQMNSLRAEDTAVYYCSNDQFDPWGQGTLVTVSSR |
| SEQ ID NO: 66<br>SYVLTQPPSVSVAPGQTARITCGGNNIGSKSVNWFQQKPGQAPVLVVYDDSGRPSGVPNRFSGST<br>SGNTATLTISRVEAGDEADYYCQVWDSSSDHVVFGGGTKLTVLGGGGSGGGGSGGGGSGGGGS<br>QVQLVESGGGVVQPGRSLRLSCAASGFTLSYYGMHWVRQAPGKGLEWVAAISHDGSDKYYAD<br>SVKGRFTISRDNSKNTLYLQMNSLRAEDTAVYYCSNDQFDPWGQGTLVTVSSR |
| SEQ ID NO: 67<br>SYVLTQPPSVSVAPGQTARITCGGNNIGSKSVNWFQQKPGQAPVLVVYDDSGRPSGVPSRFSGST<br>SGNTATLTISRVEAGDEADYYCQVWDSSSDHVVFGGGTKLTVLGGGGSGGGGSGGGGSGGGGS<br>QVQLVESGGGVVQPGRSLRLSCAASGFTLSYYGMHVVVRQAPGKGLEWVAAISHDGSDKYYAD<br>SVKGRFTISRDNSKNTLYLQMNSLRAEDTAVYYCSNDQFDPWGQGTLVTVSSR |
| SEQ ID NO: 68<br>SYVLTQPPSVSVAPGQTARITCGGNNIGSKSVNWFQQKPGQAPVLVVYDDSGRPSGIPKRFSGST<br>SGNTATLTISRVEAGDEADYYCQVWDSSSDHVVFGGGTKLTVLGGGGSGGGGSGGGGSGGGGS<br>QVQLVESGGGVVQPGRSLRLSCAASGFTLSYYGMHWVRQAPGKGLEWVAAISHDGSDKYYAD<br>SVKGRFTISRDNSKNTLYLQMNSLRAEDTAVYYCSNDQFDPWGQGTLVTVSSR |
| SEQ ID NO: 69<br>SYVLTQPPSVSVAPGQTARITCGGNNIGSKSVNWFQQKPGQAPVLVVYDDSGRPSGIPARFSGST<br>SGNTATLTISRVEAGDEADYYCQVWDSSSDHVVFGGGTKLTVLGGGGSGGGGSGGGGSGGGGS<br>QVQLVESGGGVVQPGRSLRLSCAASGFTLSYYGMHWVRQAPGKGLEWVAAISHDGSDKYYAD<br>SVKGRFTISRDNSKNRLYLQMNSLRAEDTAVYYCSNDQFDPWGQGTLVTVSSR |
| SEQ ID NO: 70<br>SYVLTQPPSVSVAPGQTARITCGGNNIGSKSVNWFQQKPGQAPVLVVYDDSGRPSGVPNRFSGST<br>SGNTATLTISRVEAGDEADYYCQVWDSSSDHVVFGGGTKLTVLGGGGSGGGGSGGGGSGGGGS<br>QVQLVESGGGVVQPGRSLRLSCAASGFTLSYYGMHWVRQAPGKGLEWVAAISHDGSDKYYAD<br>SVKGRFTISRDNSKNRLYLQMNSLRAEDTAVYYCSNDQFDPWGQGTLVTVSSR |
| SEQ ID NO: 71<br>SYVLTQPPSVSVAPGQTARITCGGNNIGSKSVNWFQQKPGQAPVLVVYDDSGRPSGVPSRFSGST<br>SGNTATLTISRVEAGDEADYYCQVWDSSSDHVVFGGGTKLTVLGGGGSGGGGSGGGGSGGGGS<br>QVQLVESGGGVVQPGRSLRLSCAASGFTLSYYGMHWVRQAPGKGLEWVAAISHDGSDKYYAD<br>SVKGRFTISRDNSKNRLYLQMNSLRAEDTAVYYCSNDQFDPWGQGTLVTVSSR |
| SEQ ID NO: 72<br>SYVLTQPPSVSVAPGQTARITCGGNNIGSKSVNWFQQKPGQAPVLVVYDDSGRPSGIPKRFSGST<br>SGNTATLTISRVEAGDEADYYCQVWDSSSDHVVFGGGTKLTVLGGGGSGGGGSGGGGSGGGGS<br>QVQLVESGGGVVQPGRSLRLSCAASGFTLSYYGMHWVRQAPGKGLEWVAAISHDGSDKYYAD<br>SVKGRFTISRDNSKNRLYLQMNSLRAEDTAVYYCSNDQFDPWGQGTLVTVSSR |

-continued

| SEQUENCES |
|---|

SEQ ID NO: 73
SYVLTQPPSVSVAPGKTARITCGGNNIGSKSVNWFQQKPGQAPVLVVYDDSGRPSGIPARFSGST
SGNTATLTISRVEAGDEADYYCQVWDSSSDHVVFGGGTKLTVLGGGGSGGGGSGGGGSGGGGS
QVQLVESGGGVVQPGRSLRLSCAASGFTLSYYGMHWVRQAPGKGLEWVAAISHDGSDKYYAD
SVKGRFTISRDNSKNRLYLQMNSLRAEDTAVYYCSNDQFDPWGQGTLVTVSSR

SEQ ID NO: 74
SYVLTQPPSVSVAPGKTARITCGGNNIGSKSVNWFQQKPGQAPVLVVYDDSGRPSGVPNRFSGST
SGNTATLTISRVEAGDEADYYCQVWDSSSDHVVFGGGTKLTVLGGGGSGGGGSGGGGSGGGGS
QVQLVESGGGVVQPGRSLRLSCAASGFTLSYYGMHWVRQAPGKGLEWVAAISHDGSDKYYAD
SVKGRFTISRDNSKNRLYLQMNSLRAEDTAVYYCSNDQFDPWGQGTLVTVSSR

SEQ ID NO: 75
SYVLTQPPSVSVAPGKTARITCGGNNIGSKSVNWFQQKPGQAPVLVVYDDSGRPSGVPSRFSGST
SGNTATLTISRVEAGDEADYYCQVWDSSSDHVVFGGGTKLTVLGGGGSGGGGSGGGGSGGGGS
QVQLVESGGGVVQPGRSLRLSCAASGFTLSYYGMHWVRQAPGKGLEWVAAISHDGSDKYYAD
SVKGRFTISRDNSKNRLYLQMNSLRAEDTAVYYCSNDQFDPWGQGTLVTVSSR

SEQ ID NO: 76
SYVLTQPPSVSVAPGKTARITCGGNNIGSKSVNWFQQKPGQAPVLVVYDDSGRPSGIPKRFSGST
SGNTATLTISRVEAGDEADYYCQVWDSSSDHVVFGGGTKLTVLGGGGSGGGGSGGGGSGGGGS
QVQLVESGGGVVQPGRSLRLSCAASGFTLSYYGMHWVRQAPGKGLEWVAAISHDGSDKYYAD
SVKGRFTISRDNSKNRLYLQMNSLRAEDTAVYYCSNDQFDPWGQGTLVTVSSR

SEQ ID NO: 77
QVQLQQPGAELVKPGASVKLSCEASGYTFTSYWINWVKQRPGQGLEWIGNIYPGSSTTNYNEKF
KSKATLTVDTSSSTAYMQLSSLTSDDSAVFYCASFSDGYYAYAMDYWVQGTSVTVSSGGGGSG
GGGSGGGGSGGGGSDIQMTQTTSSLSASLGDRVTITCRASQDISNYLNWYQQKPDGTVKLLIYYT
SRLHSGVPSRFSGGGSGTDYSLTISNLEQEDIATYFCQQGYTLPYTFGGGTKLEIKR

SEQ ID NO: 78
EVQLVQSGAEVKKPGASVKVSCKASGYTFTSYWMNWVRQAPGQGLEWMGNIYPSGGSTNYAQ
KFQGRVTMTVDTSTSTVYMELSSLRSEDTAVYYCASFSDGYYAYAMDYWGQGTLVTVSSGGG
GSGGGGSGGGGSGGGGSEIVMTQSPATLSLSPGERATLSCRASQSVSSYLNWYQQKPGQAPRLLI
YYASRRHTGIPARFSGSGSGTDFTLTISSLQPEDFAVYYCQQGYNLPYTFGQGTKVEIKEPKSSDK
THTCPPCPAPPAAAPSVFLFPPKPKDTLMISRTPEVTCVVVDVSHEDPEVKFNWYVDGVEVHNA
KTKPREEQYNSTYRVVSVLTVLHQDWLNGKEYKCAVSNKALPAPIEKTISKAKGQPREPQVYTL
PPSRDELTKNQVSLTCLVKGFYPSDIAVEWESNGQPENNYKTTPPVLDSDGSFFLYSKLTVDKSR
WQQGNVFSCSVMHEALHNHYTQKSLSLSPGGGGSPSSYVLTQPPSVSVAPGQTARITCGGNNIGS
KSVNWFQQKPGQAPVLVVYDDSGRPSGIPERFSGSTSGNTATLTISRVEAGDEADYYCQVWDSS
SDHVVFGGGTKLTVLGGGGSGGGGSGGGGSGGGGSQVQLVESGGGVVQPGRSLRLSCAASGFT
LSYYGMHWVRQAPGKGLEWVAAISHDGSDKYYADSVKGRFTISRDNSKNTLYLQMNSLRAED
TAVYYCSNDQFDPWGQGTLVTVSSR

SEQ ID NO: 79
EVQLVQSGAEVKKPGASVKVSCKASGYTFTSYWMNWVRQAPGQGLEWMGNIYPSGGSTNYAQ
KFQGRVTMTVDTSTSTVYMELSSLRSEDTAVYYCASFSDGYYAYAMDYWGQGTLVTVSSGGG
GSGGGGSGGGGSGGGGSEIVMTQSPATLSLSPGERATLSCRASQSVSSYLNWYQQKPGQAPRLLI
YYASRRHTGIPARFSGSGSGTDFTLTISSLQPEDFAVYYCQQGYNLPYTFGQGTKVEIKEPKSSDK
THTCPPCPAPPAAAPSVFLFPPKPKDTLMISRTPEVTCVVVDVSHEDPEVKFNWYVDGVEVHNA
KTKPREEQYNSTYRVVSVLTVLHQDWLNGKEYKCAVSNKALPAPIEKTISKAKGQPREPQVYTL
PPSRDELTKNQVSLTCLVKGFYPSDIAVEWESNGQPENNYKTTPPVLDSDGSFFLYSKLTVDKSR
WQQGNVFSCSVMHEALHNHYTQKSLSLSPGGGGSPSSYVLTQPPSVSVAPGKTARITCGGNNIGS
KSVNWFQQKPGQAPVLVVYDDSGRPSGIPERFSGSTSGNTATLTISRVEAGDEADYYCQVWDSS
SDHVVFGGGTKLTVLGGGGSGGGGSGGGGSGGGGSQVQLVESGGGVVQPGRSLRLSCAASGFT
LSYYGMHWVRQAPGKGLEWVAAISHDGSDKYYADSVKGRFTISRDNSKNTLYLQMNSLRAED
TAVYYCSNDQFDPWGQGTLVTVSSR

SEQ ID NO: 80
EVQLVQSGAEVKKPGASVKVSCKASGYTFTSYWMNWVRQAPGQGLEWMGNIYPSGGSTNYAQ
KFQGRVTMTVDTSTSTVYMELSSLRSEDTAVYYCASFSDGYYAYAMDYWGQGTLVTVSSGGG
GSGGGGSGGGGSGGGGSEIVMTQSPATLSLSPGERATLSCRASQSVSSYLNWYQQKPGQAPRLLI
YYASRRHTGIPARFSGSGSGTDFTLTISSLQPEDFAVYYCQQGYNLPYTFGQGTKVEIKEPKSSDK
THTCPPCPAPPAAAPSVFLFPPKPKDTLMISRTPEVTCVVVDVSHEDPEVKFNWYVDGVEVHNA
KTKPREEQYNSTYRVVSVLTVLHQDWLNGKEYKCAVSNKALPAPIEKTISKAKGQPREPQVYTL
PPSRDELTKNQVSLTCLVKGFYPSDIAVEWESNGQPENNYKTTPPVLDSDGSFFLYSKLTVDKSR
WQQGNVFSCSVMHEALHNHYTQKSLSLSPGGGGSPSSYVLTQPPSVSVAPGQTARITCGGNNIGS
KSVNWFQQKPGQAPVLVVYDDSGRPSGIPERFSGSTSGNTATLTISRVEAGDEADYYCQVWDSS
SDHVVFGGGTKLTVLGGGGSGGGGSGGGGSGGGGSQVQLVESGGGVVQPGRSLRLSCAASGFT
LSYYGMHWVRQAPGKGLEWVAAISHDGSDKYYADSVKGRFTISRDNSKNRLYLQMNSLRAED
TAVYYCSNDQFDPWGQGTLVTVSSR

SEQ ID NO: 81
EVQLVQSGAEVKKPGASVKVSCKASGYTFTSYWMNWVRQAPGQGLEWMGNIYPSGGSTNYAQ
KFQGRVTMTVDTSTSTVYMELSSLRSEDTAVYYCASFSDGYYAYAMDYWGQGTLVTVSSGGG
GSGGGGSGGGGSGGGGSEIVMTQSPATLSLSPGERATLSCRASQSVSSYLNWYQQKPGQAPRLLI

-continued

| SEQUENCES |
| --- |

YYASRRHTGIPARFSGSGSGTDFTLTISSLQPEDFAVYYCQQGYNLPYTFGQGTKVEIKEPKSSDK
THTCPPCPAPPAAAPSVFLFPPKPKDTLMISRTPEVTCVVVDVSHEDPEVKFNWYVDGVEVHNA
KTKPREEQYNSTYRVVSVLTVLHQDWLNGKEYKCAVSNKALPAPIEKTISKAKGQPREPQVYTL
PPSRDELTKNQVSLTCLVKGFYPSDIAVEWESNGQPENNYKTTPPVLDSDGSFFLYSKLTVDKSR
WQQGNVFSCSVMHEALHNHYTQKSLSLSPGGGGSPSSYVLTQPPSVSVAPGKTARITCGGNNIGS
KSVNWFQQKPGQAPVLVVYDDSGRPSGIPERFSGSTSGNTATLTISRVEAGDEADYYCQVWDSS
SDHVVFGGGTKLTVLGGGGSGGGGSGGGGSGGGGSQVQLVESGGGVVQPGRSLRLSCAASGFT
LSYYGMHWVRQAPGKGLEWVAAISHDGSDKYYADSVKGRFTISRDNSKNRLYLQMNSLRAED
TAVYYCSNDQFDPWGQGTLVTVSSR

SEQ ID NO: 82
EIVMTQSPATLSLSPGERATLSCRASQSVSSYLNWYQQKPGQAPRLLIYYASRRHTGIPARFSGSG
SGTDFTLTISSLQPEDFAVYYCQQGYNLPYTFGQGTKVEIKGGGGSGGGGSGGGGSGGGGSEVQ
LVQSGAEVKKPGASVKVSCKASGYTFTSYWMNWVRQAPGQGLEWMGNIYPSGGSTNYAQKFQ
GRVTMTVDTSTSTVYMELSSLRSEDTAVYYCASFSDGYYAYAMDYWGQGTLVTVEPKSSDKTH
TCPPCPAPPAAAPSVFLFPPKPKDTLMISRTPEVTCVVVDVSHEDPEVKFNWYVDGVEVHNAKT
KPREEQYNSTYRVVSVLTVLHQDWLNGKEYKCAVSNKALPAPIEKTISKAKGQPREPQVYTLPPS
RDELTKNQVSLTCLVKGFYPSDIAVEWESNGQPENNYKTTPPVLDSDGSFFLYSKLTVDKSRWQ
QGNVFSCSVMHEALHNHYTQKSLSLSPGGGGSPSSYVLTQPPSVSVAPGQTARITCGGNNIGSKS
VNWFQQKPGQAPVLVVYDDSGRPSGIPERFSGSTSGNTATLTISRVEAGDEADYYCQVWDSSSD
HVVFGGGTKLTVLGGGGSGGGGSGGGGSGGGGSQVQLVESGGGVITQPGRSLRLSCAASGFTLS
YYGMEIWVRQAPGKGLEWVAAISHDGSDKYYADSVKGRFTISRDNSKNTLYLQMNSLRAEDTA
VYYCSNDQFDPWGQGTLVTVSSR

SEQ ID NO: 83
EIVMTQSPATLSLSPGERATLSCRASQSVSSYLNWYQQKPGQAPRLLIYYASRRHTGIPARFSGSG
SGTDFTLTISSLQPEDFAVYYCQQGYNLPYTFGQGTKVEIKGGGGSGGGGSGGGGSGGGGSEVQ
LVQSGAEVKKPGASVKVSCKASGYTFTSYWMNWVRQAPGQGLEWMGNIYPSGGSTNYAQKFQ
GRVTMTVDTSTSTVYMELSSLRSEDTAVYYCASFSDGYYAYAMDYWGQGTLVTVEPKSSDKTH
TCPPCPAPPAAAPSVFLFPPKPKDTLMISRTPEVTCVVVDVSHEDPEVKFNWYVDGVEVHNAKT
KPREEQYNSTYRVVSVLTVLHQDWLNGKEYKCAVSNKALPAPIEKTISKAKGQPREPQVYTLPPS
RDELTKNQVSLTCLVKGFYPSDIAVEWESNGQPENNYKTTPPVLDSDGSFFLYSKLTVDKSRWQ
QGNVFSCSVMHEALHNHYTQKSLSLSPGGGGSPSSYVLTQPPSVSVAPGKTARITCGGNNIGSKS
VNWFQQKPGQAPVLVVYDDSGRPSGIPERFSGSTSGNTATLTISRVEAGDEADYYCQVWDSSSD
HVVFGGGTKLTVLGGGGSGGGGSGGGGSGGGGSQVQLVESGGGVAIQPGRSLRLSCAASGFTLS
YYGMEIWVRQAPGKGLEWVAAISHDGSDKYYADSVKGRFTISRDNSKNTLYLQMNSLRAEDTA
VYYCSNDQFDPWGQGTLVTVSSR

SEQ ID NO: 84
EIVMTQSPATLSLSPGERATLSCRASQSVSSYLNWYQQKPGQAPRLLIYYASRRHTGIPARFSGSG
SGTDFTLTISSLQPEDFAVYYCQQGYNLPYTFGQGTKVEIKGGGGSGGGGSGGGGSGGGGSEVQ
LVQSGAEVKKPGASVKVSCKASGYTFTSYWMNWVRQAPGQGLEWMGNIYPSGGSTNYAQKFQ
GRVTMTVDTSTSTVYMELSSLRSEDTAVYYCASFSDGYYAYAMDYWGQGTLVTVEPKSSDKTH
TCPPCPAPPAAAPSVFLFPPKPKDTLMISRTPEVTCVVVDVSHEDPEVKFNWYVDGVEVHNAKT
KPREEQYNSTYRVVSVLTVLHQDWLNGKEYKCAVSNKALPAPIEKTISKAKGQPREPQVYTLPPS
RDELTKNQVSLTCLVKGFYPSDIAVEWESNGQPENNYKTTPPVLDSDGSFFLYSKLTVDKSRWQ
QGNVFSCSVMHEALHNHYTQKSLSLSPGGGGSPSSYVLTQPPSVSVAPGQTARITCGGNNIGSKS
ITNWFQQKPGQAPVLVVYDDSGRPSGIPERFSGSTSGNTATLTISRVEAGDEADYYCQVWDSSSD
HVVFGGGTKLTVLGGGGSGGGGSGGGGSGGGGSQVQLVESGGGVVQPGRSLRLSCAASGFTLS
YYGMEIWVRQAPGKGLEWVAAISHDGSDKYYADSVKGRFTISRDNSKNRLYLQMNSLRAEDTA
VYYCSNDQFDPWGQGTLVTVSSR

SEQ ID NO: 85
EIVMTQSPATLSLSPGERATLSCRASQSVSSYLNWYQQKPGQAPRLLIYYASRRHTGIPARFSGSG
SGTDFTLTISSLQPEDFAVYYCQQGYNLPYTFGQGTKVEIKGGGGSGGGGSGGGGSGGGGSEVQ
LVQSGAEVKKPGASVKVSCKASGYTFTSYWMNWVRQAPGQGLEWMGNIYPSGGSTNYAQKFQ
GRVTMTVDTSTSTVYMELSSLRSEDTAVYYCASFSDGYYAYAMDYWGQGTLVTVEPKSSDKTH
TCPPCPAPPAAAPSVFLFPPKPKDTLMISRTPEVTCVVVDVSHEDPEVKFNWYVDGVEVHNAKT
KPREEQYNSTYRVVSVLTVLHQDWLNGKEYKCAVSNKALPAPIEKTISKAKGQPREPQVYTLPPS
RDELTKNQVSLTCLVKGFYPSDIAVEWESNGQPENNYKTTPPVLDSDGSFFLYSKLTVDKSRWQ
QGNVFSCSVMHEALHNHYTQKSLSLSPGGGGSPSSYVLTQPPSVSVAPGKTARITCGGNNIGSKS
VNWFQQKPGQAPVLVVYDDSGRPSGIPERFSGSTSGNTATLTISRVEAGDEADYYCQVWDSSSD
HVVFGGGTKLTVLGGGGSGGGGSGGGGSGGGGSQVQLVESGGGVITQPGRSLRLSCAASGFTLS
YYGMHWVRQAPGKGLEWVAAISHDGSDKYYADSVKGRFTISRDNSKNRLYLQMNSLRAEDTA
VYYCSNDQFDPWGQGTLVTVSSR

SEQ ID NO: 86
EVQLVQSGAEVKKPGASVKVSCKASGYTFTSYWMNWVRQAPGQGLEWMGNIYPGSSTTNYAQ
KFQGRVTMTVDTSTSTVYMELSSLRSEDTAVYYCASFSDGYYAYAMDYWGQGTLVTVSSGGG
GSGGGGSGGGGSGGGGSEIVMTQSPATLSLSPGERATLSCRASQDISNYLNWYQQKPGQAVRLLI
YYTSRLHSGIPARFSGSGSGTDYTLTISSLQPEDFAVYFCQQGYTLPYTFGQGTKVEIKEPKSSDKT
HTCPPCPAPPAAAPSVFLFPPKPKDTLMISRTPEVTCVVVDVSHEDPEVKFNWYVDGVEVHNAK
TKPREEQYNSTYRVVSVLTVLHQDWLNGKEYKCAVSNKALPAPIEKTISKAKGQPREPQVYTLP
PSRDELTKNQVSLTCLVKGFYPSDIAVEWESNGQPENNYKTTPPVLDSDGSFFLYSKLTVDKSRW
QQGNVFSCSVMHEALHNHYTQKSLSLSPGGGGSPSSYVLTQPPSVSVAPGQTARITCGGNNIGSK
SVNWFQQKPGQAPVLVVYDDSGRPSGIPERFSGSTSGNTATLTISRVEAGDEADYYCQVWDSSS
DHVVFGGGTKLTVLGGGGSGGGGSGGGGSGGGGSQVQLVESGGGVVQPGRSLRLSCAASGFTL

-continued

| SEQUENCES |
|---|

SYYGMHWVRQAPGKGLEWVAAISHDGSDKYYADSVKGRFTISRDNSKNTLYLQMNSLRAEDT
AVYYCSNDQFDPWGQGTLVTVSSR

SEQ ID NO: 87
SYVLTQPPSVSVAPGQTARITCGGNNIGSKSVNWFQQKPGQAPVLVVYDDSGRPSGIPERFSGSTS
GNTATLTISRVEAGDEADYYCQVWDSSSDHVVFGGGTKLTVLGGGGSGGGGSGGGGSGGGGSQ
VQLVESGGGVVQPGRSLRLSCAASGFTLSYYGMHWVRQAPGKGLEWVAVISHDGSDKYYADS
VKGRFTISRDNSKNTLYLQMNSLRAEDTAVYYCSNDQFDPWGQGTLVTVEPKSSDKTHTCPPCP
APPAAAPSVFLFPPKPKDTLMISRTPEVTCVVVDVSHEDPEVKFNWYVDGVEVHNAKTKPREEQ
YNSTYRVVSVLTVLHQDWLNGKEYKCAVSNKALPAPIEKTISKAKGQPREPQVYTLPPSRDELT
KNQVSLTCLVKGFYPSDIAVEWESNGQPENNYKTTPPVLDSDGSFFLYSKLTVDKSRWQQGNVF
ScSVMHEALHNHYTQKSLSLSPGGGGSPSEVQLVQSGAEVKKPGASVKVSCKASGYTFTSYWM
NWVRQAPGQGLEWMGNIYPGSSTTNYAQKFQGRVTMTVDTSTSTVYMELSSLRSEDTAVYYCA
SFSDGYYAYAMDYWGQGTLVTVSSGGGGSGGGGSGGGGSGGGGSEIVMTQSPATLSLSPGERA
TLSCRASQDISNYLNWYQQKPGQAVRLLIYYTSRLHSGIPARFSGSGSGTDYTLTISSLQPEDFAV
YFCQQGYTLPYTFGQGTKVEIKR

SEQ ID NO: 88
SYVLTQPPSVSVAPGQTARITCGGNNIGSKSVNWFQQKPGQAPVLVVYDDSGRPSGIPERFSGSTS
GNTATLTISRVEAGDEADYYCQVWDSSSDHVVFGGGTKLTVLGGGGSGGGGSGGGGSGGGGSQ
VQLVESGGGVVQPGRSLRLSCAASGFTLSYYGMHWVRQAPGKGLEWVAVISHDGSDKYYADS
VKGRFTISRDNSKNTLYLQMNSLRAEDTAVYYCSNDQFDPWGQGTLVTVEPKSSDKTHTCPPCP
APPAAAPSVFLFPPKPKDTLMISRTPEVTCVVVDVSHEDPEVKFNWYVDGVEVHNAKTKPREEQ
YNSTYRVVSVLTVLHQDWLNGKEYKCAVSNKALPAPIEKTISKAKGQPREPQVYTLPPSRDELT
KNQVSLTCLVKGFYPSDIAVEWESNGQPENNYKTTPPVLDSDGSFFLYSKLTVDKSRWQQGNVF
SCSVMHEALHNHYTQKSLSLSPGGGGSPSEVQLVQSGAEVKKPGASVKVSCKASGYTFTSYWM
NWVRQAPGQGLEWMGNIYPSGGSTNYAQKFQGRVTMTVDTSTSTVYMELSSLRSEDTAVYYC
ASFSDGYYAYAMDYWGQGTLVTVSSGGGGSGGGGSGGGGSGGGGSEIVMTQSPATLSLSPGER
ATLSCRASQSVSSYLNWYQQKPGQAPRLLIYYASRRHTGIPARFSGSGSGTDFTLTISSLQPEDFA
VYYCQQGYNLPYTFGQGTKVEIKR

SEQ ID NO: 89
EVQLVQSGAEVKKPGASVKVSCKASGYTFTSYWMNWVRQAPGQGLEWMGNIYPSGGSTNYAQ
KFQGRVTMTVDTSTSTVYMELSSLRSEDTAVYYCASFSDGYYAYAMDYWGQGTLVTVSSGGG
GSGGGGSGGGGSGGGGSEIVMTQSPATLSLSPGERATLSCRASQSVSSYLNWYQQKPGQAPRLLI
YYASRRHTGIPARFSGSGSGTDFTLTISSLQPEDFAVYYCQQGYNLPYTFGQGTKVEIKEPKSSDK
THTCPPCPAPPAAAPSVFLFPPKPKDTLMISRTPEVTCVVVDVSHEDPEVKFNWYVDGVEVHNA
KTKPREEQYNSTYRVVSVLTVLHQDWLNGKEYKCAVSNKALPAPIEKTISKAKGQPREPQVYTL
PPSRDELTKNQVSLTCLVKGFYPSDIAVEWESNGQPENNYKTTPPVLDSDGSFFLYSKLTVDKSR
WQQGNVFSCSVMHEALHNHYTQKSLSLSPGGGGSPSSYVLTQPPSVSVAPGQTARITCGGNNIGS
KSVNWFQQKPGQAPVLVVYDDSGRPSGIPARFSGSTSGNTATLTISRVEAGDEADYYCQVWDSS
SDHVVFGGGTKLTVLGGGGSGGGGSGGGGSGGGGSQVQLVESGGGVVQPGRSLRLSCAASGFT
LSYYGMHWVRQAPGKGLEWVAAISHDGSDKYYADSVKGRFTISRDNSKNTLYLQMNSLRAED
TAVYYCSNDQFDPWGQGTLVTVSSR

SEQ ID NO: 90
EVQLVQSGAEVKKPGASVKVSCKASGYTFTSYWMNWVRQAPGQGLEWMGNIYPSGGSTNYAQ
KFQGRVTMTVDTSTSTVYMELSSLRSEDTAVYYCASFSDGYYAYAMDYWGQGTLVTVSSGGG
GSGGGGSGGGGSGGGGSEIVMTQSPATLSLSPGERATLSCRASQSVSSYLNWYQQKPGQAPRLLI
YYASRRHTGIPARFSGSGSGTDFTLTISSLQPEDFAVYYCQQGYNLPYTFGQGTKVEIKEPKSSDK
THTCPPCPAPPAAAPSVFLFPPKPKDTLMISRTPEVTCVVVDVSHEDPEVKFNWYVDGVEVHNA
KTKPREEQYNSTYRVVSVLTVLHQDWLNGKEYKCAVSNKALPAPIEKTISKAKGQPREPQVYTL
PPSRDELTKNQVSLTCLVKGFYPSDIAVEWESNGQPENNYKTTPPVLDSDGSFFLYSKLTVDKSR
WQQGNVFSCSVMHEALHNHYTQKSLSLSPGGGGSPSSYVLTQPPSVSVAPGQTARITCGGNNIGS
KSVNWFQQKPGQAPVLVVYDDSGRPSGVPNRFSGSTSGNTATLTISRVEAGDEADYYCQVWDS
SSDHVVFGGGTKLTVLGGGGSGGGGSGGGGSGGGGSQVQLVESGGGVVQPGRSLRLSCAASGF
TLSYYGMHWVRQAPGKGLEWVAAISHDGSDKYYADSVKGRFTISRDNSKNTLYLQMNSLRAE
DTAVYYCSNDQFDPWGQGTLVTVSSR

SEQ ID NO: 91
EVQLVQSGAEVKKPGASVKVSCKASGYTFTSYWMNWVRQAPGQGLEWMGNIYPSGGSTNYAQ
KFQGRVTMTVDTSTSTVYMELSSLRSEDTAVYYCASFSDGYYAYAMDYWGQGTLVTVSSGGG
GSGGGGSGGGGSGGGGSEIVMTQSPATLSLSPGERATLSCRASQSVSSYLNWYQQKPGQAPRLLI
YYASRRHTGIPARFSGSGSGTDFTLTISSLQPEDFAVYYCQQGYNLPYTFGQGTKVEIKEPKSSDK
THTCPPCPAPPAAAPSVFLFPPKPKDTLMISRTPEVTCVVVDVSHEDPEVKFNWYVDGVEVHNA
KTKPREEQYNSTYRVVSVLTVLHQDWLNGKEYKCAVSNKALPAPIEKTISKAKGQPREPQVYTL
PPSRDELTKNQVSLTCLVKGFYPSDIAVEWESNGQPENNYKTTPPVLDSDGSFFLYSKLTVDKSR
WQQGNVFSCSVMHEALHNHYTQKSLSLSPGGGGSPSSYVLTQPPSVSVAPGQTARITCGGNNIGS
KSVNWFQQKPGQAPVLVVYDDSGRPSGVPSRFSGSTSGNTATLTISRVEAGDEADYYCQVWDSS
SDHVVFGGGTKLTVLGGGGSGGGGSGGGGSGGGGSQVQLVESGGGVVQPGRSLRLSCAASGFT
LSYYGMHWVRQAPGKGLEWVAAISHDGSDKYYADSVKGRFTISRDNSKNTLYLQMNSLRAED
TAVYYCSNDQFDPWGQGTLVTVSSR

SEQ ID NO: 92
EVQLVQSGAEVKKPGASVKVSCKASGYTFTSYWMNWVRQAPGQGLEWMGNIYPSGGSTNYAQ
KFQGRVTMTVDTSTSTVYMELSSLRSEDTAVYYCASFSDGYYAYAMDYWGQGTLVTVSSGGG
GSGGGGSGGGGSGGGGSEIVMTQSPATLSLSPGERATLSCRASQSVSSYLNWYQQKPGQAPRLLI

-continued

| SEQUENCES |
|---|

YYASRRHTGIPARFSGSGSGTDFTLTISSLQPEDFAVYYCQQGYNLPYTFGQGTKVEIKEPKSSDK
THTCPPCPAPPAAAPSVFLFPPKPKDTLMISRTPEVTCVVVDVSHEDPEVKFNWYVDGVEVHNA
KTKPREEQYNSTYRVVSVLTVLHQDWLNGKEYKCAVSNKALPAPIEKTISKAKGQPREPQVYTL
PPSRDELTKNQVSLTCLVKGFYPSDIAVEWESNGQPENNYKTTPPVLDSDGSFFLYSKLTVDKSR
WQQGNVFSCSVMHEALHNHYTQKSLSLSPGGGGSPSSYVLTQPPSVSVAPGQTARITCGGNNIGS
KSVNWFQQKPGQAPVLVVYDDSGRPSGIPKRFSGSTSGNTATLTISRVEAGDEADYYCQVWDSS
SDHVVFGGGTKLTVLGGGGSGGGGSGGGGSGGGGSQVQLVESGGGVVQPGRSLRLSCAASGFT
LSYYGMHWVRQAPGKGLEWVAAISHDGSDKYYADSVKGRFTISRDNSKNTLYLQMNSLRAED
TAVYYCSNDQFDPWGQGTLVTVSSR

SEQ ID NO: 93
EVQLVQSGAEVKKPGASVKVSCKASGYTFTSYWMNWVRQAPGQGLEWMGNIYPSGGSTNYAQ
KFQGRVTMTVDTSTSTVYMELSSLRSEDTAVYYCASFSDGYYAYAMDYWGQGTLVTVSSGGG
GSGGGGSGGGGSGGGGSEIVMTQSPATLSLSPGERATLSCRASQSVSSYLNWYQQKPGQAPRLLI
YYASRRHTGIPARFSGSGSGTDFTLTISSLQPEDFAVYYCQQGYNLPYTFGQGTKVEIKEPKSSDK
THTCPPCPAPPAAAPSVFLFPPKPKDTLMISRTPEVTCVVVDVSHEDPEVKFNWYVDGVEVHNA
KTKPREEQYNSTYRVVSVLTVLHQDWLNGKEYKCAVSNKALPAPIEKTISKAKGQPREPQVYTL
PPSRDELTKNQVSLTCLVKGFYPSDIAVEWESNGQPENNYKTTPPVLDSDGSFFLYSKLTVDKSR
WQQGNVFSCSVMHEALHNHYTQKSLSLSPGGGGSPSSYVLTQPPSVSVAPGQTARITCGGNNIGS
KSVNWFQQKPGQAPVLVVYDDSGRPSGIPARFSGSTSGNTATLTISRVEAGDEADYYCQVWDSS
SDHVVFGGGTKLTVLGGGGSGGGGSGGGGSGGGGSQVQLVESGGGVVQPGRSLRLSCAASGFT
LSYYGMHWVRQAPGKGLEWVAAISHDGSDKYYADSVKGRFTISRDNSKNRLYLQMNSLRAED
TAVYYCSNDQFDPWGQGTLVTVSSR

SEQ ID NO: 94
EVQLVQSGAEVKKPGASVKVSCKASGYTFTSYWMNWVRQAPGQGLEWMGNIYPSGGSTNYAQ
KFQGRVTMTVDTSTSTVYMELSSLRSEDTAVYYCASFSDGYYAYAMDYWGQGTLVTVSSGGG
GSGGGGSGGGGSGGGGSEIVMTQSPATLSLSPGERATLSCRASQSVSSYLNWYQQKPGQAPRLLI
YYASRRHTGIPARFSGSGSGTDFTLTISSLQPEDFAVYYCQQGYNLPYTFGQGTKVEIKEPKSSDK
THTCPPCPAPPAAAPSVFLFPPKPKDTLMISRTPEVTCVVVDVSHEDPEVKFNWYVDGVEVHNA
KTKPREEQYNSTYRVVSVLTVLHQDWLNGKEYKCAVSNKALPAPIEKTISKAKGQPREPQVYTL
PPSRDELTKNQVSLTCLVKGFYPSDIAVEWESNGQPENNYKTTPPVLDSDGSFFLYSKLTVDKSR
WQQGNVFSCSVMHEALHNHYTQKSLSLSPGGGGSPSSYVLTQPPSVSVAPGQTARITCGGNNIGS
KSVNWFQQKPGQAPVLVVYDDSGRPSGVPNRFSGSTSGNTATLTISRVEAGDEADYYCQVWDS
SSDHVVFGGGTKLTVLGGGGSGGGGSGGGGSGGGGSQVQLVESGGGVVQPGRSLRLSCAASGF
TLSYYGMHWVRQAPGKGLEWVAAISHDGSDKYYADSVKGRFTISRDNSKNRLYLQMNSLRAE
DTAVYYCSNDQFDPWGQGTLVTVSSR

SEQ ID NO: 95
EVQLVQSGAEVKKPGASVKVSCKASGYTFTSYWMNWVRQAPGQGLEWMGNIYPSGGSTNYAQ
KFQGRVTMTVDTSTSTVYMELSSLRSEDTAVYYCASFSDGYYAYAMDYWGQGTLVTVSSGGG
GSGGGGSGGGGSGGGGSEIVMTQSPATLSLSPGERATLSCRASQSVSSYLNWYQQKPGQAPRLLI
YYASRRHTGIPARFSGSGSGTDFTLTISSLQPEDFAVYYCQQGYNLPYTFGQGTKVEIKEPKSSDK
THTCPPCPAPPAAAPSVFLFPPKPKDTLMISRTPEVTCVVVDVSHEDPEVKFNWYVDGVEVHNA
KTKPREEQYNSTYRVVSVLTVLHQDWLNGKEYKCAVSNKALPAPIEKTISKAKGQPREPQVYTL
PPSRDELTKNQVSLTCLVKGFYPSDIAVEWESNGQPENNYKTTPPVLDSDGSFFLYSKLTVDKSR
WQQGNVFSCSVMHEALHNHYTQKSLSLSPGGGGSPSSYVLTQPPSVSVAPGQTARITCGGNNIGS
KSVNWFQQKPGQAPVLVVYDDSGRPSGVPSRFSGSTSGNTATLTISRVEAGDEADYYCQVWDSS
SDHVVFGGGTKLTVLGGGGSGGGGSGGGGSGGGGSQVQLVESGGGVVQPGRSLRLSCAASGFT
LSYYGMHWVRQAPGKGLEWVAAISHDGSDKYYADSVKGRFTISRDNSKNRLYLQMNSLRAED
TAVYYCSNDQFDPWGQGTLVTVSSR

SEQ ID NO: 96
EVQLVQSGAEVKKPGASVKVSCKASGYTFTSYWMNWVRQAPGQGLEWMGNIYPSGGSTNYAQ
KFQGRVTMTVDTSTSTVYMELSSLRSEDTAVYYCASFSDGYYAYAMDYWGQGTLVTVSSGGG
GSGGGGSGGGGSGGGGSEIVMTQSPATLSLSPGERATLSCRASQSVSSYLNWYQQKPGQAPRLLI
YYASRRHTGIPARFSGSGSGTDFTLTISSLQPEDFAVYYCQQGYNLPYTFGQGTKVEIKEPKSSDK
THTCPPCPAPPAAAPSVFLFPPKPKDTLMISRTPEVTCVVVDVSHEDPEVKFNWYVDGVEVHNA
KTKPREEQYNSTYRVVSVLTVLHQDWLNGKEYKCAVSNKALPAPIEKTISKAKGQPREPQVYTL
PPSRDELTKNQVSLTCLVKGFYPSDIAVEWESNGQPENNYKTTPPVLDSDGSFFLYSKLTVDKSR
WQQGNVFSCSVMHEALHNHYTQKSLSLSPGGGGSPSSYVLTQPPSVSVAPGQTARITCGGNNIGS
KSVNWFQQKPGQAPVLVVYDDSGRPSGIPKRFSGSTSGNTATLTISRVEAGDEADYYCQVWDSS
SDHVVFGGGTKLTVLGGGGSGGGGSGGGGSGGGGSQVQLVESGGGVVQPGRSLRLSCAASGFT
LSYYGMHWVRQAPGKGLEWVAAISHDGSDKYYADSVKGRFTISRDNSKNRLYLQMNSLRAED
TAVYYCSNDQFDPWGQGTLVTVSSR

SEQ ID NO: 97
EVQLVQSGAEVKKPGASVKVSCKASGYTFTSYWMNWVRQAPGQGLEWMGNIYPSGGSTNYAQ
KFQGRVTMTVDTSTSTVYMELSSLRSEDTAVYYCASFSDGYYAYAMDYWGQGTLVTVSSGGG
GSGGGGSGGGGSGGGGSEIVMTQSPATLSLSPGERATLSCRASQSVSSYLNWYQQKPGQAPRLLI
YYASRRHTGIPARFSGSGSGTDFTLTISSLQPEDFAVYYCQQGYNLPYTFGQGTKVEIKEPKSSDK
THTCPPCPAPPAAAPSVFLFPPKPKDTLMISRTPEVTCVVVDVSHEDPEVKFNWYVDGVEVHNA
KTKPREEQYNSTYRVVSVLTVLHQDWLNGKEYKCAVSNKALPAPIEKTISKAKGQPREPQVYTL
PPSRDELTKNQVSLTCLVKGFYPSDIAVEWESNGQPENNYKTTPPVLDSDGSFFLYSKLTVDKSR
WQQGNVFSCSVMHEALHNHYTQKSLSLSPGGGGSPSSYVLTQPPSVSVAPGKTARITCGGNNIGS
KSVNWFQQKPGQAPVLVVYDDSGRPSGIPARFSGSTSGNTATLTISRVEAGDEADYYCQVWDSS
SDHVVFGGGTKLTVLGGGGSGGGGSGGGGSGGGGSQVQLVESGGGVVQPGRSLRLSCAASGFT

-continued

| SEQUENCES |
|---|
| LSYYGMHWVRQAPGKGLEWVAAISHDGSDKYYADSVKGRFTISRDNSKNRLYLQMNSLRAED<br>TAVYYCSNDQFDPWGQGTLVTVSSR |
| SEQ ID NO: 98<br>EVQLVQSGAEVKKPGASVKVSCKASGYTFTSYWMNWVRQAPGQGLEWMGNIYPSGGSTNYAQ<br>KFQGRVTMTVDTSTSTVYMELSSLRSEDTAVYYCASFSDGYYAYAMDYWGQGTLVTVSSGGG<br>GSGGGGSGGGGSGGGGSEIVMTQSPATLSLSPGERATLSCRASQSVSSYLNWYQQKPGQAPRLLI<br>YYASRRHTGIPARFSGSGSGTDFTLTISSLQPEDFAVYYCQQGYNLPYTFGQGTKVEIKEPKSSDK<br>THTCPPCPAPPAAAPSVFLFPPKPKDTLMISRTPEVTCVVVDVSHEDPEVKFNWYVDGVEVHNA<br>KTKPREEQYNSTYRVVSVLTVLHQDWLNGKEYKCAVSNKALPAPIEKTISKAKGQPREPQVYTL<br>PPSRDELTKNQVSLTCLVKGFYPSDIAVEWESNGQPENNYKTTPPVLDSDGSFFLYSKLTVDKSR<br>WQQGNVFSCSVMHEALHNHYTQKSLSLSPGGGGSPSSYVLTQPPSVSVAPGKTARITCGGNNIGS<br>KSVNWFQQKPGQAPVLVVYDDSGRPSGVPNRFSGSTSGNTATLTISRVEAGDEADYYCQVWDS<br>SSDHVVFGGGTKLTVLGGGGSGGGGSGGGGSGGGGSQVQLVESGGGVVQPGRSLRLSCAASGF<br>TLSYYGMHWVRQAPGKGLEWVAAISHDGSDKYYADSVKGRFTISRDNSKNRLYLQMNSLRAE<br>DTAVYYCSNDQFDPWGQGTLVTVSSR |
| SEQ ID NO: 99<br>EVQLVQSGAEVKKPGASVKVSCKASGYTFTSYWMNWVRQAPGQGLEWMGNIYPSGGSTNYAQ<br>KFQGRVTMTVDTSTSTVYMELSSLRSEDTAVYYCASFSDGYYAYAMDYWGQGTLVTVSSGGG<br>GSGGGGSGGGGSGGGGSEIVMTQSPATLSLSPGERATLSCRASQSVSSYLNWYQQKPGQAPRLLI<br>YYASRRHTGIPARFSGSGSGTDFTLTISSLQPEDFAVYYCQQGYNLPYTFGQGTKVEIKEPKSSDK<br>THTCPPCPAPPAAAPSVFLFPPKPKDTLMISRTPEVTCVVVDVSHEDPEVKFNWYVDGVEVHNA<br>KTKPREEQYNSTYRVVSVLTVLHQDWLNGKEYKCAVSNKALPAPIEKTISKAKGQPREPQVYTL<br>PPSRDELTKNQVSLTCLVKGFYPSDIAVEWESNGQPENNYKTTPPVLDSDGSFFLYSKLTVDKSR<br>WQQGNVFSCSVMHEALHNHYTQKSLSLSPGGGGSPSSYVLTQPPSVSVAPGKTARITCGGNNIGS<br>KSVNWFQQKPGQAPVLVVYDDSGRPSGVPSRFSGSTSGNTATLTISRVEAGDEADYYCQVWDSS<br>SDHVVFGGGTKLTVLGGGGSGGGGSGGGGSGGGGSQVQLVESGGGVVQPGRSLRLSCAASGFT<br>LSYYGMHWVRQAPGKGLEWVAAISHDGSDKYYADSVKGRFTISRDNSKNRLYLQMNSLRAED<br>TAVYYCSNDQFDPWGQGTLVTVSSR |
| SEQ ID NO: 100<br>EVQLVQSGAEVKKPGASVKVSCKASGYTFTSYWMNWVRQAPGQGLEWMGNIYPSGGSTNYAQ<br>KFQGRVTMTVDTSTSTVYMELSSLRSEDTAVYYCASFSDGYYAYAMDYWGQGTLVTVSSGGG<br>GSGGGGSGGGGSGGGGSEIVMTQSPATLSLSPGERATLSCRASQSVSSYLNWYQQKPGQAPRLLI<br>YYASRRHTGIPARFSGSGSGTDFTLTISSLQPEDFAVYYCQQGYNLPYTFGQGTKVEIKEPKSSDK<br>THTCPPCPAPPAAAPSVFLFPPKPKDTLMISRTPEVTCVVVDVSHEDPEVKFNWYVDGVEVHNA<br>KTKPREEQYNSTYRVVSVLTVLHQDWLNGKEYKCAVSNKALPAPIEKTISKAKGQPREPQVYTL<br>PPSRDELTKNQVSLTCLVKGFYPSDIAVEWESNGQPENNYKTTPPVLDSDGSFFLYSKLTVDKSR<br>WQQGNVFSCSVMHEALHNHYTQKSLSLSPGGGGSPSSYVLTQPPSVSVAPGKTARITCGGNNIGS<br>KSVNWFQQKPGQAPVLVVYDDSGRPSGIPKRFSGSTSGNTATLTISRVEAGDEADYYCQVWDSS<br>SDHVVFGGGTKLTVLGGGGSGGGGSGGGGSGGGGSQVQLVESGGGVVQPGRSLRLSCAASGFT<br>LSYYGMHWVRQAPGKGLEWVAAISHDGSDKYYADSVKGRFTISRDNSKNRLYLQMNSLRAED<br>TAVYYCSNDQFDPWGQGTLVTVSSR |
| SEQ ID NO: 101<br>SSEPKSSDKTHTCPPCPAPELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIEKTISKAKGQ<br>PREPQVYTLPPSRDELTKNQVSLTCLVKGFYPSDIAVEWESNGQPENNYKTTPPVLDSDGSFFLYS<br>KLTVDKSRWQQGNVFSCSVMHEALHNHYTQKSLSLSPGGGGSPSQVQLQQPGAELVKPGASVK<br>LSCEASGYTFTSYWINWVKQRPGQGLEWIGNIYPGSSTTNYNEKFKSKATLTVDTSSSTAYMQLS<br>SLTSDDSAVFYCASFSDGYYAYAMDYWVQGTSVTVSSGGGGSGGGGSGGGGSGGGGSDIQMT<br>QTTSSLSASLGDRVTITCRASQDISNYLNWYQQKPDGTVKLLIYYTSRLHSGVPSRFSGGGSGTD<br>YSLTISNLEQEDIATYFCQQGYTLPYTFGGGTKLEIKR |
| SEQ ID NO: 102<br>SYVLTQPPSVSVAPGQTARITCGGNNIGSKSVHWFQQKPGQAPALVVYDDSGRPSGIPERFSGSTS<br>GNTATLTISRVEAGDEADYYCQVWDSSSDHVVFGGGTKLTVLGGGGSGGGGSGGGGSGGGGSQ<br>VQLVESGGGVVQPGRSLRLSCAASGFTLSYYGMHWVRQAPGKGLEWVAVISHDGSDKYYADS<br>VKGRFTISRDNSKNTLYLQMDSLRAEDTALYYCSNDQFDPWGQGTLVTVSSSEPKSSDKTHTCPP<br>CPAPELLGGPSVFLFPPKPKDTLMISRTPEVTCVVVDVSHEDPEVKFNWYVDGVEVHNAKTKPR<br>EEQYNSTYRVVSYLTVLHQDWLNGKEYKCKVSNKALPAPIEKTISKAKGQPREPQVYTLPPSRD<br>ELTKNQVSLTCLVKGFYPSDIAVEWESNGQPENNYKTTPPVLDSDGSFFLYSKLTVDKSRWQQG<br>NVFSCSVMHEALHNHYTQKSLSLSPGK |
| SEQ ID NO: 103 (HUMAN CD137 ECD-AVI-FLAG-HIS)<br>LQDPCSNCPAGTFCDNNRNQICSPCPPNSFSSAGGQRTCDICRQCKGVFRTRKECSSTSNAECDCT<br>PGFHCLGAGCSMCEQDCKQGQELTKKGCKDCCFGTFNDQKRGICRPWTNCSLDGKSVLVNGTK<br>ERDVVCGPSPADLSPGASSVTPPAPAREPGHSPQSSSLNDIFEAQKIEWHEDYKDDDDKDYKDDD<br>DKDYKDDDDKHHHHHHHHHH |
| SEQ ID NO: 104 (Human CD137 ECD-mFc)<br>LQDPCSNCPAGTFCDNNRNQICSPCPPNSFSSAGGQRTCDICRQCKGVFRTRKECSSTSNAECDCT<br>PGFHCLGAGCSMCEQDCKQGQELTKKGCKDCCFGTFNDQKRGICRPWTNCSLDGKSVLVNGTK<br>ERDVVCGPSPADLSPGASSVTPPAPAREPGHSPQSSSEPRGPTIKPCPPCKCPAPNLLGGPSVFIFPP<br>KIKDVLMISLSPIVTCVVVDVSEDDPDVQISWFVNNVEVHTAQTQTHREDYNSTLRVVSALPIQH |

-continued

| SEQUENCES |
| --- |

QDWMSGKEFKCKVNNKDLPAPIERTISKPKGSVRAPQVYVLPPPEEEMTKKQVTLTCMVTDFMP
EDIYVEWTNNGKTELNYKNTEPVLDSDGSYFMYSKLRVEKKNWVERNSYSCSVVHEGLHNHHT
TKSFSRTPGK

SEQ ID NO: 105 (Cyno CD137 ECD-avi-flag-his)
LQDLCSNCPAGTFCDNNRSQICSPCPPNSFS SAGGQRTCDICRQCKGVFKTRKECSSTSNAECDCI
SGYHCLGAECSMCEQDCKQGQELTKKGCKDCCFGTFNDQKRGICRPWTNCSLDGKSVLVNGTK
ERDVVCGPSPADLSPGASSATPPAPAREPGHSPQSSSLNDIFEAQKIEWHEDYKDDDDKDYKDDD
DKDYKDDDDKHHHHHHHHHH SEQ ID NO: 106 (Cyno CD137 ECD-mFc)
LQDLCSNCPAGTFCDNNRSQICSPCPPNSFSSAGGQRTCDICRQCKGVFKTRKECSSTSNAECDCI
SGYHCLGAECSMCEQDCKQGQELTKKGCKDCCFGTFNDQKRGICRPWTNCSLDGKSYLVNGTK
ERDVVCGPSPADLSPGASSATPPAPAREPGHSPQSSSEPRGPTIKPCPPCKCPAPNLLGGPSVFIFPP
KIKDVLMISLSPIVTCVVVDVSEDDPDVQISWFVNNVEVHTAQTQTHREDYNSTLRVVSALPIQH
QDWMSGKEFKCKVNNKDLPAPIERTISKPKGSVRAPQVYVLPPPEEEMTKKQVTLTCMVTDFMP
EDIYVEWTNNGKTELNYKNTEPVLDSDGSYFMYSKLRVEKKNWVERNSYSCSVVHEGLHNHHT
TKSFSRTPGK SEQ ID NO: 107 (Human OX40 ECD-avi-flag-his)
LHCVGDTYPSNDRCCHECRPGNGMVSRCSRSQNTVCRPCGPGFYNDVVSSKPCKPCTWCNLRS
GSERKQLCTATQDTVCRCRAGTQPLDSYKPGVDCAPCPPGHFSPGDNQACKPWTNCTLAGKHT
LQPASNSSDAICEDRDPPATQPQETQGPPARPITVQPTEAWPRTSQGPSTRPVEVPGGRATGLNDI
FEAQKIEWHEDYKDDDDKDYKDDDDKDYKDDDDKHHHHHH SEQ ID NO: 108 (Cyno OX40 ECD-avi-flag-his)
KLHCVGDTYPSNDRCCQECRPGNGMVSRCNRSQNTVCRPCGPGFYNDVVSAKPCKACTWCNL
RSGSERKQPCTATQDTVCRCRAGTQPLDSYKPGVDCAPCPPGHFSPGDNQACKPWTNCTLAGK
HTLQPASNSSDAICEDRDPPPTQPQETQGPPARPTTVQPTEAWPRTSQRPSTRPVEVPRGPATGLN
DIFEAQKIEWHEDYKDDDDKDYKDDDDKDYKDDDDKHHHHHH SEQ ID NO: 109 (linker)
AGGGGSGGGGSGGGGSPS

SEQ ID NO: 110 (LINKER)
AGGGGSPS

SEQ ID NO: 111 (K332A)
EPKSSDKTHTCPPCPAPEAAGAPSVFLFPPKPKDTLMISRTPEVTCVVVDVSHEDPEVKFNWYVD
GVEVHNAKTKPREEQYNSTYRVVSVLTVLHQDWLNGKEYKCAVSNKALPAPIEKTISKAKGQP
REPQVYTLPPSRDELTKNQVSLTCLVKGFYPSDIAVEWESNGQPENNYKTTPPVLDSDGSFFLYS
KLTVDKSRWQQGNVFSCSVMHEALHNHYTQKSLSLSPG

SEQ ID NO: 112 (PVAG TSC01004)
EPKSSDKTHTCPPCPAPPVAGAPSVFLFPPKPKDTLMISRTPEVTCVVVDVSHEDPEVKFNWYVD
GVEVHNAKTKPREEQYNSTYRVVSVLTVLHQDWLNGKEYKCAVSNKALPAPIEKTISKAKGQP
REPQVYTLPPSRDELTKNQVSLTCLVKGFYPSDIAVEWESNGQPENNYKTTPPVLDSDGSFFLYS
KLTVDKSRWQQGNVFSCSVMHEALHNHYTQKSLSLSPG

SEQ ID NO: 113 (PVAdel TSC01005)
EPKSSDKTHTCPPCPAPPVAAPSVFLFPPKPKDTLMISRTPEVTCVANDVSHEDPEVKFNWYVDG
VEVHNAKTKPREEQYNSTYRVVSVLTVLHQDWLNGKEYKCAVSNKALPAPIEKTISKAKGQPRE
PQVYTLPPSRDELTKNQVSLTCLVKGFYPSDIAVEWESNGQPENNYKTTPPVLDSDGSFFLYSKL
TVDKSRWQQGNVFSCSVMHEALHNHYTQKSLSLSPG SEQ ID NO: 114 (PAAG TSC01006)
EPKSSDKTHTCPPCPAPPAAGAPSVFLFPPKPKDTLMISRTPEVTCVVVDVSHEDPEVKFNWYVD
GVEVHNAKTKPREEQYNSTYRVVSVLTVLHQDWLNGKEYKCAVSNKALPAPIEKTISKAKGQP
REPQVYTLPPSRDELTKNQVSLTCLVKGFYPSDIAVEWESNGQPENNYKTTPPVLDSDGSFFLYS
KLTVDKSRWQQGNVFSCSVMHEALHNHYTQKSLSLSPG SEQ ID NO: 115 (PAAdel TSC01007)
EPKSSDKTHTCPPCPAPPAAAPSVFLFPPKPKDTLMISRTPEVTCVANDVSHEDPEVKFNWYVDG
VEVHNAKTKPREEQYNSTYRVVSVLTVLHQDWLNGKEYKCAVSNKALPAPIEKTISKAKGQPRE
PQVYTLPPSRDELTKNQVSLTCLVKGFYPSDIAVEWESNGQPENNYKTTPPVLDSDGSFFLYSKL
TVDKSRWQQGNVFSCSVMHEALHNHYTQKSLSLSPG SEQ ID NO: 143
QVQLQQPGAELVKPGASVKLSCEASGYTFTSYWINWVKQRPGQGLEWIGNIYPGSSTTNYNEKF
KSKATLTVDTSSSTAYMQLSSLTSDDSAVFYCASFSDGYYAYAMDYWVQGTSVTVSS SEQ ID NO: 144
QVQLQQPGAELVKPGASVKLSCKASGYTFTSYWINWVKQRPGQGLEWIGNIYPGSSTTNYNEKF
KSKATLTVDTSSSTAYMQLSSLTSDDSAVFYCASFSDGYYAYAMDYWVQGTSVTVSSGGGGSG
GGGSGGGGSGGGGSDIQMTQTTSSLSASLGDRVTITCRASQDISNYLNWYQQKPDGTVKLLIYYT
SRLHSGVPSRFSGGGSGTDYSLTISNLEQEDIATYFCQQGYTLPYTFGGGTKLEIKSSSEPKSSDKT
HTCPPCPAPELLGGPSVFLFPPKPKDTLMISRTPEVTCVIIVDVSHEDPEVKFNWYVDGVEVHNAK -continued

| SEQUENCES |
| --- |

TKPREEQYNSTYRVVSVLTVLHQDWLNGKEYKCKVSNKALPAPIEKTISKAKGQPREPQVYTLP
PSRDELTKNQVSLTCLVKGFYPSDIAVEWESNGQPENNYKTTPPVLDSDGSFFLYSKLTVDKSRW
QQGNVFSCSVMHEALHNHYTQKSLSLSPGSGGGGSGGGGSGGGGSPSSYVLTQPPSVSVAPGQT
ARITCGGNNIGSKSVHWFQQKPGQAPALVVYDDSGRPSGIPERFSGSTSGNTATLTISRVEAGDEA
DYYCQVWDSSSDHVVFGGGTKLTVLGGGGSGGGGSGGGGSGGGGSQVQLVESGGGVVQPGRS
LRLSCAASGFTLSYYGMHWVRQAPGKGLEWVAVISHDGSDKYYADSVKGRFTISRDNSKNTLY
LQMDSLRAEDTALYYCSNDQFDPWGQGTLVTVSSR

SEQ ID NO: 145
QVQLQQPGAELVKPGASVKLSCKASGYTFTSYWINWVKQRPGQGLEWIGNIYPGSSTTNYNEKF
KSKATLTVDTSSSTAYMQLSSLTSDDSAVFYCASFSDGYYAYAMDWVQGTSVTVSSGGGGSG
GGGSGGGGSGGGGSDIQMTQTTSSLSASLGDRVTITCRASQDISNYLNWYQQKPDGTVKLLIYYT
SRLHSGVPSRFSGGGSGTDYSLTISNLEQEDIATYFCQQGYTLPYTFGGGTKLEIKSSS

SEQ ID NO: 146
SYVLTQPPSVSVAPGQTARITCGGNNIGSKSVHWFQQKPGQAPALVVYDDSGRPSGIPERFSGSTS
GNTATLTISRVEAGDEADYYCQVWDSSSDHVVFGGGTKLTVLGGGGSGGGGSGGGGSGGGGSQ
VQLVESGGGVVQPGRSLRLSCAASGFTLSYYGMHWVRQAPGKGLEWVAVISHDGSDKYYADS
VKGRFTISRDNSKNTLYLQMDSLRAEDTALYYCSNDQFDPWGQGTLVTVSSR

SEQ ID NO: 147 (FXX01066 ANTI 4-1BB SCFV X ANTI OX40 SCFV ADAPTIR NUCLEOTIDE SEQUENCE)
GAGGTGCAACTGGTGCAATCAGGAGCTGAGGTGAAAAAACCGGGTGCCAGTGTTAAAGTTA
GCTGTAAGGCATCCGGGTACACGTTTACATCTTACTGGATGAATTGGGTCCGACAGGCCCCA
GGCCAAGGGTTGGAATGGATGGGAAATATTTATCCGTCCGGAGGTAGCACCAATTACGCTCA
AAAATTTCAGGGAAGGGTGACAATGACGGTGGACACTAGCACCAGTACTGTGTACATGGAG
TTGTCAAGTCTTCGCTCCGAAGATACTGCCGTGTATTACTGTGCTTCATTTAGTGATGGGTAT
TATGCGTACGCTATGGATTATTGGGGTCAGGGGACCTTGGTGACGGTGTCCAGTGGTGGTGG
AGGTAGTGGTGGAGGCGGATCTGGCGGCGGCGGTTCAGGAGGTGGTGGATCCGAGATAGTG
ATGACTCAATCTCCGGCTACTTTGTCTCTCAGTCCAGGGGAGCGAGCCACTCTGAGCTGCAG
GGCAAGTCAGTCCGTCTCCAGCTATCTTAATTGGTACCAACAGAAGCCGGGACAGGCTCCAC
GATTGTTGATCTACTACGCTAGTCGCAGGCACACAGGCATACCTGCTCGCTTTTCTGGAAGC
GGGTCAGGAACAGACTTCACTTTGACAATCTCATCACTTCAGCCGGAGGACTTTGCTGTGTA
TTACTGCCAACAAGGCTACAACCTCCCCTATACGTTTGGGCAGGGCACAAAAGTAGAGATTA
AGGAGCCCAAATCTTCTGACAAAACTCACACATGCCCACCGTGCCCAGCACCTCCAGCCGCT
GCACCGTCAGTCTTCCTCTTCCCCCCAAAACCCAAGGACACCCTCATGATCTCCCGGACCCCT
GAGGTCACATGCGTGGTGGTGGACGTGAGCCACGAAGACCCTGAGGTCAAGTTCAACTGGT
ACGTGGACGGCGTGGAGGTGCATAATGCCAAGACAAAGCCGCGGGAGGAGCAGTACAACA
GCACGTACCGTGTGGTCAGCGTCCTCACCGTCCTGCACCAGGACTGGCTGAATGGCAAGGAA
TACAAGTGCGCGGTCTCCAACAAAGCCCTCCCAGCCCCCATCGAGAAAACCATCTCCAAAGC
CAAAGGGCAGCCCCGAGAACCACAGGTGTACACCCTGCCCCCATCCCGGGATGAGCTGACC
AAGAACCAGGTCAGCCTGACCTGCCTGGTCAAAGGCTTCTATCCAAGCGACATCGCCGTGGA
GTGGGAGAGCAATGGGCAGCCGGAGAACAACTACAAGACCACGCCTCCCGTGCTGGACTCC
GACGGCTCCTTCTTCCTCTACAGCAAGCTCACCGTGGACAAGAGCAGGTGGCAGCAGGGGA
ACGTCTTCTCATGCTCCGTGATGCATGAGGCTCTGCACAACCACTACACGCAGAAGAGCCTC
TCCCTGTCTCCGGGCGGCGGGGGATCCCCGTCATCCTATGTGCTGACTCAGCCACCCTCGGTG
TCGGTGGCCCCAGGACAGACGGCCAGGATTACCTGTGGGGGAAACAACATTGGAAGTAAAA
GTGTGAACTGGTTCCAGCAGAAGCCAGGCCAGGCCCCTGTACTGGTCGTCTATGATGATAGC
GGCCGGCCCTCAGGGATCCCTGAGCGATTCTCTGGCTCCACCTCTGGGAACACGGCCACCCT
GACCATCAGCAGGGTCGAAGCCGGGGATGAGGCCGACTATTACTGTCAGGTGTGGGATAGT
AGTAGTGATCATGTGGTATTCGGCGGAGGGACCAAGCTGACCGTCCTAGGTGGAGGCGGTTC
AGGCGGAGGTGGATCCGGCGGTGGCGGCTCCGGTGGCGGCGGATCTCAGGTGCAACTGGTG
GAGTCTGGGGGAGGCGTGGTCCAGCCTGGGAGGTCCCTGAGACTCTCCTGTGCAGCCTCTGG
ATTCACCCTCAGTTACTATGGCATGCACTGGGTCCGCCAGGCTCCAGGCAAGGGGCTGGAGT
GGGTGGCAGCTATATCACATGATGGAAGTGATAAATACTATGCAGACTCCGTGAAGGGCCG
ATTCACCATCTCCAGAGACAATTCCAAGAACACGCTGTATCTGCAAATGAACAGCCTGAGAG
CTGAAGACACGGCCGTGTATTACTGTTCGAATGACCAGTTTGACCCCTGGGGCCAGGGAACC
CTGGTCACCGTCTCCTCGCGC

SEQ ID NO: 148 (FXX01102 ANTI 4-1BB SCFV X ANTI OX40 SCFV ADAPTIR NUCLEOTIDE SEQUENCE)
GAGGTGCAACTGGTGCAATCAGGAGCTGAGGTGAAAAAACCGGGTGCCAGTGTTAAAGTTA
GCTGTAAGGCATCCGGGTACACGTTTACATCTTACTGGATGAATTGGGTCCGACAGGCCCCA
GGCCAAGGGTTGGAATGGATGGGAAATATTTATCCGTCCGGAGGTAGCACCAATTACGCTCA
AAAATTTCAGGGAAGGGTGACAATGACGGTGGACACTAGCACCAGTACTGTGTACATGGAG
TTGTCAAGTCTTCGCTCCGAAGATACTGCCGTGTATTACTGTGCTTCATTTAGTGATGGGTAT
TATGCGTACGCTATGGATTATTGGGGTCAGGGGACCTTGGTGACGGTGTCCAGTGGTGGTGG
AGGTAGTGGTGGAGGCGGATCTGGCGGCGGCGGTTCAGGAGGTGGTGGATCCGAGATAGTG
ATGACTCAATCTCCGGCTACTTTGTCTCTCAGTCCAGGGGAGCGAGCCACTCTGAGCTGCAG
GGCAAGTCAGTCCGTCTCCAGCTATCTTAATTGGTACCAACAGAAGCCGGGACAGGCTCCAC
GATTGTTGATCTACTACGCTAGTCGCAGGCACACAGGCATACCTGCTCGCTTTTCTGGAAGC
GGGTCAGGAACAGACTTCACTTTGACAATCTCATCACTTCAGCCGGAGGACTTTGCTGTGTA
TTACTGCCAACAAGGCTACAACCTCCCCTATACGTTTGGGCAGGGCACAAAAGTAGAGATTA
AGGAGCCCAAATCTTCTGACAAAACTCACACATGCCCACCGTGCCCAGCACCTCCAGCCGCT
GCACCGTCAGTCTTCCTCTTCCCCCCAAAACCCAAGGACACCCTCATGATCTCCCGGACCCCT
GAGGTCACATGCGTGGTGGTGGACGTGAGCCACGAAGACCCTGAGGTCAAGTTCAACTGGT
ACGTGGACGGCGTGGAGGTGCATAATGCCAAGACAAAGCCGCGGGAGGAGCAGTACAACA

-continued

SEQUENCES

GCACGTACCGTGTGGTCAGCGTCCTCACCGTCCTGCACCAGGACTGGCTGAATGGCAAGGAA
TACAAGTGCGCGGTCTCCAACAAAGCCCTCCCAGCCCCCATCGAGAAAACCATCTCCAAAGC
CAAAGGGCAGCCCCGAGAACCACAGGTGTACACCCTGCCCCCATCCCGGGATGAGCTGACC
AAGAACCAGGTCAGCCTGACCTGCCTGGTCAAAGGCTTCTATCCAAGCGACATCGCCGTGGA
GTGGGAGAGCAATGGGCAGCCGGAGAACAACTACAAGACCACGCCTCCCGTGCTGGACTCC
GACGGCTCCTTCTTCCTCTACAGCAAGCTCACCGTGGACAAGAGCAGGTGGCAGCAGGGGA
ACGTCTTCTCATGCTCCGTGATGCATGAGGCTCTGCACAACCACTACACGCAGAAGAGCCTC
TCCCTGTCTCCGGGCGGCGGGGGATCCCCGTCATCCTATGTGCTGACTCAGCCACCCTCGGTG
TCGGTGGCCCCAGGAAAAACGGCCAGGATTACCTGTGGGGGAAACAACATTGGAAGTAAAA
GTGTGAACTGGTTCCAGCAGAAGCCAGGCCAGGCCCCTGTACTGGTCGTCTATGATGATAGC
GGCCGGCCCTCAGGGATCCCTGAGCGATTCTCTGGCTCCACCTCTGGGAACACGGCCACCCT
GACCATCAGCAGGGTCGAAGCCGGGGATGAGGCCGACTATTACTGTCAGGTGTGGGATAGT
AGTAGTGATCATGTGGTATTCGGCGGAGGGACCAAGCTGACCGTCCTAGGTGGAGGCGGTTC
AGGCGGAGGTGGATCCGGCGGTGGCGGCTCCGGTGGCGGCGGATCTCAGGTGCAACTGGTG
GAGTCTGGGGGAGGCGTGGTCCAGCCTGGGAGGTCCCTGAGACTCTCCTGTGCAGCCTCTGG
ATTCACCCTCAGTTACTATGGCATGCACTGGGTCCGCCAGGCTCCAGGCAAGGGGCTGGAGT
GGGTGGCAGCTATATCACATGATGGAAGTGATAAATACTATGCAGACTCCGTGAAGGGCCG
ATTCACCATCTCCAGAGACAATTCCAAGAACAGACTGTATCTGCAAATGAACAGCCTGAGAG
CTGAAGACACGGCCGTGTATTACTGTTCGAATGACCAGTTTGACCCCTGGGGCCAGGGAACC
CTGGTCACCGTCTCCTCGCGC

SEQ ID NO: 149 (FXX01111 anti 4-1BB scFV X anti OX40 scFV ADAPTIR nucleotide sequence)
GAGGTGCAACTGGTGCAATCAGGAGCTGAGGTGAAAAAACCGGGTGCCAGTGTTAAAGTTA
GCTGTAAGGCATCCGGGTACACGTTTACATCTTACTGGATGAATTGGGTCCGACAGGCCCCA
GGCCAAGGGTTGGAATGGATGGGAAATATTTATCCGTCCGGAGGTAGCACCAATTACGCTCA
AAAATTTCAGGGAAGGGTGACAATGACGGTGGACACTAGCACCAGTACTGTGTACATGGAG
TTGTCAAGTCTTCGCTCCGAAGATACTGCCGTGTATTACTGTGCTTCATTTAGTGATGGGTAT
TATGCGTACGCTATGGATTATTGGGGTCAGGGGACCTTGGTGACGGTGTCCAGTGGTGGTGG
AGGTAGTGGTGGAGGCGGATCTGGCGGCGGCGGTTCAGGAGGTGGTGGATCCGAGATAGTG
ATGACTCAATCTCCGGCTACTTTGTCTCTCAGTCCAGGGGAGCGAGCCACTCTGAGCTGCAG
GGCAAGTCAGTCCGTCTCCAGCTATCTTAATTGGTACCAACAGAAGCCGGGACAGGCTCCAC
GATTGTTGATCTACTACGCTAGTCGCAGGCACACAGGCATACCTGCTCGCTTTTCTGGAAGC
GGGTCAGGAACAGACTTCACTTTGACAATCTCATCACTTCAGCCGGAGGACTTTGCTGTGTA
TTACTGCCAACAAGGCTACAACCTCCCCTATACGTTTGGGCAGGGCACAAAAGTAGAGATTA
AGGAGCCCAAATCTTCTGACAAAACTCACACATGCCCACCGTGCCCAGCACCTCCAGCCGCT
GCACCGTCAGTCTTCCTCTTCCCCCCAAAACCCAAGGACACCCTCATGATCTCCCGGACCCCT
GAGGTCACATGCGTGGTGGTGGACGTGAGCCACGAAGACCCTGAGGTCAAGTTCAACTGGT
ACGTGGACGGCGTGGAGGTGCATAATGCCAAGACAAAGCCGCGGGAGGAGCAGTACAACA
GCACGTACCGTGTGGTCAGCGTCCTCACCGTCCTGCACCAGGACTGGCTGAATGGCAAGGAA
TACAAGTGCGCGGTCTCCAACAAAGCCCTCCCAGCCCCCATCGAGAAAACCATCTCCAAAGC
CAAAGGGCAGCCCCGAGAACCACAGGTGTACACCCTGCCCCCATCCCGGGATGAGCTGACC
AAGAACCAGGTCAGCCTGACCTGCCTGGTCAAAGGCTTCTATCCAAGCGACATCGCCGTGGA
GTGGGAGAGCAATGGGCAGCCGGAGAACAACTACAAGACCACGCCTCCCGTGCTGGACTCC
GACGGCTCCTTCTTCCTCTACAGCAAGCTCACCGTGGACAAGAGCAGGTGGCAGCAGGGGA
ACGTCTTCTCATGCTCCGTGATGCATGAGGCTCTGCACAACCACTACACGCAGAAGAGCCTC
TCCCTGTCTCCGGGCGGCGGGGGATCCCCGTCATCCTATGTGCTGACTCAGCCACCCTCGGTG
TCGGTGGCCCCAGGACAGACGGCCAGGATTACCTGTGGGGGAAACAACATTGGAAGTAAAA
GTGTGAACTGGTTCCAGCAGAAGCCAGGCCAGGCCCCTGTACTGGTCGTCTATGATGATAGC
GGCCGGCCCTCAGGGGTTCCTAACCGATTCTCTGGCTCCACCTCTGGGAACACGGCCACCCT
GACCATCAGCAGGGTCGAAGCCGGGGATGAGGCCGACTATTACTGTCAGGTGTGGGATAGT
AGTAGTGATCATGTGGTATTCGGCGGAGGGACCAAGCTGACCGTCCTAGGTGGAGGCGGTTC
AGGCGGAGGTGGATCCGGCGGTGGCGGCTCCGGTGGCGGCGGATCTCAGGTGCAACTGGTG
GAGTCTGGGGGAGGCGTGGTCCAGCCTGGGAGGTCCCTGAGACTCTCCTGTGCAGCCTCTGG
ATTCACCCTCAGTTACTATGGCATGCACTGGGTCCGCCAGGCTCCAGGCAAGGGGCTGGAGT
GGGTGGCAGCTATATCACATGATGGAAGTGATAAATACTATGCAGACTCCGTGAAGGGCCG
ATTCACCATCTCCAGAGACAATTCCAAGAACACGCTGTATCTGCAAATGAACAGCCTGAGAG
CTGAAGACACGGCCGTGTATTACTGTTCGAATGACCAGTTTGACCCCTGGGGCCAGGGAACC
CTGGTCACCGTCTCCTCGCGC

What is claimed:

1. A bispecific antibody comprising a polypeptide comprising, in order from amino-terminus to carboxyl-terminus, (i) a first single chain variable fragment (scFv), (ii) a linker, (iii) an immunoglobulin constant region, wherein the immunoglobulin constant region comprises immunoglobulin CH2 and CH3 domains of IgG1, IgG2, IgG3, or IgG4, and (iv) a second scFv, wherein (a) the first scFv comprises a human 4-1BB antigen-binding domain, and the second scFv comprises a human OX40 antigen-binding domain or (b) the first scFv comprises a human OX40 antigen-binding domain and the second scFv comprises a human 4-1BB antigen-binding domain, wherein the human 4-1BB antigen-binding domain comprises (i) a VH-CDR1 comprising the amino acid sequence of GYTFTSYW (SEQ ID NO:5); (ii) a VH-CDR2 comprising the amino acid sequence of IYPSGGST (SEQ ID NO:6); (iii) a VH-CDR3 comprising the amino acid sequence of ASFSDGYYAYAMDY (SEQ ID NO:7); (iv) a light chain variable domain (VL)-CDR1 comprising the amino acid sequence of QSVSSY (SEQ ID NO:8); (v) a VL-CDR2 comprising the amino acid sequence of YAS (SEQ ID NO:9); and (vi) a VL-CDR3 comprising the amino acid sequence of QQGYNLPYT (SEQ ID NO: 10) or (i) a VH-CDR1 comprising the amino acid sequence of GYTFTSYW (SEQ ID NO:5); (ii) a VH-CDR2 comprising the amino acid sequence of IYPGSSTT (SEQ ID NO: 119); (iii) a VH-CDR3 comprising the amino acid sequence of ASFSDGYYAYAMDY (SEQ ID NO:7); (iv) a light chain variable domain (VL)-CDR1 comprising the amino acid sequence of QDISNY (SEQ ID NO: 120); (v) a VL-CDR2 comprising the amino acid sequence of YTS (SEQ ID NO:121); and (vi) a VL-CDR3 comprising the amino acid sequence of QQGYTLPYT (SEQ ID NO:122), and wherein the human OX40 binding domain comprises (i) a VH-CDR1 comprising the amino acid sequence of GFTLSYYG (SEQ ID NO:11); (ii) a VH-CDR2 comprising the amino acid sequence of ISHDGSDK (SEQ ID NO:12); (iii) a VH-CDR3 comprising the amino acid sequence of SNDQFDP (SEQ ID NO:13); (iv) a light chain variable domain (VL)-CDR1 comprising the amino acid sequence of NIGSKS (SEQ ID NO:14); (v) a VL-CDR2 comprising the amino acid sequence of DDS (SEQ ID NO:15); and (vi) a VL-CDR3 comprising the amino acid sequence of QVWDSSSDHVV (SEQ ID NO:16).

2. The bispecific antibody of claim 1, wherein the human 4-1BB binding domain comprises (a) a VH comprising the amino acid sequence of SEQ ID NO:17 and a VL comprising the amino acid sequence of SEQ ID NO:18, (b) a VH comprising the amino acid sequence of SEQ ID NO: 19 and a VL comprising the amino acid sequence of SEQ ID NO: 20, (c) a VH comprising the amino acid sequence of SEQ ID NO:21 and a VL comprising the amino acid sequence of SEQ ID NO:22, (d) a VH comprising the amino acid sequence of SEQ ID NO:23 and a VL comprising the amino acid sequence of SEQ ID NO: 24, (e) a VH comprising the amino acid sequence of SEQ ID NO:32 and a VL comprising the amino acid sequence of SEQ ID NO:18, or (f) a VH comprising the amino acid sequence of SEQ ID NO:143 and a VL comprising the amino acid sequence of SEQ ID NO: 20 and wherein the human OX40 binding domain comprises (a) a VH comprising the amino acid sequence of SEQ ID NO:25 and a VL comprising the amino acid sequence of SEQ ID NO:26, (b) a VH comprising the amino acid sequence of SEQ ID NO:27 and a VL comprising the amino acid sequence of SEQ ID NO:28, (c) a VH comprising the amino acid sequence of SEQ ID NO:29 and a VL comprising the amino acid sequence of SEQ ID NO: 26, (d) a VH comprising the amino acid sequence of SEQ ID NO:29 and a VL comprising the amino acid sequence of SEQ ID NO:30, (e) a VH comprising the amino acid sequence of SEQ ID NO:31 and a VL comprising the amino acid sequence of SEQ ID NO: 28, (f) a VH comprising the amino acid sequence of SEQ ID NO:31 and a VL comprising the amino acid sequence of SEQ ID NO:30, (g) a VH comprising the amino acid sequence of SEQ ID NO:33 and a VL comprising the amino acid sequence of SEQ ID NO: 28, (h) a VH comprising the amino acid sequence of SEQ ID NO:29 and a VL comprising the amino acid sequence of SEQ ID NO:34, (i) a VH comprising the amino acid sequence of SEQ ID NO:29 and a VL comprising the amino acid sequence of SEQ ID NO: 35, (j) a VH comprising the amino acid sequence of SEQ ID NO:29 and a VL comprising the amino acid sequence of SEQ ID NO:36, (k) a VH comprising the amino acid sequence of SEQ ID NO:29 and a VL comprising the amino acid sequence of SEQ ID NO: 37, (l) a VH comprising the amino acid sequence of SEQ ID NO:31 and a VL comprising the amino acid sequence of SEQ ID NO:34, (m) a VH comprising the amino acid sequence of SEQ ID NO:31 and a VL comprising the amino acid sequence of SEQ ID NO: 35, (n) a VH comprising the amino acid sequence of SEQ ID NO:31 and a VL comprising the amino acid sequence of SEQ ID NO:36, (o) a VH comprising the amino acid sequence of SEQ ID NO:31 and a VL comprising the amino acid sequence of SEQ ID NO: 37, (p) a VH comprising the amino acid sequence of SEQ ID NO:31 and a VL comprising the amino acid sequence of SEQ ID NO:38, (q) a VH comprising the amino acid sequence of SEQ ID NO:31 and a VL comprising the amino acid sequence of SEQ ID NO: 39, (r) a VH comprising the amino acid sequence of SEQ ID NO:31 and a VL comprising the amino acid sequence of SEQ ID NO:40, or(s) a VH comprising the amino acid sequence of SEQ ID NO:31 and a VL comprising the amino acid sequence of SEQ ID NO: 41.

3. The bispecific antibody of claim 1, wherein the linker is a hinge region.

4. The bispecific antibody of claim 1, wherein the 4-1BB antigen-binding domain comprises (i) a VH-CDR 1 comprising the amino acid sequence of GYTFTSYW (SEQ ID NO: 5); (ii) a VH-CDR2 comprising the amino acid sequence of IYPSGGST (SEQ ID NO: 6); (iii) a VH-CDR3 comprising the amino acid sequence of ASFSDGYYAYAMDY (SEQ ID NO:7); (iv) a light chain variable domain (VL)-CDR1 comprising the amino acid sequence of QSVSSY (SEQ ID NO:8); (v) a VL-CDR2 comprising the amino acid sequence of YAS (SEQ ID NO:9); and (vi) a VL-CDR3 comprising the amino acid sequence of QQGYNLPYT (SEQ ID NO:10); and the OX40 antigen-binding domain comprises (i) a VH-CDR1 comprising the amino acid sequence of GFTLSYYG (SEQ ID NO:11); (ii) a VH-CDR2 comprising the amino acid sequence of ISHDGSDK (SEQ ID NO:12); (iii) a VH-CDR3 comprising the amino acid sequence of SNDQFDP (SEQ ID NO:13); (iv) a VL-CDR1 comprising the amino acid sequence of NIGSKS (SEQ ID NO:14); (v) a VL-CDR2 comprising the amino acid sequence of DDS (SEQ ID NO:15); and (vi) a VL-CDR3 comprising the amino acid sequence of QVWDSSSDHVV (SEQ ID NO:16).

5. The bispecific antibody of claim 1, wherein the human 4-1BB antigen binding domain comprises a VH comprising the amino acid sequence of SEQ ID NO:17 and a VL comprising the amino acid sequence of SEQ ID NO: 18 and wherein the human OX40 antigen binding domain comprises (a) a VH comprising the amino acid sequence of SEQ ID NO: 31 and a VL comprising the amino acid sequence of SEQ ID NO:30.

6. The bispecific antibody of claim 1, wherein the human 4-1BB antigen binding domain comprises an scFv comprising the amino acid sequence of SEQ ID NO:58 and wherein the human OX40 antigen binding domain comprises an scFv comprising the amino acid sequence of SEQ ID NOs: 62.

7. A pharmaceutical composition comprising the antibody of claim 1, and a pharmaceutically acceptable excipient.

8. A method for enhancing an immune response in a subject, increasing the number of tumor infiltrating lymphocytes in a subject, increasing the expression of granzymes by effector cells in a subject, and/or reducing the number of tumor cells in a subject, the method comprising administering to the subject an effective amount of the antibody of claim 1.

9. A method of treating cancer in a subject, the method comprising administering to the subject an effective amount of the antibody of claim 1.

10. A bispecific antibody comprising (a) a human 4-1BB antigen-binding domain and (b) a human OX40 antigen-binding domain, wherein the 4-1BB antigen-binding domain comprises (i) a VH-CDR 1 comprising the amino acid sequence of GYTFTSYW (SEQ ID NO:5); (ii) a VH-CDR2 comprising the amino acid sequence of IYPSGGST (SEQ ID NO:6); (iii) a VH-CDR3 comprising the amino acid sequence of ASFSDGYYAYAMDY (SEQ ID NO:7); (iv) a light chain variable domain (VL)-CDR1 comprising the amino acid sequence of QSVSSY (SEQ ID NO:8); (v) a VL-CDR2 comprising the amino acid sequence of YAS (SEQ ID NO:9); and (vi) a VL-CDR3 comprising the amino acid sequence of QQGYNLPYT (SEQ ID NO:10); and the OX40 antigen-binding domain comprises (i) a VH-CDR1 comprising the amino acid sequence of GFTLSYYG (SEQ ID NO:11); (ii) a VH-CDR2 comprising the amino acid sequence of ISHDGSDK (SEQ ID NO:12); (iii) a VH-CDR3 comprising the amino acid sequence of SNDQFDP (SEQ ID NO:13); (iv) a VL-CDR1 comprising the amino acid sequence of NIGSKS (SEQ ID NO:14); (v) a VL-CDR2 comprising the amino acid sequence of DDS (SEQ ID NO:15); and (vi) a VL-CDR3 comprising the amino acid sequence of QVWDSSSDHVV (SEQ ID NO:16).

11. A pharmaceutical composition comprising the antibody of claim 10, and a pharmaceutically acceptable excipient.

12. An antibody comprising a human 4-1BB binding domain and a human OX-40 binding domain, wherein the human 4-1BB binding domain comprises a VH comprising the amino acid sequence of SEQ ID NO:17 and a VL comprising the amino acid sequence of SEQ ID NO:18 and wherein the human OX40 binding domain comprises (a) a VH comprising the amino acid sequence of SEQ ID NO:29 and a VL comprising the amino acid sequence of SEQ ID NO:28, (b) a VH comprising the amino acid sequence of SEQ ID NO: 31 and a VL comprising the amino acid sequence of SEQ ID NO:30, or (c) a VH comprising the amino acid sequence of SEQ ID NO:29 and a VL comprising the amino acid sequence of SEQ ID NO:35.

13. The antibody of claim 12, wherein the human 4-1BB binding domain comprises a VH comprising the amino acid sequence of SEQ ID NO:17 and a VL comprising the amino acid sequence of SEQ ID NO:18 and wherein the human OX40 binding domain comprises a VH comprising the amino acid sequence of SEQ ID NO:31 and a VL comprising the amino acid sequence of SEQ ID NO:30.

14. An antibody comprising a human 4-1BB binding domain and a human OX40 binding domain, wherein the human 4-1BB binding domain comprises an scFv comprising the amino acid sequence of SEQ ID NO:58 and wherein the human OX40 binding domain comprises an scFv comprising the amino acid sequence of any one of SEQ ID NOs: 59, 62, or 66.

15. The antibody of claim 14, wherein the human 4-1BB binding domain comprises an scFv comprising the amino acid sequence of SEQ ID NO:58 and wherein the human OX40 binding domain comprises an scFv comprising the amino acid sequence of SEQ ID NOs: 62.

16. A bispecific antibody that comprises a human 4-1BB antigen-binding domain and a human OX40 antigen-binding domain, wherein the antibody comprises the amino acid sequence selected from the group consisting of SEQ ID NOs: 78-100 and 144.

17. The antibody of claim 16, wherein the antibody is a homodimer comprising two identical polypeptides, each polypeptide comprising the amino acid sequence selected from the group consisting of SEQ ID NOs: 78-100 and 144.

18. The bispecific antibody of claim 16, wherein the antibody comprises the amino acid of SEQ ID NO:81.

19. The antibody of claim 16, wherein the antibody is a homodimer comprising two identical polypeptides, each polypeptide comprising the amino acid sequence of SEQ ID NO: 81.

20. A pharmaceutical composition comprising the antibody of claim 19, and a pharmaceutically acceptable excipient.

* * * * *

SEQUENCE LISTING

<160> NUMBER OF SEQ ID NOS: 184

<210> SEQ ID NO 1
<211> LENGTH: 232
<212> TYPE: PRT
<213> ORGANISM: Artificial Sequence
<220> FEATURE:
<223> OTHER INFORMATION: Synthetic Peptide

<400> SEQUENCE: 1

```
Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
    50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Val Thr Pro Pro Ala Pro Ala Arg Glu Pro Gly His
145                 150                 155                 160

Ser Pro Gln Ile Ile Ser Phe Phe Leu Ala Leu Thr Ser Thr Ala Leu
                165                 170                 175

Leu Phe Leu Leu Phe Phe Leu Thr Leu Arg Phe Ser Val Val Lys Arg
            180                 185                 190

Gly Arg Lys Lys Leu Leu Tyr Ile Phe Lys Gln Pro Phe Met Arg Pro
        195                 200                 205

Val Gln Thr Thr Gln Glu Glu Asp Gly Cys Ser Cys Arg Phe Pro Glu
    210                 215                 220

Glu Glu Glu Gly Gly Cys Glu Leu
225                 230
```

<210> SEQ ID NO 2
<211> LENGTH: 231
<212> TYPE: PRT
<213> ORGANISM: Artificial Sequence
<220> FEATURE:
<223> OTHER INFORMATION: Synthetic Peptide

<400> SEQUENCE: 2

```
Leu Gln Asp Leu Cys Ser Asn Cys Pro Ala Gly Thr Phe Cys Asp Asn
1               5                   10                  15

Asn Arg Ser Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Lys Thr Arg Lys Glu Cys Ser Ser Thr Ser Asn Ala Glu Cys Asp
    50                  55                  60

Cys Ile Ser Gly Tyr His Cys Leu Gly Ala Glu Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125
```

```
Lys Glu Arg Asp Val Val Cys Gly Pro Ser Pro Ala Asp Leu Ser Pro
    130                 135                 140

Gly Ala Ser Ser Ala Thr Pro Pro Ala Pro Ala Arg Glu Pro Gly His
145                 150                 155                 160

Ser Pro Gln Ile Ile Phe Phe Leu Ala Leu Thr Ser Thr Val Val Leu
                165                 170                 175

Phe Leu Leu Phe Phe Leu Val Leu Arg Phe Ser Val Val Lys Arg Ser
            180                 185                 190

Arg Lys Lys Leu Leu Tyr Ile Phe Lys Gln Pro Phe Met Arg Pro Val
        195                 200                 205

Gln Thr Thr Gln Glu Glu Asp Gly Cys Ser Cys Arg Phe Pro Glu Glu
    210                 215                 220

Glu Glu Gly Gly Cys Glu Leu
225                 230


<210> SEQ ID NO 3
<211> LENGTH: 249
<212> TYPE: PRT
<213> ORGANISM: Artificial Sequence
<220> FEATURE:
<223> OTHER INFORMATION: Synthetic Peptide

<400> SEQUENCE: 3

Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
        35                  40                  45

Ser Ser Lys Pro Cys Lys Pro Cys Thr Trp Cys Asn Leu Arg Ser Gly
    50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
    130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala Val Ala Ala Ile Leu Gly
            180                 185                 190

Leu Gly Leu Val Leu Gly Leu Leu Gly Pro Leu Ala Ile Leu Leu Ala
        195                 200                 205

Leu Tyr Leu Leu Arg Arg Asp Gln Arg Leu Pro Pro Asp Ala His Lys
    210                 215                 220

Pro Pro Gly Gly Gly Ser Phe Arg Thr Pro Ile Gln Glu Glu Gln Ala
225                 230                 235                 240

Asp Ala His Ser Thr Leu Ala Lys Ile
                245
```

<210> SEQ ID NO 4
<211> LENGTH: 250
<212> TYPE: PRT
<213> ORGANISM: Artificial Sequence
<220> FEATURE:
<223> OTHER INFORMATION: Synthetic Peptide

<400> SEQUENCE: 4

Lys Leu His Cys Val Gly Asp Thr Tyr Pro Ser Asn Asp Arg Cys Cys
1 5 10 15

Gln Glu Cys Arg Pro Gly Asn Gly Met Val Ser Arg Cys Asn Arg Ser
20 25 30

Gln Asn Thr Val Cys Arg Pro Cys Gly Pro Gly Phe Tyr Asn Asp Val
35 40 45

Val Ser Ala Lys Pro Cys Lys Ala Cys Thr Trp Cys Asn Leu Arg Ser
50 55 60

Gly Ser Glu Arg Lys Gln Pro Cys Thr Ala Thr Gln Asp Thr Val Cys
65 70 75 80

Arg Cys Arg Ala Gly Thr Gln Pro Leu Asp Ser Tyr Lys Pro Gly Val
85 90 95

Asp Cys Ala Pro Cys Pro Pro Gly His Phe Ser Pro Gly Asp Asn Gln
100 105 110

Ala Cys Lys Pro Trp Thr Asn Cys Thr Leu Ala Gly Lys His Thr Leu
115 120 125

Gln Pro Ala Ser Asn Ser Ser Asp Ala Ile Cys Glu Asp Arg Asp Pro
130 135 140

Pro Pro Thr Gln Pro Gln Glu Thr Gln Gly Pro Pro Ala Arg Pro Thr
145 150 155 160

Thr Val Gln Pro Thr Glu Ala Trp Pro Arg Thr Ser Gln Arg Pro Ser
165 170 175

Thr Arg Pro Val Glu Val Pro Arg Gly Pro Ala Val Ala Ala Ile Leu
180 185 190

Gly Leu Gly Leu Ala Leu Gly Leu Leu Gly Pro Leu Ala Met Leu Leu
195 200 205

Ala Leu Leu Leu Leu Arg Arg Asp Gln Arg Leu Pro Pro Asp Ala Pro
210 215 220

Lys Ala Pro Gly Gly Gly Ser Phe Arg Thr Pro Ile Gln Glu Glu Gln
225 230 235 240

Ala Asp Ala His Ser Ala Leu Ala Lys Ile
245 250

<210> SEQ ID NO 5
<211> LENGTH: 8
<212> TYPE: PRT
<213> ORGANISM: Artificial Sequence
<220> FEATURE:
<223> OTHER INFORMATION: Heavy Chain CDR1

<400> SEQUENCE: 5

Gly Tyr Thr Phe Thr Ser Tyr Trp
1 5

<210> SEQ ID NO 6
<211> LENGTH: 8
<212> TYPE: PRT
<213> ORGANISM: Artificial Sequence
<220> FEATURE:
<223> OTHER INFORMATION: VH CDR2

<400> SEQUENCE: 6

Ile Tyr Pro Ser Gly Gly Ser Thr
1 5

<210> SEQ ID NO 7
<211> LENGTH: 14
<212> TYPE: PRT
<213> ORGANISM: Artificial Sequence
<220> FEATURE:
<223> OTHER INFORMATION: VH CDR3

<400> SEQUENCE: 7

Ala Ser Phe Ser Asp Gly Tyr Tyr Ala Tyr Ala Met Asp Tyr
1 5 10

<210> SEQ ID NO 8
<211> LENGTH: 6
<212> TYPE: PRT
<213> ORGANISM: Artificial Sequence
<220> FEATURE:
<223> OTHER INFORMATION: VL CDR1

<400> SEQUENCE: 8

Gln Ser Val Ser Ser Tyr
1 5

<210> SEQ ID NO 9
<211> LENGTH: 3
<212> TYPE: PRT
<213> ORGANISM: Artificial Sequence
<220> FEATURE:
<223> OTHER INFORMATION: VL CDR2

<400> SEQUENCE: 9

Tyr Ala Ser
1

<210> SEQ ID NO 10
<211> LENGTH: 9
<212> TYPE: PRT
<213> ORGANISM: Artificial Sequence
<220> FEATURE:
<223> OTHER INFORMATION: VL CDR3

<400> SEQUENCE: 10

Gln Gln Gly Tyr Asn Leu Pro Tyr Thr
1 5

<210> SEQ ID NO 11
<211> LENGTH: 8
<212> TYPE: PRT
<213> ORGANISM: Artificial Sequence
<220> FEATURE:
<223> OTHER INFORMATION: OX40 Heavy Chain CDR1 Amino Acid Sequences

<400> SEQUENCE: 11

Gly Phe Thr Leu Ser Tyr Tyr Gly
1 5

<210> SEQ ID NO 12
<211> LENGTH: 8
<212> TYPE: PRT
<213> ORGANISM: Artificial Sequence
<220> FEATURE:
<223> OTHER INFORMATION: OX40 Heavy Chain CDR2 Amino Acid Sequences

<400> SEQUENCE: 12

Ile Ser His Asp Gly Ser Asp Lys
1 5

<210> SEQ ID NO 13
<211> LENGTH: 7
<212> TYPE: PRT
<213> ORGANISM: Artificial Sequence
<220> FEATURE:
<223> OTHER INFORMATION: OX40 Heavy Chain CDR3 Amino Acid Sequences

<400> SEQUENCE: 13

Ser Asn Asp Gln Phe Asp Pro
1 5

<210> SEQ ID NO 14
<211> LENGTH: 6
<212> TYPE: PRT
<213> ORGANISM: Artificial Sequence
<220> FEATURE:
<223> OTHER INFORMATION: OX40 Light Chain CDR1 Amino Acid Sequences

<400> SEQUENCE: 14

Asn Ile Gly Ser Lys Ser
1 5

<210> SEQ ID NO 15
<211> LENGTH: 3
<212> TYPE: PRT
<213> ORGANISM: Artificial Sequence
<220> FEATURE:
<223> OTHER INFORMATION: OX40 Light Chain CDR2 Amino Acid Sequences

<400> SEQUENCE: 15

Asp Asp Ser
1

<210> SEQ ID NO 16
<211> LENGTH: 11
<212> TYPE: PRT
<213> ORGANISM: Artificial Sequence
<220> FEATURE:
<223> OTHER INFORMATION: OX40 Light Chain CDR3 Amino Acid Sequences

<400> SEQUENCE: 16

Gln Val Trp Asp Ser Ser Ser Asp His Val Val
1 5 10

<210> SEQ ID NO 17
<211> LENGTH: 121
<212> TYPE: PRT
<213> ORGANISM: Artificial Sequence
<220> FEATURE:
<223> OTHER INFORMATION: 4-1BB Variable Heavy Chain Sequences

<400> SEQUENCE: 17

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Met Asn Trp Val Arg Gln Ala Pro Gly Gln Gly Leu Glu Trp Met
35 40 45

Gly Asn Ile Tyr Pro Ser Gly Gly Ser Thr Asn Tyr Ala Gln Lys Phe
50 55 60

Gln Gly Arg Val Thr Met Thr Val Asp Thr Ser Thr Ser Thr Val Tyr

```
65                  70                  75                  80

Met Glu Leu Ser Ser Leu Arg Ser Glu Asp Thr Ala Val Tyr Tyr Cys
                85                  90                  95

Ala Ser Phe Ser Asp Gly Tyr Tyr Ala Tyr Ala Met Asp Tyr Trp Gly
            100                 105                 110

Gln Gly Thr Leu Val Thr Val Ser Ser
        115                 120


<210> SEQ ID NO 18
<211> LENGTH: 107
<212> TYPE: PRT
<213> ORGANISM: Artificial Sequence
<220> FEATURE:
<223> OTHER INFORMATION: Variable Light Chain  Amino Acid

<400> SEQUENCE: 18

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Asn Trp Tyr Gln Gln Lys Pro Gly Gln Ala Pro Arg Leu Leu Ile
        35                  40                  45

Tyr Tyr Ala Ser Arg Arg His Thr Gly Ile Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Gly Tyr Asn Leu Pro Tyr
                85                  90                  95

Thr Phe Gly Gln Gly Thr Lys Val Glu Ile Lys
            100                 105


<210> SEQ ID NO 19
<211> LENGTH: 121
<212> TYPE: PRT
<213> ORGANISM: Artificial Sequence
<220> FEATURE:
<223> OTHER INFORMATION: 4-1BB Variable Heavy Chain Sequences

<400> SEQUENCE: 19

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Gly Ser Ser Thr Thr Asn Tyr Asn Glu Lys Phe
    50                  55                  60

Lys Ser Lys Ala Thr Leu Thr Val Asp Thr Ser Ser Ser Thr Ala Tyr
65                  70                  75                  80

Met Gln Leu Ser Ser Leu Thr Ser Asp Asp Ser Ala Val Phe Tyr Cys
                85                  90                  95

Ala Ser Phe Ser Asp Gly Tyr Tyr Ala Tyr Ala Met Asp Tyr Trp Val
            100                 105                 110

Gln Gly Thr Ser Val Thr Val Ser Ser
        115                 120


<210> SEQ ID NO 20
<211> LENGTH: 107
```

```
<212> TYPE: PRT
<213> ORGANISM: Artificial Sequence
<220> FEATURE:
<223> OTHER INFORMATION: Variable Light Chain  Amino Acid

<400> SEQUENCE: 20

Asp Ile Gln Met Thr Gln Thr Thr Ser Ser Leu Ser Ala Ser Leu Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Gly Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Tyr Thr Leu Pro Tyr
                85                  90                  95

Thr Phe Gly Gly Gly Thr Lys Leu Glu Ile Lys
            100                 105


<210> SEQ ID NO 21
<211> LENGTH: 121
<212> TYPE: PRT
<213> ORGANISM: Artificial Sequence
<220> FEATURE:
<223> OTHER INFORMATION: 4-1BB Variable Heavy Chain Sequences

<400> SEQUENCE: 21

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Ile
        35                  40                  45

Gly Asn Ile Tyr Pro Gly Ser Ser Thr Thr Asn Tyr Asn Glu Lys Phe
    50                  55                  60

Lys Ser Arg Ala Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Phe Ser Asp Gly Tyr Tyr Ala Tyr Ala Met Asp Tyr Trp Gly
            100                 105                 110

Gln Gly Thr Leu Val Thr Val Ser Ser
        115                 120


<210> SEQ ID NO 22
<211> LENGTH: 107
<212> TYPE: PRT
<213> ORGANISM: Artificial Sequence
<220> FEATURE:
<223> OTHER INFORMATION: Variable Light Chain  Amino Acid

<400> SEQUENCE: 22

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Asp Ile Ser Asn Tyr
            20                  25                  30

Leu Asn Trp Tyr Gln Gln Lys Pro Gly Gln Ala Val Arg Leu Leu Ile
```

```
        35                  40                  45

Tyr Tyr Thr Ser Arg Leu His Ser Gly Ile Pro Asp Arg Phe Ser Gly
    50                  55                  60

Ser Gly Ser Gly Thr Asp Tyr Thr Leu Thr Ile Ser Arg Leu Glu Pro
65                  70                  75                  80

Glu Asp Phe Ala Val Tyr Phe Cys Gln Gln Gly Tyr Thr Leu Pro Tyr
                85                  90                  95

Thr Phe Gly Gln Gly Thr Lys Val Glu Ile Lys
            100                 105


<210> SEQ ID NO 23
<211> LENGTH: 121
<212> TYPE: PRT
<213> ORGANISM: Artificial Sequence
<220> FEATURE:
<223> OTHER INFORMATION: 4-1BB Variable Heavy Chain Sequences

<400> SEQUENCE: 23

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Asn Ile Tyr Pro Gly Ser Ser Thr Thr Asn Tyr Ala Gln Lys Phe
    50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Phe Ser Asp Gly Tyr Tyr Ala Tyr Ala Met Asp Tyr Trp Gly
            100                 105                 110

Gln Gly Thr Leu Val Thr Val Ser Ser
        115                 120


<210> SEQ ID NO 24
<211> LENGTH: 107
<212> TYPE: PRT
<213> ORGANISM: Artificial Sequence
<220> FEATURE:
<223> OTHER INFORMATION: Variable Light Chain  Amino Acid

<400> SEQUENCE: 24

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Asn Tyr
            20                  25                  30

Leu Asn Trp Tyr Gln Gln Lys Pro Gly Gln Ala Val Arg Leu Leu Ile
        35                  40                  45

Tyr Tyr Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Tyr Thr Leu Pro Tyr
                85                  90                  95

Thr Phe Gly Gln Gly Thr Lys Val Glu Ile Lys
            100                 105
```

<210> SEQ ID NO 25
<211> LENGTH: 114
<212> TYPE: PRT
<213> ORGANISM: Artificial Sequence
<220> FEATURE:
<223> OTHER INFORMATION: OX40 Variable Heavy Chain Amino Acid Sequence

<400> SEQUENCE: 25

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Ser Tyr Tyr
            20                  25                  30

Gly Met His Trp Val Arg Gln Ala Pro Gly Lys Gly Leu Glu Trp Val
        35                  40                  45

Ala Val Ile Ser His Asp Gly Ser Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Leu Tyr Tyr Cys
                85                  90                  95

Ser Asn Asp Gln Phe Asp Pro Trp Gly Gln Gly Thr Leu Val Thr Val
            100                 105                 110

Ser Ser
```

<210> SEQ ID NO 26
<211> LENGTH: 108
<212> TYPE: PRT
<213> ORGANISM: Artificial Sequence
<220> FEATURE:
<223> OTHER INFORMATION: Variable Light Chain Amino Acid Sequence

<400> SEQUENCE: 26

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Phe Gln Gln Lys Pro Gly Gln Ala Pro Ala Leu Val Val Tyr
        35                  40                  45

Asp Asp Ser Gly Arg Pro Ser Gly Ile Pro Glu Arg Phe Ser Gly Ser
    50                  55                  60

Thr Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105
```

<210> SEQ ID NO 27
<211> LENGTH: 114
<212> TYPE: PRT
<213> ORGANISM: Artificial Sequence
<220> FEATURE:
<223> OTHER INFORMATION: OX40 Variable Heavy Chain Amino Acid Sequence

<400> SEQUENCE: 27

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Ser Tyr Tyr
            20                  25                  30
```

Gly Met His Trp Val Arg Gln Ala Pro Gly Lys Gly Leu Glu Trp Val
35 40 45

Ala Val Ile Ser His Asp Gly Ser Asp Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ser Asn Asp Gln Phe Asp Pro Trp Gly Gln Gly Thr Leu Val Thr Val
100 105 110

Ser Ser

<210> SEQ ID NO 28
<211> LENGTH: 108
<212> TYPE: PRT
<213> ORGANISM: Artificial Sequence
<220> FEATURE:
<223> OTHER INFORMATION: Variable Light Chain Amino Acid Sequence

<400> SEQUENCE: 28

Ser Tyr Val Leu Thr Gln Pro Pro Ser Val Ser Val Ala Pro Gly Gln
1 5 10 15

Thr Ala Arg Ile Thr Cys Gly Gly Asn Asn Ile Gly Ser Lys Ser Val
20 25 30

Asn Trp Phe Gln Gln Lys Pro Gly Gln Ala Pro Val Leu Val Val Tyr
35 40 45

Asp Asp Ser Gly Arg Pro Ser Gly Ile Pro Glu Arg Phe Ser Gly Ser
50 55 60

Thr Ser Gly Asn Thr Ala Thr Leu Thr Ile Ser Arg Val Glu Ala Gly
65 70 75 80

Asp Glu Ala Asp Tyr Tyr Cys Gln Val Trp Asp Ser Ser Ser Asp His
85 90 95

Val Val Phe Gly Gly Gly Thr Lys Leu Thr Val Leu
100 105

<210> SEQ ID NO 29
<211> LENGTH: 114
<212> TYPE: PRT
<213> ORGANISM: Artificial Sequence
<220> FEATURE:
<223> OTHER INFORMATION: OX40 Variable Heavy Chain Amino Acid Sequence

<400> SEQUENCE: 29

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Leu Ser Tyr Tyr
20 25 30

Gly Met His Trp Val Arg Gln Ala Pro Gly Lys Gly Leu Glu Trp Val
35 40 45

Ala Ala Ile Ser His Asp Gly Ser Asp Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ser Asn Asp Gln Phe Asp Pro Trp Gly Gln Gly Thr Leu Val Thr Val
100 105 110

Ser Ser

<210> SEQ ID NO 30
<211> LENGTH: 108
<212> TYPE: PRT
<213> ORGANISM: Artificial Sequence
<220> FEATURE:
<223> OTHER INFORMATION: Variable Light Chain Amino Acid Sequence

<400> SEQUENCE: 30

Ser Tyr Val Leu Thr Gln Pro Pro Ser Val Ser Val Ala Pro Gly Lys
1 5 10 15

Thr Ala Arg Ile Thr Cys Gly Gly Asn Asn Ile Gly Ser Lys Ser Val
20 25 30

Asn Trp Phe Gln Gln Lys Pro Gly Gln Ala Pro Val Leu Val Val Tyr
35 40 45

Asp Asp Ser Gly Arg Pro Ser Gly Ile Pro Glu Arg Phe Ser Gly Ser
50 55 60

Thr Ser Gly Asn Thr Ala Thr Leu Thr Ile Ser Arg Val Glu Ala Gly
65 70 75 80

Asp Glu Ala Asp Tyr Tyr Cys Gln Val Trp Asp Ser Ser Ser Asp His
85 90 95

Val Val Phe Gly Gly Gly Thr Lys Leu Thr Val Leu
100 105

<210> SEQ ID NO 31
<211> LENGTH: 114
<212> TYPE: PRT
<213> ORGANISM: Artificial Sequence
<220> FEATURE:
<223> OTHER INFORMATION: OX40 Variable Heavy Chain Amino Acid Sequence

<400> SEQUENCE: 31

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Leu Ser Tyr Tyr
20 25 30

Gly Met His Trp Val Arg Gln Ala Pro Gly Lys Gly Leu Glu Trp Val
35 40 45

Ala Ala Ile Ser His Asp Gly Ser Asp Lys Tyr Tyr Ala Asp Ser Val
50 55 60

Lys Gly Arg Phe Thr Ile Ser Arg Asp Asn Ser Lys Asn Arg Leu Tyr
65 70 75 80

Leu Gln Met Asn Ser Leu Arg Ala Glu Asp Thr Ala Val Tyr Tyr Cys
85 90 95

Ser Asn Asp Gln Phe Asp Pro Trp Gly Gln Gly Thr Leu Val Thr Val
100 105 110

Ser Ser

<210> SEQ ID NO 32
<211> LENGTH: 119
<212> TYPE: PRT
<213> ORGANISM: Artificial Sequence
<220> FEATURE:
<223> OTHER INFORMATION: 4-1BB Variable Heavy Chain Sequences

<400> SEQUENCE: 32

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Met Asn Trp Val Arg Gln Ala Pro Gly Gln Gly Leu Glu Trp Met
35 40 45

Gly Asn Ile Tyr Pro Ser Gly Gly Ser Thr Asn Tyr Ala Gln Lys Phe
50 55 60

Gln Gly Arg Val Thr Met Thr Val Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Ser Phe Ser Asp Gly Tyr Tyr Ala Tyr Ala Met Asp Tyr Trp Gly
100 105 110

Gln Gly Thr Leu Val Thr Val
115

<210> SEQ ID NO 33
<211> LENGTH: 112
<212> TYPE: PRT
<213> ORGANISM: Artificial Sequence
<220> FEATURE:
<223> OTHER INFORMATION: OX40 Variable Heavy Chain Amino Acid Sequence

<400> SEQUENCE: 33

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Leu Ser Tyr Tyr
20 25 30

Gly Met His Trp Val Arg Gln Ala Pro Gly Lys Gly Leu Glu Trp Val
35 40 45

Ala Val Ile Ser His Asp Gly Ser Asp Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ser Asn Asp Gln Phe Asp Pro Trp Gly Gln Gly Thr Leu Val Thr Val
100 105 110

<210> SEQ ID NO 34
<211> LENGTH: 108
<212> TYPE: PRT
<213> ORGANISM: Artificial Sequence
<220> FEATURE:
<223> OTHER INFORMATION: Variable Light Chain Amino Acid Sequence

<400> SEQUENCE: 34

Ser Tyr Val Leu Thr Gln Pro Pro Ser Val Ser Val Ala Pro Gly Gln
1 5 10 15

Thr Ala Arg Ile Thr Cys Gly Gly Asn Asn Ile Gly Ser Lys Ser Val
20 25 30

Asn Trp Phe Gln Gln Lys Pro Gly Gln Ala Pro Val Leu Val Val Tyr
35 40 45

Asp Asp Ser Gly Arg Pro Ser Gly Ile Pro Ala Arg Phe Ser Gly Ser
50 55 60

Thr Ser Gly Asn Thr Ala Thr Leu Thr Ile Ser Arg Val Glu Ala Gly
65 70 75 80

Asp Glu Ala Asp Tyr Tyr Cys Gln Val Trp Asp Ser Ser Ser Asp His

```
                85                  90                  95

Val Val Phe Gly Gly Gly Thr Lys Leu Thr Val Leu
            100                 105


<210> SEQ ID NO 35
<211> LENGTH: 108
<212> TYPE: PRT
<213> ORGANISM: Artificial Sequence
<220> FEATURE:
<223> OTHER INFORMATION: Variable Light Chain Amino Acid Sequence

<400> SEQUENCE: 35

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

Asn Trp Phe Gln Gln Lys Pro Gly Gln Ala Pro Val Leu Val Val Tyr
        35                  40                  45

Asp Asp Ser Gly Arg Pro Ser Gly Val Pro Asn Arg Phe Ser Gly Ser
    50                  55                  60

Thr Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105


<210> SEQ ID NO 36
<211> LENGTH: 108
<212> TYPE: PRT
<213> ORGANISM: Artificial Sequence
<220> FEATURE:
<223> OTHER INFORMATION: Variable Light Chain Amino Acid Sequence

<400> SEQUENCE: 36

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

Asn Trp Phe Gln Gln Lys Pro Gly Gln Ala Pro Val Leu Val Val Tyr
        35                  40                  45

Asp Asp Ser Gly Arg Pro Ser Gly Val Pro Ser Arg Phe Ser Gly Ser
    50                  55                  60

Thr Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105


<210> SEQ ID NO 37
<211> LENGTH: 108
<212> TYPE: PRT
<213> ORGANISM: Artificial Sequence
<220> FEATURE:
<223> OTHER INFORMATION: Variable Light Chain Amino Acid Sequence

<400> SEQUENCE: 37

Ser Tyr Val Leu Thr Gln Pro Pro Ser Val Ser Val Ala Pro Gly Gln
1               5                   10                  15
```

```
Thr Ala Arg Ile Thr Cys Gly Gly Asn Asn Ile Gly Ser Lys Ser Val
            20                  25                  30

Asn Trp Phe Gln Gln Lys Pro Gly Gln Ala Pro Val Leu Val Val Tyr
        35                  40                  45

Asp Asp Ser Gly Arg Pro Ser Gly Ile Pro Lys Arg Phe Ser Gly Ser
    50                  55                  60

Thr Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105


<210> SEQ ID NO 38
<211> LENGTH: 108
<212> TYPE: PRT
<213> ORGANISM: Artificial Sequence
<220> FEATURE:
<223> OTHER INFORMATION: Variable Light Chain Amino Acid Sequence

<400> SEQUENCE: 38

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

Asn Trp Phe Gln Gln Lys Pro Gly Gln Ala Pro Val Leu Val Val Tyr
        35                  40                  45

Asp Asp Ser Gly Arg Pro Ser Gly Ile Pro Ala Arg Phe Ser Gly Ser
    50                  55                  60

Thr Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105


<210> SEQ ID NO 39
<211> LENGTH: 108
<212> TYPE: PRT
<213> ORGANISM: Artificial Sequence
<220> FEATURE:
<223> OTHER INFORMATION: Variable Light Chain Amino Acid Sequence

<400> SEQUENCE: 39

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

Asn Trp Phe Gln Gln Lys Pro Gly Gln Ala Pro Val Leu Val Val Tyr
        35                  40                  45

Asp Asp Ser Gly Arg Pro Ser Gly Val Pro Asn Arg Phe Ser Gly Ser
    50                  55                  60

Thr Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
```

100 105

<210> SEQ ID NO 40
<211> LENGTH: 108
<212> TYPE: PRT
<213> ORGANISM: Artificial Sequence
<220> FEATURE:
<223> OTHER INFORMATION: Variable Light Chain Amino Acid Sequence

<400> SEQUENCE: 40

Ser Tyr Val Leu Thr Gln Pro Pro Ser Val Ser Val Ala Pro Gly Lys
1 5 10 15

Thr Ala Arg Ile Thr Cys Gly Gly Asn Asn Ile Gly Ser Lys Ser Val
20 25 30

Asn Trp Phe Gln Gln Lys Pro Gly Gln Ala Pro Val Leu Val Val Tyr
35 40 45

Asp Asp Ser Gly Arg Pro Ser Gly Val Pro Ser Arg Phe Ser Gly Ser
50 55 60

Thr Ser Gly Asn Thr Ala Thr Leu Thr Ile Ser Arg Val Glu Ala Gly
65 70 75 80

Asp Glu Ala Asp Tyr Tyr Cys Gln Val Trp Asp Ser Ser Ser Asp His
85 90 95

Val Val Phe Gly Gly Gly Thr Lys Leu Thr Val Leu
100 105

<210> SEQ ID NO 41
<211> LENGTH: 108
<212> TYPE: PRT
<213> ORGANISM: Artificial Sequence
<220> FEATURE:
<223> OTHER INFORMATION: Variable Light Chain Amino Acid Sequence

<400> SEQUENCE: 41

Ser Tyr Val Leu Thr Gln Pro Pro Ser Val Ser Val Ala Pro Gly Lys
1 5 10 15

Thr Ala Arg Ile Thr Cys Gly Gly Asn Asn Ile Gly Ser Lys Ser Val
20 25 30

Asn Trp Phe Gln Gln Lys Pro Gly Gln Ala Pro Val Leu Val Val Tyr
35 40 45

Asp Asp Ser Gly Arg Pro Ser Gly Ile Pro Lys Arg Phe Ser Gly Ser
50 55 60

Thr Ser Gly Asn Thr Ala Thr Leu Thr Ile Ser Arg Val Glu Ala Gly
65 70 75 80

Asp Glu Ala Asp Tyr Tyr Cys Gln Val Trp Asp Ser Ser Ser Asp His
85 90 95

Val Val Phe Gly Gly Gly Thr Lys Leu Thr Val Leu
100 105

<210> SEQ ID NO 42
<211> LENGTH: 249
<212> TYPE: PRT
<213> ORGANISM: Artificial Sequence
<220> FEATURE:
<223> OTHER INFORMATION: Synthetic Peptide

<400> SEQUENCE: 42

Glu Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Ser Tyr
20 25 30

```
Trp Ile Asn Trp Val Arg Gln Ala Pro Gly Gln Gly Leu Glu Trp Ile
        35                  40                  45

Gly Asn Ile Tyr Pro Gly Ser Ser Thr Thr Asn Tyr Asn Glu Lys Phe
    50                  55                  60

Lys Ser Arg Ala Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Phe Ser Asp Gly Tyr Tyr Ala Tyr Ala Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Glu Ile Val
    130                 135                 140

Met Thr Gln Ser Pro Gly Thr Leu Ser Leu Ser Pro Gly Glu Arg Ala
145                 150                 155                 160

Thr Leu Ser Cys Arg Ala Ser Gln Asp Ile Ser Asn Tyr Leu Asn Trp
                165                 170                 175

Tyr Gln Gln Lys Pro Gly Gln Ala Val Arg Leu Leu Ile Tyr Tyr Thr
            180                 185                 190

Ser Arg Leu His Ser Gly Ile Pro Asp Arg Phe Ser Gly Ser Gly Ser
        195                 200                 205

Gly Thr Asp Tyr Thr Leu Thr Ile Ser Arg Leu Glu Pro Glu Asp Phe
    210                 215                 220

Ala Val Tyr Phe Cys Gln Gln Gly Tyr Thr Leu Pro Tyr Thr Phe Gly
225                 230                 235                 240

Gln Gly Thr Lys Val Glu Ile Lys Arg
                245
```

<210> SEQ ID NO 43
<211> LENGTH: 500
<212> TYPE: PRT
<213> ORGANISM: Artificial Sequence
<220> FEATURE:
<223> OTHER INFORMATION: Synthetic Peptide

<400> SEQUENCE: 43

```
Ser Ser Glu Pro Lys Ser Ser Asp Lys Thr His Thr Cys Pro Pro Cys
1               5                   10                  15

Pro Ala Pro Glu Leu Leu Gly Gly Pro Ser Val Phe Leu Phe Pro Pro
            20                  25                  30

Lys Pro Lys Asp Thr Leu Met Ile Ser Arg Thr Pro Glu Val Thr Cys
        35                  40                  45

Val Val Val Asp Val Ser His Glu Asp Pro Glu Val Lys Phe Asn Trp
    50                  55                  60

Tyr Val Asp Gly Val Glu Val His Asn Ala Lys Thr Lys Pro Arg Glu
65                  70                  75                  80

Glu Gln Tyr Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Ala Leu Pro Ala Pro Ile Glu Lys Thr Ile Ser Lys Ala Lys Gly
        115                 120                 125

Gln Pro Arg Glu Pro Gln Val Tyr Thr Leu Pro Pro Ser Arg Asp Glu
    130                 135                 140
```

```
Leu Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Lys Leu Thr Val Asp Lys Ser Arg Trp Gln Gln Gly Asn
        195                 200                 205

Val Phe Ser Cys Ser Val Met His Glu Ala Leu His Asn His Tyr Thr
    210                 215                 220

Gln Lys Ser Leu Ser Leu Ser Pro Gly Ser Gly Gly Gly Gly Ser Gly
225                 230                 235                 240

Gly Gly Gly Ser Gly Gly Gly Gly Ser Pro Ser Glu Val Gln Leu Val
                245                 250                 255

Gln Ser Gly Ala Glu Val Lys Lys Pro Gly Ser Ser Val Lys Val Ser
            260                 265                 270

Cys Lys Ala Ser Gly Tyr Thr Phe Thr Ser Tyr Trp Ile Asn Trp Val
        275                 280                 285

Arg Gln Ala Pro Gly Gln Gly Leu Glu Trp Ile Gly Asn Ile Tyr Pro
    290                 295                 300

Gly Ser Ser Thr Thr Asn Tyr Asn Glu Lys Phe Lys Ser Arg Ala Thr
305                 310                 315                 320

Leu Thr Val Asp Thr Ser Thr Ser Thr Ala Tyr Met Glu Leu Ser Ser
                325                 330                 335

Leu Arg Ser Glu Asp Thr Ala Val Tyr Tyr Cys Ala Ser Phe Ser Asp
            340                 345                 350

Gly Tyr Tyr Ala Tyr Ala Met Asp Tyr Trp Gly Gln Gly Thr Leu Val
        355                 360                 365

Thr Val Ser Ser Gly Gly Gly Gly Ser Gly Gly Gly Gly Ser Gly Gly
    370                 375                 380

Gly Gly Ser Gly Gly Gly Gly Ser Glu Ile Val Met Thr Gln Ser Pro
385                 390                 395                 400

Gly Thr Leu Ser Leu Ser Pro Gly Glu Arg Ala Thr Leu Ser Cys Arg
                405                 410                 415

Ala Ser Gln Asp Ile Ser Asn Tyr Leu Asn Trp Tyr Gln Gln Lys Pro
            420                 425                 430

Gly Gln Ala Val Arg Leu Leu Ile Tyr Tyr Thr Ser Arg Leu His Ser
        435                 440                 445

Gly Ile Pro Asp Arg Phe Ser Gly Ser Gly Ser Gly Thr Asp Tyr Thr
    450                 455                 460

Leu Thr Ile Ser Arg Leu Glu Pro Glu Asp Phe Ala Val Tyr Phe Cys
465                 470                 475                 480

Gln Gln Gly Tyr Thr Leu Pro Tyr Thr Phe Gly Gln Gly Thr Lys Val
                485                 490                 495

Glu Ile Lys Arg
            500
```

<210> SEQ ID NO 44
<211> LENGTH: 249
<212> TYPE: PRT
<213> ORGANISM: Artificial Sequence
<220> FEATURE:
<223> OTHER INFORMATION: Synthetic Peptide

<400> SEQUENCE: 44

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Asn Ile Tyr Pro Gly Ser Ser Thr Thr Asn Tyr Ala Gln Lys Phe
    50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Phe Ser Asp Gly Tyr Tyr Ala Tyr Ala Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Glu Ile Val
    130                 135                 140

Met Thr Gln Ser Pro Ala Thr Leu Ser Leu Ser Pro Gly Glu Arg Ala
145                 150                 155                 160

Thr Leu Ser Cys Arg Ala Ser Gln Asp Ile Ser Asn Tyr Leu Asn Trp
                165                 170                 175

Tyr Gln Gln Lys Pro Gly Gln Ala Val Arg Leu Leu Ile Tyr Tyr Thr
            180                 185                 190

Ser Arg Leu His Ser Gly Ile Pro Ala Arg Phe Ser Gly Ser Gly Ser
        195                 200                 205

Gly Thr Asp Tyr Thr Leu Thr Ile Ser Ser Leu Gln Pro Glu Asp Phe
    210                 215                 220

Ala Val Tyr Phe Cys Gln Gln Gly Tyr Thr Leu Pro Tyr Thr Phe Gly
225                 230                 235                 240

Gln Gly Thr Lys Val Glu Ile Lys Arg
                245


<210> SEQ ID NO 45
<211> LENGTH: 500
<212> TYPE: PRT
<213> ORGANISM: Artificial Sequence
<220> FEATURE:
<223> OTHER INFORMATION: Synthetic Peptide

<400> SEQUENCE: 45

Ser Ser Glu Pro Lys Ser Ser Asp Lys Thr His Thr Cys Pro Pro Cys
1               5                   10                  15

Pro Ala Pro Glu Leu Leu Gly Gly Pro Ser Val Phe Leu Phe Pro Pro
            20                  25                  30

Lys Pro Lys Asp Thr Leu Met Ile Ser Arg Thr Pro Glu Val Thr Cys
        35                  40                  45

Val Val Val Asp Val Ser His Glu Asp Pro Glu Val Lys Phe Asn Trp
    50                  55                  60

Tyr Val Asp Gly Val Glu Val His Asn Ala Lys Thr Lys Pro Arg Glu
65                  70                  75                  80

Glu Gln Tyr Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110
```

```
Lys Ala Leu Pro Ala Pro Ile Glu Lys Thr Ile Ser Lys Ala Lys Gly
        115                 120                 125

Gln Pro Arg Glu Pro Gln Val Tyr Thr Leu Pro Pro Ser Arg Asp Glu
    130                 135                 140

Leu Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Lys Leu Thr Val Asp Lys Ser Arg Trp Gln Gln Gly Asn
        195                 200                 205

Val Phe Ser Cys Ser Val Met His Glu Ala Leu His Asn His Tyr Thr
    210                 215                 220

Gln Lys Ser Leu Ser Leu Ser Pro Gly Ser Gly Gly Gly Gly Ser Gly
225                 230                 235                 240

Gly Gly Gly Ser Gly Gly Gly Gly Ser Pro Ser Glu Val Gln Leu Val
                245                 250                 255

Gln Ser Gly Ala Glu Val Lys Lys Pro Gly Ala Ser Val Lys Val Ser
            260                 265                 270

Cys Lys Ala Ser Gly Tyr Thr Phe Thr Ser Tyr Trp Met Asn Trp Val
        275                 280                 285

Arg Gln Ala Pro Gly Gln Gly Leu Glu Trp Met Gly Asn Ile Tyr Pro
    290                 295                 300

Gly Ser Ser Thr Thr Asn Tyr Ala Gln Lys Phe Gln Gly Arg Val Thr
305                 310                 315                 320

Met Thr Val Asp Thr Ser Thr Ser Thr Val Tyr Met Glu Leu Ser Ser
                325                 330                 335

Leu Arg Ser Glu Asp Thr Ala Val Tyr Tyr Cys Ala Ser Phe Ser Asp
            340                 345                 350

Gly Tyr Tyr Ala Tyr Ala Met Asp Tyr Trp Gly Gln Gly Thr Leu Val
        355                 360                 365

Thr Val Ser Ser Gly Gly Gly Gly Ser Gly Gly Gly Gly Ser Gly Gly
    370                 375                 380

Gly Gly Ser Gly Gly Gly Gly Ser Glu Ile Val Met Thr Gln Ser Pro
385                 390                 395                 400

Ala Thr Leu Ser Leu Ser Pro Gly Glu Arg Ala Thr Leu Ser Cys Arg
                405                 410                 415

Ala Ser Gln Asp Ile Ser Asn Tyr Leu Asn Trp Tyr Gln Gln Lys Pro
            420                 425                 430

Gly Gln Ala Val Arg Leu Leu Ile Tyr Tyr Thr Ser Arg Leu His Ser
        435                 440                 445

Gly Ile Pro Ala Arg Phe Ser Gly Ser Gly Ser Gly Thr Asp Tyr Thr
    450                 455                 460

Leu Thr Ile Ser Ser Leu Gln Pro Glu Asp Phe Ala Val Tyr Phe Cys
465                 470                 475                 480

Gln Gln Gly Tyr Thr Leu Pro Tyr Thr Phe Gly Gln Gly Thr Lys Val
                485                 490                 495

Glu Ile Lys Arg
            500
```

<210> SEQ ID NO 46
<211> LENGTH: 243

<212> TYPE: PRT
<213> ORGANISM: Artificial Sequence
<220> FEATURE:
<223> OTHER INFORMATION: Synthetic Peptide

<400> SEQUENCE: 46

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Ser Tyr Tyr
            20                  25                  30

Gly Met His Trp Val Arg Gln Ala Pro Gly Lys Gly Leu Glu Trp Val
        35                  40                  45

Ala Val Ile Ser His Asp Gly Ser Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Leu Tyr Tyr Cys
                85                  90                  95

Ser Asn Asp Gln Phe Asp Pro Trp Gly Gln Gly Thr Leu Val Thr Val
            100                 105                 110

Ser Ser Gly Gly Gly Gly Ser Gly Gly Gly Gly Ser Gly Gly Gly Gly
        115                 120                 125

Ser Gly Gly Gly Gly Ser Ser Tyr Val Leu Thr Gln Pro Pro Ser Val
    130                 135                 140

Ser Val Ala Pro Gly Gln Thr Ala Arg Ile Thr Cys Gly Gly Asn Asn
145                 150                 155                 160

Ile Gly Ser Lys Ser Val His Trp Phe Gln Gln Lys Pro Gly Gln Ala
                165                 170                 175

Pro Ala Leu Val Val Tyr Asp Asp Ser Gly Arg Pro Ser Gly Ile Pro
            180                 185                 190

Glu Arg Phe Ser Gly Ser Thr Ser Gly Asn Thr Ala Thr Leu Thr Ile
        195                 200                 205

Ser Arg Val Glu Ala Gly Asp Glu Ala Asp Tyr Tyr Cys Gln Val Trp
    210                 215                 220

Asp Ser Ser Ser Asp His Val Val Phe Gly Gly Gly Thr Lys Leu Thr
225                 230                 235                 240

Val Leu Arg
```

<210> SEQ ID NO 47
<211> LENGTH: 243
<212> TYPE: PRT
<213> ORGANISM: Artificial Sequence
<220> FEATURE:
<223> OTHER INFORMATION: Synthetic Peptide

<400> SEQUENCE: 47

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Phe Gln Gln Lys Pro Gly Gln Ala Pro Ala Leu Val Val Tyr
        35                  40                  45

Asp Asp Ser Gly Arg Pro Ser Gly Ile Pro Glu Arg Phe Ser Gly Ser
    50                  55                  60

Thr Ser Gly Asn Thr Ala Thr Leu Thr Ile Ser Arg Val Glu Ala Gly
65                  70                  75                  80
```

Asp Glu Ala Asp Tyr Tyr Cys Gln Val Trp Asp Ser Ser Ser Asp His
85 90 95

Val Val Phe Gly Gly Gly Thr Lys Leu Thr Val Leu Gly Gly Gly Gly
100 105 110

Ser Gly Gly Gly Gly Ser Gly Gly Gly Gly Ser Gly Gly Gly Gly Ser
115 120 125

Gln Val Gln Leu Val Glu Ser Gly Gly Gly Val Val Gln Pro Gly Arg
130 135 140

Ser Leu Arg Leu Ser Cys Ala Ala Ser Gly Phe Thr Leu Ser Tyr Tyr
145 150 155 160

Gly Met His Trp Val Arg Gln Ala Pro Gly Lys Gly Leu Glu Trp Val
165 170 175

Ala Val Ile Ser His Asp Gly Ser Asp Lys Tyr Tyr Ala Asp Ser Val
180 185 190

Lys Gly Arg Phe Thr Ile Ser Arg Asp Asn Ser Lys Asn Thr Leu Tyr
195 200 205

Leu Gln Met Asp Ser Leu Arg Ala Glu Asp Thr Ala Leu Tyr Tyr Cys
210 215 220

Ser Asn Asp Gln Phe Asp Pro Trp Gly Gln Gly Thr Leu Val Thr Val
225 230 235 240

Ser Ser Arg

<210> SEQ ID NO 48
<211> LENGTH: 742
<212> TYPE: PRT
<213> ORGANISM: Artificial Sequence
<220> FEATURE:
<223> OTHER INFORMATION: Synthetic Peptide

<400> SEQUENCE: 48

Asp Ile Gln Met Thr Gln Ser Pro Ser Ser Leu Ser Ala Ser Val Gly
1 5 10 15

Asp Arg Val Thr Ile Asn Cys Gln Ala Ser Gln Ser Ile Asp Ser Asn
20 25 30

Leu Ala Trp Phe Gln Gln Lys Pro Gly Gln Pro Pro Lys Leu Leu Ile
35 40 45

Tyr Arg Ala Ser Asn Leu Ala Ser Gly Val Pro Asp Arg Phe Ser Gly
50 55 60

Ser Gly Ser Gly Thr Asp Phe Thr Leu Thr Ile Ser Ser Leu Glu Ala
65 70 75 80

Glu Asp Val Ala Thr Tyr Tyr Cys Leu Gly Gly Val Gly Ala Val Ser
85 90 95

Tyr Arg Thr Ser Phe Gly Gly Gly Thr Lys Val Glu Ile Lys Gly Gly
100 105 110

Gly Gly Ser Gly Gly Gly Gly Ser Gly Gly Gly Gly Ser Gly Gly Gly
115 120 125

Gly Ser Glu Val Gln Leu Val Glu Ser Gly Gly Gly Leu Val Gln Pro
130 135 140

Gly Arg Ser Leu Arg Leu Ser Cys Thr Ala Ser Gly Ser Asp Ile Asn
145 150 155 160

Asp Tyr Pro Ile Thr Trp Val Arg Gln Ala Pro Gly Gln Gly Leu Glu
165 170 175

Trp Ile Gly Phe Ile Asn Ser Gly Gly Ser Thr Trp Tyr Ala Ser Trp
180 185 190

Val Lys Gly Arg Phe Thr Ile Ser Arg Asp Asp Ser Lys Ser Ile Ala

-continued

```
        195                 200                 205

Tyr Leu Gln Met Asn Ser Leu Lys Thr Glu Asp Thr Ala Val Tyr Tyr
    210                 215                 220

Cys Ala Arg Gly Tyr Ser Thr Tyr Tyr Arg Asp Phe Asn Ile Trp Gly
225                 230                 235                 240

Gln Gly Thr Leu Val Thr Val Ser Ser Ser Glu Pro Lys Ser Ser Asp
                245                 250                 255

Lys Thr His Thr Cys Pro Pro Cys Pro Ala Pro Glu Ala Ala Gly Ala
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Ala Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Ala Gly Gly Gly Gly Ser Gly Gly Gly Gly Ser Gly Gly Gly Gly
                485                 490                 495

Ser Pro Ser Gln Val Gln Leu Val Glu Ser Gly Gly Gly Val Val Gln
            500                 505                 510

Pro Gly Arg Ser Leu Arg Leu Ser Cys Ala Ala Ser Gly Phe Thr Leu
        515                 520                 525

Ser Tyr Tyr Gly Met His Trp Val Arg Gln Ala Pro Gly Lys Gly Leu
    530                 535                 540

Glu Trp Val Ala Val Ile Ser His Asp Gly Ser Asp Lys Tyr Tyr Ala
545                 550                 555                 560

Asp Ser Val Lys Gly Arg Phe Thr Ile Ser Arg Asp Asn Ser Lys Asn
                565                 570                 575

Thr Leu Tyr Leu Gln Met Asp Ser Leu Arg Ala Glu Asp Thr Ala Leu
            580                 585                 590

Tyr Tyr Cys Ser Asn Asp Gln Phe Asp Pro Trp Gly Gln Gly Thr Leu
        595                 600                 605

Val Thr Val Ser Ser Gly Gly Gly Gly Ser Gly Gly Gly Gly Ser Gly
    610                 615                 620
```

```
Gly Gly Gly Ser Gly Gly Gly Gly Ser Ser Tyr Val Leu Thr Gln Pro
625                 630                 635                 640

Pro Ser Val Ser Val Ala Pro Gly Gln Thr Ala Arg Ile Thr Cys Gly
                645                 650                 655

Gly Asn Asn Ile Gly Ser Lys Ser Val His Trp Phe Gln Gln Lys Pro
            660                 665                 670

Gly Gln Ala Pro Ala Leu Val Val Tyr Asp Asp Ser Gly Arg Pro Ser
        675                 680                 685

Gly Ile Pro Glu Arg Phe Ser Gly Ser Thr Ser Gly Asn Thr Ala Thr
    690                 695                 700

Leu Thr Ile Ser Arg Val Glu Ala Gly Asp Glu Ala Asp Tyr Tyr Cys
705                 710                 715                 720

Gln Val Trp Asp Ser Ser Ser Asp His Val Val Phe Gly Gly Gly Thr
                725                 730                 735

Lys Leu Thr Val Leu Arg
            740
```

<210> SEQ ID NO 49
<211> LENGTH: 732
<212> TYPE: PRT
<213> ORGANISM: Artificial Sequence
<220> FEATURE:
<223> OTHER INFORMATION: Synthetic Peptide

<400> SEQUENCE: 49

```
Asp Ile Gln Met Thr Gln Ser Pro Ser Ser Leu Ser Ala Ser Val Gly
1               5                   10                  15

Asp Arg Val Thr Ile Asn Cys Gln Ala Ser Gln Ser Ile Asp Ser Asn
            20                  25                  30

Leu Ala Trp Phe Gln Gln Lys Pro Gly Gln Pro Pro Lys Leu Leu Ile
        35                  40                  45

Tyr Arg Ala Ser Asn Leu Ala Ser Gly Val Pro Asp Arg Phe Ser Gly
    50                  55                  60

Ser Gly Ser Gly Thr Asp Phe Thr Leu Thr Ile Ser Ser Leu Glu Ala
65                  70                  75                  80

Glu Asp Val Ala Thr Tyr Tyr Cys Leu Gly Gly Val Gly Ala Val Ser
                85                  90                  95

Tyr Arg Thr Ser Phe Gly Gly Gly Thr Lys Val Glu Ile Lys Gly Gly
            100                 105                 110

Gly Gly Ser Gly Gly Gly Gly Ser Gly Gly Gly Gly Ser Gly Gly Gly
        115                 120                 125

Gly Ser Glu Val Gln Leu Val Glu Ser Gly Gly Gly Leu Val Gln Pro
    130                 135                 140

Gly Arg Ser Leu Arg Leu Ser Cys Thr Ala Ser Gly Ser Asp Ile Asn
145                 150                 155                 160

Asp Tyr Pro Ile Thr Trp Val Arg Gln Ala Pro Gly Gln Gly Leu Glu
                165                 170                 175

Trp Ile Gly Phe Ile Asn Ser Gly Gly Ser Thr Trp Tyr Ala Ser Trp
            180                 185                 190

Val Lys Gly Arg Phe Thr Ile Ser Arg Asp Asp Ser Lys Ser Ile Ala
        195                 200                 205

Tyr Leu Gln Met Asn Ser Leu Lys Thr Glu Asp Thr Ala Val Tyr Tyr
    210                 215                 220

Cys Ala Arg Gly Tyr Ser Thr Tyr Tyr Arg Asp Phe Asn Ile Trp Gly
225                 230                 235                 240
```

```
Gln Gly Thr Leu Val Thr Val Ser Ser Ser Glu Pro Lys Ser Ser Asp
                245                 250                 255

Lys Thr His Thr Cys Pro Pro Cys Pro Ala Pro Glu Ala Ala Gly Ala
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Ala Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Ala Gly Gly Gly Gly Ser Pro Ser Gln Val Gln Leu Val Glu Ser
                485                 490                 495

Gly Gly Gly Val Val Gln Pro Gly Arg Ser Leu Arg Leu Ser Cys Ala
            500                 505                 510

Ala Ser Gly Phe Thr Leu Ser Tyr Tyr Gly Met His Trp Val Arg Gln
        515                 520                 525

Ala Pro Gly Lys Gly Leu Glu Trp Val Ala Val Ile Ser His Asp Gly
    530                 535                 540

Ser Asp Lys Tyr Tyr Ala Asp Ser Val Lys Gly Arg Phe Thr Ile Ser
545                 550                 555                 560

Arg Asp Asn Ser Lys Asn Thr Leu Tyr Leu Gln Met Asp Ser Leu Arg
                565                 570                 575

Ala Glu Asp Thr Ala Leu Tyr Tyr Cys Ser Asn Asp Gln Phe Asp Pro
            580                 585                 590

Trp Gly Gln Gly Thr Leu Val Thr Val Ser Ser Gly Gly Gly Gly Ser
        595                 600                 605

Gly Gly Gly Gly Ser Gly Gly Gly Gly Ser Gly Gly Gly Gly Ser Ser
    610                 615                 620

Tyr Val Leu Thr Gln Pro Pro Ser Val Ser Val Ala Pro Gly Gln Thr
625                 630                 635                 640

Ala Arg Ile Thr Cys Gly Gly Asn Asn Ile Gly Ser Lys Ser Val His
                645                 650                 655
```

```
Trp Phe Gln Gln Lys Pro Gly Gln Ala Pro Ala Leu Val Val Tyr Asp
            660                 665                 670

Asp Ser Gly Arg Pro Ser Gly Ile Pro Glu Arg Phe Ser Gly Ser Thr
        675                 680                 685

Ser Gly Asn Thr Ala Thr Leu Thr Ile Ser Arg Val Glu Ala Gly Asp
    690                 695                 700

Glu Ala Asp Tyr Tyr Cys Gln Val Trp Asp Ser Ser Ser Asp His Val
705                 710                 715                 720

Val Phe Gly Gly Gly Thr Lys Leu Thr Val Leu Arg
                725                 730


<210> SEQ ID NO 50
<211> LENGTH: 742
<212> TYPE: PRT
<213> ORGANISM: Artificial Sequence
<220> FEATURE:
<223> OTHER INFORMATION: Synthetic Peptide

<400> SEQUENCE: 50

Asp Ile Gln Met Thr Gln Ser Pro Ser Ser Leu Ser Ala Ser Val Gly
1               5                   10                  15

Asp Arg Val Thr Ile Asn Cys Gln Ala Ser Gln Ser Ile Asp Ser Asn
            20                  25                  30

Leu Ala Trp Phe Gln Gln Lys Pro Gly Gln Pro Pro Lys Leu Leu Ile
        35                  40                  45

Tyr Arg Ala Ser Asn Leu Ala Ser Gly Val Pro Asp Arg Phe Ser Gly
    50                  55                  60

Ser Gly Ser Gly Thr Asp Phe Thr Leu Thr Ile Ser Ser Leu Glu Ala
65                  70                  75                  80

Glu Asp Val Ala Thr Tyr Tyr Cys Leu Gly Gly Val Gly Ala Val Ser
                85                  90                  95

Tyr Arg Thr Ser Phe Gly Gly Gly Thr Lys Val Glu Ile Lys Gly Gly
            100                 105                 110

Gly Gly Ser Gly Gly Gly Gly Ser Gly Gly Gly Gly Ser Gly Gly Gly
        115                 120                 125

Gly Ser Glu Val Gln Leu Val Glu Ser Gly Gly Gly Leu Val Gln Pro
    130                 135                 140

Gly Arg Ser Leu Arg Leu Ser Cys Thr Ala Ser Gly Ser Asp Ile Asn
145                 150                 155                 160

Asp Tyr Pro Ile Thr Trp Val Arg Gln Ala Pro Gly Gln Gly Leu Glu
                165                 170                 175

Trp Ile Gly Phe Ile Asn Ser Gly Gly Ser Thr Trp Tyr Ala Ser Trp
            180                 185                 190

Val Lys Gly Arg Phe Thr Ile Ser Arg Asp Asp Ser Lys Ser Ile Ala
        195                 200                 205

Tyr Leu Gln Met Asn Ser Leu Lys Thr Glu Asp Thr Ala Val Tyr Tyr
    210                 215                 220

Cys Ala Arg Gly Tyr Ser Thr Tyr Tyr Arg Asp Phe Asn Ile Trp Gly
225                 230                 235                 240

Gln Gly Thr Leu Val Thr Val Ser Ser Ser Glu Pro Lys Ser Ser Asp
                245                 250                 255

Lys Thr His Thr Cys Pro Pro Cys Pro Ala Pro Glu Ala Ala Gly Ala
            260                 265                 270

Pro Ser Val Phe Leu Phe Pro Pro Lys Pro Lys Asp Thr Leu Met Ile
        275                 280                 285
```

```
Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Ala Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Ala Gly Gly Gly Gly Ser Gly Gly Gly Gly Ser Gly Gly Gly Gly
                485                 490                 495

Ser Pro Ser Ser Tyr Val Leu Thr Gln Pro Pro Ser Val Ser Val Ala
            500                 505                 510

Pro Gly Gln Thr Ala Arg Ile Thr Cys Gly Gly Asn Asn Ile Gly Ser
        515                 520                 525

Lys Ser Val His Trp Phe Gln Gln Lys Pro Gly Gln Ala Pro Ala Leu
    530                 535                 540

Val Val Tyr Asp Asp Ser Gly Arg Pro Ser Gly Ile Pro Glu Arg Phe
545                 550                 555                 560

Ser Gly Ser Thr Ser Gly Asn Thr Ala Thr Leu Thr Ile Ser Arg Val
                565                 570                 575

Glu Ala Gly Asp Glu Ala Asp Tyr Tyr Cys Gln Val Trp Asp Ser Ser
            580                 585                 590

Ser Asp His Val Val Phe Gly Gly Gly Thr Lys Leu Thr Val Leu Gly
        595                 600                 605

Gly Gly Gly Ser Gly Gly Gly Gly Ser Gly Gly Gly Gly Ser Gly Gly
    610                 615                 620

Gly Gly Ser Gln Val Gln Leu Val Glu Ser Gly Gly Gly Val Val Gln
625                 630                 635                 640

Pro Gly Arg Ser Leu Arg Leu Ser Cys Ala Ala Ser Gly Phe Thr Leu
                645                 650                 655

Ser Tyr Tyr Gly Met His Trp Val Arg Gln Ala Pro Gly Lys Gly Leu
            660                 665                 670

Glu Trp Val Ala Val Ile Ser His Asp Gly Ser Asp Lys Tyr Tyr Ala
        675                 680                 685

Asp Ser Val Lys Gly Arg Phe Thr Ile Ser Arg Asp Asn Ser Lys Asn
    690                 695                 700

Thr Leu Tyr Leu Gln Met Asp Ser Leu Arg Ala Glu Asp Thr Ala Leu
```

705 710 715 720

Tyr Tyr Cys Ser Asn Asp Gln Phe Asp Pro Trp Gly Gln Gly Thr Leu
725 730 735

Val Thr Val Ser Ser Arg
740

<210> SEQ ID NO 51
<211> LENGTH: 732
<212> TYPE: PRT
<213> ORGANISM: Artificial Sequence
<220> FEATURE:
<223> OTHER INFORMATION: Synthetic Peptide

<400> SEQUENCE: 51

Asp Ile Gln Met Thr Gln Ser Pro Ser Ser Leu Ser Ala Ser Val Gly
1 5 10 15

Asp Arg Val Thr Ile Asn Cys Gln Ala Ser Gln Ser Ile Asp Ser Asn
20 25 30

Leu Ala Trp Phe Gln Gln Lys Pro Gly Gln Pro Pro Lys Leu Leu Ile
35 40 45

Tyr Arg Ala Ser Asn Leu Ala Ser Gly Val Pro Asp Arg Phe Ser Gly
50 55 60

Ser Gly Ser Gly Thr Asp Phe Thr Leu Thr Ile Ser Ser Leu Glu Ala
65 70 75 80

Glu Asp Val Ala Thr Tyr Tyr Cys Leu Gly Gly Val Gly Ala Val Ser
85 90 95

Tyr Arg Thr Ser Phe Gly Gly Gly Thr Lys Val Glu Ile Lys Gly Gly
100 105 110

Gly Gly Ser Gly Gly Gly Gly Ser Gly Gly Gly Gly Ser Gly Gly Gly
115 120 125

Gly Ser Glu Val Gln Leu Val Glu Ser Gly Gly Gly Leu Val Gln Pro
130 135 140

Gly Arg Ser Leu Arg Leu Ser Cys Thr Ala Ser Gly Ser Asp Ile Asn
145 150 155 160

Asp Tyr Pro Ile Thr Trp Val Arg Gln Ala Pro Gly Gln Gly Leu Glu
165 170 175

Trp Ile Gly Phe Ile Asn Ser Gly Gly Ser Thr Trp Tyr Ala Ser Trp
180 185 190

Val Lys Gly Arg Phe Thr Ile Ser Arg Asp Asp Ser Lys Ser Ile Ala
195 200 205

Tyr Leu Gln Met Asn Ser Leu Lys Thr Glu Asp Thr Ala Val Tyr Tyr
210 215 220

Cys Ala Arg Gly Tyr Ser Thr Tyr Tyr Arg Asp Phe Asn Ile Trp Gly
225 230 235 240

Gln Gly Thr Leu Val Thr Val Ser Ser Ser Glu Pro Lys Ser Ser Asp
245 250 255

Lys Thr His Thr Cys Pro Pro Cys Pro Ala Pro Glu Ala Ala Gly Ala
260 265 270

Pro Ser Val Phe Leu Phe Pro Pro Lys Pro Lys Asp Thr Leu Met Ile
275 280 285

Ser Arg Thr Pro Glu Val Thr Cys Val Val Val Asp Val Ser His Glu
290 295 300

Asp Pro Glu Val Lys Phe Asn Trp Tyr Val Asp Gly Val Glu Val His
305 310 315 320

Asn Ala Lys Thr Lys Pro Arg Glu Glu Gln Tyr Asn Ser Thr Tyr Arg

```
                325                 330                 335

Val Val Ser Val Leu Thr Val Leu His Gln Asp Trp Leu Asn Gly Lys
            340                 345                 350

Glu Tyr Lys Cys Ala Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Ala Gly Gly Gly Gly Ser Pro Ser Ser Tyr Val Leu Thr Gln Pro
                485                 490                 495

Pro Ser Val Ser Val Ala Pro Gly Gln Thr Ala Arg Ile Thr Cys Gly
            500                 505                 510

Gly Asn Asn Ile Gly Ser Lys Ser Val His Trp Phe Gln Gln Lys Pro
        515                 520                 525

Gly Gln Ala Pro Ala Leu Val Val Tyr Asp Asp Ser Gly Arg Pro Ser
    530                 535                 540

Gly Ile Pro Glu Arg Phe Ser Gly Ser Thr Ser Gly Asn Thr Ala Thr
545                 550                 555                 560

Leu Thr Ile Ser Arg Val Glu Ala Gly Asp Glu Ala Asp Tyr Tyr Cys
                565                 570                 575

Gln Val Trp Asp Ser Ser Ser Asp His Val Val Phe Gly Gly Gly Thr
            580                 585                 590

Lys Leu Thr Val Leu Gly Gly Gly Gly Ser Gly Gly Gly Gly Ser Gly
        595                 600                 605

Gly Gly Gly Ser Gly Gly Gly Gly Ser Gln Val Gln Leu Val Glu Ser
    610                 615                 620

Gly Gly Gly Val Val Gln Pro Gly Arg Ser Leu Arg Leu Ser Cys Ala
625                 630                 635                 640

Ala Ser Gly Phe Thr Leu Ser Tyr Tyr Gly Met His Trp Val Arg Gln
                645                 650                 655

Ala Pro Gly Lys Gly Leu Glu Trp Val Ala Val Ile Ser His Asp Gly
            660                 665                 670

Ser Asp Lys Tyr Tyr Ala Asp Ser Val Lys Gly Arg Phe Thr Ile Ser
        675                 680                 685

Arg Asp Asn Ser Lys Asn Thr Leu Tyr Leu Gln Met Asp Ser Leu Arg
    690                 695                 700

Ala Glu Asp Thr Ala Leu Tyr Tyr Cys Ser Asn Asp Gln Phe Asp Pro
705                 710                 715                 720

Trp Gly Gln Gly Thr Leu Val Thr Val Ser Ser Arg
                725                 730
```

<210> SEQ ID NO 52

<211> LENGTH: 243
<212> TYPE: PRT
<213> ORGANISM: Artificial Sequence
<220> FEATURE:
<223> OTHER INFORMATION: Synthetic Peptide

<400> SEQUENCE: 52

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

Asn Trp Phe Gln Gln Lys Pro Gly Gln Ala Pro Val Leu Val Val Tyr
        35                  40                  45

Asp Asp Ser Gly Arg Pro Ser Gly Ile Pro Glu Arg Phe Ser Gly Ser
    50                  55                  60

Thr Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Glu Ser Gly Gly Gly Val Val Gln Pro Gly Arg
    130                 135                 140

Ser Leu Arg Leu Ser Cys Ala Ala Ser Gly Phe Thr Leu Ser Tyr Tyr
145                 150                 155                 160

Gly Met His Trp Val Arg Gln Ala Pro Gly Lys Gly Leu Glu Trp Val
                165                 170                 175

Ala Val Ile Ser His Asp Gly Ser Asp Lys Tyr Tyr Ala Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Val Tyr Tyr Cys
    210                 215                 220

Ser Asn Asp Gln Phe Asp Pro Trp Gly Gln Gly Thr Leu Val Thr Val
225                 230                 235                 240

Ser Ser Arg

<210> SEQ ID NO 53
<211> LENGTH: 482
<212> TYPE: PRT
<213> ORGANISM: Artificial Sequence
<220> FEATURE:
<223> OTHER INFORMATION: Synthetic Peptide

<400> SEQUENCE: 53

Ser Ser Glu Pro Lys Ser Ser Asp Lys Thr His Thr Cys Pro Pro Cys
1               5                   10                  15

Pro Ala Pro Glu Leu Leu Gly Gly Pro Ser Val Phe Leu Phe Pro Pro
            20                  25                  30

Lys Pro Lys Asp Thr Leu Met Ile Ser Arg Thr Pro Glu Val Thr Cys
        35                  40                  45

Val Val Val Asp Val Ser His Glu Asp Pro Glu Val Lys Phe Asn Trp
    50                  55                  60

Tyr Val Asp Gly Val Glu Val His Asn Ala Lys Thr Lys Pro Arg Glu
65                  70                  75                  80

```
Glu Gln Tyr Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Ala Leu Pro Ala Pro Ile Glu Lys Thr Ile Ser Lys Ala Lys Gly
        115                 120                 125

Gln Pro Arg Glu Pro Gln Val Tyr Thr Leu Pro Pro Ser Arg Asp Glu
    130                 135                 140

Leu Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Lys Leu Thr Val Asp Lys Ser Arg Trp Gln Gln Gly Asn
        195                 200                 205

Val Phe Ser Cys Ser Val Met His Glu Ala Leu His Asn His Tyr Thr
    210                 215                 220

Gln Lys Ser Leu Ser Leu Ser Pro Gly Gly Gly Gly Ser Pro Ser Ser
225                 230                 235                 240

Tyr Val Leu Thr Gln Pro Pro Ser Val Ser Val Ala Pro Gly Gln Thr
                245                 250                 255

Ala Arg Ile Thr Cys Gly Gly Asn Asn Ile Gly Ser Lys Ser Val Asn
            260                 265                 270

Trp Phe Gln Gln Lys Pro Gly Gln Ala Pro Val Leu Val Val Tyr Asp
        275                 280                 285

Asp Ser Gly Arg Pro Ser Gly Ile Pro Glu Arg Phe Ser Gly Ser Thr
    290                 295                 300

Ser Gly Asn Thr Ala Thr Leu Thr Ile Ser Arg Val Glu Ala Gly Asp
305                 310                 315                 320

Glu Ala Asp Tyr Tyr Cys Gln Val Trp Asp Ser Ser Ser Asp His Val
                325                 330                 335

Val Phe Gly Gly Gly Thr Lys Leu Thr Val Leu Gly Gly Gly Gly Ser
            340                 345                 350

Gly Gly Gly Gly Ser Gly Gly Gly Gly Ser Gly Gly Gly Gly Ser Gln
        355                 360                 365

Val Gln Leu Val Glu Ser Gly Gly Gly Val Val Gln Pro Gly Arg Ser
    370                 375                 380

Leu Arg Leu Ser Cys Ala Ala Ser Gly Phe Thr Leu Ser Tyr Tyr Gly
385                 390                 395                 400

Met His Trp Val Arg Gln Ala Pro Gly Lys Gly Leu Glu Trp Val Ala
                405                 410                 415

Val Ile Ser His Asp Gly Ser Asp Lys Tyr Tyr Ala Asp Ser Val Lys
            420                 425                 430

Gly Arg Phe Thr Ile Ser Arg Asp Asn Ser Lys Asn Thr Leu Tyr Leu
        435                 440                 445

Gln Met Asn Ser Leu Arg Ala Glu Asp Thr Ala Val Tyr Tyr Cys Ser
    450                 455                 460

Asn Asp Gln Phe Asp Pro Trp Gly Gln Gly Thr Leu Val Thr Val Ser
465                 470                 475                 480

Ser Arg
```

<210> SEQ ID NO 54
<211> LENGTH: 243
<212> TYPE: PRT
<213> ORGANISM: Artificial Sequence
<220> FEATURE:
<223> OTHER INFORMATION: Synthetic Peptide

<400> SEQUENCE: 54

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

Asn Trp Phe Gln Gln Lys Pro Gly Gln Ala Pro Val Leu Val Val Tyr
        35                  40                  45

Asp Asp Ser Gly Arg Pro Ser Gly Ile Pro Glu Arg Phe Ser Gly Ser
    50                  55                  60

Thr Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Glu Ser Gly Gly Gly Val Val Gln Pro Gly Arg
    130                 135                 140

Ser Leu Arg Leu Ser Cys Ala Ala Ser Gly Phe Thr Leu Ser Tyr Tyr
145                 150                 155                 160

Gly Met His Trp Val Arg Gln Ala Pro Gly Lys Gly Leu Glu Trp Val
                165                 170                 175

Ala Ala Ile Ser His Asp Gly Ser Asp Lys Tyr Tyr Ala Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Val Tyr Tyr Cys
    210                 215                 220

Ser Asn Asp Gln Phe Asp Pro Trp Gly Gln Gly Thr Leu Val Thr Val
225                 230                 235                 240

Ser Ser Arg
```

<210> SEQ ID NO 55
<211> LENGTH: 482
<212> TYPE: PRT
<213> ORGANISM: Artificial Sequence
<220> FEATURE:
<223> OTHER INFORMATION: Synthetic Peptide

<400> SEQUENCE: 55

```
Ser Ser Glu Pro Lys Ser Ser Asp Lys Thr His Thr Cys Pro Pro Cys
1               5                   10                  15

Pro Ala Pro Glu Leu Leu Gly Gly Pro Ser Val Phe Leu Phe Pro Pro
            20                  25                  30

Lys Pro Lys Asp Thr Leu Met Ile Ser Arg Thr Pro Glu Val Thr Cys
        35                  40                  45

Val Val Val Asp Val Ser His Glu Asp Pro Glu Val Lys Phe Asn Trp
    50                  55                  60

Tyr Val Asp Gly Val Glu Val His Asn Ala Lys Thr Lys Pro Arg Glu
```

-continued

```
65                  70                  75                  80

Glu Gln Tyr Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Ala Leu Pro Ala Pro Ile Glu Lys Thr Ile Ser Lys Ala Lys Gly
        115                 120                 125

Gln Pro Arg Glu Pro Gln Val Tyr Thr Leu Pro Pro Ser Arg Asp Glu
    130                 135                 140

Leu Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Lys Leu Thr Val Asp Lys Ser Arg Trp Gln Gln Gly Asn
        195                 200                 205

Val Phe Ser Cys Ser Val Met His Glu Ala Leu His Asn His Tyr Thr
    210                 215                 220

Gln Lys Ser Leu Ser Leu Ser Pro Gly Gly Gly Gly Ser Pro Ser Ser
225                 230                 235                 240

Tyr Val Leu Thr Gln Pro Pro Ser Val Ser Val Ala Pro Gly Gln Thr
                245                 250                 255

Ala Arg Ile Thr Cys Gly Gly Asn Asn Ile Gly Ser Lys Ser Val Asn
            260                 265                 270

Trp Phe Gln Gln Lys Pro Gly Gln Ala Pro Val Leu Val Val Tyr Asp
        275                 280                 285

Asp Ser Gly Arg Pro Ser Gly Ile Pro Glu Arg Phe Ser Gly Ser Thr
    290                 295                 300

Ser Gly Asn Thr Ala Thr Leu Thr Ile Ser Arg Val Glu Ala Gly Asp
305                 310                 315                 320

Glu Ala Asp Tyr Tyr Cys Gln Val Trp Asp Ser Ser Ser Asp His Val
                325                 330                 335

Val Phe Gly Gly Gly Thr Lys Leu Thr Val Leu Gly Gly Gly Gly Ser
            340                 345                 350

Gly Gly Gly Gly Ser Gly Gly Gly Gly Ser Gly Gly Gly Gly Ser Gln
        355                 360                 365

Val Gln Leu Val Glu Ser Gly Gly Gly Val Val Gln Pro Gly Arg Ser
    370                 375                 380

Leu Arg Leu Ser Cys Ala Ala Ser Gly Phe Thr Leu Ser Tyr Tyr Gly
385                 390                 395                 400

Met His Trp Val Arg Gln Ala Pro Gly Lys Gly Leu Glu Trp Val Ala
                405                 410                 415

Ala Ile Ser His Asp Gly Ser Asp Lys Tyr Tyr Ala Asp Ser Val Lys
            420                 425                 430

Gly Arg Phe Thr Ile Ser Arg Asp Asn Ser Lys Asn Thr Leu Tyr Leu
        435                 440                 445

Gln Met Asn Ser Leu Arg Ala Glu Asp Thr Ala Val Tyr Tyr Cys Ser
    450                 455                 460

Asn Asp Gln Phe Asp Pro Trp Gly Gln Gly Thr Leu Val Thr Val Ser
465                 470                 475                 480

Ser Arg
```

<210> SEQ ID NO 56
<211> LENGTH: 243
<212> TYPE: PRT
<213> ORGANISM: Artificial Sequence
<220> FEATURE:
<223> OTHER INFORMATION: Synthetic Peptide

<400> SEQUENCE: 56

Ser Tyr Val Leu Thr Gln Pro Pro Ser Val Ser Val Ala Pro Gly Gln
1 5 10 15

Thr Ala Arg Ile Thr Cys Gly Gly Asn Asn Ile Gly Ser Lys Ser Val
20 25 30

His Trp Phe Gln Gln Lys Pro Gly Gln Ala Pro Ala Leu Val Val Tyr
35 40 45

Asp Asp Ser Gly Arg Pro Ser Gly Ile Pro Glu Arg Phe Ser Gly Ser
50 55 60

Thr Ser Gly Asn Thr Ala Thr Leu Thr Ile Ser Arg Val Glu Ala Gly
65 70 75 80

Asp Glu Ala Asp Tyr Tyr Cys Gln Val Trp Asp Ser Ser Ser Asp His
85 90 95

Val Val Phe Gly Gly Gly Thr Lys Leu Thr Val Leu Gly Gly Gly Gly
100 105 110

Ser Gly Gly Gly Gly Ser Gly Gly Gly Gly Ser Gly Gly Gly Gly Ser
115 120 125

Gln Val Gln Leu Val Glu Ser Gly Gly Gly Val Val Gln Pro Gly Arg
130 135 140

Ser Leu Arg Leu Ser Cys Ala Ala Ser Gly Phe Thr Leu Ser Tyr Tyr
145 150 155 160

Gly Met His Trp Val Arg Gln Ala Pro Gly Lys Gly Leu Glu Trp Val
165 170 175

Ala Val Ile Ser His Asp Gly Ser Asp Lys Tyr Tyr Ala Asp Ser Val
180 185 190

Lys Gly Arg Phe Thr Ile Ser Arg Asp Asn Ser Lys Asn Thr Leu Tyr
195 200 205

Leu Gln Met Asp Ser Leu Arg Ala Glu Asp Thr Ala Leu Tyr Tyr Cys
210 215 220

Ser Asn Asp Gln Phe Asp Pro Trp Gly Gln Gly Thr Leu Val Thr Val
225 230 235 240

Ser Ser Arg

<210> SEQ ID NO 57
<211> LENGTH: 482
<212> TYPE: PRT
<213> ORGANISM: Artificial Sequence
<220> FEATURE:
<223> OTHER INFORMATION: Synthetic Peptide

<400> SEQUENCE: 57

Ser Ser Glu Pro Lys Ser Ser Asp Lys Thr His Thr Cys Pro Pro Cys
1 5 10 15

Pro Ala Pro Glu Leu Leu Gly Gly Pro Ser Val Phe Leu Phe Pro Pro
20 25 30

Lys Pro Lys Asp Thr Leu Met Ile Ser Arg Thr Pro Glu Val Thr Cys
35 40 45

Val Val Val Asp Val Ser His Glu Asp Pro Glu Val Lys Phe Asn Trp
50 55 60

```
Tyr Val Asp Gly Val Glu Val His Asn Ala Lys Thr Lys Pro Arg Glu
65                  70                  75                  80

Glu Gln Tyr Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Ala Leu Pro Ala Pro Ile Glu Lys Thr Ile Ser Lys Ala Lys Gly
        115                 120                 125

Gln Pro Arg Glu Pro Gln Val Tyr Thr Leu Pro Pro Ser Arg Asp Glu
    130                 135                 140

Leu Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Lys Leu Thr Val Asp Lys Ser Arg Trp Gln Gln Gly Asn
        195                 200                 205

Val Phe Ser Cys Ser Val Met His Glu Ala Leu His Asn His Tyr Thr
    210                 215                 220

Gln Lys Ser Leu Ser Leu Ser Pro Gly Gly Gly Gly Ser Pro Ser Ser
225                 230                 235                 240

Tyr Val Leu Thr Gln Pro Pro Ser Val Ser Val Ala Pro Gly Gln Thr
                245                 250                 255

Ala Arg Ile Thr Cys Gly Gly Asn Asn Ile Gly Ser Lys Ser Val His
            260                 265                 270

Trp Phe Gln Gln Lys Pro Gly Gln Ala Pro Ala Leu Val Val Tyr Asp
        275                 280                 285

Asp Ser Gly Arg Pro Ser Gly Ile Pro Glu Arg Phe Ser Gly Ser Thr
    290                 295                 300

Ser Gly Asn Thr Ala Thr Leu Thr Ile Ser Arg Val Glu Ala Gly Asp
305                 310                 315                 320

Glu Ala Asp Tyr Tyr Cys Gln Val Trp Asp Ser Ser Ser Asp His Val
                325                 330                 335

Val Phe Gly Gly Gly Thr Lys Leu Thr Val Leu Gly Gly Gly Gly Ser
            340                 345                 350

Gly Gly Gly Gly Ser Gly Gly Gly Gly Ser Gly Gly Gly Gly Ser Gln
        355                 360                 365

Val Gln Leu Val Glu Ser Gly Gly Gly Val Val Gln Pro Gly Arg Ser
    370                 375                 380

Leu Arg Leu Ser Cys Ala Ala Ser Gly Phe Thr Leu Ser Tyr Tyr Gly
385                 390                 395                 400

Met His Trp Val Arg Gln Ala Pro Gly Lys Gly Leu Glu Trp Val Ala
                405                 410                 415

Val Ile Ser His Asp Gly Ser Asp Lys Tyr Tyr Ala Asp Ser Val Lys
            420                 425                 430

Gly Arg Phe Thr Ile Ser Arg Asp Asn Ser Lys Asn Thr Leu Tyr Leu
        435                 440                 445

Gln Met Asp Ser Leu Arg Ala Glu Asp Thr Ala Leu Tyr Tyr Cys Ser
    450                 455                 460

Asn Asp Gln Phe Asp Pro Trp Gly Gln Gly Thr Leu Val Thr Val Ser
465                 470                 475                 480

Ser Arg
```

<210> SEQ ID NO 58
<211> LENGTH: 248
<212> TYPE: PRT
<213> ORGANISM: Artificial Sequence
<220> FEATURE:
<223> OTHER INFORMATION: Synthetic Peptide

<400> SEQUENCE: 58

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Met Asn Trp Val Arg Gln Ala Pro Gly Gln Gly Leu Glu Trp Met
35 40 45

Gly Asn Ile Tyr Pro Ser Gly Gly Ser Thr Asn Tyr Ala Gln Lys Phe
50 55 60

Gln Gly Arg Val Thr Met Thr Val Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Ser Phe Ser Asp Gly Tyr Tyr Ala Tyr Ala Met Asp Tyr Trp Gly
100 105 110

Gln Gly Thr Leu Val Thr Val Ser Ser Gly Gly Gly Gly Ser Gly Gly
115 120 125

Gly Gly Ser Gly Gly Gly Gly Ser Gly Gly Gly Gly Ser Glu Ile Val
130 135 140

Met Thr Gln Ser Pro Ala Thr Leu Ser Leu Ser Pro Gly Glu Arg Ala
145 150 155 160

Thr Leu Ser Cys Arg Ala Ser Gln Ser Val Ser Ser Tyr Leu Asn Trp
165 170 175

Tyr Gln Gln Lys Pro Gly Gln Ala Pro Arg Leu Leu Ile Tyr Tyr Ala
180 185 190

Ser Arg Arg His Thr Gly Ile Pro Ala Arg Phe Ser Gly Ser Gly Ser
195 200 205

Gly Thr Asp Phe Thr Leu Thr Ile Ser Ser Leu Gln Pro Glu Asp Phe
210 215 220

Ala Val Tyr Tyr Cys Gln Gln Gly Tyr Asn Leu Pro Tyr Thr Phe Gly
225 230 235 240

Gln Gly Thr Lys Val Glu Ile Lys
245

<210> SEQ ID NO 59
<211> LENGTH: 243
<212> TYPE: PRT
<213> ORGANISM: Artificial Sequence
<220> FEATURE:
<223> OTHER INFORMATION: Synthetic Peptide

<400> SEQUENCE: 59

Ser Tyr Val Leu Thr Gln Pro Pro Ser Val Ser Val Ala Pro Gly Gln
1 5 10 15

Thr Ala Arg Ile Thr Cys Gly Gly Asn Asn Ile Gly Ser Lys Ser Val
20 25 30

Asn Trp Phe Gln Gln Lys Pro Gly Gln Ala Pro Val Leu Val Val Tyr
35 40 45

Asp Asp Ser Gly Arg Pro Ser Gly Ile Pro Glu Arg Phe Ser Gly Ser

```
    50                  55                  60

Thr Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Glu Ser Gly Gly Gly Val Val Gln Pro Gly Arg
    130                 135                 140

Ser Leu Arg Leu Ser Cys Ala Ala Ser Gly Phe Thr Leu Ser Tyr Tyr
145                 150                 155                 160

Gly Met His Trp Val Arg Gln Ala Pro Gly Lys Gly Leu Glu Trp Val
                165                 170                 175

Ala Ala Ile Ser His Asp Gly Ser Asp Lys Tyr Tyr Ala Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Val Tyr Tyr Cys
    210                 215                 220

Ser Asn Asp Gln Phe Asp Pro Trp Gly Gln Gly Thr Leu Val Thr Val
225                 230                 235                 240

Ser Ser Arg


<210> SEQ ID NO 60
<211> LENGTH: 243
<212> TYPE: PRT
<213> ORGANISM: Artificial Sequence
<220> FEATURE:
<223> OTHER INFORMATION: Synthetic Peptide

<400> SEQUENCE: 60

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

Asn Trp Phe Gln Gln Lys Pro Gly Gln Ala Pro Val Leu Val Val Tyr
        35                  40                  45

Asp Asp Ser Gly Arg Pro Ser Gly Ile Pro Glu Arg Phe Ser Gly Ser
    50                  55                  60

Thr Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Glu Ser Gly Gly Gly Val Val Gln Pro Gly Arg
    130                 135                 140

Ser Leu Arg Leu Ser Cys Ala Ala Ser Gly Phe Thr Leu Ser Tyr Tyr
145                 150                 155                 160

Gly Met His Trp Val Arg Gln Ala Pro Gly Lys Gly Leu Glu Trp Val
                165                 170                 175
```

```
Ala Ala Ile Ser His Asp Gly Ser Asp Lys Tyr Tyr Ala Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Val Tyr Tyr Cys
    210                 215                 220

Ser Asn Asp Gln Phe Asp Pro Trp Gly Gln Gly Thr Leu Val Thr Val
225                 230                 235                 240

Ser Ser Arg


<210> SEQ ID NO 61
<211> LENGTH: 243
<212> TYPE: PRT
<213> ORGANISM: Artificial Sequence
<220> FEATURE:
<223> OTHER INFORMATION: Synthetic Peptide

<400> SEQUENCE: 61

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

Asn Trp Phe Gln Gln Lys Pro Gly Gln Ala Pro Val Leu Val Val Tyr
        35                  40                  45

Asp Asp Ser Gly Arg Pro Ser Gly Ile Pro Glu Arg Phe Ser Gly Ser
    50                  55                  60

Thr Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Glu Ser Gly Gly Gly Val Val Gln Pro Gly Arg
    130                 135                 140

Ser Leu Arg Leu Ser Cys Ala Ala Ser Gly Phe Thr Leu Ser Tyr Tyr
145                 150                 155                 160

Gly Met His Trp Val Arg Gln Ala Pro Gly Lys Gly Leu Glu Trp Val
                165                 170                 175

Ala Ala Ile Ser His Asp Gly Ser Asp Lys Tyr Tyr Ala Asp Ser Val
            180                 185                 190

Lys Gly Arg Phe Thr Ile Ser Arg Asp Asn Ser Lys Asn Arg Leu Tyr
        195                 200                 205

Leu Gln Met Asn Ser Leu Arg Ala Glu Asp Thr Ala Val Tyr Tyr Cys
    210                 215                 220

Ser Asn Asp Gln Phe Asp Pro Trp Gly Gln Gly Thr Leu Val Thr Val
225                 230                 235                 240

Ser Ser Arg


<210> SEQ ID NO 62
<211> LENGTH: 243
<212> TYPE: PRT
<213> ORGANISM: Artificial Sequence
<220> FEATURE:
<223> OTHER INFORMATION: Synthetic Peptide
```

<400> SEQUENCE: 62

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

Asn Trp Phe Gln Gln Lys Pro Gly Gln Ala Pro Val Leu Val Val Tyr
        35                  40                  45

Asp Asp Ser Gly Arg Pro Ser Gly Ile Pro Glu Arg Phe Ser Gly Ser
    50                  55                  60

Thr Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Glu Ser Gly Gly Gly Val Val Gln Pro Gly Arg
    130                 135                 140

Ser Leu Arg Leu Ser Cys Ala Ala Ser Gly Phe Thr Leu Ser Tyr Tyr
145                 150                 155                 160

Gly Met His Trp Val Arg Gln Ala Pro Gly Lys Gly Leu Glu Trp Val
                165                 170                 175

Ala Ala Ile Ser His Asp Gly Ser Asp Lys Tyr Tyr Ala Asp Ser Val
            180                 185                 190

Lys Gly Arg Phe Thr Ile Ser Arg Asp Asn Ser Lys Asn Arg Leu Tyr
        195                 200                 205

Leu Gln Met Asn Ser Leu Arg Ala Glu Asp Thr Ala Val Tyr Tyr Cys
    210                 215                 220

Ser Asn Asp Gln Phe Asp Pro Trp Gly Gln Gly Thr Leu Val Thr Val
225                 230                 235                 240

Ser Ser Arg

<210> SEQ ID NO 63
<211> LENGTH: 246
<212> TYPE: PRT
<213> ORGANISM: Artificial Sequence
<220> FEATURE:
<223> OTHER INFORMATION: Synthetic Peptide

<400> SEQUENCE: 63

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Asn Trp Tyr Gln Gln Lys Pro Gly Gln Ala Pro Arg Leu Leu Ile
        35                  40                  45

Tyr Tyr Ala Ser Arg Arg His Thr Gly Ile Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Gly Tyr Asn Leu Pro Tyr
                85                  90                  95

Thr Phe Gly Gln Gly Thr Lys Val Glu Ile Lys Gly Gly Gly Gly Ser

```
            100                 105                 110

Gly Gly Gly Gly Ser Gly Gly Gly Gly Ser Gly Gly Gly Gly Ser Glu
        115                 120                 125

Val Gln Leu Val Gln Ser Gly Ala Glu Val Lys Lys Pro Gly Ala Ser
    130                 135                 140

Val Lys Val Ser Cys Lys Ala Ser Gly Tyr Thr Phe Thr Ser Tyr Trp
145                 150                 155                 160

Met Asn Trp Val Arg Gln Ala Pro Gly Gln Gly Leu Glu Trp Met Gly
                165                 170                 175

Asn Ile Tyr Pro Ser Gly Gly Ser Thr Asn Tyr Ala Gln Lys Phe Gln
            180                 185                 190

Gly Arg Val Thr Met Thr Val Asp Thr Ser Thr Ser Thr Val Tyr Met
        195                 200                 205

Glu Leu Ser Ser Leu Arg Ser Glu Asp Thr Ala Val Tyr Tyr Cys Ala
    210                 215                 220

Ser Phe Ser Asp Gly Tyr Tyr Ala Tyr Ala Met Asp Tyr Trp Gly Gln
225                 230                 235                 240

Gly Thr Leu Val Thr Val
                245


<210> SEQ ID NO 64
<211> LENGTH: 240
<212> TYPE: PRT
<213> ORGANISM: Artificial Sequence
<220> FEATURE:
<223> OTHER INFORMATION: Synthetic Peptide

<400> SEQUENCE: 64

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

Asn Trp Phe Gln Gln Lys Pro Gly Gln Ala Pro Val Leu Val Val Tyr
        35                  40                  45

Asp Asp Ser Gly Arg Pro Ser Gly Ile Pro Glu Arg Phe Ser Gly Ser
    50                  55                  60

Thr Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Glu Ser Gly Gly Gly Val Val Gln Pro Gly Arg
    130                 135                 140

Ser Leu Arg Leu Ser Cys Ala Ala Ser Gly Phe Thr Leu Ser Tyr Tyr
145                 150                 155                 160

Gly Met His Trp Val Arg Gln Ala Pro Gly Lys Gly Leu Glu Trp Val
                165                 170                 175

Ala Val Ile Ser His Asp Gly Ser Asp Lys Tyr Tyr Ala Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Val Tyr Tyr Cys
```

```
    210                 215                 220

Ser Asn Asp Gln Phe Asp Pro Trp Gly Gln Gly Thr Leu Val Thr Val
225                 230                 235                 240
```

<210> SEQ ID NO 65
<211> LENGTH: 243
<212> TYPE: PRT
<213> ORGANISM: Artificial Sequence
<220> FEATURE:
<223> OTHER INFORMATION: Synthetic Peptide

<400> SEQUENCE: 65

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

Asn Trp Phe Gln Gln Lys Pro Gly Gln Ala Pro Val Leu Val Val Tyr
        35                  40                  45

Asp Asp Ser Gly Arg Pro Ser Gly Ile Pro Ala Arg Phe Ser Gly Ser
    50                  55                  60

Thr Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Glu Ser Gly Gly Gly Val Val Gln Pro Gly Arg
    130                 135                 140

Ser Leu Arg Leu Ser Cys Ala Ala Ser Gly Phe Thr Leu Ser Tyr Tyr
145                 150                 155                 160

Gly Met His Trp Val Arg Gln Ala Pro Gly Lys Gly Leu Glu Trp Val
                165                 170                 175

Ala Ala Ile Ser His Asp Gly Ser Asp Lys Tyr Tyr Ala Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Val Tyr Tyr Cys
    210                 215                 220

Ser Asn Asp Gln Phe Asp Pro Trp Gly Gln Gly Thr Leu Val Thr Val
225                 230                 235                 240

Ser Ser Arg
```

<210> SEQ ID NO 66
<211> LENGTH: 243
<212> TYPE: PRT
<213> ORGANISM: Artificial Sequence
<220> FEATURE:
<223> OTHER INFORMATION: Synthetic Peptide

<400> SEQUENCE: 66

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

Asn Trp Phe Gln Gln Lys Pro Gly Gln Ala Pro Val Leu Val Val Tyr
```

35 40 45

Asp Asp Ser Gly Arg Pro Ser Gly Val Pro Asn Arg Phe Ser Gly Ser
50 55 60

Thr Ser Gly Asn Thr Ala Thr Leu Thr Ile Ser Arg Val Glu Ala Gly
65 70 75 80

Asp Glu Ala Asp Tyr Tyr Cys Gln Val Trp Asp Ser Ser Ser Asp His
85 90 95

Val Val Phe Gly Gly Gly Thr Lys Leu Thr Val Leu Gly Gly Gly Gly
100 105 110

Ser Gly Gly Gly Gly Ser Gly Gly Gly Gly Ser Gly Gly Gly Gly Ser
115 120 125

Gln Val Gln Leu Val Glu Ser Gly Gly Gly Val Val Gln Pro Gly Arg
130 135 140

Ser Leu Arg Leu Ser Cys Ala Ala Ser Gly Phe Thr Leu Ser Tyr Tyr
145 150 155 160

Gly Met His Trp Val Arg Gln Ala Pro Gly Lys Gly Leu Glu Trp Val
165 170 175

Ala Ala Ile Ser His Asp Gly Ser Asp Lys Tyr Tyr Ala Asp Ser Val
180 185 190

Lys Gly Arg Phe Thr Ile Ser Arg Asp Asn Ser Lys Asn Thr Leu Tyr
195 200 205

Leu Gln Met Asn Ser Leu Arg Ala Glu Asp Thr Ala Val Tyr Tyr Cys
210 215 220

Ser Asn Asp Gln Phe Asp Pro Trp Gly Gln Gly Thr Leu Val Thr Val
225 230 235 240

Ser Ser Arg

<210> SEQ ID NO 67
<211> LENGTH: 243
<212> TYPE: PRT
<213> ORGANISM: Artificial Sequence
<220> FEATURE:
<223> OTHER INFORMATION: Synthetic Peptide

<400> SEQUENCE: 67

Ser Tyr Val Leu Thr Gln Pro Pro Ser Val Ser Val Ala Pro Gly Gln
1 5 10 15

Thr Ala Arg Ile Thr Cys Gly Gly Asn Asn Ile Gly Ser Lys Ser Val
20 25 30

Asn Trp Phe Gln Gln Lys Pro Gly Gln Ala Pro Val Leu Val Val Tyr
35 40 45

Asp Asp Ser Gly Arg Pro Ser Gly Val Pro Ser Arg Phe Ser Gly Ser
50 55 60

Thr Ser Gly Asn Thr Ala Thr Leu Thr Ile Ser Arg Val Glu Ala Gly
65 70 75 80

Asp Glu Ala Asp Tyr Tyr Cys Gln Val Trp Asp Ser Ser Ser Asp His
85 90 95

Val Val Phe Gly Gly Gly Thr Lys Leu Thr Val Leu Gly Gly Gly Gly
100 105 110

Ser Gly Gly Gly Gly Ser Gly Gly Gly Gly Ser Gly Gly Gly Gly Ser
115 120 125

Gln Val Gln Leu Val Glu Ser Gly Gly Gly Val Val Gln Pro Gly Arg
130 135 140

Ser Leu Arg Leu Ser Cys Ala Ala Ser Gly Phe Thr Leu Ser Tyr Tyr
145 150 155 160

Gly Met His Trp Val Arg Gln Ala Pro Gly Lys Gly Leu Glu Trp Val
165 170 175

Ala Ala Ile Ser His Asp Gly Ser Asp Lys Tyr Tyr Ala Asp Ser Val
180 185 190

Lys Gly Arg Phe Thr Ile Ser Arg Asp Asn Ser Lys Asn Thr Leu Tyr
195 200 205

Leu Gln Met Asn Ser Leu Arg Ala Glu Asp Thr Ala Val Tyr Tyr Cys
210 215 220

Ser Asn Asp Gln Phe Asp Pro Trp Gly Gln Gly Thr Leu Val Thr Val
225 230 235 240

Ser Ser Arg

<210> SEQ ID NO 68
<211> LENGTH: 243
<212> TYPE: PRT
<213> ORGANISM: Artificial Sequence
<220> FEATURE:
<223> OTHER INFORMATION: Synthetic Peptide

<400> SEQUENCE: 68

Ser Tyr Val Leu Thr Gln Pro Pro Ser Val Ser Val Ala Pro Gly Gln
1 5 10 15

Thr Ala Arg Ile Thr Cys Gly Gly Asn Asn Ile Gly Ser Lys Ser Val
20 25 30

Asn Trp Phe Gln Gln Lys Pro Gly Gln Ala Pro Val Leu Val Val Tyr
35 40 45

Asp Asp Ser Gly Arg Pro Ser Gly Ile Pro Lys Arg Phe Ser Gly Ser
50 55 60

Thr Ser Gly Asn Thr Ala Thr Leu Thr Ile Ser Arg Val Glu Ala Gly
65 70 75 80

Asp Glu Ala Asp Tyr Tyr Cys Gln Val Trp Asp Ser Ser Ser Asp His
85 90 95

Val Val Phe Gly Gly Gly Thr Lys Leu Thr Val Leu Gly Gly Gly Gly
100 105 110

Ser Gly Gly Gly Gly Ser Gly Gly Gly Gly Ser Gly Gly Gly Gly Ser
115 120 125

Gln Val Gln Leu Val Glu Ser Gly Gly Gly Val Val Gln Pro Gly Arg
130 135 140

Ser Leu Arg Leu Ser Cys Ala Ala Ser Gly Phe Thr Leu Ser Tyr Tyr
145 150 155 160

Gly Met His Trp Val Arg Gln Ala Pro Gly Lys Gly Leu Glu Trp Val
165 170 175

Ala Ala Ile Ser His Asp Gly Ser Asp Lys Tyr Tyr Ala Asp Ser Val
180 185 190

Lys Gly Arg Phe Thr Ile Ser Arg Asp Asn Ser Lys Asn Thr Leu Tyr
195 200 205

Leu Gln Met Asn Ser Leu Arg Ala Glu Asp Thr Ala Val Tyr Tyr Cys
210 215 220

Ser Asn Asp Gln Phe Asp Pro Trp Gly Gln Gly Thr Leu Val Thr Val
225 230 235 240

Ser Ser Arg

<210> SEQ ID NO 69
<211> LENGTH: 243
<212> TYPE: PRT

<213> ORGANISM: Artificial Sequence
<220> FEATURE:
<223> OTHER INFORMATION: Synthetic Peptide

<400> SEQUENCE: 69

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

Asn Trp Phe Gln Gln Lys Pro Gly Gln Ala Pro Val Leu Val Val Tyr
        35                  40                  45

Asp Asp Ser Gly Arg Pro Ser Gly Ile Pro Ala Arg Phe Ser Gly Ser
    50                  55                  60

Thr Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Glu Ser Gly Gly Gly Val Val Gln Pro Gly Arg
    130                 135                 140

Ser Leu Arg Leu Ser Cys Ala Ala Ser Gly Phe Thr Leu Ser Tyr Tyr
145                 150                 155                 160

Gly Met His Trp Val Arg Gln Ala Pro Gly Lys Gly Leu Glu Trp Val
                165                 170                 175

Ala Ala Ile Ser His Asp Gly Ser Asp Lys Tyr Tyr Ala Asp Ser Val
            180                 185                 190

Lys Gly Arg Phe Thr Ile Ser Arg Asp Asn Ser Lys Asn Arg Leu Tyr
        195                 200                 205

Leu Gln Met Asn Ser Leu Arg Ala Glu Asp Thr Ala Val Tyr Tyr Cys
    210                 215                 220

Ser Asn Asp Gln Phe Asp Pro Trp Gly Gln Gly Thr Leu Val Thr Val
225                 230                 235                 240

Ser Ser Arg
```

<210> SEQ ID NO 70
<211> LENGTH: 243
<212> TYPE: PRT
<213> ORGANISM: Artificial Sequence
<220> FEATURE:
<223> OTHER INFORMATION: Synthetic Peptide

<400> SEQUENCE: 70

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

Asn Trp Phe Gln Gln Lys Pro Gly Gln Ala Pro Val Leu Val Val Tyr
        35                  40                  45

Asp Asp Ser Gly Arg Pro Ser Gly Val Pro Asn Arg Phe Ser Gly Ser
    50                  55                  60

Thr Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
```

```
                85                  90                  95

Val Val Phe Gly Gly Gly Thr Lys Leu Thr Val Leu Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Glu Ser Gly Gly Gly Val Val Gln Pro Gly Arg
    130                 135                 140

Ser Leu Arg Leu Ser Cys Ala Ala Ser Gly Phe Thr Leu Ser Tyr Tyr
145                 150                 155                 160

Gly Met His Trp Val Arg Gln Ala Pro Gly Lys Gly Leu Glu Trp Val
                165                 170                 175

Ala Ala Ile Ser His Asp Gly Ser Asp Lys Tyr Tyr Ala Asp Ser Val
            180                 185                 190

Lys Gly Arg Phe Thr Ile Ser Arg Asp Asn Ser Lys Asn Arg Leu Tyr
        195                 200                 205

Leu Gln Met Asn Ser Leu Arg Ala Glu Asp Thr Ala Val Tyr Tyr Cys
    210                 215                 220

Ser Asn Asp Gln Phe Asp Pro Trp Gly Gln Gly Thr Leu Val Thr Val
225                 230                 235                 240

Ser Ser Arg


<210> SEQ ID NO 71
<211> LENGTH: 243
<212> TYPE: PRT
<213> ORGANISM: Artificial Sequence
<220> FEATURE:
<223> OTHER INFORMATION: Synthetic Peptide

<400> SEQUENCE: 71

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

Asn Trp Phe Gln Gln Lys Pro Gly Gln Ala Pro Val Leu Val Val Tyr
        35                  40                  45

Asp Asp Ser Gly Arg Pro Ser Gly Val Pro Ser Arg Phe Ser Gly Ser
    50                  55                  60

Thr Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Glu Ser Gly Gly Gly Val Val Gln Pro Gly Arg
    130                 135                 140

Ser Leu Arg Leu Ser Cys Ala Ala Ser Gly Phe Thr Leu Ser Tyr Tyr
145                 150                 155                 160

Gly Met His Trp Val Arg Gln Ala Pro Gly Lys Gly Leu Glu Trp Val
                165                 170                 175

Ala Ala Ile Ser His Asp Gly Ser Asp Lys Tyr Tyr Ala Asp Ser Val
            180                 185                 190

Lys Gly Arg Phe Thr Ile Ser Arg Asp Asn Ser Lys Asn Arg Leu Tyr
        195                 200                 205
```

Leu Gln Met Asn Ser Leu Arg Ala Glu Asp Thr Ala Val Tyr Tyr Cys
    210                 215                 220

Ser Asn Asp Gln Phe Asp Pro Trp Gly Gln Gly Thr Leu Val Thr Val
225                 230                 235                 240

Ser Ser Arg

<210> SEQ ID NO 72
<211> LENGTH: 243
<212> TYPE: PRT
<213> ORGANISM: Artificial Sequence
<220> FEATURE:
<223> OTHER INFORMATION: Synthetic Peptide

<400> SEQUENCE: 72

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

Asn Trp Phe Gln Gln Lys Pro Gly Gln Ala Pro Val Leu Val Val Tyr
        35                  40                  45

Asp Asp Ser Gly Arg Pro Ser Gly Ile Pro Lys Arg Phe Ser Gly Ser
    50                  55                  60

Thr Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Glu Ser Gly Gly Gly Val Val Gln Pro Gly Arg
    130                 135                 140

Ser Leu Arg Leu Ser Cys Ala Ala Ser Gly Phe Thr Leu Ser Tyr Tyr
145                 150                 155                 160

Gly Met His Trp Val Arg Gln Ala Pro Gly Lys Gly Leu Glu Trp Val
                165                 170                 175

Ala Ala Ile Ser His Asp Gly Ser Asp Lys Tyr Tyr Ala Asp Ser Val
            180                 185                 190

Lys Gly Arg Phe Thr Ile Ser Arg Asp Asn Ser Lys Asn Arg Leu Tyr
        195                 200                 205

Leu Gln Met Asn Ser Leu Arg Ala Glu Asp Thr Ala Val Tyr Tyr Cys
    210                 215                 220

Ser Asn Asp Gln Phe Asp Pro Trp Gly Gln Gly Thr Leu Val Thr Val
225                 230                 235                 240

Ser Ser Arg

<210> SEQ ID NO 73
<211> LENGTH: 243
<212> TYPE: PRT
<213> ORGANISM: Artificial Sequence
<220> FEATURE:
<223> OTHER INFORMATION: Synthetic Peptide

<400> SEQUENCE: 73

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
20 25 30

Asn Trp Phe Gln Gln Lys Pro Gly Gln Ala Pro Val Leu Val Val Tyr
35 40 45

Asp Asp Ser Gly Arg Pro Ser Gly Ile Pro Ala Arg Phe Ser Gly Ser
50 55 60

Thr Ser Gly Asn Thr Ala Thr Leu Thr Ile Ser Arg Val Glu Ala Gly
65 70 75 80

Asp Glu Ala Asp Tyr Tyr Cys Gln Val Trp Asp Ser Ser Ser Asp His
85 90 95

Val Val Phe Gly Gly Gly Thr Lys Leu Thr Val Leu Gly Gly Gly Gly
100 105 110

Ser Gly Gly Gly Gly Ser Gly Gly Gly Gly Ser Gly Gly Gly Gly Ser
115 120 125

Gln Val Gln Leu Val Glu Ser Gly Gly Gly Val Val Gln Pro Gly Arg
130 135 140

Ser Leu Arg Leu Ser Cys Ala Ala Ser Gly Phe Thr Leu Ser Tyr Tyr
145 150 155 160

Gly Met His Trp Val Arg Gln Ala Pro Gly Lys Gly Leu Glu Trp Val
165 170 175

Ala Ala Ile Ser His Asp Gly Ser Asp Lys Tyr Tyr Ala Asp Ser Val
180 185 190

Lys Gly Arg Phe Thr Ile Ser Arg Asp Asn Ser Lys Asn Arg Leu Tyr
195 200 205

Leu Gln Met Asn Ser Leu Arg Ala Glu Asp Thr Ala Val Tyr Tyr Cys
210 215 220

Ser Asn Asp Gln Phe Asp Pro Trp Gly Gln Gly Thr Leu Val Thr Val
225 230 235 240

Ser Ser Arg

<210> SEQ ID NO 74
<211> LENGTH: 243
<212> TYPE: PRT
<213> ORGANISM: Artificial Sequence
<220> FEATURE:
<223> OTHER INFORMATION: Synthetic Peptide

<400> SEQUENCE: 74

Ser Tyr Val Leu Thr Gln Pro Pro Ser Val Ser Val Ala Pro Gly Lys
1 5 10 15

Thr Ala Arg Ile Thr Cys Gly Gly Asn Asn Ile Gly Ser Lys Ser Val
20 25 30

Asn Trp Phe Gln Gln Lys Pro Gly Gln Ala Pro Val Leu Val Val Tyr
35 40 45

Asp Asp Ser Gly Arg Pro Ser Gly Val Pro Asn Arg Phe Ser Gly Ser
50 55 60

Thr Ser Gly Asn Thr Ala Thr Leu Thr Ile Ser Arg Val Glu Ala Gly
65 70 75 80

Asp Glu Ala Asp Tyr Tyr Cys Gln Val Trp Asp Ser Ser Ser Asp His
85 90 95

Val Val Phe Gly Gly Gly Thr Lys Leu Thr Val Leu Gly Gly Gly Gly
100 105 110

Ser Gly Gly Gly Gly Ser Gly Gly Gly Gly Ser Gly Gly Gly Gly Ser
115 120 125

Gln Val Gln Leu Val Glu Ser Gly Gly Gly Val Val Gln Pro Gly Arg

```
    130                 135                 140

Ser Leu Arg Leu Ser Cys Ala Ala Ser Gly Phe Thr Leu Ser Tyr Tyr
145                 150                 155                 160

Gly Met His Trp Val Arg Gln Ala Pro Gly Lys Gly Leu Glu Trp Val
                165                 170                 175

Ala Ala Ile Ser His Asp Gly Ser Asp Lys Tyr Tyr Ala Asp Ser Val
            180                 185                 190

Lys Gly Arg Phe Thr Ile Ser Arg Asp Asn Ser Lys Asn Arg Leu Tyr
        195                 200                 205

Leu Gln Met Asn Ser Leu Arg Ala Glu Asp Thr Ala Val Tyr Tyr Cys
    210                 215                 220

Ser Asn Asp Gln Phe Asp Pro Trp Gly Gln Gly Thr Leu Val Thr Val
225                 230                 235                 240

Ser Ser Arg


<210> SEQ ID NO 75
<211> LENGTH: 243
<212> TYPE: PRT
<213> ORGANISM: Artificial Sequence
<220> FEATURE:
<223> OTHER INFORMATION: Synthetic Peptide

<400> SEQUENCE: 75

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

Asn Trp Phe Gln Gln Lys Pro Gly Gln Ala Pro Val Leu Val Val Tyr
        35                  40                  45

Asp Asp Ser Gly Arg Pro Ser Gly Val Pro Ser Arg Phe Ser Gly Ser
    50                  55                  60

Thr Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Glu Ser Gly Gly Gly Val Val Gln Pro Gly Arg
    130                 135                 140

Ser Leu Arg Leu Ser Cys Ala Ala Ser Gly Phe Thr Leu Ser Tyr Tyr
145                 150                 155                 160

Gly Met His Trp Val Arg Gln Ala Pro Gly Lys Gly Leu Glu Trp Val
                165                 170                 175

Ala Ala Ile Ser His Asp Gly Ser Asp Lys Tyr Tyr Ala Asp Ser Val
            180                 185                 190

Lys Gly Arg Phe Thr Ile Ser Arg Asp Asn Ser Lys Asn Arg Leu Tyr
        195                 200                 205

Leu Gln Met Asn Ser Leu Arg Ala Glu Asp Thr Ala Val Tyr Tyr Cys
    210                 215                 220

Ser Asn Asp Gln Phe Asp Pro Trp Gly Gln Gly Thr Leu Val Thr Val
225                 230                 235                 240

Ser Ser Arg
```

<210> SEQ ID NO 76
<211> LENGTH: 243
<212> TYPE: PRT
<213> ORGANISM: Artificial Sequence
<220> FEATURE:
<223> OTHER INFORMATION: Synthetic Peptide

<400> SEQUENCE: 76

Ser Tyr Val Leu Thr Gln Pro Pro Ser Val Ser Val Ala Pro Gly Lys
1 5 10 15

Thr Ala Arg Ile Thr Cys Gly Gly Asn Asn Ile Gly Ser Lys Ser Val
20 25 30

Asn Trp Phe Gln Gln Lys Pro Gly Gln Ala Pro Val Leu Val Val Tyr
35 40 45

Asp Asp Ser Gly Arg Pro Ser Gly Ile Pro Lys Arg Phe Ser Gly Ser
50 55 60

Thr Ser Gly Asn Thr Ala Thr Leu Thr Ile Ser Arg Val Glu Ala Gly
65 70 75 80

Asp Glu Ala Asp Tyr Tyr Cys Gln Val Trp Asp Ser Ser Ser Asp His
85 90 95

Val Val Phe Gly Gly Gly Thr Lys Leu Thr Val Leu Gly Gly Gly Gly
100 105 110

Ser Gly Gly Gly Gly Ser Gly Gly Gly Gly Ser Gly Gly Gly Gly Ser
115 120 125

Gln Val Gln Leu Val Glu Ser Gly Gly Gly Val Val Gln Pro Gly Arg
130 135 140

Ser Leu Arg Leu Ser Cys Ala Ala Ser Gly Phe Thr Leu Ser Tyr Tyr
145 150 155 160

Gly Met His Trp Val Arg Gln Ala Pro Gly Lys Gly Leu Glu Trp Val
165 170 175

Ala Ala Ile Ser His Asp Gly Ser Asp Lys Tyr Tyr Ala Asp Ser Val
180 185 190

Lys Gly Arg Phe Thr Ile Ser Arg Asp Asn Ser Lys Asn Arg Leu Tyr
195 200 205

Leu Gln Met Asn Ser Leu Arg Ala Glu Asp Thr Ala Val Tyr Tyr Cys
210 215 220

Ser Asn Asp Gln Phe Asp Pro Trp Gly Gln Gly Thr Leu Val Thr Val
225 230 235 240

Ser Ser Arg

<210> SEQ ID NO 77
<211> LENGTH: 249
<212> TYPE: PRT
<213> ORGANISM: Artificial Sequence
<220> FEATURE:
<223> OTHER INFORMATION: Synthetic Peptide

<400> SEQUENCE: 77

Gln Val Gln Leu Gln Gln Pro Gly Ala Glu Leu Val Lys Pro Gly Ala
1 5 10 15

Ser Val Lys Leu Ser Cys Glu Ala Ser Gly Tyr Thr Phe Thr Ser Tyr
20 25 30

Trp Ile Asn Trp Val Lys Gln Arg Pro Gly Gln Gly Leu Glu Trp Ile
35 40 45

Gly Asn Ile Tyr Pro Gly Ser Ser Thr Thr Asn Tyr Asn Glu Lys Phe
50 55 60

Lys Ser Lys Ala Thr Leu Thr Val Asp Thr Ser Ser Ser Thr Ala Tyr
65 70 75 80

Met Gln Leu Ser Ser Leu Thr Ser Asp Asp Ser Ala Val Phe Tyr Cys
85 90 95

Ala Ser Phe Ser Asp Gly Tyr Tyr Ala Tyr Ala Met Asp Tyr Trp Val
100 105 110

Gln Gly Thr Ser Val Thr Val Ser Ser Gly Gly Gly Gly Ser Gly Gly
115 120 125

Gly Gly Ser Gly Gly Gly Gly Ser Gly Gly Gly Gly Ser Asp Ile Gln
130 135 140

Met Thr Gln Thr Thr Ser Ser Leu Ser Ala Ser Leu Gly Asp Arg Val
145 150 155 160

Thr Ile Thr Cys Arg Ala Ser Gln Asp Ile Ser Asn Tyr Leu Asn Trp
165 170 175

Tyr Gln Gln Lys Pro Asp Gly Thr Val Lys Leu Leu Ile Tyr Tyr Thr
180 185 190

Ser Arg Leu His Ser Gly Val Pro Ser Arg Phe Ser Gly Gly Gly Ser
195 200 205

Gly Thr Asp Tyr Ser Leu Thr Ile Ser Asn Leu Glu Gln Glu Asp Ile
210 215 220

Ala Thr Tyr Phe Cys Gln Gln Gly Tyr Thr Leu Pro Tyr Thr Phe Gly
225 230 235 240

Gly Gly Thr Lys Leu Glu Ile Lys Arg
245

<210> SEQ ID NO 78
<211> LENGTH: 727
<212> TYPE: PRT
<213> ORGANISM: Artificial Sequence
<220> FEATURE:
<223> OTHER INFORMATION: Synthetic Peptide

<400> SEQUENCE: 78

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Met Asn Trp Val Arg Gln Ala Pro Gly Gln Gly Leu Glu Trp Met
35 40 45

Gly Asn Ile Tyr Pro Ser Gly Gly Ser Thr Asn Tyr Ala Gln Lys Phe
50 55 60

Gln Gly Arg Val Thr Met Thr Val Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Ser Phe Ser Asp Gly Tyr Tyr Ala Tyr Ala Met Asp Tyr Trp Gly
100 105 110

Gln Gly Thr Leu Val Thr Val Ser Ser Gly Gly Gly Gly Ser Gly Gly
115 120 125

Gly Gly Ser Gly Gly Gly Gly Ser Gly Gly Gly Gly Ser Glu Ile Val
130 135 140

Met Thr Gln Ser Pro Ala Thr Leu Ser Leu Ser Pro Gly Glu Arg Ala
145 150 155 160

Thr Leu Ser Cys Arg Ala Ser Gln Ser Val Ser Ser Tyr Leu Asn Trp
165 170 175

-continued

```
Tyr Gln Gln Lys Pro Gly Gln Ala Pro Arg Leu Leu Ile Tyr Tyr Ala
            180                 185                 190

Ser Arg Arg His Thr Gly Ile Pro Ala Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Val Tyr Tyr Cys Gln Gln Gly Tyr Asn Leu Pro Tyr Thr Phe Gly
225                 230                 235                 240

Gln Gly Thr Lys Val Glu Ile Lys Glu Pro Lys Ser Ser Asp Lys Thr
                245                 250                 255

His Thr Cys Pro Pro Cys Pro Ala Pro Pro Ala Ala Ala Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Ala Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Gly Gly
465                 470                 475                 480

Gly Ser Pro Ser Ser Tyr Val Leu Thr Gln Pro Pro Ser Val Ser Val
                485                 490                 495

Ala Pro Gly Gln Thr Ala Arg Ile Thr Cys Gly Gly Asn Asn Ile Gly
            500                 505                 510

Ser Lys Ser Val Asn Trp Phe Gln Gln Lys Pro Gly Gln Ala Pro Val
        515                 520                 525

Leu Val Val Tyr Asp Asp Ser Gly Arg Pro Ser Gly Ile Pro Glu Arg
    530                 535                 540

Phe Ser Gly Ser Thr Ser Gly Asn Thr Ala Thr Leu Thr Ile Ser Arg
545                 550                 555                 560

Val Glu Ala Gly Asp Glu Ala Asp Tyr Tyr Cys Gln Val Trp Asp Ser
                565                 570                 575

Ser Ser Asp His Val Val Phe Gly Gly Gly Thr Lys Leu Thr Val Leu
            580                 585                 590

Gly Gly Gly Gly Ser Gly Gly Gly Gly Ser Gly Gly Gly Gly Ser Gly
```

```
        595                 600                 605

Gly Gly Gly Ser Gln Val Gln Leu Val Glu Ser Gly Gly Gly Val Val
    610                 615                 620

Gln Pro Gly Arg Ser Leu Arg Leu Ser Cys Ala Ala Ser Gly Phe Thr
625                 630                 635                 640

Leu Ser Tyr Tyr Gly Met His Trp Val Arg Gln Ala Pro Gly Lys Gly
                645                 650                 655

Leu Glu Trp Val Ala Ala Ile Ser His Asp Gly Ser Asp Lys Tyr Tyr
            660                 665                 670

Ala Asp Ser Val Lys Gly Arg Phe Thr Ile Ser Arg Asp Asn Ser Lys
        675                 680                 685

Asn Thr Leu Tyr Leu Gln Met Asn Ser Leu Arg Ala Glu Asp Thr Ala
    690                 695                 700

Val Tyr Tyr Cys Ser Asn Asp Gln Phe Asp Pro Trp Gly Gln Gly Thr
705                 710                 715                 720

Leu Val Thr Val Ser Ser Arg
                725


<210> SEQ ID NO 79
<211> LENGTH: 727
<212> TYPE: PRT
<213> ORGANISM: Artificial Sequence
<220> FEATURE:
<223> OTHER INFORMATION: Synthetic Peptide

<400> SEQUENCE: 79

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Asn Ile Tyr Pro Ser Gly Gly Ser Thr Asn Tyr Ala Gln Lys Phe
    50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Phe Ser Asp Gly Tyr Tyr Ala Tyr Ala Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Glu Ile Val
    130                 135                 140

Met Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ser Tyr Leu Asn Trp
                165                 170                 175

Tyr Gln Gln Lys Pro Gly Gln Ala Pro Arg Leu Leu Ile Tyr Tyr Ala
            180                 185                 190

Ser Arg Arg His Thr Gly Ile Pro Ala Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Val Tyr Tyr Cys Gln Gln Gly Tyr Asn Leu Pro Tyr Thr Phe Gly
```

```
225                 230                 235                 240

Gln Gly Thr Lys Val Glu Ile Lys Glu Pro Lys Ser Ser Asp Lys Thr
                245                 250                 255

His Thr Cys Pro Pro Cys Pro Ala Pro Pro Ala Ala Ala Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Ala Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Gly Gly
465                 470                 475                 480

Gly Ser Pro Ser Ser Tyr Val Leu Thr Gln Pro Pro Ser Val Ser Val
                485                 490                 495

Ala Pro Gly Lys Thr Ala Arg Ile Thr Cys Gly Gly Asn Asn Ile Gly
            500                 505                 510

Ser Lys Ser Val Asn Trp Phe Gln Gln Lys Pro Gly Gln Ala Pro Val
        515                 520                 525

Leu Val Val Tyr Asp Asp Ser Gly Arg Pro Ser Gly Ile Pro Glu Arg
    530                 535                 540

Phe Ser Gly Ser Thr Ser Gly Asn Thr Ala Thr Leu Thr Ile Ser Arg
545                 550                 555                 560

Val Glu Ala Gly Asp Glu Ala Asp Tyr Tyr Cys Gln Val Trp Asp Ser
                565                 570                 575

Ser Ser Asp His Val Val Phe Gly Gly Gly Thr Lys Leu Thr Val Leu
            580                 585                 590

Gly Gly Gly Gly Ser Gly Gly Gly Gly Ser Gly Gly Gly Gly Ser Gly
        595                 600                 605

Gly Gly Gly Ser Gln Val Gln Leu Val Glu Ser Gly Gly Gly Val Val
    610                 615                 620

Gln Pro Gly Arg Ser Leu Arg Leu Ser Cys Ala Ala Ser Gly Phe Thr
625                 630                 635                 640

Leu Ser Tyr Tyr Gly Met His Trp Val Arg Gln Ala Pro Gly Lys Gly
                645                 650                 655
```

```
Leu Glu Trp Val Ala Ala Ile Ser His Asp Gly Ser Asp Lys Tyr Tyr
            660                 665                 670

Ala Asp Ser Val Lys Gly Arg Phe Thr Ile Ser Arg Asp Asn Ser Lys
        675                 680                 685

Asn Thr Leu Tyr Leu Gln Met Asn Ser Leu Arg Ala Glu Asp Thr Ala
    690                 695                 700

Val Tyr Tyr Cys Ser Asn Asp Gln Phe Asp Pro Trp Gly Gln Gly Thr
705                 710                 715                 720

Leu Val Thr Val Ser Ser Arg
                725
```

<210> SEQ ID NO 80
<211> LENGTH: 727
<212> TYPE: PRT
<213> ORGANISM: Artificial Sequence
<220> FEATURE:
<223> OTHER INFORMATION: Synthetic Peptide

<400> SEQUENCE: 80

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Asn Ile Tyr Pro Ser Gly Gly Ser Thr Asn Tyr Ala Gln Lys Phe
    50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Phe Ser Asp Gly Tyr Tyr Ala Tyr Ala Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Glu Ile Val
    130                 135                 140

Met Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ser Tyr Leu Asn Trp
                165                 170                 175

Tyr Gln Gln Lys Pro Gly Gln Ala Pro Arg Leu Leu Ile Tyr Tyr Ala
            180                 185                 190

Ser Arg Arg His Thr Gly Ile Pro Ala Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Val Tyr Tyr Cys Gln Gln Gly Tyr Asn Leu Pro Tyr Thr Phe Gly
225                 230                 235                 240

Gln Gly Thr Lys Val Glu Ile Lys Glu Pro Lys Ser Ser Asp Lys Thr
                245                 250                 255

His Thr Cys Pro Pro Cys Pro Ala Pro Pro Ala Ala Ala Pro Ser Val
            260                 265                 270

Phe Leu Phe Pro Pro Lys Pro Lys Asp Thr Leu Met Ile Ser Arg Thr
        275                 280                 285
```

```
Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Ala Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Gly Gly
465                 470                 475                 480

Gly Ser Pro Ser Ser Tyr Val Leu Thr Gln Pro Pro Ser Val Ser Val
                485                 490                 495

Ala Pro Gly Gln Thr Ala Arg Ile Thr Cys Gly Gly Asn Asn Ile Gly
            500                 505                 510

Ser Lys Ser Val Asn Trp Phe Gln Gln Lys Pro Gly Gln Ala Pro Val
        515                 520                 525

Leu Val Val Tyr Asp Asp Ser Gly Arg Pro Ser Gly Ile Pro Glu Arg
    530                 535                 540

Phe Ser Gly Ser Thr Ser Gly Asn Thr Ala Thr Leu Thr Ile Ser Arg
545                 550                 555                 560

Val Glu Ala Gly Asp Glu Ala Asp Tyr Tyr Cys Gln Val Trp Asp Ser
                565                 570                 575

Ser Ser Asp His Val Val Phe Gly Gly Gly Thr Lys Leu Thr Val Leu
            580                 585                 590

Gly Gly Gly Gly Ser Gly Gly Gly Gly Ser Gly Gly Gly Gly Ser Gly
        595                 600                 605

Gly Gly Gly Ser Gln Val Gln Leu Val Glu Ser Gly Gly Gly Val Val
    610                 615                 620

Gln Pro Gly Arg Ser Leu Arg Leu Ser Cys Ala Ala Ser Gly Phe Thr
625                 630                 635                 640

Leu Ser Tyr Tyr Gly Met His Trp Val Arg Gln Ala Pro Gly Lys Gly
                645                 650                 655

Leu Glu Trp Val Ala Ala Ile Ser His Asp Gly Ser Asp Lys Tyr Tyr
            660                 665                 670

Ala Asp Ser Val Lys Gly Arg Phe Thr Ile Ser Arg Asp Asn Ser Lys
        675                 680                 685

Asn Arg Leu Tyr Leu Gln Met Asn Ser Leu Arg Ala Glu Asp Thr Ala
    690                 695                 700
```

```
Val Tyr Tyr Cys Ser Asn Asp Gln Phe Asp Pro Trp Gly Gln Gly Thr
705                 710                 715                 720

Leu Val Thr Val Ser Ser Arg
                725


<210> SEQ ID NO 81
<211> LENGTH: 727
<212> TYPE: PRT
<213> ORGANISM: Artificial Sequence
<220> FEATURE:
<223> OTHER INFORMATION: Synthetic Peptide

<400> SEQUENCE: 81

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Asn Ile Tyr Pro Ser Gly Gly Ser Thr Asn Tyr Ala Gln Lys Phe
    50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Phe Ser Asp Gly Tyr Tyr Ala Tyr Ala Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Glu Ile Val
    130                 135                 140

Met Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ser Tyr Leu Asn Trp
                165                 170                 175

Tyr Gln Gln Lys Pro Gly Gln Ala Pro Arg Leu Leu Ile Tyr Tyr Ala
            180                 185                 190

Ser Arg Arg His Thr Gly Ile Pro Ala Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Val Tyr Tyr Cys Gln Gln Gly Tyr Asn Leu Pro Tyr Thr Phe Gly
225                 230                 235                 240

Gln Gly Thr Lys Val Glu Ile Lys Glu Pro Lys Ser Ser Asp Lys Thr
                245                 250                 255

His Thr Cys Pro Pro Cys Pro Ala Pro Pro Ala Ala Ala Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335
```

```
Val Leu Thr Val Leu His Gln Asp Trp Leu Asn Gly Lys Glu Tyr Lys
            340                 345                 350

Cys Ala Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Gly Gly
465                 470                 475                 480

Gly Ser Pro Ser Ser Tyr Val Leu Thr Gln Pro Pro Ser Val Ser Val
                485                 490                 495

Ala Pro Gly Lys Thr Ala Arg Ile Thr Cys Gly Gly Asn Asn Ile Gly
            500                 505                 510

Ser Lys Ser Val Asn Trp Phe Gln Gln Lys Pro Gly Gln Ala Pro Val
        515                 520                 525

Leu Val Val Tyr Asp Asp Ser Gly Arg Pro Ser Gly Ile Pro Glu Arg
    530                 535                 540

Phe Ser Gly Ser Thr Ser Gly Asn Thr Ala Thr Leu Thr Ile Ser Arg
545                 550                 555                 560

Val Glu Ala Gly Asp Glu Ala Asp Tyr Tyr Cys Gln Val Trp Asp Ser
                565                 570                 575

Ser Ser Asp His Val Val Phe Gly Gly Gly Thr Lys Leu Thr Val Leu
            580                 585                 590

Gly Gly Gly Gly Ser Gly Gly Gly Gly Ser Gly Gly Gly Gly Ser Gly
        595                 600                 605

Gly Gly Gly Ser Gln Val Gln Leu Val Glu Ser Gly Gly Gly Val Val
    610                 615                 620

Gln Pro Gly Arg Ser Leu Arg Leu Ser Cys Ala Ala Ser Gly Phe Thr
625                 630                 635                 640

Leu Ser Tyr Tyr Gly Met His Trp Val Arg Gln Ala Pro Gly Lys Gly
                645                 650                 655

Leu Glu Trp Val Ala Ala Ile Ser His Asp Gly Ser Asp Lys Tyr Tyr
            660                 665                 670

Ala Asp Ser Val Lys Gly Arg Phe Thr Ile Ser Arg Asp Asn Ser Lys
        675                 680                 685

Asn Arg Leu Tyr Leu Gln Met Asn Ser Leu Arg Ala Glu Asp Thr Ala
    690                 695                 700

Val Tyr Tyr Cys Ser Asn Asp Gln Phe Asp Pro Trp Gly Gln Gly Thr
705                 710                 715                 720

Leu Val Thr Val Ser Ser Arg
                725
```

<210> SEQ ID NO 82
<211> LENGTH: 725
<212> TYPE: PRT

<213> ORGANISM: Artificial Sequence
<220> FEATURE:
<223> OTHER INFORMATION: Synthetic Peptide

<400> SEQUENCE: 82

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Asn Trp Tyr Gln Gln Lys Pro Gly Gln Ala Pro Arg Leu Leu Ile
        35                  40                  45

Tyr Tyr Ala Ser Arg Arg His Thr Gly Ile Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Gly Tyr Asn Leu Pro Tyr
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Glu
        115                 120                 125

Val Gln Leu Val Gln Ser Gly Ala Glu Val Lys Lys Pro Gly Ala Ser
    130                 135                 140

Val Lys Val Ser Cys Lys Ala Ser Gly Tyr Thr Phe Thr Ser Tyr Trp
145                 150                 155                 160

Met Asn Trp Val Arg Gln Ala Pro Gly Gln Gly Leu Glu Trp Met Gly
                165                 170                 175

Asn Ile Tyr Pro Ser Gly Gly Ser Thr Asn Tyr Ala Gln Lys Phe Gln
            180                 185                 190

Gly Arg Val Thr Met Thr Val Asp Thr Ser Thr Ser Thr Val Tyr Met
        195                 200                 205

Glu Leu Ser Ser Leu Arg Ser Glu Asp Thr Ala Val Tyr Tyr Cys Ala
    210                 215                 220

Ser Phe Ser Asp Gly Tyr Tyr Ala Tyr Ala Met Asp Tyr Trp Gly Gln
225                 230                 235                 240

Gly Thr Leu Val Thr Val Glu Pro Lys Ser Ser Asp Lys Thr His Thr
                245                 250                 255

Cys Pro Pro Cys Pro Ala Pro Pro Ala Ala Ala Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Ala
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Arg Asp Glu Leu Thr Lys Asn Gln Val Ser Leu Thr Cys Leu Val Lys

```
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Gly Gly Gly Ser
465                 470                 475                 480

Pro Ser Ser Tyr Val Leu Thr Gln Pro Pro Ser Val Ser Val Ala Pro
                485                 490                 495

Gly Gln Thr Ala Arg Ile Thr Cys Gly Gly Asn Asn Ile Gly Ser Lys
            500                 505                 510

Ser Val Asn Trp Phe Gln Gln Lys Pro Gly Gln Ala Pro Val Leu Val
        515                 520                 525

Val Tyr Asp Asp Ser Gly Arg Pro Ser Gly Ile Pro Glu Arg Phe Ser
    530                 535                 540

Gly Ser Thr Ser Gly Asn Thr Ala Thr Leu Thr Ile Ser Arg Val Glu
545                 550                 555                 560

Ala Gly Asp Glu Ala Asp Tyr Tyr Cys Gln Val Trp Asp Ser Ser Ser
                565                 570                 575

Asp His Val Val Phe Gly Gly Gly Thr Lys Leu Thr Val Leu Gly Gly
            580                 585                 590

Gly Gly Ser Gly Gly Gly Gly Ser Gly Gly Gly Gly Ser Gly Gly Gly
        595                 600                 605

Gly Ser Gln Val Gln Leu Val Glu Ser Gly Gly Gly Val Val Gln Pro
    610                 615                 620

Gly Arg Ser Leu Arg Leu Ser Cys Ala Ala Ser Gly Phe Thr Leu Ser
625                 630                 635                 640

Tyr Tyr Gly Met His Trp Val Arg Gln Ala Pro Gly Lys Gly Leu Glu
                645                 650                 655

Trp Val Ala Ala Ile Ser His Asp Gly Ser Asp Lys Tyr Tyr Ala Asp
            660                 665                 670

Ser Val Lys Gly Arg Phe Thr Ile Ser Arg Asp Asn Ser Lys Asn Thr
        675                 680                 685

Leu Tyr Leu Gln Met Asn Ser Leu Arg Ala Glu Asp Thr Ala Val Tyr
    690                 695                 700

Tyr Cys Ser Asn Asp Gln Phe Asp Pro Trp Gly Gln Gly Thr Leu Val
705                 710                 715                 720

Thr Val Ser Ser Arg
                725


<210> SEQ ID NO 83
<211> LENGTH: 725
<212> TYPE: PRT
<213> ORGANISM: Artificial Sequence
<220> FEATURE:
<223> OTHER INFORMATION: Synthetic Peptide

<400> SEQUENCE: 83

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
```

```
            20                  25                  30

Leu Asn Trp Tyr Gln Gln Lys Pro Gly Gln Ala Pro Arg Leu Leu Ile
        35                  40                  45

Tyr Tyr Ala Ser Arg Arg His Thr Gly Ile Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Gly Tyr Asn Leu Pro Tyr
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Glu
        115                 120                 125

Val Gln Leu Val Gln Ser Gly Ala Glu Val Lys Lys Pro Gly Ala Ser
    130                 135                 140

Val Lys Val Ser Cys Lys Ala Ser Gly Tyr Thr Phe Thr Ser Tyr Trp
145                 150                 155                 160

Met Asn Trp Val Arg Gln Ala Pro Gly Gln Gly Leu Glu Trp Met Gly
                165                 170                 175

Asn Ile Tyr Pro Ser Gly Gly Ser Thr Asn Tyr Ala Gln Lys Phe Gln
            180                 185                 190

Gly Arg Val Thr Met Thr Val Asp Thr Ser Thr Ser Thr Val Tyr Met
        195                 200                 205

Glu Leu Ser Ser Leu Arg Ser Glu Asp Thr Ala Val Tyr Tyr Cys Ala
    210                 215                 220

Ser Phe Ser Asp Gly Tyr Tyr Ala Tyr Ala Met Asp Tyr Trp Gly Gln
225                 230                 235                 240

Gly Thr Leu Val Thr Val Glu Pro Lys Ser Ser Asp Lys Thr His Thr
                245                 250                 255

Cys Pro Pro Cys Pro Ala Pro Pro Ala Ala Ala Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Ala
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445
```

Gln Gly Asn Val Phe Ser Cys Ser Val Met His Glu Ala Leu His Asn
450 455 460

His Tyr Thr Gln Lys Ser Leu Ser Leu Ser Pro Gly Gly Gly Gly Ser
465 470 475 480

Pro Ser Ser Tyr Val Leu Thr Gln Pro Pro Ser Val Ser Val Ala Pro
485 490 495

Gly Lys Thr Ala Arg Ile Thr Cys Gly Gly Asn Asn Ile Gly Ser Lys
500 505 510

Ser Val Asn Trp Phe Gln Gln Lys Pro Gly Gln Ala Pro Val Leu Val
515 520 525

Val Tyr Asp Asp Ser Gly Arg Pro Ser Gly Ile Pro Glu Arg Phe Ser
530 535 540

Gly Ser Thr Ser Gly Asn Thr Ala Thr Leu Thr Ile Ser Arg Val Glu
545 550 555 560

Ala Gly Asp Glu Ala Asp Tyr Tyr Cys Gln Val Trp Asp Ser Ser Ser
565 570 575

Asp His Val Val Phe Gly Gly Gly Thr Lys Leu Thr Val Leu Gly Gly
580 585 590

Gly Gly Ser Gly Gly Gly Gly Ser Gly Gly Gly Gly Ser Gly Gly Gly
595 600 605

Gly Ser Gln Val Gln Leu Val Glu Ser Gly Gly Gly Val Val Gln Pro
610 615 620

Gly Arg Ser Leu Arg Leu Ser Cys Ala Ala Ser Gly Phe Thr Leu Ser
625 630 635 640

Tyr Tyr Gly Met His Trp Val Arg Gln Ala Pro Gly Lys Gly Leu Glu
645 650 655

Trp Val Ala Ala Ile Ser His Asp Gly Ser Asp Lys Tyr Tyr Ala Asp
660 665 670

Ser Val Lys Gly Arg Phe Thr Ile Ser Arg Asp Asn Ser Lys Asn Thr
675 680 685

Leu Tyr Leu Gln Met Asn Ser Leu Arg Ala Glu Asp Thr Ala Val Tyr
690 695 700

Tyr Cys Ser Asn Asp Gln Phe Asp Pro Trp Gly Gln Gly Thr Leu Val
705 710 715 720

Thr Val Ser Ser Arg
725

<210> SEQ ID NO 84
<211> LENGTH: 725
<212> TYPE: PRT
<213> ORGANISM: Artificial Sequence
<220> FEATURE:
<223> OTHER INFORMATION: Synthetic Peptide

<400> SEQUENCE: 84

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Asn Trp Tyr Gln Gln Lys Pro Gly Gln Ala Pro Arg Leu Leu Ile
35 40 45

Tyr Tyr Ala Ser Arg Arg His Thr Gly Ile Pro Ala Arg Phe Ser Gly
50 55 60

Ser Gly Ser Gly Thr Asp Phe Thr Leu Thr Ile Ser Ser Leu Gln Pro
65 70 75 80

```
Glu Asp Phe Ala Val Tyr Tyr Cys Gln Gln Gly Tyr Asn Leu Pro Tyr
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Glu
        115                 120                 125

Val Gln Leu Val Gln Ser Gly Ala Glu Val Lys Lys Pro Gly Ala Ser
    130                 135                 140

Val Lys Val Ser Cys Lys Ala Ser Gly Tyr Thr Phe Thr Ser Tyr Trp
145                 150                 155                 160

Met Asn Trp Val Arg Gln Ala Pro Gly Gln Gly Leu Glu Trp Met Gly
                165                 170                 175

Asn Ile Tyr Pro Ser Gly Gly Ser Thr Asn Tyr Ala Gln Lys Phe Gln
            180                 185                 190

Gly Arg Val Thr Met Thr Val Asp Thr Ser Thr Ser Thr Val Tyr Met
        195                 200                 205

Glu Leu Ser Ser Leu Arg Ser Glu Asp Thr Ala Val Tyr Tyr Cys Ala
    210                 215                 220

Ser Phe Ser Asp Gly Tyr Tyr Ala Tyr Ala Met Asp Tyr Trp Gly Gln
225                 230                 235                 240

Gly Thr Leu Val Thr Val Glu Pro Lys Ser Ser Asp Lys Thr His Thr
                245                 250                 255

Cys Pro Pro Cys Pro Ala Pro Pro Ala Ala Ala Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Ala
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Gly Gly Gly Ser
465                 470                 475                 480

Pro Ser Ser Tyr Val Leu Thr Gln Pro Pro Ser Val Ser Val Ala Pro
                485                 490                 495
```

```
Gly Gln Thr Ala Arg Ile Thr Cys Gly Gly Asn Asn Ile Gly Ser Lys
            500                 505                 510

Ser Val Asn Trp Phe Gln Gln Lys Pro Gly Gln Ala Pro Val Leu Val
        515                 520                 525

Val Tyr Asp Asp Ser Gly Arg Pro Ser Gly Ile Pro Glu Arg Phe Ser
    530                 535                 540

Gly Ser Thr Ser Gly Asn Thr Ala Thr Leu Thr Ile Ser Arg Val Glu
545                 550                 555                 560

Ala Gly Asp Glu Ala Asp Tyr Tyr Cys Gln Val Trp Asp Ser Ser Ser
                565                 570                 575

Asp His Val Val Phe Gly Gly Gly Thr Lys Leu Thr Val Leu Gly Gly
            580                 585                 590

Gly Gly Ser Gly Gly Gly Gly Ser Gly Gly Gly Gly Ser Gly Gly Gly
        595                 600                 605

Gly Ser Gln Val Gln Leu Val Glu Ser Gly Gly Gly Val Val Gln Pro
    610                 615                 620

Gly Arg Ser Leu Arg Leu Ser Cys Ala Ala Ser Gly Phe Thr Leu Ser
625                 630                 635                 640

Tyr Tyr Gly Met His Trp Val Arg Gln Ala Pro Gly Lys Gly Leu Glu
                645                 650                 655

Trp Val Ala Ala Ile Ser His Asp Gly Ser Asp Lys Tyr Tyr Ala Asp
            660                 665                 670

Ser Val Lys Gly Arg Phe Thr Ile Ser Arg Asp Asn Ser Lys Asn Arg
        675                 680                 685

Leu Tyr Leu Gln Met Asn Ser Leu Arg Ala Glu Asp Thr Ala Val Tyr
    690                 695                 700

Tyr Cys Ser Asn Asp Gln Phe Asp Pro Trp Gly Gln Gly Thr Leu Val
705                 710                 715                 720

Thr Val Ser Ser Arg
                725
```

```
<210> SEQ ID NO 85
<211> LENGTH: 725
<212> TYPE: PRT
<213> ORGANISM: Artificial Sequence
<220> FEATURE:
<223> OTHER INFORMATION: Synthetic Peptide

<400> SEQUENCE: 85
```

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Asn Trp Tyr Gln Gln Lys Pro Gly Gln Ala Pro Arg Leu Leu Ile
        35                  40                  45

Tyr Tyr Ala Ser Arg Arg His Thr Gly Ile Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Gly Tyr Asn Leu Pro Tyr
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Glu
        115                 120                 125
```

```
Val Gln Leu Val Gln Ser Gly Ala Glu Val Lys Lys Pro Gly Ala Ser
    130                 135                 140

Val Lys Val Ser Cys Lys Ala Ser Gly Tyr Thr Phe Thr Ser Tyr Trp
145                 150                 155                 160

Met Asn Trp Val Arg Gln Ala Pro Gly Gln Gly Leu Glu Trp Met Gly
                165                 170                 175

Asn Ile Tyr Pro Ser Gly Gly Ser Thr Asn Tyr Ala Gln Lys Phe Gln
            180                 185                 190

Gly Arg Val Thr Met Thr Val Asp Thr Ser Thr Ser Thr Val Tyr Met
        195                 200                 205

Glu Leu Ser Ser Leu Arg Ser Glu Asp Thr Ala Val Tyr Tyr Cys Ala
    210                 215                 220

Ser Phe Ser Asp Gly Tyr Tyr Ala Tyr Ala Met Asp Tyr Trp Gly Gln
225                 230                 235                 240

Gly Thr Leu Val Thr Val Glu Pro Lys Ser Ser Asp Lys Thr His Thr
                245                 250                 255

Cys Pro Pro Cys Pro Ala Pro Pro Ala Ala Ala Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Ala
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Gly Gly Gly Ser
465                 470                 475                 480

Pro Ser Ser Tyr Val Leu Thr Gln Pro Pro Ser Val Ser Val Ala Pro
                485                 490                 495

Gly Lys Thr Ala Arg Ile Thr Cys Gly Gly Asn Asn Ile Gly Ser Lys
            500                 505                 510

Ser Val Asn Trp Phe Gln Gln Lys Pro Gly Gln Ala Pro Val Leu Val
        515                 520                 525

Val Tyr Asp Asp Ser Gly Arg Pro Ser Gly Ile Pro Glu Arg Phe Ser
    530                 535                 540

Gly Ser Thr Ser Gly Asn Thr Ala Thr Leu Thr Ile Ser Arg Val Glu
```

545 550 555 560

Ala Gly Asp Glu Ala Asp Tyr Tyr Cys Gln Val Trp Asp Ser Ser Ser
565 570 575

Asp His Val Val Phe Gly Gly Gly Thr Lys Leu Thr Val Leu Gly Gly
580 585 590

Gly Gly Ser Gly Gly Gly Gly Ser Gly Gly Gly Gly Ser Gly Gly Gly
595 600 605

Gly Ser Gln Val Gln Leu Val Glu Ser Gly Gly Gly Val Val Gln Pro
610 615 620

Gly Arg Ser Leu Arg Leu Ser Cys Ala Ala Ser Gly Phe Thr Leu Ser
625 630 635 640

Tyr Tyr Gly Met His Trp Val Arg Gln Ala Pro Gly Lys Gly Leu Glu
645 650 655

Trp Val Ala Ala Ile Ser His Asp Gly Ser Asp Lys Tyr Tyr Ala Asp
660 665 670

Ser Val Lys Gly Arg Phe Thr Ile Ser Arg Asp Asn Ser Lys Asn Arg
675 680 685

Leu Tyr Leu Gln Met Asn Ser Leu Arg Ala Glu Asp Thr Ala Val Tyr
690 695 700

Tyr Cys Ser Asn Asp Gln Phe Asp Pro Trp Gly Gln Gly Thr Leu Val
705 710 715 720

Thr Val Ser Ser Arg
725

<210> SEQ ID NO 86
<211> LENGTH: 727
<212> TYPE: PRT
<213> ORGANISM: Artificial Sequence
<220> FEATURE:
<223> OTHER INFORMATION: Synthetic Peptide

<400> SEQUENCE: 86

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Met Asn Trp Val Arg Gln Ala Pro Gly Gln Gly Leu Glu Trp Met
35 40 45

Gly Asn Ile Tyr Pro Gly Ser Ser Thr Thr Asn Tyr Ala Gln Lys Phe
50 55 60

Gln Gly Arg Val Thr Met Thr Val Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Ser Phe Ser Asp Gly Tyr Tyr Ala Tyr Ala Met Asp Tyr Trp Gly
100 105 110

Gln Gly Thr Leu Val Thr Val Ser Ser Gly Gly Gly Gly Ser Gly Gly
115 120 125

Gly Gly Ser Gly Gly Gly Gly Ser Gly Gly Gly Gly Ser Glu Ile Val
130 135 140

Met Thr Gln Ser Pro Ala Thr Leu Ser Leu Ser Pro Gly Glu Arg Ala
145 150 155 160

Thr Leu Ser Cys Arg Ala Ser Gln Asp Ile Ser Asn Tyr Leu Asn Trp
165 170 175

Tyr Gln Gln Lys Pro Gly Gln Ala Val Arg Leu Leu Ile Tyr Tyr Thr

```
            180                 185                 190

Ser Arg Leu His Ser Gly Ile Pro Ala Arg Phe Ser Gly Ser Gly Ser
        195                 200                 205

Gly Thr Asp Tyr Thr Leu Thr Ile Ser Ser Leu Gln Pro Glu Asp Phe
    210                 215                 220

Ala Val Tyr Phe Cys Gln Gln Gly Tyr Thr Leu Pro Tyr Thr Phe Gly
225                 230                 235                 240

Gln Gly Thr Lys Val Glu Ile Lys Glu Pro Lys Ser Ser Asp Lys Thr
                245                 250                 255

His Thr Cys Pro Pro Cys Pro Ala Pro Pro Ala Ala Ala Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Ala Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Gly Gly
465                 470                 475                 480

Gly Ser Pro Ser Ser Tyr Val Leu Thr Gln Pro Pro Ser Val Ser Val
                485                 490                 495

Ala Pro Gly Gln Thr Ala Arg Ile Thr Cys Gly Gly Asn Asn Ile Gly
            500                 505                 510

Ser Lys Ser Val Asn Trp Phe Gln Gln Lys Pro Gly Gln Ala Pro Val
        515                 520                 525

Leu Val Val Tyr Asp Asp Ser Gly Arg Pro Ser Gly Ile Pro Glu Arg
    530                 535                 540

Phe Ser Gly Ser Thr Ser Gly Asn Thr Ala Thr Leu Thr Ile Ser Arg
545                 550                 555                 560

Val Glu Ala Gly Asp Glu Ala Asp Tyr Tyr Cys Gln Val Trp Asp Ser
                565                 570                 575

Ser Ser Asp His Val Val Phe Gly Gly Gly Thr Lys Leu Thr Val Leu
            580                 585                 590

Gly Gly Gly Gly Ser Gly Gly Gly Gly Ser Gly Gly Gly Gly Ser Gly
        595                 600                 605
```

```
Gly Gly Gly Ser Gln Val Gln Leu Val Glu Ser Gly Gly Gly Val Val
    610                 615                 620

Gln Pro Gly Arg Ser Leu Arg Leu Ser Cys Ala Ala Ser Gly Phe Thr
625                 630                 635                 640

Leu Ser Tyr Tyr Gly Met His Trp Val Arg Gln Ala Pro Gly Lys Gly
                645                 650                 655

Leu Glu Trp Val Ala Ala Ile Ser His Asp Gly Ser Asp Lys Tyr Tyr
            660                 665                 670

Ala Asp Ser Val Lys Gly Arg Phe Thr Ile Ser Arg Asp Asn Ser Lys
        675                 680                 685

Asn Thr Leu Tyr Leu Gln Met Asn Ser Leu Arg Ala Glu Asp Thr Ala
    690                 695                 700

Val Tyr Tyr Cys Ser Asn Asp Gln Phe Asp Pro Trp Gly Gln Gly Thr
705                 710                 715                 720

Leu Val Thr Val Ser Ser Arg
                725


<210> SEQ ID NO 87
<211> LENGTH: 725
<212> TYPE: PRT
<213> ORGANISM: Artificial Sequence
<220> FEATURE:
<223> OTHER INFORMATION: Synthetic Peptide

<400> SEQUENCE: 87

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

Asn Trp Phe Gln Gln Lys Pro Gly Gln Ala Pro Val Leu Val Val Tyr
        35                  40                  45

Asp Asp Ser Gly Arg Pro Ser Gly Ile Pro Glu Arg Phe Ser Gly Ser
    50                  55                  60

Thr Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Glu Ser Gly Gly Gly Val Val Gln Pro Gly Arg
    130                 135                 140

Ser Leu Arg Leu Ser Cys Ala Ala Ser Gly Phe Thr Leu Ser Tyr Tyr
145                 150                 155                 160

Gly Met His Trp Val Arg Gln Ala Pro Gly Lys Gly Leu Glu Trp Val
                165                 170                 175

Ala Val Ile Ser His Asp Gly Ser Asp Lys Tyr Tyr Ala Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Val Tyr Tyr Cys
    210                 215                 220

Ser Asn Asp Gln Phe Asp Pro Trp Gly Gln Gly Thr Leu Val Thr Val
225                 230                 235                 240
```

```
Glu Pro Lys Ser Ser Asp Lys Thr His Thr Cys Pro Pro Cys Pro Ala
                245                 250                 255

Pro Pro Ala Ala Ala Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Ala Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Gly Gly Gly Ser Pro Ser Glu Val Gln Leu
465                 470                 475                 480

Val Gln Ser Gly Ala Glu Val Lys Lys Pro Gly Ala Ser Val Lys Val
                485                 490                 495

Ser Cys Lys Ala Ser Gly Tyr Thr Phe Thr Ser Tyr Trp Met Asn Trp
            500                 505                 510

Val Arg Gln Ala Pro Gly Gln Gly Leu Glu Trp Met Gly Asn Ile Tyr
        515                 520                 525

Pro Gly Ser Ser Thr Thr Asn Tyr Ala Gln Lys Phe Gln Gly Arg Val
    530                 535                 540

Thr Met Thr Val Asp Thr Ser Thr Ser Thr Val Tyr Met Glu Leu Ser
545                 550                 555                 560

Ser Leu Arg Ser Glu Asp Thr Ala Val Tyr Tyr Cys Ala Ser Phe Ser
                565                 570                 575

Asp Gly Tyr Tyr Ala Tyr Ala Met Asp Tyr Trp Gly Gln Gly Thr Leu
            580                 585                 590

Val Thr Val Ser Ser Gly Gly Gly Gly Ser Gly Gly Gly Gly Ser Gly
        595                 600                 605

Gly Gly Gly Ser Gly Gly Gly Gly Ser Glu Ile Val Met Thr Gln Ser
    610                 615                 620

Pro Ala Thr Leu Ser Leu Ser Pro Gly Glu Arg Ala Thr Leu Ser Cys
625                 630                 635                 640

Arg Ala Ser Gln Asp Ile Ser Asn Tyr Leu Asn Trp Tyr Gln Gln Lys
                645                 650                 655
```

```
Pro Gly Gln Ala Val Arg Leu Leu Ile Tyr Tyr Thr Ser Arg Leu His
            660                 665                 670

Ser Gly Ile Pro Ala Arg Phe Ser Gly Ser Gly Ser Gly Thr Asp Tyr
        675                 680                 685

Thr Leu Thr Ile Ser Ser Leu Gln Pro Glu Asp Phe Ala Val Tyr Phe
    690                 695                 700

Cys Gln Gln Gly Tyr Thr Leu Pro Tyr Thr Phe Gly Gln Gly Thr Lys
705                 710                 715                 720

Val Glu Ile Lys Arg
                725


<210> SEQ ID NO 88
<211> LENGTH: 725
<212> TYPE: PRT
<213> ORGANISM: Artificial Sequence
<220> FEATURE:
<223> OTHER INFORMATION: Synthetic Peptide

<400> SEQUENCE: 88

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

Asn Trp Phe Gln Gln Lys Pro Gly Gln Ala Pro Val Leu Val Val Tyr
        35                  40                  45

Asp Asp Ser Gly Arg Pro Ser Gly Ile Pro Glu Arg Phe Ser Gly Ser
    50                  55                  60

Thr Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Glu Ser Gly Gly Gly Val Val Gln Pro Gly Arg
    130                 135                 140

Ser Leu Arg Leu Ser Cys Ala Ala Ser Gly Phe Thr Leu Ser Tyr Tyr
145                 150                 155                 160

Gly Met His Trp Val Arg Gln Ala Pro Gly Lys Gly Leu Glu Trp Val
                165                 170                 175

Ala Val Ile Ser His Asp Gly Ser Asp Lys Tyr Tyr Ala Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Val Tyr Tyr Cys
    210                 215                 220

Ser Asn Asp Gln Phe Asp Pro Trp Gly Gln Gly Thr Leu Val Thr Val
225                 230                 235                 240

Glu Pro Lys Ser Ser Asp Lys Thr His Thr Cys Pro Pro Cys Pro Ala
                245                 250                 255

Pro Pro Ala Ala Ala Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285
```

```
Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Ala Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Gly Gly Gly Ser Pro Ser Glu Val Gln Leu
465                 470                 475                 480

Val Gln Ser Gly Ala Glu Val Lys Lys Pro Gly Ala Ser Val Lys Val
                485                 490                 495

Ser Cys Lys Ala Ser Gly Tyr Thr Phe Thr Ser Tyr Trp Met Asn Trp
            500                 505                 510

Val Arg Gln Ala Pro Gly Gln Gly Leu Glu Trp Met Gly Asn Ile Tyr
        515                 520                 525

Pro Ser Gly Gly Ser Thr Asn Tyr Ala Gln Lys Phe Gln Gly Arg Val
    530                 535                 540

Thr Met Thr Val Asp Thr Ser Thr Ser Thr Val Tyr Met Glu Leu Ser
545                 550                 555                 560

Ser Leu Arg Ser Glu Asp Thr Ala Val Tyr Tyr Cys Ala Ser Phe Ser
                565                 570                 575

Asp Gly Tyr Tyr Ala Tyr Ala Met Asp Tyr Trp Gly Gln Gly Thr Leu
            580                 585                 590

Val Thr Val Ser Ser Gly Gly Gly Gly Ser Gly Gly Gly Gly Ser Gly
        595                 600                 605

Gly Gly Gly Ser Gly Gly Gly Gly Ser Glu Ile Val Met Thr Gln Ser
    610                 615                 620

Pro Ala Thr Leu Ser Leu Ser Pro Gly Glu Arg Ala Thr Leu Ser Cys
625                 630                 635                 640

Arg Ala Ser Gln Ser Val Ser Ser Tyr Leu Asn Trp Tyr Gln Gln Lys
                645                 650                 655

Pro Gly Gln Ala Pro Arg Leu Leu Ile Tyr Tyr Ala Ser Arg Arg His
            660                 665                 670

Thr Gly Ile Pro Ala Arg Phe Ser Gly Ser Gly Ser Gly Thr Asp Phe
        675                 680                 685

Thr Leu Thr Ile Ser Ser Leu Gln Pro Glu Asp Phe Ala Val Tyr Tyr
    690                 695                 700

Cys Gln Gln Gly Tyr Asn Leu Pro Tyr Thr Phe Gly Gln Gly Thr Lys
```

705 710 715 720

Val Glu Ile Lys Arg
725

<210> SEQ ID NO 89
<211> LENGTH: 727
<212> TYPE: PRT
<213> ORGANISM: Artificial Sequence
<220> FEATURE:
<223> OTHER INFORMATION: Synthetic Peptide

<400> SEQUENCE: 89

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Met Asn Trp Val Arg Gln Ala Pro Gly Gln Gly Leu Glu Trp Met
35 40 45

Gly Asn Ile Tyr Pro Ser Gly Gly Ser Thr Asn Tyr Ala Gln Lys Phe
50 55 60

Gln Gly Arg Val Thr Met Thr Val Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Ser Phe Ser Asp Gly Tyr Tyr Ala Tyr Ala Met Asp Tyr Trp Gly
100 105 110

Gln Gly Thr Leu Val Thr Val Ser Ser Gly Gly Gly Gly Ser Gly Gly
115 120 125

Gly Gly Ser Gly Gly Gly Gly Ser Gly Gly Gly Gly Ser Glu Ile Val
130 135 140

Met Thr Gln Ser Pro Ala Thr Leu Ser Leu Ser Pro Gly Glu Arg Ala
145 150 155 160

Thr Leu Ser Cys Arg Ala Ser Gln Ser Val Ser Ser Tyr Leu Asn Trp
165 170 175

Tyr Gln Gln Lys Pro Gly Gln Ala Pro Arg Leu Leu Ile Tyr Tyr Ala
180 185 190

Ser Arg Arg His Thr Gly Ile Pro Ala Arg Phe Ser Gly Ser Gly Ser
195 200 205

Gly Thr Asp Phe Thr Leu Thr Ile Ser Ser Leu Gln Pro Glu Asp Phe
210 215 220

Ala Val Tyr Tyr Cys Gln Gln Gly Tyr Asn Leu Pro Tyr Thr Phe Gly
225 230 235 240

Gln Gly Thr Lys Val Glu Ile Lys Glu Pro Lys Ser Ser Asp Lys Thr
245 250 255

His Thr Cys Pro Pro Cys Pro Ala Pro Pro Ala Ala Ala Pro Ser Val
260 265 270

Phe Leu Phe Pro Pro Lys Pro Lys Asp Thr Leu Met Ile Ser Arg Thr
275 280 285

Pro Glu Val Thr Cys Val Val Val Asp Val Ser His Glu Asp Pro Glu
290 295 300

Val Lys Phe Asn Trp Tyr Val Asp Gly Val Glu Val His Asn Ala Lys
305 310 315 320

Thr Lys Pro Arg Glu Glu Gln Tyr Asn Ser Thr Tyr Arg Val Val Ser
325 330 335

Val Leu Thr Val Leu His Gln Asp Trp Leu Asn Gly Lys Glu Tyr Lys

```
            340                 345                 350

Cys Ala Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Gly Gly
465                 470                 475                 480

Gly Ser Pro Ser Ser Tyr Val Leu Thr Gln Pro Pro Ser Val Ser Val
                485                 490                 495

Ala Pro Gly Gln Thr Ala Arg Ile Thr Cys Gly Gly Asn Asn Ile Gly
            500                 505                 510

Ser Lys Ser Val Asn Trp Phe Gln Gln Lys Pro Gly Gln Ala Pro Val
        515                 520                 525

Leu Val Val Tyr Asp Asp Ser Gly Arg Pro Ser Gly Ile Pro Ala Arg
    530                 535                 540

Phe Ser Gly Ser Thr Ser Gly Asn Thr Ala Thr Leu Thr Ile Ser Arg
545                 550                 555                 560

Val Glu Ala Gly Asp Glu Ala Asp Tyr Tyr Cys Gln Val Trp Asp Ser
                565                 570                 575

Ser Ser Asp His Val Val Phe Gly Gly Gly Thr Lys Leu Thr Val Leu
            580                 585                 590

Gly Gly Gly Gly Ser Gly Gly Gly Gly Ser Gly Gly Gly Gly Ser Gly
        595                 600                 605

Gly Gly Gly Ser Gln Val Gln Leu Val Glu Ser Gly Gly Gly Val Val
    610                 615                 620

Gln Pro Gly Arg Ser Leu Arg Leu Ser Cys Ala Ala Ser Gly Phe Thr
625                 630                 635                 640

Leu Ser Tyr Tyr Gly Met His Trp Val Arg Gln Ala Pro Gly Lys Gly
                645                 650                 655

Leu Glu Trp Val Ala Ala Ile Ser His Asp Gly Ser Asp Lys Tyr Tyr
            660                 665                 670

Ala Asp Ser Val Lys Gly Arg Phe Thr Ile Ser Arg Asp Asn Ser Lys
        675                 680                 685

Asn Thr Leu Tyr Leu Gln Met Asn Ser Leu Arg Ala Glu Asp Thr Ala
    690                 695                 700

Val Tyr Tyr Cys Ser Asn Asp Gln Phe Asp Pro Trp Gly Gln Gly Thr
705                 710                 715                 720

Leu Val Thr Val Ser Ser Arg
                725
```

<210> SEQ ID NO 90
<211> LENGTH: 727
<212> TYPE: PRT
<213> ORGANISM: Artificial Sequence
<220> FEATURE:
<223> OTHER INFORMATION: Synthetic Peptide

<400> SEQUENCE: 90

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Asn Ile Tyr Pro Ser Gly Gly Ser Thr Asn Tyr Ala Gln Lys Phe
    50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Phe Ser Asp Gly Tyr Tyr Ala Tyr Ala Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Glu Ile Val
    130                 135                 140

Met Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ser Tyr Leu Asn Trp
                165                 170                 175

Tyr Gln Gln Lys Pro Gly Gln Ala Pro Arg Leu Leu Ile Tyr Tyr Ala
            180                 185                 190

Ser Arg Arg His Thr Gly Ile Pro Ala Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Val Tyr Tyr Cys Gln Gln Gly Tyr Asn Leu Pro Tyr Thr Phe Gly
225                 230                 235                 240

Gln Gly Thr Lys Val Glu Ile Lys Glu Pro Lys Ser Ser Asp Lys Thr
                245                 250                 255

His Thr Cys Pro Pro Cys Pro Ala Pro Pro Ala Ala Ala Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Ala Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

```
Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Gly Gly
465                 470                 475                 480

Gly Ser Pro Ser Ser Tyr Val Leu Thr Gln Pro Pro Ser Val Ser Val
                485                 490                 495

Ala Pro Gly Gln Thr Ala Arg Ile Thr Cys Gly Gly Asn Asn Ile Gly
            500                 505                 510

Ser Lys Ser Val Asn Trp Phe Gln Gln Lys Pro Gly Gln Ala Pro Val
        515                 520                 525

Leu Val Val Tyr Asp Asp Ser Gly Arg Pro Ser Gly Val Pro Asn Arg
    530                 535                 540

Phe Ser Gly Ser Thr Ser Gly Asn Thr Ala Thr Leu Thr Ile Ser Arg
545                 550                 555                 560

Val Glu Ala Gly Asp Glu Ala Asp Tyr Tyr Cys Gln Val Trp Asp Ser
                565                 570                 575

Ser Ser Asp His Val Val Phe Gly Gly Gly Thr Lys Leu Thr Val Leu
            580                 585                 590

Gly Gly Gly Gly Ser Gly Gly Gly Gly Ser Gly Gly Gly Gly Ser Gly
        595                 600                 605

Gly Gly Gly Ser Gln Val Gln Leu Val Glu Ser Gly Gly Gly Val Val
    610                 615                 620

Gln Pro Gly Arg Ser Leu Arg Leu Ser Cys Ala Ala Ser Gly Phe Thr
625                 630                 635                 640

Leu Ser Tyr Tyr Gly Met His Trp Val Arg Gln Ala Pro Gly Lys Gly
                645                 650                 655

Leu Glu Trp Val Ala Ala Ile Ser His Asp Gly Ser Asp Lys Tyr Tyr
            660                 665                 670

Ala Asp Ser Val Lys Gly Arg Phe Thr Ile Ser Arg Asp Asn Ser Lys
        675                 680                 685

Asn Thr Leu Tyr Leu Gln Met Asn Ser Leu Arg Ala Glu Asp Thr Ala
    690                 695                 700

Val Tyr Tyr Cys Ser Asn Asp Gln Phe Asp Pro Trp Gly Gln Gly Thr
705                 710                 715                 720

Leu Val Thr Val Ser Ser Arg
                725
```

<210> SEQ ID NO 91
<211> LENGTH: 727
<212> TYPE: PRT
<213> ORGANISM: Artificial Sequence
<220> FEATURE:
<223> OTHER INFORMATION: Synthetic Peptide

<400> SEQUENCE: 91

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

```
Trp Met Asn Trp Val Arg Gln Ala Pro Gly Gln Gly Leu Glu Trp Met
        35                  40                  45

Gly Asn Ile Tyr Pro Ser Gly Gly Ser Thr Asn Tyr Ala Gln Lys Phe
    50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Phe Ser Asp Gly Tyr Tyr Ala Tyr Ala Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Glu Ile Val
    130                 135                 140

Met Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ser Tyr Leu Asn Trp
                165                 170                 175

Tyr Gln Gln Lys Pro Gly Gln Ala Pro Arg Leu Leu Ile Tyr Tyr Ala
            180                 185                 190

Ser Arg Arg His Thr Gly Ile Pro Ala Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Val Tyr Tyr Cys Gln Gln Gly Tyr Asn Leu Pro Tyr Thr Phe Gly
225                 230                 235                 240

Gln Gly Thr Lys Val Glu Ile Lys Glu Pro Lys Ser Ser Asp Lys Thr
                245                 250                 255

His Thr Cys Pro Pro Cys Pro Ala Pro Pro Ala Ala Ala Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Ala Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445
```

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Gly Gly
465                 470                 475                 480

Gly Ser Pro Ser Ser Tyr Val Leu Thr Gln Pro Pro Ser Val Ser Val
                485                 490                 495

Ala Pro Gly Gln Thr Ala Arg Ile Thr Cys Gly Gly Asn Asn Ile Gly
            500                 505                 510

Ser Lys Ser Val Asn Trp Phe Gln Gln Lys Pro Gly Gln Ala Pro Val
        515                 520                 525

Leu Val Val Tyr Asp Asp Ser Gly Arg Pro Ser Gly Val Pro Ser Arg
    530                 535                 540

Phe Ser Gly Ser Thr Ser Gly Asn Thr Ala Thr Leu Thr Ile Ser Arg
545                 550                 555                 560

Val Glu Ala Gly Asp Glu Ala Asp Tyr Tyr Cys Gln Val Trp Asp Ser
                565                 570                 575

Ser Ser Asp His Val Val Phe Gly Gly Gly Thr Lys Leu Thr Val Leu
            580                 585                 590

Gly Gly Gly Gly Ser Gly Gly Gly Gly Ser Gly Gly Gly Gly Ser Gly
        595                 600                 605

Gly Gly Gly Ser Gln Val Gln Leu Val Glu Ser Gly Gly Gly Val Val
    610                 615                 620

Gln Pro Gly Arg Ser Leu Arg Leu Ser Cys Ala Ala Ser Gly Phe Thr
625                 630                 635                 640

Leu Ser Tyr Tyr Gly Met His Trp Val Arg Gln Ala Pro Gly Lys Gly
                645                 650                 655

Leu Glu Trp Val Ala Ala Ile Ser His Asp Gly Ser Asp Lys Tyr Tyr
            660                 665                 670

Ala Asp Ser Val Lys Gly Arg Phe Thr Ile Ser Arg Asp Asn Ser Lys
        675                 680                 685

Asn Thr Leu Tyr Leu Gln Met Asn Ser Leu Arg Ala Glu Asp Thr Ala
    690                 695                 700

Val Tyr Tyr Cys Ser Asn Asp Gln Phe Asp Pro Trp Gly Gln Gly Thr
705                 710                 715                 720

Leu Val Thr Val Ser Ser Arg
                725

<210> SEQ ID NO 92
<211> LENGTH: 727
<212> TYPE: PRT
<213> ORGANISM: Artificial Sequence
<220> FEATURE:
<223> OTHER INFORMATION: Synthetic Peptide

<400> SEQUENCE: 92

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Asn Ile Tyr Pro Ser Gly Gly Ser Thr Asn Tyr Ala Gln Lys Phe
    50                  55                  60

Gln Gly Arg Val Thr Met Thr Val Asp Thr Ser Thr Ser Thr Val Tyr
65                  70                  75                  80

```
Met Glu Leu Ser Ser Leu Arg Ser Glu Asp Thr Ala Val Tyr Tyr Cys
                85                  90                  95

Ala Ser Phe Ser Asp Gly Tyr Tyr Ala Tyr Ala Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Glu Ile Val
    130                 135                 140

Met Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ser Tyr Leu Asn Trp
                165                 170                 175

Tyr Gln Gln Lys Pro Gly Gln Ala Pro Arg Leu Leu Ile Tyr Tyr Ala
            180                 185                 190

Ser Arg Arg His Thr Gly Ile Pro Ala Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Val Tyr Tyr Cys Gln Gln Gly Tyr Asn Leu Pro Tyr Thr Phe Gly
225                 230                 235                 240

Gln Gly Thr Lys Val Glu Ile Lys Glu Pro Lys Ser Ser Asp Lys Thr
                245                 250                 255

His Thr Cys Pro Pro Cys Pro Ala Pro Pro Ala Ala Ala Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Ala Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Gly Gly
465                 470                 475                 480

Gly Ser Pro Ser Ser Tyr Val Leu Thr Gln Pro Pro Ser Val Ser Val
                485                 490                 495

Ala Pro Gly Gln Thr Ala Arg Ile Thr Cys Gly Gly Asn Asn Ile Gly
```

```
            500                 505                 510

Ser Lys Ser Val Asn Trp Phe Gln Gln Lys Pro Gly Gln Ala Pro Val
        515                 520                 525

Leu Val Val Tyr Asp Asp Ser Gly Arg Pro Ser Gly Ile Pro Ala Arg
    530                 535                 540

Phe Ser Gly Ser Thr Ser Gly Asn Thr Ala Thr Leu Thr Ile Ser Arg
545                 550                 555                 560

Val Glu Ala Gly Asp Glu Ala Asp Tyr Tyr Cys Gln Val Trp Asp Ser
                565                 570                 575

Ser Ser Asp His Val Val Phe Gly Gly Gly Thr Lys Leu Thr Val Leu
            580                 585                 590

Gly Gly Gly Gly Ser Gly Gly Gly Gly Ser Gly Gly Gly Gly Ser Gly
        595                 600                 605

Gly Gly Gly Ser Gln Val Gln Leu Val Glu Ser Gly Gly Gly Val Val
    610                 615                 620

Gln Pro Gly Arg Ser Leu Arg Leu Ser Cys Ala Ala Ser Gly Phe Thr
625                 630                 635                 640

Leu Ser Tyr Tyr Gly Met His Trp Val Arg Gln Ala Pro Gly Lys Gly
                645                 650                 655

Leu Glu Trp Val Ala Ala Ile Ser His Asp Gly Ser Asp Lys Tyr Tyr
            660                 665                 670

Ala Asp Ser Val Lys Gly Arg Phe Thr Ile Ser Arg Asp Asn Ser Lys
        675                 680                 685

Asn Arg Leu Tyr Leu Gln Met Asn Ser Leu Arg Ala Glu Asp Thr Ala
    690                 695                 700

Val Tyr Tyr Cys Ser Asn Asp Gln Phe Asp Pro Trp Gly Gln Gly Thr
705                 710                 715                 720

Leu Val Thr Val Ser Ser Arg
                725


<210> SEQ ID NO 93
<211> LENGTH: 727
<212> TYPE: PRT
<213> ORGANISM: Artificial Sequence
<220> FEATURE:
<223> OTHER INFORMATION: Synthetic Peptide

<400> SEQUENCE: 93

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Asn Ile Tyr Pro Ser Gly Gly Ser Thr Asn Tyr Ala Gln Lys Phe
    50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Phe Ser Asp Gly Tyr Tyr Ala Tyr Ala Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Glu Ile Val
```

```
    130                 135                 140

Met Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ser Tyr Leu Asn Trp
                165                 170                 175

Tyr Gln Gln Lys Pro Gly Gln Ala Pro Arg Leu Leu Ile Tyr Tyr Ala
            180                 185                 190

Ser Arg Arg His Thr Gly Ile Pro Ala Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Val Tyr Tyr Cys Gln Gln Gly Tyr Asn Leu Pro Tyr Thr Phe Gly
225                 230                 235                 240

Gln Gly Thr Lys Val Glu Ile Lys Glu Pro Lys Ser Ser Asp Lys Thr
                245                 250                 255

His Thr Cys Pro Pro Cys Pro Ala Pro Pro Ala Ala Ala Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Ala Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Gly Gly
465                 470                 475                 480

Gly Ser Pro Ser Ser Tyr Val Leu Thr Gln Pro Pro Ser Val Ser Val
                485                 490                 495

Ala Pro Gly Gln Thr Ala Arg Ile Thr Cys Gly Gly Asn Asn Ile Gly
            500                 505                 510

Ser Lys Ser Val Asn Trp Phe Gln Gln Lys Pro Gly Gln Ala Pro Val
        515                 520                 525

Leu Val Val Tyr Asp Asp Ser Gly Arg Pro Ser Gly Ile Pro Ala Arg
    530                 535                 540

Phe Ser Gly Ser Thr Ser Gly Asn Thr Ala Thr Leu Thr Ile Ser Arg
545                 550                 555                 560
```

```
Val Glu Ala Gly Asp Glu Ala Asp Tyr Tyr Cys Gln Val Trp Asp Ser
                565                 570                 575

Ser Ser Asp His Val Val Phe Gly Gly Gly Thr Lys Leu Thr Val Leu
            580                 585                 590

Gly Gly Gly Gly Ser Gly Gly Gly Gly Ser Gly Gly Gly Gly Ser Gly
        595                 600                 605

Gly Gly Gly Ser Gln Val Gln Leu Val Glu Ser Gly Gly Gly Val Val
    610                 615                 620

Gln Pro Gly Arg Ser Leu Arg Leu Ser Cys Ala Ala Ser Gly Phe Thr
625                 630                 635                 640

Leu Ser Tyr Tyr Gly Met His Trp Val Arg Gln Ala Pro Gly Lys Gly
                645                 650                 655

Leu Glu Trp Val Ala Ala Ile Ser His Asp Gly Ser Asp Lys Tyr Tyr
            660                 665                 670

Ala Asp Ser Val Lys Gly Arg Phe Thr Ile Ser Arg Asp Asn Ser Lys
        675                 680                 685

Asn Arg Leu Tyr Leu Gln Met Asn Ser Leu Arg Ala Glu Asp Thr Ala
    690                 695                 700

Val Tyr Tyr Cys Ser Asn Asp Gln Phe Asp Pro Trp Gly Gln Gly Thr
705                 710                 715                 720

Leu Val Thr Val Ser Ser Arg
                725


<210> SEQ ID NO 94
<211> LENGTH: 727
<212> TYPE: PRT
<213> ORGANISM: Artificial Sequence
<220> FEATURE:
<223> OTHER INFORMATION: Synthetic Peptide

<400> SEQUENCE: 94

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Asn Ile Tyr Pro Ser Gly Gly Ser Thr Asn Tyr Ala Gln Lys Phe
    50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Phe Ser Asp Gly Tyr Tyr Ala Tyr Ala Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Glu Ile Val
    130                 135                 140

Met Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ser Tyr Leu Asn Trp
                165                 170                 175

Tyr Gln Gln Lys Pro Gly Gln Ala Pro Arg Leu Leu Ile Tyr Tyr Ala
            180                 185                 190
```

```
Ser Arg Arg His Thr Gly Ile Pro Ala Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Val Tyr Tyr Cys Gln Gln Gly Tyr Asn Leu Pro Tyr Thr Phe Gly
225                 230                 235                 240

Gln Gly Thr Lys Val Glu Ile Lys Glu Pro Lys Ser Ser Asp Lys Thr
                245                 250                 255

His Thr Cys Pro Pro Cys Pro Ala Pro Pro Ala Ala Ala Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Ala Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Gly Gly
465                 470                 475                 480

Gly Ser Pro Ser Ser Tyr Val Leu Thr Gln Pro Pro Ser Val Ser Val
                485                 490                 495

Ala Pro Gly Gln Thr Ala Arg Ile Thr Cys Gly Gly Asn Asn Ile Gly
            500                 505                 510

Ser Lys Ser Val Asn Trp Phe Gln Gln Lys Pro Gly Gln Ala Pro Val
        515                 520                 525

Leu Val Val Tyr Asp Asp Ser Gly Arg Pro Ser Gly Val Pro Asn Arg
    530                 535                 540

Phe Ser Gly Ser Thr Ser Gly Asn Thr Ala Thr Leu Thr Ile Ser Arg
545                 550                 555                 560

Val Glu Ala Gly Asp Glu Ala Asp Tyr Tyr Cys Gln Val Trp Asp Ser
                565                 570                 575

Ser Ser Asp His Val Val Phe Gly Gly Gly Thr Lys Leu Thr Val Leu
            580                 585                 590

Gly Gly Gly Gly Ser Gly Gly Gly Gly Ser Gly Gly Gly Gly Ser Gly
        595                 600                 605
```

```
Gly Gly Gly Ser Gln Val Gln Leu Val Glu Ser Gly Gly Gly Val Val
    610                 615                 620

Gln Pro Gly Arg Ser Leu Arg Leu Ser Cys Ala Ala Ser Gly Phe Thr
625                 630                 635                 640

Leu Ser Tyr Tyr Gly Met His Trp Val Arg Gln Ala Pro Gly Lys Gly
                645                 650                 655

Leu Glu Trp Val Ala Ala Ile Ser His Asp Gly Ser Asp Lys Tyr Tyr
            660                 665                 670

Ala Asp Ser Val Lys Gly Arg Phe Thr Ile Ser Arg Asp Asn Ser Lys
        675                 680                 685

Asn Arg Leu Tyr Leu Gln Met Asn Ser Leu Arg Ala Glu Asp Thr Ala
    690                 695                 700

Val Tyr Tyr Cys Ser Asn Asp Gln Phe Asp Pro Trp Gly Gln Gly Thr
705                 710                 715                 720

Leu Val Thr Val Ser Ser Arg
                725


<210> SEQ ID NO 95
<211> LENGTH: 727
<212> TYPE: PRT
<213> ORGANISM: Artificial Sequence
<220> FEATURE:
<223> OTHER INFORMATION: Synthetic Peptide

<400> SEQUENCE: 95

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Asn Ile Tyr Pro Ser Gly Gly Ser Thr Asn Tyr Ala Gln Lys Phe
    50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Phe Ser Asp Gly Tyr Tyr Ala Tyr Ala Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Glu Ile Val
    130                 135                 140

Met Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ser Tyr Leu Asn Trp
                165                 170                 175

Tyr Gln Gln Lys Pro Gly Gln Ala Pro Arg Leu Leu Ile Tyr Tyr Ala
            180                 185                 190

Ser Arg Arg His Thr Gly Ile Pro Ala Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Val Tyr Tyr Cys Gln Gln Gly Tyr Asn Leu Pro Tyr Thr Phe Gly
225                 230                 235                 240
```

```
Gln Gly Thr Lys Val Glu Ile Lys Glu Pro Lys Ser Ser Asp Lys Thr
                245                 250                 255

His Thr Cys Pro Pro Cys Pro Ala Pro Pro Ala Ala Ala Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Ala Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Gly Gly
465                 470                 475                 480

Gly Ser Pro Ser Ser Tyr Val Leu Thr Gln Pro Pro Ser Val Ser Val
                485                 490                 495

Ala Pro Gly Gln Thr Ala Arg Ile Thr Cys Gly Gly Asn Asn Ile Gly
            500                 505                 510

Ser Lys Ser Val Asn Trp Phe Gln Gln Lys Pro Gly Gln Ala Pro Val
        515                 520                 525

Leu Val Val Tyr Asp Asp Ser Gly Arg Pro Ser Gly Val Pro Ser Arg
    530                 535                 540

Phe Ser Gly Ser Thr Ser Gly Asn Thr Ala Thr Leu Thr Ile Ser Arg
545                 550                 555                 560

Val Glu Ala Gly Asp Glu Ala Asp Tyr Tyr Cys Gln Val Trp Asp Ser
                565                 570                 575

Ser Ser Asp His Val Val Phe Gly Gly Gly Thr Lys Leu Thr Val Leu
            580                 585                 590

Gly Gly Gly Gly Ser Gly Gly Gly Gly Ser Gly Gly Gly Gly Ser Gly
        595                 600                 605

Gly Gly Gly Ser Gln Val Gln Leu Val Glu Ser Gly Gly Gly Val Val
    610                 615                 620

Gln Pro Gly Arg Ser Leu Arg Leu Ser Cys Ala Ala Ser Gly Phe Thr
625                 630                 635                 640

Leu Ser Tyr Tyr Gly Met His Trp Val Arg Gln Ala Pro Gly Lys Gly
                645                 650                 655

Leu Glu Trp Val Ala Ala Ile Ser His Asp Gly Ser Asp Lys Tyr Tyr
```

```
            660                 665                 670

Ala Asp Ser Val Lys Gly Arg Phe Thr Ile Ser Arg Asp Asn Ser Lys
        675                 680                 685

Asn Arg Leu Tyr Leu Gln Met Asn Ser Leu Arg Ala Glu Asp Thr Ala
    690                 695                 700

Val Tyr Tyr Cys Ser Asn Asp Gln Phe Asp Pro Trp Gly Gln Gly Thr
705                 710                 715                 720

Leu Val Thr Val Ser Ser Arg
                725


<210> SEQ ID NO 96
<211> LENGTH: 727
<212> TYPE: PRT
<213> ORGANISM: Artificial Sequence
<220> FEATURE:
<223> OTHER INFORMATION: Synthetic Peptide

<400> SEQUENCE: 96

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Asn Ile Tyr Pro Ser Gly Gly Ser Thr Asn Tyr Ala Gln Lys Phe
    50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Phe Ser Asp Gly Tyr Tyr Ala Tyr Ala Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Glu Ile Val
    130                 135                 140

Met Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ser Tyr Leu Asn Trp
                165                 170                 175

Tyr Gln Gln Lys Pro Gly Gln Ala Pro Arg Leu Leu Ile Tyr Tyr Ala
            180                 185                 190

Ser Arg Arg His Thr Gly Ile Pro Ala Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Val Tyr Tyr Cys Gln Gln Gly Tyr Asn Leu Pro Tyr Thr Phe Gly
225                 230                 235                 240

Gln Gly Thr Lys Val Glu Ile Lys Glu Pro Lys Ser Ser Asp Lys Thr
                245                 250                 255

His Thr Cys Pro Pro Cys Pro Ala Pro Pro Ala Ala Ala Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
```

```
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Ala Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Gly Gly
465                 470                 475                 480

Gly Ser Pro Ser Ser Tyr Val Leu Thr Gln Pro Pro Ser Val Ser Val
                485                 490                 495

Ala Pro Gly Gln Thr Ala Arg Ile Thr Cys Gly Gly Asn Asn Ile Gly
            500                 505                 510

Ser Lys Ser Val Asn Trp Phe Gln Gln Lys Pro Gly Gln Ala Pro Val
        515                 520                 525

Leu Val Val Tyr Asp Asp Ser Gly Arg Pro Ser Gly Ile Pro Lys Arg
    530                 535                 540

Phe Ser Gly Ser Thr Ser Gly Asn Thr Ala Thr Leu Thr Ile Ser Arg
545                 550                 555                 560

Val Glu Ala Gly Asp Glu Ala Asp Tyr Tyr Cys Gln Val Trp Asp Ser
                565                 570                 575

Ser Ser Asp His Val Val Phe Gly Gly Gly Thr Lys Leu Thr Val Leu
            580                 585                 590

Gly Gly Gly Gly Ser Gly Gly Gly Gly Ser Gly Gly Gly Gly Ser Gly
        595                 600                 605

Gly Gly Gly Ser Gln Val Gln Leu Val Glu Ser Gly Gly Gly Val Val
    610                 615                 620

Gln Pro Gly Arg Ser Leu Arg Leu Ser Cys Ala Ala Ser Gly Phe Thr
625                 630                 635                 640

Leu Ser Tyr Tyr Gly Met His Trp Val Arg Gln Ala Pro Gly Lys Gly
                645                 650                 655

Leu Glu Trp Val Ala Ala Ile Ser His Asp Gly Ser Asp Lys Tyr Tyr
            660                 665                 670

Ala Asp Ser Val Lys Gly Arg Phe Thr Ile Ser Arg Asp Asn Ser Lys
        675                 680                 685

Asn Arg Leu Tyr Leu Gln Met Asn Ser Leu Arg Ala Glu Asp Thr Ala
    690                 695                 700

Val Tyr Tyr Cys Ser Asn Asp Gln Phe Asp Pro Trp Gly Gln Gly Thr
705                 710                 715                 720
```

```
Leu Val Thr Val Ser Ser Arg
                725


<210> SEQ ID NO 97
<211> LENGTH: 727
<212> TYPE: PRT
<213> ORGANISM: Artificial Sequence
<220> FEATURE:
<223> OTHER INFORMATION: Synthetic Peptide

<400> SEQUENCE: 97

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Asn Ile Tyr Pro Ser Gly Gly Ser Thr Asn Tyr Ala Gln Lys Phe
    50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Phe Ser Asp Gly Tyr Tyr Ala Tyr Ala Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Glu Ile Val
    130                 135                 140

Met Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ser Tyr Leu Asn Trp
                165                 170                 175

Tyr Gln Gln Lys Pro Gly Gln Ala Pro Arg Leu Leu Ile Tyr Tyr Ala
            180                 185                 190

Ser Arg Arg His Thr Gly Ile Pro Ala Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Val Tyr Tyr Cys Gln Gln Gly Tyr Asn Leu Pro Tyr Thr Phe Gly
225                 230                 235                 240

Gln Gly Thr Lys Val Glu Ile Lys Glu Pro Lys Ser Ser Asp Lys Thr
                245                 250                 255

His Thr Cys Pro Pro Cys Pro Ala Pro Pro Ala Ala Ala Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350
```

```
Cys Ala Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Gly Gly
465                 470                 475                 480

Gly Ser Pro Ser Ser Tyr Val Leu Thr Gln Pro Pro Ser Val Ser Val
                485                 490                 495

Ala Pro Gly Lys Thr Ala Arg Ile Thr Cys Gly Gly Asn Asn Ile Gly
            500                 505                 510

Ser Lys Ser Val Asn Trp Phe Gln Gln Lys Pro Gly Gln Ala Pro Val
        515                 520                 525

Leu Val Val Tyr Asp Asp Ser Gly Arg Pro Ser Gly Ile Pro Ala Arg
    530                 535                 540

Phe Ser Gly Ser Thr Ser Gly Asn Thr Ala Thr Leu Thr Ile Ser Arg
545                 550                 555                 560

Val Glu Ala Gly Asp Glu Ala Asp Tyr Tyr Cys Gln Val Trp Asp Ser
                565                 570                 575

Ser Ser Asp His Val Val Phe Gly Gly Gly Thr Lys Leu Thr Val Leu
            580                 585                 590

Gly Gly Gly Gly Ser Gly Gly Gly Gly Ser Gly Gly Gly Gly Ser Gly
        595                 600                 605

Gly Gly Gly Ser Gln Val Gln Leu Val Glu Ser Gly Gly Gly Val Val
    610                 615                 620

Gln Pro Gly Arg Ser Leu Arg Leu Ser Cys Ala Ala Ser Gly Phe Thr
625                 630                 635                 640

Leu Ser Tyr Tyr Gly Met His Trp Val Arg Gln Ala Pro Gly Lys Gly
                645                 650                 655

Leu Glu Trp Val Ala Ala Ile Ser His Asp Gly Ser Asp Lys Tyr Tyr
            660                 665                 670

Ala Asp Ser Val Lys Gly Arg Phe Thr Ile Ser Arg Asp Asn Ser Lys
        675                 680                 685

Asn Arg Leu Tyr Leu Gln Met Asn Ser Leu Arg Ala Glu Asp Thr Ala
    690                 695                 700

Val Tyr Tyr Cys Ser Asn Asp Gln Phe Asp Pro Trp Gly Gln Gly Thr
705                 710                 715                 720

Leu Val Thr Val Ser Ser Arg
                725
```

<210> SEQ ID NO 98
<211> LENGTH: 727
<212> TYPE: PRT
<213> ORGANISM: Artificial Sequence
<220> FEATURE:

<223> OTHER INFORMATION: Synthetic Peptide

<400> SEQUENCE: 98

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Asn Ile Tyr Pro Ser Gly Gly Ser Thr Asn Tyr Ala Gln Lys Phe
    50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Phe Ser Asp Gly Tyr Tyr Ala Tyr Ala Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Glu Ile Val
    130                 135                 140

Met Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ser Tyr Leu Asn Trp
                165                 170                 175

Tyr Gln Gln Lys Pro Gly Gln Ala Pro Arg Leu Leu Ile Tyr Tyr Ala
            180                 185                 190

Ser Arg Arg His Thr Gly Ile Pro Ala Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Val Tyr Tyr Cys Gln Gln Gly Tyr Asn Leu Pro Tyr Thr Phe Gly
225                 230                 235                 240

Gln Gly Thr Lys Val Glu Ile Lys Glu Pro Lys Ser Ser Asp Lys Thr
                245                 250                 255

His Thr Cys Pro Pro Cys Pro Ala Pro Pro Ala Ala Ala Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Ala Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
405 410 415

Gly Gln Pro Glu Asn Asn Tyr Lys Thr Thr Pro Pro Val Leu Asp Ser
420 425 430

Asp Gly Ser Phe Phe Leu Tyr Ser Lys Leu Thr Val Asp Lys Ser Arg
435 440 445

Trp Gln Gln Gly Asn Val Phe Ser Cys Ser Val Met His Glu Ala Leu
450 455 460

His Asn His Tyr Thr Gln Lys Ser Leu Ser Leu Ser Pro Gly Gly Gly
465 470 475 480

Gly Ser Pro Ser Ser Tyr Val Leu Thr Gln Pro Pro Ser Val Ser Val
485 490 495

Ala Pro Gly Lys Thr Ala Arg Ile Thr Cys Gly Gly Asn Asn Ile Gly
500 505 510

Ser Lys Ser Val Asn Trp Phe Gln Gln Lys Pro Gly Gln Ala Pro Val
515 520 525

Leu Val Val Tyr Asp Asp Ser Gly Arg Pro Ser Gly Val Pro Asn Arg
530 535 540

Phe Ser Gly Ser Thr Ser Gly Asn Thr Ala Thr Leu Thr Ile Ser Arg
545 550 555 560

Val Glu Ala Gly Asp Glu Ala Asp Tyr Tyr Cys Gln Val Trp Asp Ser
565 570 575

Ser Ser Asp His Val Val Phe Gly Gly Gly Thr Lys Leu Thr Val Leu
580 585 590

Gly Gly Gly Gly Ser Gly Gly Gly Gly Ser Gly Gly Gly Gly Ser Gly
595 600 605

Gly Gly Gly Ser Gln Val Gln Leu Val Glu Ser Gly Gly Gly Val Val
610 615 620

Gln Pro Gly Arg Ser Leu Arg Leu Ser Cys Ala Ala Ser Gly Phe Thr
625 630 635 640

Leu Ser Tyr Tyr Gly Met His Trp Val Arg Gln Ala Pro Gly Lys Gly
645 650 655

Leu Glu Trp Val Ala Ala Ile Ser His Asp Gly Ser Asp Lys Tyr Tyr
660 665 670

Ala Asp Ser Val Lys Gly Arg Phe Thr Ile Ser Arg Asp Asn Ser Lys
675 680 685

Asn Arg Leu Tyr Leu Gln Met Asn Ser Leu Arg Ala Glu Asp Thr Ala
690 695 700

Val Tyr Tyr Cys Ser Asn Asp Gln Phe Asp Pro Trp Gly Gln Gly Thr
705 710 715 720

Leu Val Thr Val Ser Ser Arg
725

<210> SEQ ID NO 99
<211> LENGTH: 727
<212> TYPE: PRT
<213> ORGANISM: Artificial Sequence
<220> FEATURE:
<223> OTHER INFORMATION: Synthetic Peptide

<400> SEQUENCE: 99

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

```
Trp Met Asn Trp Val Arg Gln Ala Pro Gly Gln Gly Leu Glu Trp Met
        35                  40                  45

Gly Asn Ile Tyr Pro Ser Gly Gly Ser Thr Asn Tyr Ala Gln Lys Phe
    50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Phe Ser Asp Gly Tyr Tyr Ala Tyr Ala Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Glu Ile Val
    130                 135                 140

Met Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ser Tyr Leu Asn Trp
                165                 170                 175

Tyr Gln Gln Lys Pro Gly Gln Ala Pro Arg Leu Leu Ile Tyr Tyr Ala
            180                 185                 190

Ser Arg Arg His Thr Gly Ile Pro Ala Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Val Tyr Tyr Cys Gln Gln Gly Tyr Asn Leu Pro Tyr Thr Phe Gly
225                 230                 235                 240

Gln Gly Thr Lys Val Glu Ile Lys Glu Pro Lys Ser Ser Asp Lys Thr
                245                 250                 255

His Thr Cys Pro Pro Cys Pro Ala Pro Pro Ala Ala Ala Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Ala Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
```

```
    450                 455                 460

His Asn His Tyr Thr Gln Lys Ser Leu Ser Leu Ser Pro Gly Gly Gly
465                 470                 475                 480

Gly Ser Pro Ser Ser Tyr Val Leu Thr Gln Pro Pro Ser Val Ser Val
                485                 490                 495

Ala Pro Gly Lys Thr Ala Arg Ile Thr Cys Gly Gly Asn Asn Ile Gly
            500                 505                 510

Ser Lys Ser Val Asn Trp Phe Gln Gln Lys Pro Gly Gln Ala Pro Val
        515                 520                 525

Leu Val Val Tyr Asp Asp Ser Gly Arg Pro Ser Gly Val Pro Ser Arg
    530                 535                 540

Phe Ser Gly Ser Thr Ser Gly Asn Thr Ala Thr Leu Thr Ile Ser Arg
545                 550                 555                 560

Val Glu Ala Gly Asp Glu Ala Asp Tyr Tyr Cys Gln Val Trp Asp Ser
                565                 570                 575

Ser Ser Asp His Val Val Phe Gly Gly Gly Thr Lys Leu Thr Val Leu
            580                 585                 590

Gly Gly Gly Gly Ser Gly Gly Gly Gly Ser Gly Gly Gly Gly Ser Gly
        595                 600                 605

Gly Gly Gly Ser Gln Val Gln Leu Val Glu Ser Gly Gly Gly Val Val
    610                 615                 620

Gln Pro Gly Arg Ser Leu Arg Leu Ser Cys Ala Ala Ser Gly Phe Thr
625                 630                 635                 640

Leu Ser Tyr Tyr Gly Met His Trp Val Arg Gln Ala Pro Gly Lys Gly
                645                 650                 655

Leu Glu Trp Val Ala Ala Ile Ser His Asp Gly Ser Asp Lys Tyr Tyr
            660                 665                 670

Ala Asp Ser Val Lys Gly Arg Phe Thr Ile Ser Arg Asp Asn Ser Lys
        675                 680                 685

Asn Arg Leu Tyr Leu Gln Met Asn Ser Leu Arg Ala Glu Asp Thr Ala
    690                 695                 700

Val Tyr Tyr Cys Ser Asn Asp Gln Phe Asp Pro Trp Gly Gln Gly Thr
705                 710                 715                 720

Leu Val Thr Val Ser Ser Arg
                725


<210> SEQ ID NO 100
<211> LENGTH: 727
<212> TYPE: PRT
<213> ORGANISM: Artificial Sequence
<220> FEATURE:
<223> OTHER INFORMATION: Synthetic Peptide

<400> SEQUENCE: 100

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Asn Ile Tyr Pro Ser Gly Gly Ser Thr Asn Tyr Ala Gln Lys Phe
    50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
```

-continued

```
                85                  90                  95

Ala Ser Phe Ser Asp Gly Tyr Tyr Ala Tyr Ala Met Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Glu Ile Val
    130                 135                 140

Met Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ser Tyr Leu Asn Trp
                165                 170                 175

Tyr Gln Gln Lys Pro Gly Gln Ala Pro Arg Leu Leu Ile Tyr Tyr Ala
            180                 185                 190

Ser Arg Arg His Thr Gly Ile Pro Ala Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Val Tyr Tyr Cys Gln Gln Gly Tyr Asn Leu Pro Tyr Thr Phe Gly
225                 230                 235                 240

Gln Gly Thr Lys Val Glu Ile Lys Glu Pro Lys Ser Ser Asp Lys Thr
                245                 250                 255

His Thr Cys Pro Pro Cys Pro Ala Pro Pro Ala Ala Ala Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Ala Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Gly Gly
465                 470                 475                 480

Gly Ser Pro Ser Ser Tyr Val Leu Thr Gln Pro Pro Ser Val Ser Val
                485                 490                 495

Ala Pro Gly Lys Thr Ala Arg Ile Thr Cys Gly Gly Asn Asn Ile Gly
            500                 505                 510
```

```
Ser Lys Ser Val Asn Trp Phe Gln Gln Lys Pro Gly Gln Ala Pro Val
        515                 520                 525

Leu Val Val Tyr Asp Asp Ser Gly Arg Pro Ser Gly Ile Pro Lys Arg
    530                 535                 540

Phe Ser Gly Ser Thr Ser Gly Asn Thr Ala Thr Leu Thr Ile Ser Arg
545                 550                 555                 560

Val Glu Ala Gly Asp Glu Ala Asp Tyr Tyr Cys Gln Val Trp Asp Ser
                565                 570                 575

Ser Ser Asp His Val Val Phe Gly Gly Gly Thr Lys Leu Thr Val Leu
            580                 585                 590

Gly Gly Gly Gly Ser Gly Gly Gly Gly Ser Gly Gly Gly Gly Ser Gly
        595                 600                 605

Gly Gly Gly Ser Gln Val Gln Leu Val Glu Ser Gly Gly Gly Val Val
    610                 615                 620

Gln Pro Gly Arg Ser Leu Arg Leu Ser Cys Ala Ala Ser Gly Phe Thr
625                 630                 635                 640

Leu Ser Tyr Tyr Gly Met His Trp Val Arg Gln Ala Pro Gly Lys Gly
                645                 650                 655

Leu Glu Trp Val Ala Ala Ile Ser His Asp Gly Ser Asp Lys Tyr Tyr
            660                 665                 670

Ala Asp Ser Val Lys Gly Arg Phe Thr Ile Ser Arg Asp Asn Ser Lys
        675                 680                 685

Asn Arg Leu Tyr Leu Gln Met Asn Ser Leu Arg Ala Glu Asp Thr Ala
    690                 695                 700

Val Tyr Tyr Cys Ser Asn Asp Gln Phe Asp Pro Trp Gly Gln Gly Thr
705                 710                 715                 720

Leu Val Thr Val Ser Ser Arg
                725


<210> SEQ ID NO 101
<211> LENGTH: 488
<212> TYPE: PRT
<213> ORGANISM: Artificial Sequence
<220> FEATURE:
<223> OTHER INFORMATION: Synthetic Peptide

<400> SEQUENCE: 101

Ser Ser Glu Pro Lys Ser Ser Asp Lys Thr His Thr Cys Pro Pro Cys
1               5                   10                  15

Pro Ala Pro Glu Leu Leu Gly Gly Pro Ser Val Phe Leu Phe Pro Pro
            20                  25                  30

Lys Pro Lys Asp Thr Leu Met Ile Ser Arg Thr Pro Glu Val Thr Cys
        35                  40                  45

Val Val Val Asp Val Ser His Glu Asp Pro Glu Val Lys Phe Asn Trp
    50                  55                  60

Tyr Val Asp Gly Val Glu Val His Asn Ala Lys Thr Lys Pro Arg Glu
65                  70                  75                  80

Glu Gln Tyr Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Ala Leu Pro Ala Pro Ile Glu Lys Thr Ile Ser Lys Ala Lys Gly
        115                 120                 125

Gln Pro Arg Glu Pro Gln Val Tyr Thr Leu Pro Pro Ser Arg Asp Glu
    130                 135                 140
```

Leu Thr Lys Asn Gln Val Ser Leu Thr Cys Leu Val Lys Gly Phe Tyr
145 150 155 160

Pro Ser Asp Ile Ala Val Glu Trp Glu Ser Asn Gly Gln Pro Glu Asn
165 170 175

Asn Tyr Lys Thr Thr Pro Pro Val Leu Asp Ser Asp Gly Ser Phe Phe
180 185 190

Leu Tyr Ser Lys Leu Thr Val Asp Lys Ser Arg Trp Gln Gln Gly Asn
195 200 205

Val Phe Ser Cys Ser Val Met His Glu Ala Leu His Asn His Tyr Thr
210 215 220

Gln Lys Ser Leu Ser Leu Ser Pro Gly Gly Gly Gly Ser Pro Ser Gln
225 230 235 240

Val Gln Leu Gln Gln Pro Gly Ala Glu Leu Val Lys Pro Gly Ala Ser
245 250 255

Val Lys Leu Ser Cys Glu Ala Ser Gly Tyr Thr Phe Thr Ser Tyr Trp
260 265 270

Ile Asn Trp Val Lys Gln Arg Pro Gly Gln Gly Leu Glu Trp Ile Gly
275 280 285

Asn Ile Tyr Pro Gly Ser Ser Thr Thr Asn Tyr Asn Glu Lys Phe Lys
290 295 300

Ser Lys Ala Thr Leu Thr Val Asp Thr Ser Ser Ser Thr Ala Tyr Met
305 310 315 320

Gln Leu Ser Ser Leu Thr Ser Asp Asp Ser Ala Val Phe Tyr Cys Ala
325 330 335

Ser Phe Ser Asp Gly Tyr Tyr Ala Tyr Ala Met Asp Tyr Trp Val Gln
340 345 350

Gly Thr Ser Val Thr Val Ser Ser Gly Gly Gly Gly Ser Gly Gly Gly
355 360 365

Gly Ser Gly Gly Gly Gly Ser Gly Gly Gly Gly Ser Asp Ile Gln Met
370 375 380

Thr Gln Thr Thr Ser Ser Leu Ser Ala Ser Leu Gly Asp Arg Val Thr
385 390 395 400

Ile Thr Cys Arg Ala Ser Gln Asp Ile Ser Asn Tyr Leu Asn Trp Tyr
405 410 415

Gln Gln Lys Pro Asp Gly Thr Val Lys Leu Leu Ile Tyr Tyr Thr Ser
420 425 430

Arg Leu His Ser Gly Val Pro Ser Arg Phe Ser Gly Gly Gly Ser Gly
435 440 445

Thr Asp Tyr Ser Leu Thr Ile Ser Asn Leu Glu Gln Glu Asp Ile Ala
450 455 460

Thr Tyr Phe Cys Gln Gln Gly Tyr Thr Leu Pro Tyr Thr Phe Gly Gly
465 470 475 480

Gly Thr Lys Leu Glu Ile Lys Arg
485

<210> SEQ ID NO 102
<211> LENGTH: 475
<212> TYPE: PRT
<213> ORGANISM: Artificial Sequence
<220> FEATURE:
<223> OTHER INFORMATION: Synthetic Peptide

<400> SEQUENCE: 102

Ser Tyr Val Leu Thr Gln Pro Pro Ser Val Ser Val Ala Pro Gly Gln
1 5 10 15

-continued

```
Thr Ala Arg Ile Thr Cys Gly Gly Asn Asn Ile Gly Ser Lys Ser Val
            20                  25                  30

His Trp Phe Gln Gln Lys Pro Gly Gln Ala Pro Ala Leu Val Val Tyr
        35                  40                  45

Asp Asp Ser Gly Arg Pro Ser Gly Ile Pro Glu Arg Phe Ser Gly Ser
    50                  55                  60

Thr Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Glu Ser Gly Gly Gly Val Val Gln Pro Gly Arg
    130                 135                 140

Ser Leu Arg Leu Ser Cys Ala Ala Ser Gly Phe Thr Leu Ser Tyr Tyr
145                 150                 155                 160

Gly Met His Trp Val Arg Gln Ala Pro Gly Lys Gly Leu Glu Trp Val
                165                 170                 175

Ala Val Ile Ser His Asp Gly Ser Asp Lys Tyr Tyr Ala Asp Ser Val
            180                 185                 190

Lys Gly Arg Phe Thr Ile Ser Arg Asp Asn Ser Lys Asn Thr Leu Tyr
        195                 200                 205

Leu Gln Met Asp Ser Leu Arg Ala Glu Asp Thr Ala Leu Tyr Tyr Cys
    210                 215                 220

Ser Asn Asp Gln Phe Asp Pro Trp Gly Gln Gly Thr Leu Val Thr Val
225                 230                 235                 240

Ser Ser Ser Glu Pro Lys Ser Ser Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430
```

```
Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475


<210> SEQ ID NO 103
<211> LENGTH: 214
<212> TYPE: PRT
<213> ORGANISM: Artificial Sequence
<220> FEATURE:
<223> OTHER INFORMATION: HUMAN CD137 ECD-AVI-FLAG-HIS

<400> SEQUENCE: 103

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
    50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Val Thr Pro Pro Ala Pro Ala Arg Glu Pro Gly His
145                 150                 155                 160

Ser Pro Gln Ser Ser Ser Leu Asn Asp Ile Phe Glu Ala Gln Lys Ile
                165                 170                 175

Glu Trp His Glu Asp Tyr Lys Asp Asp Asp Asp Lys Asp Tyr Lys Asp
            180                 185                 190

Asp Asp Asp Lys Asp Tyr Lys Asp Asp Asp Asp Lys His His His His
        195                 200                 205

His His His His His His
    210


<210> SEQ ID NO 104
<211> LENGTH: 399
<212> TYPE: PRT
<213> ORGANISM: Artificial Sequence
<220> FEATURE:
<223> OTHER INFORMATION: Human CD137 ECD-mFc

<400> SEQUENCE: 104

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45
```

Phe Arg Thr Arg Lys Glu Cys Ser Ser Thr Ser Asn Ala Glu Cys Asp
    50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Val Thr Pro Pro Ala Pro Ala Arg Glu Pro Gly His
145                 150                 155                 160

Ser Pro Gln Ser Ser Ser Glu Pro Arg Gly Pro Thr Ile Lys Pro Cys
                165                 170                 175

Pro Pro Cys Lys Cys Pro Ala Pro Asn Leu Leu Gly Gly Pro Ser Val
            180                 185                 190

Phe Ile Phe Pro Pro Lys Ile Lys Asp Val Leu Met Ile Ser Leu Ser
        195                 200                 205

Pro Ile Val Thr Cys Val Val Val Asp Val Ser Glu Asp Asp Pro Asp
    210                 215                 220

Val Gln Ile Ser Trp Phe Val Asn Asn Val Glu Val His Thr Ala Gln
225                 230                 235                 240

Thr Gln Thr His Arg Glu Asp Tyr Asn Ser Thr Leu Arg Val Val Ser
                245                 250                 255

Ala Leu Pro Ile Gln His Gln Asp Trp Met Ser Gly Lys Glu Phe Lys
            260                 265                 270

Cys Lys Val Asn Asn Lys Asp Leu Pro Ala Pro Ile Glu Arg Thr Ile
        275                 280                 285

Ser Lys Pro Lys Gly Ser Val Arg Ala Pro Gln Val Tyr Val Leu Pro
    290                 295                 300

Pro Pro Glu Glu Glu Met Thr Lys Lys Gln Val Thr Leu Thr Cys Met
305                 310                 315                 320

Val Thr Asp Phe Met Pro Glu Asp Ile Tyr Val Glu Trp Thr Asn Asn
                325                 330                 335

Gly Lys Thr Glu Leu Asn Tyr Lys Asn Thr Glu Pro Val Leu Asp Ser
            340                 345                 350

Asp Gly Ser Tyr Phe Met Tyr Ser Lys Leu Arg Val Glu Lys Lys Asn
        355                 360                 365

Trp Val Glu Arg Asn Ser Tyr Ser Cys Ser Val Val His Glu Gly Leu
    370                 375                 380

His Asn His His Thr Thr Lys Ser Phe Ser Arg Thr Pro Gly Lys
385                 390                 395

<210> SEQ ID NO 105
<211> LENGTH: 214
<212> TYPE: PRT
<213> ORGANISM: Artificial Sequence
<220> FEATURE:
<223> OTHER INFORMATION: Cyno CD137 ECD-avi-flag-his

<400> SEQUENCE: 105

Leu Gln Asp Leu Cys Ser Asn Cys Pro Ala Gly Thr Phe Cys Asp Asn
1               5                   10                  15

```
Asn Arg Ser Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Lys Thr Arg Lys Glu Cys Ser Ser Thr Ser Asn Ala Glu Cys Asp
    50                  55                  60

Cys Ile Ser Gly Tyr His Cys Leu Gly Ala Glu Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Ala Thr Pro Pro Ala Pro Ala Arg Glu Pro Gly His
145                 150                 155                 160

Ser Pro Gln Ser Ser Ser Leu Asn Asp Ile Phe Glu Ala Gln Lys Ile
                165                 170                 175

Glu Trp His Glu Asp Tyr Lys Asp Asp Asp Asp Lys Asp Tyr Lys Asp
            180                 185                 190

Asp Asp Asp Lys Asp Tyr Lys Asp Asp Asp Asp Lys His His His His
        195                 200                 205

His His His His His His
    210


<210> SEQ ID NO 106
<211> LENGTH: 399
<212> TYPE: PRT
<213> ORGANISM: Artificial Sequence
<220> FEATURE:
<223> OTHER INFORMATION: Cyno CD137 ECD-mFc

<400> SEQUENCE: 106

Leu Gln Asp Leu Cys Ser Asn Cys Pro Ala Gly Thr Phe Cys Asp Asn
1               5                   10                  15

Asn Arg Ser Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Lys Thr Arg Lys Glu Cys Ser Ser Thr Ser Asn Ala Glu Cys Asp
    50                  55                  60

Cys Ile Ser Gly Tyr His Cys Leu Gly Ala Glu Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Ala Thr Pro Pro Ala Pro Ala Arg Glu Pro Gly His
145                 150                 155                 160
```

```
Ser Pro Gln Ser Ser Ser Glu Pro Arg Gly Pro Thr Ile Lys Pro Cys
                165                 170                 175

Pro Pro Cys Lys Cys Pro Ala Pro Asn Leu Leu Gly Gly Pro Ser Val
            180                 185                 190

Phe Ile Phe Pro Pro Lys Ile Lys Asp Val Leu Met Ile Ser Leu Ser
        195                 200                 205

Pro Ile Val Thr Cys Val Val Val Asp Val Ser Glu Asp Asp Pro Asp
    210                 215                 220

Val Gln Ile Ser Trp Phe Val Asn Asn Val Glu Val His Thr Ala Gln
225                 230                 235                 240

Thr Gln Thr His Arg Glu Asp Tyr Asn Ser Thr Leu Arg Val Val Ser
                245                 250                 255

Ala Leu Pro Ile Gln His Gln Asp Trp Met Ser Gly Lys Glu Phe Lys
            260                 265                 270

Cys Lys Val Asn Asn Lys Asp Leu Pro Ala Pro Ile Glu Arg Thr Ile
        275                 280                 285

Ser Lys Pro Lys Gly Ser Val Arg Ala Pro Gln Val Tyr Val Leu Pro
    290                 295                 300

Pro Pro Glu Glu Glu Met Thr Lys Lys Gln Val Thr Leu Thr Cys Met
305                 310                 315                 320

Val Thr Asp Phe Met Pro Glu Asp Ile Tyr Val Glu Trp Thr Asn Asn
                325                 330                 335

Gly Lys Thr Glu Leu Asn Tyr Lys Asn Thr Glu Pro Val Leu Asp Ser
            340                 345                 350

Asp Gly Ser Tyr Phe Met Tyr Ser Lys Leu Arg Val Glu Lys Lys Asn
        355                 360                 365

Trp Val Glu Arg Asn Ser Tyr Ser Cys Ser Val Val His Glu Gly Leu
    370                 375                 380

His Asn His His Thr Thr Lys Ser Phe Ser Arg Thr Pro Gly Lys
385                 390                 395
```

<210> SEQ ID NO 107
<211> LENGTH: 232
<212> TYPE: PRT
<213> ORGANISM: Artificial Sequence
<220> FEATURE:
<223> OTHER INFORMATION: Human OX40 ECD-avi-flag-his

<400> SEQUENCE: 107

```
Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
        35                  40                  45

Ser Ser Lys Pro Cys Lys Pro Cys Thr Trp Cys Asn Leu Arg Ser Gly
    50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125
```

Pro Ala Ser Asn Ser Ser Asp Ala Ile Cys Glu Asp Arg Asp Pro Pro
130 135 140

Ala Thr Gln Pro Gln Glu Thr Gln Gly Pro Pro Ala Arg Pro Ile Thr
145 150 155 160

Val Gln Pro Thr Glu Ala Trp Pro Arg Thr Ser Gln Gly Pro Ser Thr
165 170 175

Arg Pro Val Glu Val Pro Gly Gly Arg Ala Thr Gly Leu Asn Asp Ile
180 185 190

Phe Glu Ala Gln Lys Ile Glu Trp His Glu Asp Tyr Lys Asp Asp Asp
195 200 205

Asp Lys Asp Tyr Lys Asp Asp Asp Asp Lys Asp Tyr Lys Asp Asp Asp
210 215 220

Asp Lys His His His His His His
225 230

<210> SEQ ID NO 108
<211> LENGTH: 233
<212> TYPE: PRT
<213> ORGANISM: Artificial Sequence
<220> FEATURE:
<223> OTHER INFORMATION: Cyno OX40 ECD-avi-flag-his

<400> SEQUENCE: 108

Lys Leu His Cys Val Gly Asp Thr Tyr Pro Ser Asn Asp Arg Cys Cys
1 5 10 15

Gln Glu Cys Arg Pro Gly Asn Gly Met Val Ser Arg Cys Asn Arg Ser
20 25 30

Gln Asn Thr Val Cys Arg Pro Cys Gly Pro Gly Phe Tyr Asn Asp Val
35 40 45

Val Ser Ala Lys Pro Cys Lys Ala Cys Thr Trp Cys Asn Leu Arg Ser
50 55 60

Gly Ser Glu Arg Lys Gln Pro Cys Thr Ala Thr Gln Asp Thr Val Cys
65 70 75 80

Arg Cys Arg Ala Gly Thr Gln Pro Leu Asp Ser Tyr Lys Pro Gly Val
85 90 95

Asp Cys Ala Pro Cys Pro Pro Gly His Phe Ser Pro Gly Asp Asn Gln
100 105 110

Ala Cys Lys Pro Trp Thr Asn Cys Thr Leu Ala Gly Lys His Thr Leu
115 120 125

Gln Pro Ala Ser Asn Ser Ser Asp Ala Ile Cys Glu Asp Arg Asp Pro
130 135 140

Pro Pro Thr Gln Pro Gln Glu Thr Gln Gly Pro Pro Ala Arg Pro Thr
145 150 155 160

Thr Val Gln Pro Thr Glu Ala Trp Pro Arg Thr Ser Gln Arg Pro Ser
165 170 175

Thr Arg Pro Val Glu Val Pro Arg Gly Pro Ala Thr Gly Leu Asn Asp
180 185 190

Ile Phe Glu Ala Gln Lys Ile Glu Trp His Glu Asp Tyr Lys Asp Asp
195 200 205

Asp Asp Lys Asp Tyr Lys Asp Asp Asp Asp Lys Asp Tyr Lys Asp Asp
210 215 220

Asp Asp Lys His His His His His His
225 230

<210> SEQ ID NO 109

<211> LENGTH: 18
<212> TYPE: PRT
<213> ORGANISM: Artificial Sequence
<220> FEATURE:
<223> OTHER INFORMATION: linker

<400> SEQUENCE: 109

```
Ala Gly Gly Gly Gly Ser Gly Gly Gly Gly Ser Gly Gly Gly Gly Ser
1               5                   10                  15

Pro Ser
```

<210> SEQ ID NO 110
<211> LENGTH: 8
<212> TYPE: PRT
<213> ORGANISM: Artificial Sequence
<220> FEATURE:
<223> OTHER INFORMATION: AGGGGSPS

<400> SEQUENCE: 110

```
Ala Gly Gly Gly Gly Ser Pro Ser
1               5
```

<210> SEQ ID NO 111
<211> LENGTH: 231
<212> TYPE: PRT
<213> ORGANISM: Artificial Sequence
<220> FEATURE:
<223> OTHER INFORMATION: Synthetic Peptide

<400> SEQUENCE: 111

```
Glu Pro Lys Ser Ser Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Ala Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
```

225 230

<210> SEQ ID NO 112
<211> LENGTH: 231
<212> TYPE: PRT
<213> ORGANISM: Artificial Sequence
<220> FEATURE:
<223> OTHER INFORMATION: PVAG TSC01004

<400> SEQUENCE: 112

Glu Pro Lys Ser Ser Asp Lys Thr His Thr Cys Pro Pro Cys Pro Ala
1 5 10 15

Pro Pro Val Ala Gly Ala Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Ala Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Tyr Thr Leu Pro Pro Ser Arg Asp Glu Leu Thr
130 135 140

Lys Asn Gln Val Ser Leu Thr Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly
225 230

<210> SEQ ID NO 113
<211> LENGTH: 230
<212> TYPE: PRT
<213> ORGANISM: Artificial Sequence
<220> FEATURE:
<223> OTHER INFORMATION: PVAdel TSC01005

<400> SEQUENCE: 113

Glu Pro Lys Ser Ser Asp Lys Thr His Thr Cys Pro Pro Cys Pro Ala
1 5 10 15

Pro Pro Val Ala Ala Pro Ser Val Phe Leu Phe Pro Pro Lys Pro Lys
20 25 30

Asp Thr Leu Met Ile Ser Arg Thr Pro Glu Val Thr Cys Val Val Val
35 40 45

Asp Val Ser His Glu Asp Pro Glu Val Lys Phe Asn Trp Tyr Val Asp
50 55 60

```
Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Ala Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly
225                 230


<210> SEQ ID NO 114
<211> LENGTH: 231
<212> TYPE: PRT
<213> ORGANISM: Artificial Sequence
<220> FEATURE:
<223> OTHER INFORMATION: PAAG TSC01006

<400> SEQUENCE: 114

Glu Pro Lys Ser Ser Asp Lys Thr His Thr Cys Pro Pro Cys Pro Ala
1               5                   10                  15

Pro Pro Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Ala Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190
```

```
Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230


<210> SEQ ID NO 115
<211> LENGTH: 230
<212> TYPE: PRT
<213> ORGANISM: Artificial Sequence
<220> FEATURE:
<223> OTHER INFORMATION: PAAdel TSC01007

<400> SEQUENCE: 115

Glu Pro Lys Ser Ser Asp Lys Thr His Thr Cys Pro Pro Cys Pro Ala
1               5                   10                  15

Pro Pro Ala Ala Ala Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Ala Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly
225                 230


<210> SEQ ID NO 116
<211> LENGTH: 21
<212> TYPE: PRT
<213> ORGANISM: Artificial Sequence
<220> FEATURE:
<223> OTHER INFORMATION: peptide linker

<400> SEQUENCE: 116

Gly Gly Gly Gly Ser Ser Ser Gly Gly Gly Gly Ser Ser Ser Gly Gly
1               5                   10                  15

Gly Gly Ser Ser Ser
            20
```

<210> SEQ ID NO 117
<211> LENGTH: 5
<212> TYPE: PRT
<213> ORGANISM: Artificial Sequence
<220> FEATURE:
<223> OTHER INFORMATION: peptide linker
<220> FEATURE:
<221> NAME/KEY: misc_feature
<222> LOCATION: (1)..(5)
<223> OTHER INFORMATION: wherein the sequence can be repeated between
1-5 times

<400> SEQUENCE: 117

Gly Gly Gly Gly Ser
1 5

<210> SEQ ID NO 118
<211> LENGTH: 6
<212> TYPE: PRT
<213> ORGANISM: Artificial Sequence
<220> FEATURE:
<223> OTHER INFORMATION: peptide linker

<400> SEQUENCE: 118

Gly Gly Gly Ser Pro Ser
1 5

<210> SEQ ID NO 119
<211> LENGTH: 8
<212> TYPE: PRT
<213> ORGANISM: Artificial Sequence
<220> FEATURE:
<223> OTHER INFORMATION: VH CDR2

<400> SEQUENCE: 119

Ile Tyr Pro Gly Ser Ser Thr Thr
1 5

<210> SEQ ID NO 120
<211> LENGTH: 6
<212> TYPE: PRT
<213> ORGANISM: Artificial Sequence
<220> FEATURE:
<223> OTHER INFORMATION: VL CDR1

<400> SEQUENCE: 120

Gln Asp Ile Ser Asn Tyr
1 5

<210> SEQ ID NO 121
<211> LENGTH: 3
<212> TYPE: PRT
<213> ORGANISM: Artificial Sequence
<220> FEATURE:
<223> OTHER INFORMATION: VL CDR2

<400> SEQUENCE: 121

Tyr Thr Ser
1

<210> SEQ ID NO 122
<211> LENGTH: 9
<212> TYPE: PRT
<213> ORGANISM: Artificial Sequence
<220> FEATURE:
<223> OTHER INFORMATION: VL CDR3

<400> SEQUENCE: 122

Gln Gln Gly Tyr Thr Leu Pro Tyr Thr
1 5

<210> SEQ ID NO 123
<211> LENGTH: 98
<212> TYPE: PRT
<213> ORGANISM: Artificial Sequence
<220> FEATURE:
<223> OTHER INFORMATION: Peptide Sequence

<400> SEQUENCE: 123

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Tyr Met His Trp Val Arg Gln Ala Pro Gly Gln Gly Leu Glu Trp Met
35 40 45

Gly Ile Ile Asn Pro Ser Gly Gly Ser Thr Ser Tyr Ala Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg

<210> SEQ ID NO 124
<211> LENGTH: 98
<212> TYPE: PRT
<213> ORGANISM: Artificial Sequence
<220> FEATURE:
<223> OTHER INFORMATION: Peptide Sequence

<400> SEQUENCE: 124

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Met Asn Trp Val Arg Gln Ala Pro Gly Gln Gly Leu Glu Trp Met
35 40 45

Gly Asn Ile Tyr Pro Ser Gly Gly Ser Thr Asn Tyr Ala Gln Lys Phe
50 55 60

Gln Gly Arg Val Thr Met Thr Val Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Ser

<210> SEQ ID NO 125
<211> LENGTH: 98
<212> TYPE: PRT
<213> ORGANISM: Artificial Sequence
<220> FEATURE:
<223> OTHER INFORMATION: Peptide Sequence

<400> SEQUENCE: 125

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr

```
            20                  25                  30

Trp Met Asn Trp Val Arg Gln Ala Pro Gly Gln Gly Leu Glu Trp Met
        35                  40                  45

Gly Asn Ile Tyr Pro Gly Ser Ser Thr Thr Asn Tyr Ala Gln Lys Phe
    50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser


<210> SEQ ID NO 126
<211> LENGTH: 98
<212> TYPE: PRT
<213> ORGANISM: Artificial Sequence
<220> FEATURE:
<223> OTHER INFORMATION: Peptide Sequence

<400> SEQUENCE: 126

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile Asn Trp Val Arg Gln Ala Pro Gly Gln Gly Leu Glu Trp Ile
        35                  40                  45

Gly Asn Ile Tyr Pro Gly Ser Ser Thr Thr Asn Tyr Asn Glu Lys Phe
    50                  55                  60

Lys Ser Arg Ala Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser


<210> SEQ ID NO 127
<211> LENGTH: 98
<212> TYPE: PRT
<213> ORGANISM: Artificial Sequence
<220> FEATURE:
<223> OTHER INFORMATION: Peptide Sequence

<400> SEQUENCE: 127

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Gly Ser Ser Thr Thr Asn Tyr Asn Glu Lys Phe
    50                  55                  60

Lys Ser Lys Ala Thr Leu Thr Val Asp Thr Ser Ser Ser Thr Ala Tyr
65                  70                  75                  80

Met Gln Leu Ser Ser Leu Thr Ser Asp Asp Ser Ala Val Phe Tyr Cys
                85                  90                  95

Ala Ser


<210> SEQ ID NO 128
<211> LENGTH: 15
```

<212> TYPE: PRT
<213> ORGANISM: Artificial Sequence
<220> FEATURE:
<223> OTHER INFORMATION: IGHJ4*01

<400> SEQUENCE: 128

Tyr Phe Asp Tyr Trp Gly Gln Gly Thr Leu Val Thr Val Ser Ser
1 5 10 15

<210> SEQ ID NO 129
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 129

Ala Met Asp Tyr Trp Gly Gln Gly Thr Leu Val Thr Val Ser Ser
1 5 10 15

<210> SEQ ID NO 130
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 130

Ala Met Asp Tyr Trp Gly Gln Gly Thr Leu Val Thr Val Ser Ser
1 5 10 15

<210> SEQ ID NO 131
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 131

Ala Met Asp Tyr Trp Gly Gln Gly Thr Leu Val Thr Val Ser Ser
1 5 10 15

<210> SEQ ID NO 132
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 132

Ala Met Asp Tyr Trp Val Gln Gly Thr Ser Val Thr Val Ser Ser
1 5 10 15

<210> SEQ ID NO 133
<211> LENGTH: 96
<212> TYPE: PRT
<213> ORGANISM: Artificial Sequence
<220> FEATURE:
<223> OTHER INFORMATION: IGKV3D-7*01

<400> SEQUENCE: 133

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ser Trp Tyr Gln Gln Lys Pro Gly Gln Ala Pro Arg Leu Leu

```
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95


<210> SEQ ID NO 134
<211> LENGTH: 95
<212> TYPE: PRT
<213> ORGANISM: Artificial Sequence
<220> FEATURE:
<223> OTHER INFORMATION: Synthetic Peptide

<400> SEQUENCE: 134

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Asn Trp Tyr Gln Gln Lys Pro Gly Gln Ala Pro Arg Leu Leu Ile
        35                  40                  45

Tyr Tyr Ala Ser Arg Arg His Thr Gly Ile Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Gly Tyr Asn Leu Pro
                85                  90                  95


<210> SEQ ID NO 135
<211> LENGTH: 95
<212> TYPE: PRT
<213> ORGANISM: Artificial Sequence
<220> FEATURE:
<223> OTHER INFORMATION: Synthetic Peptide

<400> SEQUENCE: 135

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Asn Tyr
            20                  25                  30

Leu Asn Trp Tyr Gln Gln Lys Pro Gly Gln Ala Val Arg Leu Leu Ile
        35                  40                  45

Tyr Tyr Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Tyr Thr Leu Pro
                85                  90                  95


<210> SEQ ID NO 136
<211> LENGTH: 95
<212> TYPE: PRT
<213> ORGANISM: Artificial Sequence
<220> FEATURE:
<223> OTHER INFORMATION: Synthetic Peptide

<400> SEQUENCE: 136

Glu Ile Val Met Thr Gln Ser Pro Gly Thr Leu Ser Leu Ser Pro Gly
1               5                   10                  15
```

Glu Arg Ala Thr Leu Ser Cys Arg Ala Ser Gln Asp Ile Ser Asn Tyr
20 25 30

Leu Asn Trp Tyr Gln Gln Lys Pro Gly Gln Ala Val Arg Leu Leu Ile
35 40 45

Tyr Tyr Thr Ser Arg Leu His Ser Gly Ile Pro Asp Arg Phe Ser Gly
50 55 60

Ser Gly Ser Gly Thr Asp Tyr Thr Leu Thr Ile Ser Arg Leu Glu Pro
65 70 75 80

Glu Asp Phe Ala Val Tyr Phe Cys Gln Gln Gly Tyr Thr Leu Pro
85 90 95

<210> SEQ ID NO 137
<211> LENGTH: 95
<212> TYPE: PRT
<213> ORGANISM: Artificial Sequence
<220> FEATURE:
<223> OTHER INFORMATION: Synthetic Peptide

<400> SEQUENCE: 137

Asp Ile Gln Met Thr Gln Thr Thr Ser Ser Leu Ser Ala Ser Leu Gly
1 5 10 15

Asp Arg Val Thr Ile Thr Cys Arg Ala Ser Gln Asp Ile Ser Asn Tyr
20 25 30

Leu Asn Trp Tyr Gln Gln Lys Pro Asp Gly Thr Val Lys Leu Leu Ile
35 40 45

Tyr Tyr Thr Ser Arg Leu His Ser Gly Val Pro Ser Arg Phe Ser Gly
50 55 60

Gly Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Tyr Thr Leu Pro
85 90 95

<210> SEQ ID NO 138
<211> LENGTH: 12
<212> TYPE: PRT
<213> ORGANISM: Artificial Sequence
<220> FEATURE:
<223> OTHER INFORMATION: IGKJ1*01

<400> SEQUENCE: 138

Trp Thr Phe Gly Gln Gly Thr Lys Val Glu Ile Lys
1 5 10

<210> SEQ ID NO 139
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 139

Tyr Thr Phe Gly Gln Gly Thr Lys Val Glu Ile Lys
1 5 10

<210> SEQ ID NO 140
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 140

```
Tyr Thr Phe Gly Gln Gly Thr Lys Val Glu Ile Lys
1               5                   10


<210> SEQ ID NO 141
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 141

Tyr Thr Phe Gly Gln Gly Thr Lys Val Glu Ile Lys
1               5                   10


<210> SEQ ID NO 142
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 142

Tyr Thr Phe Gly Gly Gly Thr Lys Leu Glu Ile Lys
1               5                   10


<210> SEQ ID NO 143
<211> LENGTH: 121
<212> TYPE: PRT
<213> ORGANISM: Artificial Sequence
<220> FEATURE:
<223> OTHER INFORMATION: 4-1BB Variable Heavy Chain Sequences

<400> SEQUENCE: 143

Gln Val Gln Leu Gln Gln Pro Gly Ala Glu Leu Val Lys Pro Gly Ala
1               5                   10                  15

Ser Val Lys Leu Ser Cys Glu Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Gly Ser Ser Thr Thr Asn Tyr Asn Glu Lys Phe
    50                  55                  60

Lys Ser Lys Ala Thr Leu Thr Val Asp Thr Ser Ser Ser Thr Ala Tyr
65                  70                  75                  80

Met Gln Leu Ser Ser Leu Thr Ser Asp Asp Ser Ala Val Phe Tyr Cys
                85                  90                  95

Ala Ser Phe Ser Asp Gly Tyr Tyr Ala Tyr Ala Met Asp Tyr Trp Val
            100                 105                 110

Gln Gly Thr Ser Val Thr Val Ser Ser
        115                 120


<210> SEQ ID NO 144
<211> LENGTH: 743
<212> TYPE: PRT
<213> ORGANISM: Artificial Sequence
<220> FEATURE:
<223> OTHER INFORMATION: Peptide Sequence

<400> SEQUENCE: 144

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30
```

```
Trp Ile Asn Trp Val Lys Gln Arg Pro Gly Gln Gly Leu Glu Trp Ile
        35                  40                  45

Gly Asn Ile Tyr Pro Gly Ser Ser Thr Thr Asn Tyr Asn Glu Lys Phe
    50                  55                  60

Lys Ser Lys Ala Thr Leu Thr Val Asp Thr Ser Ser Ser Thr Ala Tyr
65                  70                  75                  80

Met Gln Leu Ser Ser Leu Thr Ser Asp Asp Ser Ala Val Phe Tyr Cys
                85                  90                  95

Ala Ser Phe Ser Asp Gly Tyr Tyr Ala Tyr Ala Met Asp Tyr Trp Val
            100                 105                 110

Gln Gly Thr Ser Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Thr Thr Ser Ser Leu Ser Ala Ser Leu Gly Asp Arg Val
145                 150                 155                 160

Thr Ile Thr Cys Arg Ala Ser Gln Asp Ile Ser Asn Tyr Leu Asn Trp
                165                 170                 175

Tyr Gln Gln Lys Pro Asp Gly Thr Val Lys Leu Leu Ile Tyr Tyr Thr
            180                 185                 190

Ser Arg Leu His Ser Gly Val Pro Ser Arg Phe Ser Gly Gly Gly Ser
        195                 200                 205

Gly Thr Asp Tyr Ser Leu Thr Ile Ser Asn Leu Glu Gln Glu Asp Ile
    210                 215                 220

Ala Thr Tyr Phe Cys Gln Gln Gly Tyr Thr Leu Pro Tyr Thr Phe Gly
225                 230                 235                 240

Gly Gly Thr Lys Leu Glu Ile Lys Ser Ser Ser Glu Pro Lys Ser Ser
                245                 250                 255

Asp Lys Thr His Thr Cys Pro Pro Cys Pro Ala Pro Glu Leu Leu Gly
            260                 265                 270

Gly Pro Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
        355                 360                 365

Glu Lys Thr Ile Ser Lys Ala Lys Gly Gln Pro Arg Glu Pro Gln Val
    370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Lys Leu Thr Val
        435                 440                 445
```

```
Asp Lys Ser Arg Trp Gln Gln Gly Asn Val Phe Ser Cys Ser Val Met
    450                 455                 460

His Glu Ala Leu His Asn His Tyr Thr Gln Lys Ser Leu Ser Leu Ser
465                 470                 475                 480

Pro Gly Ser Gly Gly Gly Gly Ser Gly Gly Gly Gly Ser Gly Gly Gly
                485                 490                 495

Gly Ser Pro Ser Ser Tyr Val Leu Thr Gln Pro Pro Ser Val Ser Val
            500                 505                 510

Ala Pro Gly Gln Thr Ala Arg Ile Thr Cys Gly Gly Asn Asn Ile Gly
        515                 520                 525

Ser Lys Ser Val His Trp Phe Gln Gln Lys Pro Gly Gln Ala Pro Ala
    530                 535                 540

Leu Val Val Tyr Asp Asp Ser Gly Arg Pro Ser Gly Ile Pro Glu Arg
545                 550                 555                 560

Phe Ser Gly Ser Thr Ser Gly Asn Thr Ala Thr Leu Thr Ile Ser Arg
                565                 570                 575

Val Glu Ala Gly Asp Glu Ala Asp Tyr Tyr Cys Gln Val Trp Asp Ser
            580                 585                 590

Ser Ser Asp His Val Val Phe Gly Gly Gly Thr Lys Leu Thr Val Leu
        595                 600                 605

Gly Gly Gly Gly Ser Gly Gly Gly Gly Ser Gly Gly Gly Gly Ser Gly
    610                 615                 620

Gly Gly Gly Ser Gln Val Gln Leu Val Glu Ser Gly Gly Gly Val Val
625                 630                 635                 640

Gln Pro Gly Arg Ser Leu Arg Leu Ser Cys Ala Ala Ser Gly Phe Thr
                645                 650                 655

Leu Ser Tyr Tyr Gly Met His Trp Val Arg Gln Ala Pro Gly Lys Gly
            660                 665                 670

Leu Glu Trp Val Ala Val Ile Ser His Asp Gly Ser Asp Lys Tyr Tyr
        675                 680                 685

Ala Asp Ser Val Lys Gly Arg Phe Thr Ile Ser Arg Asp Asn Ser Lys
    690                 695                 700

Asn Thr Leu Tyr Leu Gln Met Asp Ser Leu Arg Ala Glu Asp Thr Ala
705                 710                 715                 720

Leu Tyr Tyr Cys Ser Asn Asp Gln Phe Asp Pro Trp Gly Gln Gly Thr
                725                 730                 735

Leu Val Thr Val Ser Ser Arg
            740


<210> SEQ ID NO 145
<211> LENGTH: 251
<212> TYPE: PRT
<213> ORGANISM: Artificial Sequence
<220> FEATURE:
<223> OTHER INFORMATION: Peptide Sequence

<400> SEQUENCE: 145

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Gly Ser Ser Thr Thr Asn Tyr Asn Glu Lys Phe
    50                  55                  60
```

```
Lys Ser Lys Ala Thr Leu Thr Val Asp Thr Ser Ser Ser Thr Ala Tyr
65                  70                  75                  80

Met Gln Leu Ser Ser Leu Thr Ser Asp Asp Ser Ala Val Phe Tyr Cys
                85                  90                  95

Ala Ser Phe Ser Asp Gly Tyr Tyr Ala Tyr Ala Met Asp Tyr Trp Val
            100                 105                 110

Gln Gly Thr Ser Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Thr Thr Ser Ser Leu Ser Ala Ser Leu Gly Asp Arg Val
145                 150                 155                 160

Thr Ile Thr Cys Arg Ala Ser Gln Asp Ile Ser Asn Tyr Leu Asn Trp
                165                 170                 175

Tyr Gln Gln Lys Pro Asp Gly Thr Val Lys Leu Leu Ile Tyr Tyr Thr
            180                 185                 190

Ser Arg Leu His Ser Gly Val Pro Ser Arg Phe Ser Gly Gly Gly Ser
        195                 200                 205

Gly Thr Asp Tyr Ser Leu Thr Ile Ser Asn Leu Glu Gln Glu Asp Ile
    210                 215                 220

Ala Thr Tyr Phe Cys Gln Gln Gly Tyr Thr Leu Pro Tyr Thr Phe Gly
225                 230                 235                 240

Gly Gly Thr Lys Leu Glu Ile Lys Ser Ser Ser
                245                 250


<210> SEQ ID NO 146
<211> LENGTH: 243
<212> TYPE: PRT
<213> ORGANISM: Artificial Sequence
<220> FEATURE:
<223> OTHER INFORMATION: Peptide Sequence

<400> SEQUENCE: 146

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Phe Gln Gln Lys Pro Gly Gln Ala Pro Ala Leu Val Val Tyr
        35                  40                  45

Asp Asp Ser Gly Arg Pro Ser Gly Ile Pro Glu Arg Phe Ser Gly Ser
    50                  55                  60

Thr Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Val Glu Ser Gly Gly Gly Val Val Gln Pro Gly Arg
    130                 135                 140

Ser Leu Arg Leu Ser Cys Ala Ala Ser Gly Phe Thr Leu Ser Tyr Tyr
145                 150                 155                 160

Gly Met His Trp Val Arg Gln Ala Pro Gly Lys Gly Leu Glu Trp Val
                165                 170                 175
```

```
Ala Val Ile Ser His Asp Gly Ser Asp Lys Tyr Tyr Ala Asp Ser Val
            180                 185                 190

Lys Gly Arg Phe Thr Ile Ser Arg Asp Asn Ser Lys Asn Thr Leu Tyr
        195                 200                 205

Leu Gln Met Asp Ser Leu Arg Ala Glu Asp Thr Ala Leu Tyr Tyr Cys
    210                 215                 220

Ser Asn Asp Gln Phe Asp Pro Trp Gly Gln Gly Thr Leu Val Thr Val
225                 230                 235                 240

Ser Ser Arg


<210> SEQ ID NO 147
<211> LENGTH: 2181
<212> TYPE: DNA
<213> ORGANISM: Artificial Sequence
<220> FEATURE:
<223> OTHER INFORMATION: FXX01066 ANTI 4-1BB SCFV X ANTI OX40 SCFV
      ADAPTIR NUCLEOTIDE SEQUENCE

<400> SEQUENCE: 147

gaggtgcaac tggtgcaatc aggagctgag gtgaaaaaac cgggtgccag tgttaaagtt     60

agctgtaagg catccgggta cacgtttaca tcttactgga tgaattgggt ccgacaggcc    120

ccaggccaag ggttggaatg gatgggaaat atttatccgt ccggaggtag caccaattac    180

gctcaaaaat ttcagggaag ggtgacaatg acggtggaca ctagcaccag tactgtgtac    240

atggagttgt caagtcttcg ctccgaagat actgccgtgt attactgtgc ttcatttagt    300

gatgggtatt atgcgtacgc tatggattat tggggtcagg ggaccttggt gacggtgtcc    360

agtggtggtg gaggtagtgg tggaggcgga tctggcggcg gcggttcagg aggtggtgga    420

tccgagatag tgatgactca atctccggct actttgtctc tcagtccagg ggagcgagcc    480

actctgagct gcagggcaag tcagtccgtc tccagctatc ttaattggta ccaacagaag    540

ccgggacagg ctccacgatt gttgatctac tacgctagtc gcaggcacac aggcatacct    600

gctcgctttt ctggaagcgg gtcaggaaca gacttcactt tgacaatctc atcacttcag    660

ccggaggact ttgctgtgta ttactgccaa caaggctaca acctccccta tacgtttggg    720

cagggcacaa aagtagagat taaggagccc aaatcttctg acaaaactca cacatgccca    780

ccgtgcccag cacctccagc cgctgcaccg tcagtcttcc tcttcccccc aaaacccaag    840

gacaccctca tgatctcccg gacccctgag gtcacatgcg tggtggtgga cgtgagccac    900

gaagaccctg aggtcaagtt caactggtac gtggacggcg tggaggtgca taatgccaag    960

acaaagccgc gggaggagca gtacaacagc acgtaccgtg tggtcagcgt cctcaccgtc   1020

ctgcaccagg actggctgaa tggcaaggaa tacaagtgcg cggtctccaa caaagccctc   1080

ccagccccca tcgagaaaac catctccaaa gccaaagggc agccccgaga accacaggtg   1140

tacaccctgc ccccatcccg ggatgagctg accaagaacc aggtcagcct gacctgcctg   1200

gtcaaaggct tctatccaag cgacatcgcc gtggagtggg agagcaatgg gcagccggag   1260

aacaactaca agaccacgcc tcccgtgctg gactccgacg gctccttctt cctctacagc   1320

aagctcaccg tggacaagag caggtggcag caggggaacg tcttctcatg ctccgtgatg   1380

catgaggctc tgcacaacca ctacacgcag aagagcctct ccctgtctcc gggcggcggg   1440

ggatccccgt catcctatgt gctgactcag ccaccctcgg tgtcggtggc cccaggacag   1500

acggccagga ttacctgtgg gggaaacaac attggaagta aaagtgtgaa ctggttccag   1560

cagaagccag gccaggcccc tgtactggtc gtctatgatg atagcggccg gccctcaggg   1620
```

atccctgagc gattctctgg ctccacctct gggaacacgg ccaccctgac catcagcagg 1680
gtcgaagccg gggatgaggc cgactattac tgtcaggtgt gggatagtag tagtgatcat 1740
gtggtattcg gcggagggac caagctgacc gtcctaggtg gaggcggttc aggcggaggt 1800
ggatccggcg gtggcggctc cggtggcggc ggatctcagg tgcaactggt ggagtctggg 1860
ggaggcgtgg tccagcctgg gaggtccctg agactctcct gtgcagcctc tggattcacc 1920
ctcagttact atggcatgca ctgggtccgc caggctccag gcaaggggct ggagtgggtg 1980
gcagctatat cacatgatgg aagtgataaa tactatgcag actccgtgaa gggccgattc 2040
accatctcca gagacaattc caagaacacg ctgtatctgc aaatgaacag cctgagagct 2100
gaagacacgg ccgtgtatta ctgttcgaat gaccagtttg acccctgggg ccagggaacc 2160
ctggtcaccg tctcctcgcg c 2181

<210> SEQ ID NO 148
<211> LENGTH: 2181
<212> TYPE: DNA
<213> ORGANISM: Artificial Sequence
<220> FEATURE:
<223> OTHER INFORMATION: FXX01102 ANTI 4-1BB SCFV X ANTI OX40 SCFV ADAPTIR NUCLEOTIDE SEQUENCE

<400> SEQUENCE: 148
gaggtgcaac tggtgcaatc aggagctgag gtgaaaaaac cgggtgccag tgttaaagtt 60
agctgtaagg catccgggta cacgtttaca tcttactgga tgaattgggt ccgacaggcc 120
ccaggccaag ggttggaatg gatgggaaat atttatccgt ccggaggtag caccaattac 180
gctcaaaaat ttcagggaag ggtgacaatg acggtggaca ctagcaccag tactgtgtac 240
atggagttgt caagtcttcg ctccgaagat actgccgtgt attactgtgc ttcatttagt 300
gatgggtatt atgcgtacgc tatggattat tggggtcagg ggaccttggt gacggtgtcc 360
agtggtggtg gaggtagtgg tggaggcgga tctggcggcg gcggttcagg aggtggtgga 420
tccgagatag tgatgactca atctccggct actttgtctc tcagtccagg ggagcgagcc 480
actctgagct gcagggcaag tcagtccgtc tccagctatc ttaattggta ccaacagaag 540
ccgggacagg ctccacgatt gttgatctac tacgctagtc gcaggcacac aggcatacct 600
gctcgctttt ctggaagcgg gtcaggaaca gacttcactt tgacaatctc atcacttcag 660
ccggaggact ttgctgtgta ttactgccaa caaggctaca acctccccta tacgtttggg 720
cagggcacaa aagtagagat taaggagccc aaatcttctg acaaaactca cacatgccca 780
ccgtgcccag cacctccagc cgctgcaccg tcagtcttcc tcttcccccc aaaacccaag 840
gacaccctca tgatctcccg gacccctgag gtcacatgcg tggtggtgga cgtgagccac 900
gaagaccctg aggtcaagtt caactggtac gtggacggcg tggaggtgca taatgccaag 960
acaaagccgc gggaggagca gtacaacagc acgtaccgtg tggtcagcgt cctcaccgtc 1020
ctgcaccagg actggctgaa tggcaaggaa tacaagtgcg cggtctccaa caaagccctc 1080
ccagccccca tcgagaaaac catctccaaa gccaaagggc agccccgaga accacaggtg 1140
tacaccctgc ccccatcccg ggatgagctg accaagaacc aggtcagcct gacctgcctg 1200
gtcaaaggct tctatccaag cgacatcgcc gtggagtggg agagcaatgg gcagccggag 1260
aacaactaca agaccacgcc tcccgtgctg gactccgacg gctccttctt cctctacagc 1320
aagctcaccg tggacaagag caggtggcag caggggaacg tcttctcatg ctccgtgatg 1380
catgaggctc tgcacaacca ctacacgcag aagagcctct ccctgtctcc gggcggcggg 1440
ggatccccgt catcctatgt gctgactcag ccaccctcgg tgtcggtggc cccaggaaaa 1500
acggccagga ttacctgtgg gggaaacaac attggaagta aaagtgtgaa ctggttccag 1560
cagaagccag gccaggcccc tgtactggtc gtctatgatg atagcggccg gccctcaggg 1620
atccctgagc gattctctgg ctccacctct gggaacacgg ccaccctgac catcagcagg 1680
gtcgaagccg gggatgaggc cgactattac tgtcaggtgt gggatagtag tagtgatcat 1740
gtggtattcg gcggagggac caagctgacc gtcctaggtg gaggcggttc aggcggaggt 1800
ggatccggcg gtggcggctc cggtggcggc ggatctcagg tgcaactggt ggagtctggg 1860
ggaggcgtgg tccagcctgg gaggtccctg agactctcct gtgcagcctc tggattcacc 1920
ctcagttact atggcatgca ctgggtccgc caggctccag gcaaggggct ggagtgggtg 1980
gcagctatat cacatgatgg aagtgataaa tactatgcag actccgtgaa gggccgattc 2040
accatctcca gagacaattc caagaacaga ctgtatctgc aaatgaacag cctgagagct 2100
gaagacacgg ccgtgtatta ctgttcgaat gaccagtttg accccctgggg ccagggaacc 2160 ctggtcaccg tctcctcgcg c 2181

<210> SEQ ID NO 149
<211> LENGTH: 2181
<212> TYPE: DNA
<213> ORGANISM: Artificial Sequence
<220> FEATURE:
<223> OTHER INFORMATION: FXX01111 anti 4-1BB scFV X anti OX40 scFV
ADAPTIR nucleotide sequence

<400> SEQUENCE: 149
gaggtgcaac tggtgcaatc aggagctgag gtgaaaaaac cgggtgccag tgttaaagtt 60
agctgtaagg catccgggta cacgtttaca tcttactgga tgaattgggt ccgacaggcc 120
ccaggccaag ggttggaatg gatgggaaat atttatccgt ccggaggtag caccaattac 180
gctcaaaaat ttcagggaag ggtgacaatg acggtggaca ctagcaccag tactgtgtac 240
atggagttgt caagtcttcg ctccgaagat actgccgtgt attactgtgc ttcatttagt 300
gatgggtatt atgcgtacgc tatggattat tggggtcagg ggaccttggt gacggtgtcc 360
agtggtggtg gaggtagtgg tggaggcgga tctggcggcg gcggttcagg aggtggtgga 420
tccgagatag tgatgactca atctccggct actttgtctc tcagtccagg ggagcgagcc 480
actctgagct gcagggcaag tcagtccgtc tccagctatc ttaattggta ccaacagaag 540
ccgggacagg ctccacgatt gttgatctac tacgctagtc gcaggcacac aggcatacct 600
gctcgctttt ctggaagcgg gtcaggaaca gacttcactt tgacaatctc atcacttcag 660
ccggaggact ttgctgtgta ttactgccaa caaggctaca acctccccta tacgtttggg 720
cagggcacaa aagtagagat taaggagccc aaatcttctg acaaaactca cacatgccca 780
ccgtgcccag cacctccagc cgctgcaccg tcagtcttcc tcttcccccc aaaacccaag 840
gacaccctca tgatctcccg gacccctgag gtcacatgcg tggtggtgga cgtgagccac 900
gaagaccctg aggtcaagtt caactggtac gtggacggcg tggaggtgca taatgccaag 960
acaaagccgc gggaggagca gtacaacagc acgtaccgtg tggtcagcgt cctcaccgtc 1020
ctgcaccagg actggctgaa tggcaaggaa tacaagtgcg cggtctccaa caaagccctc 1080
ccagccccca tcgagaaaac catctccaaa gccaaagggc agccccgaga accacaggtg 1140
tacaccctgc ccccatcccg ggatgagctg accaagaacc aggtcagcct gacctgcctg 1200
gtcaaaggct tctatccaag cgacatcgcc gtggagtggg agagcaatgg gcagccggag 1260
aacaactaca agaccacgcc tcccgtgctg gactccgacg gctccttctt cctctacagc 1320
aagctcaccg tggacaagag caggtggcag caggggaacg tcttctcatg ctccgtgatg 1380
catgaggctc tgcacaacca ctacacgcag aagagcctct ccctgtctcc gggcggcggg 1440
ggatccccgt catcctatgt gctgactcag ccaccctcgg tgtcggtggc cccaggacag 1500
acggccagga ttacctgtgg gggaaacaac attggaagta aaagtgtgaa ctggttccag 1560
cagaagccag gccaggcccc tgtactggtc gtctatgatg atagcggccg gccctcaggg 1620
gttcctaacc gattctctgg ctccacctct gggaacacgg ccaccctgac catcagcagg 1680
gtcgaagccg gggatgaggc cgactattac tgtcaggtgt gggatagtag tagtgatcat 1740
gtggtattcg gcggagggac caagctgacc gtcctaggtg gaggcggttc aggcggaggt 1800
ggatccggcg gtggcggctc cggtggcggc ggatctcagg tgcaactggt ggagtctggg 1860
ggaggcgtgg tccagcctgg gaggtccctg agactctcct gtgcagcctc tggattcacc 1920
ctcagttact atggcatgca ctgggtccgc caggctccag gcaaggggct ggagtgggtg 1980
gcagctatat cacatgatgg aagtgataaa tactatgcag actccgtgaa gggccgattc 2040
accatctcca gagacaattc caagaacacg ctgtatctgc aaatgaacag cctgagagct 2100
gaagacacgg ccgtgtatta ctgttcgaat gaccagtttg acccctgggg ccagggaacc 2160
ctggtcaccg tctcctcgcg c 2181

<210> SEQ ID NO 150
<211> LENGTH: 15
<212> TYPE: PRT
<213> ORGANISM: Artificial Sequence
<220> FEATURE:
<223> OTHER INFORMATION: sss(s)-hIgG1 hinge

<400> SEQUENCE: 150

Glu Pro Lys Ser Ser Asp Lys Thr His Thr Ser Pro Pro Ser Ser
1 5 10 15

<210> SEQ ID NO 151
<211> LENGTH: 15
<212> TYPE: PRT
<213> ORGANISM: Artificial Sequence
<220> FEATURE:
<223> OTHER INFORMATION: csc(s)-hIgG1 hinge

<400> SEQUENCE: 151

Glu Pro Lys Ser Cys Asp Lys Thr His Thr Ser Pro Pro Cys Ser
1 5 10 15

<210> SEQ ID NO 152
<211> LENGTH: 15
<212> TYPE: PRT
<213> ORGANISM: Artificial Sequence
<220> FEATURE:
<223> OTHER INFORMATION: ssc(s)-hIgG1 hinge

<400> SEQUENCE: 152

Glu Pro Lys Ser Ser Asp Lys Thr His Thr Ser Pro Pro Cys Ser
1 5 10 15

<210> SEQ ID NO 153
<211> LENGTH: 15
<212> TYPE: PRT
<213> ORGANISM: Artificial Sequence
<220> FEATURE:
<223> OTHER INFORMATION: scc(s)-hIgG1 hinge

<400> SEQUENCE: 153

Glu Pro Lys Ser Ser Asp Lys Thr His Thr Cys Pro Pro Cys Ser
1 5 10 15

<210> SEQ ID NO 154
<211> LENGTH: 15
<212> TYPE: PRT
<213> ORGANISM: Artificial Sequence
<220> FEATURE:
<223> OTHER INFORMATION: css(s)-hIgG1 hinge

<400> SEQUENCE: 154

Glu Pro Lys Ser Cys Asp Lys Thr His Thr Ser Pro Pro Ser Ser
1 5 10 15

<210> SEQ ID NO 155
<211> LENGTH: 15
<212> TYPE: PRT
<213> ORGANISM: Artificial Sequence
<220> FEATURE:
<223> OTHER INFORMATION: scs(s)-hIgG1 hinge

<400> SEQUENCE: 155

Glu Pro Lys Ser Ser Asp Lys Thr His Thr Cys Pro Pro Ser Ser
1 5 10 15

<210> SEQ ID NO 156
<211> LENGTH: 15
<212> TYPE: PRT
<213> ORGANISM: Artificial Sequence
<220> FEATURE:
<223> OTHER INFORMATION: ccc(s)-hIgG1 hinge

<400> SEQUENCE: 156

Glu Pro Lys Ser Cys Asp Lys Thr His Thr Ser Pro Pro Cys Ser
1 5 10 15

<210> SEQ ID NO 157
<211> LENGTH: 15
<212> TYPE: PRT
<213> ORGANISM: Artificial Sequence
<220> FEATURE:
<223> OTHER INFORMATION: ccc(p)-hIgG1 hinge

<400> SEQUENCE: 157

Glu Pro Lys Ser Cys Asp Lys Thr His Thr Ser Pro Pro Cys Pro
1 5 10 15

<210> SEQ ID NO 158
<211> LENGTH: 15
<212> TYPE: PRT
<213> ORGANISM: Artificial Sequence
<220> FEATURE:
<223> OTHER INFORMATION: sss(p)-hIgG1 hinge

<400> SEQUENCE: 158

Glu Pro Lys Ser Ser Asp Lys Thr His Thr Ser Pro Pro Ser Pro
1 5 10 15

<210> SEQ ID NO 159
<211> LENGTH: 15
<212> TYPE: PRT
<213> ORGANISM: Artificial Sequence
<220> FEATURE:
<223> OTHER INFORMATION: csc(p)-hIgG1 hinge

<400> SEQUENCE: 159

Glu Pro Lys Ser Cys Asp Lys Thr His Thr Ser Pro Pro Cys Pro
1 5 10 15

<210> SEQ ID NO 160
<211> LENGTH: 15
<212> TYPE: PRT
<213> ORGANISM: Artificial Sequence
<220> FEATURE:
<223> OTHER INFORMATION: ssc(p)-hIgG1 hinge

<400> SEQUENCE: 160

Glu Pro Lys Ser Ser Asp Lys Thr His Thr Ser Pro Pro Cys Pro
1 5 10 15

<210> SEQ ID NO 161
<211> LENGTH: 15
<212> TYPE: PRT
<213> ORGANISM: Artificial Sequence
<220> FEATURE:
<223> OTHER INFORMATION: scc(p)-hIgG1 hinge

<400> SEQUENCE: 161

Glu Pro Lys Ser Ser Asp Lys Thr His Thr Cys Pro Pro Cys Pro
1 5 10 15

<210> SEQ ID NO 162
<211> LENGTH: 15
<212> TYPE: PRT
<213> ORGANISM: Artificial Sequence
<220> FEATURE:
<223> OTHER INFORMATION: css(p)-hIgG1 hinge

<400> SEQUENCE: 162

Glu Pro Lys Ser Cys Asp Lys Thr His Thr Ser Pro Pro Ser Pro
1 5 10 15

<210> SEQ ID NO 163
<211> LENGTH: 15
<212> TYPE: PRT
<213> ORGANISM: Artificial Sequence
<220> FEATURE:
<223> OTHER INFORMATION: scs(p)-hIgG1 hinge

<400> SEQUENCE: 163

Glu Pro Lys Ser Ser Asp Lys Thr His Thr Cys Pro Pro Ser Pro
1 5 10 15

<210> SEQ ID NO 164
<211> LENGTH: 6
<212> TYPE: PRT
<213> ORGANISM: Artificial Sequence
<220> FEATURE:
<223> OTHER INFORMATION: Synthetic sequence

<400> SEQUENCE: 164

Ser Cys Pro Pro Cys Pro
1 5

<210> SEQ ID NO 165
<211> LENGTH: 20
<212> TYPE: PRT
<213> ORGANISM: Artificial Sequence
<220> FEATURE:
<223> OTHER INFORMATION: STD1

<400> SEQUENCE: 165

Asn Tyr Gly Gly Gly Gly Ser Gly Gly Gly Gly Ser Gly Gly Gly Gly
1 5 10 15

Ser Gly Asn Ser
20

<210> SEQ ID NO 166
<211> LENGTH: 38
<212> TYPE: PRT
<213> ORGANISM: Artificial Sequence
<220> FEATURE:
<223> OTHER INFORMATION: STD2

<400> SEQUENCE: 166

Asn Tyr Gly Gly Gly Gly Ser Gly Gly Gly Gly Ser Gly Gly Gly Gly
1 5 10 15

Ser Gly Asn Tyr Gly Gly Gly Gly Ser Gly Gly Gly Gly Ser Gly Gly
20 25 30

Gly Gly Ser Gly Asn Ser
35

<210> SEQ ID NO 167
<211> LENGTH: 2
<212> TYPE: PRT
<213> ORGANISM: Artificial Sequence
<220> FEATURE:
<223> OTHER INFORMATION: Synthetic peptide

<400> SEQUENCE: 167

Asn Ser
1

<210> SEQ ID NO 168
<211> LENGTH: 8
<212> TYPE: PRT
<213> ORGANISM: Artificial Sequence
<220> FEATURE:
<223> OTHER INFORMATION: Synthetic peptide

<400> SEQUENCE: 168

Gly Gly Gly Gly Ser Gly Asn Ser
1 5

<210> SEQ ID NO 169
<211> LENGTH: 10
<212> TYPE: PRT
<213> ORGANISM: Artificial Sequence
<220> FEATURE:
<223> OTHER INFORMATION: Synthetic peptide

<400> SEQUENCE: 169

Asn Tyr Gly Gly Gly Gly Ser Gly Asn Ser
1 5 10

<210> SEQ ID NO 170
<211> LENGTH: 13
<212> TYPE: PRT
<213> ORGANISM: Artificial Sequence
<220> FEATURE:
<223> OTHER INFORMATION: Synthetic peptide

<400> SEQUENCE: 170

Gly Gly Gly Gly Ser Gly Gly Gly Gly Ser Gly Asn Ser
1 5 10

<210> SEQ ID NO 171

```
<211> LENGTH: 15
<212> TYPE: PRT
<213> ORGANISM: Artificial Sequence
<220> FEATURE:
<223> OTHER INFORMATION: Synthetic peptide

<400> SEQUENCE: 171

Asn Tyr Gly Gly Gly Gly Ser Gly Gly Gly Gly Ser Gly Asn Ser
1               5                   10                  15


<210> SEQ ID NO 172
<211> LENGTH: 18
<212> TYPE: PRT
<213> ORGANISM: Artificial Sequence
<220> FEATURE:
<223> OTHER INFORMATION: Synthetic peptide

<400> SEQUENCE: 172

Gly Gly Gly Gly Ser Gly Gly Gly Gly Ser Gly Gly Gly Gly Ser Gly
1               5                   10                  15

Asn Ser


<210> SEQ ID NO 173
<211> LENGTH: 8
<212> TYPE: PRT
<213> ORGANISM: Artificial Sequence
<220> FEATURE:
<223> OTHER INFORMATION: Synthetic peptide

<400> SEQUENCE: 173

Gly Cys Pro Pro Cys Pro Asn Ser
1               5


<210> SEQ ID NO 174
<211> LENGTH: 15
<212> TYPE: PRT
<213> ORGANISM: Artificial Sequence
<220> FEATURE:
<223> OTHER INFORMATION: Synthetic peptide

<400> SEQUENCE: 174

Gly Gly Gly Gly Ser Gly Gly Gly Gly Ser Gly Gly Gly Gly Ser
1               5                   10                  15


<210> SEQ ID NO 175
<211> LENGTH: 16
<212> TYPE: PRT
<213> ORGANISM: Artificial Sequence
<220> FEATURE:
<223> OTHER INFORMATION: Synthetic peptide

<400> SEQUENCE: 175

Ser Gly Gly Gly Gly Ser Gly Gly Gly Gly Ser Gly Gly Gly Gly Ser
1               5                   10                  15


<210> SEQ ID NO 176
<211> LENGTH: 20
<212> TYPE: PRT
<213> ORGANISM: Artificial Sequence
<220> FEATURE:
<223> OTHER INFORMATION: Synthetic peptide

<400> SEQUENCE: 176

Gly Gly Gly Gly Ser Gly Gly Gly Gly Ser Gly Gly Gly Gly Ser Gly
1               5                   10                  15

Gly Gly Gly Ser
```

20

<210> SEQ ID NO 177
<211> LENGTH: 21
<212> TYPE: PRT
<213> ORGANISM: Artificial Sequence
<220> FEATURE:
<223> OTHER INFORMATION: H75 (NKG2A quadruple mutant)

<400> SEQUENCE: 177

Gln Arg His Asn Asn Ser Ser Leu Asn Thr Gly Thr Gln Met Ala Gly
1               5                   10                  15

His Ser Pro Asn Ser
            20

<210> SEQ ID NO 178
<211> LENGTH: 16
<212> TYPE: PRT
<213> ORGANISM: Artificial Sequence
<220> FEATURE:
<223> OTHER INFORMATION: H83 (NKG2A derived)

<400> SEQUENCE: 178

Ser Ser Leu Asn Thr Gly Thr Gln Met Ala Gly His Ser Pro Asn Ser
1               5                   10                  15

<210> SEQ ID NO 179
<211> LENGTH: 18
<212> TYPE: PRT
<213> ORGANISM: Artificial Sequence
<220> FEATURE:
<223> OTHER INFORMATION: H106 (NKG2A derived)

<400> SEQUENCE: 179

Gln Arg His Asn Asn Ser Ser Leu Asn Thr Gly Thr Gln Met Ala Gly
1               5                   10                  15

His Ser

<210> SEQ ID NO 180
<211> LENGTH: 14
<212> TYPE: PRT
<213> ORGANISM: Artificial Sequence
<220> FEATURE:
<223> OTHER INFORMATION: H81 (NKG2D derived)

<400> SEQUENCE: 180

Glu Val Gln Ile Pro Leu Thr Glu Ser Tyr Ser Pro Asn Ser
1               5                   10

<210> SEQ ID NO 181
<211> LENGTH: 20
<212> TYPE: PRT
<213> ORGANISM: Artificial Sequence
<220> FEATURE:
<223> OTHER INFORMATION: H91 (NKG2D derived)

<400> SEQUENCE: 181

Asn Ser Leu Ala Asn Gln Glu Val Gln Ile Pro Leu Thr Glu Ser Tyr
1               5                   10                  15

Ser Pro Asn Ser
            20

<210> SEQ ID NO 182
<211> LENGTH: 19
<212> TYPE: PRT

```
<213> ORGANISM: Artificial Sequence
<220> FEATURE:
<223> OTHER INFORMATION: Synthetic Peptide

<400> SEQUENCE: 182

Ser Gly Gly Gly Gly Ser Gly Gly Gly Gly Ser Gly Gly Gly Gly Ser
1               5                   10                  15

Pro Asn Ser


<210> SEQ ID NO 183
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 183

Ser Gly Gly Gly Gly Ser Gly Gly Gly Gly Ser Gly Gly Gly Gly Ser
1               5                   10                  15

Pro Gly Ser


<210> SEQ ID NO 184
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 184

Gly Gly Gly Gly Ser Gly Gly Gly Gly Ser Gly Gly Gly Gly Ser Pro
1               5                   10                  15

Ser
```